United States Patent
Wilson et al.

(10) Patent No.: US 9,226,922 B2
(45) Date of Patent: Jan. 5, 2016

(54) COMPOUNDS THAT ARE ERK INHIBITORS

(71) Applicant: Merck Sharp & Dohme Corp., Rahway, NJ (US)

(72) Inventors: Kevin J. Wilson, Boston, MA (US); David J. Witter, Norfolk, MA (US); Matthew H. Daniels, Somerville, MA (US); Angie R. Angeles, Boston, MA (US); Phieng Siliphaivanh, Newton, MA (US); David Sloman, Brookline, MA (US); Brendan O'Boyle, Pittsburgh, PA (US); Danielle Falcone, Brookline, MA (US); Catherine White, Newton Center, MA (US); Ron Ferguson, Scotch Plains, NJ (US); Wei Zhou, Scotch Plains, NJ (US); Kathryn Lipford, Boston, MA (US); Umar Faruk Mansoor, Framingham, MA (US); Salem Fevrier, Cranford, NJ (US); Xianhai Huang, Warren, NJ (US); Ravi Kurukulasuriya, Niantic, CT (US); Judson E. Richard, Kittery, ME (US); Shuyi Tang, Belmont, MA (US); Christopher Boyce, Flemington, NJ (US); Joseph Kozlowski, Princeton, NJ (US); Raman Kumar Bakshi, Bangalore (IN); Ganesh Babu Karunakaran, Bangalore (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/431,485

(22) PCT Filed: Sep. 26, 2013

(86) PCT No.: PCT/US2013/061884
§ 371 (c)(1),
(2) Date: Mar. 26, 2015

(87) PCT Pub. No.: WO2014/052566
PCT Pub. Date: Apr. 3, 2014

(65) Prior Publication Data
US 2015/0258074 A1   Sep. 17, 2015

Related U.S. Application Data

(60) Provisional application No. 61/707,091, filed on Sep. 28, 2012.

(51) Int. Cl.
| | |
|---|---|
| C07D 401/14 | (2006.01) |
| A61K 31/437 | (2006.01) |
| C07D 471/04 | (2006.01) |
| A61K 45/06 | (2006.01) |
| A61K 31/4545 | (2006.01) |

(52) U.S. Cl.
CPC ........... *A61K 31/437* (2013.01); *A61K 31/4545* (2013.01); *A61K 45/06* (2013.01); *C07D 471/04* (2013.01)

(58) Field of Classification Search
CPC ............................. C07D 401/14; A61K 31/437
USPC .......................................... 546/119; 514/303
See application file for complete search history.

(56) References Cited

U.S. PATENT DOCUMENTS

| | | | |
|---|---|---|---|
| 6,706,711 B2 | 3/2004 | Hale | |
| 7,348,339 B2 | 3/2008 | Bailey et al. | |
| 7,485,643 B2 | 2/2009 | Wallace et al. | |
| 7,566,784 B2 | 7/2009 | Borzilleri et al. | |
| 9,023,865 B2 * | 5/2015 | Lim ..................... | C07D 471/04 514/303 |
| 2006/0142572 A1 | 6/2006 | Martinez-Botella et al. | |
| 2009/0163488 A1 | 6/2009 | Oguro et al. | |
| 2010/0273776 A1 | 10/2010 | Lindquist et al. | |
| 2011/0189192 A1 | 8/2011 | Cooper et al. | |
| 2011/0251199 A1 | 10/2011 | De Morin et al. | |
| 2012/0214823 A1 | 8/2012 | Zhu et al. | |

FOREIGN PATENT DOCUMENTS

| | | |
|---|---|---|
| WO | 2012000595 A1 | 1/2012 |
| WO | 2012058127 A2 | 5/2012 |

* cited by examiner

*Primary Examiner* — Niloofar Rahmani
(74) *Attorney, Agent, or Firm* — Richard S. Parr; Laura M. Ginkel

(57) ABSTRACT

Disclosed are the ERK inhibitors of formula (1.0), having a pyrazolopyridine base structure, and the pharmaceutically acceptable salts thereof. Also disclosed are methods of treating cancer using the compounds of formula (1.0).

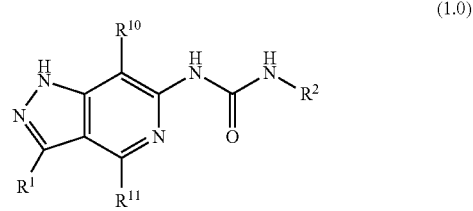

(1.0)

15 Claims, No Drawings

COMPOUNDS THAT ARE ERK INHIBITORS

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

SUMMARY OF THE INVENTION

This invention provides compounds that inhibit the activity of ERK2.

Thus, this invention provides compounds that are ERK inhibitors (i.e., ERK2 inhibitors), said compounds being of the formula (1.0):

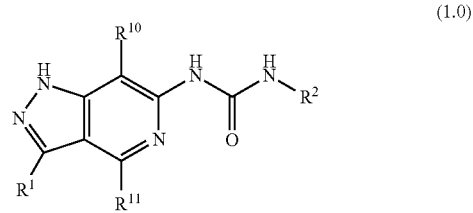

(1.0)

or a pharmaceutically acceptable salt, ester, solvate or prodrug thereof, wherein $R^1$, $R^2$, $R^{10}$ and $R^{11}$ are defined below.

This invention provides: (1) compounds of formula (1.0); (2) compounds of formula (1.0) in pure or isolated form; (3) pharmaceutically acceptable salts of the compounds of formula (1.0); (4) solvates of the compounds of formula (1.0); (5) compounds of formula (1.0) wherein from one to all of the hydrogens are deuterium; (6) compounds of formula (1.0) wherein at least one H is deuterium; (7) compounds of formula (1.0) wherein 1 to 5H are deuterium; (8) compounds of formula (1.0) wherein 1 to 2H are deuterium; and (9) compounds of formula (1.0) wherein one H is deuterium.

This invention also provides the final compounds of Examples 1 to 81.

This invention also provides the final compounds of Examples 100-113 and 200-579.

This invention also provides a pharmaceutical composition comprising an effective amount of at least one (e.g., 1) compound of formula (1.0) and a pharmaceutically acceptable carrier. This invention also provides a pharmaceutical composition comprising an effective amount of at least one (e.g., 1) compound of formula (1.0) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK2) in a patient in need of such treatment comprising administering to said patient an effective amount of at least one (e.g., 1) compound of formula (1.0).

This invention also provides a method for treating cancer in a patient in need of such treatment, said method comprising administering to said patient an effective amount of at least one (e.g., 1) compound of formula (1.0). This invention also provides a method for treating cancer in a patient in need of such treatment, said method comprising administering to said patient an effective amount of at least one (e.g., 1) compound of formula (1.0), in combination with an effective amount of at least one chemotherapeutic agent. The methods of this invention include the administration of a pharmaceutical composition comprising at least one (e.g., 1) compound of this invention and a pharmaceutically acceptable carrier. This invention also provides any of the above methods of treating cancer wherein the cancer is colorectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: Bipphos is 5-(di-tert-butylphosphino)-1',3',5'-triphenyl-1'H-1,4'-bipyrazole; Bn is benzyl; BOC Anhydride is di-tert-butyl dicarbonate; Brettphos is 2-(Dicyclohexylphosphino)3,6-dimethoxy-2',4',6'-triisopropyl-1,1'-biphenyl; CDI is carbonyl diimidazole; DCM is dichloromethane; DIBAL-H is diisobutylaluminum hydride; DIEA is diisopropylethylamine; DMA is dimethyl acetamide; DME is dimethoxyethane; DMF is dimethylformamide; DMSO is dimethyl sulfoxide; DPPA is diphenyl phosphorazidate; EtOAc is ethyl acetate; IPA is i-propanol; Me is methyl; MeOH is methanol; NBS is N-bromosuccinimide; $Pd_2(dba)_3$ is tris(dibenzylidene-acetone)dipalladium(0); $Pd(OAc)_2$ is palladium (II) acetate; PS—$HCO_3$ cartridge is bicarbonate polystyrene copolymere, anion exchanger cartridge; Selectfluor® is 1-chloromethyl-4-fluoro-1,4-diazoniabicyclo[2.2.2]octane bis(tetrafluoroborate); SFC is Supercritcal fluid chromatography; RT is room temperature; TEA is triethylamine; TFA is trifluoroacetic acid; THF is tetrahydrofuran; TrCl is triphenyl methane chloride; Trt is trityl or triphenylmethane; XantPhos is 4,5-Bis(diphenylphosphino)-9,9-dimethylxanthene As used herein, unless otherwise specified, the terms below have the meaning indicated.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (i.e., a chemotherapeutic agent).

The term "at least one" means one or more than one. In one example "at least one" means 1-4, and in another example 1-3, and in another example 1-2, and in another example 1.

The meaning of "at least one" with reference to the number of compounds of this invention is independent of the meaning with reference to the number of chemotherapeutic agents.

The term "chemotherapeutic agent" means a drug (medicament or pharmaceutically active ingredient) for treating cancer (i.e., antineoplastic agent);

The term "compound" with reference to the antineoplastic agents, includes the agents that are antibodies.

The term "consecutively" means one following the other.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK2) activity and phosphorylation. The reduction in ERK activity may be determined by the analysis of pharmacodynamic markers such as phosphorylated RSK1,2 using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period after the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is $H_2O$.

The term "fused" with reference to, for example, two fused rings, means that the two rings have two atoms in common.

The term "monocyclic", as used to describe a ring, means the ring is a single ring (i.e., the ring is not a fused ring). Thus, for example, a "monocyclic heteroaryl ring" means a single heteroaryl ring. A bridged monocyclic ring means a monocyclic ring wherein two atoms in the ring are connected by a bridge. Thus, for example, a "bridged monocyclic heterocycloalkyl ring" means a monocyclic heterocycloalkyl ring wherein two atoms in the ring are connected by a bridge.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e., moiety or substituent) apply when that term is used individually or as a component of another term (e.g., the definition of heteroaryl is the same for heteroaryl and for the heteroaryl portion of -alkylheteroaryl, and the like).

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term -alkylcycloalkyl (or cycloalkylalkyl-) means a cycloalkyl, as defined below, bound to an alkyl, as defined above, wherein the cycloalkyl moiety is bound to the rest of the molecule through the alkyl group.

The term "alkylene" (including the alkylene portions of other moieties) means a chain comprising at least one —(CH$_2$)— group. Examples of alkylene chains include, but are not limited to: —(CH$_2$)$_{1-6}$—, —(CH$_2$)$_{1-4}$—, —(CH$_2$)$_{1-2}$— and —(CH$_2$)—.

The term "amino" means an —NH$_2$ group.

The term "aryl" (including the aryl portions of other moieties, and sometimes abbreviated "ar") means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "cycloalkyl" means a non-aromatic mono- or multicyclic ring system comprising about 3 to about 7, or 3 to about 6, carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system (e.g., a fused ring system) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. The heteroaryl multicyclic ring system includes two rings fused together (i.e., there are two atoms common to both rings). Examples of the heteroaryl multicyclic ring system include fused heteroarylaryl rings (i.e., a heteroaryl ring fused to an aryl ring), and fused heteroarylheteroaryl rings (i.e., a heteroaryl ring fused to a heteroaryl ring). Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, benzopyrazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine (e.g., ![furopyridine structure])

and the like.

The term "heteroarylalkyl-" (or heteroaralkyl-, or -alkylheteroaryl) means a heteroaryl-group (as defined above), bound to an alkyl- group (as defined above), wherein the heteroaryl group is bound to the rest of the molecule through the alkyl group; preferred heteroarylalkyls comprise an alkyl group that is a lower alkyl group; non-limiting examples of suitable heteroaralkyl groups include pyridyl-CH$_2$—, pyrimidinyl-CH$_2$—, imidazolyl-CH$_2$; pyrazinyl-CH$_2$—, and thiazolyl-CH$_2$—.

The term "heterocycloalkyl" (or "heterocyclyl") means a non-aromatic saturated monocyclic or multicyclic ring system comprising about 3 to about 10 ring atoms, preferably about 5 to about 10 ring atoms, and in one example 4 to 6 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl rings. The term "bridged heterocycloalkyl" (or "bridged heterocyclyl") means a heterocycloalkyl group as defined above having an alkylene chain (generally a 1 or 2 carbon alkylene chain, not counting the atoms in the ring to which the alkylene chain is bound to) bridging two carbon atoms in the ring.

The term -heterocycloalkylaryl (or arylheterocycloalkyl-) means a heterocycloalkyl, as defined above, bound to an aryl, as defined above, wherein the aryl moiety is bound to the rest of the molecule through the heterocycloalkyl group.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled the art will appreciate that formulas showing a bond that does not have a substituent at the end of the bond represents a methyl group. Thus, for example,

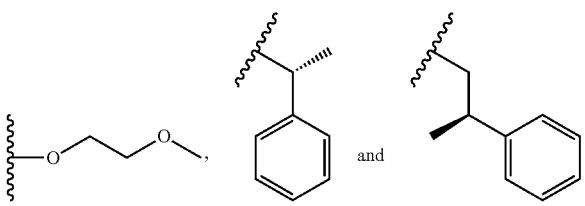

are the same moieties as:

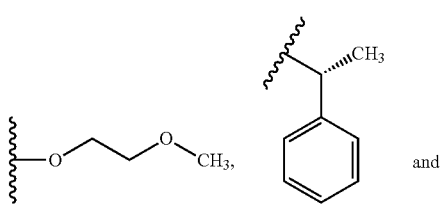

-continued

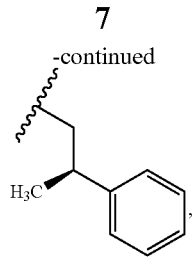

respectively.

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

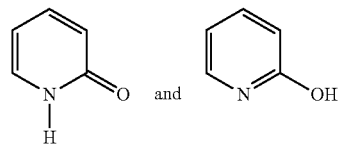 [SMILES: O=c1cccc[nH]1 ; Oc1ccccn1]

are considered equivalent in certain embodiments of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1.0) may be atropisomers and are considered as part of this invention. Enantiomers can also be separated by use of chiral HPLC column.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1.0) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1.0), and of the salts, solvates and prodrugs of the compounds of formula (1.0), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N¹-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free forms of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

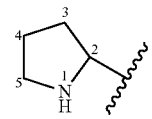

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{123}$I, respectively.

Certain isotopically-labelled compounds of formula (1.0) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (1.0) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of Formula (1.0), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

This invention provides compounds that are ERK inhibitors (i.e., ERK2 inhibitors), said compounds being of the formula (1.0):

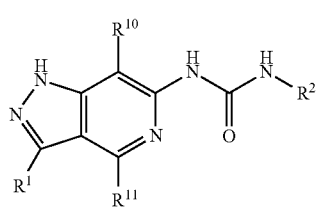

(1.0)

or a pharmaceutically acceptable salt, ester, solvate or prodrug thereof, wherein:

$R^1$ is selected from the group consisting of: —OR$^4$ and —S(O)$_t$R$^5$;

t is 0, 1 or 2;

$R^2$ is selected from the group consisting of: H, (C$_6$-C$_{10}$) aryl-(C$_1$-C$_3$alkyl)-heterocycloalkyl-, —(C$_1$-C$_6$alkyl), —(C$_1$-C$_6$alkyl)-O—(C$_1$-C$_6$alkyl), —(C$_1$-C$_6$alkyl)-heterocycloalkyl-(C$_6$-C$_{10}$aryl), —(C$_1$-C$_6$alkyl)(C$_6$-C$_{10}$) aryl, —(C$_1$-C$_4$alkyl)heteroaryl, —(C$_3$-C$_6$cycloalkyl)-(C$_6$-C$_{10}$aryl), -heterocycloalkyl-(C$_6$-C$_{10}$aryl), -fused (heterocycloalkyl)(C$_6$-C$_{10}$)aryl wherein said heterocycloalkyl is a 5 to 8 membered ring (including the two atoms common with said aryl) comprising 1-3 heteroatoms selected from the group consisting of: O, S and N, and wherein the remaining atoms are carbon, -fused ((C$_3$-C$_6$cycloalkyl))(C$_6$-C$_{10}$)aryl, -heterocycloalkyl-C(O)O—(C$_1$-C$_6$alkyl)-(C$_6$-C$_{10}$)aryl, -heterocycloalkyl-(C$_1$-C$_6$alkyl)-heteroaryl, heterocycloalkyl, (C$_3$-C$_6$cycloalkyl)-(C$_1$-C$_6$alkyl)- and —(C$_3$-C$_6$cycloalkyl);

and wherein said aryl (including the aryl moiety of said fused heterocycloalkylaryl, and fused cycloalkylaryl groups), heterocycloalkyl (including the heterocycloalkyl moiety of said fused heterocycloalkylaryl group), heteroaryl, and cycloalkyl (including the cycloalkyl moiety of said fused cycloalkylaryl group) moieties of said R$^2$ groups are optionally substituted with 1-3 substituents independently selected from the group consisting of: halo (e.g., F, Br, and Cl), —O—(C$_1$-C$_6$alkyl), —OH, —CF$_3$, —(C$_1$-C$_6$alkyl), —S(O)$_r$(C$_1$-C$_6$alkyl) wherein r is 0, 1 or 2, —(C$_1$-C$_6$alkyl)-(C$_3$-C$_6$cycloalkyl), —C(O)—(C$_1$-C$_6$alkyl)-OH, (hydroxyl substituted —(C$_1$-C$_6$alkyl)), —(C$_1$-C$_6$alkyl)(C$_6$-C$_{10}$) aryl, —(C$_1$-C$_6$alkyl)(halo substituted (C$_6$-C$_{10}$)aryl), —C(O)O(C$_1$-C$_6$alkyl), —C(O)(C$_1$-C$_6$alkyl), (halo substituted —(C$_1$-C$_6$alkyl)), —O-(halo substituted (C$_1$-C$_6$alkyl)), —C(O)N(C$_1$-C$_6$alkyl)$_2$ wherein each alkyl is selected independently, —C(O)NH(C$_1$-C$_6$alkyl), —N(C$_1$-C$_6$alkyl)$_2$ wherein each alkyl is independently selected, and —NH(C$_1$-C$_6$alkyl);

and wherein said alkyl moieties of said R$^2$ groups are optionally substituted with 1-3 substituents independently selected from the group consisting of: halo (e.g., F, Br, and Cl), —O—(C$_1$-C$_6$alkyl), —OH and —CF$_3$, —S(O)$_r$(C$_1$-C$_6$alkyl) wherein r is 0, 1 or 2, —(C$_3$-C$_6$cycloalkyl), (hydroxy substituted —(C$_3$-C$_6$cycloalkyl)), heteroaryl, -heteroaryl-(C$_1$-C$_6$alkyl), heterocycloalkyl, —S(O)$_t$(C$_1$-C$_6$alkyl) (wherein t is 0, 1, or 2), —C(O)O(C$_1$-C$_6$alkyl), —O-(halo substituted —(C$_1$-C$_6$alkyl)), —O(C$_1$-C$_6$alkyl)-O—(C$_1$-C$_6$alkyl), —N(C$_1$-C$_6$alkyl)$_2$ wherein each alkyl is independently selected, and —NH(C$_1$-C$_6$alkyl);

$R^4$ is selected from the group consisting of: —(C$_1$-C$_6$alkyl)-O—(C$_1$-C$_6$alkyl), —(C$_1$-C$_6$alkyl)(C$_6$-C$_{10}$aryl), —(C$_1$-C$_6$alkyl), —(C$_1$-C$_6$alkyl)-heteroaryl, —(C$_1$-C$_6$alkyl)-C(O)—N(C$_1$-C$_6$alkyl)$_2$ (wherein each alkyl moiety is independently selected), —(C$_1$-C$_6$alkyl)-heterocycloalkyl, heterocycloalkyl, —(C$_1$-C$_6$alkyl)-(C$_3$-C$_6$cycloalkyl), —(C$_1$-C$_6$alkyl)-N(C$_1$-C$_6$alkyl)$_2$ wherein each alkyl is independently selected, -(hydroxy substituted (C$_1$-C$_6$alkyl)), -heteroaryl and —(C$_3$-C$_6$cycloalkyl);

and wherein said aryl, cycloalkyl, heteroaryl, and heterocycloalkyl moieties of said R$^4$ groups are optionally substituted with 1-3 substitutents independently selected from the group consisting of: halo (e.g., F, Br, and Cl, and in one example F), =O, —CN, —O(C$_1$-C$_6$alkyl) and —(C$_1$-C$_6$ alkyl);

and wherein the alkyl moieties of said R$^4$ groups are optionally substituted with 1-3 substituents independently selected from the group consisting of: —OH, halo (e.g., F, Br, and Cl, and in one example F), and —O(C$_1$-C$_6$alkyl);

$R^5$ is selected from the group consisting of: —(C$_1$-C$_6$alkyl), and —(C$_1$-C$_6$alkyl)-O—(C$_1$-C$_6$alkyl); and wherein said alkyl moieties of said R$^5$ groups are optionally substituted with 1-3 substitutents independently selected from the group consisting of: halo (e.g., F, Br, and Cl, and in one example F), and —O(C$_1$-C$_6$alkyl); and $R^{10}$ and $R^{11}$ are each independently selected from the group consisting of: H, halo, —(C$_1$ to C$_6$alkyl), —(C$_3$-C$_6$ cycloalkyl), hydroxy substituted —(C$_1$-C$_6$alkyl), —(C$_1$-C$_6$alkyl)-O—(C$_1$-C$_6$alkyl), —(C$_1$-C$_6$alkyl)-N(C$_1$-C$_6$alkyl)$_2$ wherein each alkyl is independently selected, —(C$_1$-C$_6$alkyl)-heterocycloalkyl, —NH$_2$, —N(C$_1$-C$_6$alkyl)$_2$ wherein each alkyl is independently selected, —NH(C$_1$-C$_6$alkyl), —(C$_1$-C$_6$alkyl)NH(C$_1$-C$_6$alkyl), —(C$_1$-C$_6$alkyl)NH$_2$, —NHC(O)(C$_1$-C$_6$alkyl), —NH—(C$_6$-C$_{10}$aryl)-O(C$_1$-C$_6$alkyl), —C(O)OH, —CN, heteroaryl, -(heteroaryl-((C$_1$-C$_6$alkyl)-OH), —((C$_1$-C$_6$alkyl)heteroaryl), —C(O)-heterocycloalkyl, -oxoheteroaryl, —C(O)NH$_2$, —C(O)N(C$_1$-C$_6$alkyl)$_2$ wherein each alkyl is independently selected, —C(O)NH(C$_1$-C$_6$alkyl), —(C$_1$-C$_6$alkyl)-(C$_3$-C$_6$cycloalkyl), (hydroxy substituted —($C_1$-$C_6$alkyl)-($C_3$-$C_6$cycloalkyl)), —($C_1$-$C_6$alkyl)-O—C(O)—($C_1$-$C_6$alkyl), —C(O)—($C_1$-$C_6$alkyl), —($C_1$-$C_6$alkyl)-O—C(O)—NH($C_1$-$C_6$alkyl), —($C_1$-$C_6$alkyl)-O—C(O)—N($C_1$-$C_6$alkyl)$_2$ wherein each alkyl is independently selected, —($C_1$-$C_6$alkyl)-(oxoheterocycloalkyl), —($C_1$-$C_6$alkyl)-O-heterocyloalkyl, halo substituted ($C_1$-$C_6$alkyl), —($C_1$-$C_6$alkyl)heteroaryl, —($C_1$-$C_6$alkyl)-(($C_1$-$C_6$)alkoxy) substituted heteroaryl), —($C_1$-$C_6$alkyl)-O—($C_1$-$C_6$alkyl)-OH, —($C_1$-$C_6$alkyl)-O—($C_3$-$C_6$cycloalkyl)-OH, and —($C_1$-$C_6$alkyl)-OH.

In one example, this invention provides the compounds of formula (1.0)

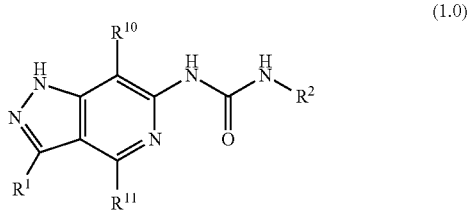

(1.0)

or a pharmaceutically acceptable salt, ester, solvate or prodrug thereof, wherein:

$R^1$ is selected from the group consisting of: —$OR^4$ and —$S(O)_tR^5$;

t is 0, 1 or 2;

$R^2$ is selected from the group consisting of: H, ($C_6$-$C_{10}$)aryl-($C_1$-$C_3$alkyl)-, heterocycloalkyl-, —($C_1$-$C_6$alkyl), —($C_1$-$C_6$alkyl)-O—($C_1$-$C_6$alkyl), —($C_1$-$C_6$alkyl)-heterocycloalkyl-($C_6$-$C_{10}$aryl), —($C_1$-$C_4$alkyl)($C_6$-$C_{10}$)aryl, —($C_1$-$C_3$alkyl)heteroaryl, —($C_3$-$C_6$cycloalkyl)-($C_6$-$C_{10}$aryl), and heterocycloalkyl-($C_6$-$C_{10}$aryl);

and wherein said aryl, heterocycloalkyl, heteroaryl, and cycloalkyl moieties of said $R^2$ groups are optionally substituted with 1-3 substituents independently selected from the group consisting of: halo (e.g., F, Br, and Cl), —O—($C_1$-$C_6$alkyl), —OH, —$CF_3$, and —($C_1$-$C_6$alkyl);

and wherein said alkyl moieties of said $R^2$ groups are optionally substituted with 1-3 substituents independently selected from the group consisting of: halo (e.g., F, Br, and Cl), —O—($C_1$-$C_6$alkyl), —OH and —$CF_3$;

$R^4$ is selected from the group consisting of: —($C_1$-$C_6$alkyl)-O—($C_1$-$C_6$alkyl), —($C_1$-$C_6$alkyl)($C_6$-$C_{10}$aryl), —($C_1$-$C_6$alkyl), —($C_1$-$C_6$alkyl)-heteroaryl, —($C_1$-$C_6$alkyl)-C(O)—N($C_1$-$C_6$alkyl)$_2$ (wherein each alkyl moiety is independently selected), —($C_1$-$C_6$alkyl)-heterocycloalkyl, heterocycloalkyl, —($C_1$-$C_6$alkyl)-($C_3$-$C_6$cycloalkyl), —($C_1$-$C_6$alkyl)-OH;

and wherein said aryl, heteroaryl, and heterocycloalkyl moieties of said $R^4$ groups are optionally substituted with 1-3 substitutents independently selected from the group consisting of: halo (e.g., F, Br, and Cl, and in one example F), —O($C_1$-$C_6$alkyl) and —($C_1$-$C_6$ alkyl);

and wherein the alkyl moieties of said $R^4$ groups are optionally substituted with 1-3 substituents independently selected from the group consisting of: halo (e.g., F, Br, and Cl, and in one example F), and —O($C_1$-$C_6$alkyl);

$R^5$ is selected from the group consisting of: —($C_1$-$C_6$alkyl), and —($C_1$-$C_6$alkyl)-O—($C_1$-$C_6$alkyl); and wherein said alkyl moieties of said $R^5$ groups are optionally substituted with 1-3 substitutents independently selected from the group consisting of: halo (e.g., F, Br, and Cl, and in one example F), and —O($C_1$-$C_6$alkyl); and $R^{10}$ and $R^{11}$ are each independently selected from the group consisting of: H, halo, —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl.

For the $R^2$, $R^4$, $R^{10}$ and $R^{11}$ groups comprising a heterocycloalkyl, each heterocycloalkyl is independently selected and each heterocycloalkyl is a 4 to 6 membered ring comprising 1 to 3 heteroatoms independently selected from the group consisting of: O, N and S, and the remaining ring atoms are carbon. In one example, the heterocycloalkyl is a 4 to 6 membered ring comprising 1-2 heteroatoms independently selected from the group consisting of: O, N and S, and the remaining ring atoms are carbon. In another example, the heterocycloalkyl is a 4 to 6 membered ring comprising 1-2 heteroatoms independently selected from the group consisting of: O and N, and the remaining ring atoms are carbon. In another example, the heterocycloalkyl is a 4 to 6 membered ring comprising 1 heteroatom selected from the group consisting of: O, N and S, and the remaining ring atoms are carbon. In another example, the heterocycloalkyl is a 4 to 6 membered ring comprising 1 heteroatom selected from the group consisting of: O and N, and the remaining ring atoms are carbon. In another example the heterocycloalkyl is a 4 to 6 membered ring comprising 1-2 N atoms, and the remaining ring atoms are carbon. In another example the heterocycloalkyl is a 4 to 6 membered ring comprising 1 heteroatom and said heteroatom is O. In another example the $R^4$ heterocycloalkyl is a 4 membered ring, in another example a 5 membered ring, and in another example a 6 membered ring. Examples of the heterocycloalkyl include, but are not limited to: oxetanyl, tetrahydrofuranyl, tetrahydropyranyl, azetidinyl, pyrrolidinyl, piperidinyl, piperazinyl, morpholinyl, thietanyl, tetrahydrothiophenyl(tetrahydrothienyl), and tetrahydrothiopyranyl. In one example the heterocycloalkyl is

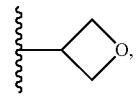 [SMILES: *C1COC1]

and another example is

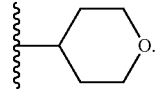

In another example, the hetereocycloalkyl is selected from the group consisting of: piperidinyl, pyrrolidinyl, azetidinyl, piperazinyl, and morpholinyl. In another example the heterocycloalkyl is piperidinyl. Examples the $R^2$ heterocycloalkyl include, but are not limited to, piperidinyl, pyrrolidinyl, azetidinyl, piperazinyl, and morpholinyl. In another example the heterocycloalkyl is piperidinyl. Examples of the $R^4$ heterocycloalkyl include, but are not limited to: oxetanyl, tetrahydrofuranyl, tetrahydropyranyl, azetidinyl, pyrrolidinyl, piperidinyl, piperazinyl, morpholinyl, thietanyl, tetrahydrothiophenyl(tetrahydrothienyl), and tetrahydrothiopyranyl. In one example the $R^4$ heterocycloalkyl is

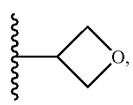

and another example is

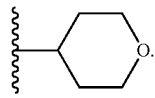 [SMILES: *C1CCOCC1]

Examples the $R^{10}$ heterocycloalkyl include, but are not limited to, piperidinyl, pyrrolidinyl azetidinyl, piperazinyl, and morpholinyl. In another example the heterocycloalkyl is piperidinyl. Examples the $R^{11}$ heterocycloalkyl include, but are not limited to, piperidinyl, pyrrolidinyl, azetidinyl, piperazinyl, and morpholinyl. In another example the heterocycloalkyl is piperidinyl.

For the $R^2$ groups comprising a heteroaryl, said heteroaryl is a 5 to 6 membered ring comprising 1 to 3 heteroatoms independently selected from the group consisting of: O, N and S, and the remaining ring atoms are carbon. In one example the heteroaryl is a 6 membered ring comprising 1 or 2 heteroatoms independently selected from the group consisting of: O, N and S. In another example the heteroaryl is a 6 membered ring comprising 1 or 2 N atoms. In another example the heteroaryl is a 6 membered ring comprising 1 N.

For the $R^4$ groups comprising a heteroaryl, said heteroaryl is a 5 to 6 membered ring comprising 1 to 3 heteroatoms independently selected from the group consisting of: O, N and S, and the remaining ring atoms are carbon. In one example the heteroaryl is a 6 membered ring comprising 1 or 2 heteroatoms independently selected from the group consisting of: O, N and S. In another example the heteroaryl is a 6 membered ring comprising 1 or 2 N atoms. In another example the heteroaryl ring is a 6 membered ring comprising 1 N.

For the $R^2$ groups comprising a $C_6$-$C_{10}$ aryl, said $C_6$-$C_{10}$ aryl is a single ring or two fused rings, and the total number of carbons is 6 to 10. In one example of the $C_6$-$C_{10}$ aryl is phenyl. Another example of the $C_6$-$C_{10}$ aryl is naphthyl.

For the $R^4$ groups comprising a $C_6$-$C_{10}$ aryl, said $C_6$-$C_{10}$ aryl is a single ring or two fused rings, and the total number of carbons is 6 to 10. In one example of the $C_6$-$C_{10}$ aryl is phenyl. Another example of the $C_6$-$C_{10}$ aryl is naphthyl.

For the $R^2$ optional substituent —O—($C_1$-$C_6$alkyl), one example of the alkyl moiety is —($C_1$-$C_4$alkyl), and another is —($C_1$-$C_2$alkyl), and another is methyl.

For the $R^2$ optional substituent —($C_1$-$C_6$alkyl), one example of the alkyl moiety is —($C_1$-$C_4$alkyl), and another is —($C_1$-$C_2$alkyl), and another is methyl.

In one example $R^1$ is —$OR^4$.

In one example the $R^4$ groups are optionally substituted, and in another example the $R^4$ groups are not optionally substituted.

In one example $R^4$ is —($C_1$-$C_6$alkyl)-O—(—$C_1$-$C_6$alkyl). One example of this $R^4$ group is —($C_1$-$C_4$alkyl)-O—($C_1$-$C_4$alkyl), another is —($C_1$-$C_3$alkyl)-O—(—$C_1$-$C_3$alkyl), and another is —($C_1$-$C_2$alkyl)-O—($C_1$-$C_2$alkyl). In one example $R^4$ is —$CH_2CH_2$—$OCH_3$. In one example $R^4$ is —$CH_2C(CH_3)_2OCH_3$, and in another example —$(CH_2)_2OCH_3$, and in another example —$CH(CH_3)CH_2OCH_3$. In another example $R^4$ is a substituted —($C_1$-$C_6$alkyl)-O—(—$C_1$-$C_6$alkyl), such as, for example a substituted —($C_1$-Calkyl)-O—($C_1$-$C_2$alkyl), and in one example a halo (e.g., F) substituted —($C_1$-Calkyl)-O—($C_1$-$C_2$alkyl), and in another example, —$(CH_2)_2OCF_3$, and in another example —$(CH_2)_2OCHF_2$.

In one example $R^4$ is —($C_1$-$C_6$alkyl)($C_6$-$C_{10}$aryl). One example of this $R^4$ group is —($C_1$-$C_4$alkyl)($C_6$-$C_{10}$aryl), another is —($C_1$-$C_3$alkyl)($C_6$-$C_{10}$aryl), another is —($C_1$-$C_2$alkyl)($C_6$-$C_{10}$aryl), and another is —$CH_2$($C_6$-$C_{10}$aryl). In one example the aryl moiety in any one of the —($C_1$-$C_6$alkyl)($C_6$-$C_{10}$aryl) $R^4$ groups is phenyl. In one example $R^4$ is —$CH_2$-phenyl.

In one example $R^4$ is —($C_1$-$C_6$alkyl). One example of this $R^4$ group is —($C_1$-$C_4$alkyl), and another is —($C_1$-$C_2$alkyl). One example of $R^4$ is —$CH_3$. Another example of $R^4$ is —$CH_2CH_3$. Another example of $R^4$ is —$C(D)_3$ (wherein D represents deuterium).

In one example $R^4$ is substituted —($C_1$-$C_6$alkyl). One example of this $R^4$ group is substituted —($C_1$-$C_4$alkyl), and another example is substituted —($C_1$-$C_2$alkyl). In one example $R^4$ is —($C_1$-$C_6$alkyl) substituted with 1-3 independently selected halo atoms, and in another example 1-2 independently selected halo atoms. In another example $R^4$ is —($C_1$-$C_4$alkyl) substituted with 1-3 independently selected halo atoms, and in another example 1-2 independently selected halo atoms. In another example $R^4$ is —($C_1$-$C_2$alkyl) substituted with 1-3 independently selected halo atoms, and in another example 1-2 independently selected halo atoms. In another example $R^4$ is —($C_1$-$C_6$alkyl) substituted with 1-3 F atoms, and in another example 1-2 F atoms. In another example $R^4$ is —($C_1$-$C_4$alkyl) substituted with 1-3 F atoms, and in another example 1-2 F atoms. In another example $R^4$ is —($C_1$-$C_2$alkyl) substituted with 1-3 F atoms, and in another example 1-2 F atoms. In another example $R^4$ is —$CH(F)_2$. In another example $R^4$ is —$CH_2CHF_2$, and in another example —$(CH_2)_3CF_3$. In another example $R^4$ is a hydroxy substituted —($C_1$-$C_6$alkyl), such as, for example, a hydroxyl substituted —($C_1$-$C_2$alkyl), such as, for example, —$(CH_2)_2OH$. In another example $R^4$ is a hydroxyl and halo (e.g., F) substituted-($C_1$-$C_6$alkyl). In another example, $R^4$ is a —$CH_2CH(OH)CF_3$.

In one example $R^4$ is —($C_1$-$C_6$alkyl)-heteroaryl. One example of this $R^4$ group is —($C_1$-$C_4$alkyl)-heteroaryl, and another is —($C_1$-$C_3$alkyl)-heteroaryl, and another is —($C_1$-$C_2$alkyl)-heteroaryl, and another is —$CH_2$-heteroaryl. In other examples of these $R^4$ groups the heteroaryl moiety is pyridyl. One example of $R^4$ is —$CH_2$-pyridyl. Another example of $R^4$ is

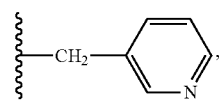

and another example is

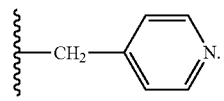 [SMILES: *Cc1ccncc1]

In another example $R^4$ is —$CH_2$thiazolyl, and in another example —$CH_2$-thiazolyl, and in another example —$CH_2$-methylisoxazolyl, and in another example $R^4$—$(CH_2)_2$pyrazolyl, and in another example —$(CH_2)_2$-methylimidazolyl.

In one example $R^4$ is —($C_1$-$C_6$alkyl)-C(O)—N($C_1$-$C_6$alkyl)$_2$ wherein each alkyl is independently selected. One example of this $R^4$ group is —($C_1$-$C_4$alkyl)-C(O)—N($C_1$-$C_4$alkyl)$_2$, and another is —($C_1$-$C_2$alkyl)-C(O)—N($C_1$-$C_4$alkyl)$_2$, and another is —($C_1$-$C_2$alkyl)-C(O)—N($C_1$-$C_2$alkyl)$_2$, and another is —$CH_2$—C(O)—N($C_1$-$C_4$alkyl)$_2$, and another is —$CH_2$—C(O)—N($C_1$-$C_2$alkyl)$_2$, and wherein in each example each alkyl is independently selected. One example of this $R^4$ is —$CH_2$—C(O)—N($CH_3$)$_2$.

In one example $R^4$ is —($C_1$-$C_6$alkyl)-heterocycloalkyl. One example of this $R^4$ group is —($C_1$-$C_4$alkyl)-heterocycloalkyl, and another is —($C_1$-$C_2$alkyl)-heterocycloalkyl, and another is —$CH_2$-heterocycloalkyl. In one example $R^4$ is —$CH_2$-tetrahydropyran, and in another example —$CH_2$-tetrahydrofuran, and in another example —$CH_2$oxopyrrolidinyl, and in another example —($CH_2$)$_2$oxopyrrolidinyl, and in another example —($CH_2$)$_2$piperidinyl.

In one example $R^4$ is —($C_1$-$C_6$alkyl)-(($C_3$-$C_6$)cycloalkyl). One example of this $R^4$ group is —($C_1$-$C_4$alkyl)-(($C_3$-$C_6$)cycloalkyl), and another is —($C_1$-$C_2$alkyl)-(($C_3$-$C_6$)cycloalkyl), and another is —$CH_2$—(($C_3$-$C_6$)cycloalkyl), and another is —($C_1$-$C_4$alkyl)-(($C_3$-$C_4$)cycloalkyl), and another is —($C_1$-$C_2$alkyl)-(($C_3$-$C_4$)cycloalkyl), and another is —$CH_2$—(($C_3$-$C_4$)cycloalkyl). Examples of the cycloalkyl moiety in any one of these $R^4$ groups include, but are not limited to: cyclopropyl, cyclobutyl, cyclopentyl, and cyclohexyl. One example of this $R^4$ is —$CH_2$-cyclopropyl.

In one example $R^4$ is a -(hydroxy substituted ($C_1$-$C_6$alkyl)) group. Said group comprises 1-3 hydroxy groups in the ($C_1$-$C_6$alkyl) group. In one example said $R^4$ group is a -(hydroxy substituted ($C_1$-$C_4$alkyl)) group. In one example, said $R^4$-(hydroxy substituted ($C_1$-$C_6$alkyl)) group is a —($C_1$-$C_6$alkyl)-OH group. In another example, said $R^4$-(hydroxy substituted ($C_1$-$C_6$alkyl)) group is —$CH_2CH(OH)CH_2CH_3$, in another example —$CH_2CH(OH)CH_2OH$. In another example said $R^4$ group is substituted with 1-3 halo atoms (such as, for example, F). An example of said $R^4$ group is —$CH_2CH(OH)CH_2F$.

In one example $R^4$ is —($C_1$-$C_6$alkyl)-OH. One example of this $R^4$ group is —($C_1$-$C_4$alkyl)-OH, and another is —($C_1$-$C_3$alkyl)-OH, and another is —($C_1$-$C_2$alkyl)-OH. One example of this $R^4$ is —$CH_2CH_2$—OH. Another example of said $R^4$ group is —$CH_2CH(CH_3)CH_2OH$, and another example is —$CH_2CH(CH_3)OH$.

In one example $R^4$ is heterocycloalkyl, such as, for example, a 5 to 6 membered ring comprising 1-2 heteroatoms independently selected from the group consisting of O and N. In one example said heterocycloalkyl is a 5-6 membered ring comprising one heteroatom selected from the group consisting of O and N. In one example $R^4$ is pyrrolidinyl, and in another example tetrahydrofuran, and in another example tetrahydrofuranyl, and in another example tetrahydropyranyl, and in another example piperidinyl. Examples of the $R^4$ heterocycloalkyl group also include heterocycloalkyls substituted with 1-2-($C_1$-$C_6$alkyl) (e.g., —($C_1$-$C_3$alkyl) groups. In one example the substituted heterocycloalkyl has one oxygen atom in the ring, and is substituted with 1-2 —($C_1$-$C_6$alkyl) (e.g., —($C_1$-$C_3$alkyl) groups. In another example said substituted heterocycloalkyl is a 6 membered ring having one oxygen atom in the ring and is substituted with a —($C_1$-$C_6$alkyl) (e.g., —($C_1$-$C_3$alkyl, such as, in one example methyl). In one example said $R^4$ substituted heterocycloalkyl is methyltetrahydropyran, in another example dimethyltetrahydropyran.

In one example $R^4$ is —($C_1$-$C_6$alkyl)-N($C_1$-$C_6$alkyl)$_2$ wherein each alkyl is independently selected. In another example said $R^4$ group is —($C_1$-$C_3$alkyl)-N($C_1$-$C_3$alkyl)$_2$ wherein each alkyl is independently selected. In another example said $R^4$ group is —($CH_2$)$_2$N($CH_3$)$_2$.

In one example $R^4$ is —($C_1$-$C_6$alkyl), such as, for example, —($C_1$-$C_2$alkyl). In one example $R^4$ is —$CH_3$, and in another example —$CH_2CH_3$.

In one example $R^4$ is ($C_3$-$C_6$) cycloalkyl (e.g., cyclohexyl). In another example said cycloalkyl is substituted with 1-2 substituents. In another example said cycloalkyl is substituted with 1-2 substituents independently selected from the group consisting of: —CN, —($C_1$-$C_6$alkyl) (e.g., —($C_1$-$C_3$alkyl), and —O($C_1$-$C_6$alkyl)(e.g., —O($C_1$-$C_3$alkyl). In another example said cycloalkyl is substituted with a CN. In another example said cycloalkyl is substituted with a —($C_1$-$C_6$alkyl) (e.g., —($C_1$-$C_3$alkyl, such as, in one example methyl) and is substituted with a —O($C_1$-$C_6$alkyl) (e.g., —O($C_1$-$C_3$alkyl, such as, in one example methoxy). In another example said substituted cycloalkyl is cyanocyclohexyl, in another example methoxymethylcyclohexyl In one example $R^1$ is —S(O)$_t$$R^5$.

In one example the $R^5$ groups are unsubstituted, and in another example the $R^5$ groups are substituted.

In one example $R^1$ is —$SR^5$ (i.e., t is 0). In another example $R^1$ is —S(O)$R^5$ (i.e., t is 1). In another example $R^1$ is —S(O)$_2R^5$ (i.e., t is 2).

In one example $R^5$ is —($C_1$-$C_6$alkyl). One example of this $R^5$ group is —($C_1$-$C_4$alkyl), and another is —($C_1$-$C_2$alkyl). One example of $R^5$ is —$CH_3$. Another example of $R^5$ is —$CH_2CH_3$. Another example of $R^5$ is —$C(D)_3$ (wherein D represents deuterium).

In one example $R^5$ is a —($C_1$-$C_6$alkyl) substituted with 1-3 halo atoms selected from the group consisting of F, Br, and Cl, and in another example —($C_1$-$C_6$alkyl) substituted with 1-3 F atoms, and in another —($C_1$-$C_2$alkyl) substituted with 1-3 halo atoms selected from the group consisting of F, Br, and Cl, and in another example —($C_1$-$C_2$alkyl) substituted with 1-3 F atoms. In one example $R^5$ is —$CF_3$.

In one example $R^5$ is —($C_1$-$C_6$alkyl)-O—(—$C_1$-$C_6$alkyl). One example of this $R^5$ group is —($C_1$-$C_4$alkyl)-O—($C_1$-$C_4$alkyl), and another is —($C_1$-$C_3$alkyl)-O—(—$C_1$-$C_3$alkyl), and another is —($C_1$-$C_2$alkyl)-O—($C_1$-$C_2$alkyl). In one example $R^5$ is —O—$CH_2CH_2$—$OCH_3$.

In one example $R^1$ is selected from the group consisting of: —O—$CH_2CH_2$—$OCH_3$, —O—$CH_2$-phenyl, —O—$CH_3$, —O—$CD_3$, —$OCH(F)_2$, —$OCH_2CH_3$, —$OCH_2CHF_2$, —$O(CH_2)_3CF_3$, —$OCH_2C(CH_3)_2OCH_3$, —$O(CH_2)NCH_3)_2$, —$OCH_2CH(OH)CH_2CH_3$, —$OCH_2CH(OH)CH_2OH$, —$OCH_2CH(CH_3)CH_2OH$, —$OCH_2CH(CH_3)OH$, —$OCH_2CH(OH)CH_2F$, —$OCH_2CH(OH)CF_3$, —$OCH_2CH_2OCHF_2$, —$OCH_2CH_2OCF_3$, —$O(CH_2)_2OH$, —$O(CH_2)_2OCH_3$, —$OCH(CH_3)CH_2OCH_3$, —$O(CH_2)_2OCH_3$, —$O(CH_2)_2OCH_2CH_3$, —O—$CH_2$-pyridyl, —O—$CH_2$—C(O)—N($CH_3$)$_2$, —O—$CH_2$-oxetanyl, —O—$CH_2$-tetrahydrofuranyl, —O—$CH_2$-tetrahydropyranyl, —O—$CH_2$-azetidinyl, —O—$CH_2$-pyrrolidinyl, —O—$CH_2$-piperidinyl, —O—$CH_2$-piperazinyl, —O—$CH_2$-morpholinyl, —O—$CH_2$-thietanyl, —O—$CH_2$-tetrahydrothiophenyl(O—$CH_2$-tetrahydrothienyl), —O—$CH_2$-tetrahydrothiopyranyl, —O—$CH_2$-thiazolyl, —O—$CH_2$-methylisoxazolyl, —O—($CH_2$)$_2$-pyrazolyl, —O—($CH_2$)$_2$-methylimidazolyl, —$OCH_2$oxopyrrolidinyl, —$O(CH_2)_2$oxopyrrolidinyl, —$O(CH_2)_2$piperidinyl, —O-phenyl, —Otetrahydrofuranyl, —Opiperidinyl, —Omethyltetrahydropyranyl, —Ocyanocyclohexyl, —Omethoxymethylcyclohexyl, —Odimethyltetrahydropyranyl, —O-oxetanyl, —O-tetrahydropyranyl, —O-azetidinyl, —O-pyrrolidinyl, —O-piperazinyl, —O-morpholinyl, —O-thietanyl, —O-tetrahydrothiophenyl (—O-tetrahydrothienyl), —O-tetrahydrothiopyranyl, —CH₂-cyclopropyl, —CH₂-cyclobutyl, —CH₂-cyclopentyl, —CH₂-cyclohexyl, —O—CH₂CH₂—OH, —SCF₃, —SCH₃, —SCH₂CH₃, —SCH₂CH₂—O—CH₃, and —S(O)₂CH₃.

In one example R¹ is selected from the group consisting of: —O—CH₂CH₂—OCH₃, —O—CH₂-phenyl, —O—CH₃, —O—CD₃, —OCH(F)₂, —O—CH₂-pyridyl, —O—CH₂—C(O)—N(CH₃)₂, —O—CH₂-oxetanyl, —O—CH₂-tetrahydrofuranyl, —O—CH₂-tetrahydropyranyl, —O—CH₂-azetidinyl, —O—CH₂-pyrrolidinyl, —O—CH₂-piperidinyl, —O—CH₂-piperazinyl, —O—CH₂-morpholinyl, —O—CH₂-thietanyl, —O—CH₂-tetrahydrothiophenyl(O—CH₂-tetrahydrothienyl), —O—CH₂-tetrahydrothiopyranyl, —O-oxetanyl, —O-tetrahydrofuranyl, —O-tetrahydropyranyl, —O-azetidinyl, —O-pyrrolidinyl, —O-piperidinyl, —O-piperazinyl, —O-morpholinyl, —O-thietanyl, —O-tetrahydrothiophenyl (—O-tetrahydrothienyl), —O-tetrahydrothiopyranyl, —CH₂-cyclopropyl, —CH₂-cyclobutyl, —CH₂-cyclopentyl, —CH₂-cyclohexyl, —O—CH₂CH₂—OH, —SCH₃, —SCH₂CH₃, —SCH₂CH₂—O—CH₃, and —S(O)₂CH₃.

In another example R¹ is selected from the group consisting of: —SCH₃, —SCH₂CH₃, —SCH₂CH₂—O—CH₃, and —S(O)₂CH₃. In another example R¹ is —SCH₃. In another example R¹ is —SCH₂CH₃. In another example R¹ is —SCH₂CH₂—OCH₃.

In another example R¹ is selected from the group consisting of: —O—CH₂CH₂—OCH₃, —O—CH₂-phenyl, —O—CH₃, —O—CD₃, —OCH(F)₂, —OCH₂CH₃, —OCH₂CHF₂, —O(CH₂)₃CF₃, —OCH₂C(CH₃)₂OCH₃, —O(CH₂)NCH₃)₂, —OCH₂CH(OH)CH₂CH₃, —OCH₂CH(OH)CH₂OH, —OCH₂CH(CH₃)CH₂OH, —OCH₂CH(CH₃)OH, —OCH₂CH(OH)CH₂F, —OCH₂CH(OH)CF₃, —OCH₂CH₂OCHF₂, —OCH₂CH₂OCF₃, —O(CH₂)₂OH, —O(CH₂)₂OCH₃, —OCH(CH₃)CH₂OCH₃, —O(CH₂)₂OCH₃, —O(CH₂)₂OCH₂CH₃, —O—CH₂-pyridyl, —O—CH₂—C(O)—N(CH₃)₂, —O—CH₂-oxetanyl, —O—CH₂-tetrahydrofuranyl, —O—CH₂-tetrahydropyranyl, —O—CH₂-azetidinyl, —O—CH₂-pyrrolidinyl, —O—CH₂-piperidinyl, —O—CH₂-piperazinyl, —O—CH₂-morpholinyl, —O—CH₂-thietanyl, —O—CH₂-tetrahydrothiophenyl(O—CH₂-tetrahydrothienyl), —O—CH₂-tetrahydrothiopyranyl, —O—CH₂-thiazolyl, —O—CH₂-methylisoxazolyl, —O—(CH₂)₂-pyrazolyl, —O—(CH₂)₂-methylimidazolyl, —OCH₂oxopyrrolidinyl, —O(CH₂)₂oxopyrrolidinyl, —O(CH₂)₂piperidinyl, —O-phenyl, —Otetrahydrofuranyl, —Opiperidinyl, —Omethyltetrahydropyranyl, —Ocyanocyclohexyl, —Omethoxymethylcyclohexyl, —Odimethyltetrahydropyranyl, —O-oxetanyl, —O-tetrahydrofuranyl, —O-tetrahydropyranyl, —O-azetidinyl, —O-pyrrolidinyl, —O-piperidinyl, —O-piperazinyl, —O-morpholinyl, —O-thietanyl, —O-tetrahydrothiophenyl (—O-tetrahydrothienyl), —O-tetrahydrothiopyranyl, —CH₂-cyclopropyl, —CH₂-cyclobutyl, —CH₂-cyclopentyl, —CH₂-cyclohexyl, and —O—CH₂CH₂—OH.

In another example R¹ is selected from the group consisting of: —O—CH₂CH₂—OCH₃, —O—CH₂-phenyl, —O—CH₃, —O—CD₃, —OCH(F)₂, —O—CH₂-pyridyl, —O—CH₂—C(O)—N(CH₃)₂, —O—CH₂-oxetanyl, —O—CH₂-tetrahydrofuranyl, —O—CH₂-tetrahydropyranyl, —O—CH₂-azetidinyl, —O—CH₂-pyrrolidinyl, —O—CH₂-piperidinyl, —O—CH₂-piperazinyl, —O—CH₂-morpholinyl, —O—CH₂-thietanyl, —O—CH₂-tetrahydrothiophenyl(O—CH₂-tetrahydrothienyl), —O—CH₂-tetrahydrothiopyranyl, —O-oxetanyl, —O-tetrahydrofuranyl, —O-tetrahydropyranyl, —O-azetidinyl, —O-pyrrolidinyl, —O-piperidinyl, —O-piperazinyl, —O-morpholinyl, —O-thietanyl, —O-tetrahydro-hiophenyl (—O-tetrahydrothienyl), —O-tetrahydrothiopyranyl, —CH₂-cyclopropyl, —CH₂-cyclobutyl, —CH₂-cyclopentyl, —CH₂-cyclohexyl, and —O—CH₂CH₂—OH.

In another example R¹ is selected from the group consisting of: —O—CH₂CH₂—OCH₃, —O—CH₂-phenyl, —OCH₃, —O—CH₂CH₃, —O—C(D)₃, —O—CH(F)₂, —O—CH₂—C(O)—N(CH₃)₂, —O—CH₂-cyclopropyl, —O—CH₂CH₂—OH, —SCH₃, —SCH₂CH₃, —SCH₂CH₂—O—CH₃, —S(O)₂CH₃,

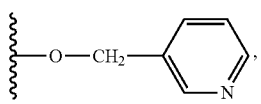
A1

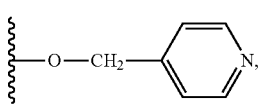
A2

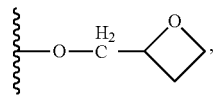
A3

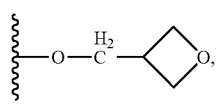
A4

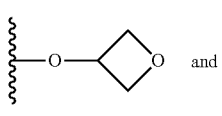
A5 and

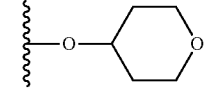
A6

In another example R¹ is selected from the group consisting of: —O—CH₂CH₂—OCH₃, —O—CH₂-phenyl, —OCH₃, —O—CH₂CH₃, —O—C(D)₃, —O—CH(F)₂, —O—CH₂—C(O)—N(CH₃)₂, —O—CH₂-cyclopropyl, —O—CH₂CH₂—OH, A1, A2, A3, A4, A5, and A6.

In another example R¹ is selected from the group consisting of: —OCH₃, —OCH₂CH₂OCH₃, —OCH₂CH₃, —OCH₂CH₂OH, —O—CH₂-phenyl, A2, A4 and A6.

In another example R¹ is —OCH₃. In another example R¹ is —OCH₂CH₂OCH₃. In another example R¹ is —OCH₂CH₃. In another example R¹ is —OCH₂CH₃. In another example R¹ is —OCH₂CH₂OH. In another example R¹ is —O—CH₂-phenyl. In another example R¹ is A2. In another example R¹ is A4. In another example R¹ is —OCH₂CHF₂. In another example R¹ is —O(CH₂)₃CF₃.

In one example R² is selected from the group consisting of:
H,
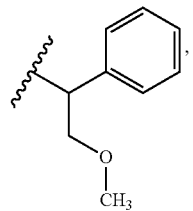 B1
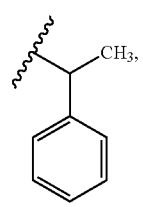 B2
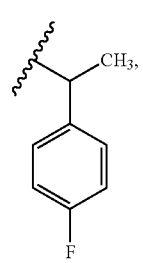 B3
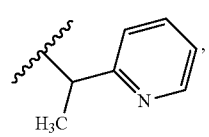 B4
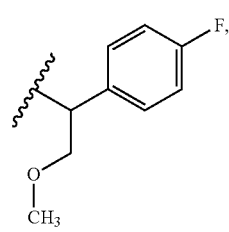 B5
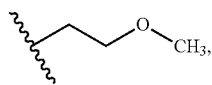 B6
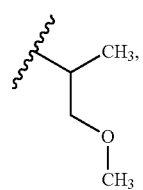 B7
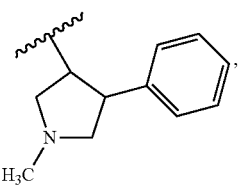 B8
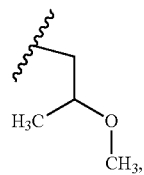 B9
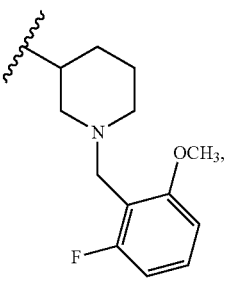 B10
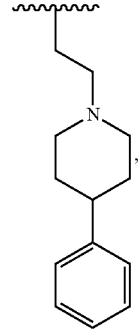 B11
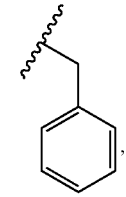 B12
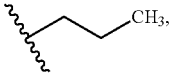 B13
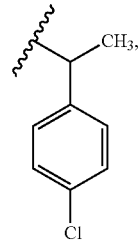 B14
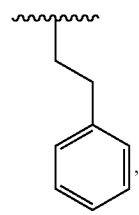 B15

B16 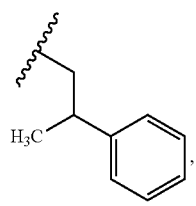
B17 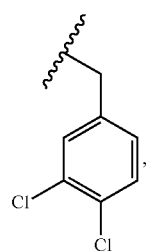
B18 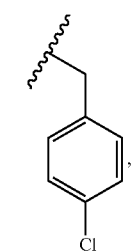
B19 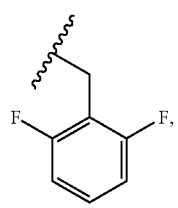
B20 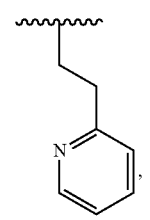
B21 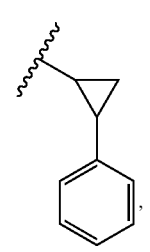
B22 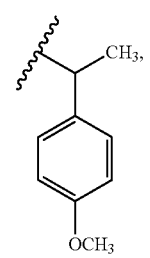
B23 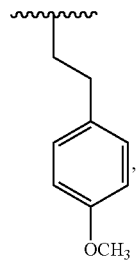
B24 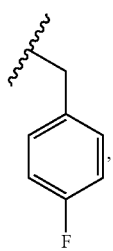
B25 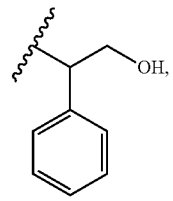
B26 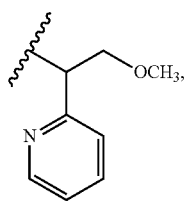
B27 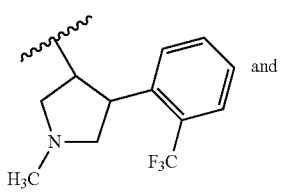 and
B28 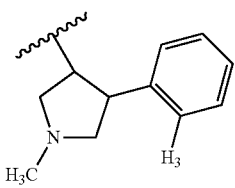

In another example R² is selected from the group consisting of: H,
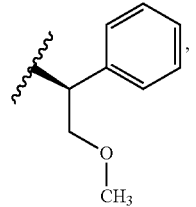
B29
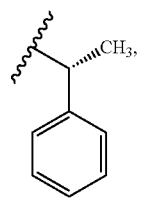
B30
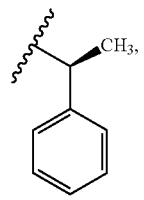
B31
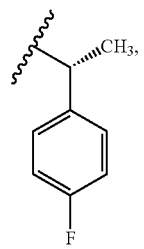
B32
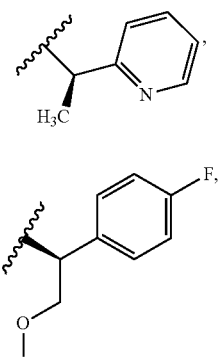
B33
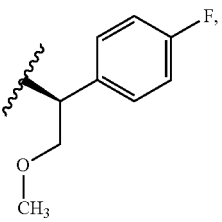
B34
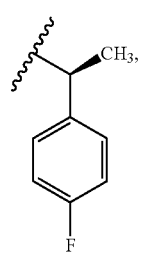
B35
-continued
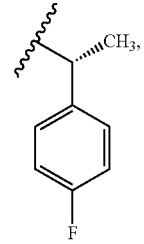
B36
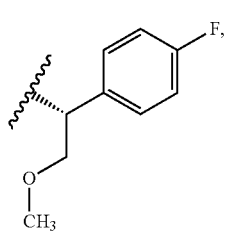
B37
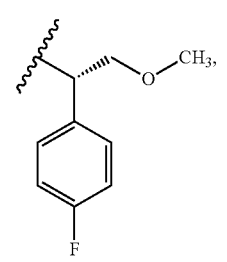
B38
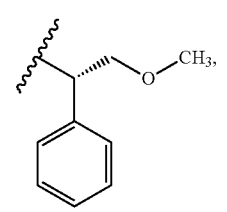
B39
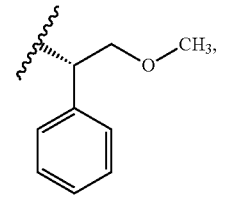
B40
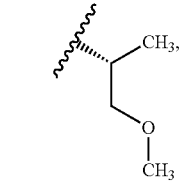
B41
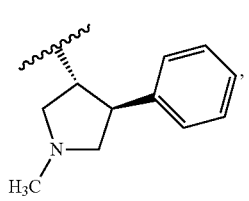
B42

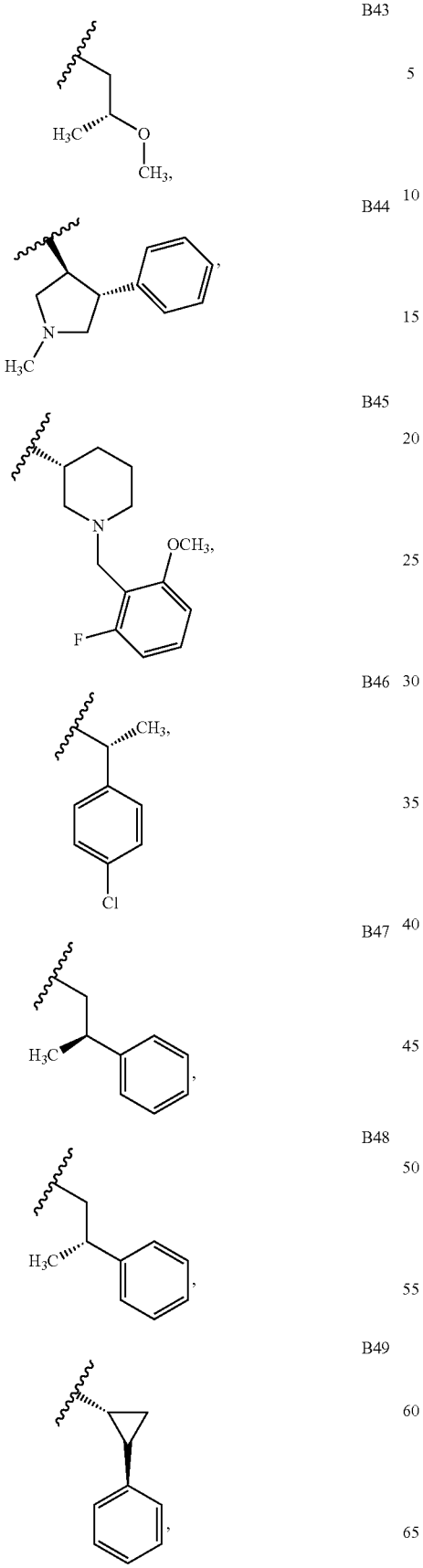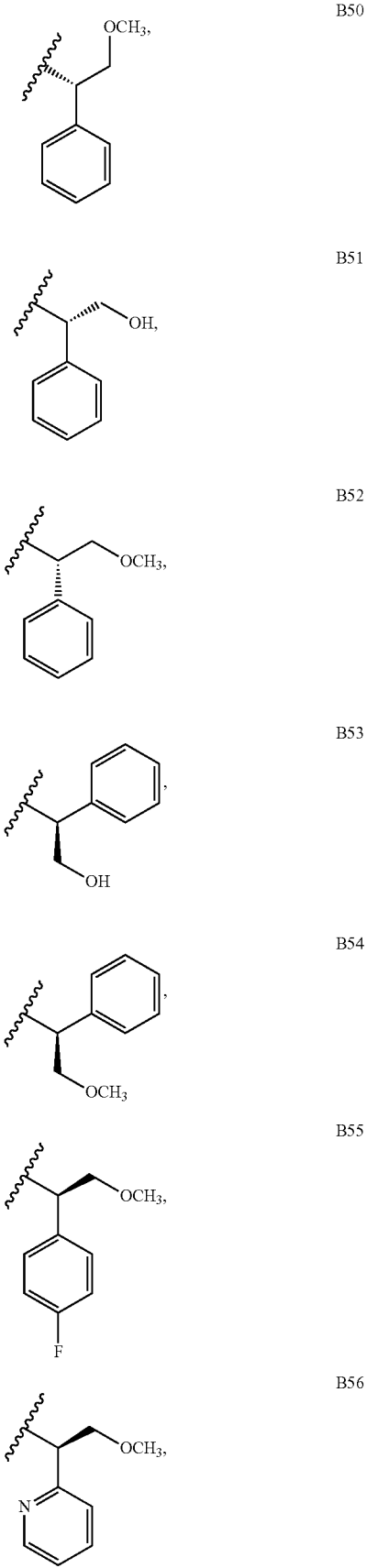

-continued

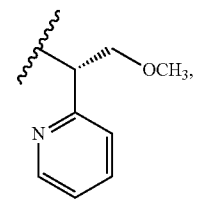  B57

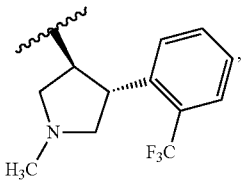  B58

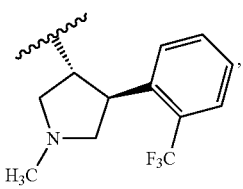  B59

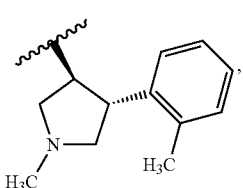  B60

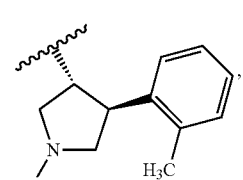  B61

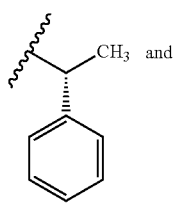  B62 and

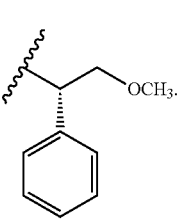  B63

In one example $R^2$ is $(C_6$-$C_{10}$aryl$)$-$(C_1$-$C_3$alkyl$)$-heterocycloalkyl-. One example of this $R^2$ group is $(C_6$-$C_{10}$aryl$)$-$(C_1$-$C_2$alkyl$)$-heterocycloalkyl-, and another is phenyl-$(C_1$-$C_2$alkyl$)$-heterocycloalkyl-, and another is phenyl-$CH_2$-heterocycloalkyl-. In another example $R^2$ is a substituted $(C_6$-$C_{10}$aryl$)$-$(C_1$-$C_3$alkyl$)$-heterocycloalkyl- and in another example substituted $(C_6$-$C_{10}$aryl$)$-$(C_1$-$C_2$alkyl$)$-heterocycloalkyl-, and in another example substituted phenyl-$(C_1$-$C_2$alkyl$)$-heterocycloalkyl-, and in another example substituted phenyl-$CH_2$-heterocycloalkyl-. In another example the phenyl moiety is substituted with 1-3 substituents, and in another example 1-2 substituents, independently selected from the group consisting of: halo (e.g., F, Br, and Cl), and —O—$(C_1$-$C_6$alkyl) (and in one example —O—$(C_1$-$C_2)$alkyl). In another example the phenyl moiety is substituted with 1-2 substituents independently selected from the group consisting of: F and —O—$(C_1$-$C_6$alkyl) (and in one example —O—$(C_1$-$C_2)$alkyl, and in another —OCH$_3$). In one example the heterocycloalkyl moiety is piperidinyl. One example of the $R^2$ substituted $(C_6$-$C_{10}$aryl$)$-$(C_1$-$C_3$alkyl$)$-heterocycloalkyl- group is (F, OCH$_3$-phenyl)-CH$_2$-piperidinyl-. In another example $R^2$ is -piperidinyl-CH$_2$—(F-phenyl). In another example $R^2$ is:

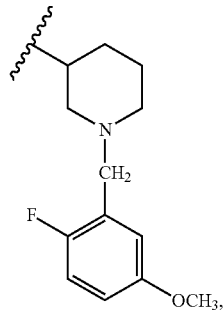  B64 and in another example

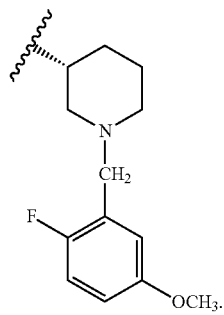  B65

The aryl and heterocycloalkyl moieties of the $R^2$—$(C_1$-$C_6$alkyl$)$-heterocycloalkyl-$(C_6$-$C_{10})$aryl are defined the same as for the $(C_6$-$C_{10}$aryl$)$-$(C_1$-$C_3$alkyl$)$-heterocycloalkyl- described above. One example of the —$(C_1$-$C_6$alkyl) moiety of the —$(C_1$-$C_6$alkyl$)$-heterocycloalkyl-$(C_6$-$C_{10}$aryl) is —$(C_1$-$C_4$alkyl), and another is —$(C_1$-$C_2$alkyl). One example of the $R^2$—$(C_1$-$C_6$alkyl$)$-heterocycloalkyl-$(C_6$-$C_{10}$aryl) group is —CH$_2$CH$_2$-heterocycloalkyl-phenyl, and another example is —CH$_2$CH$_2$-piperidyl-phenyl. The $R^2$—$(C_1$-$C_6$alkyl$)$-heterocycloalkyl-$(C_6$-$C_{10}$aryl) group can be optionally substituted with 1-3 substituents independently selected from the group consisting of: halo (e.g., F, Br, and Cl), and —O—$(C_1$-$C_6$alkyl) (and in one example —O—$(C_1$-$C_2)$alkyl). The $R^2$ $(C_6$-$C_{10}$aryl$)$-heterocycloalkyl- group can be optionally substituted with 1-3 substituents independently selected from the group consisting of: halo (e.g., F, Br and Cl) and O—$(C_1$-$C_6$alkyl) (and in one example —O—$(C_1$-$C_2)$alkyl). One example of the $R^2$—$(C_1$-$C_6$alkyl$)$-heterocycloalkyl-$(C_6$-$C_{10})$aryl is:

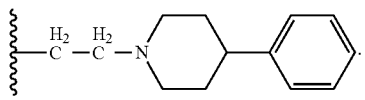
B66

One example of the —($C_1$-$C_6$alkyl) $R^2$ group is —($C_1$-$C_4$alkyl), and another is —($C_1$-$C_3$alkyl), and another is —($C_1$-$C_2$alkyl). One example of $R^2$ is methyl, another example is ethyl and another example is propyl.

In one example $R^2$ is —($C_1$-$C_6$alkyl)($C_6$-$C_{10}$)aryl (e.g., —($C_1$-$C_6$alkyl)phenyl). In another example $R^2$ is —($C_1$-$C_5$alkyl)($C_6$-$C_{10}$)aryl. In another example $R^2$ is —($C_1$-$C_5$alkyl)($C_6$-$C_{10}$)phenyl. In another example $R^2$ is —($C_1$-$C_4$alkyl)($C_6$-$C_{10}$)aryl. In another example $R^2$ is —($C_1$-$C_4$alkyl)($C_6$-$C_{10}$)phenyl. In another example $R^2$ is a substituted —($C_1$-$C_6$alkyl)($C_6$-$C_{10}$)phenyl.

In one example $R^2$ is —($C_1$-$C_4$alkyl)($C_6$-$C_{10}$aryl). One example of this group is —($C_1$-$C_2$alkyl)($C_6$-$C_{10}$aryl), another example is —($C_1$-$C_2$alkyl)phenyl. In one example the $R^2$—($C_1$-$C_4$alkyl)($C_6$-$C_{10}$aryl) group is —CH(CH$_3$)phenyl, in another example —CH-phenyl, and in another example —CH$_2$CH$_2$phenyl, and in another example —CH$_2$CH(CH$_3$)phenyl. In another example $R^2$ is:

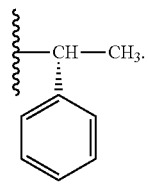
B67

In another example the $R^2$—($C_1$-$C_4$alkyl)($C_6$-$C_{10}$aryl) group is substituted with 1-3 substituents independently selected from the group consisting of: halo (e.g., F, Br, and Cl), —O—($C_1$-$C_6$alkyl) (and in one example —O—($C_1$-$C_2$) alkyl), and —OH. In one example the $R^2$ group is —CH(CH$_3$)-methoxyphenyl, and in another example —(CH$_2$)$_2$-methoxyphenyl. Examples of —O—($C_1$-$C_6$alkyl) substituted $R^2$ groups include, but are not limited to:

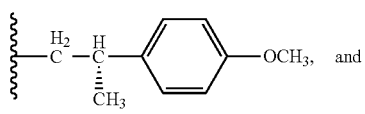
B68

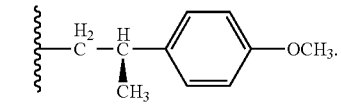
B69

In one example the $R^2$—($C_1$-$C_4$alkyl)-($C_6$-$C_{10}$aryl) group is substituted on the ($C_1$-$C_4$alkyl) moiety with a —O—($C_1$-$C_6$alkyl). An example of this $R^2$ group is —CH($C_6$-$C_{10}$aryl)($C_1$-$C_3$alkyl)-O—($C_1$-$C_6$alkyl). Another example is —CH($C_6$-$C_{10}$aryl)($C_1$-$C_3$alkyl)-O—($C_1$-$C_3$alkyl). Another example is —CH($C_6$-$C_{10}$aryl)($C_1$-$C_3$alkyl)-O—($C_1$-$C_2$alkyl). Another example is —CH(phenyl)($C_1$-$C_3$alkyl)-O—($C_1$-$C_6$alkyl), another example is —CH(phenyl)($C_1$-$C_3$alkyl)-O—($C_1$-$C_4$alkyl), and another example is —CH(phenyl)($C_1$-$C_3$alkyl)-O—($C_1$-$C_2$alkyl). In one example $R^2$ is —CH(CH$_2$OCH$_3$)-phenyl, and in another example —CH(CH$_2$OH)-phenyl. In another example the ($R^2$—CH($C_6$-$C_{10}$aryl)($C_1$-$C_3$alkyl)-O—($C_1$-$C_6$alkyl) group is substituted with 1-3 substituents independently selected from the group consisting of: halo (e.g., F, Br, and Cl), —O—($C_1$-$C_6$alkyl) (and in one example —O—($C_1$-$C_2$)alkyl), and —OH. In another example the $R^2$ group is substituted —CH(phenyl)($C_1$-$C_3$alkyl)-O—($C_1$-$C_4$alkyl), and in another example substituted —CH(phenyl)($C_1$-$C_3$alkyl)-O—($C_1$-$C_2$alkyl), wherein in each example the $R^2$ group is substituted with 1-3 substituents independently selected from the group consisting of: halo (e.g., F, Br, and Cl), —O—($C_1$-$C_6$alkyl) (and in one example —O—($C_1$-$C_2$)alkyl), and —OH. In one example the $R^2$ group is —CH(fluorophenyl)CH$_2$OCH$_3$. Examples of the $R^2$ groups include, but are not limited to:

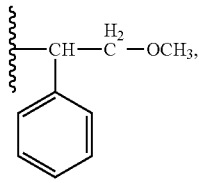
B70

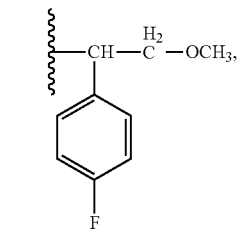
B71

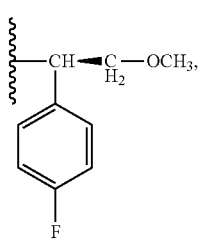
B72

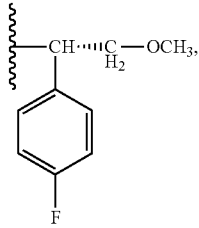
B73

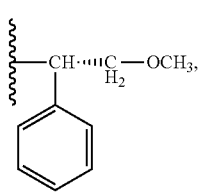
B74

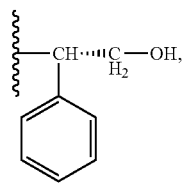
B75

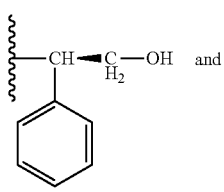 and
B76

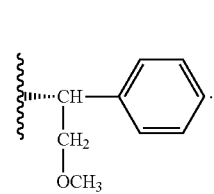
B77

In one example, the $R^2$—$(C_1$-$C_4$alkyl)$(C_6$-$C_{10}$aryl) (and in another —$(C_1$-$C_2$alkyl)$(C_6$-$C_{10}$)aryl), and in another —$(C_1$-$C_2$alkyl)phenyl, and in another —CH(CH$_3$)phenyl, and in another —CH-phenyl, and in another —CH$_2$CH$_2$phenyl, and in another —CH$_2$CH(CH$_3$)phenyl) is substituted with 1-3 independently selected halo atoms, and in another example, 1-2 independently selected halo atoms, and in another example one halo atom. In one example the $R^2$—$(C_1$-$C_3$alkyl)$(C_6$-$C_{10}$aryl) group is —CH(CH$_3$)fluorophenyl, and in another example —CH(CH$_3$)-chlorophenyl, and in another example —CH$_2$-chlorophenyl, and in another example —CH$_2$-dichlorophenyl, and in another example —CH$_2$-difluorophenyl, and in another example —CH$_2$fluorophenyl. Examples of the halo substituted $R^2$—$(C_1$-$C_4$alkyl)$(C_6$-$C_{10}$aryl) groups include, but are not limited to:

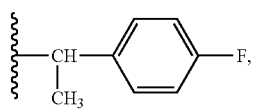
B78

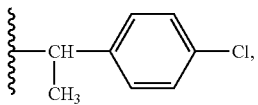
B79

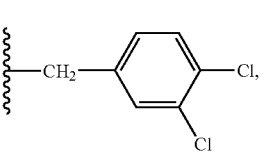
B80

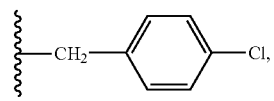
B81

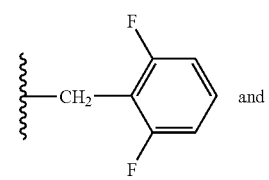 and
B82

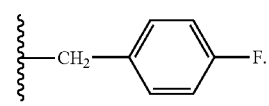
B83

Examples of the $R^2$ substituted —$(C_1$-$C_6$alkyl)$(C_6$-$C_{10}$aryl) (e.g., —$(C_1$-$C_6$alkyl)(phenyl)) group, include, for example, (Cl,F)-phenyl-CH$_2$—, (CH$_3$,Cl)-phenyl-CH$_2$—, CH$_3$O-phenyl-CH$_2$—, F$_2$CHO-phenyl-CH$_2$—, (CH$_3$O,F)-phenyl-CH$_2$—, Cl-phenyl-CH(CH$_2$CH$_3$)—, —CH(CH$_2$OCH$_3$)(p-F-phenyl), —CH(Cl,CF$_3$)-phenyl, —CH(Cl, OCF$_3$)-phenyl, —CH(Cl,OCH$_3$)-phenyl, —CH(Cl,OH)-phenyl, —CH(CH$_2$OH)(di-Cl-phenyl), —CH(C(O)OCH$_3$)(p-F-phenyl), —CH(C(CH$_3$)$_2$OH)(di-F-phenyl), —CH(C(CH$_3$)$_2$OH)(p-Cl-phenyl), —CH(C(CH$_3$)$_2$OH)(di-Cl-phenyl), —CH(methylpyrazolyl)phenyl, —CH(C(CH$_3$)$_2$OH)(F, Cl-phenyl), —CH(C(CH$_3$)$_2$OH)(F, CH$_3$-phenyl), —CH(CH$_2$OCH$_3$)(p-F-phenyl), —CH(CH$_2$OCH$_3$)phenyl, —CH(CH$_2$OCH$_2$CH$_3$)phenyl, —CH(phenyl)CH(OH)CH(CH$_3$)$_2$, —CH(phenyl)CH(OH)CH$_2$OH, —CH(phenyl)CH(OH)CH$_2$-morpholinyl, —CH(phenyl)CH(OH)CH$_2$OCH$_3$, —CH(CH$_2$OH)phenyl, —CH(phenyl)CH$_2$O—(CH$_2$)$_2$OCH$_3$, —CH(p-F-phenyl)CH(CH$_3$)OH, —CH(CH$_2$OCH$_3$)(phenyl), —CH(p-F-phenyl)-C(O)N(CH$_3$)$_2$, —CH(p-F-phenyl)C(O)NH(CH$_3$), —CH(p-F-phenyl)C(CH$_3$)$_2$OCH$_3$, —CH(phenyl)C(CH$_3$)$_2$OCH$_3$, and —CH(phenyl)CH(CH$_3$)OH.

In one example $R^2$ is —$(C_1$-$C_4$alkyl)heteroaryl. In another example $R^2$ is —CH(C(CH$_3$)$_2$OH)pyridyl.

In one example $R^2$ is —$(C_1$-$C_3$alkyl)heteroaryl. One example of the —$(C_1$-$C_3$alkyl)heteroaryl $R^2$ group is —$(C_1$-$C_2$alkyl)heteroaryl, and another is —$(C_1$-$C_3$alkyl)pyridyl, and another is —$(C_1$-$C_2$alkyl)pyridyl. In one example $R^2$ is —CH$_2$CH$_2$-pyridyl, and in another example $R^2$ is

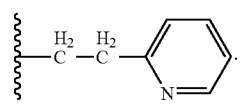
B84

In one example the $R^2$—$(C_1$-$C_3$alkyl)heteroaryl group is substituted on the $(C_1$-$C_4$alkyl) moiety with a —O—$(C_1$-$C_6$alkyl). Thus, in one example $R^2$ is —CH(heteroaryl)-$(C_1$-$C_6$alkyl)-O—$(C_1$-$C_6$alkyl). Examples of this $R^2$ group include, but are not limited to: —CH(heteroaryl)-$(C_1$-

C₄alkyl)-O—(C₁-C₄alkyl), —CH(heteroaryl)-(C₁-C₂alkyl)-O—(C₁-C₂alkyl), and —CH(pridyl)-(C₁-C₂alkyl)-O—(C₁-C₂alkyl). In one example the R² group is —CH(pyridyl)-CH₂—OCH₃. In another example the R² group is)

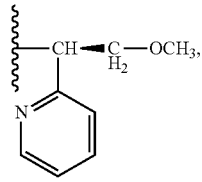

B85 and in another example

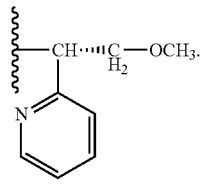

B86

In another example said R²—(C₁-C₃alkyl)heteroaryl group is —CH(CH₂CH₃)pyridyl.

In another example the R²—(C₁-C₃alkyl)heteroaryl group is substituted on the heteroaryl with a —O—(C₁-C₆alkyl) (such as an —O—(C₁-C₃alkyl). In one example, the substituted —(C₁-C₃alkyl)heteroaryl group is a —(C₁-C₃alkyl)pyridyl substituted on the pyridyl with a —O—(C₁-C₆alkyl) (such as an —O—(C₁-C₃alkyl) group. In one example said R² group is —CH₂—(OCH₂CH₃-pyridyl).

In another example the R²—(C₁-C₃alkyl)heteroaryl is substituted on the alkyl moiety with a —C(O)O(C₁-C₆alkyl). In one example said R² is —CH(C(O)OCH₃)pyridyl.

In one example R² is —(C₃-C₆cycloalkyl)-(C₆-C₁₀aryl). One example of this R² group is —(C₃-C₆cycloalkyl)-phenyl, another is (C₃-C₄cycloalkyl)-phenyl, and another is -cyclopropyl-phenyl. In another example, said R² is -cyclopentyl-phenyl.

In one example R² is -heterocycloalkyl-(C₆-C₁₀aryl). One example of this R² group is -heterocycloalkyl-phenyl, and another is a -pyrrolidinyl-phenyl. In another example R² is -heteroacycloalkyl-(C₆-C₁₀aryl) substituted with 1-3 substitutents independently selected from the group consisting of: —CF₃, and —(C₁-C₆alkyl) (and in one example —(C₁-C₄alkyl), and in another example —(C₁-C₂alkyl), and in another example methyl). In one example R² is:

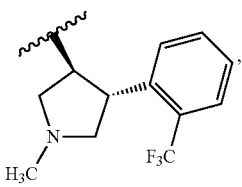

B87 and in another example and in another example

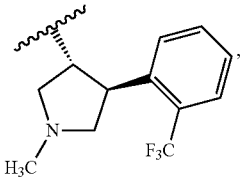

B88 and in another example

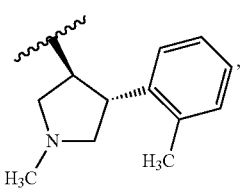

B89 and in another example

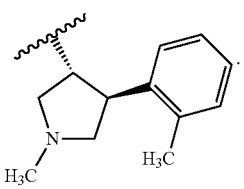

B90

In one example the R²-heterocycloalkyl-(C₆-C₁₀aryl) group (e.g., a -pyrrolidinyl-phenyl group) is substituted with a —(C₁-C₆alkyl)-(C₃-C₆ cycloalkyl) substituent, such as, for example a —(C₁-C₂alkyl)-(C₃-C₆ cycloalkyl), such as, for example —CH₂cyclopropyl.

In one example the R²-heterocycloalkyl-(C₆-C₁₀aryl) group (e.g., a -pyrrolidinyl-phenyl group) is substituted with a —C(O)—(C₁-C₆alkyl)-OH, such as, for example, a —C(O)—(C₁-C₂alkyl)-OH, such as for example, —C(O)CH₂OH.

Other examples of said R²-heterocycloalkyl-(C₆-C₁₀aryl) group include, for example, -((difluoromethyl)-methyl)(phenyl)pyrrolidinyl.

Examples of the R²—(C₁-C₆alkyl) optional substituent include, for example, methyl, ethyl, propyl, and —CH₂CH(CH₃)₂.

Examples of the R²—(C₁-C₆alkyl)-(C₃-C₆cycloalkyl) optional substituent include, for example, —(C₁-C₂alkyl)-(C₃-C₆ cycloalkyl), and in another example —(C₁-C₂alkyl)-(C₃-C₄ cycloalkyl), a nd in another example —CH₂-cyclopropyl.

Examples of the R²—C(O)—(C₁-C₆alkyl)-OH optional substituent include, for example, —C(O)—(C₁-C₂alkyl)-OH, and in another example —C(O)CH₂OH.

Examples of the R²—(C₃-C₆cycloalkyl) optional substituent include, for example, —(C₃-C₅cycloalkyl), and in another example, cyclopropyl, and in another example, cyclobutyl, and in another example cyclopentyl.

Examples of the R² hydroxy substituted —(C₃-C₆cycloalkyl) optional substituent include, for example, hydroxyl substituted —(C₃-C₅cycloalkyl), and in another example, hydroxycyclopropyl-, and in another example, hydroxycyclobutyl-, and in another example hydroxylcyclopentyl-. Other examples include the hydroxyl cycloalkyl groups mentioned in this paragraph wherein the —OH is bound to the same carbon of the cycloalkyl that binds the cycloalkyl to the rest of the molecule.

Examples of the $R^2$ (hydroxyl substituted —($C_1$-$C_6$alkyl)) optional substituent include, for example, —$CH_2CH_2OH$.

Examples of the $R^2$—($C_1$-$C_6$alkyl)($C_6$-$C_{10}$)aryl) optional substituent include, for example, —($C_1$-$C_2$alkyl)(($C_6$-$C_{10}$) aryl), and in another example —($C_1$-$C_2$alkyl)(phenyl), and in another example —$CH_2$-phenyl.

Examples of the $R^2$—($C_1$-$C_6$alkyl)(halo substituted ($C_6$-$C_{10}$)aryl) optional substituent include, for example, —($C_1$-$C_2$alkyl)(halo substituted ($C_6$-$C_{10}$)aryl), and in another example —($C_1$-$C_2$alkyl)(mono or di halo substituted ($C_6$-$C_{10}$)aryl), and in another example —($C_1$-$C_2$alkyl)(halo substituted phenyl), and in another example —($C_1$-$C_2$alkyl) (mono or di halo substituted phenyl). When there is more than one halo atom each halo atom is independently selected. In other examples of the $R^2$ groups in this paragraph, the halo atoms are selected from Br, Cl and F, and in other examples the halo is F. In one example the $R^2$ group is —$CH_2$(F-phenyl), such as, for example, —$CH_2$(p-F-phenyl).

Examples of the $R^2$—C(O)O($C_1$-$C_6$alkyl) optional substituent include, for example, —C(O)O($C_1$-$C_2$alkyl), such as, for example, —C(O)$OCH_3$.

Examples of the $R^2$—C(O)($C_1$-$C_6$alkyl) optional substituent include, for example, —C(O)($C_1$-$C_2$alkyl), such as, for example, —C(O)$CH_3$.

Examples of the $R^2$ heteroaryl optional substituent include, for example, oxazolyl, and in another example furan.

Examples of the $R^2$-heteroaryl-($C_1$-$C_6$alkyl) optional substituent include, for example, $R^2$-heteroaryl-($C_1$-$C_3$alkyl). In another example the heteroaryl moiety of the $R^2$-heteroaryl-($C_1$-$C_6$alkyl) optional substituent is a 5-6 membered ring comprising 1-2 heteroatoms selected from the group consisting of O, N, and S. In another example the heteroaryl moiety of the $R^2$-heteroaryl-($C_1$-$C_6$alkyl) optional substituent is a 5-6 membered ring comprising 1-2 heteroatoms selected from the group consisting of O, N, and S, and said —($C_1$-$C_6$alkyl) moiety is a —($C_1$-$C_3$alkyl) moiety. In another example the heteroaryl moiety of the $R^2$-heteroaryl-($C_1$-$C_6$alkyl) optional substituent is a 5-6 membered ring comprising 1-2 N atoms. In another example the $R^2$-heteroaryl-($C_1$-$C_6$alkyl) optional substituent is -heteroaryl-($C_1$-$C_2$alkyl) wherein said heteroaryl is a 5-6 membered ring comprising 1-2 N atoms. In another example said $R^2$ substituent is —CH-methylpyrazolyl.

Examples of the $R^2$ heterocycloalkyl optional substituent include, for example, morpholinyl, and in another example tetrahydrofuran.

Examples of the $R^2$ (halo substituted —($C_1$-$C_6$alkyl)) optional substituent include, for example, (halo substituted —($C_1$-$C_6$alkyl)) wherein there are 1-3 independently halo atoms. In another example the 1-3 halo atoms are selected from the group consisting of Br, Cl and F. In another example, the $R^2$ (halo substituted —($C_1$-$C_6$alkyl)) optional substituent is (trifluoro substituted —($C_1$-$C_6$alkyl)). In another example the optional substituent is —$CH_2CF_3$, and in another example —$CF_3$, and in another example —$CHF_2$.

Examples of the $R^2$—S(O)$_t$($C_1$-$C_6$alkyl) (wherein t is 0, 1, or 2) optional substituent include, for example, said substituent wherein t is 0, and in another example wherein t is 1, and in another example wherein t is 2. Other examples of the $R^2$—S(O)$_t$($C_1$-$C_6$alkyl) optional substituent include, for example, —S(O)($C_1$-$C_2$alkyl), and in another example —S(O)$_2$($C_1$-$C_2$alkyl). In another example said $R^2$ optional substituent is —S(O)$_2CH_3$, and in another example, —S(O)$CH_3$.

For the $R^2$—O-(halo substituted ($C_1$-$C_6$alkyl)) optional substituent said alkyl group is substituted with 1-3 independently selected halo (e.g., Br, Cl, and F) atoms, and in one example 1-3 F atoms. Examples of this $R^2$ optional group include, for example, —O-(halo substituted ($C_1$-$C_3$alkyl)) wherein there are 1-3 halo atoms and said halo atoms are independently selected from the group consisting of Br, Cl, and F. In another example said $R^2$ optional group is a —O-(halo substituted ($C_1$-$C_3$alkyl)) wherein there are 1-3 F atoms. In another example said $R^2$ optional group is —$OCHF_2$, and in another example —$OCF_3$.

Examples of the $R^2$—C(O)O($C_1$-$C_6$alkyl) optional substituent include, for example, —C(O)O($C_1$-$C_2$alkyl). In one example, said $R^2$ optional substituent is —C(O)$OCH_3$.

Examples of the $R^2$—S(O)$_r$($C_1$-$C_6$alkyl), wherein r is 0, 1, or 2, optional substituent include, for example, —S($C_1$-$C_6$alkyl), —S(O)($C_1$-$C_6$alkyl), and —S(O)$_2$($C_1$-$C_6$alkyl). In another example said $R^2$ optional substituent is —$SCH_3$, and in another example —S(O)$_2CH_3$.

Examples of the $R^2$—C(O)N($C_1$-$C_6$alkyl)$_2$ (wherein each alkyl is selected independently) optional substituent include, for example, —C(O)N($C_1$-$C_3$alkyl)$_2$ (wherein each alkyl is independently selected). In one example said —C(O)N($C_1$-$C_6$alkyl)$_2$ is —C(O)N($CH_3$)$_2$.

Examples of the $R^2$—C(O)NH($C_1$-$C_6$alkyl) optional substituent include, for example, —C(O)NH($C_1$-$C_3$alkyl). In one example, said —C(O)NH($C_1$-$C_6$alkyl) is —C(O)$NHCH_3$. In another example said —C(O)NH($C_1$-$C_6$alkyl) is —C(O)NH($CH_2CH_3$).

In one example $R^2$ is a -fused (heterocycloalkyl)($C_6$-$C_{10}$) aryl group. In another example said $R^2$ group is a -fused (heterocycloalkyl)($C_6$-$C_{10}$)aryl wherein said heterocycloalkyl moiety is a seven membered ring (including the two atoms in common with said aryl). In another example said $R^2$ group is a -fused (heterocycloalkyl)(phenyl) group. In another example said $R^2$ group is a -fused (heterocycloalkyl) (phenyl) group wherein said heterocycloalkyl moiety is a seven membered ring (including the two atoms in common with said phenyl ring). In another example said $R^2$ is a tetrahydrobenzoxepine, and in another example tetrahydroquinolinyl, and in another example dihydrochromenyl. In another example said -fused (heterocycloalkyl)($C_6$-$C_{10}$)aryl group is substituted, and in one example substituted with —OH. In one example said -fused (heterocycloalkyl)($C_6$-$C_{10}$)aryl group is hydroxytetrahydrobenzoxepine.

In one example $R^2$ is a fused (($C_3$-$C_6$cycloalkyl))($C_6$-$C_{10}$) aryl, and in one example, a fused (($C_3$-$C_6$cycloalkyl))phenyl. In another example said $R^2$ is a substituted fused (($C_3$-$C_6$cycloalkyl))phenyl, and in another example said $R^2$ is a hydroxyl substituted fused (($C_3$-$C_6$cycloalkyl))phenyl. In one example $R^2$ is hydroxydihydroindenyl.

Examples of the $R^2$-heterocycloalkyl-C(O)O—($C_1$-$C_6$alkyl)-($C_6$-$C_{10}$)aryl group include, for example, -heterocycloalkyl-C(O)O—($C_1$-$C_2$alkyl)-($C_6$-$C_{10}$)aryl, and in another example, -heterocycloalkyl-C(O)O—($C_1$-$C_2$alkyl)-phenyl, and in another example -heterocycloalkyl-C(O)O—($C_1$-$C_2$alkyl)-phenyl wherein said heterocycloalkyl is a 5-6 membered ring comprising 1-2 nitrogens, and in another example one nitrogen. In one example said $R^2$ is -piperidinyl-C(O)$OCH_2$phenyl.

Examples of the $R^2$-heterocycloalkyl-($C_1$-$C_6$alkyl)-heteroaryl group include, for example, -heterocycloalkyl-($C_1$-$C_2$alkyl)-heteroaryl, and in another example, -heterocycloalkyl-($C_1$-$C_2$alkyl)-pyridyl, and in another example -heterocycloalkyl-C(O)O—(C₁-C₂alkyl)-pyridyl wherein said heterocycloalkyl is a 5-6 membered ring comprising 1-2 nitrogens, and in another example one nitrogen. In one example said R² is -piperidinyl-CH₂-pyridyl. In other examples of the R² group in this paragraph, the heteroaryl, or pyridyl, moiety is substituted with 1-2 (C₁-C₆alkyl) groups. In another example said alkyl group is methyl. In one example said R² group is piperidinyl-CH₂-(methylpyridyl).

Examples of the R² heterocycloalkyl group include 5-6 membered heterocyclic rings comprising 1-2 independently selected heteroatoms. In example the R² heterocycloalkyl group include 5-6 membered heterocyclic rings comprising 1-2 independently selected heteroatoms wherein said heteroatoms are independently selected from O and N. In one example the heteroatom is nitrogen. One example of the R² heterocycloalkyl group is pyrrolidinyl. In another example the R² heterocycloalkyl group is substituted. In another example the R² heterocycloalkyl group is a 5-6 membered ring comprising 1-2 nitrogen atoms wherein said heterocycloalkyl is substituted with a (halo substituted —(C₁-C₆alkyl)) group, and in another example the (halo substituted —(C₁-C₆alkyl)) is bound to a ring nitrogen of said heterocycloalkyl group. In another example the R² heterocycloalkyl group is a 5-6 membered ring comprising 1-2 nitrogen atoms wherein said heterocycloalkyl is substituted with a —(C₁-C₆alkyl) (e.g., a —(C₁-C₂alkyl)) group, and a —O—(C₁-C₆alkyl) (e.g., a —O—(C₁-C₃alkyl)). In one example the R² group is a pyrrolidinyl, and in another example a substituted pyrrolidinyl. In another example the R² group is a N—(CH₂CF₃)pyrrolidinyl, and in another example methoxymethylpyrrolidinyl, and in another example ethoxymethylpyrrolidinyl.

Examples of the R² (C₃-C₆ cycloalkyl)-(C₁-C₆alkyl)- group include, for example, (C₃-C₆ cycloalkyl)-(C₁-C₃alkyl)-, and in another example, (C₅-C₆cycloalkyl)-(C₁-C₃alkyl)-, and in another example, cyclohexyl-CH(CH₃)—, Examples of the R²—N(C₁-C₆alkyl)₂ (wherein each alkyl is independently selected) optional substituent include, for example, the —N(C₁-C₃alkyl)₂, and in another example —N(CH₃)₂.

Examples of the R²—NH(C₁-C₆alkyl) optional substituent include, for example, —NH(C₁-C₃alkyl), and in another example —NH(CH₃).

Examples of the R²—(C₁-C₆alkyl)-O—(C₁-C₆alkyl) group include, for example, —(C₁-C₂alkyl)-O—(C₁-C₂alkyl), such as, for example, —(CH₂)₂OCH₃.

Examples of R²—(C₃-C₆cycloalkyl) include substituted —(C₃-C₆cycloalkyl), such as, for example, —(C₃-C₆cycloalkyl) substituted with —O—(C₁-C₆alkyl), and in one example —(C₃-C₆cycloalkyl) substituted with —O—(C₁-C₂alkyl). In one example the —(C₃-C₆cycloalkyl) is substituted with —OCH₃, and in another the substituted —(C₃-C₆cycloalkyl) is methoxycyclopentyl.

Examples of substituted R² groups include groups comprising a phenyl substituted with 1 to 3 substitutents independently selected from the group consisting of: halo (e.g., F and Cl), —CF₃, and —(C₁-C₃alkyl) (and in one example methyl). Examples of substituted R² groups include groups comprising a heterocycloalkyl (e.g., pyrrolidinyl) substituted with a —(C₁-C₂alkyl) (and in one example methyl).

In one example R² is —(C₁-C₆alkyl)-O—(C₁-C₆alkyl). One example of this R² group is —(C₁-C₃alkyl)-O—(C₁-C₃alkyl). In one example R² is —(CH₂)₂—O—CH₃, and in another —CH(CH₃)CH₂—O—CH₃.

In one example R² is selected from the group consisting of: (F, OCH₃-phenyl)-CH₂-piperidinyl-, —CH₂CH₂-piperidyl-phenyl, methyl, ethyl, propyl, —CH(CH₃)phenyl, —CH-phenyl, —CH₂CH₂phenyl, —CH₂CH(CH₃)phenyl, —CH(CH₃)-methoxyphenyl, —(CH₂)₂-methoxyphenyl, —CH(CH₂OCH₃)-phenyl, —CH(CH₂OH)-phenyl, —CH(fluorophenyl)CH₂OCH₃, —CH(CH₃)phenyl, —CH(CH₃) fluorophenyl, —CH(CH₃)-chlorophenyl, —CH₂-chlorophenyl, —CH₂-dichlorophenyl, —CH₂-difluorophenyl, —CH₂fluorophenyl, —CH₂CH₂-pyridyl, —CH(pyridyl)-CH₂—OCH₃, -cyclopropyl-phenyl, -pyrrolidinyl-phenyl, B64-B89, and B90.

Other examples of R² include, but are not limited to:

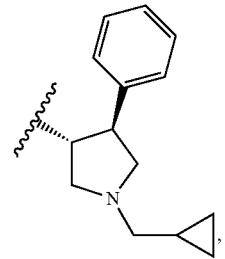

B100

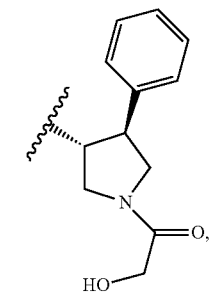

B101

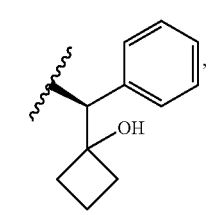

B102

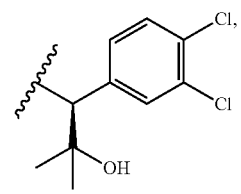

B103

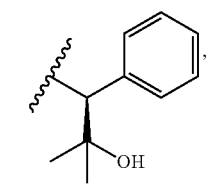

B104

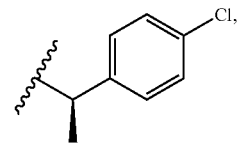

B105

| | |
|---|---|
| B106 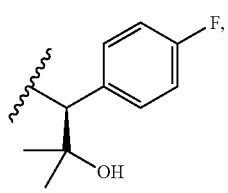 | B114 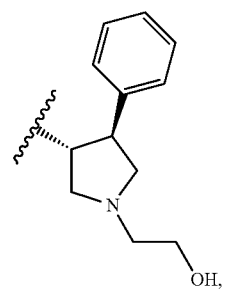 |
| B107 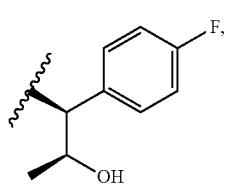 | B115 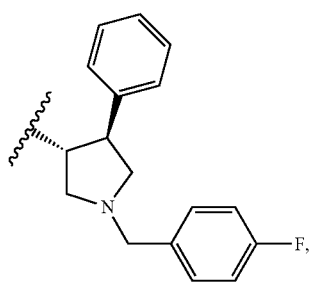 |
| B108 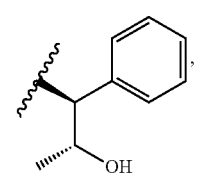 | B116 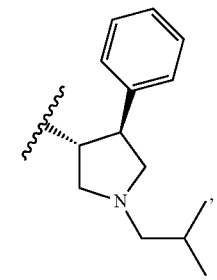 |
| B109 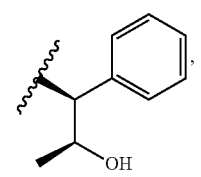 | B117 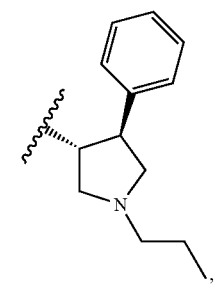 |
| B110 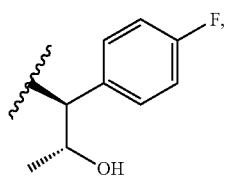 | B118 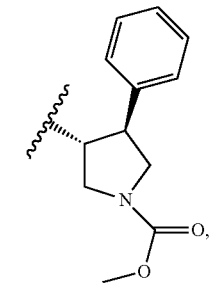 |
| B111 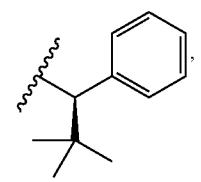 | |
| B113 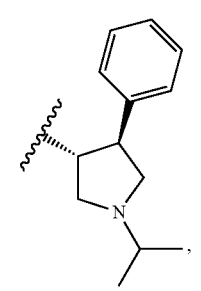 | |

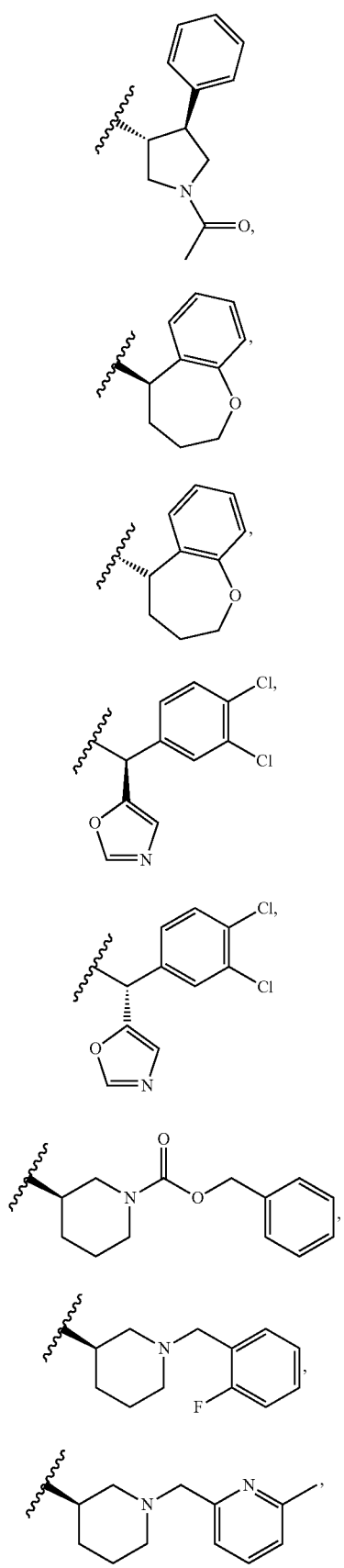
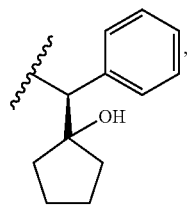
B127
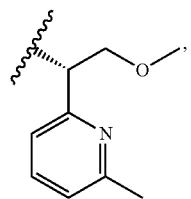
B128
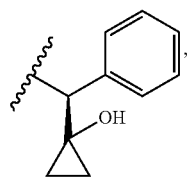
B129
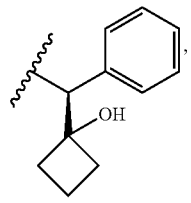
B130
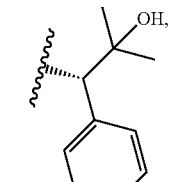
B131
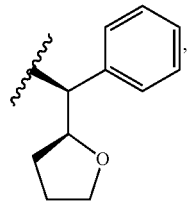
B132
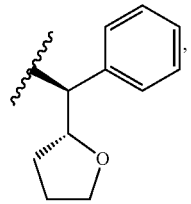
B133

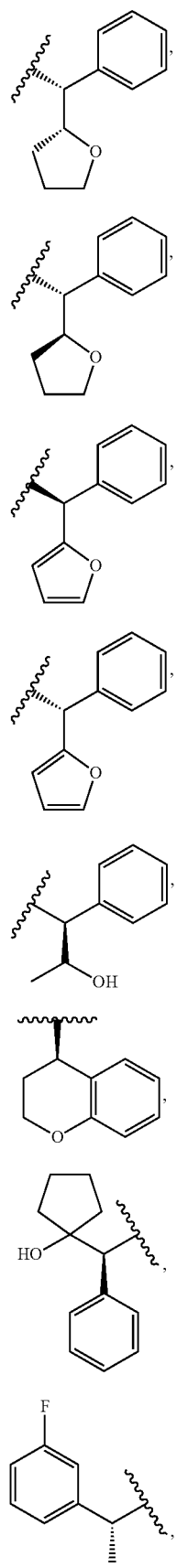
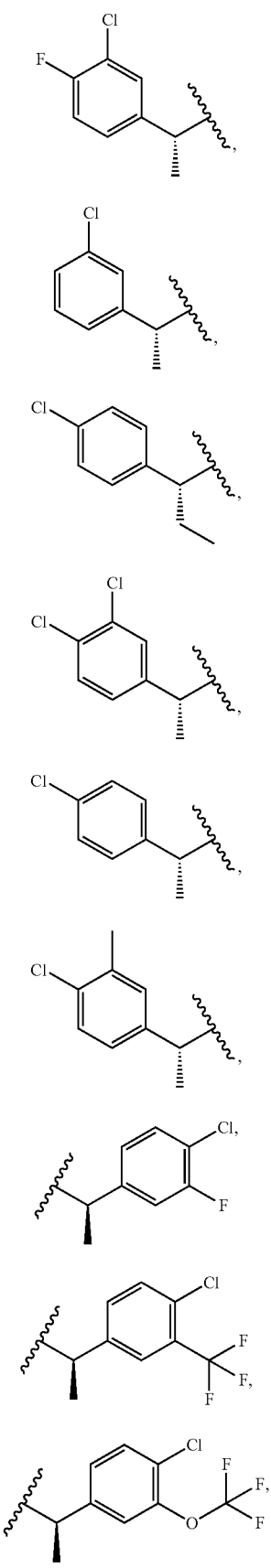

| | |
|---|---|
| 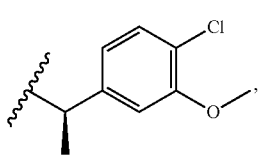 | B151 |
| 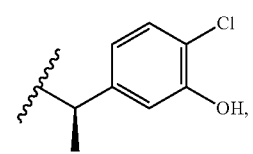 | B152 |
| 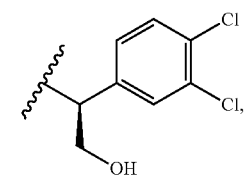 | B153 |
| 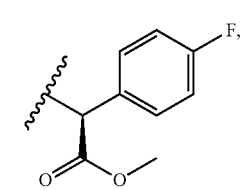 | B154 |
| 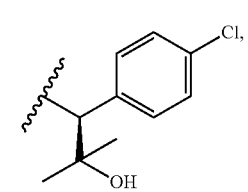 | B155 |
| 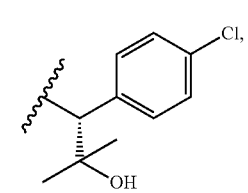 | B156 |
| 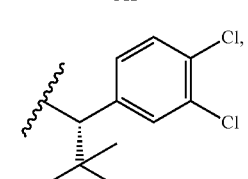 | B157 |
| 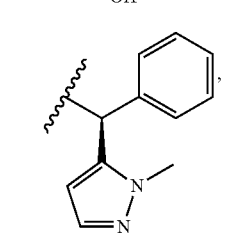 | B158 |
| 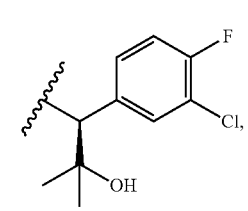 | B159 |
| 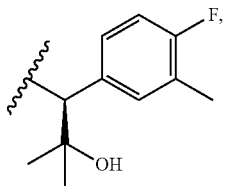 | B160 |
| 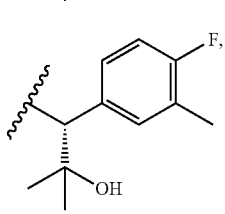 | B161 |
| 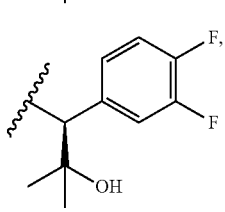 | B162 |
| 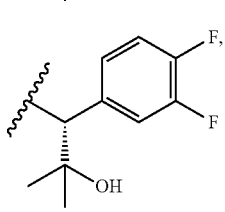 | B163 |
| 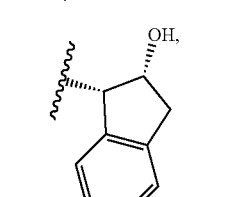 | B164 |
| 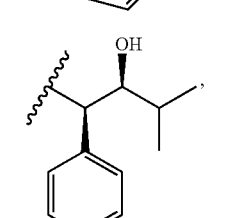 | B165 |
| 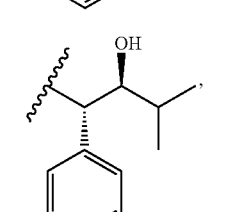 | B166 |
| 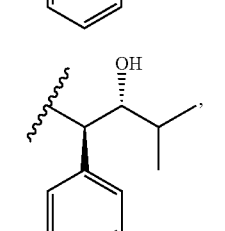 | B167 |

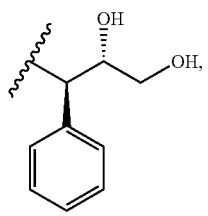 B168
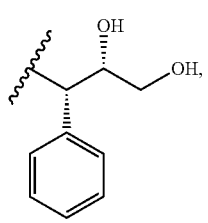 B169
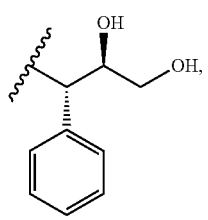 B170
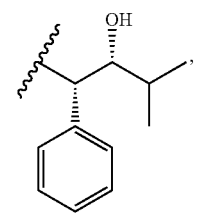 B171
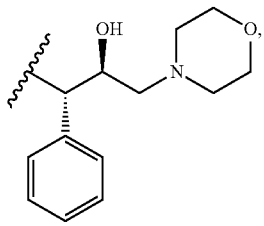 B172
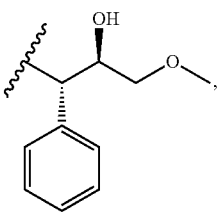 B173
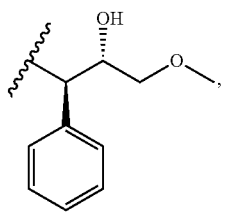 B174
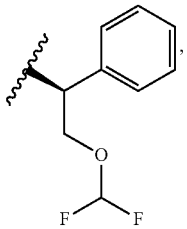 B175
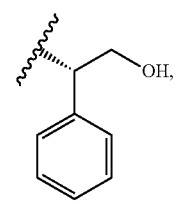 B176
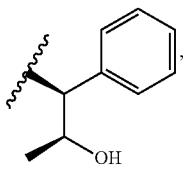 B177
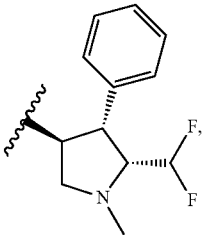 B178
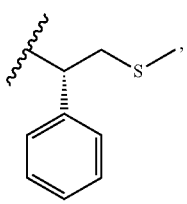 B179
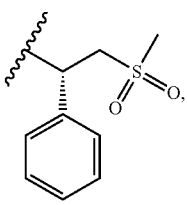 B180
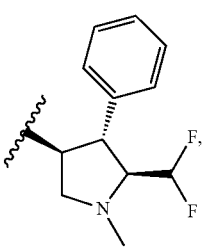 B181

| | |
|---|---|
| 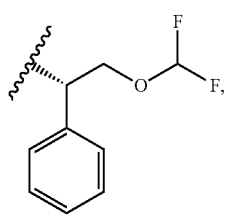 B182 | 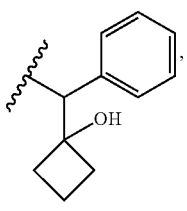 B189 |
| 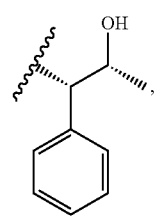 B183 | 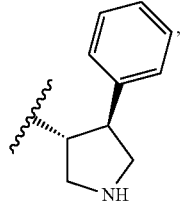 B190 |
| 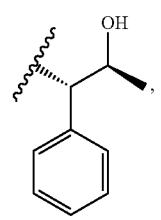 B184 | 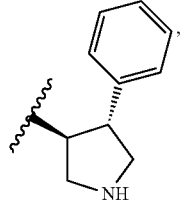 B191 |
| 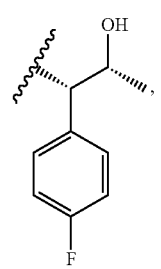 B185 | 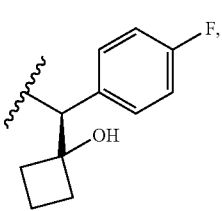 B192 |
| 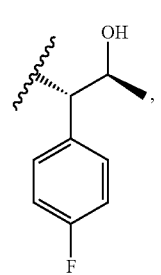 B186 | B193 |
| 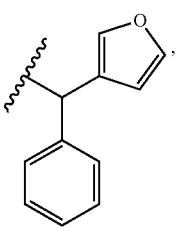 B187 | B194 |
| 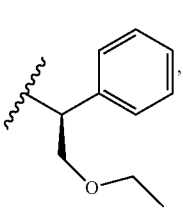 B188 | 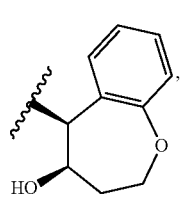 B195 |
| | 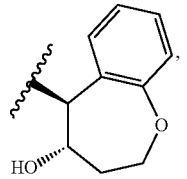 B196 |

B197
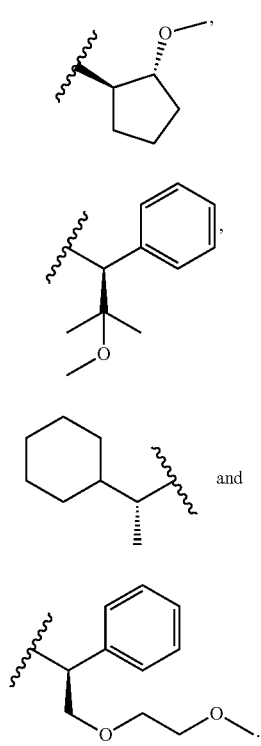
Other examples of R² include, but are not limited to:
B201 B202 B203
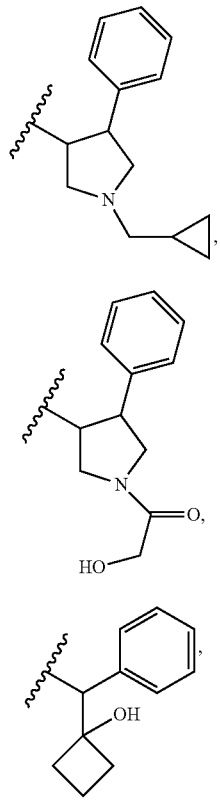
B204
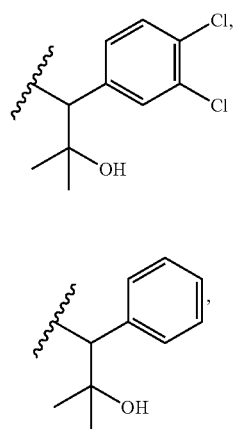
B205 B206 B207 B208 B209 B210 B211
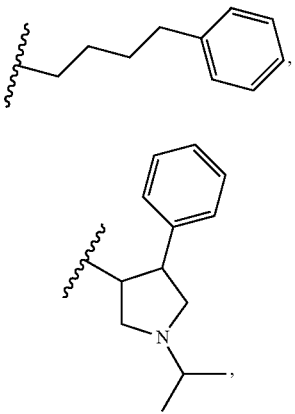

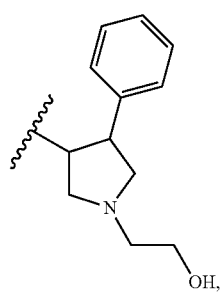 B212
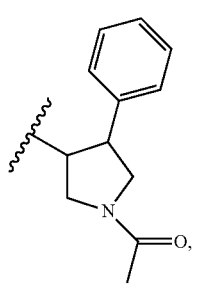 B217
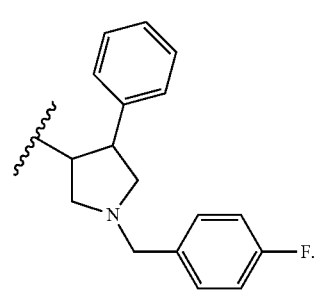 B213
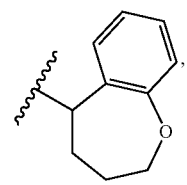 B218
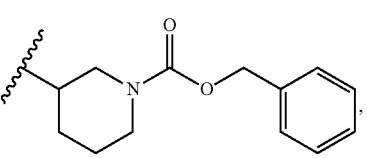 B219
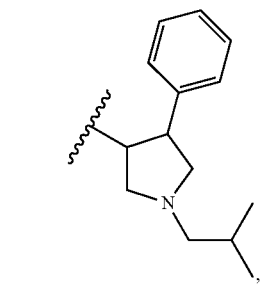 B214
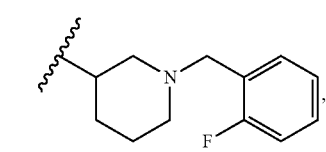 B220
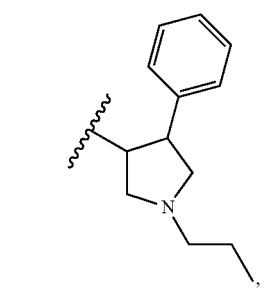 B215
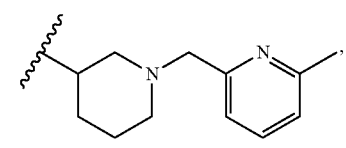 B221
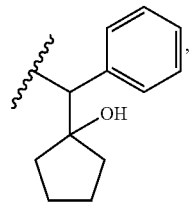 B222
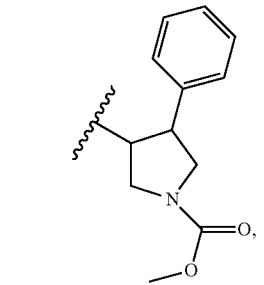 B216
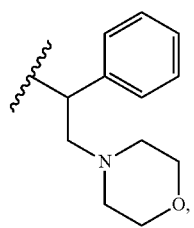 B223
B224

-continued
B225 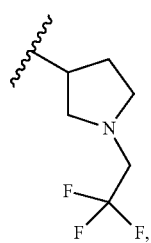
B226 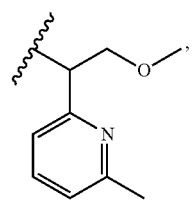
B227 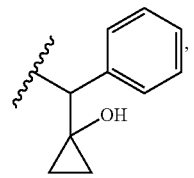
B228 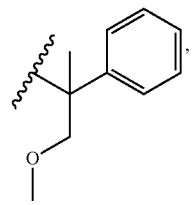
B229 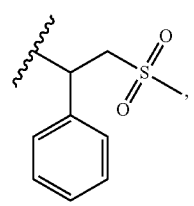
B230 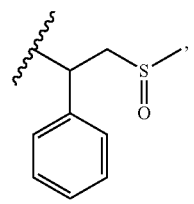
B231 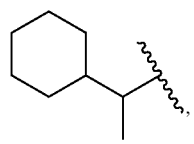
B232 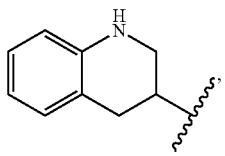
-continued
B233 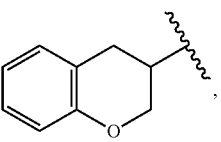
A234 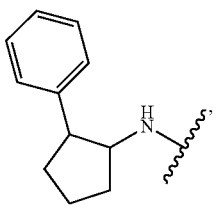
A235 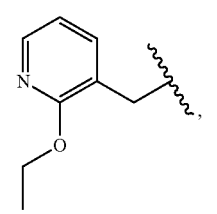
A236 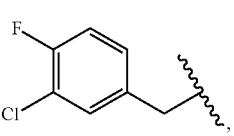
A237 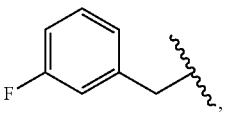
A238 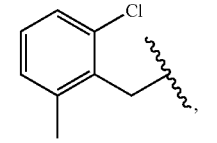
A239 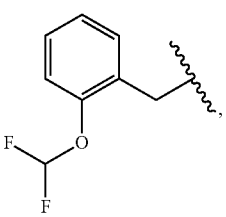
A240 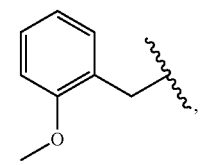
B241 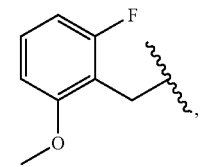

B242 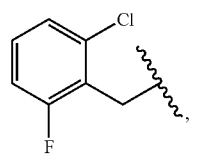
B243 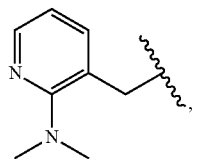
B244 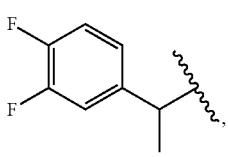
B245 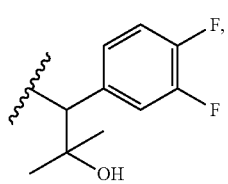
B246 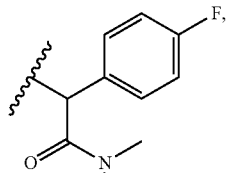
B247 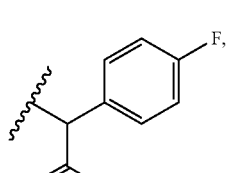
B248 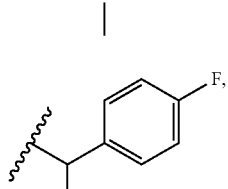
B249 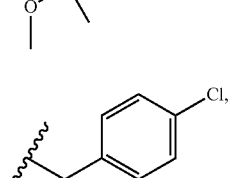
B250 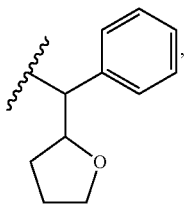
B251 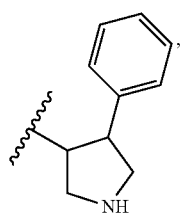
B252 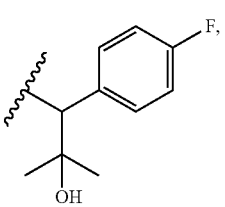
B253 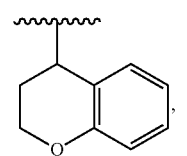
B254 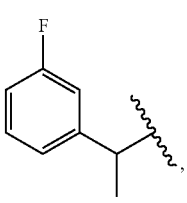
B255 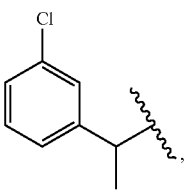
B256 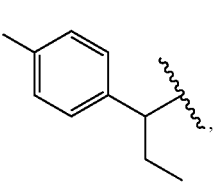
B257 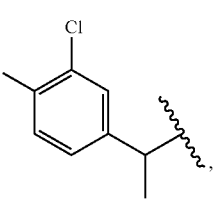

| | |
|---|---|
| 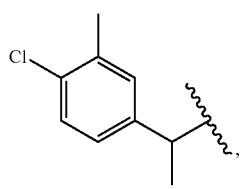 | B258 |
| 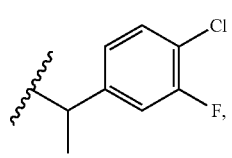 | B259 |
| 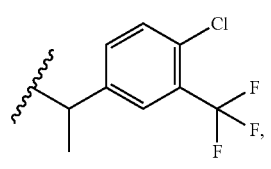 | B260 |
| 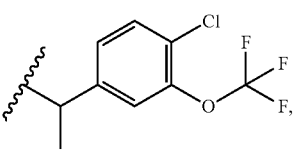 | B261 |
| 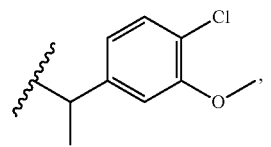 | B262 |
| 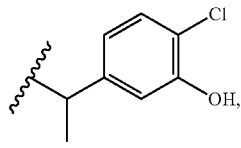 | B263 |
| 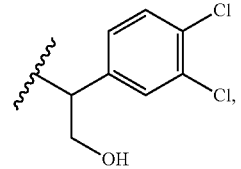 | B264 |
| 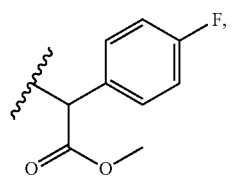 | B265 |
| 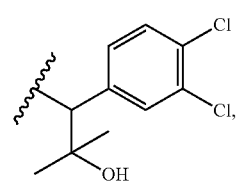 | B266 |
| 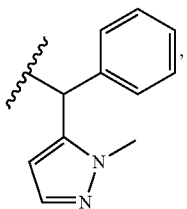 | B267 |
| 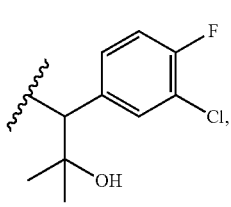 | B268 |
| 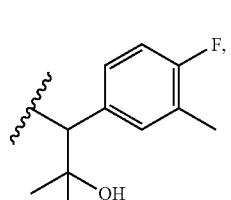 | B269 |
| 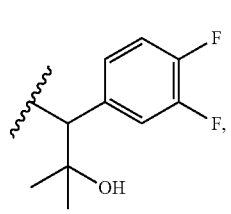 | B270 |
| 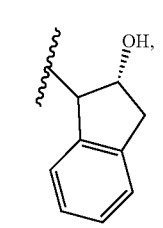 | B271 |
| 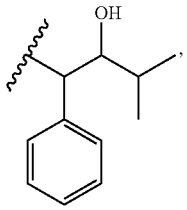 | B272 |
| 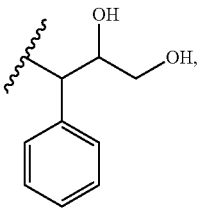 | B273 |

63
-continued

B274 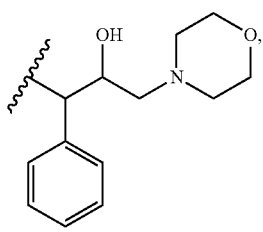

B275 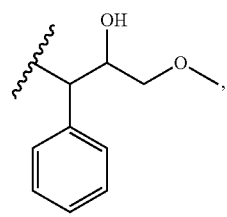

B276 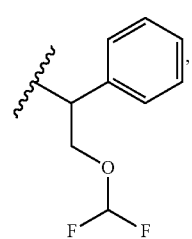

B277 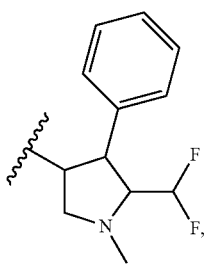

B278 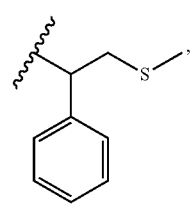

B279 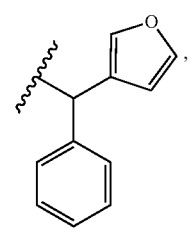

B280 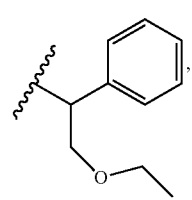

64
-continued

B281 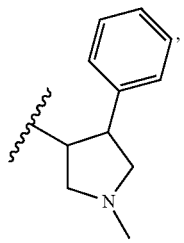

B282 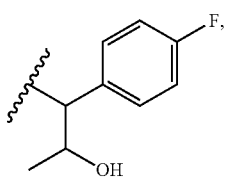

B283 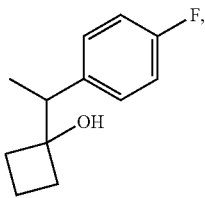

B284 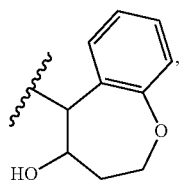

B285 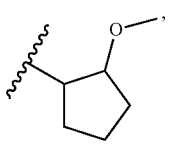

B286 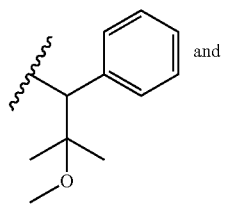

and

B287 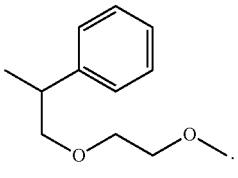

In another example $R^2$ is selected from the group consisting of: B1, B2, B3, B5, B8, B10, and B25. In another example $R^2$ is selected from the group consisting of: B11, B31, B32, B38, B39, B44, B46, B50, B51, B53, B54, and B62.

In one example $R^2$ is B1. In another example $R^2$ is B2. In another example $R^2$ is B3. In another example $R^2$ is B4. In another example $R^2$ is B5. In another example $R^2$ is B6. In another example $R^2$ is B7. In another example $R^2$ is B8. In another example $R^2$ is B9. In another example $R^2$ is B10. In another example $R^2$ is B11. In another example $R^2$ is B12. In another example $R^2$ is B13. In another example $R^2$ is B14. In another example $R^2$ is B15. In another example $R^2$ is B16. In another example $R^2$ is B17. In another example $R^2$ is B18. In another example $R^2$ is B19. In another example $R^2$ is B20. In another example $R^2$ is B21. In another example $R^2$ is B22. In another example $R^2$ is B23. In another example $R^2$ is B24. In another example $R^2$ is B25. In another example $R^2$ is B26. In another example $R^2$ is B27. In another example $R^2$ is B28. In another example $R^2$ is B29. In another example $R^2$ is B30. In another example $R^2$ is B31. In another example $R^2$ is B32. In another example $R^2$ is B33. In another example $R^2$ is B34. In another example $R^2$ is B35. In another example $R^2$ is B36. In another example $R^2$ is B37. In another example $R^2$ is B38. In another example $R^2$ is B39. In another example $R^2$ is B40. In another example $R^2$ is B41. In another example $R^2$ is B42. In another example $R^2$ is B43. In another example $R^2$ is B44. In another example $R^2$ is B45. In another example $R^2$ is B46. In another example $R^2$ is B47. In another example $R^2$ is B48. In another example $R^2$ is B49. In another example $R^2$ is B50. In another example $R^2$ is B51. In another example $R^2$ is B52. In another example $R^2$ is B53. In another example $R^2$ is B54. In another example $R^2$ is B55. In another example $R^2$ is B56. In another example $R^2$ is B57. In another example $R^2$ is B58. In another example $R^2$ is B59. In another example $R^2$ is B60. In another example $R^2$ is B61. In another example $R^2$ is B62. In another example $R^2$ is B63. In another example $R^2$ is B64. In another example $R^2$ is B65. In another example $R^2$ is B66. In another example $R^2$ is B67. In another example $R^2$ is B68. In another example $R^2$ is B69. In another example $R^2$ is B70. In another example $R^2$ is B71. In another example $R^2$ is B72. In another example $R^2$ is B73. In another example $R^2$ is B74. In another example $R^2$ is B75. In another example $R^2$ is B76. In another example $R^2$ is B77. In another example $R^2$ is B78. In another example $R^2$ is B79. In another example $R^2$ is B80. In another example $R^2$ is B81. In another example $R^2$ is B82. In another example $R^2$ is B83. In another example $R^2$ is B84. In another example $R^2$ is B85. In another example $R^2$ is B86. In another example $R^2$ is B87. In another example $R^2$ is B88. In another example $R^2$ is B89. In another example $R^2$ is B90.

Other examples of $R^2$ are any one of B100-B111 and B113-B287, as if each was listed individually as a separate example in this paragraph. Thus, for example, one example of $R^2$ is B100, and another is B102, and another is B107, and another is B109, and another is B110, and the like.

In another example, $R^2$ is H.

In another example $R^2$ is selected from the group consisting of: —$(C_1$-$C_3$alkyl)$(C_6$-$C_{10}$aryl), —CH$(C_6$-$C_{10}$aryl)$((C_1$-$C_3$alkyl)-O—$(C_1$-$C_3$alkyl)), —$(C_1$-$C_3$alkyl)heteroaryl, -heterocycloalkyl$(C_6$-$C_{10}$aryl), and —$(C_1$-$C_6$alkyl)-O—$(C_1$-$C_6$alkyl), as these groups are described above (in any of the definitions of $R^2$). For example, $R^2$ is selected from the group consisting of: (1) —$(C_1$-$C_3$alkyl)$(C_6$-$C_{10}$aryl) (such as, for example, —$(C_1$-$C_2$alkyl)$(C_6$-$C_{10}$aryl), —$(C_1$-$C_3$alkyl)phenyl, —CH(CH$_3$)phenyl, —CH$_2$CH$_2$phenyl, and —CH$_2$phenyl), (2) —CH$(C_6$-$C_{10}$aryl)$((C_1$-$C_3$alkyl)-O—$(C_1$-$C_3$alkyl)) (such as, for example, —CH(phenyl)-$((C_1$-$C_2$alkyl)-O—$(C_1$-$C_2$alkyl)), and —CH(phenyl)CH$_2$OCH$_3$), (3) —$(C_1$-$C_3$alkyl)heteroaryl (such as, for example, —$(C_1$-$C_2$alkyl)heteroaryl, —$(C_1$-$C_3$alkyl)pyridyl, —$(C_1$-$C_2$alkyl)pyridyl, and —CH(CH$_3$)pyridyl), (4) -heterocycloalkyl$(C_6$-$C_{10}$aryl) (such as, for example, -heterocycloalkylphenyl, and -pyrrolidinylphenyl), (5) —$(C_1$-$C_6$alkyl)-O—$(C_1$-$C_6$alkyl) (such as, for example, —$(C_1$-$C_3$alkyl)-O—$(C_1$-$C_2$alkyl), —$(CH_2)_2$—O—$CH_3$, and —CH(CH$_3$)CH$_2$OCH$_3$), (6) any one of the groups in (1), (2), (3), and (4) wherein the aryl, heteroaryl or heterocycloalkyl moiety is substituted with 1-3 substituents independently selected from the group consisting of halo (e.g., F, Br, and Cl, and in one example F) and —$(C_1$-$C_6$alkyl) (e.g., —$(C_1$-$C_4$alkyl), —$(C_1$-$C_3$alkyl), and —$(C_1$-$C_2$alkyl), and in one example methyl), (7) any one of the groups in (1), (2), (3), and (4) wherein the aryl, heteroaryl or heterocycloalkyl moiety is substituted with 1 substituent selected from the group consisting of halo (e.g., F, Br, and Cl, and in one example F) and —$(C_1$-$C_6$alkyl) (e.g., —$(C_1$-$C_4$alkyl), —$(C_1$-$C_3$alkyl), and —$(C_1$-$C_2$alkyl), and in one example methyl), (8) any one of the groups in (1), (2), (3), and (4) wherein the aryl, heteroaryl or heterocycloalkyl moiety is substituted with 1 substituent selected from the group consisting of F and methyl, and (9) any one of the groups in (1), (2), (3), and (4) wherein the aryl (e.g., phenyl) is substituted with 1-3 independently selected halos (e.g., F, Br, and Cl, and in one example F) and the heteroaryl (e.g., pyridyl) or heterocycloalkyl (e.g., pyrrolidine) moiety is substituted with 1-3 substituents independently selected from —$(C_1$-$C_6$alkyl) (e.g., —$(C_1$-$C_4$alkyl), —$(C_1$-$C_3$alkyl), and —$(C_1$-$C_2$alkyl), and in one example methyl), (10) any one of the groups in (1), (2), (3), and (4) wherein the aryl (e.g., phenyl) is substituted with 1 halo (e.g., F, Br, or Cl, and in one example F) and the heteroaryl (e.g., pyridyl) or heterocycloalkyl (e.g., pyrrolidine) moiety is substituted with 1 —$(C_1$-$C_6$alkyl) (e.g., —$(C_1$-$C_4$alkyl), —$(C_1$-$C_3$alkyl), and —$(C_1$-$C_2$alkyl), and in one example methyl), and (11) any one of the groups in (1), (2), (3), and (5) wherein the alkyl is substituted with 1-3 substituents independently selected from the group consisting of: halo (e.g., F, Br, and Cl), —O—$(C_1$-$C_6$alkyl), —OH and —CF$_3$.

Examples of the $R^{10}$ and $R^{11}$ heteroaryl group include, for example, pyridyl, and in another example pyrazolyl, and in another example oxazolyl.

Examples of the $R^{10}$ and $R^{11}$—$(C_1$-$C_6$alkyl)heteroaryl group include —$(C_1$-$C_2$alkyl)heteroaryl, and in one example —$(C_1$-$C_2$alkyl)heteroaryl wherein said heteroaryl is a 5-6 membered ring comprising 1-3 heteroatoms independently selected from the group consisting of: O, N and S, and in one example —$(C_1$-$C_2$alkyl)heteroaryl wherein said heteroaryl is a 5-6 membered ring comprising 1-2 nitrogen atoms. In another example the —$(C_1$-$C_6$alkyl)heteroaryl group is —CH$_2$-pyrazolyl, and in another example —CH$_2$triazolyl, and in another example —CH$_2$imidazolyl.

Examples of the $R^{10}$ and $R^{11}$—$(C_1$-$C_6$alkyl)-$((C_1$-$C_6)$alkyloxy) substituted heteroaryl) include, for example, —$(C_1$-$C_2$alkyl)-$((C_1$-$C_3)$alkoxy) substituted heteroaryl), and in one example —$(C_1$-$C_2$alkyl)-$((C_1$-$C_3)$alkoxy) substituted heteroaryl) wherein said heteroaryl is a 5-6 membered ring comprising 1-3 heteroatoms independently selected from the group consisting of: O, N and S, and in one example —$(C_1$-$C_2$alkyl)heteroaryl wherein said heteroaryl is a 5-6 membered ring comprising 1-2 nitrogen atoms, and in another example wherein said heteroaryl is a 5-6 membered ring comprising 3 nitrogen atoms. In one example, said —$(C_1$-$C_6$alkyl)-$((C_1$-$C_6)$alkyloxy) substituted heteroaryl) is —CH$_2$ (methoxypyrazolyl).

Examples of the $R^{10}$ and $R^{11}$, -(heteroaryl-$((C_1$-$C_6$alkyl)-OH) group include, for example, -heteroryl-$((C_1$-$C_3$alkyl)-OH), and in another example -heteroryl-(CH$_2$OH), and in another example, -pyridyl-$((C_1$-$C_3$alkyl)-OH), and in another example -pyridyl-(CH$_2$OH).

Examples of the $R^{10}$ and $R^{11}$—C(O)-heterocycloalkyl group include, for example, —C(O)-morpholinyl.

Examples of the $R^{10}$ and $R^{11}$ hydroxy substituted —$(C_1$-$C_6$alkyl) group include, for example, hydroxy substituted —$(C_1$-$C_3$alkyl), and in another example —CH$_2$OH, and in another example —CH(OH)CH$_3$, and in another example —CH(OH)CH$_2$CH$_3$.

Examples of the $R^{10}$ and $R^{11}$—$(C_1$-$C_6$alkyl)-$(C_3$-$C_6$cycloalkyl) group include, for example, —$(C_1$-$C_2$alkyl)-$(C_3$-$C_6$cycloalkyl), and in another example, —$(C_1$-$C_2$alkyl)-cyclopropyl, and in another example, —$CH_2$cyclopropyl.

Examples of the $R^{10}$ and $R^{11}$-(hydroxyl substituted $C_1$-$C_6$alkyl)-$(C_3$-$C_6$cycloalkyl) group include, for example, -(hydroxyl substitute $C_1$-$C_2$alkyl)-$(C_3$-$C_6$cycloalkyl), and in another example, -(hydroxyl substituted $C_1$-$C_2$alkyl)-cyclopropyl, and in another example, —$CH(OH)$cyclopropyl.

Examples of the $R^{10}$ and $R^{11}$—$(C_1$-$C_6$alkyl)-O—C(O)—$(C_1$-$C_6$alkyl) group include, for example, —$(C_1$-$C_2$alkyl)-O—C(O)—$(C_1$-$C_2$alkyl), and another example is —$CH_2OC(O)CH_3$.

Examples of the $R^{10}$ and $R^{11}$—C(O)—$(C_1$-$C_6$alkyl) group include, for example, —C(O)—$(C_1$-$C_2$alkyl), and in another example, —$C(O)CH_3$.

Examples of the $R^{10}$ and $R^{11}$—$((C_1$-$C_6$alkyl)heteroaryl) (i.e., a heteroaryl substituted with a $C_1$-$C_6$alkyl group) include, for example, —$((C_1$-$C_6$alkyl)heteroaryl) wherein said heteroaryl is a 5-6 membered ring comprising 1-2 heteroatoms independently selected from the group consisting of O, S and N (and in one example 1-2 nitrogen atoms), and in another example, —$((C_1$-$C_2$alkyl)heteroaryl) wherein said heteroaryl is a 5-6 membered ring comprising 1-2 heteroatoms independently selected from the group consisting of: O, N and S, and in another example —$((C_1$-$C_2$alkyl)heteroaryl) wherein said heteroaryl is a 5-6 membered ring comprising 1-2 nitrogen atoms. In one example said —$((C_1$-$C_6$alkyl)heteroaryl) is methylpyrimidinyl-, and in another example methylpyrazolyl- (e.g., N-methylpyrazolyl-), and in another methyloxadiazolyl-, and in another example methylthiadiazolyl-, and in another example methylpyridyl-.

Examples of the $R^{10}$ and $R^{11}$—$C(O)NH(C_1$-$C_6$alkyl) group include, for example, —$C(O)NH(C_1$-$C_2$alkyl). In one example said —$C(O)NH(C_1$-$C_2$alkyl) is —$C(O)NH(CH_3)$.

Examples of the $R^{10}$ and $R^{11}$—$C(O)N(C_1$-$C_6$alkyl)_2$ group include, for example, —$C(O)N(C_1$-$C_2$alkyl)_2$. In one example said —$C(O)N(C_1$-$C_2$alkyl)_2$ is —$C(O)N(CH_3)_2$.

Examples of the $R^{10}$ and $R^{11}$—$NH(C_1$-$C_6$alkyl) include, for example, —$NH(C_1$-$C_2$alkyl). In one example said —$NH(C_1$-$C_2$alkyl) is —$NH(CH_3)$, and in another example —$NH(CH_3)_2$, Examples of the $R^{10}$ and $R^{11}$—$C(O)N(C_1$-$C_6$alkyl)_2$ include, for example, —$C(O)N(C_1$-$C_2$alkyl)_2$. In one example said —$C(O)N(C_1$-$C_2$alkyl)_2$ is —$C(O)N(CH_3)_2$.

Examples of the $R^{10}$ and $R^{11}$—$NHC(O)(C_1$-$C_6$alkyl) group include, for example, —$NHC(O)(C_1$-$C_2$alkyl), and in one example is —$NHC(O)CH_3$.

Examples of the $R^{10}$ and $R^{11}$—$NH$—$(C_6$-$C_{10}$aryl)-$O(C_1$-$C_6$alkyl), group include, for example, —$NH$—$(C_6$-$C_{10}$aryl)-$O(C_1$-$C_2$alkyl)), and in another example —$NH$-(phenyl)-O$(C_1$-$C_2$alkyl), and in another example, —$NH$-phenyl-O—$CH_3$.

Examples of the $R^{10}$ and $R^{11}$-oxoheteroaryl (i.e., a heteroaryl substituted with an =O) include, for example, oxodihydrooxadiazolyl-.

Examples of the $R^{10}$ and $R^{11}$—$(C_1$-$C_6$alkyl)-heterocycloalkyl include, for example, —$(C_1$-$C_2$alkyl)-heterocycloalkyl, and in one example said heterocycloalkyl ring is a 5-6 membered ring comprising 1-2 heteroatoms independently selected from the group consisting of O, S, and N. In another example of said —$(C_1$-$C_2$alkyl)-heterocycloalkyl the heterocycloalkyl is a 5-6 membered ring (and in one example 5) comprising 1-2 nitrogen atoms (and in one example one nitrogen atom). In another example of said —$(C_1$-$C_2$alkyl)-heterocycloalkyl the heterocycloalkyl is a 5-6 membered ring (and in one example 5) comprising one nitrogen and one oxygen. In one example said —$(C_1$-$C_6$alkyl)-heterocycloalkyl is —$CH_2$oxazolidinyl, and in another example —$CH_2$pyrrolidinyl.

Examples of the $R^{10}$ and $R^{11}$—$(C_1$-$C_6$alkyl)-(oxoheterocycloalkyl) (i.e., said heterocycloalkyl is substituted with =O) include, for example, —$(C_1$-$C_2$alkyl)-(oxoheterocycloalkyl), and in one example said oxoheterocycloalkyl ring is a 5-6 membered ring comprising 1-2 heteroatoms independently selected from the group consisting of O, S, and N. In another example of said —$(C_1$-$C_2$alkyl)-(oxoheterocycloalkyl) the heterocycloalkyl is a 5-6 membered ring (and in one example 5) comprising 1-2 nitrogen atoms (and in one example one nitrogen atom). In another example of said —$(C_1$-$C_2$alkyl)-(oxoheterocycloalkyl) the heterocycloalkyl is a 5-6 membered ring (and in one example 5) comprising one nitrogen and one oxygen. In one example said —$(C_1$-$C_6$alkyl)-(oxoheterocycloalkyl) is —$CH_2$oxooxazolidinyl, and in another example —$CH_2$oxopyrrolidinyl.

Examples of the $R^{10}$ and $R^{11}$—$(C_1$-$C_6$alkyl)-O—$(C_1$-$C_6$alkyl) include, for example, —$(C_1$-$C_2$alkyl)-O—$(C_1$-$C_2$alkyl), and in another example —$CH_2OCH_3$.

Examples of the $R^{10}$ and $R^{11}$—$(C_1$-$C_6$alkyl)-O—C(O)—$NH(C_1$-$C_6$alkyl) group include, for example, —$(C_1$-$C_2$alkyl)-O—C(O)—$NH(C_1$-$C_2$alkyl), and in another example —$CH_2OC(O)NHCH_3$.

Examples of the $R^{10}$ and $R^{11}$—$(C_1$-$C_6$alkyl)-O—C(O)—$N(C_1$-$C_6$alkyl)_2$ wherein each alkyl is independently selected, include, for example, —$(C_1$-$C_2$alkyl)-O—C(O)—$N(C_1$-$C_2$alkyl)_2$ wherein each alkyl is independently selected, and in another example —$CH_2OC(O)N(CH_3)(CH_2CH_3)$.

Examples of the $R^{10}$ and $R^{11}$—$(C_1$-$C_6$alkyl)-O-heterocycloalkyl include, for example, —$(C_1$-$C_2$alkyl)-O-heterocycloalkyl, and in another example, —$(C_1$-$C_2$alkyl)-O-heterocycloalkyl wherein said heterocycloalkyl ring is a 4-5 membered ring comprising 1 heteroatom selected from the group consisting of O, N and S, and in another example, —$(C_1$-$C_2$alkyl)-O-heterocyloalkyl wherein said heterocycloalkyl ring is a 4-5 membered ring comprising one 0. In one example said —$(C_1$-$C_6$alkyl)-O-heterocyloalkyl is —$CH_2$—O-oxetanyl.

Examples of the $R^{10}$ and $R^{11}$ halo substituted $(C_1$-$C_6$alkyl) include, for example, halo substituted $(C_1$-$C_4$alkyl), and in another example halo substituted $(C_1$-$C_2$alkyl). The halo substituted alkyl moiety is substituted with 1-3 independently selected halo atoms. In one example the halo substituted alkyl moiety is substituted with 1-3 halo atoms independently selected from the group consisting of: Cl, Br, and F. In another example the substituted alkyl moiety is substituted with 1-3 F atoms. In one example said halo substituted $(C_1$-$C_6$alkyl) is —$CF_3$, in another example —$CHF_2$.

Examples of the $R^{10}$ and $R^{11}$—$(C_1$-$C_6$alkyl)-$N(C_1$-$C_6$alkyl)_2$, —$(C_1$-$C_6$alkyl)NH$(C_1$-$C_6$alkyl), and —$(C_1$-$C_6$alkyl)NH_2$, groups include, for example, —$(C_1$-$C_4$alkyl)-$N(C_1$-$C_4$alkyl)_2$, —$(C_1$-$C_4$alkyl)NH$(C_1$-$C_4$alkyl), and —$(C_1$-$C_4$alkyl)NH_2$. Examples of the $R^{10}$ and $R^{11}$—$(C_1$-$C_6$alkyl)-$NH(C_1$-$C_6$alkyl) include, for example, —$CH_2NH(CH_3)$, and in another example —$CH_2OCH_2CH(CH_3)OH$.

Examples of the $R^{10}$ and $R^{11}$—$(C_1$-$C_6$alkyl)-O—$(C_1$-$C_6$alkyl)-OH include, for example, —$(C_1$-$C_2$alkyl)-O—$(C_1$-$C_3$alkyl)-OH, and in one example, —$CH_2O(CH_2)_2OH$.

Examples of the $R^{10}$ and $R^{11}$—$(C_1$-$C_6$alkyl)-O—$(C_3$-$C_6$cycloalkyl)-OH include, for example, —$(C_1$-$C_2$alkyl)-O—$(C_3$-$C_5$cycloalkyl)-OH, and in one example —$CH_2O$-(hydroxycyclopentyl).

Examples of the $R^{10}$ and $R^{11}$—$(C_1$-$C_6$alkyl)-OH group include, for example, —$(C_1$-$C_3$alkyl)-OH, and in one example —$CH(CH_3)OH$.

In one example $R^{10}$ is selected from the group consisting of: H, F, Cl, Br, methyl, ethyl, isopropyl, cyclopropyl, —CH(OH)CH$_3$, —CH$_2$OCH$_3$, —CH$_2$—N(CH$_3$)$_2$, and —CH$_2$-morpholinyl.

In another example $R^{10}$ is selected from the group consisting of: H, F, Br and methyl. In another example $R^{10}$ is selected from the group consisting of: H, F and methyl. In another example $R^{10}$ is Br.

In one example $R^{11}$ is selected from the group consisting of: H, F, Cl, Br, —CF$_3$, —CHF$_2$, —CN, —NH$_2$, —NH(CH$_3$), —NH(CH$_3$)$_2$, —NHC(O)CH$_3$, —NH-phenyl-O—CH$_3$, methyl, ethyl, isopropyl, cyclopropyl, —CH$_2$OC(O)OCH$_3$, —CH$_2$OH, —CH(OH)CH$_3$, —CH(OH)CH$_2$CH$_3$, —CH$_2$OCH$_3$, —CH$_2$—N(CH$_3$)$_2$, —CH(OH)cyclopropyl, —C(O)CH$_3$, —CH$_2$-morpholinyl, methyloxadiazolyl-, methylpyridyl-, methylthiadiazolyl-, pyrazolyl, oxodihydrooxadiazolyl-, C(O)NHCH$_3$, —C(O)N(CH$_3$)$_2$, —NH$_2$, —CH$_2$OC(O)NHCH$_3$, —CH$_2$O(CH$_2$)$_2$OH, —CH$_2$oxooxazolidinyl, —CH$_2$oxopyrrolidinyl, —CH$_2$—O-oxetanyl, —CH$_2$pyrazolyl, —CH$_2$NHCH$_3$, —CH$_2$OCH$_2$CH$_3$, methylpyrimidinyl-, methylpyrazolyl-(e.g., N-methylpyrazolyl-), —CH$_2$(methoxypyrazolyl), —CH$_2$triazolyl, —CH$_2$imidazolyl, —CH$_2$O(hydroxycyclopentyl), —CH$_2$OCH$_2$CH(CH$_3$)OH, —CH(CH$_3$)OH. In one example $R^{11}$ is selected from the group consisting of: H, F, Cl, Br, methyl, ethyl, isopropyl, cyclopropyl, —CH(OH)CH$_3$, —CH$_2$OCH$_3$, —CH$_2$—N(CH$_3$)$_2$, and —CH$_2$-morpholinyl. In another example $R^{11}$ is selected from the group consisting of: H and methyl. In another example $R^{11}$ is H, and in another —CH$_2$OH, and in another —CH$_2$(OH)CH$_3$, and in another —CH$_2$(OH)CH$_2$CH$_3$, and in another example -pyridyl-CH$_2$OH, In one example $R^{10}$ is H. In another example $R^{10}$ is halo. In another example $R^{10}$ is halo selected from the group consisting of: F, Cl and Br. In another example $R^{10}$ is F. In another example $R^{10}$ is Br, and in another example Cl. In another example $R^{10}$ is —(C$_1$-C$_6$alkyl), and in another example —(C$_1$-C$_4$alkyl), and in another example —(C$_1$-C$_3$alkyl), and in another example —(C$_1$-C$_2$alkyl). In another example $R^{10}$ is methyl. In another example $R^{10}$ is ethyl. In another example $R^{10}$ is isopropyl. In another example $R^{10}$ is —(C$_3$-C$_6$ cycloalkyl). In another example $R^{10}$ is cyclopropyl. In another example $R^{10}$ is hydroxy substituted —(C$_1$-C$_6$alkyl), and in another example hydroxy substituted —(C$_1$-C$_3$alkyl), and in another example hydroxy substituted —(C$_1$-C$_3$alkyl). In another example $R^{10}$ is —CH(OH)CH$_3$. In another example $R^{10}$ is —(C$_1$-C$_6$alkyl)-O—(C$_1$-C$_6$alkyl), and in another example —(C$_1$-C$_4$alkyl)-O—(C$_1$-C$_4$alkyl), and in another example —(C$_1$-C$_2$alkyl)-O—(C$_1$-C$_2$alkyl). In another example $R^{10}$ is —CH$_2$OCH$_3$. In another example $R^{10}$ is —(C$_1$-C$_6$alkyl)-N(C$_1$-C$_6$alkyl)$_2$ wherein each alkyl is independently selected, and in another example —(C$_1$-C$_4$alkyl)-N(C$_1$-C$_4$alkyl)$_2$ wherein each alkyl is independently selected, and in another example —(C$_1$-C$_2$alkyl)-N(C$_1$-C$_2$alkyl)$_2$ wherein each alkyl is independently selected. In another example $R^{10}$ is —CH$_2$—N(CH$_3$)$_2$. In another example $R^{10}$ is —(C$_1$-C$_6$alkyl)-heterocycloalkyl, and in another example —(C$_1$-C$_4$alkyl)-heterocycloalkyl, and in another example —(C$_1$-C$_2$alkyl)-heterocycloalkyl, and in another example —(C$_1$-C$_2$alkyl)-(6 membered heterocycloalkyl). In another example $R^{10}$ is —CH$_2$-morpholinyl.

In one example $R^{11}$ is H. In another example $R^{11}$ is halo. In another example $R^{11}$ is halo selected from the group consisting of: F, Cl and Br. In another example $R^{11}$ is F. In another example $R^{11}$ is Br, and in another example Cl. In another example $R^{11}$ is —(C$_1$-C$_6$alkyl), and in another example —(C$_1$-C$_6$alkyl), and in another example —(C$_1$-C$_4$alkyl), and in another example —(C$_1$-C$_3$alkyl), and in another example —(C$_1$-C$_2$alkyl). In another example $R^{11}$ is methyl. In another example $R^{11}$ is ethyl. In another example $R^{11}$ is isopropyl. In another example $R^{11}$ is —(C$_3$-C$_6$ cycloalkyl). In another example $R^{11}$ is cyclopropyl. In another example $R^{11}$ is hydroxyl substituted —(C$_1$-C$_6$alkyl), and in another example hydroxy substituted —(C$_1$-C$_3$alkyl), and in another example hydroxy substituted —(C$_1$-C$_3$alkyl). In another example $R^{11}$ is —CH(OH)CH$_3$. In another example $R^{11}$ is —(C$_1$-C$_6$alkyl)-O—(C$_1$-C$_6$alkyl), and in another example —(C$_1$-C$_4$alkyl)-O—(C$_1$-C$_4$alkyl), and in another example —(C$_1$-C$_2$alkyl)-O—(C$_1$-C$_2$alkyl). In another example $R^{11}$ is —CH$_2$OCH$_3$. In another example $R^{11}$ is —(C$_1$-C$_6$alkyl)-N(C$_1$-C$_6$alkyl)$_2$ wherein each alkyl is independently selected, and in another example —(C$_1$-C$_4$alkyl)-N(C$_1$-C$_4$alkyl)$_2$ wherein each alkyl is independently selected, and in another example —(C$_1$-C$_2$alkyl)-N(C$_1$-C$_2$alkyl)$_2$ wherein each alkyl is independently selected. In another example $R^{11}$ is —CH$_2$—N(CH$_3$)$_2$. In another example $R^{11}$ is —(C$_1$-C$_6$alkyl)-heterocycloalkyl, and in another example —(C$_1$-C$_4$alkyl)-heterocycloalkyl, and in another example —(C$_1$-C$_2$alkyl)-heterocycloalkyl, and in another example —(C$_1$-C$_2$alkyl)-(6 membered heterocycloalkyl). In another example $R^{11}$ is —CH$_2$-morpholinyl. In other examples $R^{10}$ is selected from the group consisting of: H, Br, Cl, F and —(C$_1$-C$_3$alkyl) (and in one example methyl, and in another example ethyl), and $R^{11}$ is as defined in any one of the examples described in this paragraph. In other examples $R^{10}$ is selected from the group consisting of: H, F and methyl, and $R^{11}$ is as defined in any one of the examples described in this paragraph.

In another example $R^{10}$ is H and $R^{11}$ is H. $R^{10}$ is halo and $R^{11}$ is H. In another example $R^{10}$ is F and $R^{11}$ is H. In another example $R^{10}$ is Br and $R^{11}$ is H. In another example $R^{10}$ is Cl and $R^{11}$ is H. In another example $R^{10}$ is —(C$_1$-C$_6$alkyl) and $R^{11}$ is H. In another example $R^{10}$ is —(C$_1$-C$_4$alkyl) and $R^{11}$ is H. In another example $R^{10}$ is —(C$_1$-C$_3$alkyl) and $R^{11}$ is H. In another example $R^{10}$ is —(C$_1$-C$_2$alkyl) and $R^{11}$ is H. In another example $R^{10}$ is methyl and $R^{11}$ is H. In another example $R^{10}$ is ethyl and $R^{11}$ is H. In other examples $R^{10}$ and $R^{11}$ are as defined in any one of the examples in this paragraph, and $R^1$ and $R^2$ are as defined in any one of the examples given above.

In another example $R^{10}$ is H and $R^{11}$ is —(C$_1$-C$_3$alkyl) (and in one example methyl, and in another example ethyl, and in another example isopropyl). In another example $R^{10}$ is H and $R^{11}$ is —(C$_3$-C$_6$1 (C$_3$-C$_6$ cycloalkyl) (and in another example cyclopropyl). In another example $R^{10}$ is H and $R^{11}$ is —(C$_1$-C$_2$alkyl)-O—(C$_1$-C$_2$alkyl) (and in another example —CH$_2$OCH$_3$). In another example $R^{10}$ is H and $R^{11}$ is —(C$_1$-C$_2$alkyl)-N(C$_1$-C$_2$alkyl)$_2$ wherein each alkyl is independently selected (and in another example —CH$_2$—N(CH$_3$)$_2$). In another example $R^{10}$ is H and $R^{11}$ is —(C$_1$-C$_2$alkyl)-heterocycloalkyl (and in another example —CH$_2$-morpholinyl). In another example $R^{10}$ is H and $R^{11}$ is hydroxy substituted —(C$_1$-C$_3$alkyl) (and in another example —CH(OH)CH$_3$). In other examples $R^{10}$ and $R^{11}$ are as defined in any one of the examples in this paragraph, and $R^1$ and $R^2$ are as defined in any one of the examples given above.

In other examples $R^{10}$ is selected from the group consisting of: H, halo (for example, F, or Br, or Cl), and —(C$_1$-C$_6$alkyl) (for example, a —(C$_1$-C$_4$alkyl), or —(C$_1$-C$_3$alkyl) or —(C$_1$-C$_2$alkyl, and in one example methyl and in another ethyl), and $R^{11}$ is selected from the group consisting of: halo (for example, F or Br or Cl), and —(C$_1$-C$_6$alkyl) (for example, a —(C$_1$-C$_4$alkyl), or —(C$_1$-C$_3$alkyl) or —(C$_1$-C$_2$alkyl, and in one example methyl and in another ethyl). In other examples $R^{10}$ is selected from the group consisting of: H, F, Br, Cl, methyl and ethyl, and $R^{11}$ is selected from the group consisting of: F, Br, Cl, methyl and ethyl. In other examples $R^{10}$ is selected from the group consisting of: H, F, methyl and ethyl, and $R^{11}$ is selected from the group consisting of: F, methyl and ethyl. In other examples $R^{10}$ is selected from the group consisting of: H, F, and methyl, and $R^{11}$ is selected from the group consisting of: F, and methyl. In other examples $R^{10}$ is H and $R^{11}$ is selected from the group consisting of: F, methyl and ethyl. In other examples $R^{10}$ is H and $R^{11}$ is selected from the group consisting of: F, and methyl. In other examples $R^{10}$ and $R^{11}$ are as defined in any one of the examples in this paragraph, and $R^1$ and $R^2$ are as defined in any one of the examples given above.

In another example $R^{10}$ is H and $R^{11}$ is —CH$_2$OH. In another example $R^{10}$ is H and $R^{11}$ is —CH(OH)CH$_3$. In another example $R^{10}$ is H and $R^{11}$ is —CH(OH)CH$_3$. In another example $R^{10}$ is H and $R^{11}$ is —CH(OH)CH$_2$CH$_3$. In another example $R^{10}$ is H and $R^{11}$ is -pyridyl-CH$_2$OH. In another example, $R^{10}$ is H and $R^{11}$ is —CH(OH)cyclopropyl. In another example $R^{10}$ is H and $R^{11}$ is —CH$_2$OC(O)CH$_3$. In another example $R^{10}$ is H and $R^{11}$ is -methyloxadiazolyl. In another example $R^{10}$ is H and $R^{11}$ is methylthiadiazolyl. In another example $R^{10}$ is H and $R^{11}$ is —NH$_2$. In another example $R^{10}$ is H and $R^{11}$ is —NHCH$_3$. In another example $R^{10}$ is H and $R^{11}$ is —NHCH$_2$CH$_3$. In another example $R^{10}$ is H and $R^{11}$ is methylpyridyl. In another example $R^{10}$ is H and $R^{11}$ is —NHC(O)CH$_3$. In another example $R^{10}$ is H and $R^{11}$ is pyrazolyl. In another example $R^{10}$ is H and $R^{11}$ is oxazolyl. In another example $R^{10}$ is H and $R^{11}$ is methylpyrimidinyl. In another example $R^{10}$ is H and $R^{11}$ is —CH$_2$O—C(O)NHCH$_3$. In another example $R^{10}$ is H and $R^{11}$ is —CH$_2$imidazolyl. In another example $R^{10}$ is H and $R^{11}$ is —CH$_3$. In another example $R^{10}$ is H and $R^{11}$ is —CHF$_2$. In another example $R^{10}$ is H and $R^{11}$ is —CH$_2$OCH$_3$. In another example $R^{10}$ is H and $R^{11}$ is —CH$_2$oxooxazolidinyl. In another example $R^{10}$ is H and $R^{11}$ is —CH$_2$O(CH$_2$)$_2$OH. In another example $R^{10}$ is H and $R^{11}$ is —CH$_2$triazolyl. In another example $R^{10}$ is H and $R^{11}$ is —CH(CH$_3$)OH.

In one example $R^1$ is —O(CH$_2$)$_2$OCH$_3$. In another example $R^1$ is —OCH$_3$. In another example $R^1$ is —O(CH$_2$)$_2$OH. In another example $R^1$ is —OCH$_2$CHF$_2$. In another example $R^1$ is —OCH$_2$CH$_3$. In another example $R^1$ is —O(CH$_2$)$_3$CF$_3$. In another example $R^1$ is —OCH$_2$CH—(OH)CH$_2$CH$_3$. In another example $R^1$ is —OCH$_2$CH(CH$_2$OH)OH. In another example $R^1$ is —OCH$_2$tetrahydropyranyl. In another example $R^1$ is —OCH$_2$CH(CH$_3$)CH$_2$OH. In another example $R^1$ is —OCH$_2$tetrahydrofuranyl. In another example $R^1$ is —OCH$_2$CH—(OH)CH$_2$F. In another example $R^1$ is —Othiazolyl. In another example $R^1$ is —O(CH$_2$)$_2$-pyrazolyl. In another example $R^1$ is —O(CH$_2$)$_2$methylimidazolyl. In another example $R^1$ is —O(CH$_2$)$_2$oxopyrrolidinyl. In another example $R^1$ is —Otetrahydrofuranyl. In another example $R^1$ is —OCH$_2$CH(OH)CF$_3$. In another example $R^1$ is —O(CH$_2$)$_2$OCHF$_2$. In another example $R^1$ is —O(CH$_2$)$_2$OCH$_3$. In another example $R^1$ is —OCH$_2$C(CF$_3$)OH. In another example $R^1$ is —O(CH$_2$)$_2$OCF$_3$. In another example $R^1$ is —Otetrahydropyranyl. In another example $R^1$ is —O(CH$_2$)$_2$OCH$_2$CH$_3$. In another example $R^1$ is —SCF$_3$. In another example $R^1$ is —OCH(CH$_3$)CH$_2$OCH$_3$. In another example $R^1$ is —OCH$_2$pyridyly. In another example $R^1$ is —Otetrahydropyranyl. In another example $R^1$ is —Ocyanocyclohexyl. In another example $R^1$ is —Omethyltetrahydropyranyl. In another example $R^1$ is —Odimethyltetrahydropyranyl. In another example $R^1$ is —OCH$_2$CH—(CH$_3$)OH. In another example $R^1$ is —OCH$_2$pyridyl. In another example $R^1$ is —O(CH$_2$)$_2$—OCH$_2$CH$_3$.

In another example $R^2$ is selected from the group consisting of: B29, B30, B31, B34, B35, B36, B39, B42, B44, B53, B54, B102, B104, B105, B106, B107, B108, B109, B114, B120, B125, B127, B129, B130, B131, B132, B138, B140, B141, B142, B143, B144, B145, B147, B148, B149, B151, B152, B155, B159, B160, B162, B169, B170, B173, B175, B176, B177, B179, B181, B182, B184, B185, B186, B131, B188, B190, B192, B193, B194, B195, B198, B199, B210, B218, B224, B229, B244, B245, B248, and B249.

In another example, (1) $R^1$ is selected from the group consisting of: —O(CH$_2$)$_2$OCH$_3$, —OCH$_3$, —O(CH$_2$)$_2$OH, —OCH$_2$CHF$_2$, —OCH$_2$CH$_3$, —O(CH$_2$)$_3$CF$_3$, —OCH$_2$CH(OH)—CH$_2$CH$_3$, —OCH$_2$CH(CH$_2$OH)OH, —OCH$_2$tetrahydropyranyl, —OCH$_2$CH(CH$_3$)CH$_2$OH, —OCH$_2$tetrahydrofuranyl, —OCH$_2$CH(OH)CH$_2$F, —Othiazolyl, —O(CH$_2$)$_2$pyrazolyl, —O(CH$_2$)$_2$methylimidazolyl, —O(CH$_2$)$_2$oxopyrrolidinyl —Otetrahydrofuranyl, —OCH$_2$CH—(OH)CF$_3$, —O(CH$_2$)$_2$O—CHF$_2$, —O(CH$_2$)$_2$OCH$_3$, —OCH$_2$C(CF$_3$)OH, —O(CH$_2$)$_2$OCF$_3$, —Otetra-hydropyranyl, —O(CH$_2$)$_2$—OCH$_2$CH$_3$, —SCF$_3$, —OCH(CH$_3$)CH$_2$OCH$_3$, —OCH$_2$pyridyly, —Otetra-hydropyranyl, —Ocyanocyclohexyl, —Omethyltetrahydropyranyl, —Odimethyltetrahydropyranyl, —OCH$_2$CH(CH$_3$)OH, —OCH$_2$pyridyl and —O(CH$_2$)$_2$OCH$_2$CH$_3$; (2) $R^2$ is selected from the group consisting of: B29, B30, B31, B34, B35, B36, B39, B42, B44, B53, B54, B102, B104, B105, B106, B107, B108, B109, B114, B120, B125, B127, B129, B130, B131, B132, B138, B140, B141, B142, B143, B144, B145, B147, B148, B149, B151, B152, B155, B159, B160, B162, B169, B170, B173, B175, B176, B177, B179, B181, B182, B184, B185, B186, B131, B188, B190, B192, B193, B194, B195, B198, B199, B210, B218, B224, B229, B244, B245, B248, and B249; (3) $R^{10}$ is selected from the group consisting of H and F; and (4) $R^{11}$ is selected from the group consisting of: —CH$_2$OH, —CH(OH)CH$_3$, —CH(OH)CH$_3$, —CH(OH)CH$_2$CH$_3$, -pyridyl-CH$_2$OH, —CH(OH)cyclopropyl, —CH$_2$OC(O)CH$_3$, -methyloxadiazolyl, -methylthiadiazolyl, —NH$_2$, —NHCH$_3$, —NHCH$_2$CH$_3$, methylpyridyl, —NHC(O)CH$_3$, pyrazolyl, oxazolyl, $R^{11}$ is methylpyrimidinyl, —CH$_2$OC(O)NHCH$_3$, —CH$_2$imidazolyl, —CH$_3$, —CHF$_2$, —CH$_2$OCH$_3$, —CH$_2$oxooxazolidinyl, —CH$_2$O(CH$_2$)$_2$OH, —CH$_2$triazolyl and —CH(CH$_3$)OH. In another example, $R^1$, $R^2$ and $R^{11}$ are selected from the groups described in this paragraph and $R^{10}$ is H.

In another example, $R^1$ is —OCH$_3$, $R^2$ is selected from the group consisting of: B31, B39 and B104, $R^{10}$ is H, and $R^{11}$ is selected from the group consisting of H and —CH$_2$OH.

In another example, $R^1$ is —O(CH$_2$)$_2$OH, $R^2$ is selected from the group consisting of: B104, B106, B107, B108, B110, and B177, $R^{10}$ is H, and $R^{11}$ is —CH$_2$OH.

In another example, $R^1$ is selected from the group consisting of: —O(CH$_2$)$_2$OCHF$_2$, —O(CH$_2$)$_2$OH, —O(CH$_2$)$_2$OCH$_3$, and —OCH$_2$CH$_3$, $R^2$ is selected from the group consisting of: B52, B53, B104, B106, B107, B109, B110, and B177, le is H, and $R^{11}$ is H.

In another example, $R^1$ is selected from the group consisting of: —OCH$_2$CH$_3$, —O(CH$_2$)$_2$OCH$_3$, —O(CH$_2$)$_2$OCH$_2$CH$_3$, —O(CH$_2$)$_2$OCHF$_2$, and —O(CH$_2$)$_2$OH, $R^2$ is selected from the group consisting of: B102, B107 and B177, $R^{10}$ is H, and $R^{11}$ is selected from the group consisting of: H and —CH$_2$OH.

In the examples below Group I represents —OCH$_3$, —OCH$_2$CH$_2$OCH$_3$, —OCH$_2$CH$_3$, —OCH$_2$CH$_2$OH, —O—CH$_2$phenyl, A2, A4 and A6.

In another example $R^1$ is selected from the group consisting of Group I; $R^2$ is selected from the group consisting of: B1, B2, B3, B5, B8, B10, and B25; $R^{10}$ is selected from the group consisting of: H and F; and $R^{11}$ is selected from the group consisting of: H and —$CH_3$.

In another example $R^1$ is selected from the group consisting of Group I; $R^2$ is selected from the group consisting of: B11, B31, B32, B38, B39, B44, B46, B50, B51, B53, B54, and B62; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B1; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B2; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B3; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B5; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B8; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B10; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B25; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B11; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B31; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B32; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B38; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B39; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B44; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B46; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B50; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B51; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B53; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B54; $R^{10}$ is selected from the group consisting of: H and F; and $R^{11}$ is selected from the group consisting of: H and —$CH_3$; and wherein Group I is as defined above.

In another example $R^1$ is selected from the group consisting of Group I; $R^2$ is B62; $R^{10}$ is selected from the group consisting of: H and F; and $R^{11}$ is selected from the group consisting of: H and —$CH_3$; and wherein Group I is as defined above.

Representative compounds of this invention include, but are not limited to the final compounds of Examples 1-81, 100-113 and 200-579. In one example the compounds of the invention are selected from the group consisting of: 1, 2, 8, 23, 29, 31, 32, 33, 34, 36, 39, 41, 43, 44, 46, 47, 48, 57, 62, 64, 69, 70, 71, 109, 110, 272, 356, 416 and 419. In another example the compounds of this invention are selected from the group consisting of: 41, 109, 110, 272, 356, 416 and 419

Representative compounds of the invention include, but are not limited to, the final compounds of Examples 1 to 81. Thus, one example of this invention is the compound of Ex. 1, another is the compound of Ex. 2, another is the compound of Ex. 3, another is the compound of Ex. 4, another is the compound of Ex. 5, another is the compound of Ex. 6, another is the compound of Ex. 7, another is the compound of Ex. 8, another is the compound of Ex. 9, another is the compound of Ex. 10, another is the compound of Ex. 11, another is the compound of Ex. 12, another is the compound of Ex. 13, another is the compound of Ex. 14, another is the compound of Ex. 15, another is the compound of Ex. 16, another is the compound of Ex. 17, another is the compound of Ex. 18, another is the compound of Ex. 19, another is the compound of Ex. 20, another is the compound of Ex. 21, another is the compound of Ex. 22, another is the compound of Ex. 23, another is the compound of Ex. 24, another is the compound of Ex. 25, another is the compound of Ex. 26, another is the compound of Ex. 27, another is the compound of Ex. 28, compound of Ex. 29, another is the compound of Ex. 30, another is the compound of Ex. 31, another is the compound of Ex. 32, another is the compound of Ex. 33, another is the compound of Ex. 34, another is the compound of Ex. 35, another is the compound of Ex. 36, another is the compound of Ex. 37, another is the compound of Ex. 38, another is the compound of Ex. 39, another is the compound of Ex. 40, another is the compound of Ex. 41, another is the compound of Ex. 42, another is the compound of Ex. 43, another is the compound of Ex. 44, another is the compound of Ex. 45, another is the compound of Ex. 46, another is the compound of Ex. 47, another is the compound of Ex. 48, another is the compound of Ex. 49, another is the compound of Ex. 50, another is the compound of Ex. 51, another is the compound of Ex. 52, another is the compound of Ex. 53, another is the compound of Ex. 54, another is the compound of Ex. 55, another is the compound of Ex. 56, another is the compound of Ex. 57, another is the compound of Ex. 58, another is the compound of Ex. 59, another is the compound of Ex. 60, another is the compound of Ex. 61, another is the compound of Ex. 62, another is the compound of Ex. 63, another is the compound of Ex. 64, another is the compound of Ex. 65, another is the compound of Ex. 66, another is the compound of Ex. 67, another is the compound of Ex. 68, another is the compound of Ex. 69, another is the compound of Ex. 70, another is the compound of Ex. 71, another is the compound of Ex. 72, another is the compound of Ex. 73, another is the compound of Ex. 74, another is the compound of Ex. 75, another is the compound of Ex. 76, another is the compound of Ex. 77, another is the compound of Ex. 78, another is the compound of Ex. 79, another is the compound of Ex. 80, and another is the compound of Ex. 81.

Other examples of the compounds of this invention are any one of the final compounds of Examples 100-113 and 200-579 as if each was listed individually in this paragraph as a separate example. Thus, for example, one example of the compounds of this invention is the compound of Ex. 102, and in another example the compound of Ex. 103, and in another example the compound of Ex. 104, and in another example the compound of Ex. 107, and in another example the compound of Ex. 108, and in another example the compound of Ex. 109, and in another example the compound of Ex. 110, and in another example the compound of Ex. 112, and in another example the compound of Ex. 113, and the like.

Other examples of this invention include pharmaceutically acceptable salts of the compounds of formula (1.0).

Other examples include the pharmaceutically acceptable salts of any one of the final compounds of Examples 1 to 81. Other examples include the pharmaceutically acceptable salts of any one of the final compounds of Examples 100-113 and 200-579.

Other examples of this invention include pharmaceutically acceptable esters of the compounds of formula (1.0). Other examples of this invention include pharmaceutically acceptable esters of any one of the final compounds of Examples 1 to 81. Other examples of this invention include pharmaceutically acceptable esters of any one of the final compounds of Examples 100-113 and 200-579.

Other examples of this invention include solvates of the compounds of formula (1.0). Other examples of this invention include the solvates of any one of the final compounds of Examples 1 to 81. Other examples of this invention include the solvates of any one of the final compounds of Examples 100-113 and 200-579.

Other examples of this invention include pharmaceutical compositions comprising at least one compound of formula (1.0), and a pharmaceutically acceptable carrier.

Other examples of this invention include pharmaceutical compositions comprising at least one compound selected from the group consisting of the final compounds of Examples 1 to 81, and a pharmaceutically acceptable carrier.

Other examples of this invention include pharmaceutical compositions comprising one compound of formula (1.0), and a pharmaceutically acceptable carrier.

Other examples of this invention include pharmaceutical compositions comprising one compound selected from the group consisting of the final compounds of Examples 1 to 81, and a pharmaceutically acceptable carrier.

Other examples of this invention include pharmaceutical compositions comprising at least one pharmaceutically acceptable salt of at least one compound of formula (1.0), and a pharmaceutically acceptable carrier.

Other examples of this invention include pharmaceutical compositions comprising at least one pharmaceutically acceptable salt of one compound selected from the group consisting of the final compounds of Examples 1 to 81, and a pharmaceutically acceptable carrier. Other examples of this invention include pharmaceutical compositions comprising at least one pharmaceutically acceptable salt of one compound selected from the group consisting of the final compounds of Examples 100-113 and 200-579, and a pharmaceutically acceptable carrier.

Other examples of this invention include pharmaceutical compositions comprising one pharmaceutically acceptable salt of one compound of formula (1.0), and a pharmaceutically acceptable carrier.

Other examples of this invention include pharmaceutical compositions comprising one pharmaceutically acceptable salt of one compound selected from the group consisting of the final compounds of Examples 1 to 81, and a pharmaceutically acceptable carrier. Other examples of this invention include pharmaceutical compositions comprising one pharmaceutically acceptable salt of one compound selected from the group consisting of the final compounds of Examples 100-113 and 200-579, and a pharmaceutically acceptable carrier.

Other examples of this invention include the compounds of formula (1.0) in pure and isolated form.

Other examples of this invention include any one of the final compounds of Examples 1 to 81 in pure and isolated form. Other examples of this invention include any one of the final compounds of Examples 100-113 and 200-579 in pure and isolated form.

Another example of this invention is a pharmaceutical composition comprising an effective amount of a compound of formula (1.0) (e.g., a final compound of Examples 1 to 81, and in another example the final compounds of Examples 100-113 and 200-579), a chemotherapeutic agent, and a pharmaceutically acceptable carrier.

The compounds of the invention are useful in preparing a medicament that is useful in treating cancer.

The compounds of this invention inhibit the activity of ERK2. Thus, this invention further provides a method of inhibiting ERK in mammals, especially humans, by the administration of an effective amount of one or more (e.g., one) compounds of this invention. The administration of the compounds of this invention to patients, to inhibit ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (1.0) can be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods comprising administering a therapeutically effective amount of a compound of the instant invention in combination with radiation therapy and/or in combination with a second compound selected from the group consisting of: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of this invention is a method of treating cancer in a patient in need of such treatment, said method comprising administering an effective amount of a compound of formula (1.0). Another example of this invention is a method of treating cancer in a patient in need of such treatment, said method comprising administering to said patient an effective amount of a compound of formula (1.0), and an effective amount of at least one (e.g., 1-3, 1-2, or 1) chemotherapeutic agent.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma, colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1.0) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of this invention the cancer treated is colo-rectal cancer (such as, for example, colon adenocarcinoma and colon adenoma). Thus, another example of this invention is a method of treating colo-rectal cancer in a patient in need of such treatment, said method comprising administering an effective amount of a compound of formula (1.0) (e.g., a final compound of Examples 1 to 81, and in another example a final compound of examples 100-113 and 200-579), or a pharmaceutically acceptable salt thereof, to said patient. Another example is a method of treating colo-rectal cancer in a patient in need of such treatment, said method comprising administering to said patient an effective amount of a compound selected from the group consisting of: the final compounds of Examples 1, 2, 8, 23, 29, 31, 32, 33, 34, 36, 39, 41, 43, 44, 46, 47, 48, 57, 62, 64, 69, 70, 71, 109, 110, 272, 356, 416 and 419, or a pharmaceutically acceptable salt thereof. Another example is a method of treating colo-rectal cancer in a patient in need of such treatment, said method comprising administering to said patient an effective amount of a compound selected from the group consisting of: the final compounds of Examples 1, 2, 8, 23, 29, 31, 32, 33, 34, 36, 43, 44, 46, 47, 48, 57, 62, 64, 69, 70, and 71 or a pharmaceutically acceptable salt thereof. Another example of this invention is a method of treating colo-rectal cancer in a patient in need of such treatment, said method comprising administering to said patient an effective amount of a compound of formula (1.0) (e.g., a final compound of Examples 1 to 81, and in another example the final compounds of Examples 100-113 and 200-579), or a pharmaceutically acceptable salt thereof, and an effective amount of at least one (e.g., 1-3, or 1-2, or 1) chemotherapeutic agent.

In one example of this invention the cancer treated is melanoma. Thus, another example of this invention is directed to a method of treating melanoma in a patient in need of such treatment, said method comprising administering an effective amount of a compound of formula (1.0) (e.g. a final compound of Examples 1 to 81, and in another example the final compounds of Examples 100-113 and 200-579), or a pharmaceutically acceptable salt thereof, to said patient. Another example is a method of treating melanoma in a patient in need of such treatment, said method comprising administering to said patient an effective amount of a compound selected from the group consisting of: the final compounds of Examples 1, 2, 8, 23, 29, 31, 32, 33, 34, 36, 39, 41, 43, 44, 46, 47, 48, 57, 62, 64, 69, 70, 71, 109, 110, 272, 356, 416 and 419, or a pharmaceutically acceptable carrier thereof. Another example is a method of treating melanoma in a patient in need of such treatment, said method comprising administering to said patient an effective amount of a compound selected from the group consisting of: the final compounds of Examples 1, 2, 8, 23, 29, 31, 32, 33, 34, 36, 43, 44, 46, 47, 48, 57, 62, 64, 69, 70, and 71, or a pharmaceutically acceptable carrier thereof. Another example of this invention is a method of treating melanoma in a patient in need of such treatment, said method comprising administering to said patient an effective amount of a compound of formula (1.0) (e.g., a final compound of Examples 1 to 81), or a pharmaceutically acceptable salt thereof, and an effective amount of at least one (e.g., 1-3, or 1-2, or 1) chemotherapeutic agent. Another example of this invention is a method of treating melanoma in a patient in need of such treatment, said method comprising administering to said patient an effective amount of a compound of formula (1.0) (e.g., a final compound of Examples 100-113 and 200-579), or a pharmaceutically acceptable salt thereof, and an effective amount of at least one (e.g., 1-3, or 1-2, or 1) chemotherapeutic agent.

The compounds of the invention are also useful in preparing a medicament that is useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu- [diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, $RPR^{109881}$, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL; see U.S. Pat. No. 5,177, 080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR$^1$) and Flk-1/KDR (VEGFR$^2$), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin. Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an IC$_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC$_{50}$ for COX-2 over IC$_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272 and U.S. Pat. No. 5,932,598, all of which are hereby incorporated by reference.

Inhibitors of COX-2 that are particularly useful in the instant method of treatment are: 3-phenyl-4-(4-(methylsulfo-nyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpynol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthalmol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, LPAM (Alkeran®); mercaotopurine, 6-MP (Ourunethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In one example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians'Desk Reference, 56th Edition, 2002 (published by Medical Economics company, Inc. Montvale, N.J. 07645-1742), the Physicians' Desk Reference, 57th Edition, 2003 (published by Thompson PDR, Montvale, N.J. 07645-1742), the Physicians' Desk Reference, 60th Edition, 2006 (published by Thompson PDR, Montvale, N.J. 07645-1742), and the Physicians' Desk Reference, 64th Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1.0) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula (1.0) hereinabove.

General Schemes

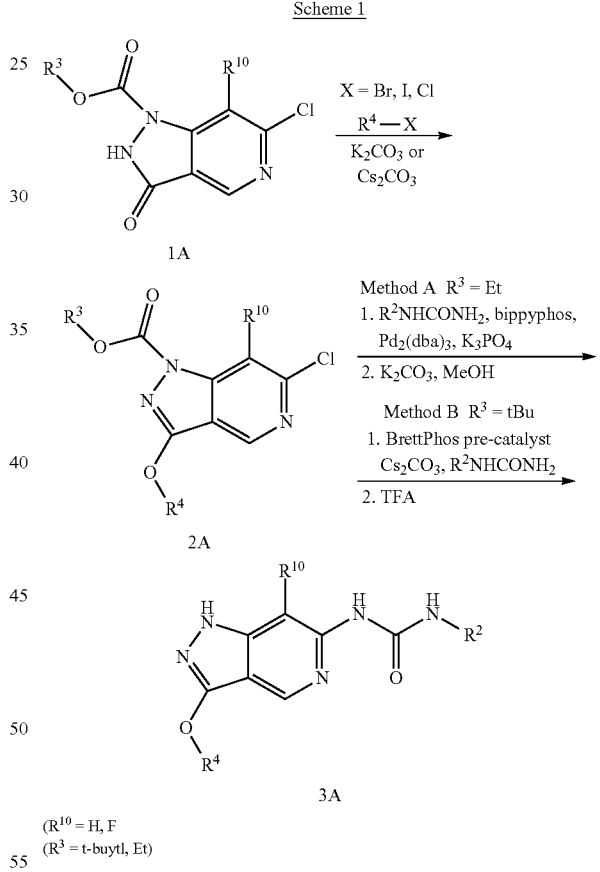

Step 1

Ether derivatives 2A have been prepared by treating 1A with the appropriate halide in the presence of a suitable base (i.e. $K_2CO_3$ or $Cs_2CO_3$) at 60° C. in DMF for 4 h or at room temperature for 16 h.

Step 2, Method A

Aryl urea derivatives have been prepared by heating 2A to 85° C. (from 2 to 16 h) with the appropriate primary urea (commercial or synthesized from heating the appropriate amine in the presence of HCl and potassium cyanate), Pd$_2$(dba)$_3$, bippyphos, and K$_3$PO$_4$ in DME. The residue was treated with K$_2$CO$_3$ in MeOH to yield the desired product 3A.

Step 2, Method B

Aryl urea derivatives have been prepared by heating 2A to 100° C. (from 1 to 16 h) with the appropriate primary urea (commercial or synthesized from heating the appropriate amine in the presence of HCl and potassium cyanate), Cs$_2$CO$_3$, and BrettPhos pre-catalyst in 1,4-dioxane. The residue was treated with TFA and triethylsilane (with or without DCM) to yield the desired product 3A.

Scheme 2

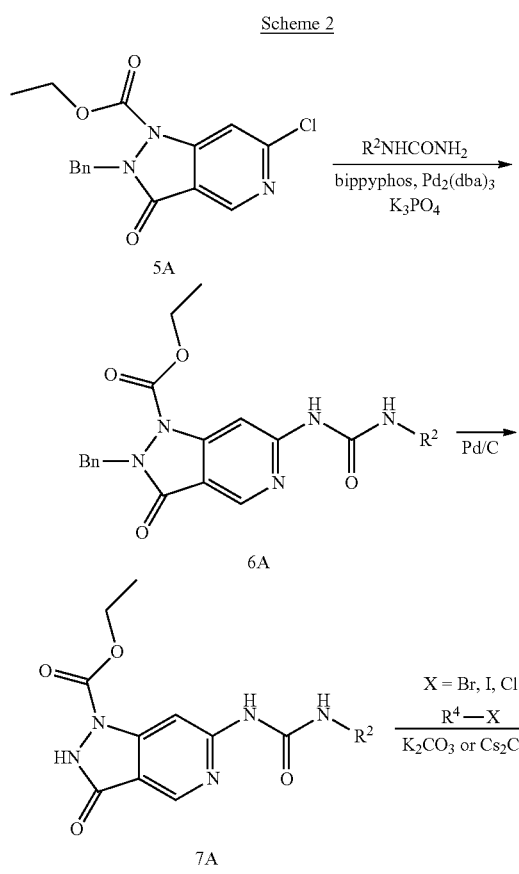

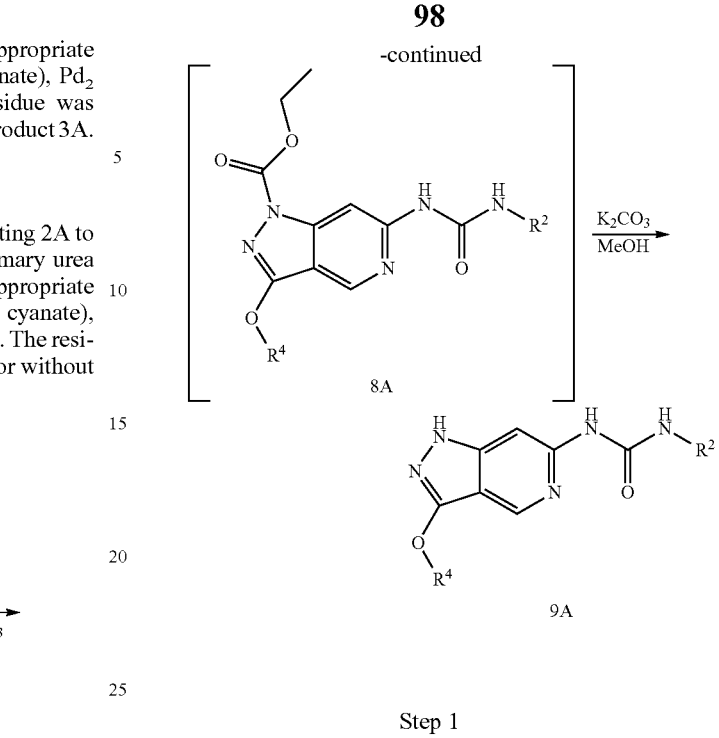

Step 1

Aryl urea derivatives have been prepared by heating ethyl 2-benzyl-6-chloro-3-oxo-2,3-dihydro-1H-pyrazolo[4,3-c]pyridine-1-carboxylate 5A to 85° C. (from 2 to 16 h) with the appropriate primary urea (commercial or synthesized from heating the appropriate amine in the presence of HCl and potassium cyanate), K$_3$PO$_4$, bippyphos, and Pd$_2$(dba)$_3$ in DME.

Step 2

6A was treated with Pd/C under a hydrogen atmosphere in EtOAc to afford 7A.

Step 3

Ether derivatives have been prepared by stirring 7A at room temperature (from 16-24 h) with the appropriate halide in the presence of a suitable base (i.e. K$_2$CO$_3$). The crude reaction mixture is treated with K$_2$CO$_3$ in MeOH to afford the desired product 9A.

Scheme 3

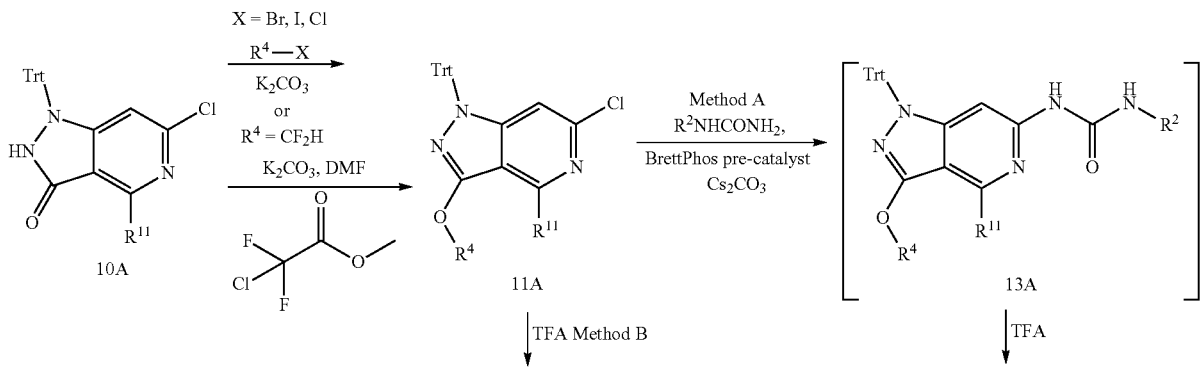

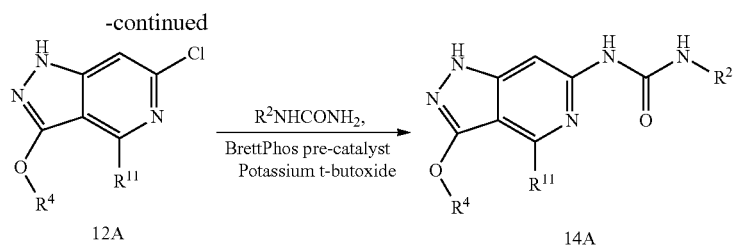

Step 1

Ether derivatives 11A have been prepared by stirring at room temperature (from 2-16 h) the appropriate halide with various 6-chloro-1-trityl-1H-pyrazolo[4,3-c]pyridin-3(2H)-one intermediates 10A in the presence of a suitable base (i.e. $K_2CO_3$) in DMF.

Step 2, Method A

Aryl urea derivatives have been prepared by heating 11A to 100° C. (from 1 to 16 h) with the appropriate primary urea (commercial or synthesized from heating the appropriate amine in the presence of HCl and potassium cyanate), $Cs_2CO_3$, and BrettPhos pre-catalyst in 1,4-dioxane. The residue was treated with TFA and triethylsilane (with or without DCM) to yield the desired product 14A.

Step 2, Method B

Aryl urea derivatives have been prepared by first treating 11A with TFA and triethylsilane to yield the deprotected product 12A.

Step 3, Method B

The corresponding 12A was then heated at 60° C. for 16 h with the appropriate primary urea, potassium tert-butoxide, and BrettPhos pre-catalyst in THF to afford the desired product 14A.

Step 1

Aryl urea derivatives 15A have been prepared by heating various 6-chloro-1-trityl-1H-pyrazolo[4,3-c]pyridin-3(2H)-one intermediates 10A to 80° C. for 24 h with the appropriate primary urea (commercial or synthesized from heating the appropriate amine in the presence of HCl and potassium cyanate), cesium carbonate, $Pd(OAc)_2$, and XantPhos in dioxane to afford the desired product 15A.

Step 2

Ether derivatives 14A have been prepared by stirring at room temperature (from 2-16 h) the appropriate halide with 15A in the presence of a suitable base (i.e. $K_2CO_3$) in DMF. The residue was treated with TFA and triethylsilane (with or without DCM) to yield the desired product 14A.

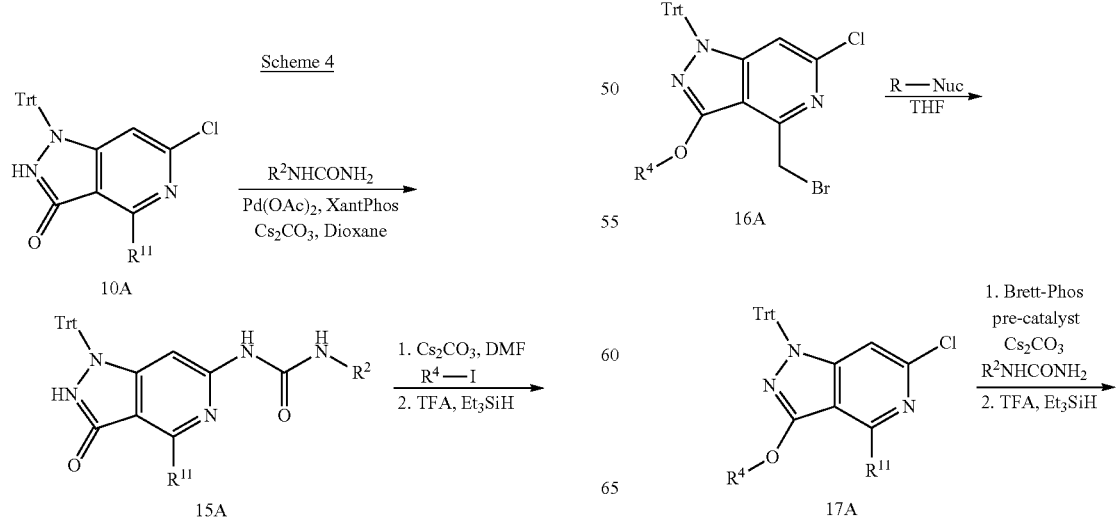

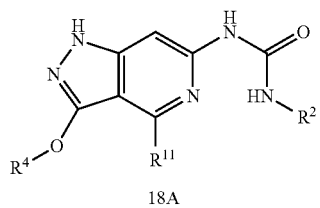

18A

R is -(C₁-C₅ alkyl), -(C₁-C₅alkyl)heterocycloalkyl, or heterocycloalkyl
R¹¹ is -(C₂-C₆ alkyl), or -(C₁-C₂alkyl)heterocycloalkyl Step 1

Alkyl derivatives 17A have been prepared by stirring at room temperature for 1 h the appropriate nucleophile with 16A (with or without a suitable base) to afford the desired product 17A.

Step 2

Aryl urea derivatives have been prepared by heating 16A to 100° C. (from 1 to 16 h) with the appropriate primary urea (commercial or synthesized from heating the appropriate amine in the presence of HCl and potassium cyanate), Cs₂CO₃, and BrettPhos pre-catalyst in 1,4-dioxane. The residue was treated with TFA and triethylsilane (with or without DCM) to yield the desired product 18A.

Scheme 6

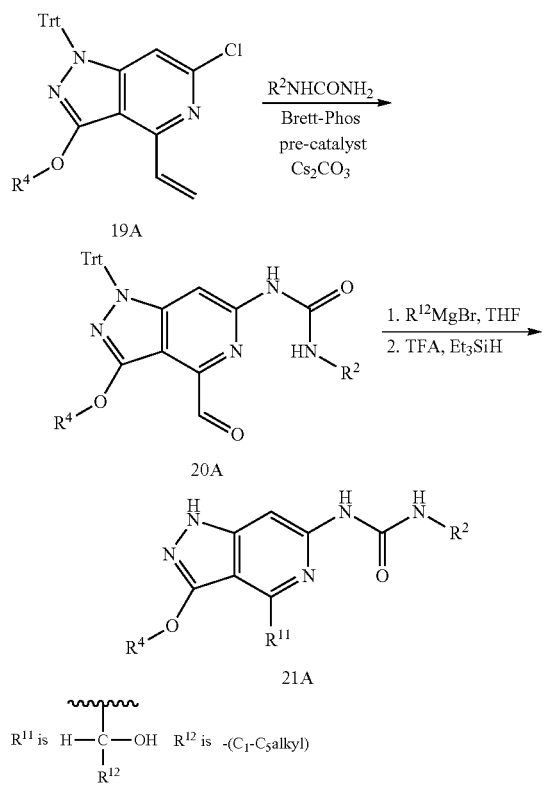

R¹¹ is H—C(R¹²)—OH    R¹² is -(C₁-C₅alkyl)

Step 1

Aryl urea derivatives have been prepared by heating 19A to 100° C. (from 1 to 16 h) with the appropriate primary urea (commercial or synthesized from heating the appropriate amine in the presence of HCl and potassium cyanate), Cs₂CO₃, and BrettPhos pre-catalyst in 1,4-dioxane.

Step 2

Secondary alcohol derivatives have been prepared by stirring 20A at −78° C. to 0° C. with the appropriate Grignard in THF. The residue was treated with TFA and triethylsilane (with or without DCM) to yield the desired product 21A, which can be further separated by chiral SFC.

Scheme 7

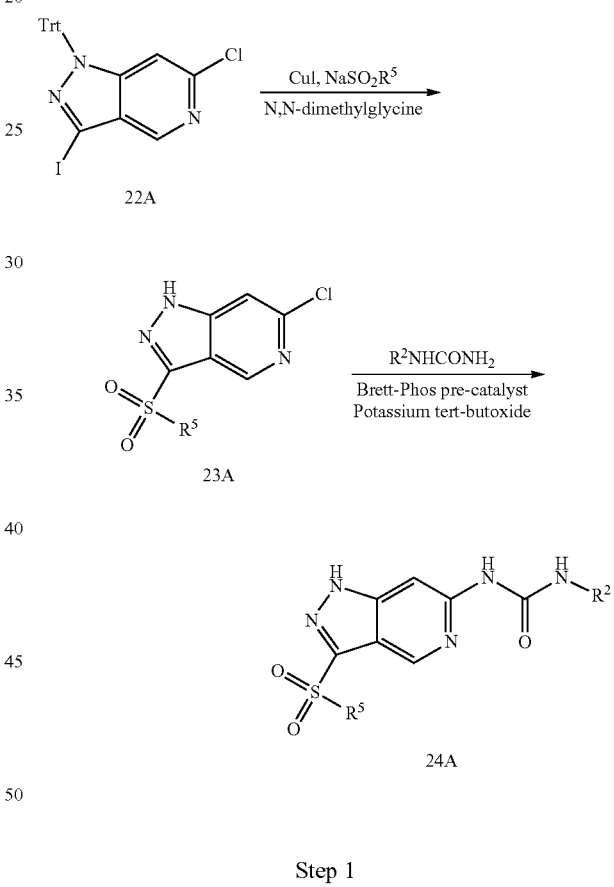

Step 1

Sulfone derivatives 23A have been prepared by heating 22A at 110° C. with the appropriate sulfinate salt, N,N-dimethylglycine, and copper(I) iodide in DMSO.

Step 2

Aryl urea derivatives have been prepared by heating 23A to 60° C. for 18 h with the appropriate primary urea (commercial or synthesized from heating the appropriate amine in the presence of HCl and potassium cyanate), potassium tert-butoxide, and BrettPhos pre-catalyst in THF to afford the desired product 24A.

Scheme 8

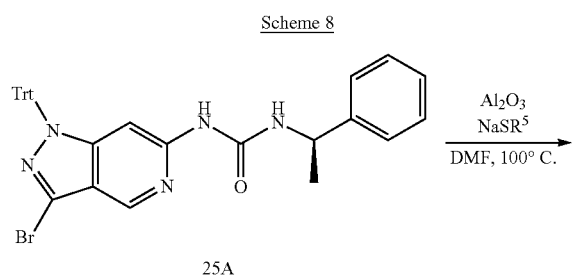
25A

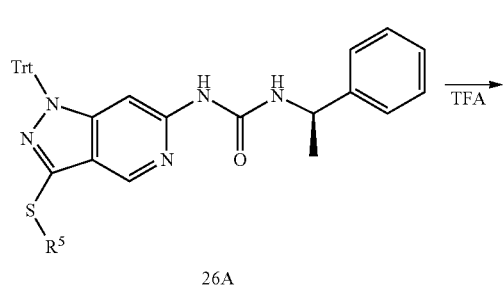
26A

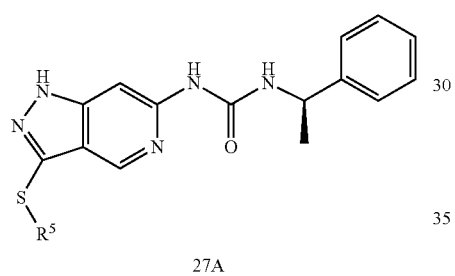
27A

Step 1

Thioether derivatives have been prepared by heating 25A at 100° C. for 1 to 3 h with the appropriate sodium thiol and aluminum oxide in DMF.

Step 2

26A was then treated with TFA and triethylsilane to yield the desired product 27A.

Scheme 9

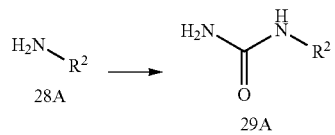

Substituted ureas are prepared by heating the appropriate amine 28A and potassium cyanate (1-5 eq.) in aqueous HCl (80-100° C., 1-3 h) to provide urea 29A. Alternatively, 28A is treated with trimethylsilyl isocyanate (3 eq) and DIPEA (3 eq) in DCM (3-18 h) to provide 29A.

Scheme 10

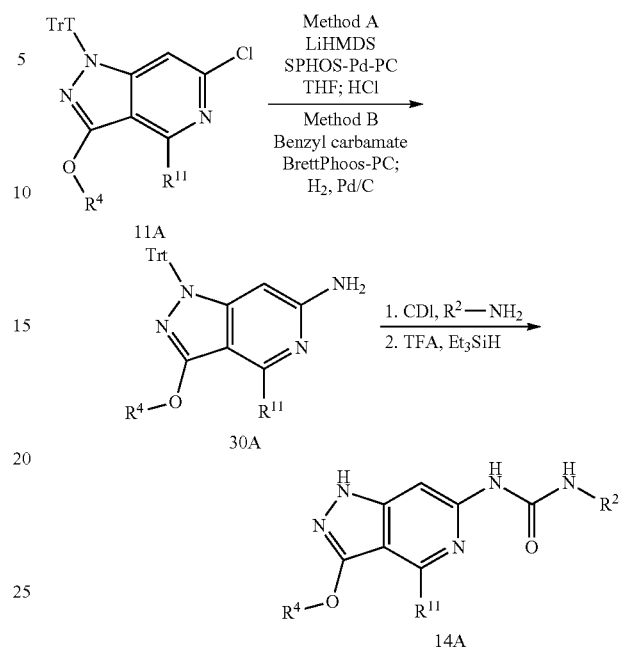

Step 1, Method A

Amine derivatives 30A have been prepared by treating various 6-chloro-3-alkoxy-1-trityl-1H-pyrazolo[4,3-c]pyridine intermediates 11A with lithium bis(trimethylsilyl)amide and SPHOS precatalyst palladacycle (60-80° C. overnight, THF sovlent) to afford 30A.

Step 1, Method B

Amine derivatives 30A were prepared by reacting 11A with benzyl carbamate (BrettPhos precatatlyst, NaOtBu, THF, 50-100° C., 3-18 h) followed by hydrogenation (H$_2$, Pd/C) to provide 30A.

Step 2

Aryl urea derivatives have been prepared by reacting 30A with an appropriate primary amine (commercial or synthesized by methods known to those in the art), CDI and imidazole or another appropriate base (THF, room temperature, overnight). The resultant products have been deprotected with TFA and triethylsilane in DCM to afford the desired product 14A.

Intermediates

Intermediate 1B

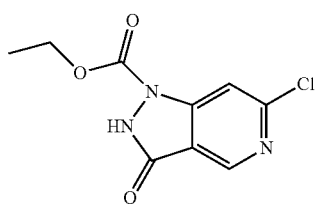 [SMILES: CCOC(=O)n1[nH]c(=O)c2cnc(Cl)cc21]

Ethyl 6-chloro-3-oxo-2,3-dihydro-1H-pyrazolo[4,3-c]pyridine-1-carboxylate

Ethyl 6-chloro-3-oxo-2,3-dihydro-1H-pyrazolo[4,3-c]pyridine-1-carboxylate was synthesized according to the following scheme and procedures.

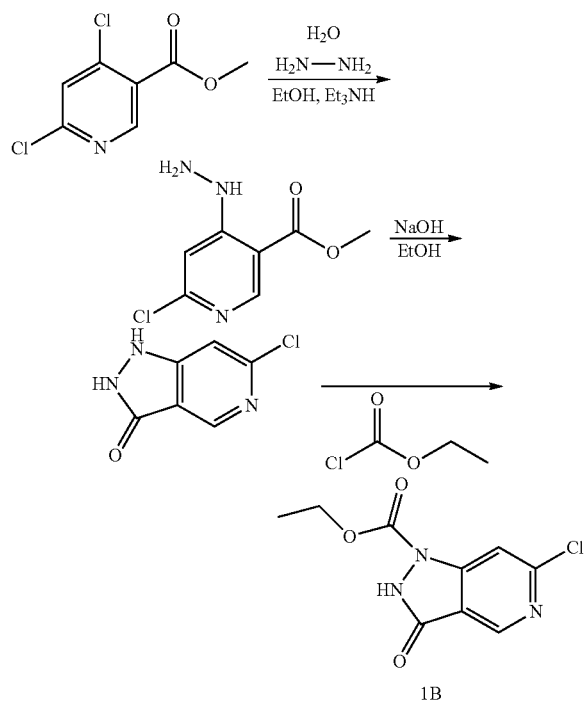

Step 1: Methyl 6-chloro-4-hydrazinylnicotinate

Into a 20-L 4-necked round-bottom flask was placed methyl 4,6-dichloropyridine-3-carboxylate (1200 g, 5.82 mol), ethanol (10 L), and triethylamine (1182 g, 11.68 mol). NH$_2$NH$_2$.H$_2$O (351 g, 7.02 mol) was then added drop-wise to the reaction mixture at 0° C. The resulting solution was heated to reflux for 1 h. The reaction mixture was cooled to room temperature. The solid was collected by filtration to give methyl 6-chloro-4-hydrazinylnicotinate, which was carried onto the next step without further purification.

Step 2:
6-Chloro-1H-pyrazolo[4,3-c]pyridin-3(2H)-one

Into a 50-L reactor was placed ethanol (22 L), sodium hydroxide (800 g, 20.00 mol), and 6-chloro-4-hydrazinylnicotinate (2700 g, 13.39 mol). The resulting solution was stirred for 2 h at room temperature. The pH value of the solution was adjusted to 7 with HCl. The solid was filtered out. The filtrate was concentrated in vacuo to give 6-chloro-1H-pyrazolo[4,3-c]pyridin-3(2H)-one, which was carried onto the next step without further purification. MS ESI calc'd. for C$_6$H$_4$ClN$_3$O [M+1]$^+$ 170. found 170.

Step 3: Ethyl 6-chloro-3-oxo-2,3-dihydro-1H-pyrazolo[4,3-c]pyridine-1-carboxylate To a solution of 6-chloro-1H-pyrazolo[4,3-c]pyridin-3(2H)-one (2.64 g, 15.57 mmol) in pyridine (10 mL) and water (14 mL) was added ethyl chloroformate (3.38 g, 31.1 mmol) drop-wise at 0° C. The reaction was removed from the ice bath and was stirred at room temperature overnight. The reaction mixture was filtered and the solid rinsed with water to afford ethyl 6-chloro-3-oxo-2,3-dihydro-1H-pyrazolo[4,3-c]pyridine-1-carboxylate, which was carried onto the next step without further purification. MS ESI calc'd. for C$_9$H$_8$ClN$_3$O$_3$ [M+1]$^+$ 242. found 242.

Intermediate 2B

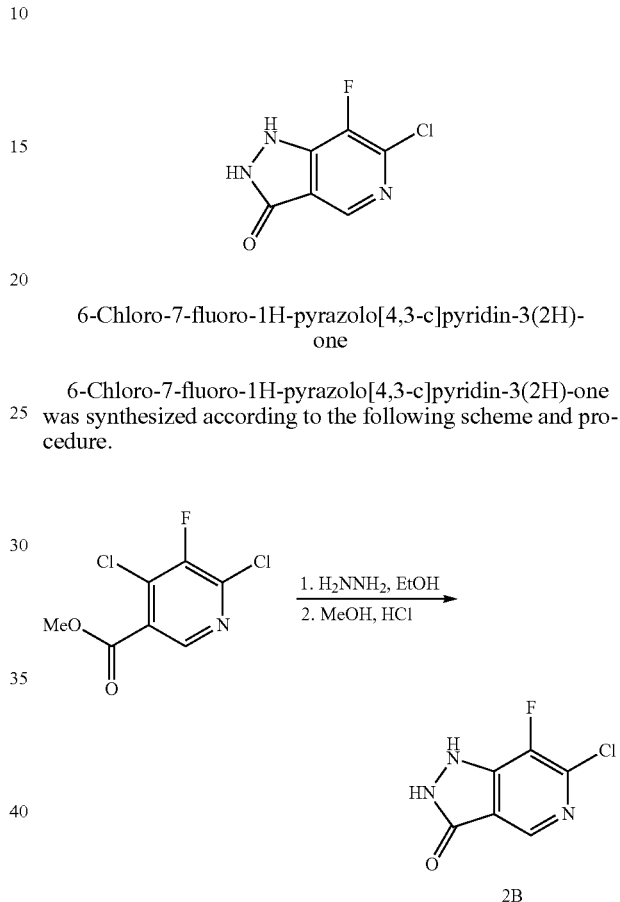

6-Chloro-7-fluoro-1H-pyrazolo[4,3-c]pyridin-3(2H)-one

6-Chloro-7-fluoro-1H-pyrazolo[4,3-c]pyridin-3(2H)-one was synthesized according to the following scheme and procedure.

Methyl 4,6-dichloro-5-fluoronicotinate (5.0 g, 22.32 mmol) and hydrazine monohydrate (1.7 mL, 22.32 mmol) were dissolved in ethanol (5 mL) and stirred at 80° C. for 1 h. The reaction mixture was filtered, dissolved in MeOH, and HCl (1 N, 0.5 mL) was added. The reaction was stirred at room temperature for 4 h. The reaction mixture was then filtered and washed with water to give 6-chloro-7-fluoro-1H-pyrazolo[4,3-c]pyridin-3(2H)-one, which was carried onto the next step without further purification. MS ESI calc'd. for C$_6$H$_{13}$ClFN$_3$O [M+1]$^+$ 188. found 188.

Intermediate 3B

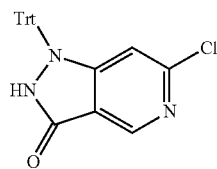

6-Chloro-1-trityl-1H-pyrazolo[4,3-c]pyridin-3(2H)-one

6-Chloro-1-trityl-1H-pyrazolo[4,3-c]pyridin-3(2H)-one was synthesized according to the following scheme and procedure.

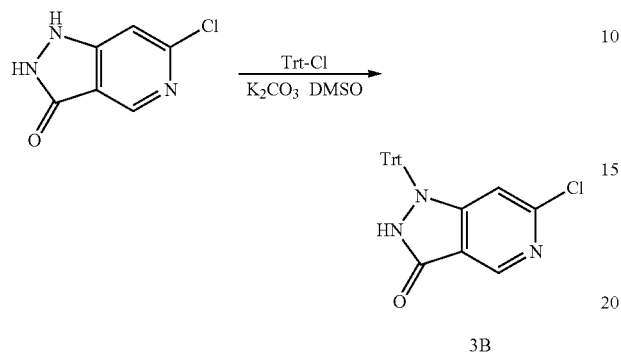

3B

Into a 2000-mL 4-necked round-bottom flask was placed 6-chloro-1H-pyrazolo[4,3-c]pyridin-3(2H)-one (Intermediate 1B, Step 2; 100 g, 589.73 mmol), Trt-Cl (328 g, 1.18 mol), potassium carbonate (244 g, 1.77 mol), and DMSO (1200 mL). The resulting solution was stirred for 30 h at 50° C. The reaction mixture was cooled to room temperature, then quenched by the addition of water/ice (4 L). The resulting solution was diluted with EtOAc (12 L). The solid was collected by filtration and washed with MeCN (1.5 L) to give 6-chloro-1-trityl-1H-pyrazolo[4,3-c]pyridin-3(2H)-one, which was carried onto the next step without further purification. MS ESI calc'd. for $C_{25}H_{18}ClN_3O$ [M+1]$^+$ 412. found 412.

Intermediate 4B

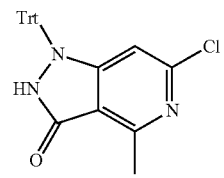

6-Chloro-4-methyl-1-trityl-1H-pyrazolo[4,3-c]pyridin-3(2H)-one

6-Chloro-4-methyl-1-trityl-1H-pyrazolo[4,3-c]pyridin-3(2H)-one was synthesized according to the following scheme and nrocedures.

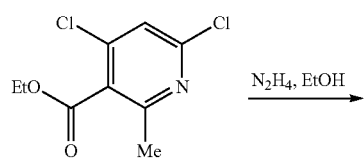

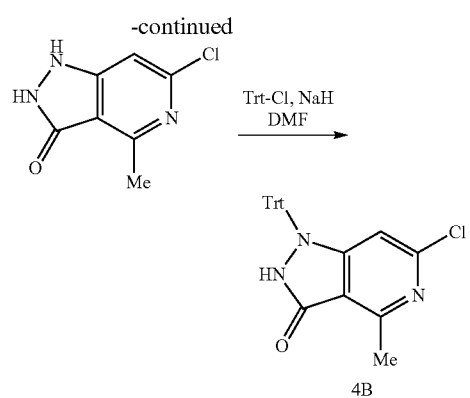

4B

Step 1: 6-Chloro-4-methyl-1H-pyrazolo[4,3-c]pyridin-3(2H)-one

A mixture of ethyl 4,6-dichloro-2-methylnicotinate (5.00 g, 21.36 mmol) and hydrazine monohydrate (2.1 mL, 43.3 mmol) in ethanol (22 mL) was heated to 80° C. and stirred for 17.5 h. The reaction was cooled to room temperature, diluted with water, filtered, rinsed with water, and dried under vacuum to provide 6-chloro-4-methyl-1H-pyrazolo[4,3-c]pyridin-3(2H)-one, which was carried onto the next step without further purification. MS ESI calc'd. for $C_7H_6ClN_3O$ [M+1]$^+$ 184. found 184.

Step 2: 6-Chloro-4-methyl-1-trityl-1H-pyrazolo[4,3-c]pyridin-3(2H)-one

A solution of 6-chloro-4-methyl-1H-pyrazolo[4,3-c]pyridin-3(2H)-one (3.1 g, 16.85 mmol) and trityl chloride (4.93 g, 17.69 mmol) in DMF (50 mL) was charged with sodium hydride (60% in mineral oil, 1.011 g, 25.3 mmol) and stirred at room temperature for 1.5 h. The reaction mixture was poured into sat. aq. NaHCO$_3$ and extracted with Et$_2$O (×3). The organic layer was washed with brine, dried over MgSO$_4$, filtered, and concentrated in vacuo. The residue was purified by flash chromatography (0-50% EtOAc/DCM) to provide 6-chloro-4-methyl-1-trityl-1H-pyrazolo[4,3-c]pyridin-3(2H)-one. MS ESI calc'd. for $C_{26}H_{20}ClN_3O$ [M+1]$^+$ 426. found 426.

Intermediate 5B

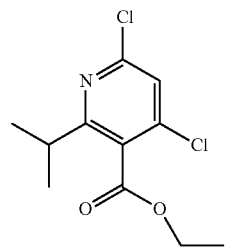 [SMILES: CCOC(=O)c1c(Cl)cc(Cl)nc1C(C)C]

Ethyl 4,6-dichloro-2-isopropylnicotinate

Ethyl 4,6-dichloro-2-isopropylnicotinate was synthesized according to the following scheme and procedures.

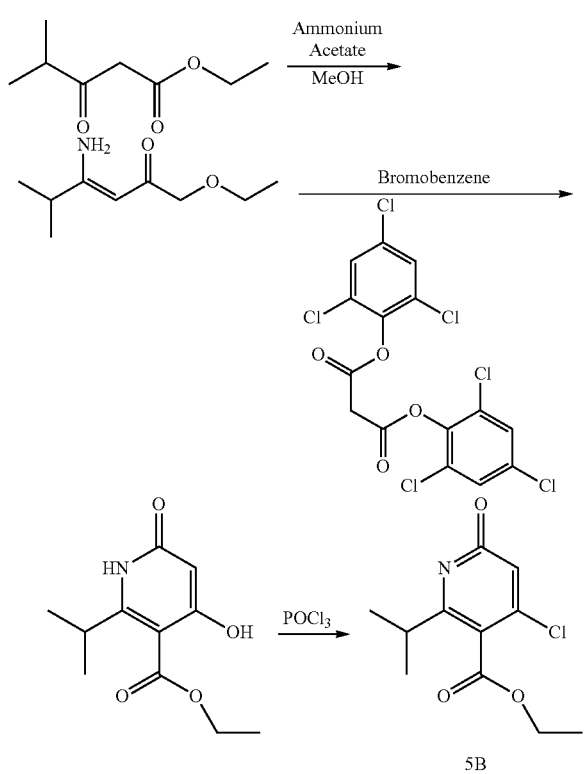

Step 1: Ethyl 3-amino-4-methylpent-2-enoate

Ethyl 4-methyl-3-oxopentanoate (4.5 mL, 27.9 mmol) and ammonium acetate (12.05 g, 156 mmol) in MeOH (50 mL) was stirred at room temperature overnight. The solvent was evaporated in vacuo and chloroform (50 mL) was added. The resulting solid was filtered and washed with chloroform (2×25 mL). The combined filtrate was washed with water (30 mL) and brine (30 mL), dried over $Na_2SO_4$, and concentrated in vacuo to give ethyl 3-amino-4-methylpent-2-enoate, which was carried onto the next step without further purification. MS ESI calc'd. for $C_8H_{15}NO_2$ $[M+1]^+$ 158. found 158.

Step 2: Ethyl 4-hydroxy-2-isopropyl-6-oxo-1,6-dihydropyridine-3-carboxylate

Malonic acid bis(2,4,6-trichlorophenyl) ester (1.4 g, 3.05 mmol) and ethyl 3-amino-4-methylpent-2-enoate (480 mg, 3.05 mmol) in bromobenzene (5 mL) was heated at 155° C. for 45 min. The reaction mixture was diluted with EtOAc/$Et_2O$ then concentrated in vacuo until a solid crashed out of solution. The solid was collected and rinsed with $Et_2O$ and ethyl acetate. The filtrate was concentrated in vacuo, diluted with DCM, and purified by flash chromatography (12-100% EtOAc/isohexane). The fractions containing pure product were concentrated in vacuo and the resulting solid triturated with $Et_2O$ and combined with the first batch of solid to give ethyl 4-hydroxy-2-isopropyl-6-oxo-1,6-dihydropyridine-3-carboxylate. MS ESI calc'd. for $C_{11}H_{15}NO_4$ $[M+1]^+$ 226. found 226.

Step 3: Ethyl 4,6-dichloro-2-isopropylnicotinate

Ethyl 4-hydroxy-2-isopropyl-6-oxo-1,6-dihydropyridine-3-carboxylate (385 mg, 1.711 mmol) and $POCl_3$ (1.0 mL, 10.73 mmol) were heated to 140° C. for 2 h. The reaction mixture was concentrated in vacuo. The residue was taken up in a small amount of ethyl acetate and an ice-water mixture was added. The mixture was neutralized with sodium carbonate while stirring until pH was basic. The aqueous solution was extracted with ethyl acetate, dried over sodium sulfate, and concentrated in vacuo to give crude ethyl 4,6-dichloro-2-isopropylnicotinate, which was carried onto the next step without further purification. MS ESI calc'd. for $C_{11}H_{13}Cl_2NO_2$ $[M+1]^+$ 262. found 262.

Intermediates 6B-7B (Table 1) were prepared following similar procedures described for Intermediate 5B using the appropriate beta keto ester, which can be achieved by those of ordinary skill in the art of organic synthesis.

TABLE 1

| Intermediate | Structure | IUPAC Name | Exact Mass [M + H]+ |
|---|---|---|---|
| 6B | 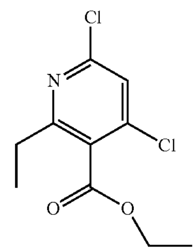 | ethyl 4,6-dichloro-2-ethylnicotinate | Calc'd 248, found 248 |
| 7B | 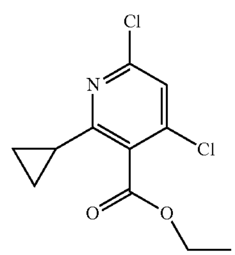 [SMILES: CCOC(=O)c1c(Cl)cc(Cl)nc1C1CC1] | ethyl 4,6-dichloro-2-cyclopropylnicotinate | Calc'd 260, found 260 |

Intermediates 8B-10B (Table 2) were prepared following similar procedures described for Intermediate 4B using the appropriate dichloropyridine carboxylate (Intermediates 5B-7B), which can be achieved by those of ordinary skill in the art of organic synthesis.

TABLE 2

| Intermediate | Structure | IUPAC Name | Exact Mass [M + H]+ |
|---|---|---|---|
| 8B | 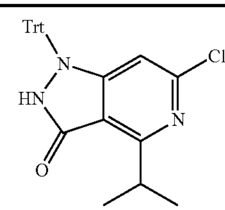 | 6-chloro-4-isopropyl-1-trityl-1H-pyrazolo[4,3-c]pyridin-3(2H)-one | Calc'd 454, found 454 |
| 9B | 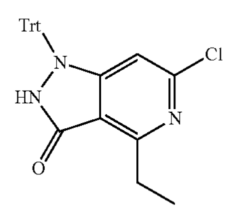 | 6-chloro-4-ethyl-1-trityl-1H-pyrazolo[4,3-c]pyridin-3(2H)-one | Calc'd 440, found 440 |

TABLE 2-continued

| Intermediate | Structure | IUPAC Name | Exact Mass [M + H]+ |
|---|---|---|---|
| 10B | 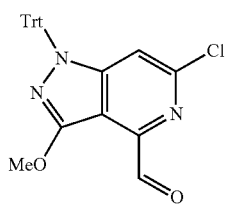 | 6-chloro-4-cyclopropyl-1-trityl-1H-pyrazolo[4,3-c]pyridin-3(2H)-one | Calc'd 452, found 452 |

Intermediate 11B

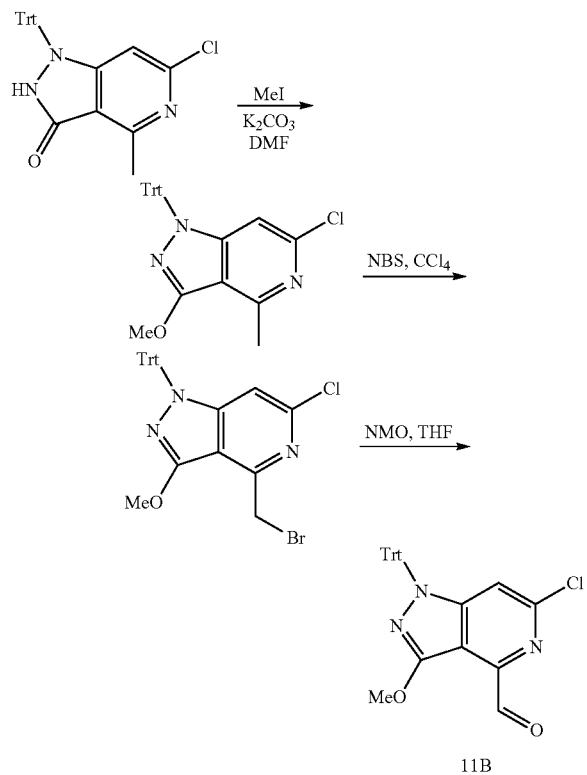

6-Chloro-3-methoxy-1-trityl-1H-pyrazolo[4,3-c]pyridine-4-carbaldehyde

6-Chloro-3-methoxy-1-trityl-1H-pyrazolo[4,3-c]pyridine-4-carbaldehyde was synthesized according to the following scheme and procedures.

Step 1: 6-Chloro-3-methoxy-4-methyl-1-trityl-1H-pyrazolo[4,3-c]pyridine

A solution of 6-chloro-4-methyl-1-trityl-1H-pyrazolo[4,3-c]pyridin-3(2H)-one (Intermediate 4B; 406 mg, 0.953 mmol) in DMF (3 mL) was charged with potassium carbonate (348 mg, 2.52 mmol) and methyl iodide (0.089 mL, 1.430 mmol) and stirred at room temperature for 1 h. The reaction mixture was diluted with water, filtered, and dried under vacuum to give 6-chloro-3-methoxy-4-methyl-1-trityl-1H-pyrazolo[4,3-c]pyridine, which was carried onto the next step without further purification. MS ESI calc'd. for $C_{27}H_{22}ClN_3O$ [M+1]$^+$ 440. found 440.

Step 2: 4-(Bromomethyl)-6-chloro-3-methoxy-1-trityl-1H-pyrazolo[4,3-c]pyridine 6-Chloro-3-methoxy-4-methyl-1-trityl-1H-pyrazolo[4,3-c]pyridine (1.5 g, 3.41 mmol) was dissolved in $CCl_4$ (10 mL), charged with NBS (637 mg, 3.58 mmol) and AIBN (56.0 mg, 0.341 mmol), and heated to 70° C. overnight. The reaction was diluted with DCM (10 mL) and purified by flash chromatography (5-25% EtOAc/hexanes) to give 4-(bromomethyl)-6-chloro-3-methoxy-1-trityl-1H-pyrazolo[4,3-c]pyridine. MS ESI calc'd. for $C_{27}H_{21}BrClN_3O$ [M+1]$^+$ 519. found 519.

Step 3: 6-Chloro-3-methoxy-1-trityl-1H-pyrazolo[4,3-c]pyridine-4-carbaldehyde 4-(Bromomethyl)-6-chloro-3-methoxy-1-trityl-1H-pyrazolo[4,3-c]pyridine (165 mg, 0.318 mmol) was dissolved in THF (4 mL), charged with NMO (112 mg, 0.954 mmol), and stirred at room temperature overnight. The reaction mixture was concentrated in vacuo and the residue was purified by flash chromatography (10-50% EtOAc/hexanes) to give 6-chloro-3-methoxy-1-trityl-1H-pyrazolo[4,3-c]pyridine-4-carbaldehyde. $^1$H NMR (500 MHz, CDCl$_3$) δ 10.41 (s, 1H), 7.31 (m, 10H), 7.20 (m, 5H), 6.08 (s, 1H), 4.00 (s, 3H).

Alternatively, intermediate 11B was synthesized directly in one step from 6-chloro-3-methoxy-4-methyl-1-trityl-1H-pyrazolo[4,3-c]pyridine (4B):

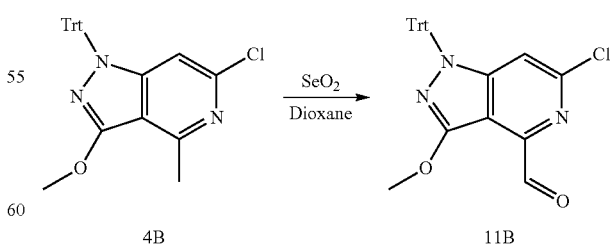

6-chloro-3-methoxy-4-methyl-1-trityl-1H-pyrazolo[4,3-c]pyridine (25 g, 45.5 mmol) was charged with 1,4-dioxane (200 ml) and selenium dioxide (15.13 g, 136 mmol) and heated to reflux overnight. The white slurry eventually dissolved to a dark yellow solution. TLC and LC/MS showed good conversion to product, with some SM left. The reaction was filtered through celite, washed with DCM and purified on silica gel, 10-50% EtOAc/hexanes to provide 6-chloro-3-methoxy-1-trityl-1H-pyrazolo[4,3-c]pyridine-4-carbaldehyde (15.7 g, 34.6 mmol, 76% yield).

Intermediate 12B

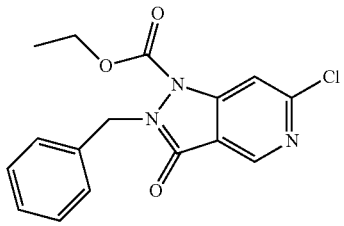

Ethyl 2-benzyl-6-chloro-3-oxo-2,3-dihydro-1H-pyrazolo[4,3-c]pyridine-1-carboxylate Ethyl 2-benzyl-6-chloro-3-oxo-2,3-dihydro-1H-pyrazolo [4,3-c]pyridine-1-carboxylate was synthesized according to the following scheme and procedure.

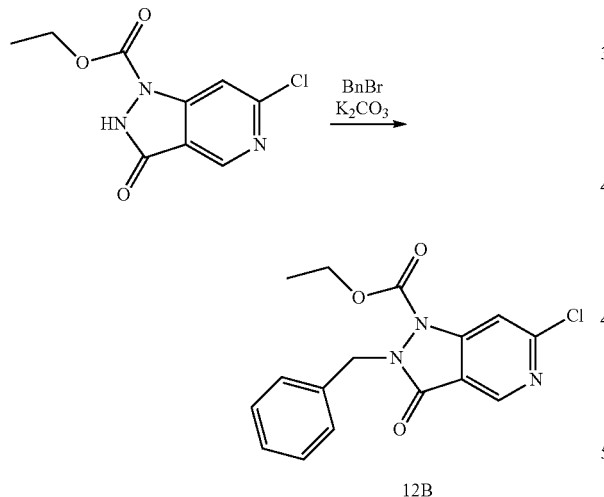

12B

Ethyl 6-chloro-3-oxo-2,3-dihydro-1H-pyrazolo[4,3-c]pyridine-1-carboxylate (Intermediate 1B; 582 mg, 2.41 mmol), potassium carbonate (666 mg, 4.82 mmol), and benzyl bromide (0.345 mL, 2.9 mmol) were stirred in DMF (10 mL) at room temperature for 16 h. Water was added and the products extracted into EtOAc (×2). The combined organic extracts were washed with brine, dried over Na$_2$SO$_4$, filtered, and concentrated in vacuo. Purification of the residue by flash chromatography (6-50% EtOAc-hexanes) gave ethyl 2-benzyl-6-chloro-3-oxo-2,3-dihydro-1H-pyrazolo[4,3-c]pyridine-1-carboxylate. MS ESI calc'd. for C$_{16}$H$_{14}$ClN$_3$O$_3$ [M+1]$^+$ 332. found 332. Ethyl 3-(benzyloxy)-6-chloro-1H-pyrazdo[4,3-c]pyridine-1-carboxylate was also obtained. MS ESI calc'd. for C$_{16}$H$_{14}$ClN$_3$O$_3$ [M+1]$^+$ 332. found 332.

Intermediate 13B

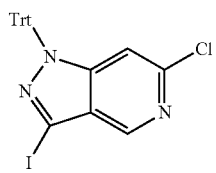

6-Chloro-3-iodo-1-trityl-1H-pyrazolo[4,3-c]pyridine

6-Chloro-3-iodo-1-trityl-1H-pyrazolo[4,3-c]pyridine was synthesized according to the following scheme and procedures.

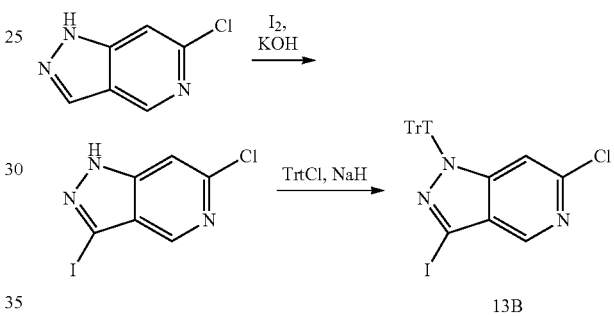

13B

Step 1: 6-Chloro-3-iodo-1H-pyrazolo[4,3-c]pyridine

A flask was charged with 6-chloro-1H-pyrazolo[4,3-c]pyridine (3.0 g, 19.54 mmol), iodine (13.11 g, 51.7 mmol), KOH (3.29 g, 58.6 mmol), and DMF (60 mL). The mixture was heated at 40° C. for 16 h and then additional iodine (7.8 g, 30.7 mmol) and KOH (1.6 g, 28.4 mmol) were added. The mixture was heated at 70° C. for 3 h then quenched with 1 N Na$_2$S$_2$O$_3$ and extracted with EtOAc. The organic phase was washed with water, brine, and dried over Na$_2$SO$_4$. After evaporation of volatiles DCM was added. A solid precipitated and was collected by filtration to yield 6-chloro-3-iodo-1H-pyrazolo[4,3-c]pyridine, which was carried onto the next step without further purification. MS ESI calc'd. for C$_6$H$_4$ClIN$_3$ [M+1]$^+$ 280. found 280.

Step 2: 6-Chloro-3-iodo-1-trityl-1H-pyrazolo[4,3-c] pyridine

A solution of 6-chloro-3-iodo-1H-pyrazolo[4,3-c]pyridine (1.874 g, 6.71 mmol) in THF (20 mL) was treated with NaH (60% in mineral oil; 0.402 g, 10.06 mmol) at 0° C. and the mixture was stirred for 50 min. Trityl chloride (2.244 g, 8.05 mmol) was added at 0° C. and the mixture was stirred for 16 h at room temperature, quenched with saturated NH$_4$Cl, and extracted with EtOAc. The organic phase was washed with water, brine, dried over Na$_2$SO$_4$, and concentrated in vacuo. The residue was purified via flash chromatography (0-10%

EtOAc-hexanes) to yield 6-chloro-3-iodo-1-trityl-1H-pyrazolo[4,3-c]pyridine. MS ESI calc'd. for $C_{25}H_{18}ClIN_3$ $[M+1]^+$ 522. found 522.

Intermediate 14B

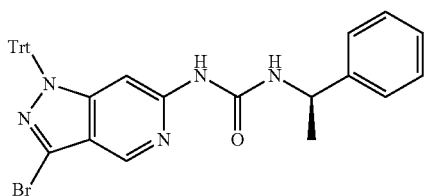

(R)-1-(3-Bromo-1-trityl-1H-pyrazolo[4,3-c]pyridin-6-yl)-3-(1-phenylethyl)urea (R)-1-(3-Bromo-1-trityl-1H-pyrazolo[4,3-c]pyridin-6-yl)-3-(1-phenylethyl)urea was synthesized according to the following scheme and procedures.

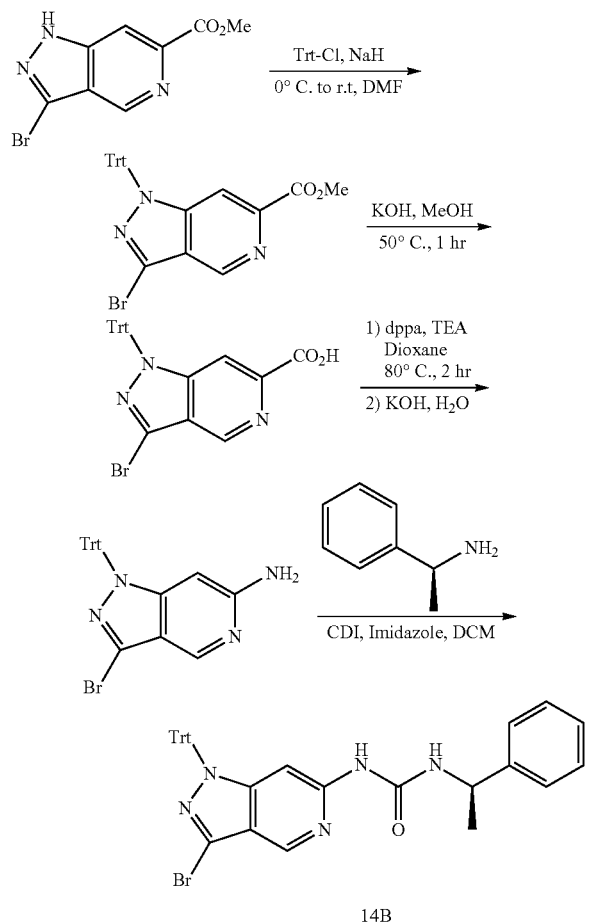

14B

Step 1: Methyl 3-bromo-1-trityl-1H-pyrazolo[4,3-c]pyridine-6-carboxylate

At 0° C., NaH (60% in mineral oil, 1.172 g, 29.3 mmol) was added in portions to a suspension of methyl 3-bromo-1H-pyrazolo[4,3-c]pyridine-6-carboxylate (5.0 g, 19.53 mmol) in DMF (50 mL). The reaction mixture was stirred at 0° C. for 30 min, then a solution of triphenylmethyl chloride (6.53 g, 23.43 mmol) in DMF (50 mL) was added drop-wise. The reaction mixture was slowly warmed to room temperature overnight, quenched with $H_2O$, and extracted with EtOAc. The combined organic layers were washed with brine, dried over $Na_2SO_4$, filtered, and concentrated in vacuo. The residue was purified by flash chromatography (20% EtOAc/hexanes) to give methyl 3-bromo-1-trityl-1H-pyrazolo[4,3-c]pyridine-6-carboxylate. MS ESI calc'd. for $C_{27}H_{21}BrN_3O_2$ $[M+H]^+$ 498. found 498.

Step 2: 3-Bromo-1-trityl-1H-pyrazolo[4,3-c]pyridine-6-carboxylic acid

To a suspension of methyl 3-bromo-1-trityl-1H-pyrazolo[4,3-c]pyridine-6-carboxylate (6.0 g, 12.04 mmol) in MeOH (60 mL) was added KOH (1 N, 42.1 mL, 42.1 mmol). The reaction mixture was heated to 50° C. for 1 h. After cooling down to room temperature, 1 N HCl was added until the pH of the reaction mixture reached 4. The solid was collected by filtration and washed with $H_2O$ to afford 3-bromo-1-trityl-1H-pyrazolo[4,3-c]pyridine-6-carboxylic acid. MS ESI calc'd. for $C_{26}H_{19}BrN_3O_2$ $[M+H]^+$ 484. found 484.

Step 3: 3-Bromo-1-trityl-1H-pyrazolo[4,3-c]pyridin-6-amine

To a suspension of 3-bromo-1-trityl-1H-pyrazolo[4,3-c]pyridine-6-carboxylic acid (1.95 g, 4.03 mmol) and diphenylphosphoryl azide (1.047 mL, 4.83 mmol) in 1,4-dioxane (19.50 mL) was added a mixture of TEA (0.842 mL, 6.04 mmol) in 1,4-dioxane (10 mL) drop-wise over 5 min. The reaction mixture was heated to 80° C. for 2 h. A solution of KOH (1 N, 20.13 mL, 20.13 mmol) was added at 80° C. The reaction mixture was stirred overnight. Room temperature was obtained and the reaction mixture was extracted with EtOAc. The combined organic layers were washed with brine, dried over $Na_2SO_4$, filtered, and concentrated in vacuo. The residue was purified by flash chromatography (50% EtOAc/hexanes) to give 3-bromo-1-trityl-1H-pyrazolo[4,3-c]pyridin-6-amine MS ESI calc'd. for $C_{25}H_{20}BrN_4$ $[M+H]^+$ 455. found 455.

Step 4: (R)-1-(3-Bromo-1-trityl-1H-pyrazolo[4,3-c]pyridin-6-yl)-3-(1-phenylethyl)urea A flask was charged with 3-bromo-1-trityl-1H-pyrazolo[4,3-c]pyridin-6-amine (1.00 g, 2.196 mmol), CDI (1.068 g, 6.59 mmol), and imidazole (0.748 g, 10.98 mmol). DCM (10 mL) was added and the reaction was stirred at room temperature overnight. (R)-Methyl-benzylamine (0.532 g, 4.39 mmol) was added and the reaction was stirred at room temperature for 1 h. The reaction was diluted with EtOAc and washed with 1 N NaOH. The combined organic layers were dried over magnesium sulfate, filtered, and concentrated in vacuo. Purification of the residue by flash chromatography (0-50% DCM/EtOAc) gave (R)-1-(3-bromo-1-trityl-1H-pyrazolo[4,3-c]pyridin-6-yl)-3-(1-phenylethyl)urea. MS ESI calc'd. for $C_{34}H_{28}BrN_5O$ $[M+H]^+$ 602. found 602.

Intermediate 15B

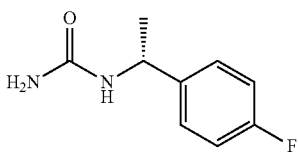

(R)-1-(1-(4-Fluorophenyl)ethyl)urea (R)-1-(1-(4-Fluorophenyl)ethyl)urea was prepared according to the following scheme and procedure.

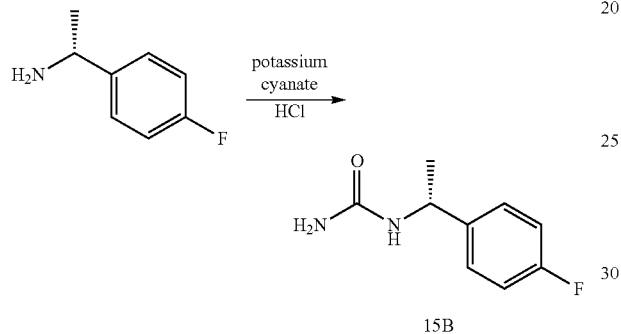

15B (R)-1-(4-Fluorophenyl)ethanamine (5.15 g, 37.0 mmol) was taken up in HCl (2N, 40 mL) and potassium cyanate (15.01 g, 185 mmol) was added. The mixture was stirred at 80° C. for 3 h. Upon cooling to room temperature, a precipitate formed which was collected by filtration and washed with water. The solid was partitioned between water and EtOAc, and the aqueous phase extracted once more with EtOAc. The combined organic extracts were dried over $Na_2SO_4$, filtered, and concentrated in vacuo to give (R)-1-(1-(4-fluorophenyl) ethyl)urea), without further purification. MS ESI calc'd. for $C_9H_{11}FN_2O$ [M+1]$^+$ 183. found 183.

Intermediate 16B

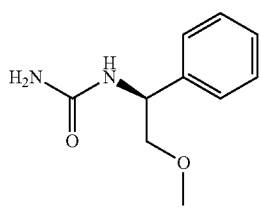

(S)-1-(2-Methoxy-1-phenylethyl)urea (S)-1-(2-Methoxy-1-phenylethyl)urea was prepared according to the following scheme and procedure.

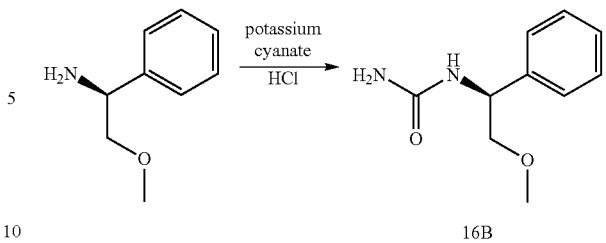

16B (S)-2-Methoxy-1-phenylethanamine (5.6 g, 37.0 mmol) and potassium cyanate (8.12 g, 100 mmol) were taken up in HCl (1 N, 40 mL, 40.0 mmol) and water (40 mL). The reaction mixture was heated to 100° C. for 3 h. Room temperature was attained, water was added, and the products extracted into EtOAc (×3) followed by 10% MeOH-DCM (×2). The combined organic extracts were washed with brine, dried over $Na_2SO_4$, filtered, and concentrated in vacuo. The residue was triturated with $Et_2O$ to give (S)-1-(2-methoxy-1-phenylethyl)urea. MS ESI calc'd. for $C_{10}H_{14}N_2O_2$ [M+1]$^+$ 195. found 195.

Intermediate 17B

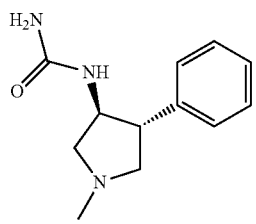 [SMILES: CN1C[C@@H](NC(N)=O)[C@H](c2ccccc2)C1]

1-((3S,4R)-1-Methyl-4-phenylpyrrolidin-3-yl)urea 1-((3S,4R)-1-Methyl-4-phenylpyrrolidin-3-yl)urea was prepared according to the following scheme and procedures.

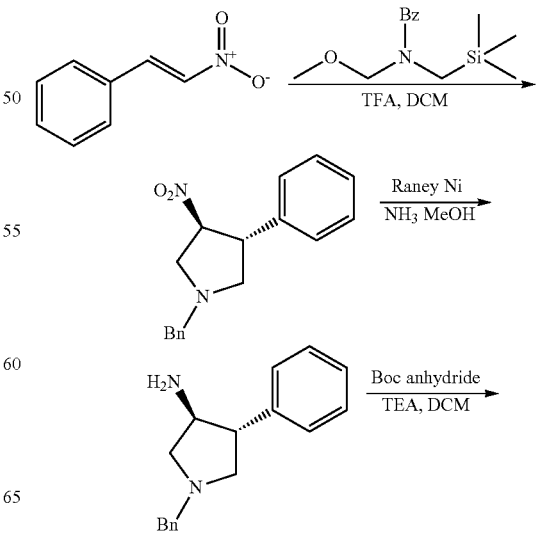

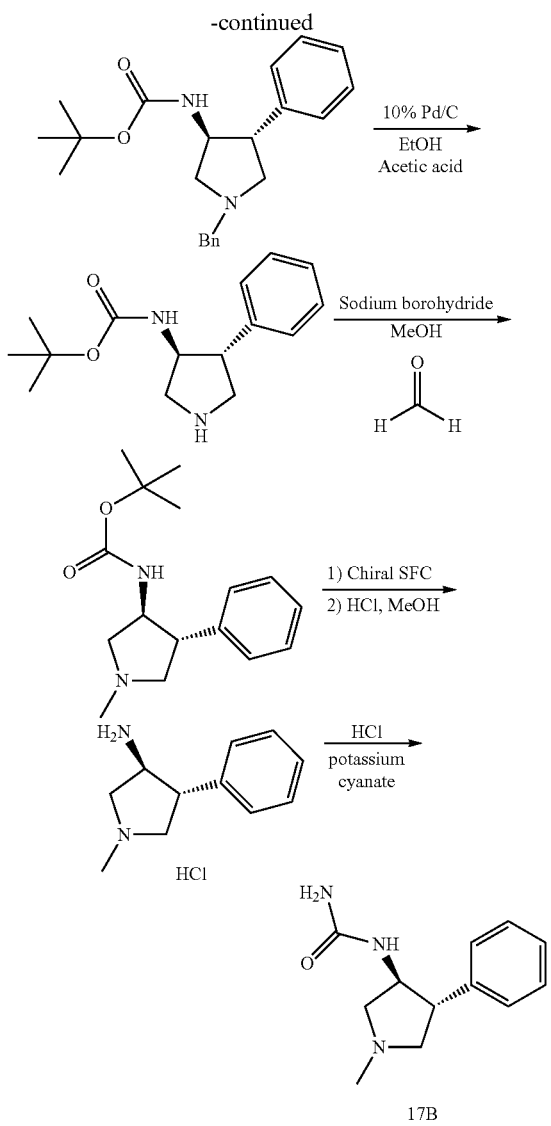

Step 1: (3S and R,4R and S)-1-Benzyl-3-nitro-4-phenylpyrrolidine

To a solution of (E)-(2-nitrovinyl)benzene (110 g, 0.738 mol) and TFA (8.42 g, 0.073 mol) in DCM (500 mL) was added N-benzyl-1-methoxy-N-((trimethylsilyl)methyl)methan-amine (351.4 g, 1.476 mol) in DCM (500 mL) drop-wise at 0° C. for a period of 30 min. Then the reaction mixture was stirred at room temperature for 48 h. After completion of the reaction, the mixture was concentrated in vacuo, dissolved in water, and extracted into EtOAc (×2, 1.0 L). The organic layer was separated, dried over anhydrous sodium sulfate, and concentrated in vacuo. The residue was purified via flash chromatography (20-80% petroleum ether/EtOAc) to afford (3S and R,4R and S)-1-benzyl-3-nitro-4-phenylpyrrolidine. MS ESI calc'd. For $C_{17}H_{18}N_2O_2$ [M+1]$^+$ 283. found 283.

Step 2: (3S and R,4R and S)-1-Benzyl-4-phenylpyrrolidin-3-amine

To a stirred solution of (3S and R,4R and S)-1-benzyl-3-nitro-4-phenylpyrrolidine (100 g, 0.354 mol) in methanolic ammonia (1 L) was added Raney Ni (20 g) at room temperature in a 2.0 L hydrogenation flask. The reaction was hydrogenated at 100 psi for 12 h at room temperature. After completion of the reaction, the mixture was filtered through Celite and the filtrate was concentrated in vacuo to afford (3S and R,4R and S)-1-benzyl-4-phenylpyrrolidin-3-amine, which was carried onto the next step without further purification. MS ESI calc'd. For $C_{12}H_{20}N_2$ [M+1]$^+$ 253. found 253.

Step 3: tert-Butyl((3S and R,4R and S)-1-benzyl-4-phenylpyrrolidin-3-yl)carbamate To a stirred solution of (3S and R,4R and S)-1-benzyl-4-phenylpyrrolidin-3-amine (120.5 g, 0.476 mol) in DCM (1.2 L) was added triethylamine (48.1 g, 0.476 mol) and the reaction mixture was cooled to 0° C. Boc anhydride (103.84 g, 0.476 mol) was added drop-wise over a period of 30 min at 0° C. The resulting reaction mixture was stirred at room temperature for 12 h. After completion of the reaction, the mixture was diluted with water (3.0 L), the separated organic layer was dried over anhydrous sodium sulfate, and concentrated in vacuo to afford tert-butyl((3S and R,4R and S)-1-benzyl-4-phenylpyrrolidin-3-yl)carbamate, which was carried onto the next step without further purification. MS ESI calc'd. For $C_{22}H_{28}N_2O_2$ [M+1]$^+$ 353. found 353.

Step 4: tert-Butyl((3S and R,4R and S)-4-phenylpyrrolidin-3-yl)carbamate

To a stirred solution of ((3S and R,4R and S)-1-benzyl-4-phenylpyrrolidin-3-yl)carbamate (115 g, 0.325 mol) and acetic acid (5 mL, 0.097 mol) in ethanol (1.5 L) was added 10% Pd—C (20 g) in a hydrogenation flask. The reaction was hydrogenated at 150 psi at 50° C. for 12 h. After completion of the reaction, the mixture was filtered through Celite and the filtrate was concentrated in vacuo. The crude compound was triturated with a minimum amount of EtOAc and dried under vacuum to afford tert-butyl((3S and R,4R and S)-4-phenylpyrrolidin-3-yl)carbamate. MS ESI calc'd. For $C_{15}H_{22}N_2O_2$ [M+1]$^+$ 263. found 263.

Step 5: tert-Butyl((3R and S, 4S and R)-1-methyl-4-phenylpyrrolidin-3-yl)carbamate tert-Butyl((3R and S, 4S and R)-4-phenylpyrrolidin-3-yl)carbamate (1 g, 3.81 mmol) and formaldehyde (0.795 mL, 10.67 mmol) were dissolved in MeOH (15.25 mL) and treated with sodium borohydride (0.433 g, 11.44 mmol) at 0° C. The reaction was warmed to room temperature and stirred overnight. The crude reaction mixture was diluted with EtOAc and washed with water and brine. The aqueous layer was extracted with EtOAc and the combined organic layers were dried over sodium sulfate, filtered, and concentrated in vacuo to afford tert-butyl((3R and S, 4S and R)-1-methyl-4-phenylpyrrolidin-3-yl)carbamate, which was carried onto the next step without further purification. MS ESI calc'd. For $C_{16}H_{24}N_2O_2$ [M+1]$^+$ 277. found 277.

Step 6: tert-Butyl((3S,4R)-1-methyl-4-phenylpyrrolidin-3-yl)carbamate and tert-Butyl((3R,4S)-1-methyl-4-phenylpyrrolidin-3-yl)carbamate The enantiomers of tert-butyl((3S and R,4R and S)-1-methyl-4-phenylpyrrolidin-3-yl)carbamate (1.22 g, 4.4 mmol) were separated by SFC (Berger Multigram II SFC, column: Chiral Technology AD-H 2.1×25 cm, 5 uM, mobile phase: 5% to 95% Ethanol+0.25% dimethyl ethylamine in $CO_{2(l)}$, flow rate: 70 mL/min, 9 min run time). The fractions were collected and the solvent evaporated in vacuo to afford tert-butyl((3S,4R)-1-methyl-4-phenylpyrrolidin-3-yl)carbamate and tert-butyl((3R,4S)-1-methyl-4-phenylpyrrolidin-3-yl) carbamate. MS ESI calc'd. For $C_{16}H_{24}N_2O_2$ $[M+1]^+$ 277. found 277. MS ESI calc'd. For $C_{16}H_{24}N_2O_2$ $[M+1]^+$ 277. found 277.

Step 7: (3S,4R)-1-Methyl-4-phenylpyrrolidin-3-amine hydrochloride tert-Butyl((3S,4R)-1-methyl-4-phenylpyrrolidin-3-yl)carbamate (521 mg, 1.885 mmol) was dissolved in methanolic HCl, (3 N, 10 mL) and heated to 50° C. for 2 h. The reaction mixture was concentrated in vacuo to afford (3S,4R)-1-methyl-4-phenylpyrrolidin-3-amine hydrochloride, which was carried onto the next step without further purification. MS ESI calc'd. For $C_{11}H_{16}N_2$ $[M+1]^+$ 177. found 177.

Step 8: 1-((3S,4R)-1-Methyl-4-phenylpyrrolidin-3-yl)urea (3S,4R)-1-Methyl-4-phenylpyrrolidin-3-amine hydrochloride (556 mg, 2.231 mmol) was dissolved in HCl (2 N, 4 mL) and potassium cyanate (905 mg, 11.16 mmol) was added. The reaction mixture was stirred at 80° C. for 3 h. The reaction was quenched with sat. sodium bicarbonate and extracted with EtOAc followed by 3:1 chloroform/IPA. The combined organic layers were dried over sodium sulfate, filtered, and concentrated in vacuo to give 1-((3S,4R)-1-methyl-4-phenylpyrrolidin-3-yl)urea, which was carried onto the next step without further purification. MS ESI calc'd. For $C_{12}H_{17}N_3O$ $[M+1]^+$ 220. found 220.

Intermediate 18B

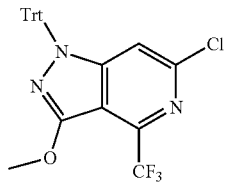

6-chloro-3-methoxy-4-(trifluoromethyl)-1-trityl-1H-pyrazolo[4,3-c]pyridine

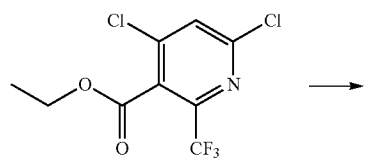

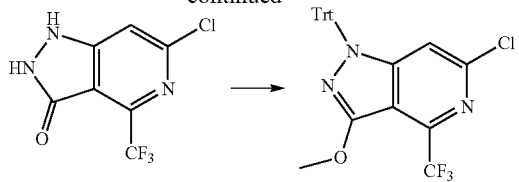

Step 1: ethyl 4,6-dichloro-2-(trifluoromethyl)nicotinate

A solution of ethyl 4,6-dihydroxy-2-(trifluoromethyl) nicotinate (1.365 g, 5.43 mmol) in DMF (1.7 ml, 21.96 mmol) was charged with $POCl_3$ (2.1 ml, 22.53 mmol) dropwise. An exotherm was observed. Sealed and heated to 90° C. for 15.5 hr, then cooled to RT. Poured into a slurry of ice/1N NaOH and extracted with $Et_2O$ (3×). Washed organics with brine, dried over $MgSO_4$, filtered and concentrated in vacuo. Purified via flash chromatography (0-50% EtOAc/Hex) to provide ethyl 4,6-dichloro-2-(trifluoromethyl)nicotinate. MS: $[M+H]^+$ m/z 288.

Step 2: 6-chloro-4-(trifluoromethyl)-1H-pyrazolo[4,3-c]pyridin-3(2H)-one

A solution of methyl 4,6-dichloro-2-(trifluoromethyl) nicotinate (535.9 mg, 1.956 mmol) in DMF (2 ml) was charged with hydrazine hydrate (190 μL, 3.92 mmol) and heated to 150° C. for 30 min under microwave irradiation. Concentrated in vacuo and washed residue with DCM. Purified via flash chromatography (0-20% MeOH/DCM) to provide 6-chloro-4-(trifluoromethyl)-1H-pyrazolo[4,3-c]pyridin-3(2H)-one MS: $[M+H]^+$ m/z 238.

Step 3: 6-chloro-3-methoxy-4-(trifluoromethyl)-1-trityl-1H-pyrazolo[4,3-c]pyridine A solution of 6-chloro-4-(trifluoromethyl)-1H-pyrazolo [4,3-c]pyridin-3(2H)-one (290 mg, 1.221 mmol) in DMF (5 ml) was charged with trityl chloride (369 mg, 1.324 mmol) followed by sodium hydride (58 mg, 1.450 mmol). Stirred at RT for 2.5 hr. Added potassium carbonate (0.53 g, 3.83 mmol) and methyl iodide (0.20 ml, 3.20 mmol) then stirred at RT for 3 hr. Quenched with water and filtered to remove ppt, which was dried under vacuum to provide crude 6-chloro-3-methoxy-4-(trifluoromethyl)-1-trityl-1H-pyrazolo[4,3-c]pyridine, used as-is. MS: $[M+H]^+$ m/z 494.

Intermediate 19B

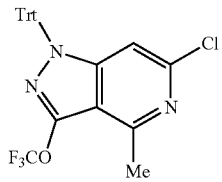

6-chloro-4-methyl-3-(trifluoromethoxy)-1-trityl-1H-pyrazolo[4,3-c]pyridine

A mixture of 6-chloro-4-methyl-1-trityl-1H-pyrazolo[4,3-c]pyridin-3(2H)-one (Intermediate 4B, 207.1 mg, 0.486 mmol), potassium carbonate (217.6 mg, 1.574 mmol) and 1-trifluoromethyl-1,2-benziodoxol-3-(1H-one (227.3 mg, 0.719 mmol) in DMF (2 ml) was stirred at RT for 16.5 hr, then heated to 60° C. for 5 hr. Added water and filtered to collect precipitate, which was purified via flash chromatography (0-100% EtOAc/Hex) to provide 6-chloro-4-methyl-3-(trifluoromethoxy)-1-trityl-1H-pyrazolo[4,3-c]pyridine. MS: [M+H]$^+$ m/z 494.

Intermediate 20B

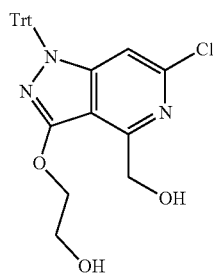

2-((6-chloro-4-(hydroxymethyl)-1-trityl-1H-pyrazolo[4,3-c]pyridin-3-yl)oxy)ethanol

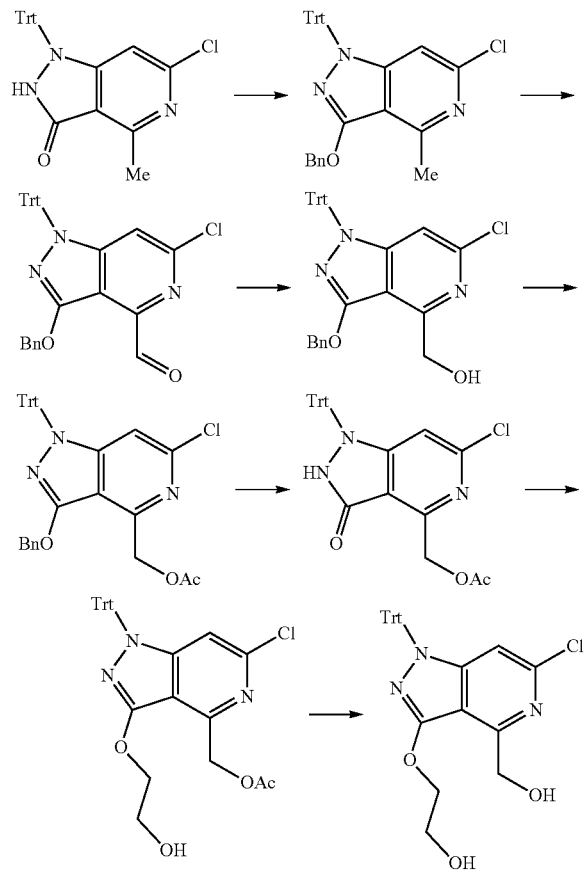

Step 1: 3-(benzyloxy)-6-chloro-4-methyl-1-trityl-1H-pyrazolo[4,3-c]pyridine

A mixture of 6-chloro-4-methyl-1-trityl-1H-pyrazolo[4,3-c]pyridin-3(2H)-one (16.10 g, 37.8 mmol, Intermediate 4B), potassium carbonate (17.75 g, 128 mmol) and benzyl bromide (6.3 ml, 53.0 mmol) in DMF (100 ml) was stirred at RT for 2 hr. Quenched with water and extracted into ether. Washed organics with brine, dried over MgSO$_4$, filtered, concentrated in vacuo and triturated with hexanes to provide 3-(benzyloxy)-6-chloro-4-methyl-1-trityl-1H-pyrazolo[4,3-c]pyridine. MS: [M+H]$^+$ m/z 516.

Step 2: 3-(benzyloxy)-6-chloro-1-trityl-1H-pyrazolo[4,3-c]pyridine-4-carbaldehyde A mixture of 3-(benzyloxy)-6-chloro-4-methyl-1-trityl-1H-pyrazolo[4,3-c]pyridine (18.72 g, 36.3 mmol) and selenium dioxide (14.42 g, 130 mmol) in dioxane (200 ml) was heated to 100° C. with attached reflux condenser for 16 hr. Added more selenium dioxide (3.35 g, 30.2 mmol) and continued to heat to 100° C. for 4.5 hr. Cooled to RT, filtered through celite, eluted with EtOAc, concentrated filtated in vacuo, took up residue in DCM, filtered through celite, eluted with DCM, concentrated filtrate in vacuo and purified via flash chromatography (0-100% EtOAc/Hex) to provide 3-(benzyloxy)-6-chloro-1-trityl-1H-pyrazolo[4,3-c]pyridine-4-carbaldehyde. MS: [M+H]$^+$ m/z 530.

Step 3: (3-(benzyloxy)-6-chloro-1-trityl-1H-pyrazolo[4,3-c]pyridin-4-yl)methanol A solution of 3-(benzyloxy)-6-chloro-1-trityl-1H-pyrazolo[4,3-c]pyridine-4-carbaldehyde (2.8884 g, 5.45 mmol) in DCM (10 ml) was charged with MeOH (20 ml) and then sodium borohydride (0.309 g, 8.17 mmol). Stirred at RT for 2 hr. Quenched with water and extracted into DCM. Dried organics over MgSO4, filtered, concentrated in vacuo and used as-is. MS: [M+H]$^+$ m/z 532.

Step 4: (3-(benzyloxy)-6-chloro-1-trityl-1H-pyrazolo[4,3-c]pyridin-4-yl)methyl acetate A solution of (3-(benzyloxy)-6-chloro-1-trityl-1H-pyrazolo[4,3-c]pyridin-4-yl)methanol (2.443 g, 4.59 mmol) and DIPEA (3.0 ml, 17.18 mmol) in DCM (25 ml) was charged with AcCl (0.70 ml, 9.84 mmol). Stirred at RT for 45 min. Diluted with DCM, washed organics with 2N HCl, dried over MgSO4, filtered, concentrated in vacuo and obtained (3-(benzyloxy)-6-chloro-1-trityl-1H-pyrazolo[4,3-c]pyridin-4-yl)methyl. MS: [M+H]$^+$ m/z 574.

Step 5: (6-chloro-3-oxo-1-trityl-2,3-dihydro-1H-pyrazolo[4,3-c]pyridin-4-yl)methyl acetate A mixture of (3-(benzyloxy)-6-chloro-1-trityl-1H-pyrazolo[4,3-c]pyridin-4-yl)methyl acetate (2.87 g, 5.00 mmol) in DCM (10 ml) and MeOH (50 ml) was evacuated and backfilled 3× with argon, charged with Pd/C (0.532 g, 0.500 mmol), evacuated and backfilled 3× with H2, then stirred at RT under a balloon of H2 for 1 hr. Filtered through celite, eluted with EtOAc and concentrated filtrate in vacuo to obtain (6-chloro-3-oxo-1-trityl-2,3-dihydro-1H-pyrazolo[4,3-c]pyridin-4-yl)methyl acetate. MS: [M+H]$^+$ m/z 484.

Step 6: (6-chloro-3-(2-hydroxyethoxy)-1-trityl-1H-pyrazolo[4,3-c]pyridin-4-yl)methyl acetate A mixture of (6-chloro-3-oxo-1-trityl-2,3-dihydro-1H-pyrazolo[4,3-c]pyridin-4-yl)methyl acetate (504.6 mg, 1.043 mmol) and potassium carbonate (558.3 mg, 4.04 mmol) in DMF (10 ml) was charged with 2-bromoethanol (0.30 ml, 4.25 mmol) and stirred at RT for 6 hr. Quenched with water and extracted 3× with Et2O. Washed organics with brine, dried over MgSO4, filtered and concentrated in vacuo. Purified via flash chromatography (0-100% EtOAc/Hex) to provide (6-chloro-3-(2-hydroxyethoxy)-1-trityl-1H-pyrazolo[4,3-c]pyridin-4-yl)methyl acetate. MS: [M+H]+ m/z 528.

Step 7: 2-((6-chloro-4-(hydroxymethyl)-1-trityl-1H-pyrazolo[4,3-c]pyridin-3-yl)oxy)ethanol A solution of (6-chloro-3-(2-hydroxyethoxy)-1-trityl-1H-pyrazolo[4,3-c]pyridin-4-yl)methyl acetate (491.9 mg, 0.932 mmol) in MeOH (2 ml) and DCM (2 ml) was charged with sodium methoxide (25 wt % in MeOH, 0.45 ml, 1.968 mmol) and stirred at RT for 2 hr. Quenched with sat aq NH4Cl and extracted 3× with DCM. Washed organics with brine, dried over Na2SO4, filtered and concentrated in vacuo to provide 2-((6-chloro-4-(hydroxymethyl)-1-trityl-1H-pyrazolo[4,3-c]pyridin-3-yl)oxy)ethanol. MS: [M+H]+ m/z 486.

Intermediate 21B

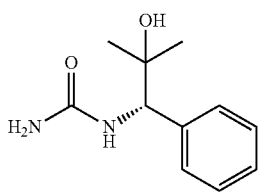

(S)-1-(2-hydroxy-2-methyl-1-phenylpropyl)urea

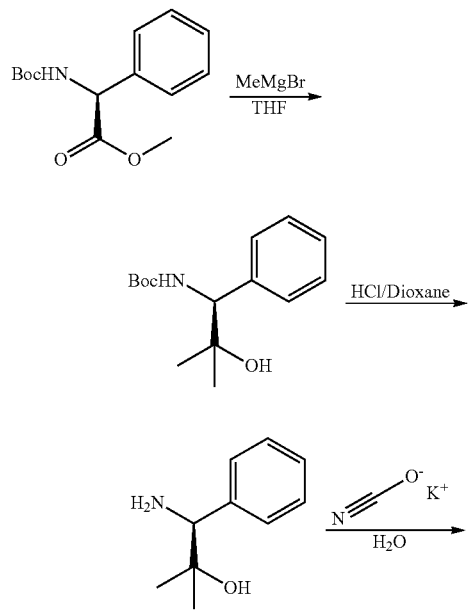

-continued

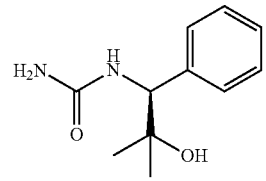

Step 1: (S)-tert-butyl(2-hydroxy-2-methyl-1-phenylpropyl)carbamate

At 0° C., to a solution of (S)-methyl 2-((tert-butoxycarbonyl)amino)-2-phenylacetate (4.0 g, 15 mmol) in THF (40 mL) was added MeMgBr (3 M solution in THF, 20 mL, 60 mmol) dropwise and the contents were stirred at ambient temperature. After 2 h, the reaction was carefully quenched with aqueous saturated NH4Cl (20 mL) and the organic contents were extracted with EtOAc (2×50 mL). The EtOAc layer was washed successively with H2O (2×10 mL), brine (1×20 mL) and the volatiles were removed under reduced pressure to afford (S)-tert-butyl(2-hydroxy-2-methyl-1-phenylpropyl)carbamate. The residue thus obtained was pure enough and is taken directly for the next step.

Step 2: (S)-1-amino-2-methyl-1-phenylpropan-2-ol

To a solution of (S)-tert-butyl(2-hydroxy-2-methyl-1-phenylpropyl)carbamate (3.5 g, 13 mmol) in CH2Cl2 (20 mL) was added dioxane saturated with HCl gas (10 mL) and the contents were stirred at ambient temperature for 30 min. The volatiles were then removed under reduced pressure and the residue thus obtained was triturated with Et2O to afford (S)-1-amino-2-methyl-1-phenylpropan-2-ol. $^{1}$H NMR (300 MHz, DMSO-$d_6$) δ 8.3 (bs, 2H), 7.47-7.37 (m, 5H), 5.34 (s, 1H), 4.1 (bs, 1H), 1.17 (s, 3H), 0.97 (s, 3H). Anal. Calcd. $C_{10}H_{15}NO$ 165.2. Found 166.2 (M+H).

Step 3: (S)-1-(2-hydroxy-2-methyl-1-phenylpropyl)urea

To a solution of (S)-1-amino-2-methyl-1-phenylpropan-2-ol (2.0 g, 10 mmol) in H2O (10 mL) was added potassium cyanate (0.85 g, 12 mmol) and the contents were stirred at ambient temperature for 2 h. The solid thus obtained was filtered and washed successively with H2O (2×5 mL) and dried in air to afford (S)-1-(2-hydroxy-2-methyl-1-phenylpropyl)urea. $^{1}$H NMR (400 MHz, DMSO-$d_6$) δ 7.25-7.15 (m, 5H), 6.52 (d, J=9.2 Hz, 1H), 5.50 (s, 2H), 4.50 (s, 1H), 4.41 (d, J=9.2 Hz, 1H), 1.10 (s, 3H), 0.93 (s, 3H). Anal. Calcd. $C_{11}H_{16}N_2O_2$ 208.3. Found 209.2 (M+H).

Intermediate 22B ((S)-1-(1-(4-fluorophenyl)-2-hydroxy-2-methylpropyl)urea) was prepared following similar procedures described for Intermediate 21B using the appropriate BOC-protected amino ester, which can be achieved by those of ordinary skill in the art of organic synthesis.

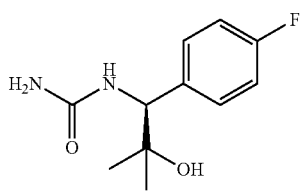

Intermediate 23B

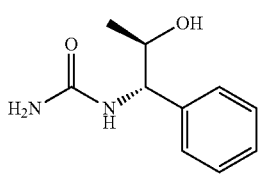

1-((1S,2R)-2-hydroxy-1-phenylpropyl)urea

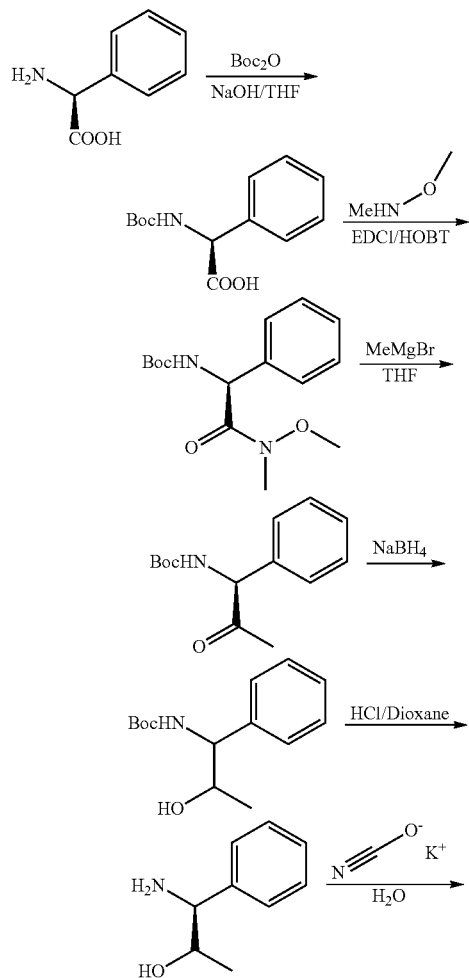

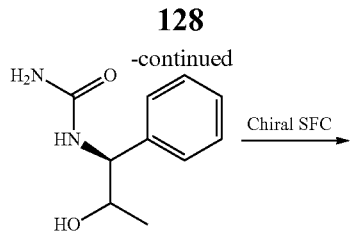

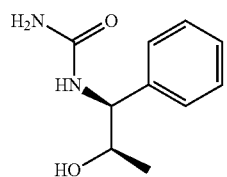

23B

Step 1: (S)-2-((tert-butoxycarbonyl)amino)-2-phenylacetic acid

At 0° C., to a solution of (S)-2-amino-2-phenylacetic acid (3.0 g, 19.9 mmol) in THF (20 mL) were added 10% NaOH solution (20 mL, 50 mmol) and Boc$_2$O (4.8 g, 22 mmol) and the contents were stirred at ambient temperature. After 3 hr, the reaction mixture was cooled to 0° C. and was acidified carefully with 50% citric acid solution (10 mL) until the pH of the solution is 4. The organic contents were extracted with EtOAc (3×25 mL) and the combined organic extracts were washed with brine (1×20 mL), dried over Na$_2$SO$_4$, concentrated to afford (S)-2-((tert-butoxycarbonyl)amino)-2-phenylacetic acid. The residue thus obtained was taken directly for step 2 without further purification. MS: [M+H]$^+$ m/z 252.

Step 2: (S)-tert-butyl(2-(methoxy(methyl)amino)-2-oxo-1-phenylethyl)carbamate To a solution of (S)-2-((tert-butoxycarbonyl)amino)-2-phenylacetic acid (1.0 g, 4.0 mmol) in dichloromethane (10 mL) were added N,O-dimethyl hydroxylamine hydrochloride (0.77 g, 8.0 mmol), EDCl (1.2 g, 6.0 mmol), HOBt (0.05 g, 0.4 mmol), Et$_3$N (0.8 g, 8.0 mmol) and the contents were stirred at ambient temperature. After 2 hr, the reaction was quenched with ice cold H$_2$O (10 mL), and the organic contents were extracted with CH$_2$Cl$_2$ (2×30 mL). The combined organic extracts were washed with brine (1×20 mL), dried over Na$_2$SO$_4$, concentrated and the residue thus obtained was purified by flash column chromatography to afford (S)-tert-butyl(2-(methoxy(methyl)amino)-2-oxo-1-phenylethyl)carbamate. $^1$H NMR (300 MHz, CDCl$_3$) δ 7.39-7.29 (m, 5H), 5.77 (bs, 1H), 5.73 (bs, 1H), 3.47 (s, 3H), 3.20 (s, 3H), 1.42 (s, 9H).

Step 3: ((S)-tert-butyl(2-oxo-1-phenylpropyl)carbamate

At 0° C., to a solution of (S)-tert-butyl(2-(methoxy(methyl)amino)-2-oxo-1-phenylethyl)carbamate (0.9 g, 3.06 mmol) in anhydrous THF (15 mL), was added MeMgBr (3M solution in Et$_2$O, 2.0 mL, 6.1 mmol) and resultant mixture was allowed to warm and stirred at ambient temperature. After 2 hrs, the reaction was carefully quenched with saturated aqueous NH$_4$Cl solution (10 mL), and the organic contents were extracted with CH$_2$Cl$_2$ (3×25 mL). The volatiles were removed under reduced pressure to afford (S)-tert-butyl (2-oxo-1-phenylpropyl)carbamate. The compound obtained is pure and no further purification is necessary. $^1$H NMR (300

MHz, CDCl₃) δ 7.40-7.33 (m, 5H), 5.88 (bs, 1H), 5.28 (bs, 1H), 2.08 (s, 3H), 1.41 (s, 9H).

Step 4:
tert-butyl((1S)-2-hydroxy-1-phenylpropyl)carbamate

At 0° C., to a solution of ((S)-tert-butyl(2-oxo-1-phenylpropyl)carbamate (0.7 g, 2.8 mmol) in MeOH (10 mL) was added NaBH₄ (0.1 g, 2.8 mmol) and the contents were stirred at ambient temperature. After 30 min, the reaction mixture was quenched carefully with ice cold H₂O (10 mL), and the organic contents were extracted with EtOAc (3×25 mL). The combined organic extracts were washed with brine (1×20 mL), dried over Na₂SO₄, concentrated to afford tert-butyl ((1S)-2-hydroxy-1-phenylpropyl)carbamate. The product thus obtained was pure and taken directly for the next step without further purification. MS: [M+H-Boc]⁺ m/z 152.

Step 5:
tert-butyl((1S)-2-hydroxy-1-phenylpropyl)carbamate

A solution of tert-butyl((1S)-2-hydroxy-1-phenylpropyl)carbamate (0.68 g, 2.7 mmol) in dioxane (2 mL) was added dioxane saturated with HCl (3 mL) and the contents were allowed to stir and ambient temperature. After 30 min, the volatiles were removed under reduced pressure. The residue thus obtained was triturated with Et₂O to afford tert-butyl ((1S)-2-hydroxy-1-phenylpropyl)carbamate. MS: [M+H]⁺ m/z 152.

Steps 6: 1-((1S)-2-hydroxy-1-phenylpropyl)urea

To a solution of (1S)-1-amino-1-phenylpropan-2-ol (0.43 g, 2 mmol) in H₂O (2 mL) was added potassium cyanate (0.23 g, 2.7 mmol) and the contents were stirred at ambient temperature for 2 hr. The solid thus obtained was filtered and washed successively with H₂O (2×5 mL) and dried in air to afford 1-((1S)-2-hydroxy-1-phenylpropyl)urea. MS: [M+H]⁺ m/z 195.

Step 7: 1-((1S,2R)-2-hydroxy-1-phenylpropyl)urea and 1-((1S,2S)-2-hydroxy-1-phenylpropyl)urea The enantiomers of 1-((1S)-2-hydroxy-1-phenylpropyl) urea (2.86 g, 14.72 mmol) were separated by SFC (Thar 80, Column: Phenomenex Lux-4 21×250 (mm), UV wavelength: 220 nM, mobile phase: 25:75 Ethanol+0.25% dimethyl ethyl amine in CO₂₍₁₎, flow rate: 70 mL/min, Run Time: 7.1 min). The fractions were collected and the solvent evaporated in vacuo to afford 1-((1S,2R)-2-hydroxy-1-phenylpropyl)urea (Intermediate 23B). MS: [M+H]⁺ m/z 195.

Intermediate 24B was prepared following similar procedures described for Intermediate 23B using the appropriate amino acid, which can be achieved by those of ordinary skill in the art of organic synthesis.

| Intermediate | Structure | IUPAC Name | Exact Mass [M + H]+ |
|---|---|---|---|
| 24B | 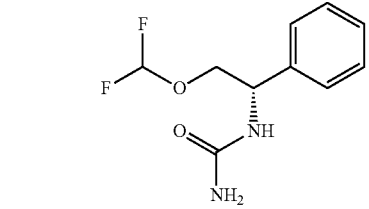 [SMILES: NC(=O)N[C@H](COC(F)F)c1ccccc1] | 1-((1S,2R)-1-(4-fluorophenyl)-2-hydroxypropyl)urea | Calc'd 213, found 213 |

Intermediate 25B

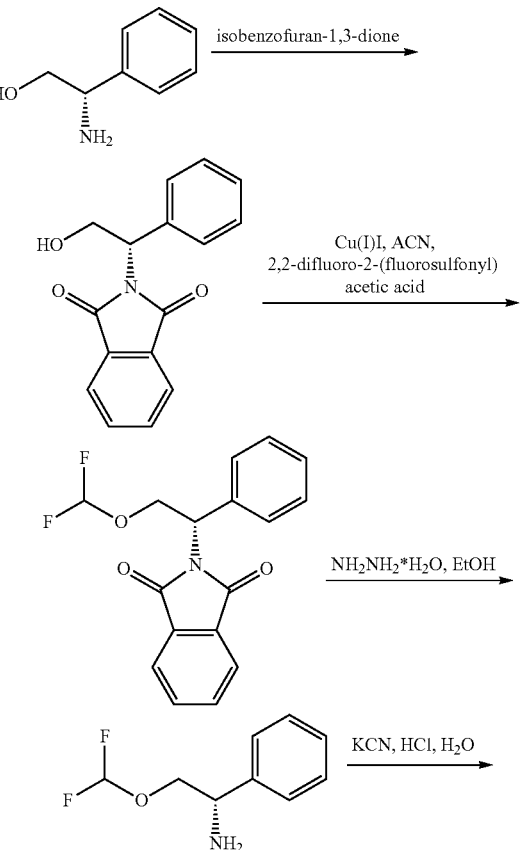

(S)-1-(2-(difluoromethoxy)-1-phenylethyl)urea

Step 1: (S)-2-(2-hydroxy-1-phenylethyl)isoindoline-1,3-dione (S)-2-amino-2-phenylethanol (2 g, 14.58 mmol) and isobenzofuran-1,3-dione (2.267 g, 15.31 mmol) were combined in a 20 mL microwave tube, sealed and heated to 150° C. for 6 hrs. The tube was cooled to ambient temperature, dilluted with DCM, loaded directly onto a 50 g SNAP column and purified 10-60% hexane/EtOAc to provide (S)-2-(2-hydroxy-1-phenylethyl)isoindoline-1,3-dione. MS: [M+H]+ m/z 268.

Step 2: (S)-2-(2-(difluoromethoxy)-1-phenylethyl)isoindoline-1,3-dione (S)-2-(2-hydroxy-1-phenylethyl)isoindoline-1,3-dione (1.06 g, 3.97 mmol) was dissolved in anhydrous acetonitrile (20 ml), charged with copper (I) iodide (1.133 g, 5.95 mmol), 2,2-difluoro-2-(fluorosulfonyl)acetic acid (0.615 ml, 5.95 mmol), degassed under nitrogen and heated to 80° C. The solution was allowed to stir at 80° C. for 1 hr. The reaction was cooled in an ice bath, quenched with 5 mL water, filtered through a 10 g celite cartridge, and the solvents were removed in vacuo. The residue was purified by MPLC 10-50% EtOAc/hexanes to provide (S)-2-(2-(difluoromethoxy)-1-phenylethyl)isoindoline-1,3-dione. MS: [M+H]+ m/z 318.

Step 3: (S)-2-(difluoromethoxy)-1-phenylethanamine (S)-2-(2-(difluoromethoxy)-1-phenylethyl)isoindoline-1,3-dione (659 mg, 2.077 mmol) was dissolved in EtOH (7 ml), charged with hydrazine hydrate (1.01 ml, 20.77 mmol) and heated to 85° C. for 90 minutes. The reaction was diluted with 10 mL EtOH, filtered, and the solvents were evaporated in vacuo. The residue was purified on silica gel 2-10% MeOH/DCM to provide (S)-2-(difluoromethoxy)-1-phenylethanamine MS: [M+H]+ m/z 188.

Step 4: (S)-1-(2-(difluoromethoxy)-1-phenylethyl)urea

To a solution of (S)-2-(difluoromethoxy)-1-phenylethanamine (169 mg, 0.903 mmol) in water (6 ml), was added HCl (3.6 ml, 3.61 mmol) 1N and potassium cyanate (366 mg, 4.51 mmol). The reaction was heated at 80° C. for 2 hrs, then allowed to cool to ambient temperature overnight. The precipitate formed was filtered, washed with water, and dried under high vacuum to provide (S)-1-(2-(difluoromethoxy)-1-phenylethyl)urea MS: [M+H]+ m/z 231. 1H NMR (500 MHz, DMSO-d6) δ 7.42-7.30 (m, 4H), 7.29-7.17 (m, 1H), 6.84-6.45 (m, 2H), 5.61 (s, 2H), 4.97-4.83 (m, 1H), 4.08-3.89 (m, 2H).

Intermediate 26B (S)-2-Amino-N-methyl-2-phenyl-acetamide

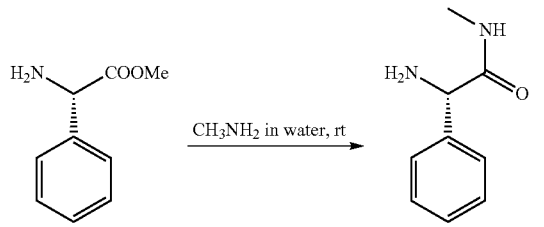

26B

Methyl amine solution (2 mL, 40% solution in water) was added to 1(0.1 g, 0.061 mmol) at 0° C. and allowed to warm up to room temperature at which it was stirred for 3 h. LCMS analysis indicated the complete consumption of the starting material. Water was removed under reduced pressure to afford the crude compound which was directly taken to next step without purification. MS: [M+H]+ m/z 165.

Intermediate 27B

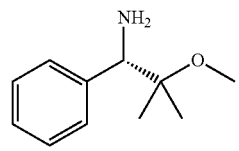

(S)-2-methoxy-2-methyl-1-phenylpropan-1-amine

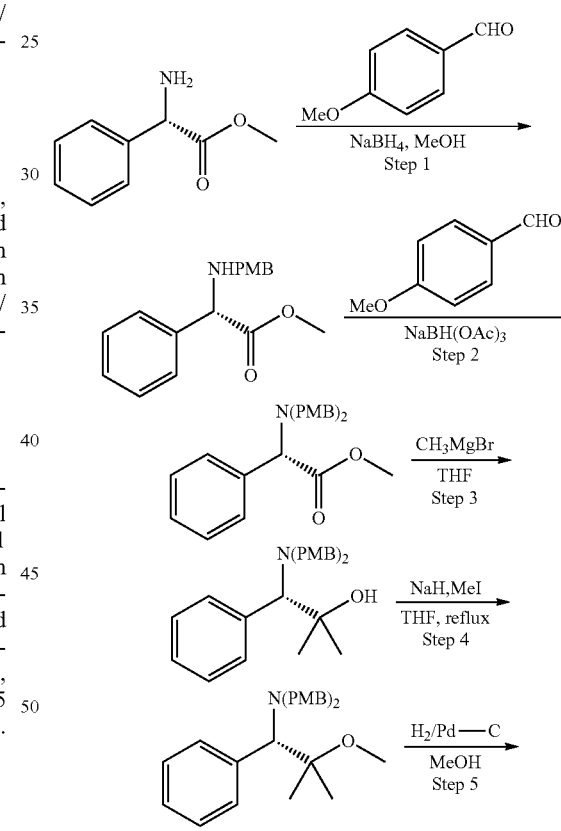

Step 1: (S)-methyl 2-((4-methoxybenzyl)amino)-2-phenylacetate

To a solution of (S)-methyl 2-amino-2-phenylacetate (1.0 g, 6.06 mmol) in anhydrous MeOH (20 mL) was added 4-methoxy benzaldehyde (0.82 g, 6.06 mmol) and few drops of HOAc. After 30 min, the reaction mixture was cooled to 0° C., NaBH$_4$ (0.69 g, 12.12 mmol) was added and the contents were stirred at ambient temperature. After 2 h, the reaction was quenched with ice cold H$_2$O (10 mL), MeOH was removed under reduced pressure and the organic contents were extracted with EtOAc (3×25 mL). The combined organic extracts were washed with brine (1×20 mL), dried over Na$_2$SO$_4$, concentrated and (S)-methyl 2-((4-methoxybenzyl)amino)-2-phenylacetate thus obtained was taken directly for step 2. MS: [M+H]$^+$ m/z 286.

Step 2: (S)-methyl 2-(bis(4-methoxybenzyl)amino)-2-phenylacetate

To a solution of (S)-methyl 2-((4-methoxybenzyl)amino)-2-phenylacetate (1.6 g, 5.61 mmol) in anhydrous dichloroethane (20 mL) was added 4-methoxy benzaldehyde (0.76 g, 5.61 mmol) and few drops of HOAc. After 30 min, the reaction mixture was cooled to 0° C., sodium triacetoxy borohydride (2.38 g, 11.22 mmol) was added and the contents were allowed to stir at ambient temperature. After 2 h, the reaction was quenched with ice cold H$_2$O (10 mL), and the organic contents were extracted with CH$_2$Cl$_2$ (2×25 mL). The combined organic extracts were washed with brine (1×20 mL), dried over Na$_2$SO$_4$, concentrated and the residue thus obtained was purified by flash column chromatography to afford (S)-methyl 2-(bis(4-methoxybenzyl)amino)-2-phenylacetate as pale yellow liquid (1.5 g, 66%). MS: [M+H]$^+$ m/z 406.

Step 3: (S)-1-(bis(4-methoxybenzyl)amino)-2-methyl-1-phenylpropan-2-ol

At 0° C., to a solution of (S)-methyl 2-(bis(4-methoxybenzyl)amino)-2-phenylacetate (1.5 g, 3.7 mmol) in anhydrous THF (15 mL), was added MeMgBr (3M solution in Et$_2$O, 12.3 mL, 37.0 mmol) and resultant mixture was allowed to warm and stirred at ambient temperature. After 10 h, the reaction was carefully quenched with saturated aqueous NH$_4$Cl solution (25 mL), and the organic contents were extracted with CH$_2$Cl$_2$ (3×50 mL). The volatiles were removed under reduced pressure and the residue thus obtained was further purified by flash column chromatography to afford (S)-1-(bis(4-methoxybenzyl)amino)-2-methyl-1-phenylpropan-2-ol (1.0 g, 68% yield). MS: [M+H]$^+$ m/z 406.

Step 4: (S)-2-methoxy-N,N-bis(4-methoxybenzyl)-2-methyl-1-phenylpropan-1-amine

At 0° C., to a suspension of NaH (0.13 g, 2.96 mmol) in anhydrous THF (5 mL), was added a solution of (S)-1-(bis(4-methoxybenzyl)amino)-2-methyl-1-phenylpropan-2-ol 4 (1.0 g, 2.47 mmol) in anhydrous THF (10 mL). After 15 min, MeI (0.55 g, 3.71 mmol) was added and the contents were heated to reflux. After 8 h, the reaction was brought back to ambient temperature, quenched carefully with ice cold H$_2$O (10 mL), and the organic contents were extracted with EtOAc (3×25 mL). The combined organic extracts were washed with brine (1×20 mL), dried over Na$_2$SO$_4$, concentrated to afford (S)-2-methoxy-N,N-bis(4-methoxybenzyl)-2-methyl-1-phenylpropan-1-amine. H$^1$NMR (CD$_3$OD, 400 MHz) δ 7.45-7.44 (m, 2H), 7.37-7.34 (m, 2H), 7.33-7.28 (m, 5H), 6.88-6.86 (m, 4H), 4.20 (s, 1H), 3.78 (s, 6H), 3.25 (s, 4H), 2.81 (s, 3H), 1.4 (s, 3H), 0.81 (s, 3H). MS: [M+H]$^+$ m/z 420.

Step 5: Synthesis of (S)-2-methoxy-2-methyl-1-phenylpropan-1-amine

A solution of (S)-2-methoxy-N,N-bis(4-methoxybenzyl)-2-methyl-1-phenylpropan-1-amine 5 (0.7 g, 1.67 mmol) in anhydrous MeOH was added Pd on C (0.1 g) and the contents were stirred at ambient temperature in H$_2$ atmosphere. After 14 h, the reaction mixture was filtered through a pad of celite and the volatiles were removed under reduced pressure. The residue thus obtained was further purified by preparative HPLC to afford (S)-2-methoxy-2-methyl-1-phenylpropan-1-amine H$^1$NMR (CDCl$_3$, 400 MHz) δ 7.45-7.44 (m, 2H), 7.35-7.33 (m, 3H), 4.1 (s, 1H), 3.32 (s, 3H), 1.2 (s, 3H), 1.12 (s, 3H).

Intermediate 28B

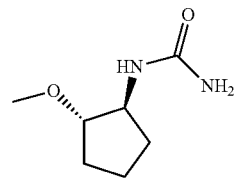

1-((trans racemic)-2-methoxycyclopentyl)urea

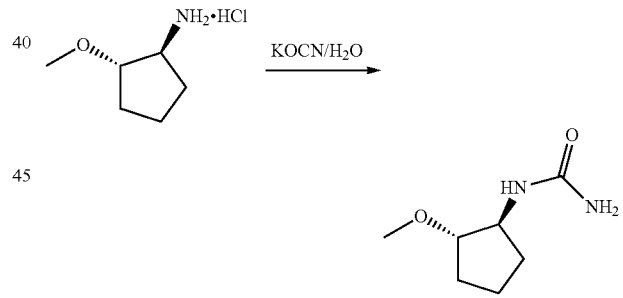

To a solution of (trans racemic)-2-methoxycyclopentanamine hydrochloride (0.5 g, 3.3 mmol) in H$_2$O (2 mL) was added potassium cyanate (0.32 g, 3.9 mmol) and the contents were stirred at ambient temperature. After 2 h the reaction mixture was diluted with H$_2$O (10 mL) and the organic contents were extracted with CH$_2$Cl$_2$ (2×10 ml). The combined organic layer were washed with brine solution (2×5 mL) and dried over Na$_2$SO$_4$. The volatiles were removed under reduced pressure to yield the title compound (0.2 g, 38% yield) which was taken further without any purification. H$^1$NMR (DMSO d$_6$, 400 MHz): δ 3.72-3.70 (m, 1H), 3.66-3.62 (m, 1H), 3.33 (s, 3H), 1.84-1.36 (m, 6H).

The following intermediates were prepared from the appropriate starting material following similar procedures described for Intermediates 27B and 28B:

| Intermediate | Structure | IUPAC Name | Exact Mass [M + H]+ |
|---|---|---|---|
| 29B | 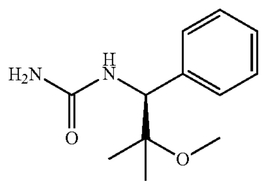 [SMILES: COC(C)(C)[C@@H](NC(N)=O)c1ccccc1] | (S)-1-(2-methoxy-2-methyl-1-phenylpropyl)urea | Calc'd 223, found 223 |
| 30B | 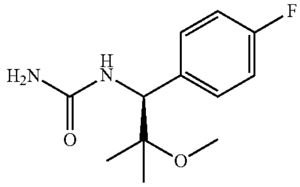 [SMILES: COC(C)(C)[C@@H](NC(N)=O)c1ccc(F)cc1] | (S)-1-(1-(4-fluorophenyl)-2-methoxy-2-methylpropyl)urea | Calc'd 241, Found 241 |

Intermediate 31B (R)-1-(2,2-dimethyl-1-phenylpropyl)urea

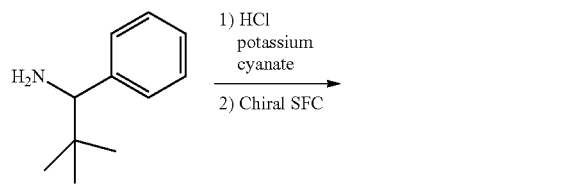

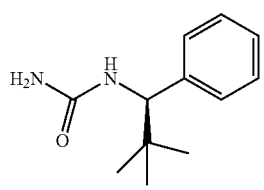

In a manner simnilar to that described for Intermediate 16B, 2,2-dimethyl-1-phenylpropan-1-amine was reacted with HCl and potassium cyanate to provide 1-(2,2-dimethyl-1-phenylpropyl)urea. MS: [M+H]+ m/z 207.

The enantiomers of (R)-1-(2,2-dimethyl-1-phenylpropyl)urea (600 mg, 2.9 mmol) were separated by SFC (Berger Multigram II SFC, column: Chiral Technology AD-H 2.1×25 cm, 5 uM, mobile phase: 20% Methanol in $CO_{2(l)}$, flow rate: 70 mL/min) The fractions were collected and the solvent evaporated in vacuo to afford (R)-1-(2,2-dimethyl-1-phenyl-propyl)urea (MS: [M+H]+ m/z 207) and (S)-1-(2,2-dimethyl-1-phenylpropyl)urea (MS: [M+H]+ m/z 207).

Intermediate 32B 3-(2-methoxyethoxy)-1-trityl-1H-pyrazolo[4,3-c]pyridin-6-amine

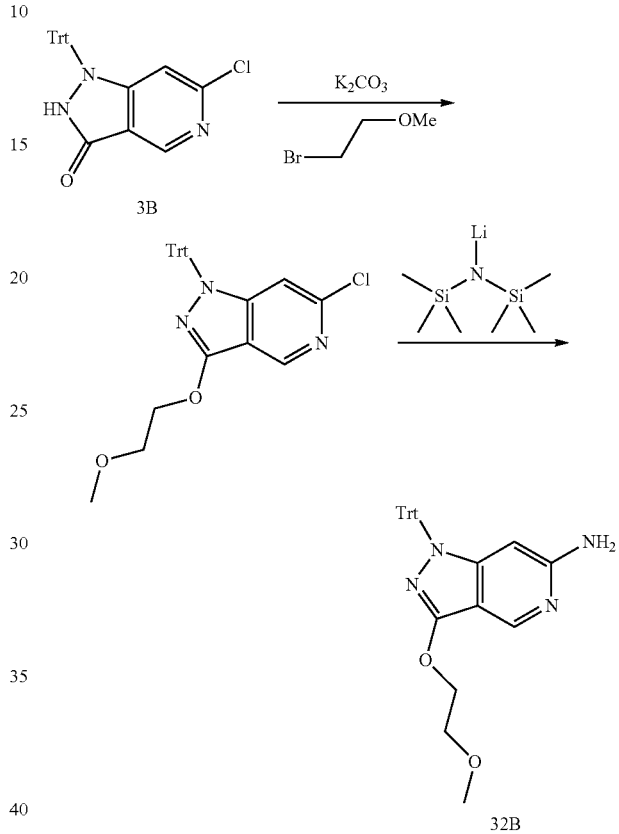

Step 1: 6-chloro-3-(2-methoxyethoxy)-1-trityl-1H-pyrazolo[4,3-c]pyridine

In a manner similar to that described in Example 1 (Step 1), 6-chloro-1-trityl-1H-pyrazolo[4,3-c]pyridin-3(2H)-one (3B) was treated with 1-bromo-2-methoxyethane and potassium carbonate (DMF, room temperature, overnight) to provide 6-chloro-3-(2-methoxyethoxy)-1-trityl-1H-pyrazolo[4,3-c]pyridine (84% yield).

Step 2: 3-(2-methoxyethoxy)-1-trityl-1H-pyrazolo[4,3-c]pyridin-6-amine 6-chloro-3-(2-methoxyethoxy)-1-trityl-1H-pyrazolo[4,3-c]pyridine (500 mg, 1.064 mmol) and SPHOS Palladacycle (162 mg, 0.213 mmol) were mixed in a pressure release vial, degassed and backfilled with Nitrogen (3×), tetrahydrofuran (8 mL) was added, followed by the addition of lithium bis(trimethylsilyl)amide (1M) (2.128 mL, 2.128 mmol), the resultant mixture was degassed and backfilled with nitrogen (3×), and heated up to 60° C. for overnight. Hydrochloric acid 1M (2 mL) was added, and the mixture was stirred at room temperature for 2 h, the mixture was basified with aqueous sodium hydroxide (1M, ~4 mL) to pH 9, and the mixture was extracted with ethyl acetate (2×10 mL). The combined organic fractions were washed with brine (saturated, 1x 10 mL), dried (MgSO$_4$), filtered and the solvent was evaporated under reduced pressure. The residue was purified by column chromatography on silica gel (40 g), eluting with EtOAc/isohexane=50%-100% to give 3-(2-methoxyethoxy)-1-trityl-1H-pyrazolo[4,3-c]pyridin-6-amine (32B, 432 mg, 0.959 mmol, 90% yield) as a brown solid. MS: [M+H]$^+$ m/z 451.

In a similar manner, intermediate 3B was reacted sequentially with 2-iodo-1,1-difluoroethane (potassium carbonate, DMF, room temperature, overnight, 95% yield) and then LiHMDS/SPHOS Palladacycle (THF, 80° C., overnight, 68% yield) to provide 3-(2,2-difluoroethoxy)-1-trityl-1H-pyrazolo[4,3-c]pyridin-6-amine (33B).

In a manner similar to that described in Scheme 10 (Step 2) and Example 102, 3-(2,2-difluoroethoxy)-1-trityl-1H-pyrazolo[4,3-c]pyridin-6-amine (33B) was treated with (3R,4S)-tert-butyl 3-amino-4-phenylpyrrolidine-1-carboxylate, CDI and imidazole (THF, room temperature, overnight, 80% yield) to afford (3R,4S)-tert-butyl 3-(3-(3-(2,2-difluoroethoxy)-1-trityl-1H-pyrazolo[4,3-c]pyridin-6-yl)ureido)-4-phenylpyrrolidine-1-carboxylate (MS: [M+H]$^+$ m/z 745). Subsequent deprotection with triethylsilane in TFA afforded 1-(3-(2,2-difluoroethoxy)-1H-pyrazolo[4,3-c]pyridin-6-O-3-43R,4S)-4-phenylpyrrolidin-3-yl)urea (34B). MS: [M+H]$^+$ m/z 403.

Intermediate 35B

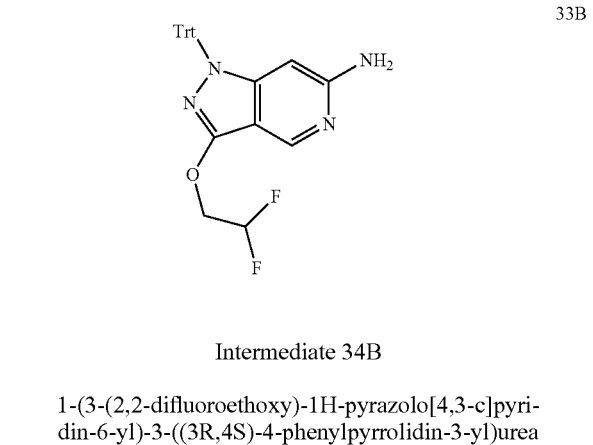

Intermediate 34B 1-(3-(2,2-difluoroethoxy)-1H-pyrazolo[4,3-c]pyridin-6-yl)-3-((3R,4S)-4-phenylpyrrolidin-3-yl)urea

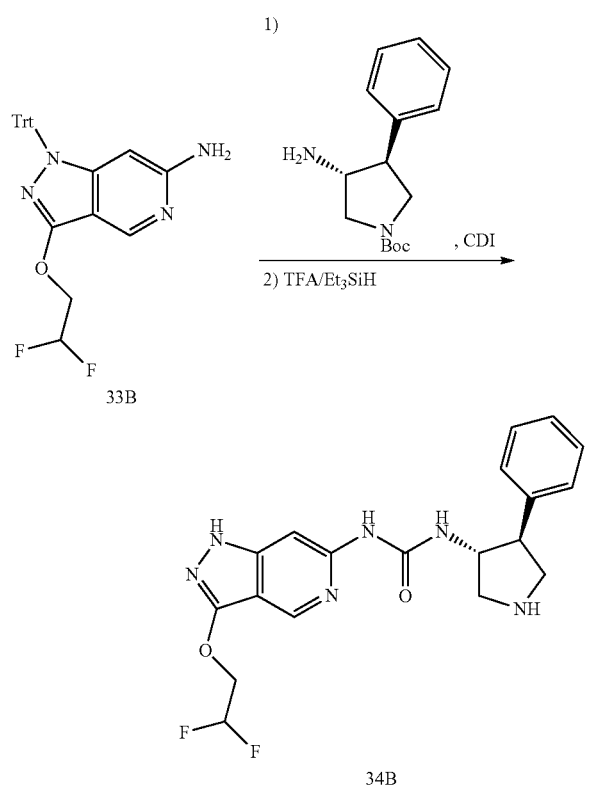

(6-chloro-3-methoxy-1-trityl-1H-pyrazolo[4,3-c]pyridin-4-yl)methanol (35B)

6-chloro-3-methoxy-1-trityl-1H-pyrazolo[4,3-c]pyridine-4-carbaldehyde (Intermediate 11B, 25 g, 55.1 mmol) was dissolved in DCM (100 ml, sonication required) and slowly charged with MeOH (100 ml). The solution was cooled in an ice bath then charged with sodium borohydride (2.60 g, 68.8 mmol) portion wise (exothermic) and allowed to stir for 1 h at RT. A large exotherm was observed and the reaction turned dark red. TLC showed product had formed after 20 minutes. The reaction was diluted with 500 mL DCM and 200 mL water. A large amount of dark red to brick red material was filtered off. The aq. layer was extracted with 1×200 mL DCM and the combined organics were washed with brine, dried over sodium sulfate, filtered and concentrated in vacuo. Purification on silica gel, 0-10% EtOAc/DCM gave (6-chloro-3-methoxy-1-trityl-1H-pyrazolo[4,3-c]pyridin-4-yl)methanol (35B, 15 g, 32.9 mmol, 59.7% yield) as a pale yellow solid. MS: [M+H]$^+$ m/z 456. $^1$H NMR (500 MHz, CDCl3) δ 7.34-7.27 (m, 10H), 7.23-7.18 (m, 5H), 5.78 (s, 1H), 4.99 (s, 2H), 3.93 (s, 3H), 3.86 (s, 1H).

Intermediate 36B 6-chloro-3-methoxy-1-trityl-1H-pyrazolo[4,3-c]pyridine-4-carboxylic acid

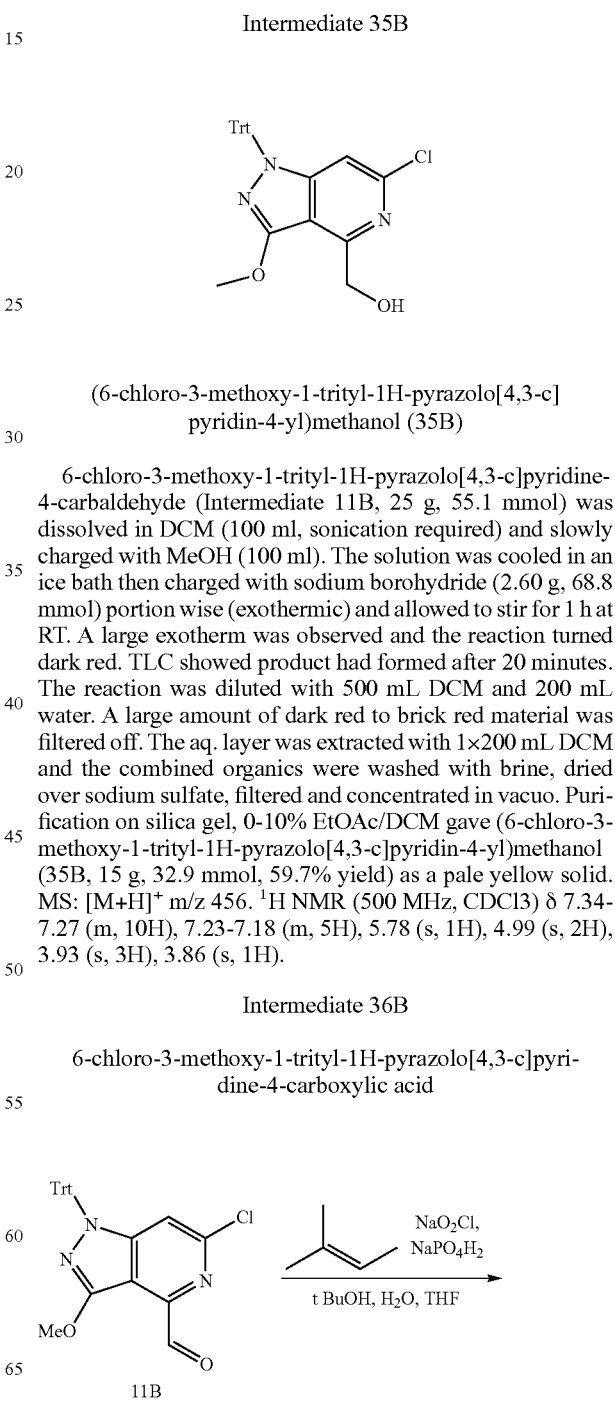

-continued

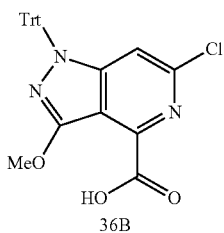

36B

Sodium chlorite (120 mg, 1.322 mmol) and sodium dihydrogen phosphate (159 mg, 1.322 mmol) were dissolved in water (1.5 ml). A suspension of 6-chloro-3-methoxy-1-trityl-1H-pyrazolo[4,3-c]pyridine-4-carbaldehyde (Intermediate 11B, 100 mg, 0.220 mmol) in tBuOH (1.5 ml) and THF (1.5 ml) and 2-methyl-2-butene (233 µl, 2.203 mmol) was then added to the aqueous mixture. The resulting solution was stirred at rt overnight. The reaction contents were concentrated in vacuo, resuspended in water, the solid was filtered, and washed with water. The solids were triturated in MeOH to give 6-chloro-3-methoxy-1-trityl-1H-pyrazolo[4,3-c]pyridine-4-carboxylic acid. MS: [M+H]$^+$ m/z 470.

Intermediate 37B 4,6-dichloro-3-methoxy-1-trityl-1H-pyrazolo[4,3-c]pyridine

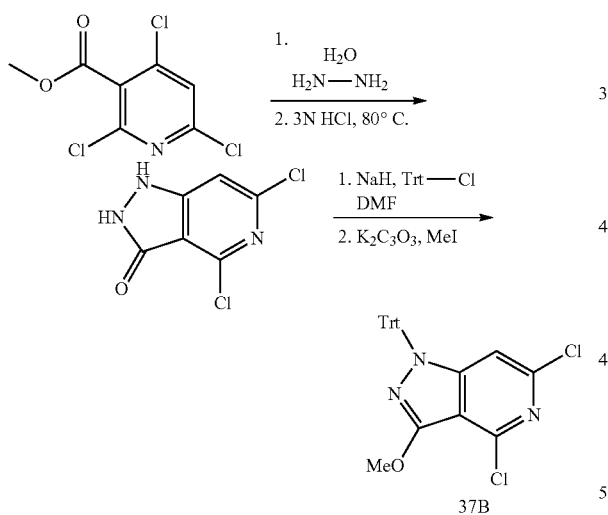

Step 1: 4,6-dichloro-1H-pyrazolo[4,3-c]pyridin-3(2H)-one

To a solution of crude methyl 2,4,6-trichloronicotinate (6 g, 24.95 mmol) in DMA was added hydrazine-hydrate (3.10 g, 40.3 mmol) at 0° C. The ice bath was removed and the reaction mixture was stirred at rt for 3 h. A solution of 2N HCl was added and the reaction was stirred at 80° C. for 12 h. The pH of the reaction mixture was adjusted to pH ~7-8 via addition of 1M NaOH, followed by addition of 20 volumes of water and the reaction was stirred at rt for 12 h. The mixture of regioisomers was filtered and separated via RF-HPLC to yield 3.56 g, 70% of the desired di-chloro aza-indazolidinone. MS: [M+H]$^+$ m/z 205.

Step 2: 4,6-dichloro-3-methoxy-1-trityl-1H-pyrazolo[4,3-c]pyridine (37B)

4,6-dichloro-1H-pyrazolo[4,3-c]pyridin-3(2H)-one (1160 mg, 5.69 mmol) was dissolved in DMF (20 ml), charged with (chloromethanetriyl)tribenzene (1744 mg, 6.25 mmol) followed by sodium hydride (341 mg, 8.53 mmol) and allowed to stir at rt for 1 h. The tritylation was complete by LC/MS. The reaction was charged with potassium carbonate (1572 mg, 11.37 mmol) followed by iodomethane (0.533 ml, 8.53 mmol) and allowed to stir overnight at rt. The alkylation was complete by LC/MS. The reaction was charged with 40 mL water, cooled to 0° C. and the precipitate was filtered and washed 2×20 mL water. The yellow solid was dissolved in 20 mL DCM and poured onto a 100 g Biotage SNAP column and purified 5-25% EtOAc/hexanes to provide 4,6-dichloro-3-methoxy-1-trityl-1H-pyrazolo[4,3-c]pyridine (37B, 1.64 g, 3.56 mmol, 62.7% yield) as a white solid. MS: [M+H]$^+$ m/z 460.

Intermediates 38B, 39B, and 40B

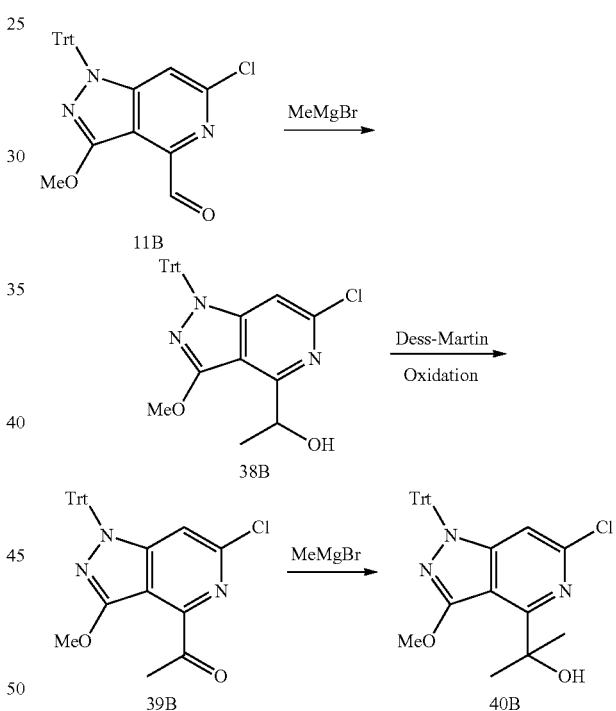

Step 1: 1-(6-chloro-3-methoxy-1-trityl-1H-pyrazolo[4,3-c]pyridin-4-yl)ethanol (38B)

Chloro-3-methoxy-1-trityl-1H-pyrazolo[4,3-c]pyridine-4-carbaldehyde (Intermediate 11B, 535 mg, 1.2 mmol) was dissolved in THF (8 ml) cooled to −78° C. and charged with methylmagnesium bromide (3M, 0.786 ml, 2.357 mmol). The reaction was allowed to stir for 1 hr, eventually reaching 0° C. The reaction was slowly quenched with saturated ammonium chloride (3 mL) and partioned between EtOAc 2×10 mL, washed with brine, dried over MgSO$_4$, filtered, and concentrated in vacuo. The residue was then loaded onto silica gel and purified by MPLC 0-25% EtOAc/hexanes to provide 1-(6-chloro-3-methoxy-1-trityl-1H-pyrazolo[4,3-c]pyridin-4-yl)ethanol (38B). MS: [M+H]+ m/z 470.

Step 2: 1-(6-chloro-3-methoxy-1-trityl-1H-pyrazolo[4,3-c]pyridin-4-yl)ethanone (39B)

1-(6-chloro-3-methoxy-1-trityl-1H-pyrazolo[4,3-c]pyridin-4-yl)ethanol (38B, 130 mg, 0.277 mmol) was taken up in DCM (2.87 ml) and Dess-Martin periodinane (141 mg, 0.332 mmol) was added. The reaction was allowed to stir at rt for 1 hr. The reaction was diluted with DCM (8 ml) and 1N NaOH was added (15 ml) and the mixture was allowed to stir. The organic phase was separated and the aqueous was washed with DCM (20 ml×3). The combined organic layers were washed with brine, dried over MgSO₄, and concentrated in vacuo to give 1-(6-chloro-3-methoxy-1-trityl-1H-pyrazolo[4,3-c]pyridin-4-yl)ethanone (Intermediate 39B). The products were carried forward without purification. MS: [M+H]+ m/z 468.

Step 3: 2-(6-chloro-3-methoxy-1-trityl-1H-pyrazolo[4,3-c]pyridin-4-yl)propan-2-ol (40B)

In an oven dried flask and under a nitrogen gas atomosphere, 1-(6-chloro-3-methoxy-1-trityl-1H-pyrazolo[4,3-c]pyridin-4-yl)ethanone (39B, 110 mg, 0.235 mmol) was dissolved in THF (2.0 ml) cooled to −78° C. and charged with methylmagnesium bromide (0.470 ml, 0.470 mmol). The reaction was allowed to stir for 1 hr, eventually reaching 0° C. The reaction was slowly quenched with saturated ammonium chloride (3 mL) and partioned between EtOAc 2×10 mL, washed with brine, dried over MgSO₄, filtered, and concentrated in vacuo to provide 2-(6-chloro-3-methoxy-1-trityl-1H-pyrazolo[4,3-c]pyridin-4-yl)propan-2-o (Intermediate 40B). The products were carried forward without purification. MS: [M+H]+ m/z 484.

Intermediate 41B

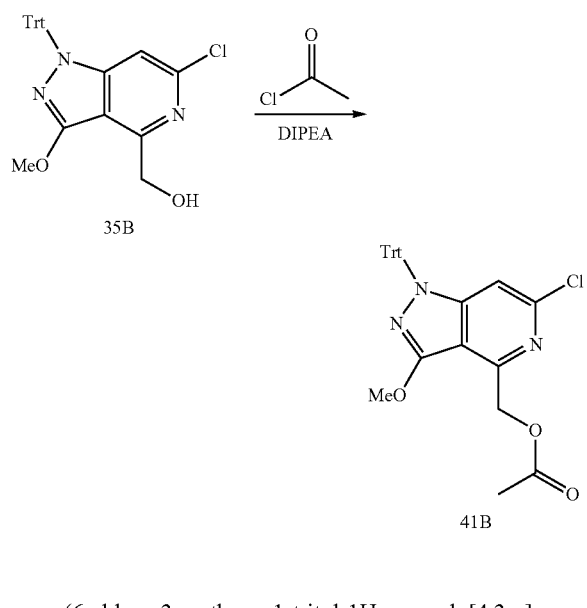

(6-chloro-3-methoxy-1-trityl-1H-pyrazolo[4,3-c]pyridin-4-yl)methyl acetate (6-chloro-3-methoxy-1-trityl-1H-pyrazolo[4,3-c]pyridin-4-yl)methanol (Intermediate 35B, 342 mg, 0.750 mmol) was dissolved in DCM (4.0 ml). The reaction mixture was charged with DIEA (0.197 ml, 1.125 mmol) followed by acetyl chloride (0.064 ml, 0.900 mmol) and allowed to stir at rt for 15 minutes. The reaction was concentrated in vacuo to provide (6-chloro-3-methoxy-1-trityl-1H-pyrazolo[4,3-c]pyridin-4-yl)methyl acetate (41B). The products were carried forward without purification. MS: [M+H]+ m/z 498.

Intermediate 42B

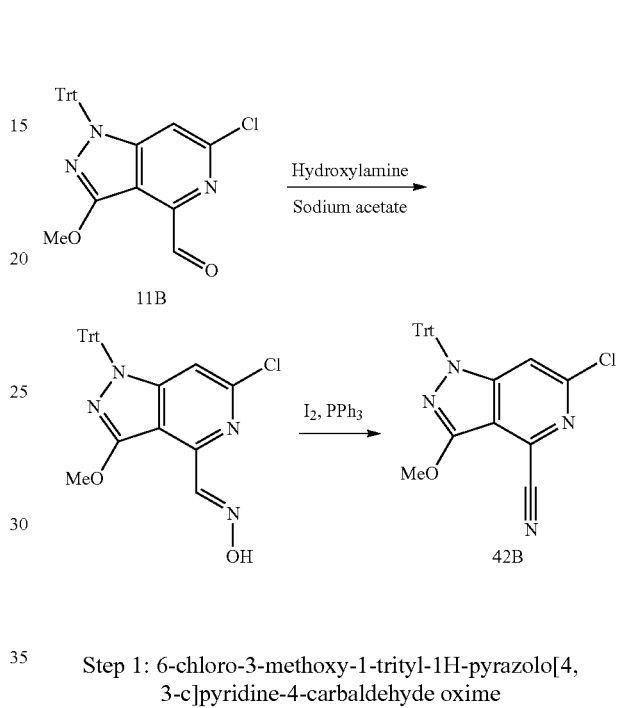

Step 1: 6-chloro-3-methoxy-1-trityl-1H-pyrazolo[4,3-c]pyridine-4-carbaldehyde oxime 6-chloro-3-methoxy-1-trityl-1H-pyrazolo[4,3-c]pyridine-4-carbaldehyde (11B, 100 mg, 0.220 mmol), sodium acetate (54.2 mg, 0.661 mmol), and hydroxylamine (21.8 mg, 0.331 mmol) were taken up in Ethanol (2.2 ml). The reaction was allowed to stir at 70° C. for 1 hour. Room temperature was attained and the reaction mixture was concentrated in vacuo. The mixture was partitioned between EtOAc and saturated NaHCO₃. The combined orgniac layers were washed with brine, dried over MgSO₄, and concentrated in vacuo to give (E)-6-chloro-3-methoxy-1-trityl-1H-pyrazolo[4,3-c]pyridine-4-carbaldehyde oxime. The products were carried forward without purification. MS: [M+H]+ m/z 469.

Step 2: 6-chloro-3-methoxy-1-trityl-1H-pyrazolo[4,3-c]pyridine-4-carbonitrile (42B)

6-chloro-3-methoxy-1-trityl-1H-pyrazolo[4,3-c]pyridine-4-carbaldehyde oxime (165 mg, 0.352 mmol) was taken up in DCM (6 ml) and triphenylphosphine (92 mg, 0.352 mmol) was added, followed by iodine (89 mg, 0.352 mmol). The resulting mixture was stirred at room temperature overnight. Saturated NaHCO₃ was added and the products extracted into EtOAc (×2). The combined organic extracts were washed with brine, dried over MgSO₄ and concentrated in vacuo. Purification of the residue by MPLC (0-25% EtOAc-hexanes) gave 6-chloro-3-methoxy-1-trityl-1H-pyrazolo[4,3-c]pyridine-4-carbonitrile (42B). ¹H NMR (500 MHz, DMSO-d₆) δ 7.37 (m, 9H), 7.13 (m, 6H), 5.89 (s, 1H), 3.40 (s, 3H).

Intermediate 43B

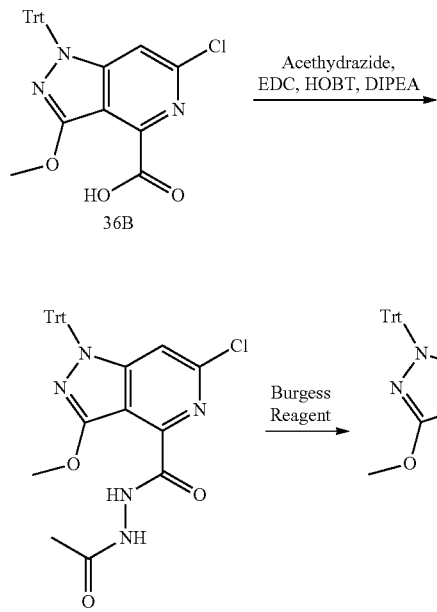

Step 1: N'-acetyl-6-chloro-3-methoxy-1-trityl-1H-pyrazolo[4,3-c]pyridine-4-carbohydrazide 6-chloro-3-methoxy-1-trityl-1H-pyrazolo[4,3-c]pyridine-4-carboxylic acid (36B, 96 mg, 0.204 mmol), acethydrazide (22.70 mg, 0.306 mmol), EDC (58.7 mg, 0.306 mmol), and HOBT (46.9 mg, 0.306 mmol) were taken up in DMF (2043 μl). DIPEA (143 μl, 0.817 mmol) was added and the reaction mixture was allowed to stir at rt overnight. The reaction was heated to 60 C for 1 hour. Saturated NH₄Cl and EtOAc were added. The products were extracted into EtOAc (2×). The combined organics were then washed with saturated NaHCO₃ and brine, then dried over MgSO₄, and concentrated in vacuo to give N'-acetyl-6-chloro-3-methoxy-1-trityl-1H-pyrazolo[4,3-c]pyridine-4-carbohydrazide. MS: [M+H]⁺ m/z 526.

Step 2: 2-(6-chloro-3-methoxy-1-trityl-1H-pyrazolo[4,3-c]pyridin-4-yl)-5-methyl-1,3,4-oxadiazole (43B)

N'-acetyl-6-chloro-3-methoxy-1-trityl-1H-pyrazolo[4,3-c]pyridine-4-carbohydrazide (48 mg, 0.091 mmol) was taken up in 1,4-dioxane (1.0 ml) and Burgess reagent (39.1 mg, 0.164 mmol) was added. The reaction mixture was stirred at 100° C. for 1 hour. Room temperature was attained. The reaction mixture was diluted with DCM and MeOH and was concentrated in vacuo while loading onto silica gel. The products were then purified by MPLC 0-25% EtOAc/hexanes to give 2-(6-chloro-3-methoxy-1-trityl-1H-pyrazolo[4,3-c]pyridin-4-yl)-5-methyl-1,3,4-oxadiazole (43B). MS: [M+H]⁺ m/z 508.

Intermediate 44B

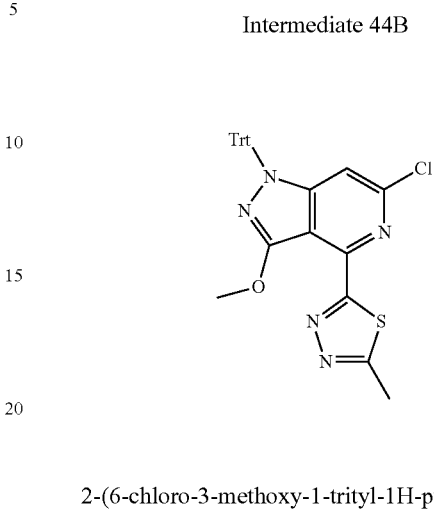

2-(6-chloro-3-methoxy-1-trityl-1H-pyrazolo[4,3-c]pyridin-4-yl)-5-methyl-1,3,4-thiadiazole N'-acetyl-6-chloro-3-methoxy-1-trityl-1H-pyrazolo[4,3-c]pyridine-4-carbohydrazide (48 mg, 0.091 mmol, see synthesis of intermediate 43B) was taken up in 1,4-dioxane (1.0 ml) and Lawesson's Reagent (27.7 mg, 0.068 mmol) was added. The reaction mixture was stirred at 100° C. for 1 hr. Room temperature was attained. The reaction mixture was diluted with DCM and MeOH and was concentrated in vacuo while loading onto silica gel. The products were purified by MPLC 5-30% EtOAc/hexanes to give 2-(6-chloro-3-methoxy-1-trityl-1H-pyrazolo[4,3-c]pyridin-4-yl)-5-methyl-1,3,4-thiadiazole (44B). MS: [M+H]⁺ m/z 524.

Intermediates 45B, 46B and 47B

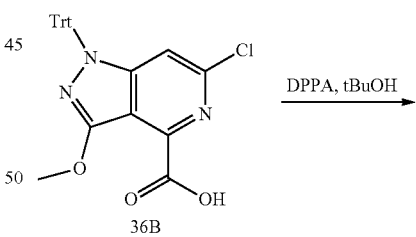

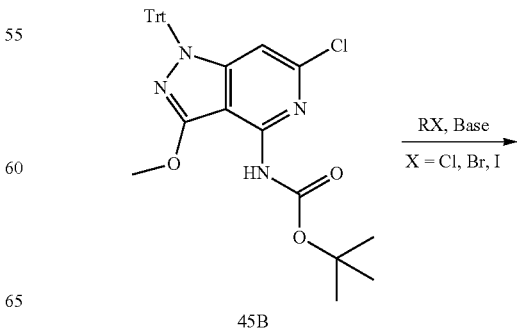

-continued

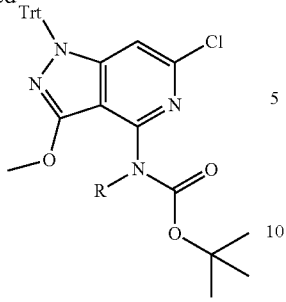

46B, R = Me
47B, R = Et

Step 1: tert-butyl(6-chloro-3-methoxy-1-trityl-1H-pyrazolo[4,3-c]pyridin-4-yl)carbamate (45B)

Triethylamine (135 µl, 0.968 mmol) followed by diphenylphosphoryl azide (163 µl, 0.754 mmol) were added to 6-chloro-3-methoxy-1-trityl-1H-pyrazolo[4,3-c]pyridine-4-carboxylic acid (Intermediate 36B, 288 mg, 0.613 mmol) in tBuOH (6.2 ml). The mixture was allowed to stir at 100° C. overnight. Room temperature was attained and the reaction mixture was diluted with water and extracted into EtOAc. The organic layers was washed with NaHCO$_3$, brine, dried over NaSO$_4$, and concentrated in vacuo. The material was loaded onto silica gel and purified by MPLC 0-25% EtOAc/hexanes to give tert-butyl(6-chloro-3-methoxy-1-trityl-1H-pyrazolo[4,3-c]pyridin-4-yl)carbamate (45B). MS: [M+H]$^+$ m/z 541.

Step 2: tert-butyl(6-chloro-3-methoxy-1-trityl-1H-pyrazolo[4,3-c]pyridin-4-yl)(methyl)carbamate (46B)

t-Butyl(6-chloro-3-methoxy-1-trityl-1H-pyrazolo[4,3-c]pyridin-4-yl)carbamate (45B, 86 mg, 0.159 mmol) was taken up in DMF (1.6 ml). Cs$_2$CO$_3$ (104 mg, 0.318 mmol) followed by iodomethane (10.93 µl, 0.175 mmol) were added. The reaction was allowed to stir at 60° C. for 2 hours. EtOAc and saturated NH$_4$Cl were added. The products were extracted into EtOAc (3×). The combined organic layers were washed with brine, dried over MgSO$_4$, and concentrated in vacuo to give tert-butyl(6-chloro-3-methoxy-1-trityl-1H-pyrazolo[4,3-c]pyridin-4-yl)(methyl)carbamate (46B). Reaction products were carrried forward without purification. MS: [M+H]$^+$ m/z 555.

In a similar manner, intermediate 45B was converted to 47B (tert-butyl(6-chloro-3-methoxy-1-trityl-1H-pyrazolo[4,3-c]pyridin-4-yl)(ethyl)carbamate). MS: [M+H]$^+$ m/z 569.

Intermediate 48B

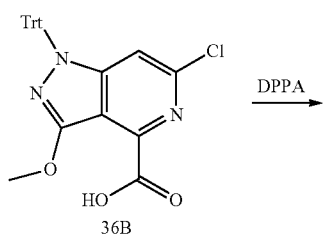

36B

-continued

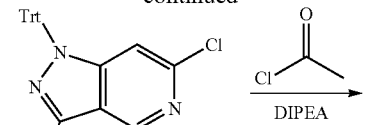

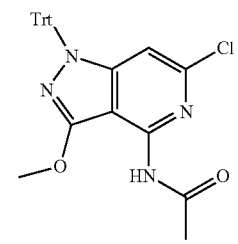

48B

Step 1: 6-chloro-3-methoxy-1-trityl-1H-pyrazolo[4,3-c]pyridin-4-amine

Triethylamine (370 µl, 2.66 mmol) followed by diphenylphosphoryl azide (447 µl, 2.068 mmol) were added to 6-chloro-3-methoxy-1-trityl-1H-pyrazolo[4,3-c]pyridine-4-carboxylic acid (36B, 790 mg, 1.681 mmol) in 1,4-dioxane (16.5 ml) a 100 ml roundbottom flask attached to a reflux condenser. The mixture was allowed to stir at 100° C. overnight. Room temperature was attained and the reaction mixture was diluted with water and extracted into EtOAc. The organic layer was washed with NaHCO$_3$, brine, dried over NaSO$_4$, and concentrated in vacuo. The material was loaded onto silica gel and purified by MPLC 0-25% EtOAc/hexanes gave 6-chloro-3-methoxy-1-trityl-1H-pyrazolo[4,3-c]pyridin-4-amine MS: [M+H]$^+$ m/z 441.

Step 2: N-(6-chloro-3-methoxy-1-trityl-1H-pyrazolo[4,3-c]pyridin-4-yl)acetamide (48B)

6-chloro-3-methoxy-1-trityl-1H-pyrazolo[4,3-c]pyridin-4-amine (115 mg, 0.261 mmol) was taken up in THF (2.6 ml) and cooled to 0° C. DIPEA (228 µl, 1.304 mmol) followed by acetyl chloride (93 µl, 1.304 mmol) was added. The mixture was allowed to stir, reaching room temperature overnight. EtOAc and saturated NH$_4$Cl were added. The products were extracted into EtOAc (3×). The combined organic layers were washed with brine, dried over Mg SO$_4$, and concentrated in vacuo to give N-(6-chloro-3-methoxy-1-trityl-1H-pyrazolo[4,3-c]pyridin-4-yl)acetamide (48B). Reaction products were carrried forward without purification. MS: [M+H]$^+$ m/z 483.

Intermediate 49B

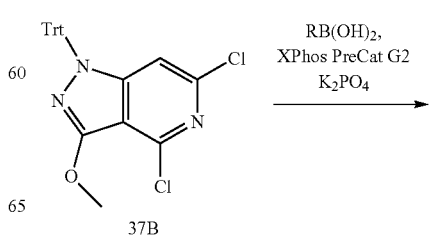

37B

147
-continued

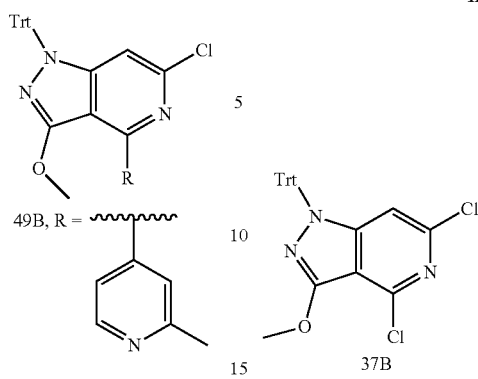

49B, R = [2-methylpyridin-4-yl]

6-chloro-3-methoxy-4-(2-methylpyridin-4-yl)-1-trityl-1H-pyrazolo[4,3-c]pyridine (49B)

4,6-dichloro-3-methoxy-1-trityl-1H-pyrazolo[4,3-c]pyridine (37B, 75 mg, 0.163 mmol), 2-methylpyridine-4-boronic acid pinacol ester (39.3 mg, 0.179 mmol), and Xphos Precatalyst $2^{nd}$ generation (10.25 mg, 0.013 mmol) were taken up in THF (1.1 ml). The mixture was evacuated and back-filled with $N_2$ gas (3×). Potassium phosphate tribasic (104 mg, 0.489 mmol) in Water (543 µl) (degassed) was then added to the reaction mixture. The reaction was allowed to stir at 60° C., for 1 hour. The reaction was then filtered through celite and loaded onto silica gel. The reaction mixture was purified by MPLC 0-50% EtOAc/DCM to give 6-chloro-3-methoxy-4-(2-methylpyridin-4-yl)-1-trityl-1H-pyrazolo[4,3-c]pyridine (49B). MS: [M+H]$^+$ m/z 517.

The following example were prepared following similar procedures described above for Intermediate 48B using the appropriate pyrazolopyridine and commercial boronic ester, which can be achieved by those of ordinary skill in the art of organic synthesis.

| Compound | Structure | IUPAC Name | Exact Mass [M + H]+ |
|---|---|---|---|
| 50B | 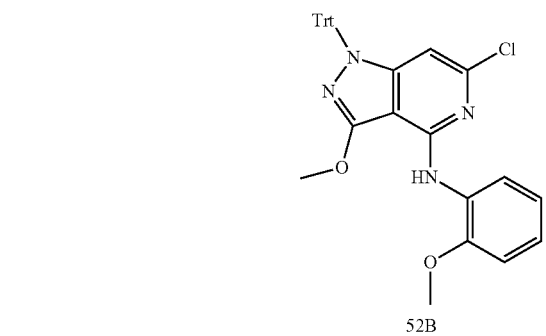 | 6-chloro-3-methoxy-4-(1-((2-(trimethylsilyl)ethoxy)methyl)-1H-pyrazol-4-yl)-1-trityl-1H-pyrazolo[4,3-c]pyridine | Calc'd 622, found 622 |
| 51B | 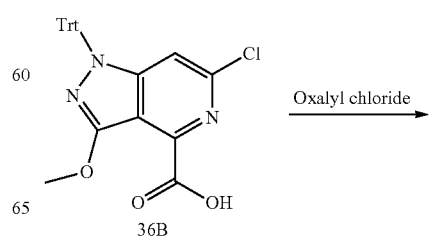 | 4-(6-chloro-3-methoxy-1-trityl-1H-pyrazolo[4,3-c]pyridin-4-yl)picolinaldehyde | Calc'd 531, found 531 |

148

Intermediate 52B

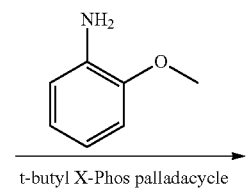

6-chloro-3-methoxy-N-(2-methoxyphenyl)-1-trityl-1H-pyrazolo[4,3-c]pyridin-4-amine (52B)

4,6-dichloro-3-methoxy-1-trityl-1H-pyrazolo[4,3-c]pyridine (Intermediate 37B, 100 mg, 0.217 mmol), 2-methoxyaniline (26.0 µl, 0.217 mmol), t-butyl X-Phos palladacycle (5.97 mg, 8.69 µmol) were combined in a 5 ml microwave vial. The vial was evacuated and backfilled (3×) with $N_2$ gas before adding THF (2.2 ml) and potassium t-butoxide (326 µl, 0.326 mmol). The reaction was allowed to stir at 80° C. for 2 hours. Room temperature was attained and the mixture was filtered through a celite frit and concentrated in vacuo while loading onto silica gel. Purifcation by MPLC 0-20% EtOAc/DCM gave 6-chloro-3-methoxy-N-(2-methoxyphenyl)-1-trityl-1H-pyrazolo[4,3-c]pyridin-4-amine (52B). MS: [M+H]$^+$ m/z 547.

Intermediate 53B

5-(6-chloro-3-methoxy-1-trityl-1H-pyrazolo[4,3-c]pyridin-4-yl)-1,3,4-oxadiazol-2(3H)-one

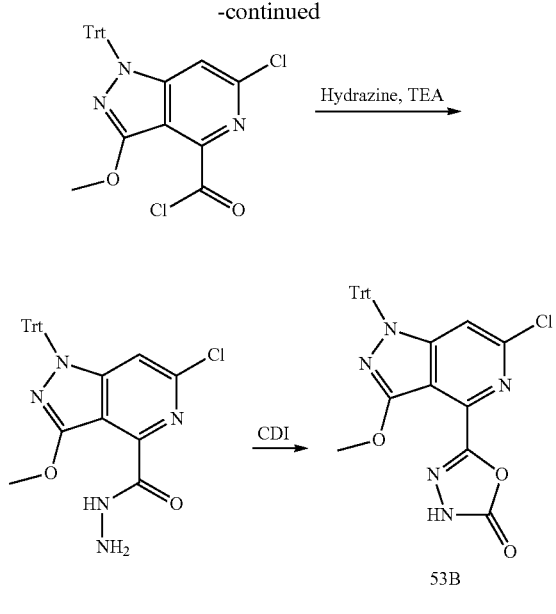

Step 1: 6-chloro-3-methoxy-1-trityl-1H-pyrazolo[4,3-c]pyridine-4-carbonyl chloride 6-chloro-3-methoxy-1-trityl-1H-pyrazolo[4,3-c]pyridine-4-carboxylic acid (Intermediate 36B, 440 mg, 0.936 mmol) was taken up in DCM (9.32 ml). DMF (93 nl) was added and the reaction was cooled to 0° C. Oxalyl chloride (164 µl, 1.873 mmol) was added and the mixture was allowed to stir for 1 hr eventually reaching room temperature. The mixture was concentrated in vacuo and then further dried under high vacuum. The residue was carried forward without further purification. MS: [M+H]+ m/z 484 (Methyl ester formed LCMS, sample prepared in MeOH).

Step 2: 6-chloro-3-methoxy-1-trityl-1H-pyrazolo[4,3-c]pyridine-4-carbohydrazide 6-chloro-3-methoxy-1-trityl-1H-pyrazolo[4,3-c]pyridine-4-carbonyl chloride (240 mg, 0.491 mmol) was taken up in acetonitrile (4 ml). TEA (0.205 ml, 1.474 mmol) was added followed by the dropwise addition of hydrazine (0.046 ml, 1.474 mmol). The reaction was allowed to stir at rt overnight. The reaction mixture was concentrated in vacuo. The mixture was then resuspended in EtOAc and saturated NH4Cl was added. The products were extracted into EtOAc (3×) and the combined organics were washed with brine, dried over MgSO4, and concentrated in vacuo to give 6-chloro-3-methoxy-1-trityl-1H-pyrazolo[4,3-c]pyridine-4-carbohydrazide. The products were carried forward without further purification. MS: [M+H]+ m/z 484.

Step 3: 5-(6-chloro-3-methoxy-1-trityl-1H-pyrazolo[4,3-c]pyridin-4-yl)-1,3,4-oxadiazol-2(3H)-one (53B)

6-chloro-3-methoxy-1-trityl-1H-pyrazolo[4,3-c]pyridine-4-carbohydrazide (122 mg, 0.252 mmol) and CDI (49.1 mg, 0.303 mmol) were taken up in 1,4-dioxane (3.0 ml). The reaction mixture was stirred at 100° C. overnight. The reaction mixture was loaded onto silica gel and purification by MPLC 0-50% EtAOc/hexanes gave 5-(6-chloro-3-methoxy-1-trityl-1H-pyrazolo[4,3-c]pyridin-4-yl)-1,3,4-oxadiazol-2(3H)-one (53B). MS: [M+H]+ m/z 510.

Intermediate 54B

Step 1: 5-(6-chloro-3-methoxy-1-trityl-1H-pyrazolo[4,3-c]pyridin-4-yl)oxazole (54B)

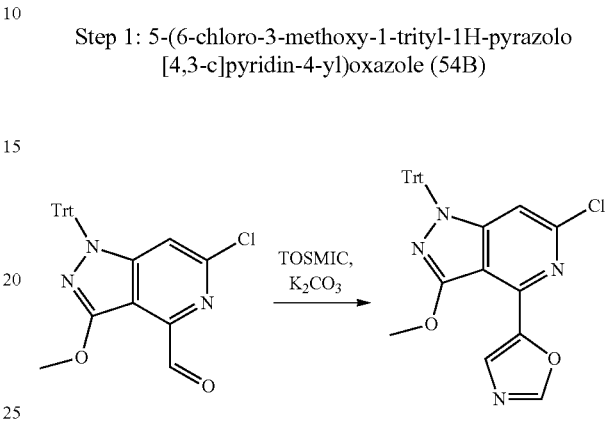

6-chloro-3-methoxy-1-trityl-1H-pyrazolo[4,3-c]pyridine-4-carbaldehyde (Intermediate 11B, 200 mg, 0.441 mmol), potassium carbonate (63.9 mg, 0.463 mmol) and 1-(isocyanomethylsulfonyl)-4-methylbenzene (90 mg, 0.463 mmol) were taken up in MeOH (1.8 ml) and were stirred at 65° C. overnight. The mixture was concentrated in vacuo while loading onto silica gel and purificied by MPLC 0-25% EtOAc/DCM to give 5-(6-chloro-3-methoxy-1-trityl-1H-pyrazolo[4,3-c]pyridin-4-yl)oxazole (54B). MS: [M+H]+ m/z 493.

Intermediate 55B 1-((1-hydroxycyclopentyl)(phenyl)methyl)urea

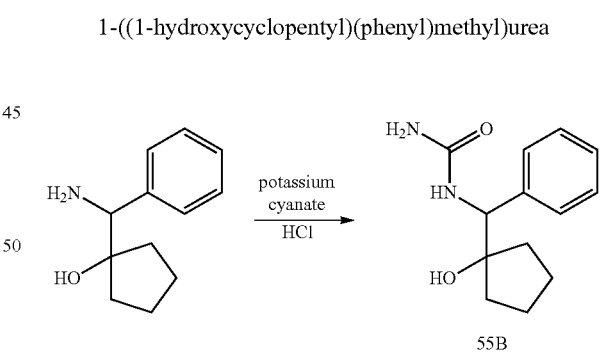

A 5 mL microwave vial was charged with 1-(amino(phenyl)methyl)cyclopentanol (191.3 mg, 1.0 mmol), potassium cyanate (406 mg, 5.00 mmol), water (1 ml) and hydrochloric acid (6N, 0.5 ml, 3.00 mmol). The vial was capped and heated to 80° C. for 1 h in a microwave. The contents of the vial were cooled to room temperature, the formed precipitate filtered, washed through with water and dried in a vacuum oven (40° C.). The crude 1-((1-hydroxycyclopentyl)(phenyl)methyl)urea was taken forward without further purification. MS: [M+H]+ m/z 235.

151

Intermediate 56B 6-chloro-3,4-dimethoxy-1-trityl-1H-pyrazolo[4,3-c]pyridine

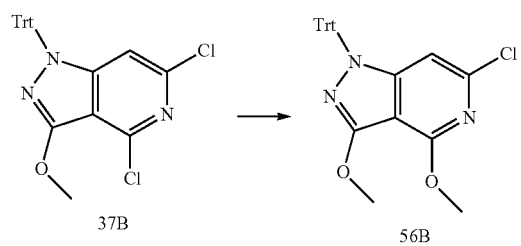

4,6-dichloro-3-methoxy-1-trityl-1H-pyrazolo[4,3-c]pyridine (Intermediate 37B, 100 mg, 0.217 mmol) in THF (1086 μl) was treated with sodium methoxide (4.6 N in MeOH) (51.9 μl, 0.239 mmol) and stirred @ 40° C. for 1 h. Reaction was diluted in with DCM and concentrated in vacuo on silica. Material was purified by normal phase column chromotography eluting with Hex/EtOAc (0-10%) affording 6-chloro-3,4-dimethoxy-1-trityl-1H-pyrazolo[4,3-c]pyridine (56B, 86 mg, 0.189 mmol, 87% yield) as a white foam. MS: [M+H]$^+$ m/z 456.

Intermediate 57B (6-chloro-3-methoxy-1-trityl-1H-pyrazolo[4,3-c]pyridin-4-yl)methyl methylcarbamate

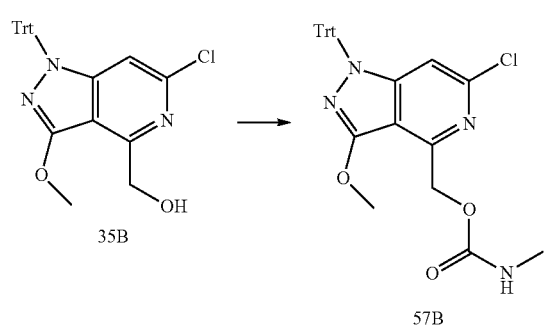

A solution of (6-chloro-3-methoxy-1-trityl-1H-pyrazolo[4,3-c]pyridin-4-yl)methanol (Intermediate 35B, 200 mg, 0.439 mmol) and methylaminoformyl chloride (45.1 mg, 0.483 mmol) in DCM (1462 μl) was treated with DIEA (153 μl, 0.877 mmol) and stirred @ 35° C. for 1 h Reaction was dilluted in with DCM and concentrated in vacuo on silica. Material was purified by normal phase column chromotography eluting with Hex/EtOAc (0-40%) affording (6-chloro-3-methoxy-1-trityl-1H-pyrazolo[4,3-c]pyridin-4-yl)methyl

152 methylcarbamate (172 mg, 0.335 mmol, 76% yield) as a white solid. MS: [M+H]$^+$ m/z 513.

Intermediates 58B and 59B

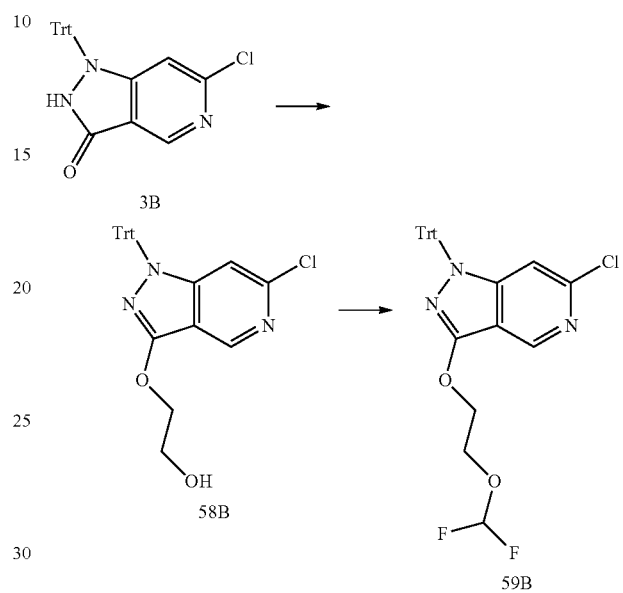

Step 1: 2-((6-chloro-1-trityl-1H-pyrazolo[4,3-c]pyridin-3-yl)oxy)ethanol (58B)

In a manner similar to that previously described (e.g. Scheme 3 and the synthesis of Intermediate 20B/Step 6), 6-Chloro-1-trityl-1H-pyrazolo[4,3-c]pyridin-3(2H)-one (3B) was converted to 2-((6-chloro-1-trityl-1H-pyrazolo[4,3-c]pyridin-3-yl)oxy)ethanol (cesium carbonate, 2-bromoethanol, DMF, 2 h, 45° C., 80% yield). MS: [M+H]$^+$ m/z 456.

Step 2: 6-chloro-3-(2-(difluoromethoxy)ethoxy)-1-trityl-1H-pyrazolo[4,3-c]pyridine (59B)

A mixture of 2-((6-chloro-1-trityl-1H-pyrazolo[4,3-c]pyridin-3-yl)oxy)ethanol (58B, 500 mg, 0.987 mmol) and copper(I) iodide (282 mg, 1.480 mmol) in acetonitrile (2861 μl) were degassed (evacuated and back filled w/Argon). 2,2-difluoro-2-(fluorosulfonyl)acetic acid (153 μl, 1.480 mmol) was added, degassed, and heated at 80° C. for 30 min. Reaction was quenched with water (1 mL), diluted with EtOAc and filtered through a celite pug. The solution was concentrated in vacuo on silica. Material was purified by normal phase column chromatography eluting with Hex/EtOAc (0-20%) affording 6-chloro-3-(2-(difluoromethoxy)ethoxy)-1-trityl- 1H-pyrazolo[4,3-c]pyridine (59B, 277 mg, 0.547 mmol, 55.5% yield) as a white crystalline solid. MS: [M+H]+ m/z 506.

Intermediates 60B, 61B, and 62B

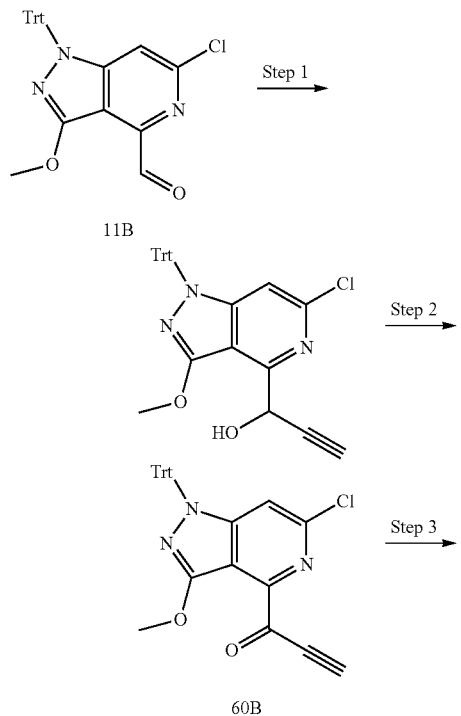

Step 1: 1-(6-chloro-3-methoxy-1-trityl-1H-pyrazolo [4,3-c]pyridin-4-yl)prop-2-yn-1-ol 6-chloro-3-methoxy-1-trityl-1H-pyrazolo[4,3-c]pyridine-4-carbaldehyde (11B, 250 mg, 0.551 mmol) was added to a oven dried 20 mL microwave vial, charged with THF (10 ml), degassed under nitrogen and cooled to −78° C. To the mixture was added ethynylmagnesium chloride (1.322 ml, 0.661 mmol) dropwise and the reaction was slowly warmed to rt over 30 minutes. The reaction was quenched with saturated ammonium chloride, extracted 3×20 mL EtOAc, washed with brine, dried over sodium sulfate filtered and concentrated in vacuo to provide crude 1-(6-chloro-3-methoxy-1-trityl-1H-pyrazolo[4,3-c]pyridin-4-yl)prop-2-yn-1-ol (257 mg, 0.535 mmol, 97% yield) which was used without further purification. MS: [M+H]+ m/z 480.

Step 2: 1-(6-chloro-3-methoxy-1-trityl-1H-pyrazolo [4,3-c]pyridin-4-yl)prop-2-yn-1-one (60B)

1-(6-chloro-3-methoxy-1-trityl-1H-pyrazolo[4,3-c]pyridin-4-yl)prop-2-yn-1-ol (257 mg, 0.535 mmol) was dissolved in DCM (5 ml) charged with Dess-MartinPeriodinane (341 mg, 0.803 mmol) and allowed to stir for 2 h at rt. The reaction was charged with 5 mL 1N sodium thiosulfate and 5 mL saturated sodium bicarbonate and allowed to stir for 15 minutes. The organic layer was separated and the solvents were concentrated in vacuo. Purification on silica gel, 10-50% EtOAc/hexanes gave 1-(6-chloro-3-methoxy-1-trityl-1H-pyrazolo[4,3-c]pyridin-4-yl)prop-2-yn-1-one (60B, 137 mg, 0.287 mmol, 53.5% yield). MS: [M+H]+ m/z 478.

Step 3: 6-chloro-3-methoxy-4-(1-methyl-1H-pyrazol-3-yl)-1-trityl-1H-pyrazolo[4,3-c]pyridine (61B) and 6-chloro-3-methoxy-4-(1-methyl-1H-pyrazol-5-yl)-1-trityl-1H-pyrazolo[4,3-c]pyridine (62B)

1-(6-chloro-3-methoxy-1-trityl-1H-pyrazolo[4,3-c]pyridin-4-yl)prop-2-yn-1-one (69 mg, 0.144 mmol) was dissolved in Ethanol, charged with methylhydrazine (9.12 µl, 0.173 mmol) and allowed to stir at 80° C. for 2 h and then at rt over the weekend. Reaction was complete by LC/MS but showed a mixture of two isomers ~3:1 by NMR. The solvents were removed in vacuo and the residue was taken on crude. MS: [M+H]+ m/z 506.

Intermediate 63B 6-chloro-3-methoxy-4-(2-methylpyrimidin-4-yl)-1-trityl-1H-pyrazolo[4,3-c]pyridine

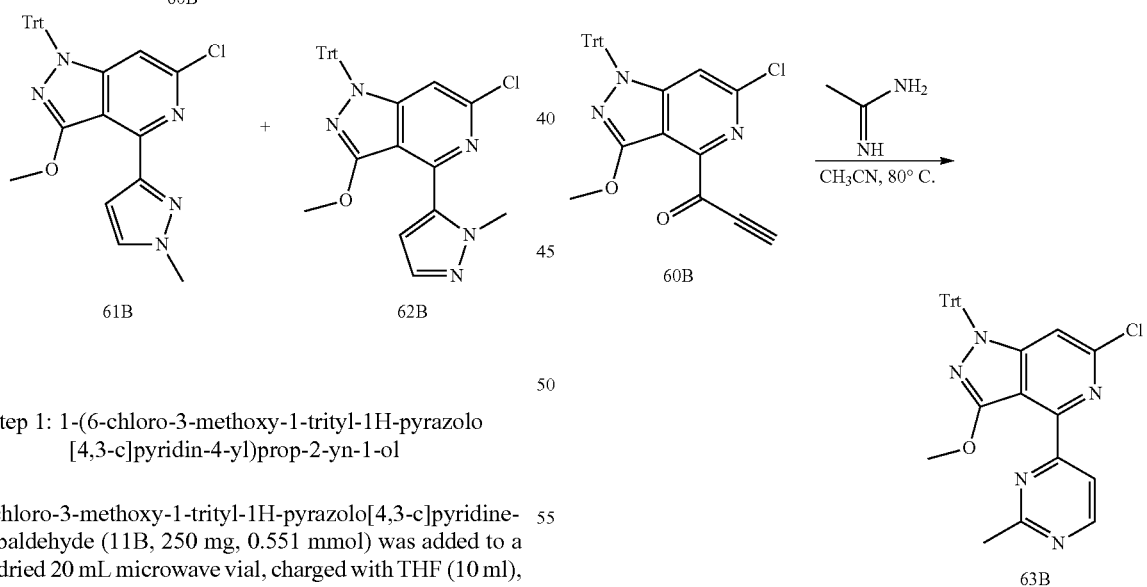

1-(6-chloro-3-methoxy-1-trityl-1H-pyrazolo[4,3-c]pyridin-4-yl)prop-2-yn-1-one (60B, 63 mg, 0.132 mmol) was dissolved in acetonitrile (3 ml), charged with acetamidine hydrochloride (14.95 mg, 0.158 mmol) and sodium carbonate (34.9 mg, 0.330 mmol) and allowed to stir at 70° C. for 2 h. The solution was filtered through a syringe filter and the solvents were removed in vacuo. The residue was purified on silica gel 2-25% EtOAc/DCM to afford 6-chloro-3-methoxy- 4-(2-methylpyrimidin-4-yl)-1-trityl-1H-pyrazolo[4,3-c]pyridine (63B, 58 mg, 0.112 mmol, 85% yield). MS: [M+H]+ m/z 518.

Intermediate 64B 6-chloro-4-(difluoromethyl)-3-methoxy-1-trityl-1H-pyrazolo[4,3-c]pyridine

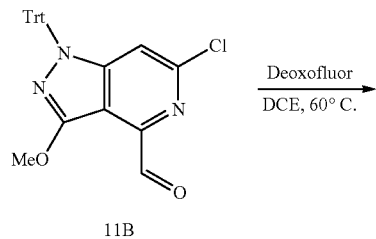

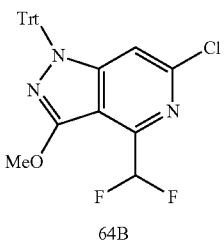

6-chloro-3-methoxy-1-trityl-1H-pyrazolo[4,3-c]pyridine-4-carbaldehyde (11B, 1 g, 2.203 mmol) was taken up in DCE (5 ml), charged with deoxofluor (4.06 ml, 22.03 mmol) and heated to 60° C. overnight. The reaction was poured into ice cold sat. aq sodium bicarbonate, extracted 2×25 mL DCM and the combined organics were washed with brine, dried over sodium sulfate, filtered and purified on silica gel to provide 6-chloro-4-(difluoromethyl)-3-methoxy-1-trityl-1H-pyrazolo[4,3-c]pyridine (64B, 150 mg, 0.315 mmol, 14.31% yield MS: [M+H]+ m/z 476.

Intermediate 65B 6-chloro-3-((trifluoromethyl)thio)-1-trityl-1H-pyrazolo[4,3-c]pyridine

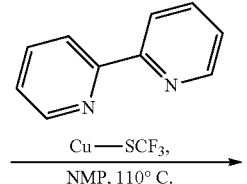
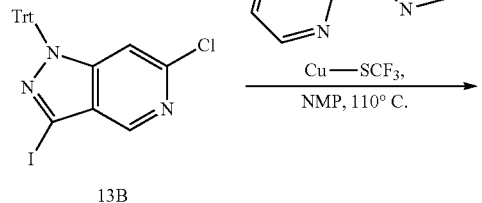

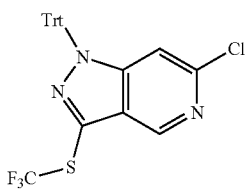

6-chloro-3-iodo-1-trityl-1H-pyrazolo[4,3-c]pyridine (13B, 1000 mg, 1.917 mmol), ((trifluoromethyl)thio)copper (592 mg, 2.87 mmol) and 2,2'-bipyridine (449 mg, 2.87 mmol) were added to a 20 mL microwave tube, evacuated under nitrogen and charged with NMP (6388 μl). The reaction was heated to 110° C. for 1 h. The reaction was poured into 20 mL water and the brown precipitate was filtered, dissolved in 10 mL DCM and loaded onto a 100 g SNAP silica column. Purification (10-40% EtOAc) gave 6-chloro-3-((trifluoromethyl)thio)-1-trityl-1H-pyrazolo[4,3-c]pyridine (65B, 755 mg, 1.522 mmol, 79% yield) as a pale pink solid. MS: [M+H]+ m/z 518.

Intermediates 66B and 67B

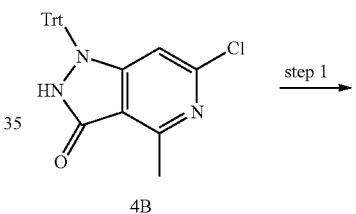

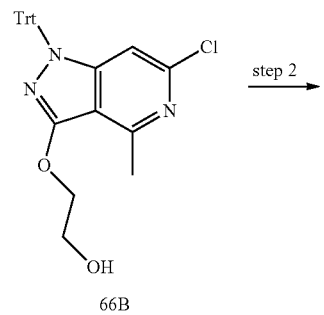

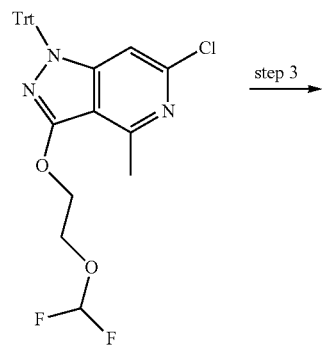

-continued

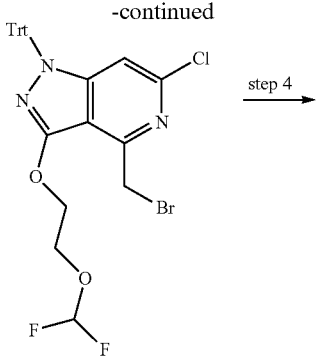

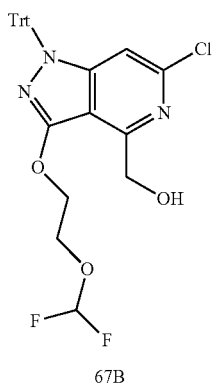

67B

Step 1: 2-((6-chloro-4-methyl-1-trityl-1H-pyrazolo[4,3-c]pyridin-3-yl)oxy)ethanol In a manner similar to that previously described (e.g. Scheme 3/Step 1 and the synthesis of Intermediate 20B/Step 6), 6-chloro-4-methyl-1-trityl-1H-pyrazolo[4,3-c]pyridin-3(2H)-one (4B) was reacted with 2-bromoethanol (K₂CO₃, DMF. 2-bromoethanol. RT, 18 h) to provide 2-((6-chloro-4-methyl-1-trityl-1H-pyrazolo[4,3-c]pyridin-3-yl)oxy)ethanol (66B). MS: [M+H]⁺ m/z 470.

Step 2: 6-chloro-3-(2-(difluoromethoxy)ethoxy)-4-methyl-1-trityl-1H-pyrazolo[4,3-c]pyridine In a manner similar to that previously described (e.g. synthesis of Intermediate 59B/Step 2), 2-((6-chloro-4-methyl-1-trityl-1H-pyrazolo[4,3-c]pyridin-3-yl)oxy)ethanol was reacted with 2,2-difluoro-2-(fluorosulfonyl)acetic acid (copper(I) iodide, acetonitrile, 80° C. 30 min) to provide 6-chloro-3-(2-(difluoromethoxy)ethoxy)-4-methyl-1-trityl-1H-pyrazolo[4,3-c]pyridine 59% yield) as a white crystalline solid. MS: [M+H]⁺ m/z 520.

Steps 3-4: 6-chloro-3-(2-(difluoromethoxy)ethoxy)-1-trityl-1H-pyrazolo[4,3-c]pyridine-4-carbaldehyde In a manner similar to that previously described (e.g. synthesis of Intermediate 11B/Steps 2-3), 6-chloro-3-(2-(difluoromethoxy)ethoxy)-4-methyl-1-trityl-1H-pyrazolo[4,3-c]pyridine was treated sequentially with NBS/AlBN (CCl₄, 70° C., 18 h, 68% yield) and then NMO (THF, RT, 18 h, 82% yield) to provide 6-chloro-3-(2-(difluoromethoxy)ethoxy)-1-trityl-1H-pyrazolo[4,3-c]pyridine-4-carbaldehyde. MS: [M+H]⁺ m/z 534.

Step 5: (6-chloro-3-(2-(difluoromethoxy)ethoxy)-1-trityl-1H-pyrazolo[4,3-c]pyridin-4-yl)methanol In a manner similar to that previously described (e.g. synthesis of Intermediate 35B), 6-chloro-3-(2-(difluoromethoxy)ethoxy)-1-trityl-1H-pyrazolo[4,3-c]pyridine-4-carbaldehyde was treated with NaBH₄ (DCM-MeOH, 1 h, RT, 75% yield) to provide (6-chloro-3-(2-(difluoromethoxy)ethoxy)-1-trityl-1H-pyrazolo[4,3-c]pyridin-4-yl)methanol (67B). MS: [M+H]⁺ m/z 536.

Intermediate 68B 6-chloro-3-phenoxy-1-trityl-1H-pyrazolo[4,3-c]pyridine

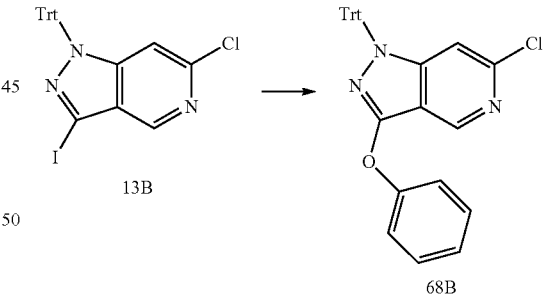

6-chloro-3-iodo-1-trityl-1H-pyrazolo[4,3-c]pyridine (160 mg, 0.307 mmol), phenol (43.3 mg, 0.460 mmol), copper(i) iodide (5.84 mg, 0.031 mmol), cesium carbonate (200 mg, 0.613 mmol) and N,N-dimethylglycine (9.49 mg, 0.092 mmol) were taken up in 1,4-Dioxane (2.0 ml) in a 25 mL microwave vial. The vial was evacuated and back-filled with N₂ (3×) and the reaction mixture was allowed to stir at 100° C. for 6 h. NH₄OH was added into the reaction mixture and extracted with EtOAc (2×). The combined organic extracts were washed with water, brine and dried over Na₂SO₄. After concentration the crude product was purified on silical gel 0-50% EtOAc/Hexanes and yielded 6-chloro-3-phenoxy-1- trityl-1H-pyrazolo[4,3-c]pyridine (120 mg, 0.246 mmol, 80% yield). MS: [M+H]$^+$ m/z 488.

Intermediate 69B 1-(4-((2-hydroxypropoxy)methyl)-3-methoxy-1-trityl-1H-pyrazolo[4,3-c]pyridin-6-yl)-3-((S)-1-phenylethyl)urea

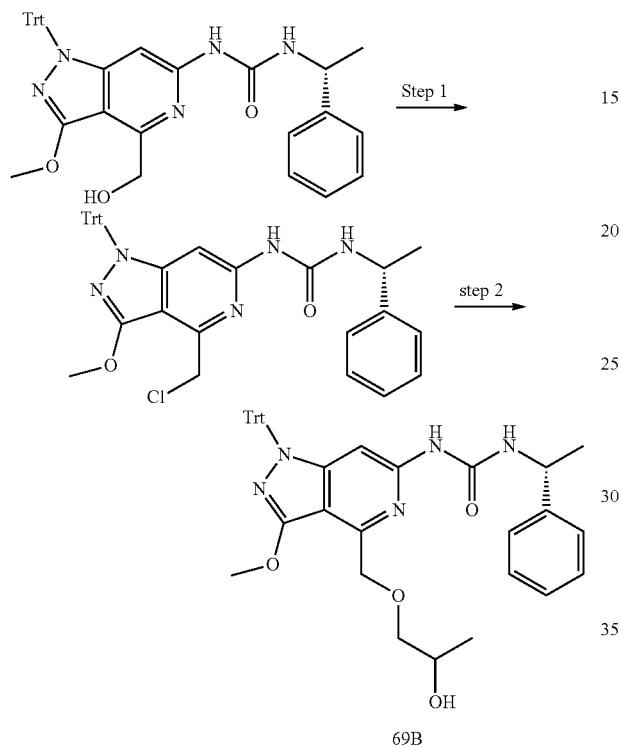

69B

Step 1: (R)-1-(4-(chloromethyl)-3-methoxy-1-trityl-1H-pyrazolo[4,3-c]pyridin-6-yl)-3-(1-phenylethyl)urea A solution of (R)-1-(4-(hydroxymethyl)-3-methoxy-1-trityl-1H-pyrazolo[4,3-c]pyridin-6-yl)-3-(1-phenylethyl)urea (800 mg, 1.371 mmol, see Example 109) and thionyl chloride (0.110 ml, 1.508 mmol) in DCM (15 ml) was allowed to stir at 50° C. for 18 h. Removed the solvent by reduced pressure and the residue was purified on silical gel 0-100% EtOAc/Hexane and yielded (R)-1-(4-(chloromethyl)-3-methoxy-1-trityl-1H-pyrazolo[4,3-c]pyridin-6-yl)-3-(1-phenylethyl)urea (402 mg, 0.668 mmol, 49% yield). MS: [M+H]$^+$ m/z 602.

Step 2: 1-(4-((2-hydroxypropoxy)methyl)-3-methoxy-1-trityl-1H-pyrazolo[4,3-c]pyridin-6-yl)-3-((S)-1-phenylethyl)urea To the solution of (S)-1-(4-(chloromethyl)-3-methoxy-1-trityl-1H-pyrazolo[4,3-c]pyridin-6-yl)-3-(1-phenylethyl) urea (50 mg, 0.083 mmol) in THF (1.0 ml) was added sodium hydride (4.98 mg, 0.125 mmol). The resulting reaction mixture was allowed to stir at rt for 10 min before (S)-1-(4-(chloromethyl)-3-methoxy-1-trityl-1H-pyrazolo[4,3-c]pyridin-6-yl)-3-(1-phenylethyl)urea (50 mg, 0.083 mmol) was added into the above solution. The reaction solution was stirred for 2 h at rt. EtOAc and water was added into the mixture and the organic layer was collected and washed by water and brine. After drying over Na$_2$SO$_4$, the solution was concentrated to give 1-(4-((2-hydroxypropoxy)methyl)-3-methoxy-1-trityl-1H-pyrazolo[4,3-c]pyridin-6-yl)-3-((S)-1-phenylethyl)urea (53.3 mg, 0.083 mmol, 100% yield) without purification. MS: [M+H]$^+$ m/z 642.

Intermediates 70R and 71R

Step 1: Synthesis of 3-methoxy-1-trityl-1H-pyrazolo[4,3-c]pyridin-6-amine (70B)

Under inert atmosphere, to a solution of 6-chloro-3-methoxy-1-trityl-1H-pyrazolo[4,3-c]pyridine (0.4 g, 0.94 mmol, see Example 40/Step 1) in anhydrous THF (10 mL) was added SPHOS Pd precatalyst (0.07 g, 0.094 mmol) and LiHMDS (1.0 M solution in Toluene, 1.9 mL, 1.9 mmol) and the contents were heated at 70° C. After 5 h, the reaction mixture was brought back to ambient temperature and quenched with NH$_4$Cl (5 mL). The organic contents were then extracted with EtOAc and the volatiles were then removed under reduced pressure. The residue thus obtained was purified by a flash column chromatography to afford the title compound. H$^1$NMR (CDCl$_3$, 400 MHz): δ 8.38 (s, 1H), 7.29-7.26 (m, 15H), 5.03 (s, 1H), 4.50 (bs, 2H), 3.93 (s, 3H).

Step 2: Synthesis of (S)-methyl 2-(3-(3-methoxy-1-trityl-1H-pyrazolo[4,3-c]pyridin-6-yl)ureido)-2-phenylacetate (71B)

To a solution of 3-methoxy-1-trityl-1H-pyrazolo[4,3-c]pyridin-6-amine (0.2 g, 0.49 mmol) in anhydrous 1,4-dioxane (5 mL) was added CDI (0.4 g, 2.46 mmol) followed by the addition of imidazole (0.16 g, 2.46 mmol) and the contents were stirred at ambient temperature. After 16 h (the completion of the reaction was confirmed by quenching small aliquot of the reaction mixture with MeOH and mass obtained corresponds to the methyl carbamate) DIPEA (0.32 g, 2.46 mmol) and (S)-methyl 2-amino-2-phenylacetate 4 (0.15 g, 0.92 mmol) were added and stirred. After 14 h, the reaction mixture was quenched with $H_2O$ and the organic contents were extracted with EtOAc (3×20 mL), dried over anhydrous $Na_2SO_4$ and concentrated. The residue thus obtained was purified by preparative HPLC to afford the title compound. MS: $[M+H]^+$ m/z 598.

EXAMPLES

The following examples were prepared according to scheme 1 method A.

Example 1

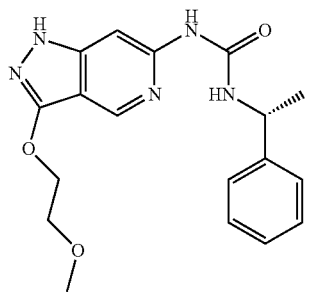 [SMILES: COCCOc1n[nH]c2cc(NC(=O)N[C@H](C)c3ccccc3)ncc12]

1-[3-(2-Methoxyethoxy)-1H-pyrazolo[4,3-c]pyridin-6-yl]-3-[(1R)-1-phenylethyl]urea

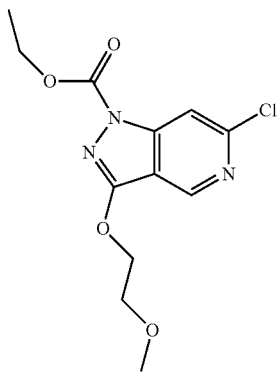 [SMILES: CCOC(=O)n1nc(OCCOC)c2cnc(Cl)cc21]

Step 1: Ethyl 6-chloro-3-(2-methoxyethoxy)-1H-pyrazolo[4,3-c]pyridine-1-carboxylate To a solution of ethyl 6-chloro-3-oxo-2,3-dihydro-1H-pyrazolo[4,3-c]pyridine-1-carboxylate (Intermediate 1B; 1 g, 4.14 mmol) in DMF (20 mL) was added cesium carbonate (18.45 g, 56.6 mmol) and the reaction mixture was stirred at room temperature for 10 min. Then, 2-bromomethyl methyl ether (3.59 mL, 37.7 mmol) was added and the reaction mixture was heated at 60° C. for 4 h. The reaction mixture was cooled to 0° C., water was slowly added, and then stirred at 0° C. for 30 min. The reaction mixture was filtered and solid washed with water to afford ethyl 6-chloro-3-(2-methoxyethoxy)-1H-pyrazolo[4,3-c]pyridine-1-carboxylate, which was carried onto the next step without further purification. MS ESI calc'd. For $C_{12}H_{14}ClN_3O_4$ $[M+1]^+$ 300. found 228.

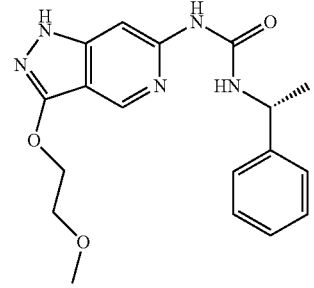 [SMILES: COCCOc1n[nH]c2cc(NC(=O)N[C@H](C)c3ccccc3)ncc12]

Step 2: 1-[3-(2-Methoxyethoxy)-1H-pyrazolo[4,3-c]pyridin-6-yl]-3-[(1R)-1-phenylethyl]urea Ethyl 6-chloro-3-(2-methoxyethoxy)-1H-pyrazolo[4,3-c]pyridine-1-carboxylate (100 mg, 0.334 mmol), (R)-1-(1-phenylethyl)urea (68.5 mg, 0.417 mmol), bippyphos (15.21 mg, 0.030 mmol), $Pd_2(dba)_3$ (7.4 mg, 8.08 μmol), and tripotassium phosphate (106 mg, 0.500 mmol) were taken up in DME (1.6 mL) in a 5 mL microwave vial. The vial was evacuated and back-filled with $N_2$ (×3) and the reaction stirred at 85° C. for 16 h. Room temperature was attained, the reaction mixture filtered through Celite, eluting with MeOH, and the filtrate was concentrated in vacuo. The residue was taken up in MeOH (3 mL) and $K_2CO_3$ (118 mg, 0.854 mmol) was added. The resulting mixture was stirred at room temperature for 3 h. The mixture was filtered through Celite and the filtrate concentrated in vacuo. The crude reaction mixture was purified by flash chromatography (0-10% MeOH-DCM) followed by purification by mass triggered, reverse phase prep-HPLC. The fractions containing pure product were concentrated in vacuo, lyophilized, and dissolved in MeOH. The solution was filtered through a PS—$HCO_3$ cartridge, eluting with MeOH. The filtrate was concentrated in vacuo to give (R)-1-(3-(2-methoxyethoxy)-1H-pyrazolo[4,3-c]pyridin-6-yl)-3-(1-phenylethyl)urea. MS ESI calc'd. For $C_{18}H_{21}N_5O_3$ $[M+1]^+$ 356. found 356. $^1H$ NMR (500 MHz, DMSO-$d_6$) δ 11.98 (s, 1H), 8.92 (s, 1H), 8.55 (s, 1H), 7.75 (br s, 1H), 7.48 (s, 1H), 7.34-7.31 (m, 4H), 7.25-7.20 (m, 1H), 4.88-4.82 (m, 1H), 4.81-4.39 (m, 2H), 3.71-3.69 (m, 2H), 3.30 (s, 3H), 1.39 (d, J=7.0 Hz, 3H).

Example 2

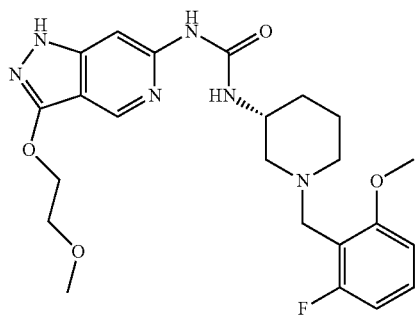

1-[(3R)-1-(2-Fluoro-6-methoxybenzyl)piperidin-3-yl]-3-[3-(2-methoxyethoxy)-1H-pyrazolo[4,3-c]pyridin-6-yl]urea

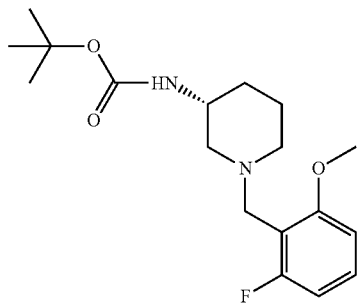 [SMILES: COc1cccc(F)c1CN1CCC[C@@H](NC(=O)OC(C)(C)C)C1]

Step 1: (R)-tert-Butyl(1-(2-fluoro-6-methoxybenzyl)piperidin-3-yl)carbamate 2-(Bromomethyl)-1-fluoro-3-methoxybenzene (3.19 g, 14.57 mmol), (R)-3-(tert-butoxycarbonylamino)piperidine (3.0 g, 12.67 mmol), and K$_2$CO$_3$ (2.63 g, 19.01 mmol) were taken up in DMF (25 mL) in a 50 mL flask. The reaction mixture was stirred at room temperature for 2 h. The mixture was diluted with EtOAc (100 mL), washed with water (50 mL, ×2), dried over MgSO$_4$, filtered, and the solvent evaporated in vacuo. The residue was purified by flash chromatography (6-50% EtOAc/hexanes) to give (R)-tert-butyl 1-(2-fluoro-6-methoxybenzyl)piperidin-3-ylcarbamate. MS ESI calc'd. For C$_{18}$H$_{22}$FN$_2$O$_3$ [M+1]$^+$ 339. found 339.

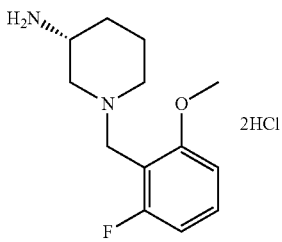 [SMILES: COc1cccc(F)c1CN1CCC[C@@H](N)C1]

Step 2: (R)-1-(2-Fluoro-6-methoxybenzyl)piperidin-3-amine hydrochloride

To (R)-tert-butyl 1-(2-fluoro-6-methoxybenzyl)piperidin-3-ylcarbamate (3.52 g, 10.40 mmol) was added methanolic HCl (3 N, 50 mL) and the reaction mixture was heated to reflux for 3 h. The volatiles were removed in vacuo to afford (R)-1-(2-fluoro-6-methoxybenzyl)-piperidin-3-amine hydrochloride. MS ESI calc'd. For C$_{13}$H$_{19}$FN$_2$O [M+1]$^+$ 239. found 239.

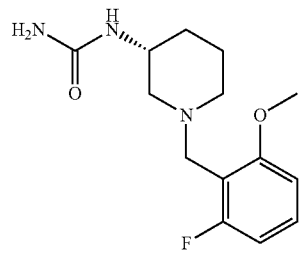 [SMILES: COc1cccc(F)c1CN1CCC[C@@H](NC(N)=O)C1]

Step 3: (R)-1-(1-(2-Fluoro-6-methoxybenzyl)piperidin-3-yl)urea (R)-1-(1-(2-Fluoro-6-methoxybenzyl)piperidin-3-yl)urea was prepared using the same procedure described for (R)-1-(1-(4-Fluorophenyl)ethyl)urea (Intermediate 15B). MS ESI calc'd. For C$_{14}$H$_{20}$FN$_3$O$_2$ [M+1]$^+$ 282. found 282.

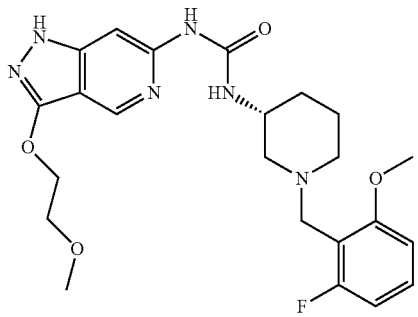 [SMILES: COCCOc1n[nH]c2cc(NC(=O)N[C@@H]3CCCN(Cc4c(F)cccc4OC)C3)ncc12]

Step 4: (R)-1-(1-(2-Fluoro-6-methoxybenzyl)piperidin-3-yl)-3-(3-(2-methoxyethoxy)-1H-pyrazolo[4,3-c]pyridin-6-yl)urea Ethyl 6-chloro-3-(2-methoxyethoxy)-1H-pyrazolo[4,3-c]pyridine-1-carboxylate (Example 1, Step 1; 35 mg, 0.117 mmol), (R)-1-(1-(2-fluoro-6-methoxybenzyl)piperidin-3-yl) urea (32.9 mg, 0.117 mmol), bippyphos (5.92 mg, 0.012 mmol), Pd$_2$(dba)$_3$ (5.35 mg, 5.84 µmol), and tripotassium phosphate (37.2 mg, 0.175 mmol) were taken up in DME (350 µL) in a 5 mL microwave vial. The vial was evacuated and back-filled with N$_2$ (×3) and the reaction was stirred at 85° C. for 16 h. Room temperature was attained, MeOH (817 µL) and K$_2$CO$_3$ (32.3 mg, 0.234 mmol) were added, and the resulting mixture stirred at room temperature for 1 h. The mixture was filtered, the filtrate concentrated in vacuo, dissolved in DMF (1.5 mL), and filtered. The residue was purified via mass triggered, reverse phase HPLC. Fractions containing pure product were combined and concentrated in vacuo to afford (R)-1-(1-(2-fluoro-6-methoxybenzyl)piperidin-3-yl)-3-(3-(2-methoxyethoxy)-1H-pyrazolo[4,3-c]pyridin-6-yl)urea as the trifluoroacetic acid salt. MS ESI calc'd. For C$_{23}$H$_{29}$FN$_6$O$_4$ [M+1]$^+$ 473. found 473. $^1$H NMR (500 MHz, DMSO-d$_6$) δ 12.09 (s, 1H), 9.53 (m, 1H), 9.17 (s, 1H), 8.57 (s, 1H), 7.53 (m, 1H), 7.46 (s, 1H), 7.02 (d, 1H), 6.96 (t, 1H), 4.41 (m, 2H), 4.30 (m, 2H), 3.96 (m, 1H), 3.88 (s, 3H), 3.70 (m, 2H), 3.46 (m, 1H), 3.34 (m, 1H), 3.30 (s, 3H), 2.98 (m, 1H), 2.88 (m, 1H), 1.91 (m, 2H), 1.73 (m, 1H), 1.42 (m, 1H).

Examples 3-25 (Table 3) were prepared according to Scheme 1 Method A following similar procedures described for Examples 1 and 2 using the appropriate halide and commercial or synthesized ureas (prepared using the same procedure as Intermediates 15B and 16B), which can be achieved by those of ordinary skill in the art of organic synthesis. Examples 11-25 were obtained as the trifluoroacetic acid salt.

TABLE 3

| Example | Structure | IUPAC Name | Exact Mass [M + H]+ |
|---|---|---|---|
| 3 | 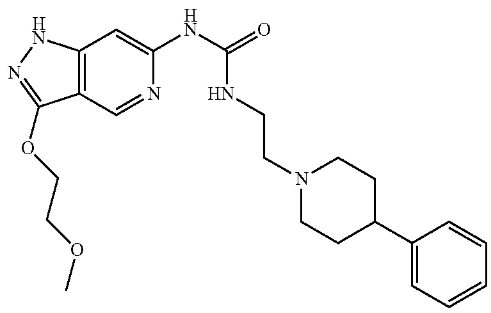 [SMILES: COCCOc1n[nH]c2cc(NC(=O)NCCN3CCC(c4ccccc4)CC3)ncc12] | 1-(3-(2-methoxyethoxy)-1H-pyrazolo[4,3-c]pyridin-6-yl)-3-(2-(4-phenylpiperidin-1-yl)ethyl)urea | Calc'd 439, found 439 |
| 4 | 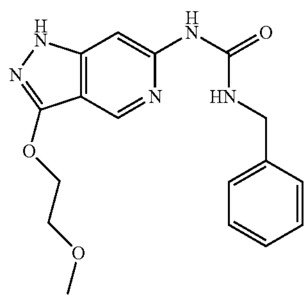 [SMILES: COCCOc1n[nH]c2cc(NC(=O)NCc3ccccc3)ncc12] | 1-benzyl-3-[3-(2-methoxyethoxy)-1H-pyrazolo[4,3-c]pyridin-6-yl]urea | Calc'd 342, found 342 |
| 5 | 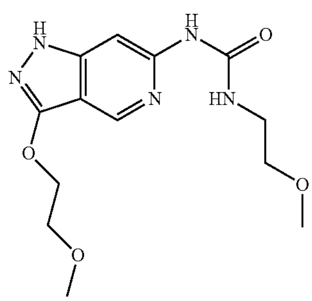 [SMILES: COCCNC(=O)Nc1cc2[nH]nc(OCCOC)c2cn1] | 1-[3-(2-methoxyethoxy)-1H-pyrazolo[4,3-c]pyridin-6-yl]-3-(2-methoxyethyl)urea | Calc'd 310, Found 310 |
| 6 | 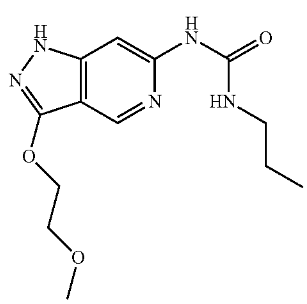 [SMILES: CCCNC(=O)Nc1cc2[nH]nc(OCCOC)c2cn1] | 1-[3-(2-methoxyethoxy)-1H-pyrazolo[4,3-c]pyridin-6-yl]-3-propylurea | Calc'd 294, Found 294 |
| 7 | 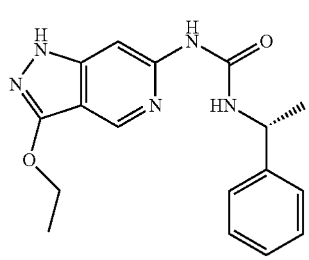 [SMILES: CCOc1n[nH]c2cc(NC(=O)N[C@H](C)c3ccccc3)ncc12] | 1-(3-ethoxy-1H-pyrazolo[4,3-c]pyridin-6-yl)-3-[(1R)-1-phenylethyl]urea | Calc'd 326, Found 326 |

TABLE 3-continued

| Example | Structure | IUPAC Name | Exact Mass [M + H]+ |
|---|---|---|---|
| 8 | 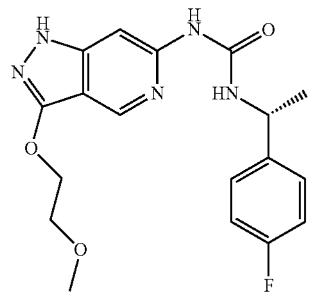 [SMILES: COCCOc1n[nH]c2cc(NC(=O)N[C@H](C)c3ccc(F)cc3)ncc12] | 1-[(1R)-1-(4-fluorophenyl)ethyl]-3-[3-(2-methoxyethoxy)-1H-pyrazolo[4,3-c]pyridin-6-yl]urea | Calc'd 374, Found 374 |
| 9 | 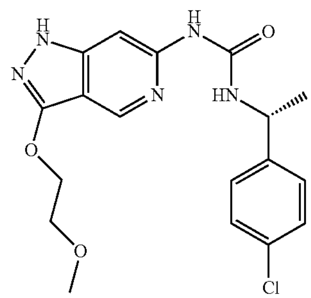 [SMILES: COCCOc1n[nH]c2cc(NC(=O)N[C@H](C)c3ccc(Cl)cc3)ncc12] | 1-[(1R)-1-(4-chlorophenyl)ethyl]-3-[3-(2-methoxyethoxy)-1H-pyrazolo[4,3-c]pyridin-6-yl]urea | Calc'd 390, Found 390 |
| 10 | 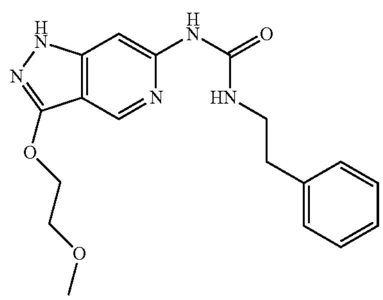 [SMILES: COCCOc1n[nH]c2cc(NC(=O)NCCc3ccccc3)ncc12] | 1-[3-(2-methoxyethoxy)-1H-pyrazolo[4,3-c]pyridin-6-yl]-3-(2-phenylethyl)urea | Calc'd 356, Found 356 |
| 11 | 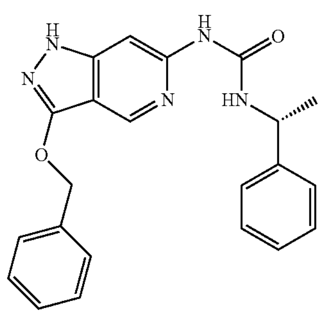 [SMILES: C[C@@H](NC(=O)Nc1cc2[nH]nc(OCc3ccccc3)c2cn1)c1ccccc1] | 1-[3-(benzyloxy)-1H-pyrazolo[4,3-c]pyridin-6-yl]-3-[(1R)-1-phenylethyl]urea | Calc'd 388, Found 388 |
| 12 | 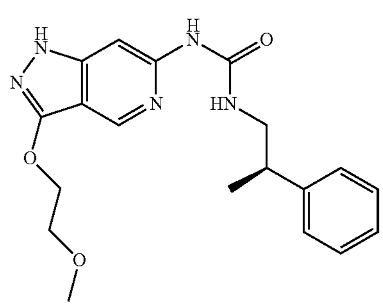 [SMILES: COCCOc1n[nH]c2cc(NC(=O)NC[C@H](C)c3ccccc3)ncc12] | 1-[3-(2-methoxyethoxy)-1H-pyrazolo[4,3-c]pyridin-6-yl]-3-[(2R)-2-phenylpropyl]-urea | Calc'd 370, Found 370 |

TABLE 3-continued

| Example | Structure | IUPAC Name | Exact Mass [M + H]+ |
|---|---|---|---|
| 13 | 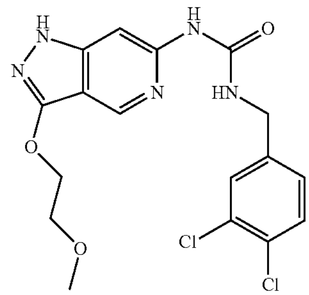 [SMILES: COCCOc1n[nH]c2cc(NC(=O)NCc3ccc(Cl)c(Cl)c3)ncc12] | 1-(3,4-dichlorobenzyl)-3-[3-(2-methoxyethoxy)-1H-pyrazolo[4,3-c]pyridin-6-yl]urea | Calc'd 410, Found 410 |
| 14 | 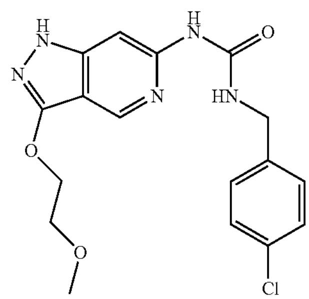 [SMILES: COCCOc1n[nH]c2cc(NC(=O)NCc3ccc(Cl)cc3)ncc12] | 1-(4-chlorobenzyl)-3-[3-(2-methoxyethoxy)-1H-pyrazolo[4,3-c]pyridin-6-yl]urea | Calc'd 376, Found 376 |
| 15 | 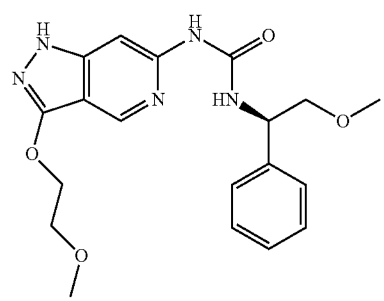 [SMILES: COCCOc1n[nH]c2cc(NC(=O)N[C@@H](COC)c3ccccc3)ncc12] | 1-[3-(2-methoxyethoxy)-1H-pyrazolo[4,3-c]pyridin-6-yl]-3-[(1R)-2-methoxy-1-phenylethyl]urea | Calc'd 386, Found 386 |
| 16 | 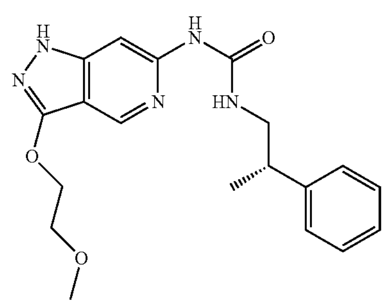 [SMILES: COCCOc1n[nH]c2cc(NC(=O)NC[C@@H](C)c3ccccc3)ncc12] | 1-[3-(2-methoxyethoxy)-1H-pyrazolo[4,3-c]pyridin-6-yl]-3-[(2S)-2-phenylpropyl]urea | Calc'd 370, Found 370 |
| 17 | 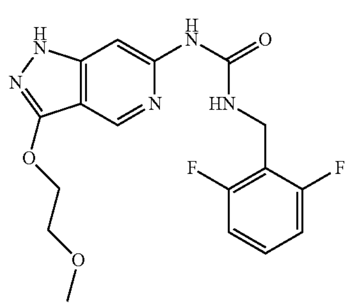 [SMILES: COCCOc1n[nH]c2cc(NC(=O)NCc3c(F)cccc3F)ncc12] | 1-(2,6-difluorobenzyl)-3-[3-(2-methoxyethoxy)-1H-pyrazolo[4,3-c]pyridin-6-yl]urea | Calc'd 378, Found 378 |

TABLE 3-continued

| Example | Structure | IUPAC Name | Exact Mass [M + H]+ |
|---------|-----------|------------|---------------------|
| 18 | 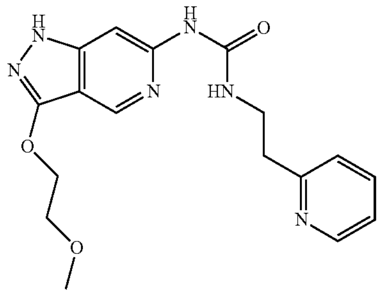 [SMILES: COCCOc1n[nH]c2cc(NC(=O)NCCc3ccccn3)ncc12] | 1-[3-(2-methoxyethoxy)-1H-pyrazolo[4,3-c]pyridin-6-yl]-3-(2-pyridin-2-ylethyl)urea | Calc'd 357, Found 357 |
| 19 | 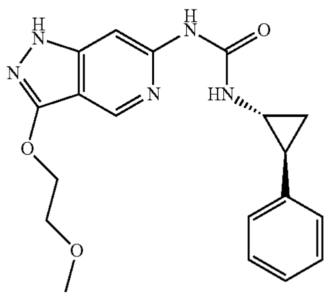 [SMILES: COCCOc1n[nH]c2cc(NC(=O)N[C@@H]3C[C@H]3c3ccccc3)ncc12] | 1-[3-(2-methoxyethoxy)-1H-pyrazolo[4,3-c]pyridin-6-yl]-3-[(1R,2S)-2-phenyl-cyclopropyl]urea | Calc'd 368, Found 368 |
| 20 | 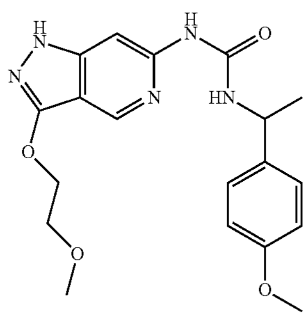 [SMILES: COCCOc1n[nH]c2cc(NC(=O)NC(C)c3ccc(OC)cc3)ncc12] | 1-[3-(2-methoxyethoxy)-1H-pyrazolo[4,3-c]pyridin-6-yl]-3-[1-(4-methoxyphenyl)ethyl]-urea | Calc'd 386, Found 386 |
| 21 | 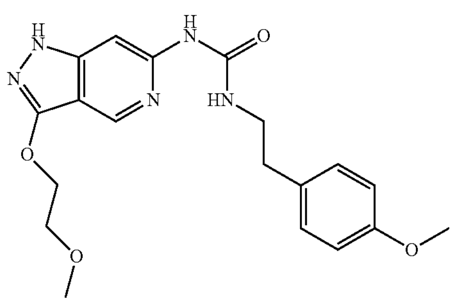 [SMILES: COCCOc1n[nH]c2cc(NC(=O)NCCc3ccc(OC)cc3)ncc12] | 1-[3-(2-methoxyethoxy)-1H-pyrazolo[4,3-c]pyridin-6-yl]-3-[2-(4-methoxyphenyl)ethyl]-urea | Calc'd 386, Found 386 |
| 22 | 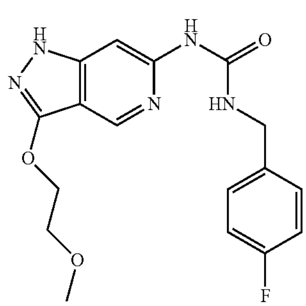 [SMILES: COCCOc1n[nH]c2cc(NC(=O)NCc3ccc(F)cc3)ncc12] | 2-(4-fluorobenzyl)-3-[3-(2-methoxyethoxy)-1H-pyrazolo[4,3-c]pyridin-6-yl]urea | Calc'd 360, Found 360 |

TABLE 3-continued

| Example | Structure | IUPAC Name | Exact Mass [M + H]+ |
|---|---|---|---|
| 23 | 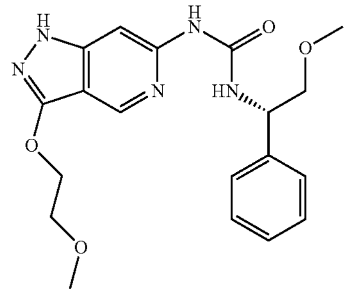 [SMILES: COCCOc1n[nH]c2cc(NC(=O)N[C@H](COC)c3ccccc3)ncc12] | 1-[3-(2-methoxyethoxy)-1H-pyrazolo[4,3-c]pyridin-6-yl]-3-[(1S)-2-methoxy-1-phenylethyl]urea | Calc'd 386, Found 386 |
| 24 | 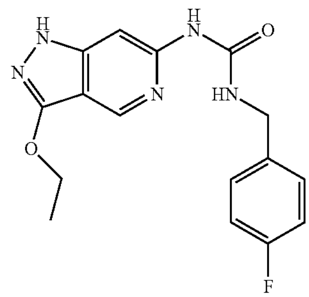 [SMILES: CCOc1n[nH]c2cc(NC(=O)NCc3ccc(F)cc3)ncc12] | 1-(3-ethoxy-1H-pyrazolo[4,3-c]pyridin-6-yl)-3-(4-fluorobenzyl)urea | Calc'd 330, Found 330 |
| 25 | 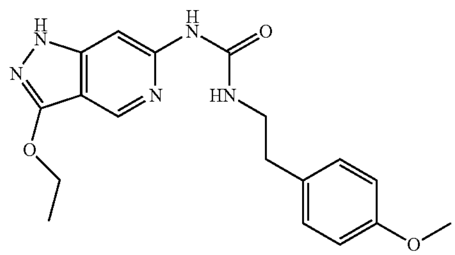 [SMILES: CCOc1n[nH]c2cc(NC(=O)NCCc3ccc(OC)cc3)ncc12] | 1-(3-ethoxy-1H-pyrazolo[4,3-c]pyridin-6-yl)-3-[2-(4-methoxyphenyl)ethyl]urea | Calc'd 356, Found 356 |

Examples 26-34 were prepared according to scheme 1 method B.

Example 26

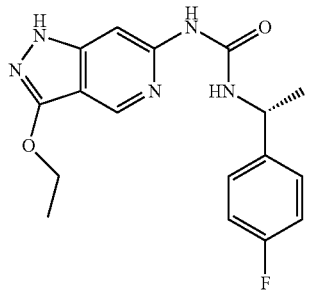 [SMILES: CCOc1n[nH]c2cc(NC(=O)N[C@H](C)c3ccc(F)cc3)ncc12]

(R)-1-(3-Ethoxy-1H-pyrazolo[4,3-c]pyridin-6-yl)-3-(1-(4-fluorophenyl)ethyl)urea

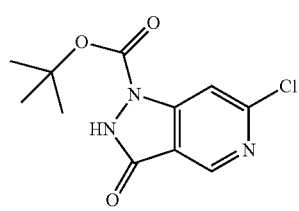 [SMILES: CC(C)(C)OC(=O)n1[nH]c(=O)c2cnc(Cl)cc21]

Step 1: tert-Butyl 6-chloro-3-oxo-2,3-dihydro-1H-pyrazolo[4,3-c]pyridine-1-carboxylate To a solution of 6-chloro-1H-pyrazolo[4,3-c]pyridin-3(2H)-one (Intermediate 1B, Step 2: 1.0 g, 5.90 mmol) and triethylamine (0.822 mL, 5.90 mmol) in DCM (9 mL) was added di-tert-butyl dicarbonate (1.506 mL, 6.49 mmol). The reaction mixture was stirred at room temperature for 5 h. Solvents were concentrated in vacuo and the crude mixture was purified via flash chromatography (0-5%-10% MeOH/DCM) to give tert-butyl 6-chloro-3-oxo-2,3-dihydro-1H-pyrazolo[4,3-c]pyridine-1-carboxylate. MS ESI calc'd. For $C_{11}H_{12}ClN_3O_3$ [M+1]$^+$ 270. found 270.

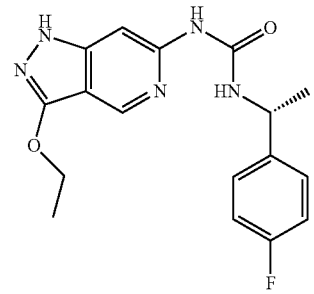

Step 3: (R)-1-(3-Ethoxy-1H-pyrazolo[4,3-c]pyridin-6-yl)-3-(1-(4-fluorophenyl)ethyl)urea tert-Butyl 6-chloro-3-ethoxy-1H-pyrazolo[4,3-c]pyridine-1-carboxylate (77 mg, 0.259 mmol), (R)-1-(1-(4-fluorophenyl)ethyl)urea (Intermediate 15B; 60 mg, 0.329 mmol), bippyphos (15.6 mg, 0.031 mmol), Pd$_2$(dba)$_3$ (9.6 mg, 10.48 µmol), and tripotassium phosphate (82 mg, 0.388 mmol) were taken up in DME (1.3 mL) in a 5 mL microwave vial. The vial was evacuated and back-filled with N$_2$ (×3) and the reaction stirred at 85° C. for 18 h. Room temperature was attained, the reaction mixture was filtered through Celite, eluting with MeOH, and the filtrate was concentrated in vacuo. The residue was dissolved in TFA (2 mL) and the solution stirred at room temperature for 3 h. The solvent was removed in vacuo, saturated NaHCO$_3$ was added, and the products extracted into EtOAc (×2). The combined organic extracts were washed with brine, dried over Na$_2$SO$_4$, filtered, and concentrated in vacuo. Purification of the residue by flash chromatography (0-100% EtOAc-DCM) gave (R)-1-(3-ethoxy-1H-pyrazolo[4,3-c]pyridin-6-yl)-3-(1-(4-fluorophenyl)ethyl)urea. MS ESI calc'd. For $C_{17}H_{18}FN_5O_2$ [M+1]$^+$ 344. found 344. $^1$H NMR (500 MHz, DMSO-d$_6$) δ $^1$H NMR (500 MHz, DMSO-d$_6$) δ 11.94 (s, 1H), 8.91 (s, 1H), 8.53 (s, 1H), 7.76 (br s, 1H), 7.46 (s, 1H), 7.39-7.33 (m, 2H), 7.15 (t, J=8.8 Hz, 2H), 4.89-4.82 (m, 1H), 4.33 (q, J=7.0 Hz, 2H), 1.41-1.34 (m, 6H).

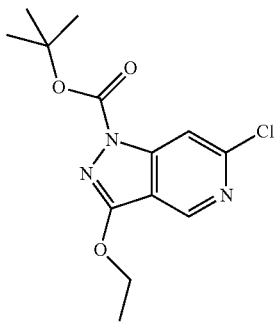 [SMILES: CCOc1nn(C(=O)OC(C)(C)C)c2cc(Cl)ncc12]

Step 2: tert-Butyl 6-chloro-3-ethoxy-1H-pyrazolo[4,3-c]pyridine-1-carboxylate tert-Butyl 6-chloro-3-oxo-2,3-dihydro-1H-pyrazolo[4,3-c]pyridine-1-carboxylate (1.19 g, 4.41 mmol), iodoethane (0.715 mL, 8.85 mmol), and cesium carbonate (4.36 g, 13.38 mmol) were stirred in DMF (15 mL) at room temperature for 16 h. Water was added and the products extracted into EtOAc (×2). The combined organic extracts were washed with brine, dried over Na$_2$SO$_4$, filtered, and concentrated in vacuo. Purification of the residue by flash chromatography (6-50% EtOAc-hexanes) gave tert-butyl 6-chloro-3-ethoxy-1H-pyrazolo[4,3-c]pyridine-1-carboxylate. MS ESI calc'd. For $C_{13}H_{16}ClN_3O_3$ [M+1]$^+$ 298. found 298.

Examples 27-34 (Table 4) were prepared according to Scheme 1 Method B following similar procedures described for Example 26 using the appropriate pyrazolopyridine (Intermediates 1B-2B), halide, and commercial or synthesized ureas (prepared using the same procedure as Intermediates 15B and 16B), which can be achieved by those of ordinary skill in the art of organic synthesis. Examples 27-34 were obtained as the trifluoroacetic acid salt.

TABLE 4

| Example | Structure | IUPAC Name | Exact Mass [M + H]+ |
|---|---|---|---|
| 27 | 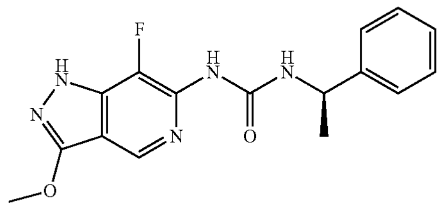 [SMILES: COc1n[nH]c2c(F)c(NC(=O)N[C@H](C)c3ccccc3)ncc12] | 1-(7-fluoro-3-methoxy-1H-pyrazolo[4,3-c]pyridin-6-yl)-3-phenylethyl]urea | Calc'd 330, Found 330 |

TABLE 4-continued

| Example | Structure | IUPAC Name | Exact Mass [M + H]+ |
|---|---|---|---|
| 28 | 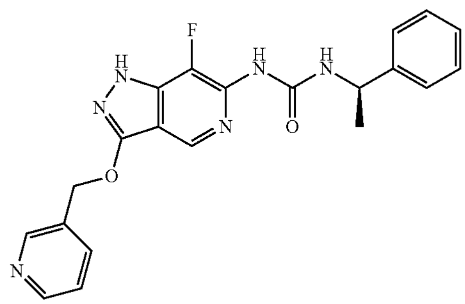 [SMILES: C[C@@H](NC(=O)Nc1ncc2c(OCc3cccnc3)n[nH]c2c1F)c1ccccc1] | 1-[7-fluoro-3-(pyridin-3-ylmethoxy)-1H-pyrazolo[4,3-c]pyridin-6-yl]-3-[(1R)-1-phenylethyl]urea | Calc'd 407, Found 407 |
| 29 | 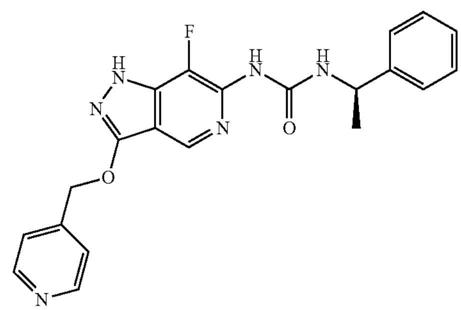 [SMILES: C[C@@H](NC(=O)Nc1ncc2c(OCc3ccncc3)n[nH]c2c1F)c1ccccc1] | 1-[7-fluoro-3-(pyridin-4-ylmethoxy)-1H-pyrazolo[4,3-c]pyridin-6-yl]-3-[(1R)-1-phenylethyl]urea | Calc'd 407, Found 407 |
| 30 | 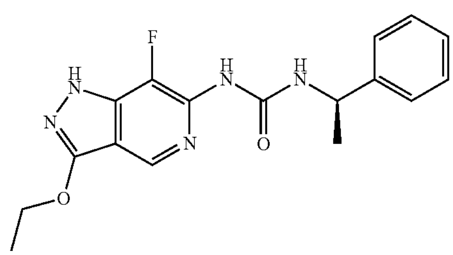 [SMILES: CCOc1n[nH]c2c(F)c(NC(=O)N[C@H](C)c3ccccc3)ncc12] | 1-(3-ethoxy-7-fluoro-1H-pyrazolo[4,3-c]pyridin-6-yl)-3-[(1R)-1-phenylethyl]urea | Calc'd 344, Found 344 |
| 31 | 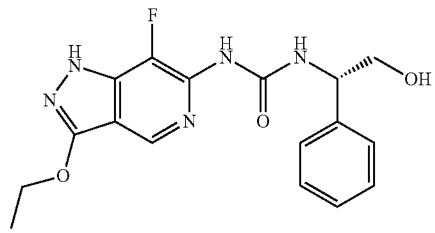 [SMILES: CCOc1n[nH]c2c(F)c(NC(=O)N[C@H](CO)c3ccccc3)ncc12] | 1-(3-ethoxy-7-fluoro-1H-pyrazolo[4,3-c]pyridin-6-yl)-3-[(1S)-2-hydroxy-1-phenylethyl]urea | Calc'd 360, Found 360 |
| 32 | 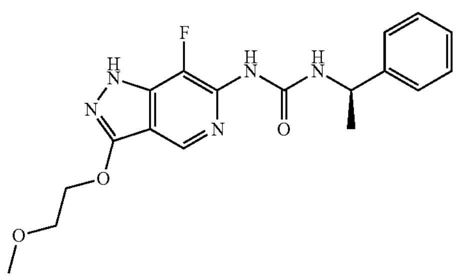 [SMILES: COCCOc1n[nH]c2c(F)c(NC(=O)N[C@H](C)c3ccccc3)ncc12] | 1-[7-fluoro-3-(2-methoxyethoxy)-1H-pyrazolo[4,3-c]pyridin-6-yl]-3-[(1R)-1-phenylethyl]urea | Calc'd 374, Found 374 |

TABLE 4-continued

| Example | Structure | IUPAC Name | Exact Mass [M + H]+ |
|---|---|---|---|
| 33 | 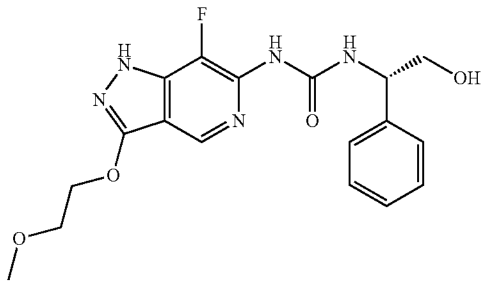 [SMILES: COCCOc1n[nH]c2c(F)c(NC(=O)N[C@H](CO)c3ccccc3)ncc12] | 1-[7-fluoro-3-(2-methoxyethoxy)-1H-pyrazolo[4,3-c]pyridin-6-yl]-3-[(1S)-2-hydroxy-1-phenylethyl]urea | Calc'd 390, Found 390 |
| 34 | 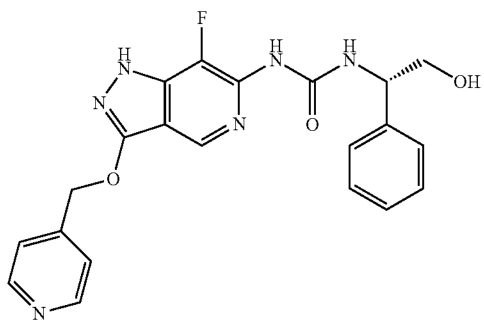 [SMILES: O=C(Nc1ncc2c(OCc3ccncc3)n[nH]c2c1F)N[C@H](CO)c1ccccc1] | 1-[7-fluoro-3-(pyridin-4-ylmethoxy)-1H-pyrazolo[4,3-c]pyridin-6-yl]-3-[(1S)-2-hydroxy-1-phenylethyl]urea | Calc'd 423, Found 423 |

Examples 35-39 were prepared according to scheme 2.

Example 35

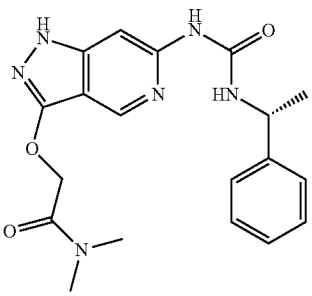 [SMILES: C[C@@H](NC(=O)Nc1cc2[nH]nc(OCC(=O)N(C)C)c2cn1)c1ccccc1]

N,N-Dimethyl-2-{[6-({[(1R)-1-phenylethyl]carbamoyl}amino)-1H-pyrazolo[4,3-c]pyridin-3-yl]oxy}acetamide

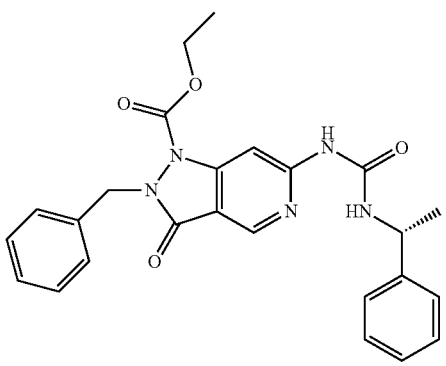 [SMILES: CCOC(=O)n1c2cc(NC(=O)N[C@H](C)c3ccccc3)ncc2c(=O)n1Cc1ccccc1]

Step 1: (R)-Ethyl 2-benzyl-3-oxo-6-(3-(1-phenylethyl)ureido)-2,3-dihydro-1H-pyrazolo[4,3-c]pyridine-1-carboxylate Ethyl 2-benzyl-6-chloro-3-oxo-2,3-dihydro-1H-pyrazolo[4,3-c]pyridine-1-carboxylate (Intermediate 12B; 71 mg, 0.214 mmol), (R)-1-(1-phenylethyl)urea (45 mg, 0.274 mmol), bippyphos (13.2 mg, 0.026 mmol), Pd$_2$(dba)$_3$ (5.4 mg, 5.90 µmol), and tripotassium phosphate (74 mg, 0.349 mmol) were taken up in DME (2 mL) in a 5 mL microwave vial. The vial was evacuated and back-filled with N$_2$ (×3) and the reaction stirred at 85° C. for 2 h. Room temperature was attained and the reaction mixture filtered through Celite, eluting with MeCN. Purification of the residue by flash chromatography (12-100% EtOAc-hexanes) gave (R)-ethyl 2-benzyl-3-oxo-6-(3-(1-phenylethyl)ureido)-2,3-dihydro-1H-pyrazolo[4,3-c]pyridine-1-carboxylate. MS ESI calc'd. For C$_{25}$H$_{25}$N$_5$O$_4$ [M+1]$^+$ 460. found 460.

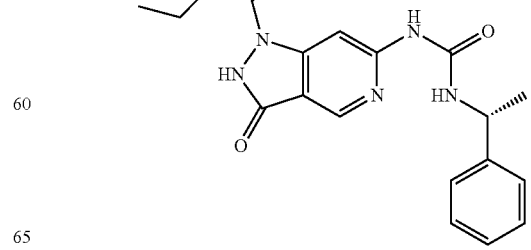

Step 2: (R)-Ethyl 3-oxo-6-(3-(1-phenylethyl)ureido)-2,3-dihydro-1H-pyrazolo[4,3-c]pyridine-1-carboxylate (R)-Ethyl 3-(benzyloxy)-6-(3-(1-phenylethyl)ureido)-1H-pyrazolo[4,3-c]pyridine-1-carboxylate (177.2 mg, 0.386 mmol) and Pd/C (4.10 mg, 0.039 mmol) were stirred in EtOAc (3.86 mL), under a balloon of hydrogen gas for 72 h. The reaction mixture was filtered through Celite, eluting with EtOAc. The filtrate was concentrated in vacuo to afford (R)-ethyl 3-oxo-6-(3-(1-phenylethyl)ureido)-2,3-dihydro-1H-pyrazolo[4,3-c]pyridine-1-carboxylate, which was carried onto the next step without further purification. MS ESI calc'd. For $C_{18}H_{19}N_5O_4$ [M+1]$^+$ 370. found 370.

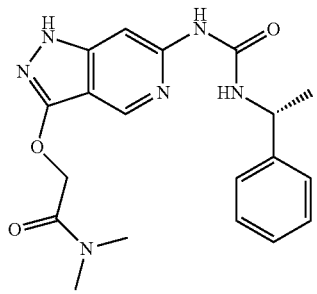 [SMILES: C[C@@H](NC(=O)Nc1cc2[nH]nc(OCC(=O)N(C)C)c2cn1)c1ccccc1]

Step 3: N,N-Dimethyl-2-{[6-({[(1R)-1-phenylethyl]carbamoyl}amino)-1H-pyrazolo[4,3-c]pyridin-3-yl]oxy}acetamide (R)-Ethyl 3-oxo-6-(3-(1-phenylethyl)ureido)-2,3-dihydro-1H-pyrazolo[4,3-c]pyridine-1-carboxylate (29 mg, 0.079 mmol), potassium carbonate (32.6 mg, 0.236 mmol), and 2-chloro-N,N-dimethylacetamide (8.8 μL, 0.087 mmol) were stirred in DMF (1 mL) at room temperature for 24 h. MeOH (0.5 mL) was added and the reaction mixture was stirred at room temperature for 1 h. The insoluble inorganics were removed by filtration and the reaction mixture was purified via mass triggered, reverse phase prep-HPLC. Fractions containing pure product were concentrated in vacuo and the residue dissolved in MeOH. The MeOH solution was passed through a PS—HCO$_3$ cartridge and the filtrate concentrated in vacuo to give (R)—N,N-dimethyl-2-(6-(3-(1-phenylethyl)ureido)-1H-pyrazolo[4,3-c]pyridin-3-yloxy)acetamide. MS ESI calc'd. For $C_{19}H_{22}N_6O_3$ [M+1]$^+$ 383. found 383. $^1$H NMR (500 MHz, DMSO-d$_6$) δ 11.94 (s, 1H), 8.94 (s, 1H), 8.58 (s, 1H), 7.77 (br s, 1H), 7.49 (s, 1H), 7.34-7.31 (m, 4H), 7.25-7.20 (m, 1H), 5.04 (s, 2H), 4.89-4.83 (m, 1H), 2.98 (s, 3H), 2.82 (s, 3H), 1.39 (d, J=7.0 Hz, 3H).

Examples 36-39 (Table 5) were prepared according to Scheme 2 following similar procedures described for Example 35 using the appropriate halides, which can be achieved by those of ordinary skill in the art of organic synthesis. Examples 37-39 were obtained as the trifluoroacetic acid salt.

TABLE 5

| Example | Structure | IUPAC Name | Exact Mass [M + H]+ |
|---|---|---|---|
| 36 | 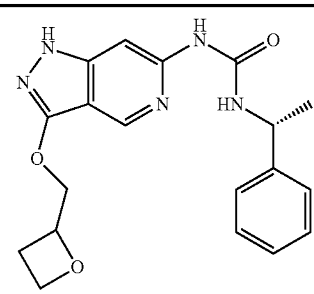 | 1-[3-(oxetan-2-ylmethoxy)-1H-pyrazolo[4,3-c]pyridin-6-yl]-3-[(1R)-1-phenylethyl]urea | Calc'd 368, Found 368 |
| 37 | 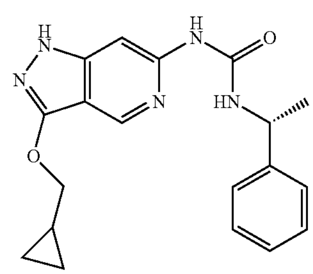 [SMILES: C[C@@H](NC(=O)Nc1cc2[nH]nc(OCC3CC3)c2cn1)c1ccccc1] | 1-[3-(cyclopropylmethoxy)-1H-pyrazolo[4,3-c]pyridin-6-yl]-3-[(1R)-1-phenylethyl]urea | Calc'd 352, Found 352 |
| 38 | 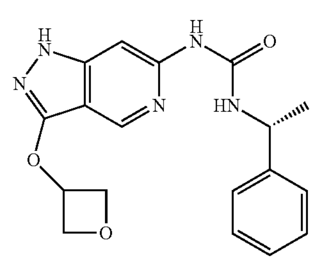 [SMILES: C[C@@H](NC(=O)Nc1cc2[nH]nc(OC3COC3)c2cn1)c1ccccc1] | 1-[3-(oxetan-3-yloxy)-1H-pyrazolo[4,3-c]pyridin-6-yl]-3-[(1R)-1-phenylethyl]urea | Calc'd 352, Found 352 |

TABLE 5-continued

| Example | Structure | IUPAC Name | Exact Mass [M + H]+ |
|---|---|---|---|
| 39 | 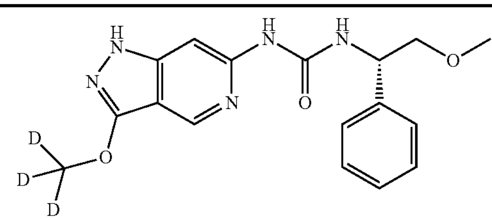 | (S)-1-(2-methoxy-1-phenylethyl)-3-(3-d₃-methoxy-1H-pyrazolo[4,3-c]pyridin-6-yl)urea | Calc'd 345, Found 345 |

Examples 40-61 were prepared according to scheme 3 method A.

Example 40

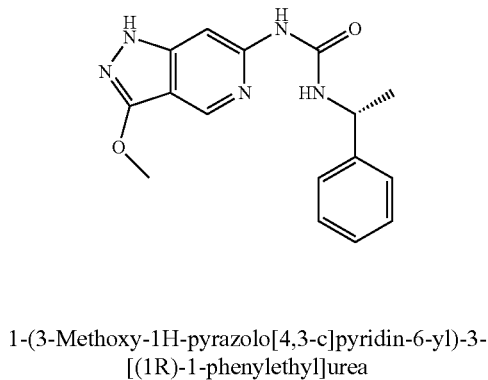

1-(3-Methoxy-1H-pyrazolo[4,3-c]pyridin-6-yl)-3-[(1R)-1-phenylethyl]urea

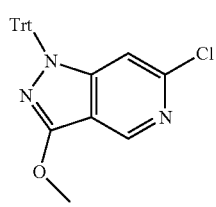

Step 1: 6-Chloro-3-methoxy-1-trityl-1H-pyrazolo[4,3-c]pyridine

6-Chloro-1-trityl-1H-pyrazolo[4,3-c]pyridin-3(2H)-one (Intermediate 3B; 194 mg, 0.471 mmol), K₂CO₃ (132 mg, 0.955 mmol), and iodomethane (0.044 mL, 0.707 mmol) were stirred in DMF (5 mL) at room temperature for 2 h. Water was added and the products extracted into EtOAc (×2). The combined organic extracts were washed with brine, dried over Na₂SO₄, filtered, and concentrated in vacuo. The residue was triturated in MeOH to give 6-chloro-3-methoxy-1-trityl-1H-pyrazolo[4,3-c]pyridine, which was carried onto the next step without further purification. MS ESI calc'd. For $C_{26}H_{20}ClN_3O$ [M+1]+ 426. found 426.

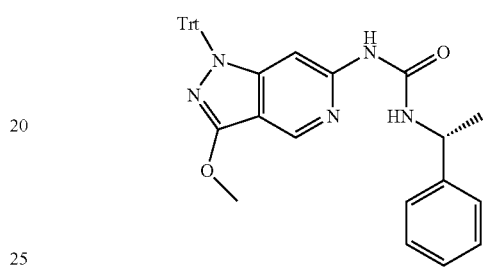

Step 2: (R)-1-(3-Methoxy-1-trityl-1H-pyrazolo[4,3-c]pyridin-6-yl)-3-(1-phenylethyl)urea 6-Chloro-3-methoxy-1-trityl-1H-pyrazolo[4,3-c]pyridine (133 mg, 0.312 mmol), (R)-1-(1-phenylethyl)urea (115 mg, 0.700 mmol), 1:1 BrettPhos:BrettPhos pre-catalyst (20.5 mg, 0.015 mmol), and cesium carbonate (254 mg, 0.781 mmol) were taken up in 1,4-dioxane (3 mL) in a 5 mL microwave vial. The vial was evacuated and back-filled with N₂ (×3) and the reaction stirred at 100° C. for 6 h. The reaction mixture was filtered through Celite, eluting with MeOH, and the filtrate was concentrated in vacuo. Purification of the residue by flash chromatography (12-100% EtOAc-hexanes) gave (R)-1-(3-methoxy-1-trityl-1H-pyrazolo[4,3-c]pyridin-6-yl)-3-(1-phenylethyl)urea. MS ESI calc'd. For $C_{35}H_{31}N_5O_2$ [M+1]+ 554. found 554.

Step 3: 1-(3-Methoxy-1H-pyrazolo[4,3-c]pyridin-6-yl)-3-[(1R)-1-phenylethyl]urea (R)-1-(3-Methoxy-1-trityl-1H-pyrazolo[4,3-c]pyridin-6-yl)-3-(1-phenylethyl)urea (156 mg, 0.282 mmol) and triethylsilane (0.068 mL, 0.423 mmol) were stirred in TFA (2 mL) at room temperature for 2 h. Saturated NaHCO₃ was added and the products extracted into EtOAc (×2). The combined organic extracts were washed with brine, dried over Na₂SO₄, filtered, and concentrated in vacuo. Purification of the residue by flash chromatography (0-15% MeOH-EtOAc) gave (R)-1-(3-methoxy-1H-pyrazolo[4,3-c]pyridin-6-yl)-3-(1-phenylethyl)urea. MS ESI calc'd. For $C_{16}H_{17}N_5O_2$ [M+1]$^+$ 312. found 312. $^1$H NMR (500 MHz, DMSO-d$_6$) δ 11.98 (s, 1H), 8.93 (s, 1H), 8.54 (s, 1H), 7.76 (br s, 1H), 7.48 (s, 1H), 7.35-7.31 (m, 4H), 7.25-7.20 (m, 1H), 4.88-4.83 (m, 1H), 3.96 (s, 3H), 1.39 (d, J=6.5 Hz, 3H).

Example 41

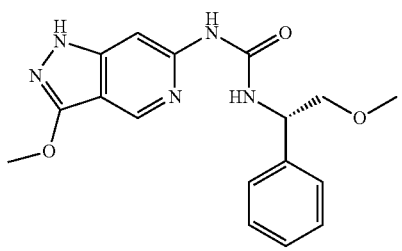

(S)-1-(2-Methoxy-1-phenylethyl)-3-(3-methoxy-1H-pyrazolo[4,3-c]pyridin-6-yl)urea

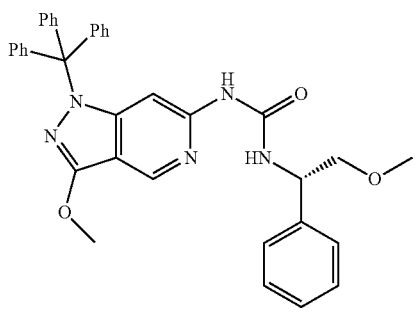 [SMILES: COC[C@@H](NC(=O)Nc1cc2c(cn1)c(OC)nn2C(c1ccccc1)(c1ccccc1)c1ccccc1)c1ccccc1]

Step 1: (S)-1-(2-Methoxy-1-phenylethyl)-3-(3-methoxy-1-trityl-1H-pyrazolo[4,3-c]pyridin-6-yl)urea 6-Chloro-3-methoxy-1-trityl-1H-pyrazolo[4,3-c]pyridine (Example 40, Step 1; 151 mg, 0.355 mmol), (S)-1-(2-methoxy-1-phenylethyl)urea (Intermediate 16B; 108 mg, 0.556 mmol), BrettPhos pre-catalyst (17.6 mg, 0.022 mmol), and cesium carbonate (337 mg, 1.034 mmol) were taken up in 1,4-dioxane (3.5 mL) in a 5 mL microwave vial. The vial was evacuated and back-filled with N$_2$ (×3) and the reaction stirred at 100° C. for 6 h. Room temperature was attained, the reaction mixture was filtered through Celite, eluting with MeOH, and the filtrate was concentrated in vacuo. Purification of the residue by flash chromatography (6-50% EtOAc-hexanes) gave (S)-1-(2-methoxy-1-phenylethyl)-3-(3-methoxy-1-trityl-1H-pyrazolo[4,3-c]pyridin-6-yl)urea. MS ESI calc'd. For $C_{36}H_{33}N_5O_3$ [M+1]$^+$ 584. found 584.

Step 2: (S)-1-(2-Methoxy-1-phenylethyl)-3-(3-methoxy-1H-pyrazolo[4,3-c]pyridin-6-yl)urea (S)-1-(2-Methoxy-1-phenylethyl)-3-(3-methoxy-1-trityl-1H-pyrazolo[4,3-c]pyridin-6-yl)urea (143 mg, 0.245 mmol) and triethylsilane (0.060 mL, 0.376 mmol) were stirred in TFA (2.5 mL) at room temperature for 30 min. Saturated NaHCO$_3$ was added and the products extracted into EtOAc (×2). The combined organic extracts were washed with brine, dried over Na$_2$SO$_4$, filtered, and concentrated in vacuo. Purification of the residue by flash chromatography (0-10% MeOH-EtOAc) gave (S)-1-(2-methoxy-1-phenylethyl)-3-(3-methoxy-1H-pyrazolo[4,3-c]pyridin-6-yl)urea. MS ESI calc'd. For $C_{12}H_{19}N_5O_3$ [M+1]$^+$ 342. found 342. $^1$H NMR (500 MHz, DMSO-d$_6$) δ 11.98 (s, 1H), 9.08 (s, 1H), 8.55 (s, 1H), 7.96 (br s, 1H), 7.48 (s, 1H), 7.34-7.30 (m, 4H), 7.25-7.21 (m, 1H), 4.98-4.93 (m, 1H), 3.96 (s, 3H), 3.55 (d, J=5.5 Hz, 2H), 3.25 (s, 3H).

Examples 42-51 (Table 6) were prepared according to Scheme 3 method A following similar procedures described for Examples 40 and 41 using the appropriate pyrazolopyridine (Intermediates 3B-4B, 8B-10B), halides, and commercial or synthesized ureas (prepared using the same procedure as Intermediates 15B-16B), which can be achieved by those of ordinary skill in the art of organic synthesis. Examples 42 and 43 were obtained as the trifluoroacetic acid salt.

TABLE 6

| Example | Structure | IUPAC Name | Exact Mass [M + H]+ |
|---|---|---|---|
| 42 | 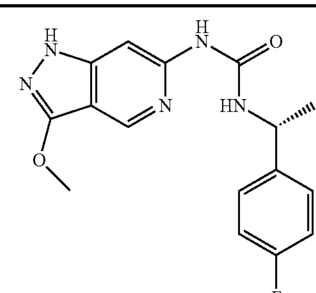 | 1-[(1R)-1-(4-fluorophenyl)ethyl]-3-(3-methoxy-1H-pyrazolo[4,3-c]pyridin-6-yl)urea | Calc'd 330, Found 330 |

TABLE 6-continued

| Example | Structure | IUPAC Name | Exact Mass [M + H]+ |
|---|---|---|---|
| 43 | 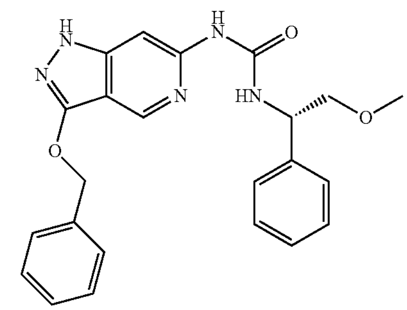 [SMILES: COC[C@@H](NC(=O)Nc1cc2[nH]nc(OCc3ccccc3)c2cn1)c1ccccc1] | 1-[3-(benzyloxy)-1H-pyrazolo[4,3-c]pyridin-6-yl]-3-[(1S)-2-methoxy-1-phenylethyl]urea | Calc'd 418, Found 418 |
| 44 | 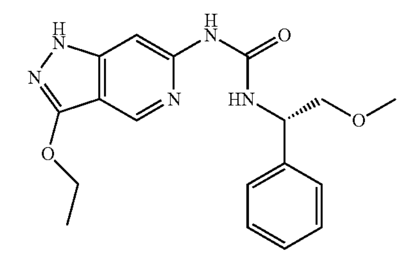 [SMILES: CCOc1n[nH]c2cc(NC(=O)N[C@H](COC)c3ccccc3)ncc12] | 1-(3-ethoxy-1H-pyrazolo[4,3-c]pyridin-6-yl)-3-[(1S)-2-methoxy-1-phenylethyl]urea | Calc'd 356, Found 356 |
| 45 | 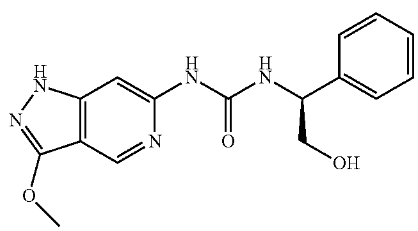 [SMILES: COc1n[nH]c2cc(NC(=O)N[C@H](CO)c3ccccc3)ncc12] | 1-[(1S)-2-hydroxy-1-phenylethyl]-3-(3-methoxy-1H-pyrazolo[4,3-c]pyridin-6-yl)urea | Calc'd 328, Found 328 |
| 46 | 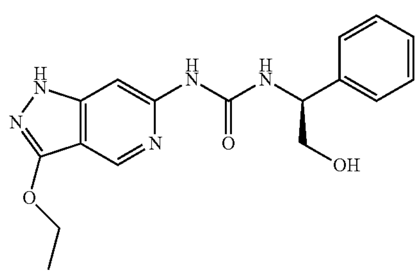 [SMILES: CCOc1n[nH]c2cc(NC(=O)N[C@H](CO)c3ccccc3)ncc12] | 1-(3-ethoxy-1H-pyrazolo[4,3-c]pyridin-6-yl)-3-[(1S)-2-hydroxy-1-phenylethyl]urea | Calc'd 342, Found 342 |
| 47 | 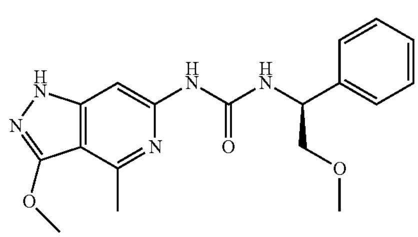 [SMILES: COC[C@@H](NC(=O)Nc1cc2[nH]nc(OC)c2c(C)n1)c1ccccc1] | 1-(3-methoxy-4-methyl-1H-pyrazolo[4,3-c]pyridin-6-yl)-3-[(1S)-2-methoxy-1-phenylethyl]urea | Calc'd 356, Found 356 |

TABLE 6-continued

| Example | Structure | IUPAC Name | Exact Mass [M + H]+ |
|---|---|---|---|
| 48 | 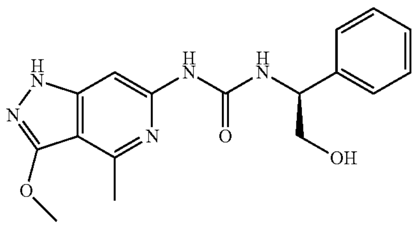 [SMILES: COc1n[nH]c2cc(NC(=O)N[C@H](CO)c3ccccc3)nc(C)c12] | 1-[(1S)-2-hydroxy-1-phenylethyl]-3-(3-methoxy-4-methyl-1H-pyrazolo[4,3-c]pyridin-6-yl)urea | Calc'd 342, Found 342 |
| 49 | 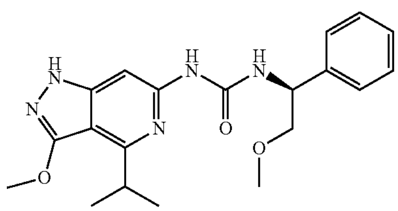 [SMILES: COC[C@@H](NC(=O)Nc1cc2[nH]nc(OC)c2c(C(C)C)n1)c1ccccc1] | 1-[3-methoxy-4-(1-methylethyl)-1H-pyrazolo[4,3-c]pyridin-6-yl]-3-[(1S)-2-methoxy-1-phenylethyl]urea | Calc'd 384, Found 384 |
| 50 | 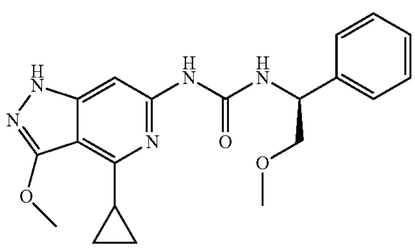 [SMILES: COC[C@@H](NC(=O)Nc1cc2[nH]nc(OC)c2c(C2CC2)n1)c1ccccc1] | 1-(4-cyclopropyl-3-methoxy-1H-pyrazolo[4,3-c]pyridin-6-yl)-3-[(1S)-2-methoxy-1-phenylethyl]urea | Calc'd 382, Found 382 |
| 51 | 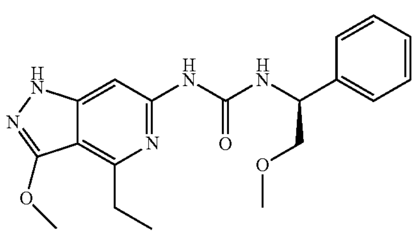 [SMILES: CCc1nc(NC(=O)N[C@H](COC)c2ccccc2)cc2[nH]nc(OC)c12] | 1-(4-ethyl-3-methoxy-1H-pyrazolo[4,3-c]pyridin-6-yl)-3-[(1S)-2-methoxy-1-phenylethyl]urea | Calc'd 370, Found 370 |

Example 52

1-[3-(Difluoromethoxy)-1H-pyrazolo[4,3-c]pyridin-6-yl]-3-[(1R)-1-phenylethyl]urea

Step 1: 6-Chloro-3-(difluoromethoxy)-1-trityl-1H-pyrazolo[4,3-c]pyridine

A solution of 6-chloro-1-trityl-1H-pyrazolo[4,3-c]pyridin-3 (2H)-one (Intermediate 3B; 368 mg, 0.893 mmol) and methyl 2-chloro-2,2-difluoroacetate (0.5 mL, 4.74 mmol) in DMF (2 mL) was charged with $K_2CO_3$ (2.5 g, 18.09 mmol) at room temperature. The reaction was stirred at 80° C. for 30 min. The reaction mixture was diluted with $H_2O$ and filtered to give 6-chloro-3-(difluoro-methoxy)-1-trityl-1H-pyrazolo[4,3-c]pyridine, which was carried onto the next step without further purification. MS ESI calc'd. For $C_{26}H_{18}ClF_2N_3O$ $[M+1]^+$ 462. found 462.

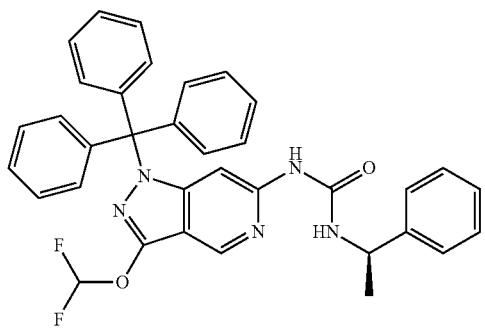 [SMILES: C[C@@H](NC(=O)Nc1cc2c(cn1)c(OC(F)F)nn2C(c1ccccc1)(c1ccccc1)c1ccccc1)c1ccccc1]

Step 2: (R)-1-(3-(Difluoromethoxy)-1-trityl-1H-pyrazolo[4,3-c]pyridin-6-yl)-3-(1-phenylethyl)urea (R)-1-(3-(Difluoromethoxy)-1-trityl-1H-pyrazolo[4,3-c]pyridin-6-yl)-3-(1-phenylethyl)urea was prepared using the same procedure as (R)-1-(3-methoxy-1-trityl-1H-pyrazolo[4,3-c]pyridin-6-yl)-3-(1-phenylethyl)urea (Example 40, Step 2). MS ESI calc'd. For $C_{35}H_{29}F_2N_5O_2$ $[M+1]^+$ 590. found 590.

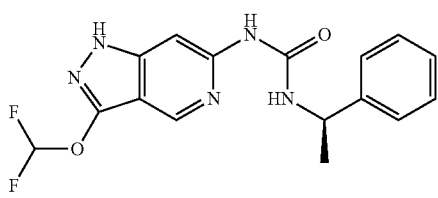 [SMILES: C[C@@H](NC(=O)Nc1cc2[nH]nc(OC(F)F)c2cn1)c1ccccc1]

Step 3: 1-[3-(Difluoromethoxy)-1H-pyrazolo[4,3-c]pyridin-6-yl]-3-[(1R)-1-phenylethyl]urea A solution of (R)-1-(3-(difluoromethoxy)-1-trityl-1H-pyrazolo[4,3-c]pyridin-6-yl)-3-(1-phenylethyl)urea (58.5 mg, 0.099 mmol) in TFA (2 mL) was stirred at room temperature for 2.5 h. The reaction mixture was diluted with DMSO (2 mL) and purified by mass-triggered reverse-phase HPLC. The fractions containing pure product were freebased with a PL-HCO3 cartridge and concentrated in vacuo to give (R)-1-(3-(difluoromethoxy)-1H-pyrazolo[4,3-c]pyridin-6-yl)-3-(1-phenylethyl)urea. MS ESI calc'd. For $C_{16}H_{15}F_2N_5O_2$ $[M+1]^+$ 348. found 348. $^1$H NMR (500 MHz, DMSO-$d_6$) δ 9.03 (s, 1H), 8.66 (s, 1H), 7.64 (m, 2H), 7.52 (t, J=7.3 Hz, 1H), 7.32 (m, 4H), 7.23 (m, 1H), 4.85 (m, 1H), 1.39 (d, J=7.0 Hz, 3H). Example 53 was prepared according to Scheme 3 method A following similar procedures described for Example 52, which can be achieved by those of ordinary skill in the art of organic synthesis.

TABLE 7

| Example | Structure | IUPAC Name | Exact Mass [M + H]+ |
|---------|-----------|------------|---------------------|
| 53 | 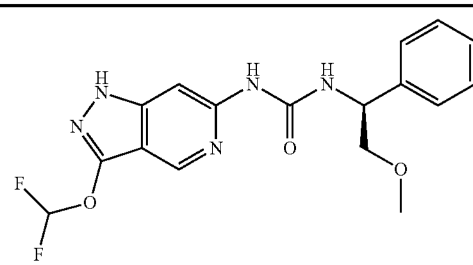 | 1-[3-(difluoromethoxy)-1H-pyrazolo[4,3-c]pyridin-6-yl]-3-[(1S)-2-methoxy-1-phenylethyl]urea | Calc'd 378, Found 378 |

Examples 54 and 55

Example 54

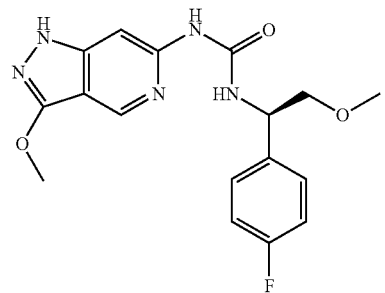

-continued

Example 55

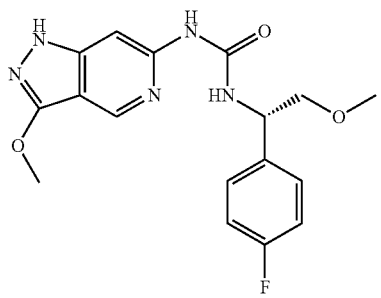

1-[(1R)-1-(4-Fluorophenyl)-2-methoxyethyl]-3-(3-methoxy-1H-pyrazolo[4,3-c]pyridin-6-yl)urea (Example 54) and 1-[(1S)-1-(4-Fluorophenyl)-2-methoxyethyl]-3-(3-methoxy-1H-pyrazolo[4,3-c]pyridin-6-yl)urea Example 55

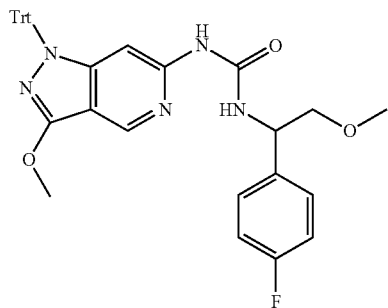

Step 1: 1-(1-(4-Fluorophenyl)-2-methoxyethyl)-3-(3-methoxy-1-trityl-1H-pyrazolo[4,3-c]pyridin-6-yl)urea 1-(1-(4-Fluorophenyl)-2-methoxyethyl)-3-(3-methoxy-1-trityl-1H-pyrazolo[4,3-c]pyridin-6-yl)urea was prepared using the same procedure described for (R)-1-(3-methoxy-1-trityl-1H-pyrazolo[4,3-c]pyridin-6-yl)-3-(1-phenylethyl)urea (Example 40, Step 2). MS ESI calc'd. For $C_{36}H_{32}FN_5O_3$ [M+1]$^+$ 602. found 602.

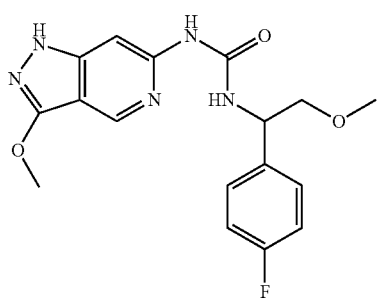 [SMILES: COCC(NC(=O)Nc1cc2[nH]nc(OC)c2cn1)c1ccc(F)cc1]

Step 2: 1-(1-(4-Fluorophenyl)-2-methoxyethyl)-3-(3-methoxy-1H-pyrazolo[4,3-c]pyridin-6-yl)urea 1-(1-(4-Fluorophenyl)-2-methoxyethyl)-3-(3-methoxy-1H-pyrazolo[4,3-c]pyridin-6-yl)urea was prepared using the same procedure described for (R)-1-(3-methoxy-1H-pyrazolo[4,3-c]pyridin-6-yl)-3-(1-phenylethyl)urea (Example 40, Step 3). MS ESI calc'd. For $C_{17}H_{18}FN_5O_3$ [M+1]$^+$ 360. found 360.

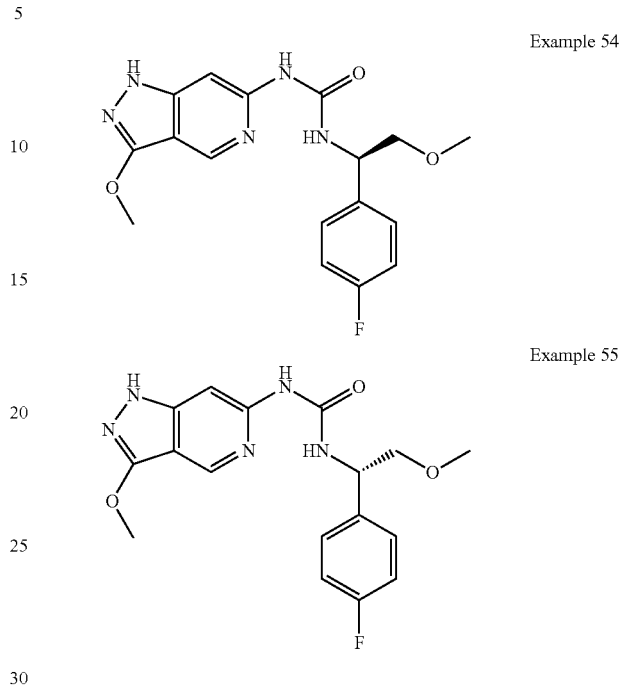

Step 3: 1-[(1R)-1-(4-Fluorophenyl)-2-methoxyethyl]-3-(3-methoxy-1H-pyrazolo[4,3-c]pyridin-6-yl)urea (Example 54) and 1-[(1S)-1-(4-Fluorophenyl)-2-methoxyethyl]-3-(3-methoxy-1H-pyrazolo[4,3-c]pyridin-6-yl)urea Example 55

The enantiomers of 1-(1-(4-fluorophenyl)-2-methoxyethyl)-3-(3-methoxy-1H-pyrazolo[4,3-c]pyridin-6-yl)urea (40 mg, 0.11 mmol) were separated by SFC (Berger Multigram II SFC, column: Phenomenex Lux 4 2.1×25 cm, 5 uM, mobile phase: 30% to 70% MeOH in $CO_{2(l)}$, flow rate: 70 mL/min, 6.5 min run time). The fractions were collected and the solvent evaporated in vacuo to afford 1-[(1R)-1-(4-fluorophenyl)-2-methoxyethyl]-3-(3-methoxy-1H-pyrazolo[4,3-c]pyridin-6-yl)urea and 1-[(1S)-1-(4-fluorophenyl)-2-methoxyethyl]-3-(3-methoxy-1H-pyrazolo[4,3-c]pyridin-6-yl)urea. MS ESI calc'd. For $C_{17}H_{18}FN_5O_3$ [M+1]$^+$ 360. found 360. $^1$H NMR (500 MHz, DMSO-$d_6$) δ 11.98 (s, 1H), 9.08 (s, 1H), 8.55 (s, 1H), 7.98 (br s, 1H), 7.47 (s, 1H), 7.36 (dd, J=8.5, 5.5 Hz, 2H), 7.15 (t, J=9.0 Hz, 2H), 4.98-4.92 (m, 1H), 3.96 (s, 3H), 3.55 (d, J=5.0 Hz, 2H), 3.25 (s, 3H) (Example 54). MS ESI calc'd. For $C_{17}H_{18}FN_5O_3$ [M+1]$^+$ 360. found 360. $^1$H NMR (500 MHz, DMSO-$d_6$) δ 11.98 (s, 1H), 9.08 (s, 1H), 8.55 (s, 1H), 7.98 (br s, 1H), 7.47 (s, 1H), 7.36 (dd, J=8.5, 5.5 Hz, 2H), 7.15 (t, J=9.0 Hz, 2H), 4.98-4.92 (m, 1H), 3.96 (s, 3H), 3.55 (d, J=5.0 Hz, 2H), 3.25 (s, 3H) (Example 55).

Examples 56-61 (Table 8) were prepared according to Scheme 3 method A following similar procedures described for Examples 54 and 55 using the appropriate halides and commercial or synthesized ureas (prepared using the same procedure as Intermediates 15B and 16B), which can be achieved by those of ordinary skill in the art of organic synthesis.

TABLE 8

| Example | Structure | IUPAC Name | Exact Mass [M + H]+ |
|---|---|---|---|
| 56 | 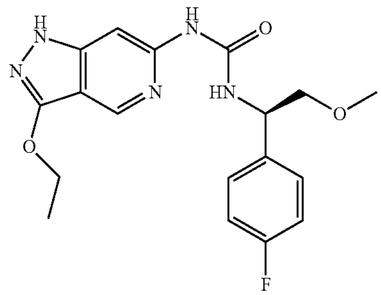 [SMILES: CCOc1n[nH]c2cc(NC(=O)N[C@@H](COC)c3ccc(F)cc3)ncc12] | 1-(3-ethoxy-1H-pyrazolo[4,3-c]pyridin-6-yl)-3-[(1R)-1-(4-fluorophenyl)-2-methoxyethyl]urea | Calc'd 374, Found 374 |
| 57 | 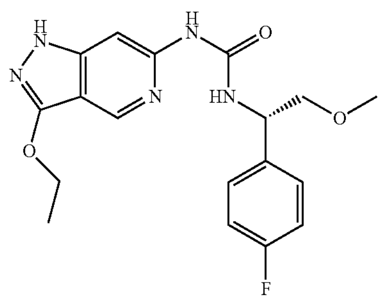 [SMILES: CCOc1n[nH]c2cc(NC(=O)N[C@H](COC)c3ccc(F)cc3)ncc12] | 1-(3-ethoxy-1H-pyrazolo[4,3-c]pyridin-6-yl)-3-[(1S)-1-(4-fluorophenyl)-2-methoxyethyl]urea | Calc'd 374, Found 374 |
| 58 | 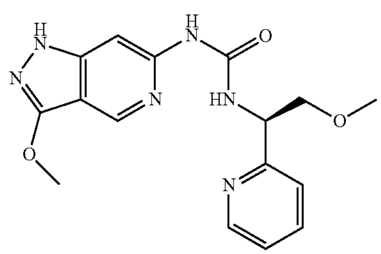 [SMILES: COC[C@H](NC(=O)Nc1cc2[nH]nc(OC)c2cn1)c1ccccn1] | 1-(3-methoxy-1H-pyrazolo[4,3-c]pyridin-6-yl)-3-[(1R)-2-methoxy-1-pyridin-2-ylethyl]urea | Calc'd 343, Found 343 |
| 59 | 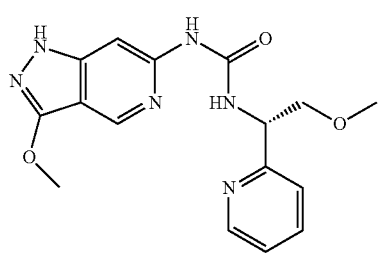 [SMILES: COC[C@@H](NC(=O)Nc1cc2[nH]nc(OC)c2cn1)c1ccccn1] | 1-(3-methoxy-1H-pyrazolo[4,3-c]pyridin-6-yl)-3-[(1S)-2-methoxy-1-pyridin-2-ylethyl]urea | Calc'd 343, Found 343 |
| 60 | 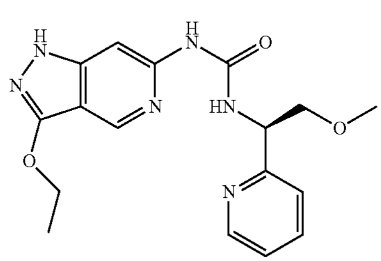 [SMILES: CCOc1n[nH]c2cc(NC(=O)N[C@@H](COC)c3ccccn3)ncc12] | 1-(3-ethoxy-1H-pyrazolo[4,3-c]pyridin-6-yl)-3-[(1R)-2-methoxy-1-pyridin-2-ylethyl]urea | Calc'd 357, Found 357 |

TABLE 8-continued

| Example | Structure | IUPAC Name | Exact Mass [M + H]+ |
|---|---|---|---|
| 61 | 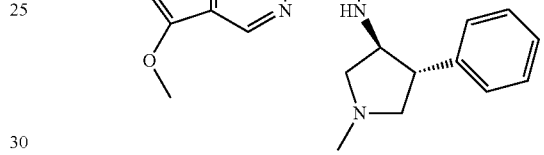 | 1-(3-ethoxy-1H-pyrazolo[4,3-c]pyridin-6-yl)-3-[(1S)-2-methoxy-1-pyridin-2-ylethyl]urea | Calc'd 357, Found 357 |

Examples 62-68 were prepared according to scheme 3 method B.

Example 62

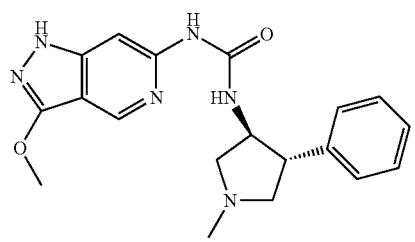 [SMILES: COc1n[nH]c2cc(NC(=O)N[C@@H]3CN(C)C[C@H]3c3ccccc3)ncc12]

1-(3-Methoxy-1H-pyrazolo[4,3-c]pyridin-6-yl)-3-[(3S,4R)-1-methyl-4-phenylpyrrolidin-3-yl]urea

Step 1: 6-Chloro-3-methoxy-1H-pyrazolo[4,3-c]pyridine

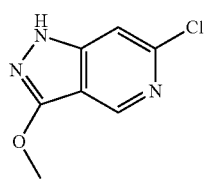

6-Chloro-3-methoxy-1-trityl-1H-pyrazolo[4,3-c]pyridine (Example 40, Step 1; 630 mg, 1.479 mmol) was dissolved in TFA (4 mL) and triethylsilane (0.354 mL, 2.219 mmol) was added. The reaction mixture was stirred at room temperature for 1 h. Saturated NaHCO₃ was added and the products extracted into EtOAc followed by 3:1 chloroform/IPA. The combined organic extracts were dried over Na₂SO₄, filtered, and concentrated in vacuo. The residue was titrated with ether to afford 6-chloro-3-methoxy-1H-pyrazolo[4,3-c]pyridine, which was carried onto the next step without further purification. MS ESI calc'd. For $C_7H_6ClN_3O$ [M+1]+ 184. found 184.

Step 2: 1-(3-Methoxy-1H-pyrazolo[4,3-c]pyridin-6-yl)-3-[(3S,4R)-1-methyl-4-phenylpyrrolidin-3-yl]urea 6-Chloro-3-methoxy-1H-pyrazolo[4,3-c]pyridine (50 mg, 0.272 mmol), 1-((3S,4R)-1-methyl-4-phenylpyrrolidin-3-yl)urea (Intermediate 17B; 90 mg, 0.409 mmol), BrettPhos precatalyst (21.75 mg, 0.027 mmol), and potassium tert-butoxide (1 M in THF, 0.817 mL, 0.817 mmol) were dissolved in THF (1 mL). The vial was degassed with argon for 5 min and the reaction stirred at 60° C. for 16 h. The reaction mixture was filtered through Celite, eluting with MeOH, and the filtrate was concentrated in vacuo while loading onto silica gel. Purification by flash chromatography (0-20% CH₂Cl₂/MeOH with 1% ammonia) gave 1-(3-methoxy-1H-pyrazolo[4,3-c]pyridin-6-yl)-3-[(3S,4R)-1-methyl-4-phenylpyrrolidin-3-yl]urea. MS ESI calc'd. For $C_{19}H_{22}N_6O_2$ [M+1]+ 367. found 367. ¹H NMR (500 MHz, DMSO-d₆) δ 11.97 (s, 1H), 8.89 (s, 1H), 8.51 (s, 1H), 7.72 (s, 1H), 7.43 (s, 1H), 7.31-7.26 (m, 3H), 7.22-7.18 (m, 2H), 4.22-4.14 (m, 1H), 3.98 (s, 3H), 3.16-3.04 (m, 1H), 2.64-2.58 (m, 2H), 2.48 (s, 3H), 2.38-2.28 (m, 2H).

Examples 63-64 (Table 9) were prepared according to Scheme 3 method B following similar procedures described for Example 62 using the appropriate halides and synthesized ureas (prepared using the same procedure as Intermediate 17B), which can be achieved by those of ordinary skill in the art of organic synthesis.

TABLE 9

| Example | Structure | IUPAC Name | Exact Mass [M + H]+ |
|---|---|---|---|
| 63 | 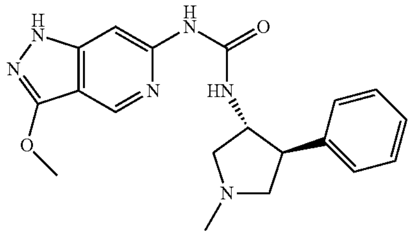 [SMILES: COc1n[nH]c2cc(NC(=O)N[C@H]3CN(C)C[C@@H]3c3ccccc3)ncc12] | 1-(3-methoxy-1H-pyrazolo[4,3-c]pyridin-6-yl)-3-[(3R,4S)-1-methyl-4-phenylpyrrolidin-3-yl]urea | Calc'd 367, Found 367 |
| 64 | 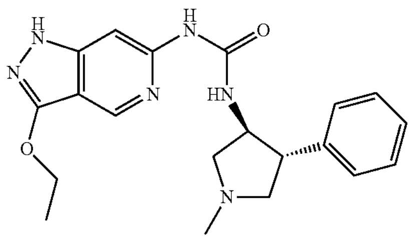 [SMILES: CCOc1n[nH]c2cc(NC(=O)N[C@@H]3CN(C)C[C@H]3c3ccccc3)ncc12] | 1-(3-ethoxy-1H-pyrazolo[4,3-c]pyridin-6-yl)-3-[(3S,4R)-1-methyl-4-phenylpyrrolidin-3-yl]urea | Calc'd 381, Found 381 |

Examples 65 and 66

Example 65

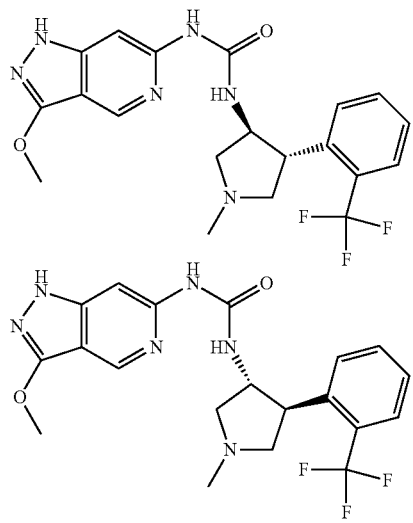

Example 66

1-(3-Methoxy-1H-pyrazolo[4,3-c]pyridin-6-yl)-3-{(3S,4R)-1-methyl-4-[2-(trifluoromethyl)phenyl]pyrrolidin-3-yl}urea (Example 65) and 1-(3-Methoxy-1H-pyrazolo[4,3-c]pyridin-6-yl)-3-{(3R,4S)-1-methyl-4-[2-(trifluoromethyl)phenyl]pyrrolidin-3-yl}urea Example 66

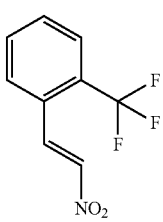 [SMILES: O=[N+]([O-])/C=C/c1ccccc1C(F)(F)F]

Step 1: (E)-1-(2-Nitrovinyl)-2-(trifluoromethyl)benzene 2-(Trifluoromethyl)benzaldehyde (0.758 mL, 5.74 mmol) was dissolved in MeOH (5 mL) and nitromethane (0.370 mL, 6.89 mmol) was added. The mixture was cooled to −10° C. and a solution of NaOH (0.241 g, 6.03 mmol) in water (2 mL) was slowly added keeping the temperature below −5° C. The mixture stirred at −5° C. for 15 min then warmed to 0° C. and stirred for 2 h. Ice water (6 mL) was added followed by HCl (6 N, 3 mL). The mixture was extracted with DCM (×2) and the combined organic layers were washed with brine, dried over $Na_2SO_4$, filtered, and concentrated in vacuo to afford (E)-1-(2-nitrovinyl)-2-(trifluoromethyl)-benzene, which was carried onto the next step without further purification. $^1$H NMR (500 MHz, DMSO-$d_6$) δ 8.28 (d, J=13.3 Hz, 1H), 8.12 (d, J=13.2 Hz, 1H), 7.91-7.7 (m, 3H), 7.54 (t, J=7.6 Hz, 1H).

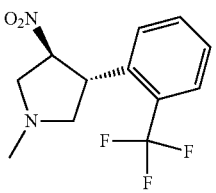 [SMILES: CN1C[C@@H]([N+](=O)[O-])[C@H](c2ccccc2C(F)(F)F)C1]

Step 2: (3S and R,4R and S)-1-Methyl-3-nitro-4-(2-(trifluoromethyl)phenyl)pyrrolidine (E)-1-(2-Nitrovinyl)-2-(trifluoromethyl)benzene (230.8 mg, 1.063 mmol) and methyl-methoxymethyltrimethylsilanyl-methylamine (206 mg, 1.275 mmol) was dissolved in DCM (4 mL) and cooled to 0° C. under $N_2$. Trifluoroacetic acid (8.19 μL, 0.106 mmol) was then added and the reaction mixture was stirred at 0° C. for 30 min then warmed to room temperature and stirred for 2 h. The reaction mixture was diluted with DCM and washed with brine. The combined organic layers were dried over $Na_2SO_4$, filtered, and concentrated in vacuo while loading onto silica gel. The residue was purified by flash chromatography (7-60% EtOAc-hexanes) to give (3S and R,4R and S)-1-methyl-3-nitro-4-(2-(trifluoromethyl)phenyl) pyrrolidine. $^1$H NMR (500 MHz, DMSO-$d_6$) δ 7.84-7.65 (m, 3H), 7.5 (t, J=7.4 Hz, 1H), 5.40-5.34 (m, 1H), 4.18-4.10 (m, 1H), 3.40 (dd, J=3.0, 11.3 Hz, 1H), 3.20 (t, J=8.4 Hz, 1H), 3.10-3.04 (m, 1H), 2.40-2.28 (m, 1H), 2.3 (s, 3H).

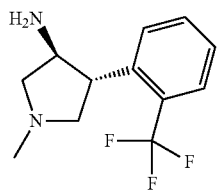

Step 3: (3S and R,4R and S)-1-Methyl-4-(2-(trifluoromethyl)phenyl)pyrrolidin-3-amine (3S and R,4R and S)-1-Methyl-3-nitro-4-(2-(trifluoromethyl)phenyl) pyrrolidine (296.8 mg, 1.082 mmol) was dissolved in MeOH (5 mL) and the reaction mixture was cooled to 0° C. Acetic acid (5 mL) and zinc (354 mg, 5.41 mmol) were added and the reaction mixture was warmed to room temperature and stirred under $N_2$ for 16 h. The suspension was filtered over Celite and washed with MeOH. The filtrate was concentrated in vacuo, the residue suspended in EtOAc, cooled in an ice bath, and basified with conc. $NH_4OH$. The organic phase was separated, washed with brine, dried over $Na_2SO_4$, filtered, and concentrated in vacuo to afford (3S and R,4R and S)-1-methyl-4-(2-(trifluoromethyl)phenyl)pyrrolidin-3-amine, which was carried onto the next step without further purification. MS ESI calc'd. For $C_{12}H_{15}F_3N_2$ [M+1]$^+$ 245. found 245.

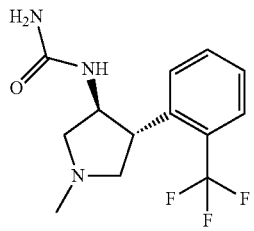 [SMILES: CN1C[C@@H](NC(N)=O)[C@H](c2ccccc2C(F)(F)F)C1]

Step 4: 1-((3S and R,4R and S)-1-Methyl-4-(2-(trifluoromethyl)phenyl)pyrrolidin-3-yl)urea 1-((3S and R,4R and S)-1-Methyl-4-(2-(trifluoromethyl) phenyl)pyrrolidin-3-yl)urea was prepared using the same procedure described for (R)-1-(1-(4-fluorophenyl)ethyl)urea (Intermediate 15B). MS ESI calc'd. For $C_{13}H_{16}F_3N_3O$ [M+1]$^+$ 288. found 288.

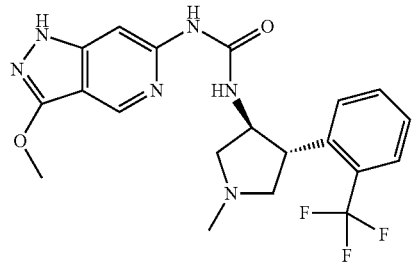

Step 5: 1-(3-Methoxy-1H-pyrazolo[4,3-c]pyridin-6-yl)-3-((3S and R,4R and S)-1-methyl-4-(2-(trifluoromethyl)phenyl)pyrrolidin-3-yl)urea 1-(3-Methoxy-1H-pyrazolo[4,3-c]pyridin-6-yl)-3-((3S and R,4R and S)-1-methyl-4-(2-(trifluoromethyl)phenyl) pyrrolidin-3-yl)urea was prepared using the same procedure described for 1-(3-methoxy-1H-pyrazolo[4,3-c]pyridin-6-yl)-3-[(3S,4R)-1-methyl-4-phenylpyrrolidin-3-yl]urea (Example 62, Step 2). MS ESI calc'd. For $C_{20}H_{21}F_3N_6O_2$ [M+1]$^+$ 435. found 435.

Example 65

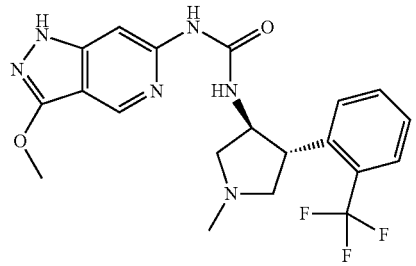 [SMILES: COc1n[nH]c2cc(NC(=O)N[C@@H]3CN(C)C[C@H]3c3ccccc3C(F)(F)F)ncc12]

Example 66

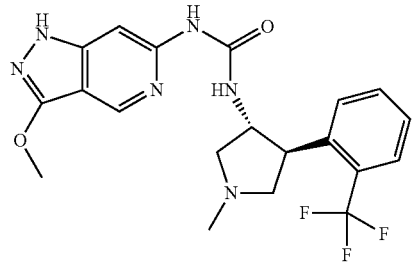

Step 6: 1-(3-Methoxy-1H-pyrazolo[4,3-c]pyridin-6-yl)-3-{(3S,4R)-1-methyl-4-[2-(trifluoromethyl)phenyl]pyrrolidin-3-yl}urea (Example 65) and 1-(3-Methoxy-1H-pyrazolo[4,3-c]pyridin-6-yl)-3-{(3R,4S)-1-methyl-4-[2-trifluoromethyl)phenyl]-pyrrolidin-3-yl}urea Example 66

The enantiomers of 1-(3-methoxy-1H-pyrazolo[4,3-c]pyridin-6-yl)-3-((3S and R, 4R and S)-1-methyl-4-(2-(trifluoromethyl)phenyl)pyrrolidin-3-yl)urea (18.6 mg, 0.043 mmol) were separated by SFC (Berger Multigram II SFC, column: Chiral Technology IC 2.1×25 cm, 5 uM, mobile phase: 25% to 75% MeOH+0.25% dimethyl ethylamine in $CO_{2(l)}$, flow rate: 70 mL/min, 7 min run time). The fractions were collected and the solvent evaporated in vacuo, dissolved in ACN/water, and lyophilized to afford 1-(3-methoxy-1H-pyrazolo[4,3-c]pyridin-6-yl)-3-{(3S,4R)-1-methyl-4-[2-(trifluoromethyl)phenyl]pyrrolidin-3-yl}urea and 1-(3-methoxy-1H-pyrazolo[4,3-c]pyridin-6-yl)-3-{(3R,4S)-1-methyl-4-[2-(trifluoromethyl)phenyl]-pyrrolidin-3-yl}urea. MS ESI calc'd. For $C_{20}H_{21}F_3N_6O_2$ [M+1]$^+$ 435. found 435. $^1$H NMR (500 MHz, DMSO-$d_6$) δ 11.94 (s, 1H), 8.89 (s, 1H), 8.50 (s, 1H), 7.80-7.74 (m, 2H), 7.68 (t, J=7.5 Hz, 1H), 7.62 (d, J=8.0 Hz, 1H), 7.41 (t, J=7.7 Hz, 1H), 7.34 (s, 1H), 4.4-4.35 (m, 1H), 3.95 (s, 3H), 3.42-3.37 (m, 1H), 3.10-2.96 (m, 2H), 2.67-2.55 (m, 1H), 2.39-2.36 (m, 1H), 2.30 (s, 3H) (Example 65). MS ESI calc'd. For $C_{20}H_{21}F_3N_6O_2$ [M+1]$^+$ 435. found 435. $^1$H NMR (500 MHz, DMSO-$d_6$) δ 11.95 (s, 1H), 8.90 (s, 1H), 8.50 (s, 1H), 7.80-7.74 (m, 2H), 7.68 (t, J=7.5 Hz, 1H), 7.62 (d, J=8.0 Hz, 1H), 7.42 (t, J=7.5 Hz, 1H), 7.34 (s, 1H), 4.4-4.35 (m, 1H), 3.95 (s, 3H), 3.42-3.37 (m, 1H), 3.07-2.92 (m, 2H), 2.67-2.55 (m, 1H), 2.39-2.36 (m, 1H), 2.30 (s, 3H) (Example 66).

Examples 67-68 (Table 10) were prepared according to Scheme 3 method B following similar procedures described for Examples 65 and 66 using the appropriate urea (prepared using the same procedure as Example 65 and 66, Steps 1-4), which can be achieved by those of ordinary skill in the art of organic synthesis.

(R)-1-(4-Methyl-3-((tetrahydro-2H-pyran-4-yl)oxy)-1H-pyrazolo[4,3-c]pyridin-6-yl)-3-(1-phenylethyl)urea

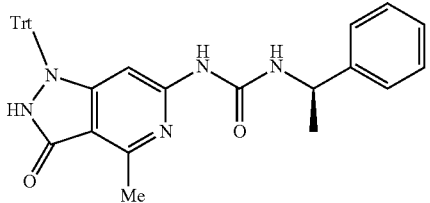

Step 1: (R)-1-(4-Methyl-3-oxo-1-trityl-2,3-dihydro-1H-pyrazolo[4,3-c]pyridin-6-yl)-3-(1-phenylethyl)urea 6-Chloro-4-methyl-1-trityl-1H-pyrazolo[4,3-c]pyridin-3(2H)-one (Intermediate 4B; 300 mg, 0.704 mmol), (R)-1-(1-

TABLE 10

| Example | Structure | IUPAC Name | Exact Mass [M + H]+ |
|---|---|---|---|
| 67 | ![structure] | 1-(3-methoxy-1H-pyrazolo-[4,3-c]pyridin-6-yl)-3-[(3S,4R)-1-methyl-4-(2-methylphenyl)pyrrolidin-3-yl]urea | Calc'd 381, Found 381 |
| 68 | ![structure] | 1-(3-methoxy-1H-pyrazolo-[4,3-c]pyridin-6-yl)-3-[(3R,4S)-1-methyl-4-(2-methylphenyl)pyrrolidin-3-yl]urea | Calc'd 381, Found 381 |

Examples 69-72 were prepared according to scheme 4.

Example 69

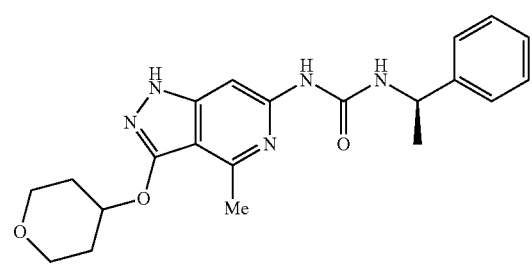 [SMILES: Cc1nc(NC(=O)N[C@H](C)c2ccccc2)cc2[nH]nc(OC3CCOCC3)c12]

phenylethyl)urea (139 mg, 0.845 mmol), palladium(II) acetate (31.6 mg, 0.141 mmol), 4,5-bis(diphenylphosphino)-9,9-dimethylxanthene (122 mg, 0.211 mmol), and cesium carbonate (574 mg, 1.761 mmol) were taken up in dioxane (10.0 mL) in a 25 mL microwave vial. The vial was evacuated and back-filled with $N_2$ (×3) then the reaction mixture was heated to 80° C. for 24 h. The reaction mixture was diluted with DCM, filtered through celite, and the filtrate was washed with water then brine. The organic layer was dried over sodium sulfate, filtered, concentrated in vacuo, and purified by flash chromatography (20-80% EtOAc/Hexanes) to give (R)-1-(4-methyl-3-oxo-1-trityl-2,3-dihydro-1H-pyrazolo[4,3-c]pyridin-6-yl)-3-(1-phenylethyl)urea. MS ESI calc'd. For $C_{35}H_{31}N_5O_2$ [M+1]$^+$ 554. found 554.

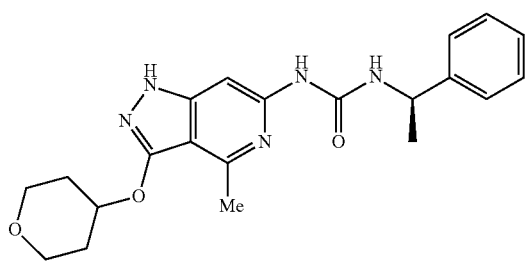 [SMILES: Cc1nc(NC(=O)N[C@H](C)c2ccccc2)cc2[nH]nc(OC3CCOCC3)c12]

Step 2: (R)-1-(4-Methyl-3-((tetrahydro-2H-pyran-4-yl)oxy)-1H-pyrazolo[4,3-c]pyridin-6-yl)-3-(1-phenylethyl)urea A mixture of (R)-1-(4-methyl-3-oxo-1-trityl-2,3-dihydro-1H-pyrazolo[4,3-c]pyridin-6-yl)-3-(1-phenylethyl)urea (50 mg, 0.090 mmol), $Cs_2CO_3$ (91 mg, 0.279 mmol), and 4-iodotetrahydro-2H-pyran (25 μL, 0.209 mmol) in DMF (1 mL) was stirred at room temperature for 18 h. The reaction was quenched with MeOH and concentrated in vacuo. The residue was dissolved in TFA (2 mL), charged with triethylsilane (0.02 mL, 0.125 mmol), and stirred at room temperature for 2 h. The reaction mixture was diluted with DMSO (4 mL) and purified by mass-triggered reverse-phase HPLC. Fractions containing pure compound were filtered through a PS—$HCO_3$ cartridge and the filtrate was concentrated in vacuo to give (R)-1-(4-methyl-3-((tetrahydro-2H-pyran-4-yl)oxy)-1H-pyrazolo[4,3-c]pyridin-6-yl)-3-(1-phenylethyl) urea. MS ESI calc'd. For $C_{21}H_{25}N_5O_3$ [M+1]$^+$ 396. found 396. $^1$H NMR (500 MHz, DMSO-$d_6$) δ 8.96 (s, 1H), 8.12 (br s, 1H), 7.33 (m, 4H), 7.22 (m, 1H), 7.16 (br s, 1H), 4.95 (m, 1H), 4.84 (quintuplet, J=7.1 Hz, 1H), 3.84 (m, 2H), 3.52 (m, 2H), 2.59 (s, 3H), 2.06 (m, 1H), 1.71 (m, 1H), 1.39 (d, J=7.1 Hz, 3H).

Examples 70-72 (Table 11) were prepared according to Scheme 4 following similar procedures described for Example 69 using the appropriate halide and commercial or synthesized ureas (prepared using the same procedure as Intermediates 15B and 16B), which can be achieved by those of ordinary skill in the art of organic synthesis. Example 71 was obtained as the trifluoroacetic acid salt.

TABLE 11

| Example | Structure | IUPAC Name | Exact Mass [M + H]+ |
|---|---|---|---|
| 70 | 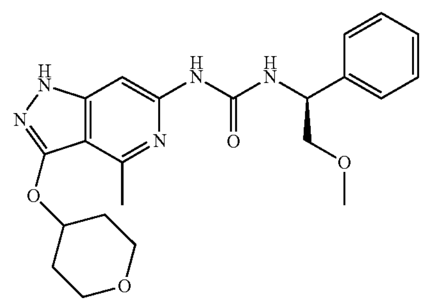 [SMILES: COC[C@@H](NC(=O)Nc1cc2[nH]nc(OC3CCOCC3)c2c(C)n1)c1ccccc1] | 1-[(1S)-2-methoxy-1-phenylethyl]-3-[4-methyl-3-(tetrahydro-2H-pyran-4-yloxy)-1H-pyrazolo[4,3-c]pyridin-6-yl]urea | Calc'd 426, Found 426 |
| 71 | 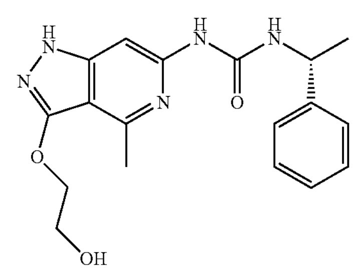 [SMILES: Cc1nc(NC(=O)N[C@H](C)c2ccccc2)cc2[nH]nc(OCCO)c12] | 1-[3-(2-hydroxyethoxy)-4-methyl-1H-pyrazolo[4,3-c]pyridin-6-yl]-3-[(1R)-1-phenylethyl]urea | Calc'd 356, Found 356 |
| 72 | 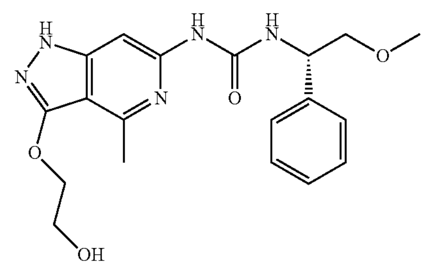 [SMILES: COC[C@@H](NC(=O)Nc1cc2[nH]nc(OCCO)c2c(C)n1)c1ccccc1] | 1-[3-(2-hydroxyethoxy)-4-methyl-1H-pyrazolo[4,3-c]pyridin-6-yl]-3-[(1S)-2-methoxy-1-phenylethyl]urea | Calc'd 386, Found 386 |

Examples 73-75 were prepared according to scheme 5.

Example 73

(R)-1-(3-Methoxy-4-(methoxymethyl)-1H-pyrazolo[4,3-c]pyridin-6-yl)-3-(1-phenylethyl)urea

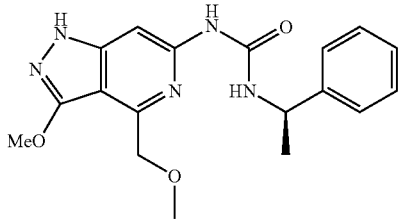 [SMILES: COCc1nc(NC(=O)N[C@H](C)c2ccccc2)cc2[nH]nc(OC)c12]

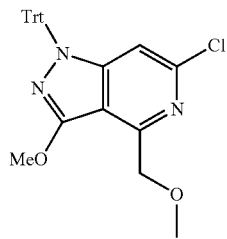

Step 1: 6-Chloro-3-methoxy-4-(methoxymethyl)-1-trityl-1H-pyrazolo[4,3-c]pyridine 4-(Bromomethyl)-6-chloro-3-methoxy-1-trityl-1H-pyrazolo[4,3-c]pyridine (from the synthesis of Intermediate 11B/Step 2; 64 mg, 0.123 mmol) was dissolved in THF (1.5 mL), charged with sodium methoxide (0.080 mL, 0.370 mmol, 4.6 M), and allowed to stir at room temperature for 30 min. The reaction mixture was diluted with water, extracted with ethyl acetate, and washed with brine. The organic layer was dried over magnesium sulfate, filtered, and concentrated in vacuo. The residue was purified by flash chromatography (5-50% EtOAc/hexanes) to give 6-chloro-3-methoxy-4-(methoxymethyl)-1-trityl-1H-pyrazolo[4,3-c]pyridine. MS ESI calc'd. For $C_{28}H_{24}ClN_3O_2$ [M+1]$^+$ 470. found 470.

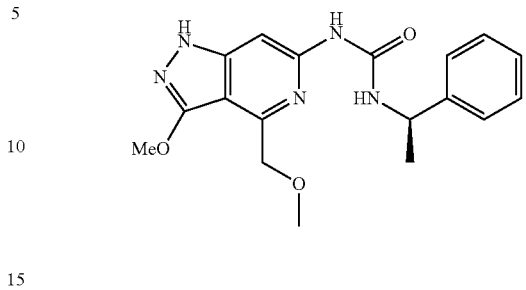

Step 2: (R)-1-(3-Methoxy-4-(methoxymethyl)-1H-pyrazolo[4,3-c]pyridin-6-yl)-3-(1-phenylethyl)urea BrettPhos pre-catalyst (6.80 mg, 8.51 µmol), 6-chloro-3-methoxy-4-(methoxymethyl)-1-trityl-1H-pyrazolo[4,3-c]pyridine (40 mg, 0.085 mmol), cesium carbonate (83 mg, 0.255 mmol), and (R)-1-(1-phenylethyl)urea (20.96 mg, 0.128 mmol) were taken up in dioxane (1 mL) in a 1.5 mL microwave vial and the vial was evacuated and back-filled with $N_2$ (×3). The reaction mixture was stirred at 90° C. for 2 h. The crude reaction mixture was diluted with DCM, filtered through a syringe filter, and the filtrate was concentrated in vacuo. The residue was dissolved in TFA (2 mL), charged with triethylsilane (100 uL), and stirred at room temperature for 10 min. The reaction mixture was concentrated in vacuo and the residue was purified by mass-triggered reverse phase HPLC. Fractions containing pure compound were filtered through a PS—HCO$_3$ cartridge and the filtrate was concentrated in vacuo to give (R)-1-(3-methoxy-4-(methoxymethyl)-1H-pyrazolo[4,3-c]pyridin-6-yl)-3-(1-phenylethyl)urea. MS ESI calc'd. For $C_{18}H_{21}N_5O_3$ [M+1]$^+$ 356. found 356. $^1$H NMR (500 MHz, CD$_3$OD) δ 7.42-7.32 (m, 4H), 7.25 (m, 4H), 6.86 (s, 1H), 5.02 (br s, 2H), 5.01-4.98 (m, 1H), 4.10 (s, 3H), 3.58 (s, 3H), 1.53 (d, J=7.0 Hz, 3H).

Examples 74-75 (Table 12) were prepared according to Scheme 5 following similar procedures described for Example 73 using the appropriate nucleophile, which can be achieved by those of ordinary skill in the art of organic synthesis.

TABLE 12

| Example | Structure | IUPAC Name | Exact Mass [M + H]+ |
|---|---|---|---|
| 74 | 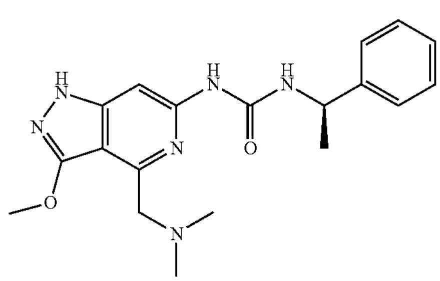 [SMILES: COc1n[nH]c2cc(NC(=O)N[C@H](C)c3ccccc3)nc(CN(C)C)c12] | 1-{4-[(dimethylamino)methyl]-3-methoxy-1H-pyrazolo[4,3-c]pyridin-6-yl}-3-[(1R)-1-phenylethyl]urea | Calc'd 369, Found 369 |

TABLE 12-continued

| Example | Structure | IUPAC Name | Exact Mass [M + H]+ |
|---|---|---|---|
| 75 | 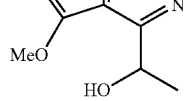 | 1-[3-methoxy-4-(morpholin-4-ylmethyl)-1H-pyrazolo-[4,3-c]pyridin-6-yl]-3-[(1R)-1-phenylethyl]urea | Calc'd 411, Found 411 |

Examples 76-77 were prepared according to scheme 6.

Examples 76 and 77

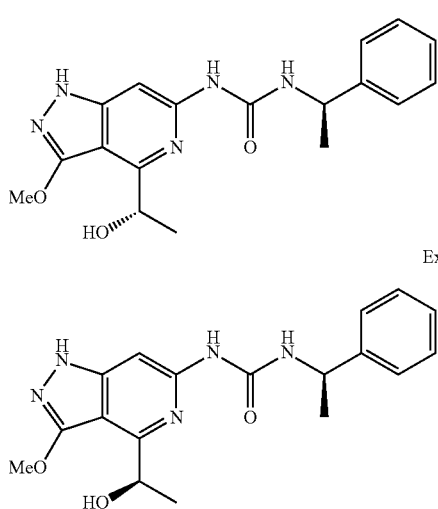

Example 76

Example 77

1-(4-((R or S)-1-Hydroxyethyl)-3-methoxy-1H-pyrazolo[4,3-c]pyridin-6-yl)-3-((R)-1-phenylethyl)urea (Example 76) and 1-(4-((S or R)-1-Hydroxyethyl)-3-methoxy-1H-pyrazolo[4,3-c]pyridin-6-yl)-3-((R)-1-phenylethyl)urea Example 77

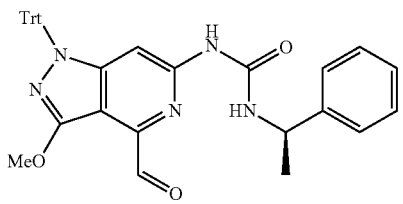

Step 1: (R)-1-(4-Formyl-3-methoxy-1-trityl-1H-pyrazolo[4,3-c]pyridin-6-yl)-3-(1-phenylethyl)urea (R)-1-(4-Formyl-3-methoxy-1-trityl-1H-pyrazolo[4,3-c]pyridin-6-yl)-3-(1-phenylethyl)urea was prepared from Intermediate 11B using the same procedure described for (R)-1-(3-methoxy-1-trityl-1H-pyrazolo[4,3-c]pyridin-6-yl)-3-(1-phenylethyl)urea (Example 40, Step 2).

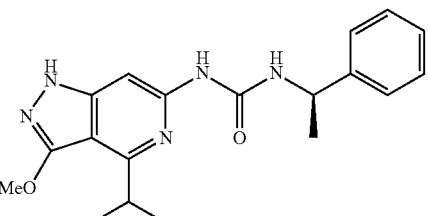

Step 2: 1-(4-(1-Hydroxyethyl)-3-methoxy-1H-pyrazolo[4,3-c]pyridin-6-yl)-3-((R)-1-phenylethyl)urea (R)-1-(4-Formyl-3-methoxy-1-trityl-1H-pyrazolo[4,3-c]pyridin-6-yl)-3-(1-phenylethyl)urea (114 mg, 0.196 mmol) was dissolved in THF (3 mL), cooled to −78° C., and charged with methylmagnesium bromide (0.196 mL, 0.588 mmol). The reaction was allowed to warm to 0° C. and stirred for 10 min. The reaction mixture was quenched with saturated ammonium chloride (3 mL), extracted with EtOAc (10 mL, ×2), washed with brine, dried over sodium sulfate, filtered, and concentrated in vacuo. The residue was dissolved in TFA (0.8 mL), charged with triethylsilane (0.031 mL, 0.196 mmol), and stirred at room temperature for 10 min. The reaction mixture was concentrated in vacuo and the residue was dissolved in DCM (2 mL) and TEA (1 mL) to free-base the product. The solvents were removed in vacuo and the residue was purified by flash chromatography (10-100% EtOAc/DCM) to give 1-(4-(1-hydroxyethyl)-3-methoxy-1H-pyrazolo[4,3-c]pyridin-6-yl)-3-((R)-1-phenylethyl)urea. MS ESI calc'd. For $C_{18}H_{21}N_5O_3$ [M+1]+ 356. found 356.

211

Example 76

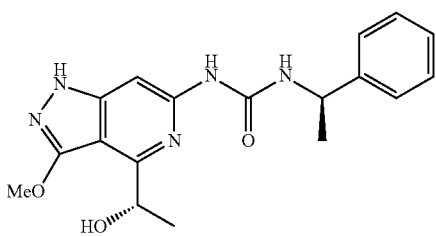

Example 77

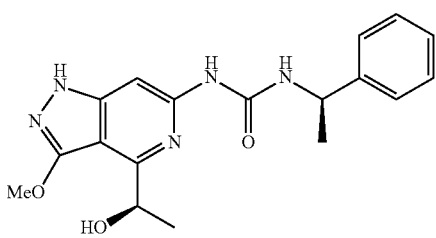 [SMILES: COc1n[nH]c2cc(NC(=O)N[C@H](C)c3ccccc3)nc(C(C)O)c12]

Step 3: 1-(4-((R or S)-1-Hydroxyethyl)-3-methoxy-1H-pyrazolo[4,3-c]pyridin-6-yl)-3-((R)-1-phenylethyl)urea (Example 76) and 1-(4-((S or R)-1-Hydroxyethyl)-3-methoxy-1H-pyrazolo[4,3-c]pyridin-6-yl)-3-((R)-1-phenylethyl)urea Example 77

The enantiomers of 1-(4-(1-hydroxyethyl)-3-methoxy-1H-pyrazolo[4,3-c]pyridin-6-yl)-3-((R)-1-phenylethyl)urea (32 mg, 0.090 mmol) were separated by SFC (Berger Multigram II SFC, column: Chiral Technology OJ-H 2.1×25 cm, 5 uM, mobile phase: 20% to 80% MeOH+0.25% dimethyl ethylamine in $CO_{2(l)}$, flow rate: 70 mL/min, 6 min run time). The fractions were collected and the solvent evaporated in vacuo to afford 1-(4-((R or S)-1-Hydroxyethyl)-3-methoxy-1H-pyrazolo[4,3-c]pyridin-6-yl)-3-((R)-1-phenylethyl)urea and 1-(4-((S or R)-1-Hydroxyethyl)-3-methoxy-1H-pyrazolo[4,3-c]pyridin-6-yl)-3-((R)-1-phenylethyl)urea. MS ESI calc'd. For $C_{18}H_{21}N_5O_3$ [M+1]$^+$ 356. found 356. $^1$H NMR (500 MHz, CD$_3$OD) δ 7.42 (d, J=7.5 Hz, 2H), 7.35-7.29 (m, 2H), 7.21 (dd, J=5.8, 13.2 Hz, 1H), 6.87 (s, 1H), 5.44-5.36 (m, 1H), 5.00 (q, J=6.9 Hz, 1H), 4.06 (s, 3H), 1.54 (d, J=7.0 Hz, 3H), 1.48 (d, J=6.5 Hz, 3H) (Example 76). MS ESI calc'd. For $C_{18}H_{21}N_5O_3$ [M+1]$^+$ 356. found 356. $^1$H NMR (500 MHz, CD$_3$OD) δ 7.40 (d, J=7.6 Hz, 2H), 7.31 (t, J=7.7 Hz, 2H), 7.20 (dd, J=6.9, 14.3 Hz, 1H), 5.42-5.36 (m, 1H), 5.02-4.95 (m,

212

1H), 4.06 (s, 3H), 1.54 (d, J=7.0 Hz, 3H), 1.51 (d, J=6.5 Hz, 3H) (Example 77).

Example 78 was prepared according to scheme 7.

Example 78

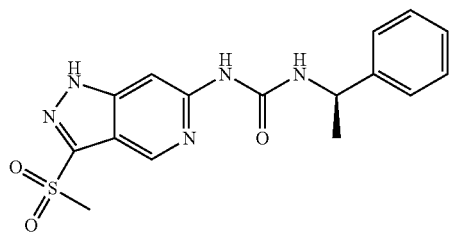 [SMILES: C[C@@H](NC(=O)Nc1cc2[nH]nc(S(C)(=O)=O)c2cn1)c1ccccc1]

(R)-1-(3-(Methylsulfonyl)-1H-pyrazolo[4,3-c]pyridin-6-yl)-3-(1-phenylethyl)urea

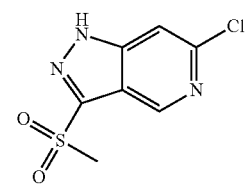

Step 1: 6-Chloro-3-(methylsulfonyl)-1H-pyrazolo[4,3-c]pyridine

6-Chloro-3-iodo-1-trityl-1H-pyrazolo[4,3-c]pyridine (Intermediate 13B; 1.0 g, 1.917 mmol), N,N-dimethylglycine (39.5 mg, 0.383 mmol), copper(I) iodide (36.5 mg, 0.192 mmol), and sodium methanesulfinate (276 mg, 2.300 mmol) were combined in a 20 mL microwave tube, evacuated under N$_2$ and charged with DMSO (7.7 mL). The reaction was degassed via vacuum under nitrogen (×3) and irradiated in a microwave reactor to 110° C. for 90 min. The crude reaction mixture was poured into water and filtered. The precipitate was purified by flash chromatography (10-50% EtOAc/DCM) to afford 6-chloro-3-(methylsulfonyl)-1H-pyrazolo[4,3-c]pyridine. MS ESI calc'd. For $C_7H_6ClN_3O_2S$ [M+1]$^+$ 232. found 232.

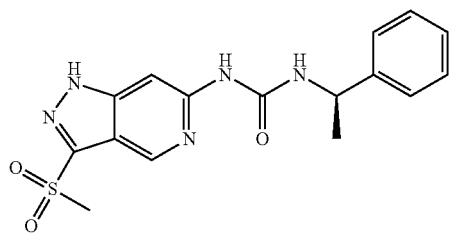 [SMILES: C[C@@H](NC(=O)Nc1cc2[nH]nc(S(C)(=O)=O)c2cn1)c1ccccc1]

Step 2: (R)-1-(3-(Methylsulfonyl)-1H-pyrazolo[4,3-c]pyridin-6-yl)-3-(1-phenylethyl)urea 6-Chloro-3-(methylsulfonyl)-1H-pyrazolo[4,3-c]pyridine (45 mg, 0.194 mmol), (R)-1-(1-phenylethyl)urea (38.3 mg, 0.233 mmol), and BrettPhos pre-catalyst (21.72 mg, 0.027 mmol) were taken up in THF (650 μL) in a 1.5 mL microwave vial. Potassium t-butoxide (1 M in THF, 583 μL, 0.583 mmol) was added and the vial was evacuated and back-filled with N₂ (×3). The reaction mixture was stirred at 60° C. for 18 h. The crude reaction mixture was filtered through a Si-Thiol cartridge (6 mL, 500 mg) to remove excess Pd. The filtrate was concentrated in vacuo, dissolved in DMSO/MeOH (with a few drops of TFA), and purified by mass triggered, reverse phase prep-HPLC. The fractions containing pure product were concentrated in vacuo to afford (R)-1-(3-(methylsulfonyl)-1H-pyrazolo[4,3-c]pyridin-6-yl)-3-(1-phenylethyl) urea. MS ESI calc'd. For $C_{16}H_{17}N_5O_3S$ [M+1]⁺ 360. found 360. ¹H NMR (500 MHz, DMSO-d₆) δ 9.21 (s, 1H), 8.92 (s, 1H), 7.87 (s, 1H), 7.50 (br s, 5H), 4.92-4.80 (m, 1H), 3.38 (s, 3H) 1.40 (d, J=7.0 Hz, 3H).

Examples 79-81 were prepared according to scheme 8.

Example 79

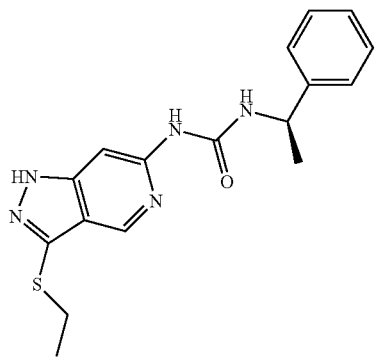 [SMILES: CCSc1n[nH]c2cc(NC(=O)N[C@H](C)c3ccccc3)ncc12]

(R)-1-(3-(Ethylthio)-1H-pyrazolo[4,3-c]pyridin-6-yl)-3-(1-phenylethyl)urea

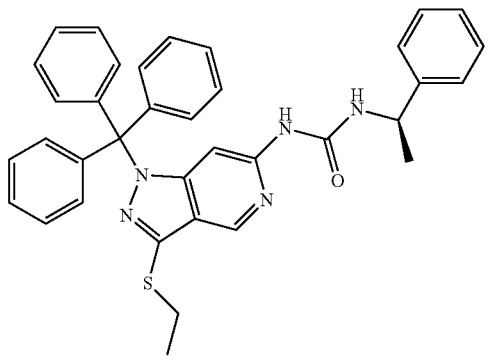 [SMILES: CCSc1nn(C(c2ccccc2)(c2ccccc2)c2ccccc2)c2cc(NC(=O)N[C@H](C)c3ccccc3)ncc12]

Step 1: (R)-1-(3-(Ethylthio)-1-trityl-1H-pyrazolo[4,3-c]pyridin-6-yl)-3-(1-phenylethyl)urea (R)-1-(3-Bromo-1-trityl-1H-pyrazolo[4,3-c]pyridin-6-yl)-3-(1-phenylethyl)urea (Intermediate 14B; 59 mg, 0.098 mmol), sodium ethanethiolate (20.59 mg, 0.245 mmol), and aluminum oxide (100 mg, 0.979 mmol) were dissolved in DMF (2 mL) and heated in a microwave reactor to 100° C. for 2 h. The reaction mixture was diluted with EtOAc, filtered, and concentrated in vacuo while loading onto silica gel. The residue was purified by flash chromatography (7-60% EtOAc/hexane) to give (R)-1-(3-(ethylthio)-1-trityl-1H-pyrazolo[4,3-c]pyridin-6-yl)-3-(1-phenylethyl)urea. MS ESI calc'd. For $C_{36}H_{33}N_5OS$ [M+1]⁺ 584. found 584.

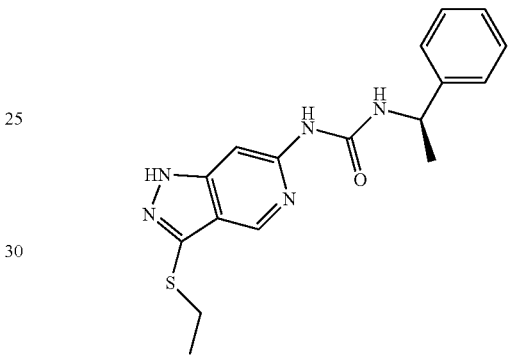

Step 2: (R)-1-(3-(Ethylthio)-1H-pyrazolo[4,3-c]pyridin-6-yl)-3-(1-phenylethyl)urea (R)-1-(3-(Ethylthio)-1-trityl-1H-pyrazolo[4,3-c]pyridin-6-yl)-3-(1-phenylethyl)urea (40.6 mg, 0.070 mmol) was dissolved in TFA (1 mL) and triethylsilane (0.017 mL, 0.104 mmol) was added. The reaction mixture stirred at room temperature for 1 h. The reaction mixture was concentrated in vacuo, diluted with DMSO (1 mL), filtered, and purified by mass-triggered reverse phase HPLC. The fractions containing pure product were concentrated in vacuo to give (R)-1-(3-(ethylthio)-1H-pyrazolo[4,3-c]pyridin-6-yl)-3-(1-phenylethyl)urea, which was obtained as the trifluoroacetic acid salt. MS ESI calc'd. For $C_{17}H_{19}N_5OS$ [M+1]⁺ 342. found 342. ¹H NMR (500 MHz, DMSO-d₆) δ 13.13 (s, 1H), 9.09 (s, 1H), 8.65 (s, 1H), 7.73 (s, 1H), 7.61 (s, 1H), 7.33 (d, J=4.4 Hz, 4H), 7.22 (dt, J=4.1, 8.6 Hz, 1H), 4.94-4.77 (m, 1H), 3.10 (q, J=7.3 Hz, 2H), 1.39 (d, J=7.0 Hz, 3H), 1.27 (t, J=7.3 Hz, 3H). Examples 80-81 (Table 13) were prepared according to Scheme 8 following similar procedures described for Example 79 using the appropriate sodium thiol, which can be achieved by those of ordinary skill in the art of organic synthesis. Example 81 was obtained as the trifluoroacetic acid.

TABLE 13

| Example | Structure | IUPAC Name | Exact Mass [M + H]+ |
|---|---|---|---|
| 80 | 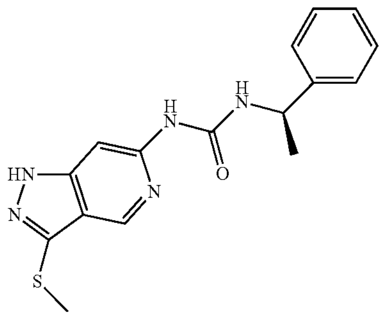 [SMILES: CSc1n[nH]c2cc(NC(=O)N[C@H](C)c3ccccc3)ncc12] | 1-[3-(methylsulfanyl)-1H-pyrazolo[4,3-c]pyridin-6-yl]-3-[(1R)-1-phenylethyl]-urea | Calc'd 328, Found 328. |
| 81 | 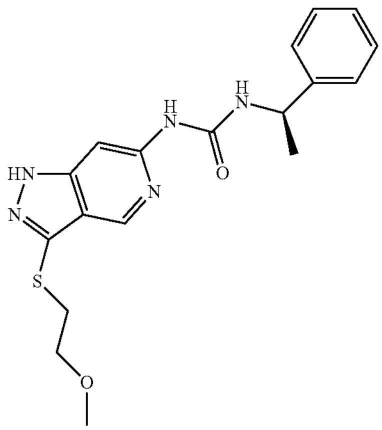 [SMILES: COCCSc1n[nH]c2cc(NC(=O)N[C@H](C)c3ccccc3)ncc12] | 1-{3-[(2-methoxyethyl)sulfanyl]-1H-pyrazolo[4,3-c]pyridin-6-yl}-3-[(1R)-1-phenylethyl]-urea | Calc'd 372, Found 372 |

Example 100

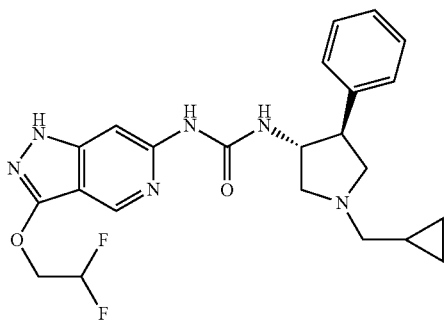 [SMILES: O=C(Nc1cc2[nH]nc(OCC(F)F)c2cn1)N[C@H]1CN(CC2CC2)C[C@@H]1c1ccccc1]

1-((3R,4S)-1-(cyclopropylmethyl)-4-phenylpyrrolidin-3-yl)-3-(3-(2,2-difluoroethoxy)-1H-pyrazolo[4,3-c]pyridin-6-yl)urea In a 4 mL, 1 dram vial were added 1-(3-(2,2-difluoroethoxy)-1H-pyrazolo[4,3-c]pyridin-6-yl)-3-43R,4S)-4-phenylpyrrolidin-3-yl)urea (20 mg, 0.050 mmol, Intermediate 34B), cyclopropane-carboxaldehyde (0.007 g, 0.099 mmol) and solid supported triacetoxyborohydride (113 mg, 0.232 mmol, Biotage MP-(OAc)3BH/800415; 2.05 mmol/g). To this was added DMA (0.5 ml) with AcOH (0.05 ml). The solution was shaken at room temperature over night. The product was analyzed by LC/MS and found to contain the desired compound. The filtered crude solution was directly injected to the Gilson, semi-preparative HPLC (0.1% TFA in ACN and Water on a Waters Sunfire C18 ODB, 5 uM, 19 mm×100 mm, Part No. 186002567 column using a gradient of 10%-60% ACN over 12 minutes). The fractions were analyzed by LC/MS and the pure fractions were concentrated to provide 1-((3R,4S)-1-(cyclopropylmethyl)-4-phenylpyrrolidin-3-yl)-3-(3-(2,2-difluoroethoxy)-1H-pyrazolo[4,3-c]pyridin-6-yl)urea (100), was isolated as an off white powder. MS: [M+H]$^+$ m/z 457.

Example 101

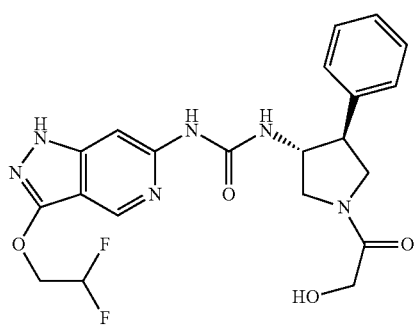 [SMILES: O=C(Nc1cc2[nH]nc(OCC(F)F)c2cn1)N[C@H]1CN(C(=O)CO)C[C@@H]1c1ccccc1]

1-(3-(2,2-difluoroethoxy)-1H-pyrazolo[4,3-c]pyridin-6-yl)-3-((3R,4S)-1-(2-hydroxyacetyl)-4-phenylpyrrolidin-3-yl)urea In a 4 mL, 1 dram vial were added 1-(3-(2,2-difluoroethoxy)-1H-pyrazolo[4,3-c]pyridin-6-yl)-3-((3R,4S)-4-phenylpyrrolidin-3-yl)urea: (20 mg, 0.050 mmol, Intermediate 34B), glycolic acid (8 mg, 0.099 mmol), HATU (37.8 mg, 0.099 mmol) and DIEA (0.025 ml, 0.149 mmol) all in DMA (0.5 ml). The solution was shaken at room temperature over night. The solution was analyzed by LC/MS and found to contain the desired compound. The filtered crude solution was directly injected to the Gilson semi-preparative HPLC (0.1% TFA in ACN and Water on a Waters Sunfire C18 ODB, 5 uM, 19 mm×100 mm, Part No. 186002567 column using a gradient of 10%-60% ACN over 12 minutes). The fractions were analyzed by LC/MS and the pure fractions were concentrated to provide 1-(3-(2,2-difluoroethoxy)-1H-pyrazolo[4,3-c]pyridin-6-yl)-3-((3R,4S)-1-(2-hydroxyacetyl)-4-phenylpyrrolidin-3-yl)urea (101), was isolated as an off white powder. MS: [M+H]+ m/z 461.

Example 102

(S)-1-((1-hydroxycyclobutyl)(phenyl)methyl)-3-(3-(2-methoxyethoxy)-1H-pyrazolo[4,3-c]pyridin-6-yl)urea

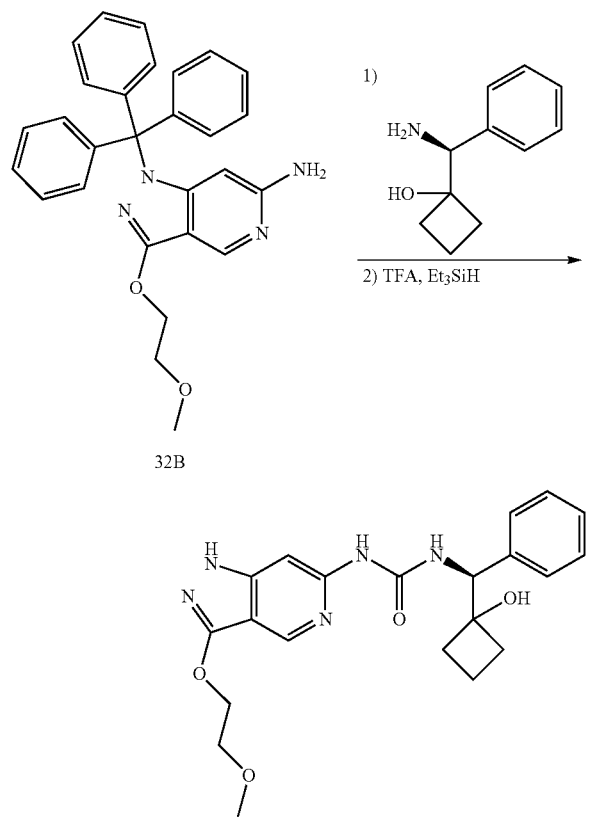

Step 1: (S)-1-((1-hydroxycyclobutyl)(phenyl)methyl)-3-(3-(2-methoxyethoxy)-1-trityl-1H-pyrazolo[4,3-c]pyridin-6-yl)urea CDI (36.0 mg, 0.222 mmol) was added to a stirred, room temperature mixture of 3-(2-methoxyethoxy)-1-trityl-1H-pyrazolo[4,3-c]pyridin-6-amine 32B (50 mg, 0.111 mmol) and imidazole (30.2 mg, 0.444 mmol) in tetrahydrofuran (1 mL), and the mixture was stirred at room temperature for overnight. The mixture turned from light yellow slurry to clear solution. (S)-1-(amino(phenyl)methyl)cyclobutanol (19.67 mg, 0.111 mmol) was added to mixture and the resultant mixture was kept stirring at room temperature for overnight. The residue was purified (24 g silica, eluting with 50% EtOAc/isohexane) to give (S)-1-((1-hydroxycyclobutyl)(phenyl)methyl)-3-(3-(2-methoxyethoxy)-1-trityl-1H-pyrazolo[4,3-c]pyridin-6-yl)urea (54 mg, 74% yield) as a white solid. MS: [M+H]+ m/z 654.

Step 2: (S)-1-((1-hydroxycyclobutyl)(phenyl)methyl)-3-(3-(2-methoxyethoxy)-1H-pyrazolo[4,3-c]pyridin-6-yl)urea (102)

In a manner similar to that described previously (e.g. Example 40, Step 3), (S)-1-((1-hydroxycyclobutyl)(phenyl)-methyl)-3-(3-(2-methoxyethoxy)-1-trityl-1H-pyrazolo[4,3-c]pyridin-6-yl)urea was treated with TFA and triethylsilane in DCM. The product (102) was purified by Reverse phase C-18 HPLC (eluting with Acetonitrile/Water+0.1% TFA). MS: [M+H]+ m/z 412. 1H NMR (500 MHz, DMSO) δ 12.24 (s, 1H), 9.48 (s, 1H), 8.61 (s, 1H), 7.85 (bs, 1H), 7.38 (t, 2H, J=7.5 Hz), 7.36 (s, 1H), 7.27 (t, 2H, J=7.5 Hz), 7.20 (t, 2H, J=7.5 Hz), 4.78 (d, 1H, J=9 Hz), 4.42 (t, 2H, J=4.5 Hz), 3.70 (t, 2H, J=4.5 Hz), 3.30 (s, 3H), 2.12 (1H, m), 2.00 (m, 2H), 1.79 (m, 1H), 1.69 (m, 1H), 1.59 (m, 1H).

Example 103

(R)-1-(4-(2-(hydroxymethyl)pyridin-4-yl)-3-methoxy-1H-pyrazolo[4,3-c]pyridin-6-yl)-3-(1-phenylethyl)urea

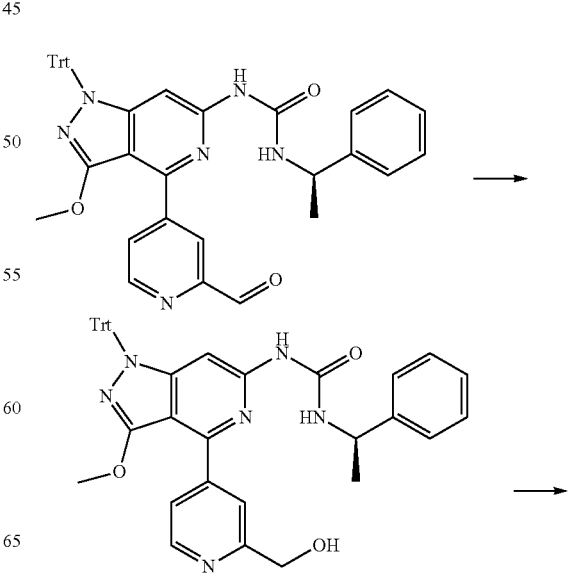

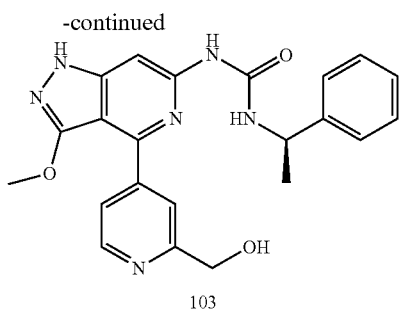

103

Step 1: (R)-1-(4-(2-(hydroxymethyl)pyridin-4-yl)-3-methoxy-1-trityl-1H-pyrazolo[4,3-c]pyridin-6-yl)-3-(1-phenylethyl)urea (R)-1-(4-(2-formyl pyridin-4-yl)-3-methoxy-1-trityl-1H-pyrazolo[4,3-c]pyridin-6-yl)-3-(1-phenylethyl)urea (60 mg, 0.091 mmol, prepared from intermediate 51B by Scheme 3/Method A) was taken up in MeOH (2 ml) and sodium borohydride (3.79 mg, 0.100 mmol) was added. The reaction was allowed to stir at rt for 2 hours—until complete by LCMS. 1 ml of 2N HCl was added and the mixture was concentrated in vacuo. Reaction products were carrried forward without purification. MS: [M+H]$^+$ m/z 661.

Step 2: (R)-1-(4-(2-(hydroxymethyl)pyridin-4-yl)-3-methoxy-1H-pyrazolo[4,3-c]pyridin-6-yl)-3-(1-phenylethyl)urea (103)

(R)-1-(4-(2-(hydroxymethyl)pyridin-4-yl)-3-methoxy-1-trityl-1H-pyrazolo[4,3-c]pyridin-6-yl)-3-(1-phenylethyl) urea was taken up in TFA (1.2 ml) at room temperature and triethylsilane (0.026 ml, 0.164 mmol) was added dropwise. The reaction was allowed to stir at rt for 20 mins. The mixture was concentrated in vacuo. The oil was suspended in DMSO and MeOH (3 ml), filtered, and purified by reverse phase mass-triggered preparative HPLC. The fractions containing product were concentrated down to give (R)-1-(4-(2-(hydroxymethyl)pyridin-4-yl)-3-methoxy-1H-pyrazolo[4,3-c]pyridin-6-yl)-3-(1-phenylethyl)urea (103) as the trifluoroacetic acid salt. MS: [M+H]$^+$ m/z 419. $^1$H NMR (500 MHz, DMSO-d$_6$) δ 12.34 (s, 1H), 9.20 (s, 1H), 8.70 (d, J=4.5 1H), 8.09 (s, 1H), 7.86 (br s, 1H), 7.76 (br s, 1H), 7.58 (s, 1H), 7.31 (m, 4H), 7.23 (m, 1H), 4.87 (m, 1H), 4.74 (s, 2H), 3.95 (s, 1H), 3.92 (s, 3H), 1.39 (d, J=7.0, 3H).

Example 104

(R)-3-methoxy-6-(3-(1-phenylethyl)ureido)-1H-pyrazolo[4,3-c]pyridine-4-carboxylic acid

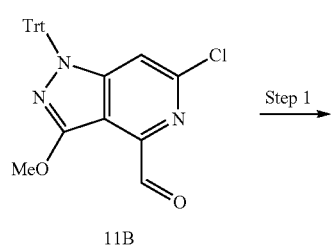

11B

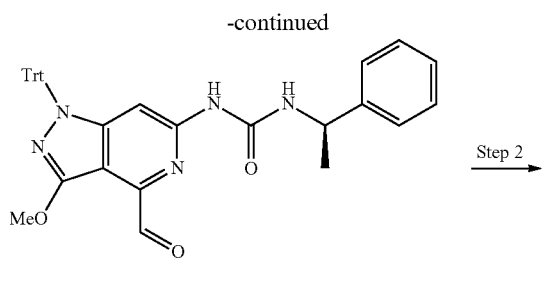

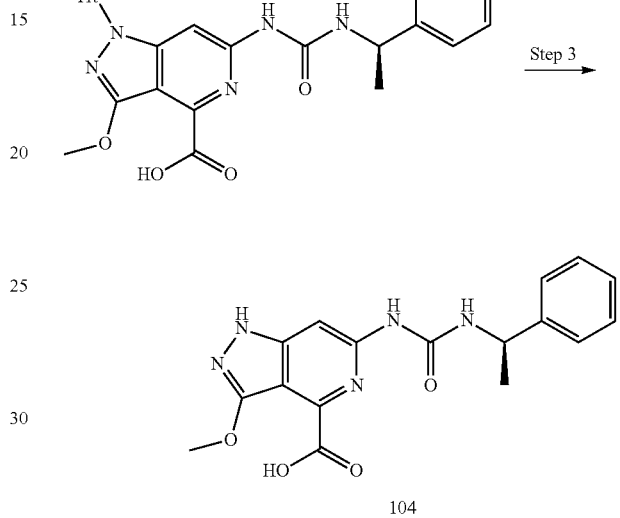

104

Step 1: (R)-1-(4-formyl-3-methoxy-1-trityl-1H-pyrazolo[4,3-c]pyridin-6-yl)-3-(1-phenylethyl)urea In a manner similar to that described previously (e.g. Scheme 3/Method A and Example 40), 6-chloro-3-methoxy-1-trityl-1H-pyrazolo[4,3-c]pyridine-4-carbaldehyde (Intermediate 11B) was reacted with converted to (R)-1-(1-phenylethyl)urea (BrettPhos PreCatalyst, cesium carbonate, dioxane, 90° C. for 4 hrs) to provide (R)-1-(4-formyl-3-methoxy-1-trityl-1H-pyrazolo[4,3-c]pyridin-6-yl)-3-(1-phenylethyl)urea. MS: [M+H]$^+$ m/z 582.

Steps 2-3: (R)-3-methoxy-6-(3-(1-phenylethyl)ureido)-1H-pyrazolo[4,3-c]pyridine-4-carboxylic acid (104)

(R)-3-methoxy-6-(3-(1-phenylethyl)ureido)-1-trityl-1H-pyrazolo[4,3-c]pyridine-4-carboxylic acid was prepared in a manner similar to that described in the preparation of Intermediate 36B. MS: [M+H]$^+$ m/z 598. Final deprotection with TFA and triethylsilane was accomplished as previously described to provide the title compound (104). MS: [M+H]$^+$ m/z 356. $^1$H NMR (500 MHz, DMSO-d$_6$) M2.24 (s, 1H), 9.26 (s, 1H), 7.96 (br s, 1H), 7.50 (s, 1H), 7.32 (m, 4H), 7.21 (m, 1H), 4.86 (m, 1H), 3.92 (s, 3H), 1.21 (d, J=7.0, 3H).

Example 105

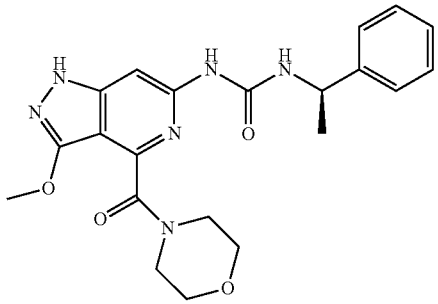 [SMILES: COc1n[nH]c2cc(NC(=O)N[C@H](C)c3ccccc3)nc(C(=O)N3CCOCC3)c12]

(R)-1-(3-methoxy-4-(morpholine-4-carbonyl)-1H-pyrazolo[4,3-c]pyridin-6-yl)-3-(1-phenylethyl)urea (105)

(R)-3-methoxy-6-(3-(1-phenylethyl)ureido)-1-trityl-1H-pyrazolo[4,3-c]pyridine-4-carboxylic acid (60 mg, 0.100 mmol, from Example 104), morpholine (8.75 mg, 0.100 mmol), EDC (28.9 mg, 0.151 mmol), and HOBT (23.06 mg, 0.151 mmol) were taken up in DMF (502 µl). DIPEA (70.1 µl, 0.402 mmol) was added and the reaction mixture was allowed to stir at rt overnight. Saturated NH₄Cl and EtOAc were added. The products were extracted into EtOAc (2×). The combined organics were then washed with saturated NaHCO₃ and brine, then dried over MgSO₄, and concentrated in vacuo. The residue was then resuspended in TFA (0.5 ml) and triethylsilane (24.05 µl, 0.151 mmol) was added. The mixture was allowed to stir at rt for 30 mins. The mixture was then concentrated in vacuo, resuspended in DMSO/MeOH and filtered. The product was then purified by reverse phase mass-triggered preparative HPLC. The fractions containing pure product were concentrated down to give (R)-1-(3-methoxy-4-(morpholine-4-carbonyl)-1H-pyrazolo[4,3-c]pyridin-6-yl)-3-(1-phenylethyl)urea (105) as the trifluoroacetic acid salt. MS: [M+H]⁺ m/z 425. ¹H NMR (500 MHz, DMSO-d₆) M2.18 (s, 1H), 9.13 (s, 1H), 7.54 (s, 1H), 7.42 (br s, 1H), 7.31 (m, 4H), 7.21 (m, 1H), 4.84 (m, 1H), 3.93 (s, 3H), 3.64 (m, 4H), 3.44 (t, J=5.5, 2H), 3.08 (m, 2H), 1.37 (d, J=7.0, 3H).

Example 106

(R)-3-methoxy-6-(3-(1-phenylethyl)ureido)-1H-pyrazolo[4,3-c]pyridine-4-carboxamide

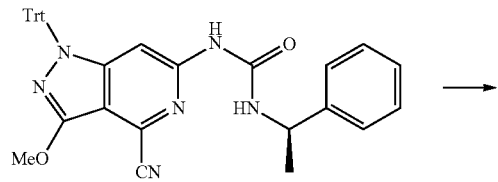

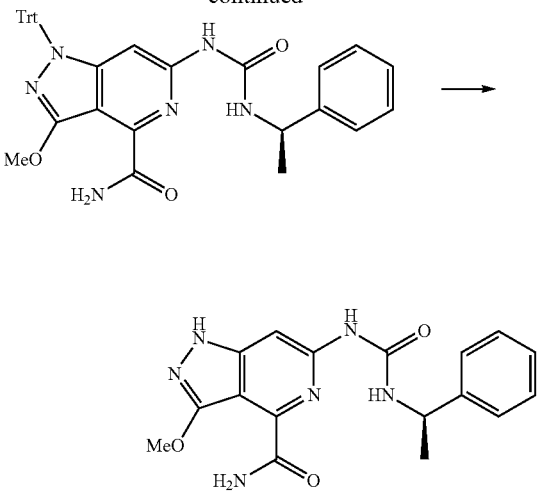

Step 1: (R)-3-methoxy-6-(3-(1-phenylethyl)ureido)-1-trityl-1H-pyrazolo[4,3-c]pyridine-4-carboxamide (R)-1-(4-cyano-3-methoxy-1-trityl-1H-pyrazolo[4,3-c]pyridin-6-yl)-3-(1-phenylethyl)urea (70 mg, 0.121 mmol, synthesized from Intermediate 42B following Scheme 3-Step 2/Method A) was taken up in DMSO (605 µl) and Ethanol (605 µl). NaOH (1.8 ml, 1.815 mmol) was added followed by dropwise addition of hydrogen peroxide (180 µl, 2.056 mmol). The reaction was heated to 60° C. and was allowed to stir for 30 minutes. Room temperature was attained and 1N HCl was added and the products were extracted into EtOAc (3×). The organic layers were washed with brine, dried over MgSO₄, and concentrated in vacuo to give (R)-3-methoxy-6-(3-(1-phenylethyl)ureido)-1-trityl-1H-pyrazolo[4,3-c]pyridine-4-carboxamide. The products were carried forward without purification. MS: [M+H]⁺ m/z 597.

Step 2: (R)-3-methoxy-6-(3-(1-phenylethyl)ureido)-1H-pyrazolo[4,3-c]pyridine-4-carboxamide (106)

(R)-3-methoxy-6-(3-(1-phenylethyl)ureido)-1-trityl-1H-pyrazolo[4,3-c]pyridine-4-carboxamide (80 mg, 0.134 mmol) was taken up in TFA (1.5 ml) and triethylsilane (0.032 ml, 0.201 mmol) was added. The reaction mixture was allowed to stir at rt for 30 mins. The mixture was concentrated in vacuo then resuspended in DMSO/MeOH and filtered. Purification by reverse phase mass-triggered preparative HPLC gave (R)-3-methoxy-6-(3-(1-phenylethyl)ureido)-1H-pyrazolo[4,3-c]pyridine-4-carboxamide (106) as the trifluoroacetic acid salt. MS: [M+H]⁺ m/z 355. ¹H NMR (500 MHz, DMSO-d₆) M2.16 (s, 1H), 9.14 (s, 1H), 7.87 (br s, 1H), 7.63 (s, 1H), 7.47 (s, 1H), 7.32 (m, 5H), 7.21 (m, 1H), 4.85 (m, 1H), 3.93 (s, 3H), 1.38 (d, J=7.0, 3H).

Example 107

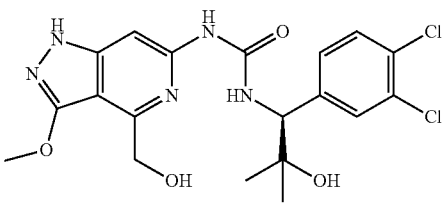 [SMILES: COc1n[nH]c2cc(NC(=O)N[C@@H](c3ccc(Cl)c(Cl)c3)C(C)(C)O)nc(CO)c12]

(S)-1-(1-(3,4-dichlorophenyl)-2-hydroxy-2-methyl-propyl)-3-(4-(hydroxymethyl)-3-methoxy-1H-pyrazolo[4,3-c]pyridin-6-yl)urea

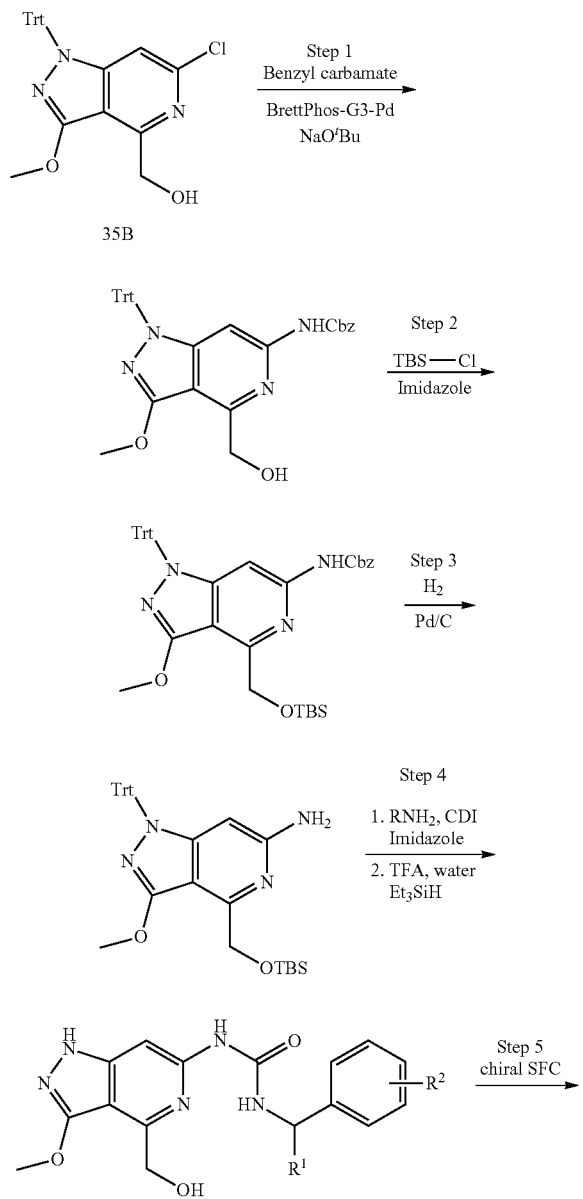

-continued

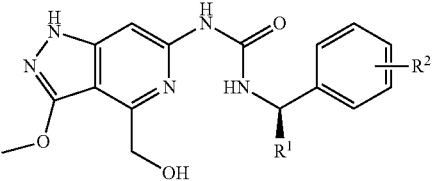

Step 1: benzyl(4-(hydroxymethyl)-3-methoxy-1-trityl-1H-pyrazolo[4,3-c]pyridin-6-yl)carbamate A 20 mL scintillation vial was charged with sodium tert-butoxide (105 mg, 1.097 mmol), (6-chloro-3-methoxy-1-trityl-1H-pyrazolo[4,3-c]pyridin-4-yl)methanol (35B, 250 mg, 0.548 mmol), benzyl carbamate (124 mg, 0.822 mmol) and BrettPhos-Pd-G3 (24.85 mg, 0.027 mmol). THF (5 ml) was added, the vial flushed with argon, capped and the contents heated to 50° C. with stirring for 10 h. The mixture was cooled, diluted with ethyl acetate (10 mL), washed with aqueous sodium hydrogen carbonate (saturated, 2×20 mL), dried (MgSO$_4$), filtered and the solvent evaporated under reduced pressure. The resulting residue was purified by column chromatography on silica gel ISCO; 24 g prepacked, eluting with EtOAc/hexanes to afford benzyl(4-(hydroxymethyl)-3-methoxy-1-trityl-1H-pyrazolo[4,3-c]pyridin-6-yl)carbamate (181 mg, 0.317 mmol, 57.8% yield) as a white solid. MS: [M+H]$^+$ m/z 571.

Step 2: benzyl(4-(((tert-butyldimethylsilyl)oxy)methyl)-3-methoxy-1-trityl-1H-pyrazolo[4,3-c]pyridin-6-yl)carbamate To a 50 mL round bottom flask charged with benzyl(4-(hydroxymethyl)-3-methoxy-1-trityl-1H-pyrazolo[4,3-c]pyridin-6-yl)carbamate (180 mg, 0.315 mmol), imidazole (42.9 mg, 0.631 mmol) and DMF (3 ml) was added tert-butyldimethylchlorosilane (57.1 mg, 0.379 mmol). The flask was capped and the contents stirred at room temperature for 2 h. LCMS analysis indicated 80% conversion to the desire product. Excess tert-butyldimethylchlorosilane (25 mg) was added, and the reaction mixture stirred at room temperature for 16 h. The reaction mixture was diluted with ethyl acetate (20 mL), washed with water (2×30 mL), dried (MgSO$_4$) and filtered. The solvent was evaporated under reduced pressure to afford crude benzyl(4-(((tert-butyldimethylsilyl)oxy)methyl)-3-methoxy-1-trityl-1H-pyrazolo[4,3-c]pyridin-6-yl)carbamate (199 mg, 0.291 mmol, 92% yield) as a colorless oil. MS: [M+H]$^+$ m/z 685.

Step 3: 4-(((tert-butyldimethylsilyl)oxy)methyl)-3-methoxy-1-trityl-1H-pyrazolo[4,3-c]pyridin-6-amine To a 50 mL round bottom flask charged with crude benzyl (4-(((tert-butyldimethylsilyl)oxy)methyl)-3-methoxy-1-trityl-1H-pyrazolo[4,3-c]pyridin-6-yl)carbamate (199 mg, 0.291 mmol) in ethyl acetate (10 ml) and methanol (5 ml) was added palladium on carbon (61.8 mg, 0.058 mmol). The flask was evacuated and back-filled with hydrogen gas using an attached balloon. This procedure was attempted a further two times. The reaction mixture was stirred under a hydrogen atmosphere at room temperature for 16 h. The palladium was filtered off by passing the reaction mixture through celite and washing through with methanol (20 mL). The volatiles were removed in vacuo to afford crude 4-(((tert-butyldimethylsilyl)oxy)methyl)-3-methoxy-1-trityl-1H-pyrazolo[4,3-c]pyridin-6-amine (132 mg, 0.240 mmol, 82% yield) as a yellow oil. The product was carried forward without purification. MS: [M+H]+ m/z 551.

Step 4: 1-(1-(3,4-dichlorophenyl)-2-hydroxy-2-methylpropyl)-3-(4-(hydroxymethyl)-3-methoxy-1H-pyrazolo[4,3-c]pyridin-6-yl)urea To a 8 mL vial charged with imidazole (31 mg, 0.45 mmol) and 4-(((tert-butyldimethylsilyl)oxy)methyl)-3-methoxy-1-trityl-1H-pyrazolo[4,3-c]pyridin-6-amine (50 mg, 0.09 mmol) in DCM (2 ml) was added 1,1'-carbonyldiimidazole (44 mg, 0.27 mmol). The reaction mixture was stirred at room temperature for 5 h, leading to a clear yellow solution. 1-amino-1-(3,4-dichlorophenyl)-2-methylpropan-2-ol (48.7 mg, 0.180 mmol, synthesized from methyl 2-amino-2-(3,4-dichlorophenyl)acetate in a manner similar to that described for Intermediate 21B) and DIEA (0.079 ml, 0.450 mmol) was added to the reaction mixture. The vial was capped and the contents stirred at room temperature for 16 h.

The reaction mixture was concentrated and the resulting residue re-dissolved in a mixture of TFA (1 ml) and water (0.5 mL) and stirred at room temperature for 2 h. Triethylsilane (0.029 ml, 0.180 mmol) was added dropwise, and the reaction mixture stirred for an additional 5 minutes. The mixture was concentrated, re-dissolved in DMSO (1.5 mL) and submitted for purification by mass-triggered prep. HPLC to afford 1-(1-(3,4-dichlorophenyl)-2-hydroxy-2-methylpropyl)-3-(4-(hydroxymethyl)-3-methoxy-1H-pyrazolo[4,3-c]pyridin-6-yl)urea as a TFA salt (107) as a white solid. MS: [M+H]+ m/z 454.

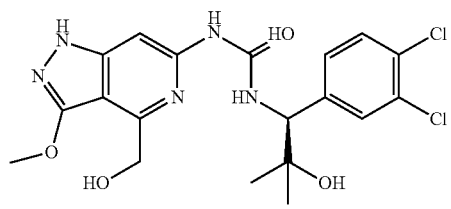

107

Step 5: (S)-1-(1-(3,4-dichlorophenyl)-2-hydroxy-2-methylpropyl)-3-(4-(hydroxymethyl)-3-methoxy-1H-pyrazolo[4,3-c]pyridin-6-yl)urea (107)

The enantiomers of 1-(1-(3,4-dichlorophenyl)-2-hydroxy-2-methylpropyl)-3-(4-(hydroxymethyl)-3-methoxy-1H-pyrazolo[4,3-c]pyridin-6-yl)urea, TFA (15 mg, 0.033 mmol) were separated by SFC (Berger Multigram II, Column: Chiralcel OJ-H, 2.1×25 cm, 5 uM, UV wavelength: 220 nM, mobile phase: 85%/15% Methanol+0.25% dimethyl ethylamine/$CO_{2(l)}$, flow rate: 70 mL/Min, 10 min run time). Elution was observed at 5.8 min. The fractions were collected and the solvent evaporated in vacuo to afford (S)-1-(1-(3,4-dichlorophenyl)-2-hydroxy-2-methylpropyl)-3-(4-(hydroxymethyl)-3-methoxy-1H-pyrazolo[4,3-c]pyridin-6-yl) urea (107, 6.2 mg, 0.014 mmol, 83.0% yield). MS: [M+H]+ m/z 454. $^1$H NMR (600 MHz, DMSO): 7.51-7.55 (m, 2H); 7.31 (dd, J=8.3, 2.0 Hz, 1H); 7.04 (s, 1H); 4.77 (s, 2H); 4.59 (d, J=8.6 Hz, 1H); 3.94 (s, 3H); 1.16 (s, 6H).

Example 108

(R)-1-(7-fluoro-4-(hydroxymethyl)-3-methoxy-1H-pyrazolo[4,3-c]pyridin-6-yl)-3-(1-phenylethyl)urea

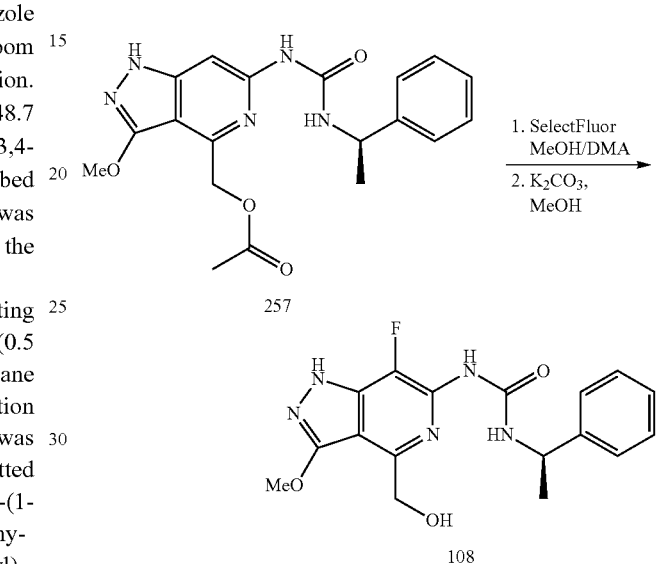

Step 1:

(R)-(3-methoxy-6-(3-(1-phenylethyl)ureido)-1H-pyrazolo[4,3-c]pyridin-4-yl)methyl acetate (108 mg, 0.282 mmol, Example 257, derived from Intermediate 41B according to Scheme 3/Method A) was dissolved in MeOH (1 mL) and charged with selectfluor (150 mg, 0.423 mmol). The reaction was allowed to stir overnight at rt. The solvents were removed in vacuo and the residue was purified on RP-HPLC 30×150 mm column (25-60% CH3CN/H2O w/0.1% TFA) to provide (R)-(7-fluoro-3-methoxy-6-(3-(1-phenylethyl)ureido)-1H-pyrazolo[4,3-c]pyridin-4-yl)methyl acetate (60 mg, 0.149 mmol, 53.1% yield) as TFA salt.

Step 2:

The white solid was dissolved in MeOH and charged with potassium carbonate (117 mg, 0.845 mmol). The reaction was allowed to stir until SM was consumed by LC/MS, ~1 h. The reaction was filtered through a syringe filter and the solvents were removed in vacuo. The residue was diluted with 20 mL EtOAc/MeOH 10:1 and charged with 5 mL sat. NH4Cl. The aq. layer was extracted a second time with 20 ml EtOAc/MeOH 10:1, the combined organics were washed with brine, dried over sodium sulfate, filtered and concentrated in vacuo. The residue was purified (silica gel, 40 g column, 20-80% EtOAc/DCM) to provide (R)-1-(7-fluoro-4-(hydroxymethyl)-3-methoxy-1H-pyrazolo[4,3-c]pyridin-6-yl)-3-(1-phenylethyl)urea (108). MS: [M+H]+ m/z 360. $^1$H NMR (500 MHz, dmso) δ 12.64 (s, 1H), 9.74 (s, 1H), 8.85 (s, 1H), 7.37

(d, J=7.3, 2H), 7.32-7.27 (m, 2H), 7.19 (m, 1H), 5.33 (q, J=5.5, 1H), 4.97-4.85 (m, 1H), 4.82-4.74 (m, 2H), 3.99 (s, 3H), 1.42 (d, J=7.0, 3H).

Example 109

1-[4-(hydroxymethyl)-3-methoxy-1H-pyrazolo[4,3-c]pyridin-6-yl]-3-[(1R)-1-phenylethyl]urea

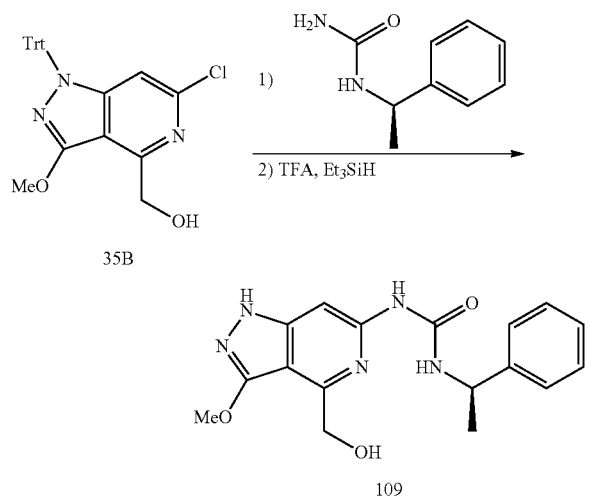

Step 1:

Chloro[2-(dicyclohexylphosphino)-3,6-dimethoxy-2'-4'-6'-tri-i-propyl-1,1'-biphenyl][2-(2-aminoethyl)phenyl]palladium(ii) (67.5 mg, 0.084 mmol), (6-chloro-3-methoxy-1-trityl-1H-pyrazolo[4,3-c]pyridin-4-yl)methanol (35B, 385 mg, 0.844 mmol), cesium carbonate (825 mg, 2.53 mmol) and (R)-1-(1-phenylethyl)urea (277 mg, 1.689 mmol) were taken up in dioxane (5 ml) in a 1.5 mL microwave vial and the vial was evacuated and back-filled with N2 (×3). The reaction mixture was stirred at 90° C. for 2 hours. The crude reaction mixture was diluted with DCM and filtered through syringe filter. The filtrate was concentrated, and purified on 80 g Redsep gold silica gel 5-25% DCM/EtOAc to provide (R)-1-(4-(hydroxymethyl)-3-methoxy-1-trityl-1H-pyrazolo[4,3-c]pyridin-6-yl)-3-(1-phenylethyl)urea. MS: [M+H]+ m/z 584.

Step 2:

The material was taken up in 2 mL DCM, charged with 1 mL TFA and 200 uL triethylsilane and allowed to stir at rt for 1 h. The solvents were removed in vacuo and the residue was neutralised with TEA/DCM 1:1 2 mL, and purified on silica gel (25-100% EtOAc/DCM) to provide (R)-1-(4-(hydroxymethyl)-3-methoxy-1H-pyrazolo[4,3-c]pyridin-6-yl)-3-(1-phenylethyl)urea (109). MS: [M+H]+ m/z 342. 1H NMR (500 MHz, dmso) δ 11.95 (s, 1H), 9.08 (s, 1H), 8.73 (br s, 1H), 7.35-7.31 (m, 4H), 7.22 (m, 1H), 7.09 (br s, 1H), 5.12 (t, J=5.0, 1H), 4.87 (m, 1H), 4.76 (d, J=5.5, 2H), 3.95 (s, 3H), 1.40 (d, J=7.0, 3H).

Example 110

1-[4-(hydroxymethyl)-3-methoxy-1H-pyrazolo[4,3-c]pyridin-6-yl]-3-[(1S)-2-hydroxy-2-methyl-1-phenylpropyl]urea Step 1:

(6-chloro-3-methoxy-1-trityl-1H-pyrazolo[4,3-c]pyridin-4-yl)methanol (35B, 500 mg, 1.097 mmol), chloro[2-(dicyclohexylphosphino)-3,6-dimethoxy-2'-4'-6'-tri-i-propyl-1, 1'-biphenyl][2-(2-aminoethyl)phenyl]palladium(ii) (88 mg, 0.110 mmol), cesium carbonate (893 mg, 2.74 mmol) and (S)-1-(2-hydroxy-2-methyl-1-phenylpropyl)urea (21B, 343 mg, 1.645 mmol) were taken up in an oven dried 2 mL round bottom flask equipped with magnetic stir bar and degassed 3× under nitrogen. Anhydrous dioxane (8 ml) was added the reaction was degassed 3× under nitrogen and heated to 95° C. for 14 hours. The crude reaction mixture was diluted with 2 mL DCM and filtered a syringe filter. The filtrate was concentrated in vacuo and the residue was purified on silica gel, 5-50% EtOAc/DCM to provide (S)-1-(2-hydroxy-2-methyl-1-phenylpropyl)-3-(4-(hydroxymethyl)-3-methoxy-1-trityl-1H-pyrazolo[4,3-c]pyridin-6-yl)urea (533 mg, 0.849 mmol, 77% yield). MS: [M+H]+ m/z 628.

Step 2:

(S)-1-(2-hydroxy-2-methyl-1-phenylpropyl)-3-(4-(hydroxymethyl)-3-methoxy-1-trityl-1H-pyrazolo[4,3-c]pyridin-6-yl)urea (533 mg, 0.849 mmol) was dissolved in DCM (3 ml), charged with triethylsilane (0.271 ml, 1.698 mmol) followed by TFA (3.27 ml, 42.5 mmol) and allowed to stir for 1 h at rt. The solvents were removed in vacuo and the residue was dissolved in 25 mL 10:1 EtOAc/MeOH and washed with 20 mL saturated sodium bicarbonate. The aq. was extracted 1×15 mL EtOAc and the combine organics were washed with brine, dried over sodium sulfate, concentrated vacuo and purified on silica gel 5-15% MeOH/DCM to provide (S)-1-(2-hydroxy-2-methyl-1-phenylpropyl)-3-(4-(hydroxymethyl)-3-methoxy-1H-pyrazolo[4,3-c]pyridin-6-yl)urea (110) as a white solid. MS: [M+H]+ m/z 386. 1H NMR (600 MHz, dmso) δ 12.00 (s, 1H), 9.20 (s, 1H), 7.31 (m, 2H), 7.25 (m, 2H), 7.15 (m, 1H), 7.07 (br s, 1H), 5.00 (t, J=6.0, 1H), 4.74 (d, J=6.0, 2H), 4.68 (s, 1H), 4.59 (d, J=9.0, 1H), 3.93 (s, 3H), 1.13 (s, 3H), 1.12 (s, 3H).

Example 111

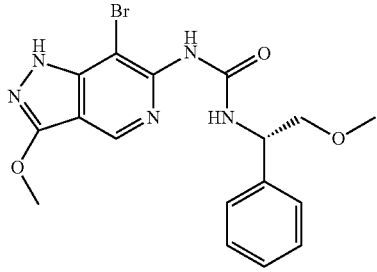 [SMILES: COC[C@@H](NC(=O)Nc1ncc2c(OC)n[nH]c2c1Br)c1ccccc1]

(S)-1-(7-bromo-3-methoxy-1H-pyrazolo[4,3-c]pyridin-6-yl)-3-(2-methoxy-1-phenylethyl)urea (S)-1-(2-Methoxy-1-phenylethyl)-3-(3-methoxy-1H-pyrazolo[4,3-c]pyridin-6-yl)urea (Example 41, 53 mg, 0.155 mmol) and NBS (35.5 mg, 0.199 mmol) were stirred in DMF (1 mL) at room temperature for 6 hours. Water was added and the products extracted into EtOAc (×2). The combined organic extracts were washed with brine, dried over Na$_2$SO$_4$, filtered and concentrated in vacuo. Purification of the residue by MPLC (12-100% EtOAc-hexanes) gave (S)-1-(7-bromo-3-methoxy-1H-pyrazolo[4,3-c]pyridin-6-yl)-3-(2-methoxy-1-phenylethyl)urea MS: [M+H]$^+$ m/z 420. $^1$H NMR (500 MHz, DMSO-d$_6$) δ 12.67 (s, 1H), 9.08 (d, J=7.0 Hz, 1H), 8.67 (s, 1H), 7.98 (s, 1H), 7.35-7.30 (m, 4H), 7.25-7.21 (m, 1H), 5.03-4.98 (m, 1H), 4.01 (s, 3H), 3.63-3.56 (m, 2H), 3.27 (s, 3H).

Example 112

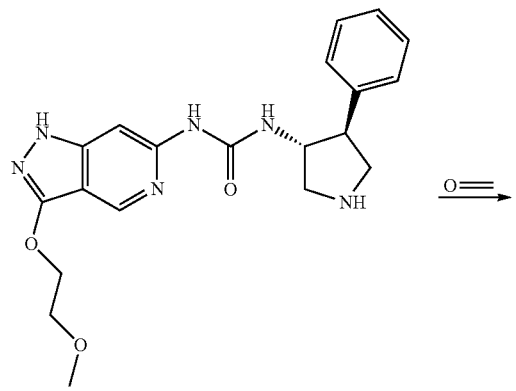

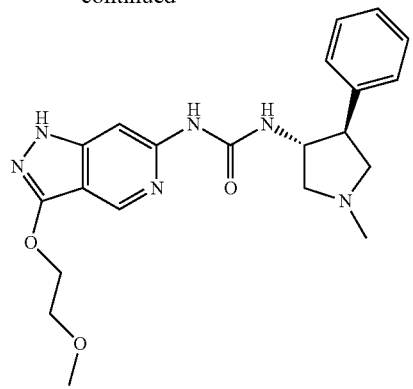

112

Step 1: 1-(3-(2-methoxyethoxy)-1H-pyrazolo[4,3-c]pyridin-6-yl)-3-((3R,4S)-1-methyl-4-phenylpyrrolidin-3-yl)urea Formaldehyde (0.014 mL, 0.189 mmol) was added to a stirred, room temperature mixture of 1-(3-(2-methoxyethoxy)-1H-pyrazolo[4,3-c]pyridin-6-yl)-3-((3R,4S)-4-phenylpyrrolidin-3-yl)urea (25 mg, 0.063 mmol, synthesized intermediate 32B in a manner analogous to that described in for intermediate 34B) in MeOH (1 mL), and the mixture was stirred at room temperature for 30 min. before the addition of sodium Borohydride (7.16 mg, 0.189 mmol), the resultant mixture was kept stirring at room temperature for 2 h. LCMS check, completed, starting material disappeared. The mixture was diluted with dichloromethane (3 mL), washed with aqueous sodium hydrogen carbonate (concentrated, 1×2 mL), dried (MgSO$_4$), filtered and the solvent was evaporated under reduced pressure. The residue was purified by preparative HPLC Reverse phase (C-18), eluting with Acetonitrile/Water+0.1% TFA, to give 1-(3-(2-methoxyethoxy)-1H-pyrazolo[4,3-c]pyridin-6-yl)-3-((3R,4S)-1-methyl-4-phenylpyrrolidin-3-yl)urea 2,2,2-trifluoroacetate (9.2 mg, 0.018 mmol, 27.8% yield) as a white solid. MS: [M+H]$^+$ m/z 411. 1H NMR (500 MHz, DMSO) δ 12.14 (s, 1H), 10.23 (bs, 1H), 9.38 (bs, 1H), 8.60 (bs, 1H), 8.06 (bs, 1H), 7.40 (m, 5H), 4.52 (m, 1H), 4.43 (m, 2H), 3.96 (m, 1H), 3.72 (m, 2H), 3.66 (m, 1H), 3.58 (m, 1H), 3.42 (m, 2H), 3.32 (s, 3H), 2.98 (d, 3H, J=4.5 Hz).

Example 113

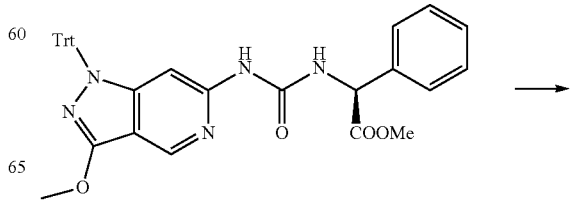

-continued

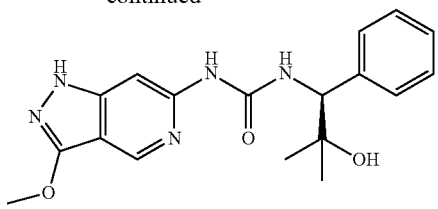

(S)-1-(2-hydroxy-2-methyl-1-phenylpropyl)-3-(3-methoxy-1H-pyrazolo[4,3-c]pyridin-6-yl)urea To the solution of (S)-methyl 2-(3-(3-methoxy-1-trityl-1H-pyrazolo[4,3-c]pyridin-6-yl)ureido)-2-phenylacetate (71B, 0.13 g, 0.22 mmol) in anhydrous $CH_2Cl_2$ (1 mL) was added TFA (1 mL) followed by $Et_3SiH$ (2 drops). The resultant mixture was stirred at ambient temperature. After 2 h of stirring, solvent was removed under reduced pressure, the residue (TFA salt) thus obtained was triturated in diethyl ether to afford the compound (0.06 g) which was taken up in anhydrous THF, cooled to 0° C. and treated with MeMgBr (3M solution in $Et_2O$, 0.6 mL, 1.7 mmol) and resultant mixture was allowed to warm and stirred at ambient temperature. After 10 h, the reaction was quenched with saturated aqueous $NH_4Cl$ solution (5 mL), and the organic contents were extracted with $CH_2Cl_2$ (3×10 mL). The volatiles were removed under reduced pressure and the residue thus obtained was further purified by prep HPLC to afford the title compound. $^1$H NMR, ($CD_3OD$, 400 MHz): δ 8.66 (s, 1H), 7.40-7.39 (m, 2H), 7.33-7.29 (m, 2H), 7.26-7.23 (m, 1H), 7.11 (s, 1H), 4.75 (s, 1H), 4.08 (s, 3H), 1.34 (s, 3H), 1.15 (s, 3H). MS: [M+H]$^+$ m/z 356.

Table 14 below provides data for additional examples, which were prepared following procedures similar to those of the indicated example/scheme and/or using methods well known to those of ordinary skill in the art of organic synthesis.

TABLE 14

| Ex | Structure | IUPAC Name | Exact Mass [M + H]+ | Route Used (Intermediate Used) |
|---|---|---|---|---|
| 200 | 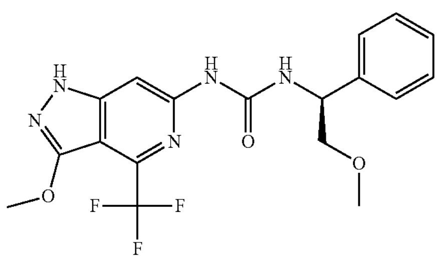 [SMILES: COC[C@@H](NC(=O)Nc1cc2[nH]nc(OC)c2c(C(F)(F)F)n1)c1ccccc1] | 1-[(1S)-2-methoxy-1-phenylethyl]-3-[3-methoxy-4-(trifluoromethyl)-1H-pyrazolo[4,3-c]pyridin-6-yl]urea | Calc'd 410, found 410 | Scheme 3/ Method A, (18B) |
| 201 | 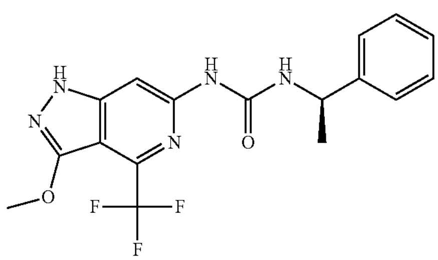 [SMILES: COc1n[nH]c2cc(NC(=O)N[C@H](C)c3ccccc3)nc(C(F)(F)F)c12] | 1-[3-methoxy-4-(trifluoromethyl)-1H-pyrazolo[4,3-c]pyridin-6-yl]-3-[(1R)-1-phenylethyl]urea | Calc'd 380, found 380 | Scheme 3/ Method A, (18B) |
| 202 | 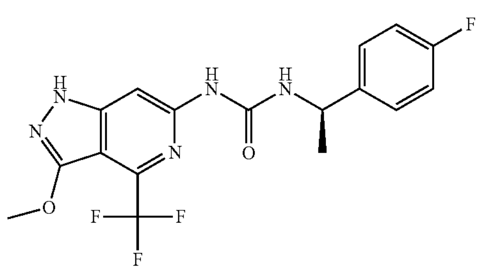 [SMILES: COc1n[nH]c2cc(NC(=O)N[C@H](C)c3ccc(F)cc3)nc(C(F)(F)F)c12] | 1-[(1R)-1-(4-fluorophenyl)ethyl]-3-[3-methoxy-4-(trifluoromethyl)-1H-pyrazolo[4,3-c]pyridin-6-yl]urea | Calc'd 398, found 398 | Scheme 3/ Method A, (18B) |
| 203 | 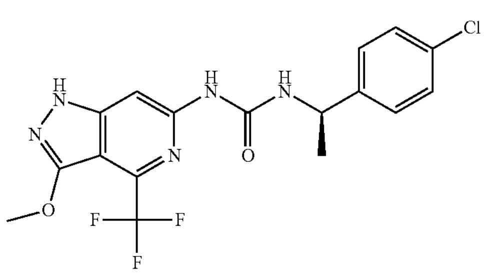 [SMILES: COc1n[nH]c2cc(NC(=O)N[C@H](C)c3ccc(Cl)cc3)nc(C(F)(F)F)c12] | 1-[(1R)-1-(4-chlorophenyl)ethyl]-3-[3-methoxy-4-(trifluoromethyl)-1H-pyrazolo[4,3-c]pyridin-6-yl]urea | Calc'd 414, found 414 | Scheme 3/ Method A, (18B) |

TABLE 14-continued

| Ex | Structure | IUPAC Name | Exact Mass [M + H]+ | Route Used (Intermediate Used) |
|---|---|---|---|---|
| 204 | 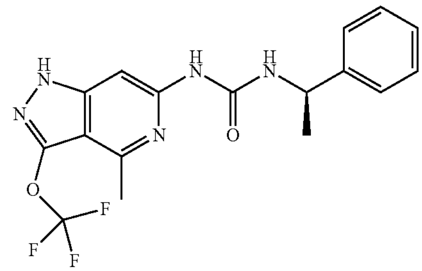 [SMILES: Cc1nc(NC(=O)N[C@H](C)c2ccccc2)cc2[nH]nc(OC(F)(F)F)c12] | 1-[4-methyl-3-(trifluoromethoxy)-1H-pyrazolo[4,3-c]pyridin-6-yl]-3-[(1R)-1-phenylethyl]urea | Calc'd 380, found 380 | Scheme 3/ Method A, (19B) |
| 205 | 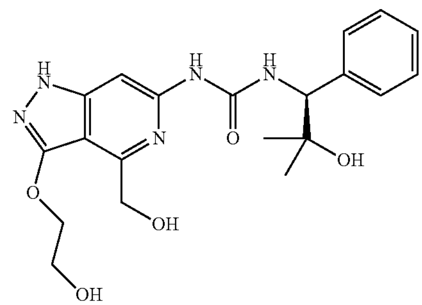 [SMILES: CC(C)(O)[C@@H](NC(=O)Nc1cc2[nH]nc(OCCO)c2c(CO)n1)c1ccccc1] | 1-[3-(2-hydroxyethoxy)-4-(hydroxymethyl)-1H-pyrazolo[4,3-c]pyridin-6-yl]-3-[(1S)-2-hydroxy-2-methyl-1-phenylpropyl]urea | Calc'd 416, found 416 | Scheme 3/ Method A, (20B, 21B) |
| 206 | 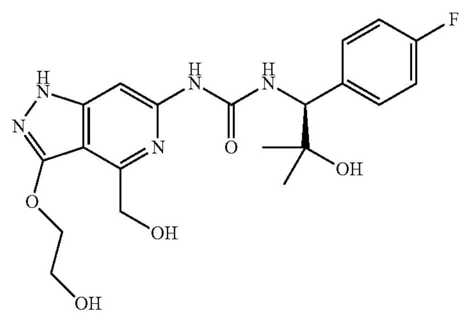 [SMILES: CC(C)(O)[C@@H](NC(=O)Nc1cc2[nH]nc(OCCO)c2c(CO)n1)c1ccc(F)cc1] | 1-[(1S)-1-(4-fluorophenyl)-2-hydroxy-2-methylpropyl]-3-[3-(2-hydroxyethoxy)-4-(hydroxymethyl)-1H-pyrazolo[4,3-c]pyridin-6-yl]urea | Calc'd 434, found 434 | Scheme 3/ Method A, (20B, 22B) |
| 207 | 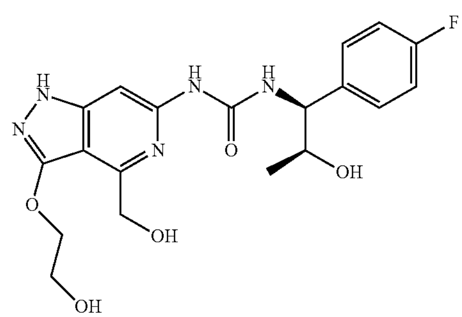 [SMILES: C[C@H](O)[C@@H](NC(=O)Nc1cc2[nH]nc(OCCO)c2c(CO)n1)c1ccc(F)cc1] | 1-[(1S,2S)-1-(4-fluorophenyl)-2-hydroxypropyl]-3-[3-(2-hydroxyethoxy)-4-(hydroxymethyl)-1H-pyrazolo[4,3-c]pyridin-6-yl]urea | Calc'd 420, found 420 | Scheme 3/ Method A, (20B, 24B) |
| 208 | 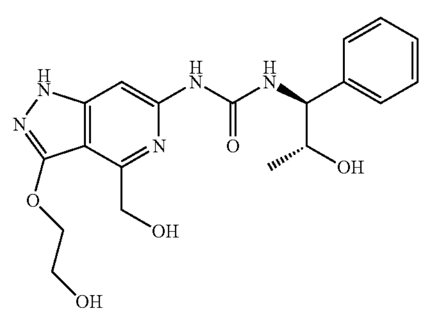 [SMILES: C[C@@H](O)[C@@H](NC(=O)Nc1cc2[nH]nc(OCCO)c2c(CO)n1)c1ccccc1] | 1-[3-(2-hydroxyethoxy)-4-(hydroxymethyl)-1H-pyrazolo[4,3-c]pyridin-6-yl]-3-[(1S,2R)-2-hydroxy-1-phenylpropyl]urea | Calc'd 402, found 402 | Scheme 3/ Method A, (20B) |

TABLE 14-continued

| Ex | Structure | IUPAC Name | Exact Mass [M + H]+ | Route Used (Intermediate Used) |
|---|---|---|---|---|
| 209 | 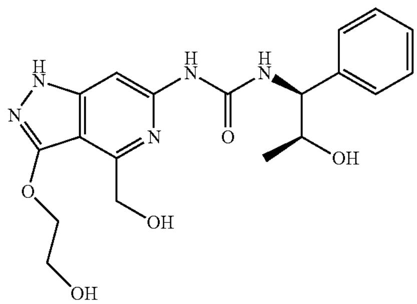 [SMILES: C[C@H](O)[C@@H](NC(=O)Nc1cc2[nH]nc(OCCO)c2c(CO)n1)c1ccccc1] | 1-[3-(2-hydroxyethoxy)-4-(hydroxymethyl)-1H-pyrazolo[4,3-c]pyridin-6-yl]-3-[(1S,2S)-2-hydroxy-1-phenylpropyl]urea | Calc'd 402, found 402 | Scheme 3/ Method A, (20B, 23B) |
| 210 | 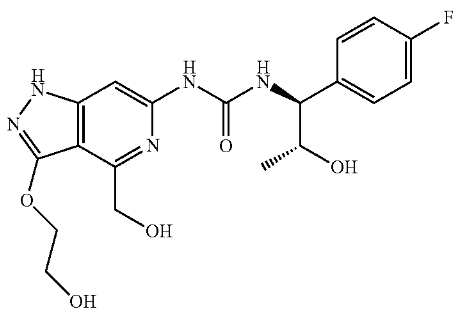 [SMILES: C[C@@H](O)[C@@H](NC(=O)Nc1cc2[nH]nc(OCCO)c2c(CO)n1)c1ccc(F)cc1] | 1-[(1S,2R)-1-(4-fluorophenyl)-2-hydroxypropyl]-3-[3-(2-hydroxyethoxy)-4-(hydroxymethyl)-1H-pyrazolo[4,3-c]pyridin-6-yl]urea | Calc'd 434, found 434 | Scheme 3/ Method A, (20B) |
| 211 | 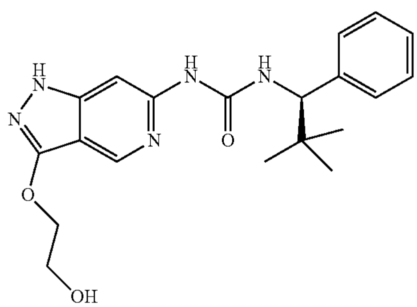 [SMILES: CC(C)(C)[C@@H](NC(=O)Nc1cc2[nH]nc(OCCO)c2cn1)c1ccccc1] | 1-[(1R)-2,2-dimethyl-1-phenylpropyl]-3-[3-(2-hydroxyethoxy)-1H-pyrazolo[4,3-c]pyridin-6-yl]urea | Calc'd 384, found 384 | Scheme 3, Method A/ Ex. 40 (31B, 58B) |
| 212 | 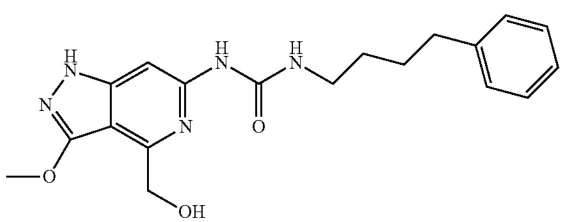 [SMILES: COc1n[nH]c2cc(NC(=O)NCCCCc3ccccc3)nc(CO)c12] | 1-[4-(hydroxymethyl)-3-methoxy-1H-pyrazolo[4,3-c]pyridin-6-yl]-3-(4-phenylbutyl)urea | Calc'd 370, found 370 | Scheme 3, Method A (35B) |
| 213 | 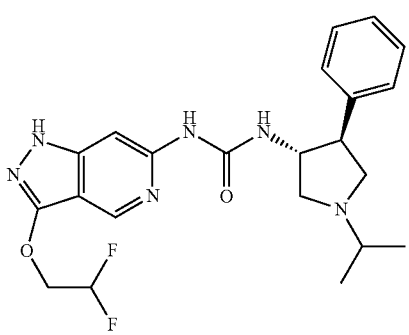 [SMILES: CC(C)N1C[C@H](NC(=O)Nc2cc3[nH]nc(OCC(F)F)c3cn2)[C@@H](c2ccccc2)C1] | 1-[3-(2,2-difluoroethoxy)-1H-pyrazolo[4,3-c]pyridin-6-yl]-3-[(3R,4S)-1-(1-methylethyl)-4-phenylpyrrolidin-3-yl]urea | Calc'd 445, found 445 | Example 100 (34B) |

TABLE 14-continued

| Ex | Structure | IUPAC Name | Exact Mass [M + H]+ | Route Used (Intermediate Used) |
|---|---|---|---|---|
| 214 | 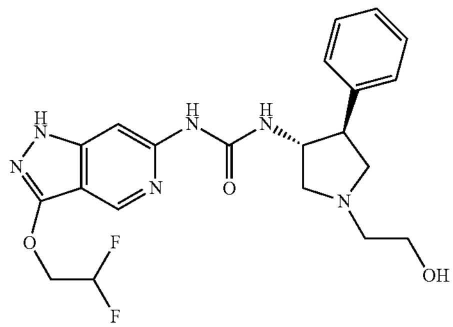 [SMILES: O=C(Nc1cc2[nH]nc(OCC(F)F)c2cn1)N[C@H]1CN(CCO)C[C@@H]1c1ccccc1] | 1-[3-(2,2-difluoroethoxy)-1H-pyrazolo[4,3-c]pyridin-6-yl]-3-[(3R,4S)-1-(2-hydroxyethyl)-4-phenylpyrrolidin-3-yl]urea | Calc'd 447, found 447 | Example 100 (34B) |
| 215 | 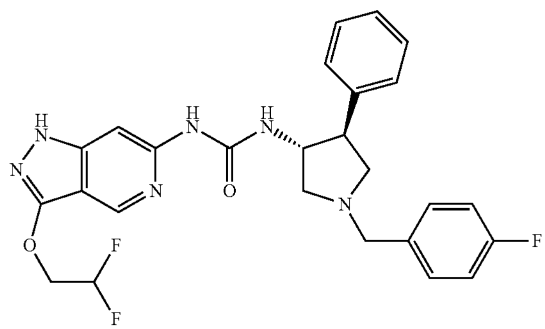 [SMILES: O=C(Nc1cc2[nH]nc(OCC(F)F)c2cn1)N[C@H]1CN(Cc2ccc(F)cc2)C[C@@H]1c1ccccc1] | 1-[3-(2,2-difluoroethoxy)-1H-pyrazolo[4,3-c]pyridin-6-yl]-3-[(3R,4S)-1-(4-fluorobenzyl)-4-phenylpyrrolidin-3-yl]urea | Calc'd 512, found 512 | Example 100 (34B) |
| 216 | 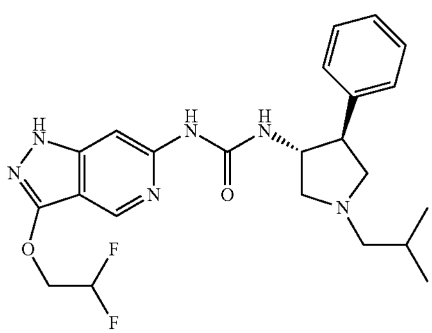 [SMILES: CC(C)CN1C[C@H](NC(=O)Nc2cc3[nH]nc(OCC(F)F)c3cn2)[C@@H](c2ccccc2)C1] | 1-[3-(2,2-difluoroethoxy)-1H-pyrazolo[4,3-c]pyridin-6-yl]-3-[(3R,4S)-1-(2-methylpropyl)-4-phenylpyrrolidin-3-yl]urea | Calc'd 460, found 460 | Example 100 (34B) |
| 217 | 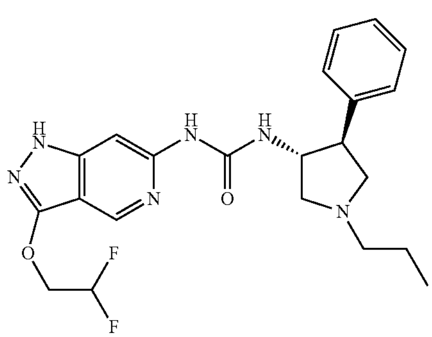 [SMILES: CCCN1C[C@H](NC(=O)Nc2cc3[nH]nc(OCC(F)F)c3cn2)[C@@H](c2ccccc2)C1] | 1-[3-(2,2-difluoroethoxy)-1H-pyrazolo[4,3-c]pyridin-6-yl]-3-[(3R,4S)-4-phenyl-1-propylpyrrolidin-3-yl]urea | Calc'd 445, found 445 | Example 100 (34B) |

TABLE 14-continued

| Ex | Structure | IUPAC Name | Exact Mass [M + H]+ | Route Used (Intermediate Used) |
|---|---|---|---|---|
| 218 | 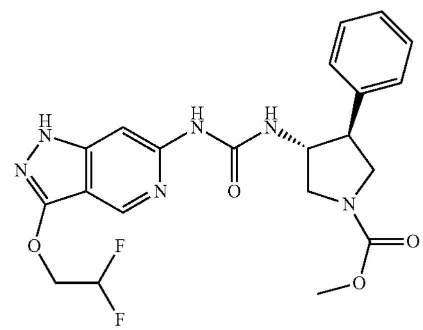 [SMILES: COC(=O)N1C[C@H](NC(=O)Nc2cc3[nH]nc(OCC(F)F)c3cn2)[C@@H](c2ccccc2)C1] | methyl (3R,4S)-3-({[3-(2,2-difluoroethoxy)-1H-pyrazolo[4,3-c]pyridin-6-yl]carbamoyl}amino)-4-phenylpyrrolidine-1-carboxylate | Calc'd 461, found 461 | Example 101 (34B) |
| 219 | 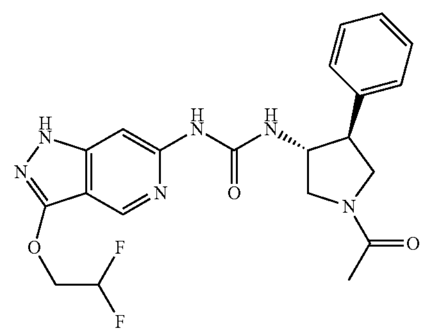 [SMILES: CC(=O)N1C[C@H](NC(=O)Nc2cc3[nH]nc(OCC(F)F)c3cn2)[C@@H](c2ccccc2)C1] | 1-[(3R,4S)-1-acetyl-4-phenylpyrrolidin-3-yl]-3-[3-(2,2-difluoroethoxy)-1H-pyrazolo[4,3-c]pyridin-6-yl]urea | Calc'd 445, found 445 | Example 101 (34B) |
| 220 | 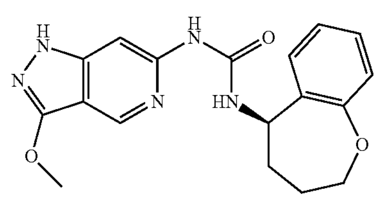 [SMILES: COc1n[nH]c2cc(NC(=O)N[C@@H]3CCCOc4ccccc43)ncc12] | 1-(3-methoxy-1H-pyrazolo[4,3-c]pyridin-6-yl)-3-[(5R)-2,3,4,5-tetrahydro-1-benzoxepin-5-yl]urea | Calc'd 354, found 354 | Scheme 3/ Method A (3B), Scheme 9 |
| 221 | 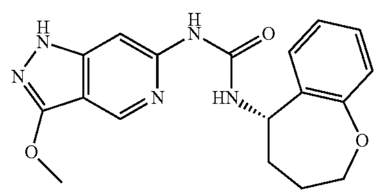 [SMILES: COc1n[nH]c2cc(NC(=O)N[C@H]3CCCOc4ccccc43)ncc12] | 1-(3-methoxy-1H-pyrazolo[4,3-c]pyridin-6-yl)-3-[(5S)-2,3,4,5-tetrahydro-1-benzoxepin-5-yl]urea | Calc'd 354, found 354 | Scheme 3/ Method A (3B), Scheme 9 |
| 222 | 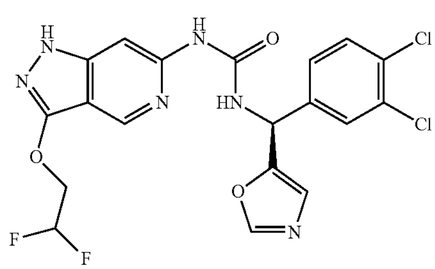 [SMILES: O=C(Nc1cc2[nH]nc(OCC(F)F)c2cn1)N[C@@H](c1ccc(Cl)c(Cl)c1)c1cnco1] | 1-[(S)-(3,4-dichlorophenyl)(1,3-oxazol-5-yl)methyl]-3-[3-(2,2-difluoroethoxy)-1H-pyrazolo[4,3-c]pyridin-6-yl]urea | Calc'd 483, found 483 | Scheme 10/ Method A (33B); amine from WO 2012/118850 |

TABLE 14-continued

| Ex | Structure | IUPAC Name | Exact Mass [M + H]+ | Route Used (Intermediate Used) |
|---|---|---|---|---|
| 223 | 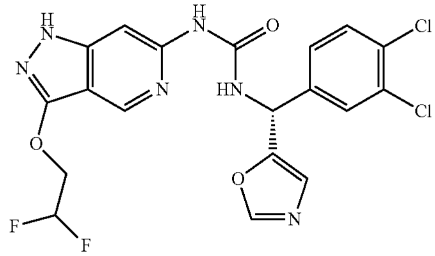 [SMILES: O=C(Nc1cc2[nH]nc(OCC(F)F)c2cn1)N[C@H](c1ccc(Cl)c(Cl)c1)c1cnco1] | 1-[(R)-(3,4-dichlorophenyl)(1,3-oxazol-5-yl)methyl]-3-[3-(2,2-difluoroethoxy)-1H-pyrazolo[4,3-c]pyridin-6-yl]urea | Calc'd 483, found 483 | Scheme 10/ Method A (33B); amine from WO 2012/118850 |
| 224 | 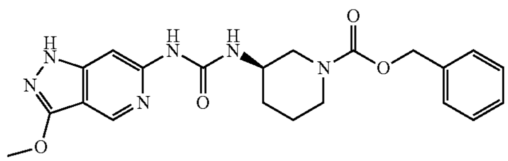 [SMILES: COc1n[nH]c2cc(NC(=O)N[C@@H]3CCCN(C(=O)OCc4ccccc4)C3)ncc12] | benzyl (3R)-3-{[(3-methoxy-1H-pyrazolo[4,3-c]pyridin-6-yl)carbamoyl]amino}piperidine-1-carboxylate | Calc'd 425, found 425 | Scheme 10/ Method A, Example 102 |
| 225 | 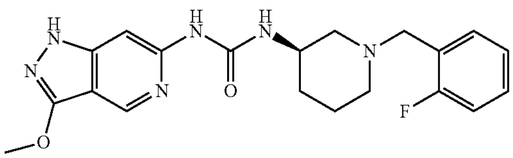 [SMILES: COc1n[nH]c2cc(NC(=O)N[C@@H]3CCCN(Cc4ccccc4F)C3)ncc12] | 1-[(3R)-1-(2-fluorobenzyl)piperidin-3-yl]-3-(3-methoxy-1H-pyrazolo[4,3-c]pyridin-6-yl)urea | Calc'd 399, found 399 | Scheme 10/ Method A, Example 102 |
| 226 | 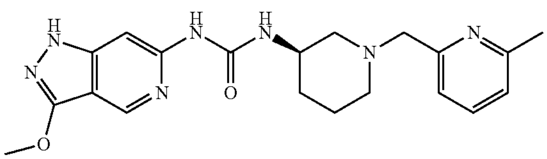 | 1-(3-methoxy-1H-pyrazolo[4,3-c]pyridin-6-yl)-3-{(3R)-1-[(6-methylpyridin-2-yl)methyl]piperidin-3-yl}urea | Calc'd 396, found 396 | Scheme 10/ Method A, Example 102 |
| 227 | 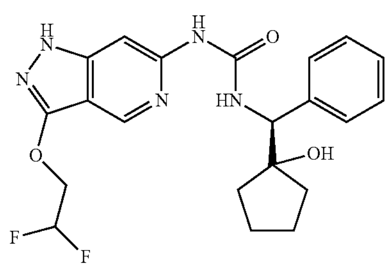 [SMILES: O=C(Nc1cc2[nH]nc(OCC(F)F)c2cn1)N[C@@H](c1ccccc1)C1(O)CCCC1] | 1-[3-(2,2-difluoroethoxy)-1H-pyrazolo[4,3-c]pyridin-6-yl]-3-[(S)-(1-hydroxycyclopentyl)(phenyl)methyl]urea | Calc'd 432, found 432 | Scheme 10/ Method A (33B), Example 102 |
| 228 | 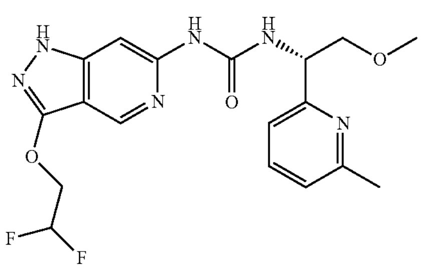 [SMILES: COC[C@@H](NC(=O)Nc1cc2[nH]nc(OCC(F)F)c2cn1)c1cccc(C)n1] | 1-[3-(2,2-difluoroethoxy)-1H-pyrazolo[4,3-c]pyridin-6-yl]-3-[(1S)-2-methoxy-1-(6-methylpyridin-2-yl)ethyl]urea | Calc'd 407, found 407 | Scheme 10/ Method A (33B), Example 102 |
| 229 | 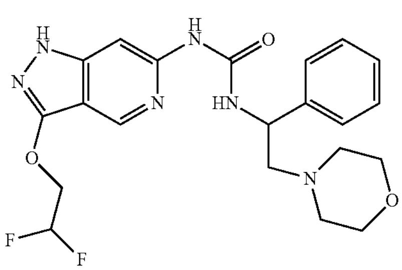 [SMILES: O=C(Nc1cc2[nH]nc(OCC(F)F)c2cn1)NC(CN1CCOCC1)c1ccccc1] | 1-[3-(2,2-difluoroethoxy)-1H-pyrazolo[4,3-c]pyridin-6-yl]-3-(2-morpholin-4-yl-1-phenylethyl)urea | Calc'd 447, found 447 | Scheme 10/ Method A (33B), Example 102 |

US 9,226,922 B2

TABLE 14-continued

| Ex | Structure | IUPAC Name | Exact Mass [M + H]+ | Route Used (Intermediate Used) |
|---|---|---|---|---|
| 230 | 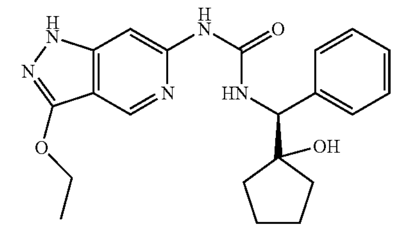 [SMILES: CCOc1n[nH]c2cc(NC(=O)N[C@@H](c3ccccc3)C3(O)CCCC3)ncc12] | 1-(3-ethoxy-1H-pyrazolo[4,3-c]pyridin-6-yl)-3-[(S)-(1-hydroxycyclopentyl)(phenyl)methyl]urea | Calc'd 396, found 396 | Scheme 10/ Method A, Example 102 |
| 231 | 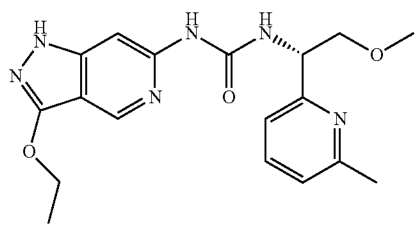 [SMILES: CCOc1n[nH]c2cc(NC(=O)N[C@H](COC)c3cccc(C)n3)ncc12] | 1-(3-ethoxy-1H-pyrazolo[4,3-c]pyridin-6-yl)-3-[(1S)-2-methoxy-1-(6-methylpyridin-2-yl)ethyl]urea | Calc'd 371, found 371 | Scheme 10/ Method A, Example 102 |
| 232 | 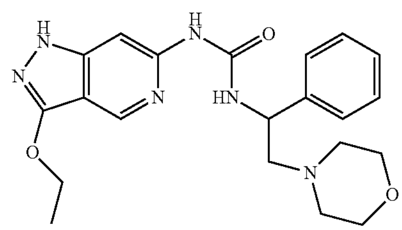 [SMILES: CCOc1n[nH]c2cc(NC(=O)NC(CN3CCOCC3)c3ccccc3)ncc12] | 1-(3-ethoxy-1H-pyrazolo[4,3-c]pyridin-6-yl)-3-(2-morpholin-4-yl-1-phenylethyl)urea | Calc'd 411, found 411 | Scheme 10/ Method A, Example 102 |
| 233 | 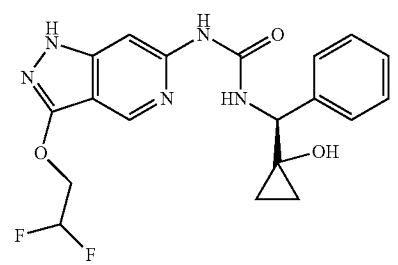 [SMILES: O=C(Nc1cc2[nH]nc(OCC(F)F)c2cn1)N[C@@H](c1ccccc1)C1(O)CC1] | 1-[3-(2,2-difluoroethoxy)-1H-pyrazolo[4,3-c]pyridin-6-yl]-3-[(S)-(1-hydroxycyclopropyl)(phenyl)methyl]urea | Calc'd 404, found 404 | Scheme 10/ Method A, Example 102 (33B) |
| 234 | 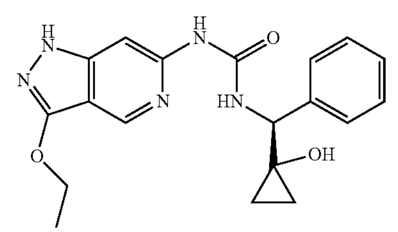 [SMILES: CCOc1n[nH]c2cc(NC(=O)N[C@@H](c3ccccc3)C3(O)CC3)ncc12] | 1-(3-ethoxy-1H-pyrazolo[4,3-c]pyridin-6-yl)-3-[(S)-(1-hydroxycyclopropyl)(phenyl)methyl]urea | Calc'd 368, found 368 | Scheme 10/ Method A, Example 102 |
| 235 | 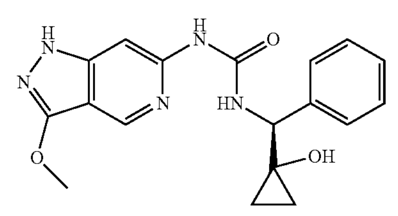 [SMILES: COc1n[nH]c2cc(NC(=O)N[C@@H](c3ccccc3)C3(O)CC3)ncc12] | 1-[(S)-(1-hydroxycyclopropyl)(phenyl)methyl]-3-(3-methoxy-1H-pyrazolo[4,3-c]pyridin-6-yl)urea | Calc'd 354, found 354 | Scheme 10/ Method A, Example 102 |

TABLE 14-continued

| Ex | Structure | IUPAC Name | Exact Mass [M + H]+ | Route Used (Intermediate Used) |
|---|---|---|---|---|
| 236 | 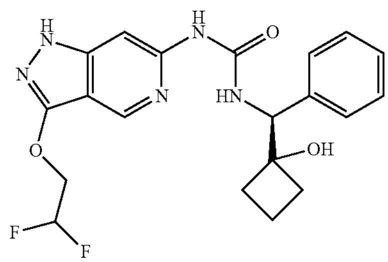 [SMILES: O=C(Nc1cc2[nH]nc(OCC(F)F)c2cn1)N[C@@H](c1ccccc1)C1(O)CCC1] | 1-[3-(2,2-difluoroethoxy)-1H-pyrazolo[4,3-c]pyridin-6-yl]-3-[(S)-(1-hydroxycyclobutyl)(phenyl)methyl]urea | Calc'd 418, found 418 | Scheme 10/ Method A, Example 102 (33B) |
| 237 | 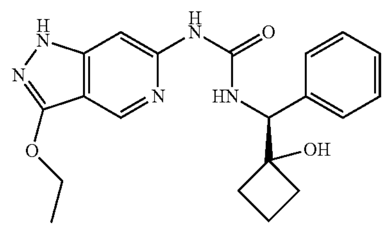 [SMILES: CCOc1n[nH]c2cc(NC(=O)N[C@@H](c3ccccc3)C3(O)CCC3)ncc12] | 1-(3-ethoxy-1H-pyrazolo[4,3-c]pyridin-6-yl)-3-[(S)-(1-hydroxycyclobutyl)(phenyl)methyl]urea | Calc'd 382, found 382 | Scheme 10/ Method A, Example 102 |
| 238 | 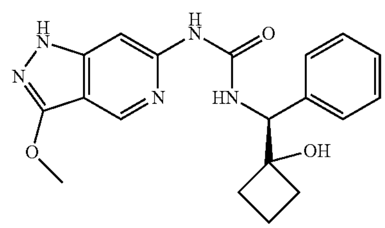 [SMILES: COc1n[nH]c2cc(NC(=O)N[C@@H](c3ccccc3)C3(O)CCC3)ncc12] | 1-[(S)-(1-hydroxycyclobutyl)(phenyl)methyl]-3-(3-methoxy-1H-pyrazolo[4,3-c]pyridin-6-yl)urea | Calc'd 368, found 368 | Scheme 10/ Method A, Example 102 |
| 239 | 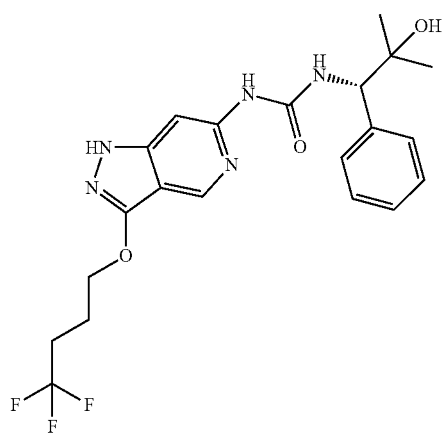 [SMILES: CC(C)(O)[C@@H](NC(=O)Nc1cc2[nH]nc(OCCCC(F)(F)F)c2cn1)c1ccccc1] | 1-[(1S)-2-hydroxy-2-methyl-1-phenylpropyl]-3-[3-(4,4,4-trifluorobutoxy)-1H-pyrazolo[4,3-c]pyridin-6-yl]urea | Calc'd 452, found 452 | Scheme 3/ Method A (3B, 21B), |
| 240 | 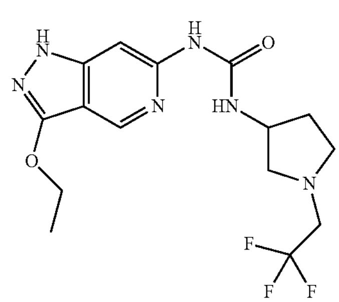 [SMILES: CCOc1n[nH]c2cc(NC(=O)NC3CCN(CC(F)(F)F)C3)ncc12] | 1-(3-ethoxy-1H-pyrazolo[4,3-c]pyridin-6-yl)-3-[1-(2,2,2-trifluoroethyl)pyrrolidin-3-yl]urea | Calc'd 373, found 373 | Scheme 3/ Method A, Example 40 |

TABLE 14-continued

| Ex | Structure | IUPAC Name | Exact Mass [M + H]+ | Route Used (Intermediate Used) |
|---|---|---|---|---|
| 241 | 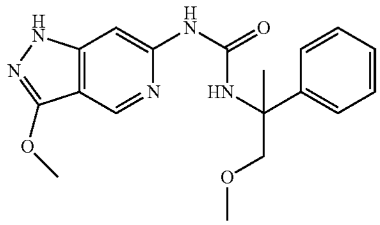 [SMILES: COCC(C)(NC(=O)Nc1cc2[nH]nc(OC)c2cn1)c1ccccc1] | 1-(2-methoxy-1-methyl-1-phenylethyl)-3-(3-methoxy-1H-pyrazolo[4,3-c]pyridin-6-yl)urea | Calc'd 356, found 356 | Scheme 3/ Method A, Example 40 |
| 242 | 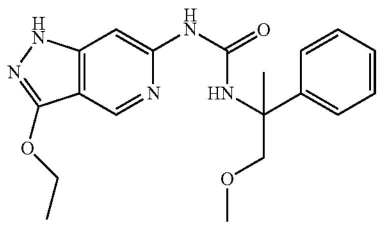 [SMILES: CCOc1n[nH]c2cc(NC(=O)NC(C)(COC)c3ccccc3)ncc12] | 1-(3-ethoxy-1H-pyrazolo[4,3-c]pyridin-6-yl)-3-(2-methoxy-1-methyl-1-phenylethyl)urea | Calc'd 370, found 370 | Scheme 3/ Method A, Example 40 |
| 243 | 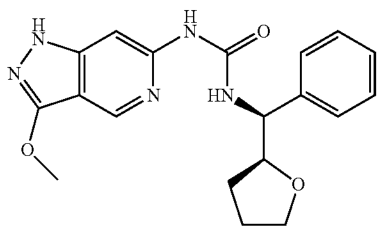 [SMILES: COc1n[nH]c2cc(NC(=O)N[C@@H](c3ccccc3)[C@@H]3CCCO3)ncc12] | 1-(3-methoxy-1H-pyrazolo[4,3-c]pyridin-6-yl)-3-{(S)-phenyl[(2S)-tetrahydrofuran-2-yl]methyl}urea | Calc'd 368, found 368 | Scheme 3/ Method A, Example 54 and 55 |
| 244 | 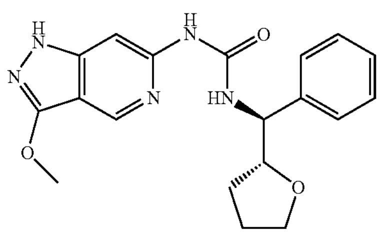 [SMILES: COc1n[nH]c2cc(NC(=O)N[C@@H](c3ccccc3)[C@H]3CCCO3)ncc12] | 1-(3-methoxy-1H-pyrazolo[4,3-c]pyridin-6-yl)-3-{(S)-phenyl[(2R)-tetrahydrofuran-2-yl]methyl}urea | Calc'd 368, found 368 | Scheme 3/ Method A, Example 54 and 55 |
| 245 | 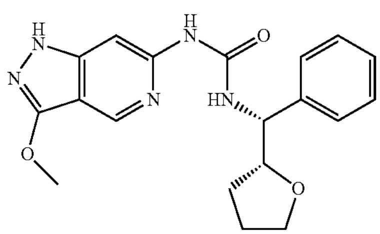 [SMILES: COc1n[nH]c2cc(NC(=O)N[C@H](c3ccccc3)[C@H]3CCCO3)ncc12] | 1-(3-methoxy-1H-pyrazolo[4,3-c]pyridin-6-yl)-3-{(R)-phenyl[(2R)-tetrahydrofuran-2-yl]methyl}urea | Calc'd 368, found 368 | Scheme 3/ Method A, Example 54 and 55 |
| 246 | 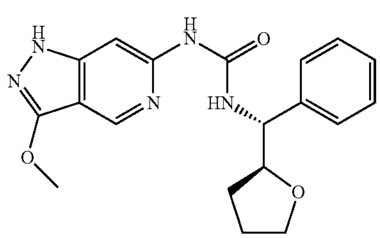 [SMILES: COc1n[nH]c2cc(NC(=O)N[C@H](c3ccccc3)[C@@H]3CCCO3)ncc12] | 1-(3-methoxy-1H-pyrazolo[4,3-c]pyridin-6-yl)-3-{(R)-phenyl[(2S)-tetrahydrofuran-2-yl]methyl}urea | Calc'd 368, found 368 | Scheme 3/ Method A, Example 54 and 55 |

TABLE 14-continued

| Ex | Structure | IUPAC Name | Exact Mass [M + H]+ | Route Used (Intermediate Used) |
|---|---|---|---|---|
| 247 | 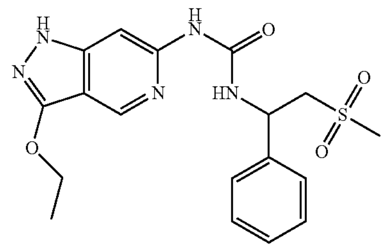 [SMILES: CCOc1n[nH]c2cc(NC(=O)NC(CS(C)(=O)=O)c3ccccc3)ncc12] | 1-(3-ethoxy-1H-pyrazolo[4,3-c]pyridin-6-yl)-3-[2-(methylsulfonyl)-1-phenylethyl]urea | Calc'd 404, found 404 | Scheme 3/ Method A |
| 248 | 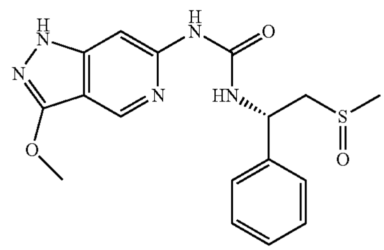 [SMILES: COc1n[nH]c2cc(NC(=O)N[C@H](CS(C)=O)c3ccccc3)ncc12] | 1-(3-methoxy-1H-pyrazolo[4,3-c]pyridin-6-yl)-3-[(1S)-2-(methylsulfinyl)-1-phenylethyl]urea | Calc'd 374, found 374 | Scheme 3/ Method A |
| 249 | 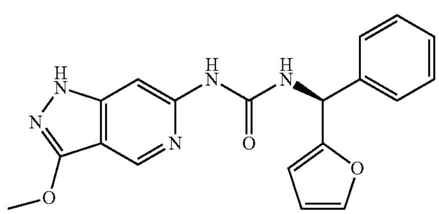 [SMILES: COc1n[nH]c2cc(NC(=O)N[C@@H](c3ccccc3)c3ccco3)ncc12] | 1-[(S)-furan-2-yl(phenyl)methyl]-3-(3-methoxy-1H-pyrazolo[4,3-c]pyridin-6-yl)urea | Calc'd 364, found 364 | Scheme 3/ Method A, Example 54 and 55 |
| 250 | 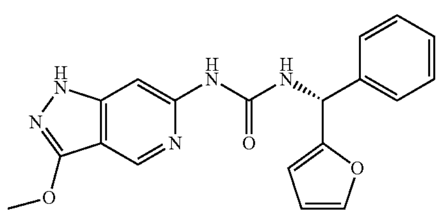 [SMILES: COc1n[nH]c2cc(NC(=O)N[C@H](c3ccccc3)c3ccco3)ncc12] | 1-[(R)-furan-2-yl(phenyl)methyl]-3-(3-methoxy-1H-pyrazolo[4,3-c]pyridin-6-yl)urea | Calc'd 364, found 364 | Scheme 3/ Method A, Example 54 and 55 |
| 251 | 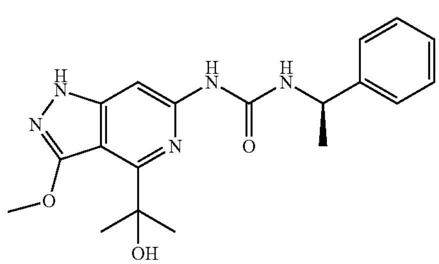 [SMILES: COc1n[nH]c2cc(NC(=O)N[C@H](C)c3ccccc3)nc(C(C)(C)O)c12] | 1-[4-(1-hydroxy-1-methylethyl)-3-methoxy-1H-pyrazolo[4,3-c]pyridin-6-yl]-3-[(1R)-1-phenylethyl]urea | Calc'd 370, found 370 | Scheme 3/ Method A (40B) |
| 252 | 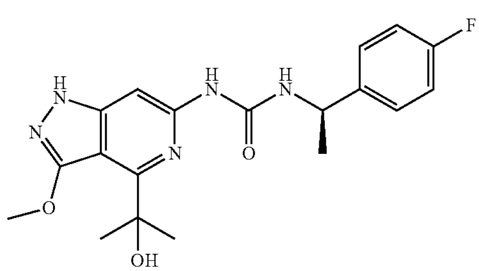 [SMILES: COc1n[nH]c2cc(NC(=O)N[C@H](C)c3ccc(F)cc3)nc(C(C)(C)O)c12] | 1-[(1R)-1-(4-fluorophenyl)ethyl]-3-[4-(1-hydroxy-1-methylethyl)-3-methoxy-1H-pyrazolo[4,3-c]pyridin-6-yl]urea | Calc'd 388, found 388 | Scheme 3/ Method A (40B) |

TABLE 14-continued

| Ex | Structure | IUPAC Name | Exact Mass [M + H]+ | Route Used (Intermediate Used) |
|---|---|---|---|---|
| 253 | 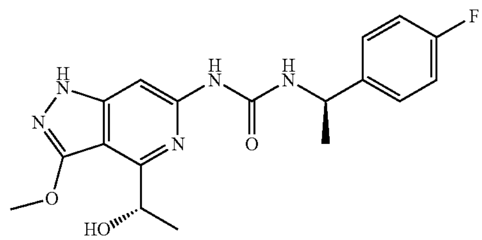 [SMILES: COc1n[nH]c2cc(NC(=O)N[C@H](C)c3ccc(F)cc3)nc([C@H](C)O)c12] | 1-[(1R)-1-(4-fluorophenyl)ethyl]-3-{4-[(1S)-1-hydroxyethyl]-3-methoxy-1H-pyrazolo[4,3-c]pyridin-6-yl}urea | Calc'd 374, found 374 | Scheme 3/ Method A (38B) |
| 254 | 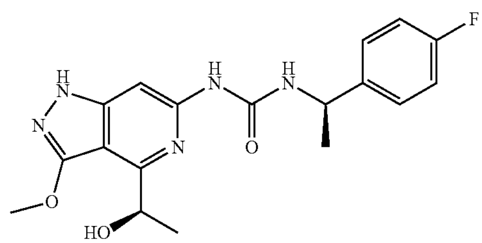 [SMILES: COc1n[nH]c2cc(NC(=O)N[C@H](C)c3ccc(F)cc3)nc([C@@H](C)O)c12] | 1-[(1R)-1-(4-fluorophenyl)ethyl]-3-{4-[(1R)-1-hydroxyethyl]-3-methoxy-1H-pyrazolo[4,3-c]pyridin-6-yl}urea | Calc'd 374, found 374 | Scheme 3/ Method A (38B) |
| 255 | 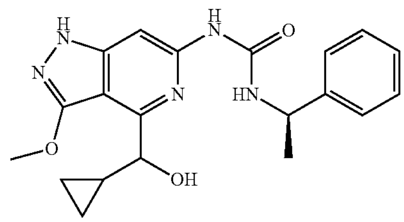 [SMILES: COc1n[nH]c2cc(NC(=O)N[C@H](C)c3ccccc3)nc(C(O)C3CC3)c12] | 1-{4-[cyclopropyl(hydroxy)methyl]-3-methoxy-1H-pyrazolo[4,3-c]pyridin-6-yl}-3-[(1R)-1-phenylethyl]urea | Calc'd 382, found 382 | Scheme 3/ Method A, procedure for 38B |
| 256 | 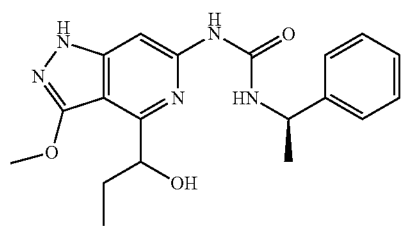 [SMILES: CCC(O)c1nc(NC(=O)N[C@H](C)c2ccccc2)cc2[nH]nc(OC)c12] | 1-[4-(1-hydroxypropyl)-3-methoxy-1H-pyrazolo[4,3-c]pyridin-6-yl]-3-[(1R)-1-phenylethyl]urea | Calc'd 370, found 370 | Scheme 3/ Method A, procedure for 38B |
| 257 | 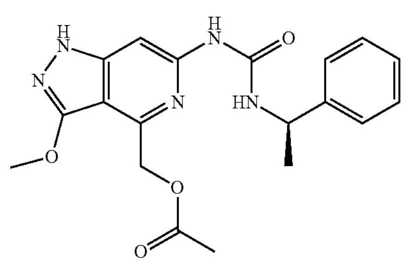 [SMILES: COc1n[nH]c2cc(NC(=O)N[C@H](C)c3ccccc3)nc(COC(C)=O)c12] | [3-methoxy-6-({[(1R)-1-phenylethyl]carbamoyl}amino)-1H-pyrazolo[4,3-c]pyridin-4-yl]methyl acetate | Calc'd 384, found 384 | Scheme 3/ Method A (41B) |
| 258 | 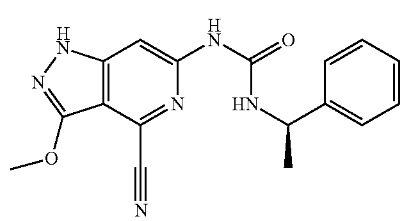 [SMILES: COc1n[nH]c2cc(NC(=O)N[C@H](C)c3ccccc3)nc(C#N)c12] | 1-(4-cyano-3-methoxy-1H-pyrazolo[4,3-c]pyridin-6-yl)-3-[(1R)-1-phenylethyl]urea | Calc'd 337, found 337 | Scheme 3/ Method A (42B) |

TABLE 14-continued

| Ex | Structure | IUPAC Name | Exact Mass [M + H]+ | Route Used (Intermediate Used) |
|---|---|---|---|---|
| 259 | 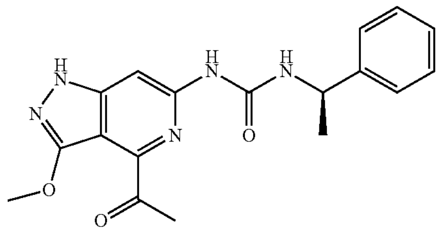 [SMILES: COc1n[nH]c2cc(NC(=O)N[C@H](C)c3ccccc3)nc(C(C)=O)c12] | 1-(4-acetyl-3-methoxy-1H-pyrazolo[4,3-c]pyridin-6-yl)-3-[(1R)-1-phenylethyl]urea | Calc'd 354, found 354 | Scheme 3/ Method A (39B) |
| 260 | 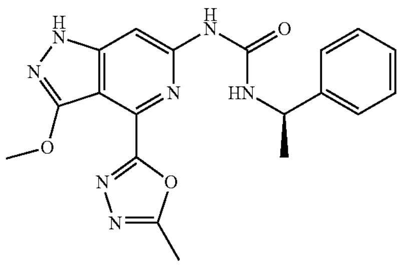 [SMILES: COc1n[nH]c2cc(NC(=O)N[C@H](C)c3ccccc3)nc(-c3nnc(C)o3)c12] | 1-[3-methoxy-4-(5-methyl-1,3,4-oxadiazol-2-yl)-1H-pyrazolo[4,3-c]pyridin-6-yl]-3-[(1R)-1-phenylethyl]urea | Calc'd 394, found 394 | Scheme 3/ Method A (43B) |
| 261 | 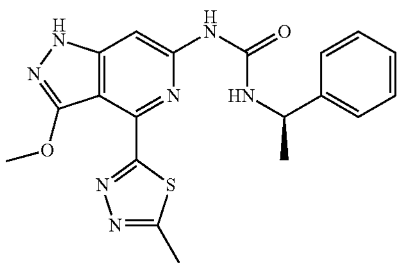 [SMILES: COc1n[nH]c2cc(NC(=O)N[C@H](C)c3ccccc3)nc(-c3nnc(C)s3)c12] | 1-[3-methoxy-4-(5-methyl-1,3,4-thiadiazol-2-yl)-1H-pyrazolo[4,3-c]pyridin-6-yl]-3-[(1R)-1-phenylethyl]urea | Calc'd 410, found 410 | Scheme 3/ Method A (44B) |
| 262 | 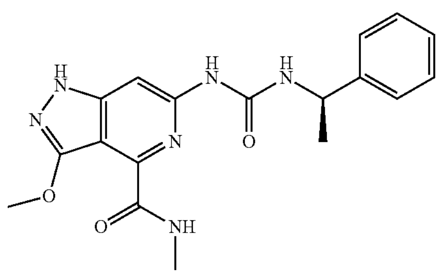 [SMILES: CNC(=O)c1nc(NC(=O)N[C@H](C)c2ccccc2)cc2[nH]nc(OC)c12] | 3-methoxy-N-methyl-6-({[(1R)-1-phenylethyl]carbamoyl}amino)-1H-pyrazolo[4,3-c]pyridine-4-carboxamide | Calc'd 369, found 369 | Example 105 |
| 263 | 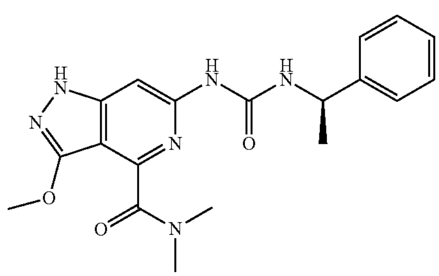 [SMILES: COc1n[nH]c2cc(NC(=O)N[C@H](C)c3ccccc3)nc(C(=O)N(C)C)c12] | 3-methoxy-N,N-dimethyl-6-({[(1R)-1-phenylethyl]carbamoyl}amino)-1H-pyrazolo[4,3-c]pyridine-4-carboxamide | Calc'd 383, found 383 | Example 105 |
| 264 | 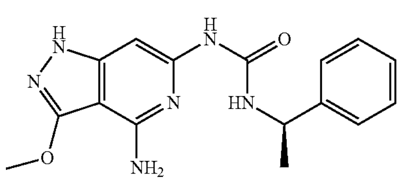 [SMILES: COc1n[nH]c2cc(NC(=O)N[C@H](C)c3ccccc3)nc(N)c12] | 1-(4-amino-3-methoxy-1H-pyrazolo[4,3-c]pyridin-6-yl)-3-[(1R)-1-phenylethyl]urea | Calc'd 327, found 327 | Scheme 3/ Method A (45B) |

TABLE 14-continued

| Ex | Structure | IUPAC Name | Exact Mass [M + H]+ | Route Used (Intermediate Used) |
|---|---|---|---|---|
| 265 | 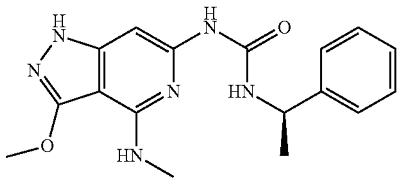 [SMILES: CNc1nc(NC(=O)N[C@H](C)c2ccccc2)cc2[nH]nc(OC)c12] | 1-[3-methoxy-4-(methylamino)-1H-pyrazolo[4,3-c]pyridin-6-yl]-3-[(1R)-1-phenylethyl]urea | Calc'd 341, found 341 | Scheme 3/ Method A (46B) |
| 266 | 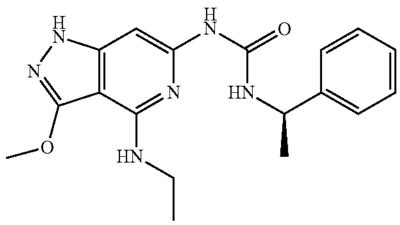 [SMILES: CCNc1nc(NC(=O)N[C@H](C)c2ccccc2)cc2[nH]nc(OC)c12] | 1-[4-(ethylamino)-3-methoxy-1H-pyrazolo[4,3-c]pyridin-6-yl]-3-[(1R)-1-phenylethyl]urea | Calc'd 355, found 355 | Scheme 3/ Method A (47B) |
| 267 | 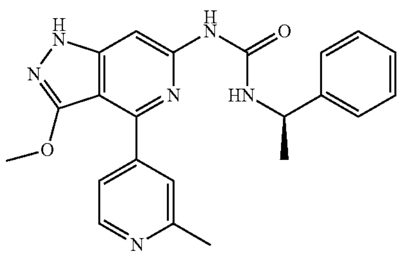 [SMILES: COc1n[nH]c2cc(NC(=O)N[C@H](C)c3ccccc3)nc(-c3ccnc(C)c3)c12] | 1-[3-methoxy-4-(2-methylpyridin-4-yl)-1H-pyrazolo[4,3-c]pyridin-6-yl]-3-[(1R)-1-phenylethyl]urea | Calc'd 403, found 403 | Scheme 3/ Method A (49B) |
| 268 | 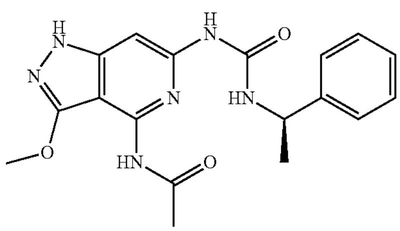 [SMILES: COc1n[nH]c2cc(NC(=O)N[C@H](C)c3ccccc3)nc(NC(C)=O)c12] | N-[3-methoxy-6-({[(1R)-1-phenylethyl]carbamoyl}amino)-1H-pyrazolo[4,3-c]pyridin-4-yl]acetamide | Calc'd 369, found 369 | Scheme 3/ Method A (48B) |
| 269 | 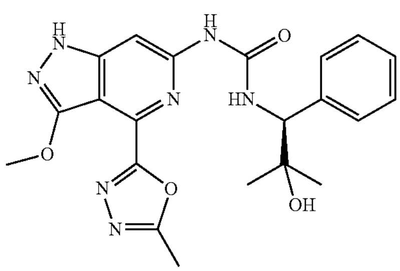 [SMILES: COc1n[nH]c2cc(NC(=O)N[C@@H](c3ccccc3)C(C)(C)O)nc(-c3nnc(C)o3)c12] | 1-[(1S)-2-hydroxy-2-methyl-1-phenylpropyl]-3-[3-methoxy-4-(5-methyl-1,3,4-oxadiazol-2-yl)-1H-pyrazolo[4,3-c]pyridin-6-yl]urea | Calc'd 438, found 438 | Scheme 3/ Method A (43B, 21B) |
| 270 | 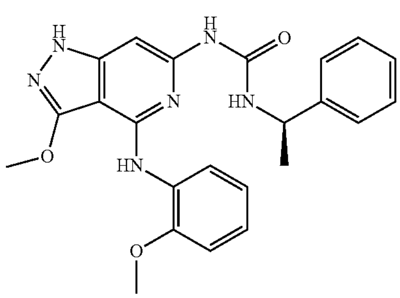 [SMILES: COc1ccccc1Nc1nc(NC(=O)N[C@H](C)c2ccccc2)cc2[nH]nc(OC)c12] | 1-{3-methoxy-4-[(2-methoxyphenyl)amino]-1H-pyrazolo[4,3-c]pyridin-6-yl}-3-[(1R)-1-phenylethyl]urea | Calc'd 433, found 433 | Scheme 3/ Method A (52B) |

TABLE 14-continued

| Ex | Structure | IUPAC Name | Exact Mass [M + H]+ | Route Used (Intermediate Used) |
|---|---|---|---|---|
| 271 | 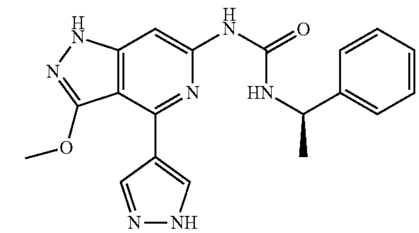 [SMILES: COc1n[nH]c2cc(NC(=O)N[C@H](C)c3ccccc3)nc(-c3cn[nH]c3)c12] | 1-[3-methoxy-4-(1H-pyrazol-4-yl)-1H-pyrazolo[4,3-c]pyridin-6-yl]-3-[(1R)-1-phenylethyl]urea | Calc'd 378, found 378 | Scheme 3/ Method A (50B) |
| 272 | 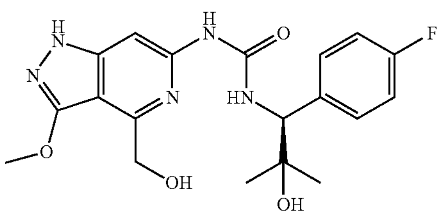 [SMILES: COc1n[nH]c2cc(NC(=O)N[C@@H](c3ccc(F)cc3)C(C)(C)O)nc(CO)c12] | 1-[(1S)-1-(4-fluorophenyl)-2-hydroxy-2-methylpropyl]-3-[4-(hydroxymethyl)-3-methoxy-1H-pyrazolo[4,3-c]pyridin-6-yl]urea | Calc'd 404, found 404 | Scheme 3/ Method A (35B, 22B) |
| 273 | 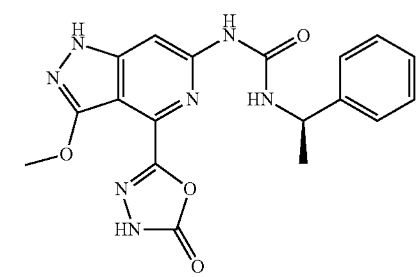 [SMILES: COc1n[nH]c2cc(NC(=O)N[C@H](C)c3ccccc3)nc(-c3n[nH]c(=O)o3)c12] | 1-[3-methoxy-4-(5-oxo-4,5-dihydro-1,3,4-oxadiazol-2-yl)-1H-pyrazolo[4,3-c]pyridin-6-yl]-3-[(1R)-1-phenylethyl]urea | Calc'd 396, found 396 | Scheme 3/ Method A (53B) |
| 274 | 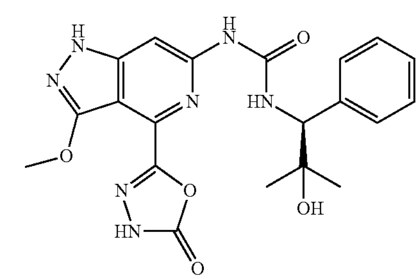 [SMILES: COc1n[nH]c2cc(NC(=O)N[C@@H](c3ccccc3)C(C)(C)O)nc(-c3n[nH]c(=O)o3)c12] | 1-[(1S)-2-hydroxy-2-methyl-1-phenylpropyl]-3-[3-methoxy-4-(5-oxo-4,5-dihydro-1,3,4-oxadiazol-2-yl)-1H-pyrazolo[4,3-c]pyridin-6-yl]urea | Calc'd 440, found 440 | Scheme 3/ Method A (53B, 21B) |
| 275 | 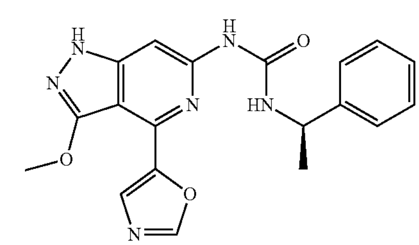 [SMILES: COc1n[nH]c2cc(NC(=O)N[C@H](C)c3ccccc3)nc(-c3cnco3)c12] | 1-[3-methoxy-4-(1,3-oxazol-5-yl)-1H-pyrazolo[4,3-c]pyridin-6-yl]-3-[(1R)-1-phenylethyl]urea | Calc'd 379, found 379 | Scheme 3/ Method A (54B) |
| 276 | 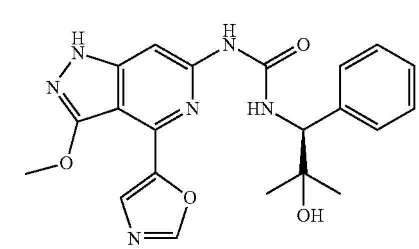 [SMILES: COc1n[nH]c2cc(NC(=O)N[C@@H](c3ccccc3)C(C)(C)O)nc(-c3cnco3)c12] | 1-[(1S)-2-hydroxy-2-methyl-1-phenylpropyl]-3-[3-methoxy-4-(1,3-oxazol-5-yl)-1H-pyrazolo[4,3-c]pyridin-6-yl]urea | Calc'd 423, found 423 | Scheme 3/ Method A (54B, 21B) |

TABLE 14-continued

| Ex | Structure | IUPAC Name | Exact Mass [M + H]+ | Route Used (Intermediate Used) |
|---|---|---|---|---|
| 277 | 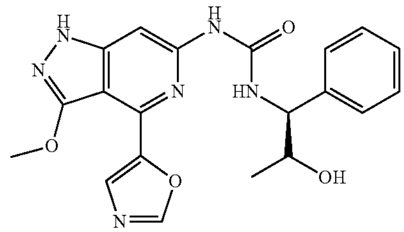 [SMILES: COc1n[nH]c2cc(NC(=O)N[C@@H](c3ccccc3)C(C)O)nc(-c3cnco3)c12] | 1-[(1S,2R)-2-hydroxy-1-phenylpropyl]-3-[3-methoxy-4-(1,3-oxazol-5-yl)-1H-pyrazolo[4,3-c]pyridin-6-yl]urea | Calc'd 409, found 409 | Scheme 3/ Method A (54B, 23B) |
| 278 | 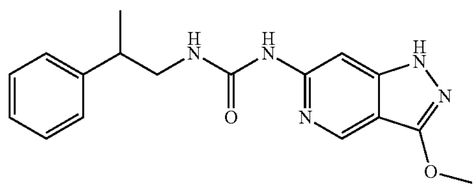 [SMILES: COc1n[nH]c2cc(NC(=O)NCC(C)c3ccccc3)ncc12] | 1-(3-methoxy-1H-pyrazolo[4,3-c]pyridin-6-yl)-3-(2-phenylpropyl)urea | Calc'd 326, found 326 | Scheme 3/ Method A, Example 40 |
| 279 | 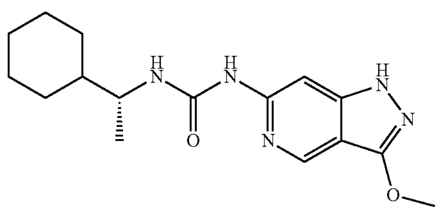 [SMILES: COc1n[nH]c2cc(NC(=O)N[C@H](C)C3CCCCC3)ncc12] | 1-[(1R)-1-cyclohexylethyl]-3-(3-methoxy-1H-pyrazolo[4,3-c]pyridin-6-yl)urea | Calc'd 318, found 318 | Scheme 3/ Method A, Example 40 |
| 280 | 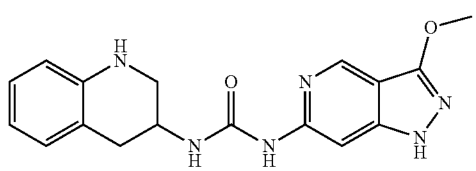 [SMILES: COc1n[nH]c2cc(NC(=O)NC3CNc4ccccc4C3)ncc12] | 1-(3-methoxy-1H-pyrazolo[4,3-c]pyridin-6-yl)-3-(1,2,3,4-tetrahydroquinolin-3-yl)urea | Calc'd 339, found 339 | Scheme 3/ Method A, Example 40 |
| 281 | 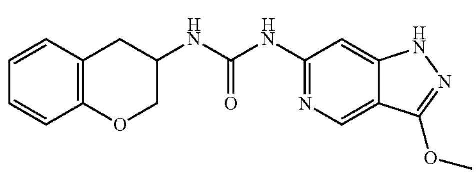 [SMILES: COc1n[nH]c2cc(NC(=O)NC3COc4ccccc4C3)ncc12] | 1-(3,4-dihydro-2H-chromen-3-yl)-3-(3-methoxy-1H-pyrazolo[4,3-c]pyridin-6-yl)urea | Calc'd 340, found 340 | Scheme 3/ Method A, Example 40 |
| 282 | 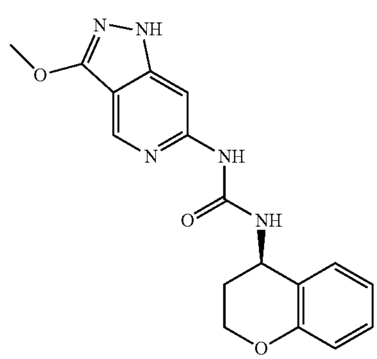 [SMILES: COc1n[nH]c2cc(NC(=O)N[C@@H]3CCOc4ccccc43)ncc12] | 1-[(4R)-3,4-dihydro-2H-chromen-4-yl]-3-(3-methoxy-1H-pyrazolo[4,3-c]pyridin-6-yl)urea | Calc'd 340, found 340 | Scheme 3/ Method A, Example 40 |

TABLE 14-continued

| Ex | Structure | IUPAC Name | Exact Mass [M + H]+ | Route Used (Intermediate Used) |
|---|---|---|---|---|
| 283 | 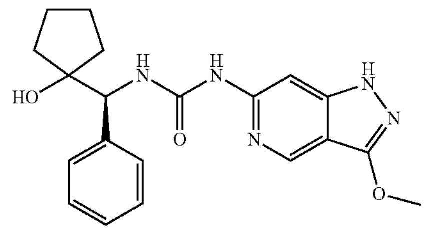 [SMILES: COc1n[nH]c2cc(NC(=O)N[C@@H](c3ccccc3)C3(O)CCCC3)ncc12] | 1-[(S)-(1-hydroxycyclopentyl)(phenyl)methyl]-3-(3-methoxy-1H-pyrazolo[4,3-c]pyridin-6-yl)urea | Calc'd 382, found 382 | Scheme 3/ Method A, Example 40 (55B) |
| 284 | 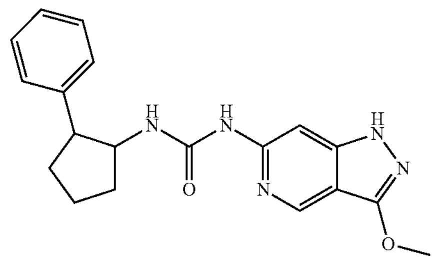 [SMILES: COc1n[nH]c2cc(NC(=O)NC3CCCC3c3ccccc3)ncc12] | 1-(3-methoxy-1H-pyrazolo[4,3-c]pyridin-6-yl)-3-(2-phenylcyclopentyl)urea | Calc'd 352, found 352 | Scheme 3/ Method A, Example 40 |
| 285 | 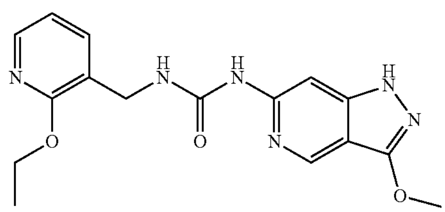 [SMILES: CCOc1ncccc1CNC(=O)Nc1cc2[nH]nc(OC)c2cn1] | 1-[(2-ethoxypyridin-3-yl)methyl]-3-(3-methoxy-1H-pyrazolo[4,3-c]pyridin-6-yl)urea | Calc'd 343, found 343 | Scheme 3/ Method A, Example 40 |
| 286 | 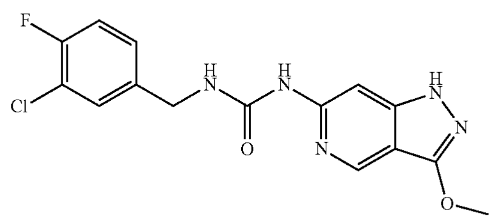 [SMILES: COc1n[nH]c2cc(NC(=O)NCc3ccc(F)c(Cl)c3)ncc12] | 1-(3-chloro-4-fluorobenzyl)-3-(3-methoxy-1H-pyrazolo[4,3-c]pyridin-6-yl)urea | Calc'd 350, found 350 | Scheme 3/ Method A, Example 40 |
| 287 | 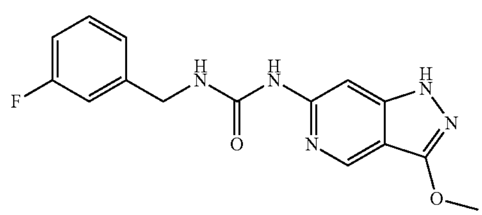 [SMILES: COc1n[nH]c2cc(NC(=O)NCc3cccc(F)c3)ncc12] | 1-(3-fluorobenzyl)-3-(3-methoxy-1H-pyrazolo[4,3-c]pyridin-6-yl)urea | Calc'd 316, found 316 | Scheme 3/ Method A, Example 40 |
| 288 | 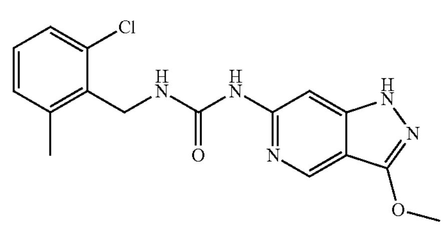 [SMILES: COc1n[nH]c2cc(NC(=O)NCc3c(C)cccc3Cl)ncc12] | 1-(2-chloro-6-methylbenzyl)-3-(3-methoxy-1H-pyrazolo[4,3-c]pyridin-6-yl)urea | Calc'd 346, found 346 | Scheme 3/ Method A, Example 40 |

TABLE 14-continued

| Ex | Structure | IUPAC Name | Exact Mass [M + H]+ | Route Used (Intermediate Used) |
|---|---|---|---|---|
| 289 | 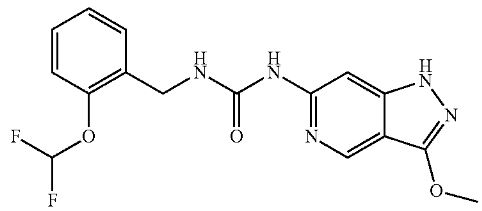 [SMILES: COc1n[nH]c2cc(NC(=O)NCc3ccccc3OC(F)F)ncc12] | 1-[2-(difluoromethoxy)benzyl]-3-(3-methoxy-1H-pyrazolo[4,3-c]pyridin-6-yl)urea | Calc'd 364, found 364 | Scheme 3/ Method A, Example 40 |
| 290 | 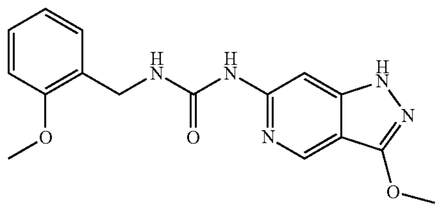 [SMILES: COc1ccccc1CNC(=O)Nc1cc2[nH]nc(OC)c2cn1] | 1-(2-methoxybenzyl)-3-(3-methoxy-1H-pyrazolo[4,3-c]pyridin-6-yl)urea | Calc'd 328, found 328 | Scheme 3/ Method A, Example 40 |
| 291 | 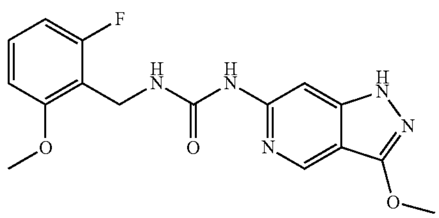 [SMILES: COc1cccc(F)c1CNC(=O)Nc1cc2[nH]nc(OC)c2cn1] | 1-(2-fluoro-6-methoxybenzyl)-3-(3-methoxy-1H-pyrazolo[4,3-c]pyridin-6-yl)urea | Calc'd 346, found 346 | Scheme 3/ Method A, Example 40 |
| 292 | 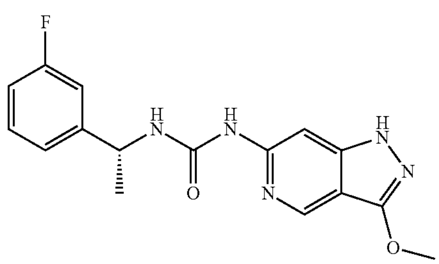 [SMILES: COc1n[nH]c2cc(NC(=O)N[C@H](C)c3cccc(F)c3)ncc12] | 1-[(1R)-1-(3-fluorophenyl)ethyl]-3-(3-methoxy-1H-pyrazolo[4,3-c]pyridin-6-yl)urea | Calc'd 330, found 330 | Scheme 3/ Method A, Example 40 |
| 293 | 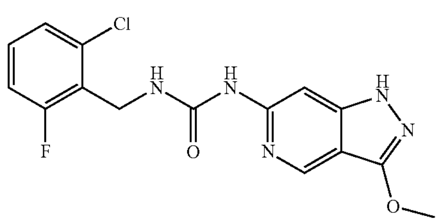 | 1-(2-chloro-6-fluorobenzyl)-3-(3-methoxy-1H-pyrazolo[4,3-c]pyridin-6-yl)urea | Calc'd 350, found 350 | Scheme 3/ Method A, Example 40 |
| 294 | 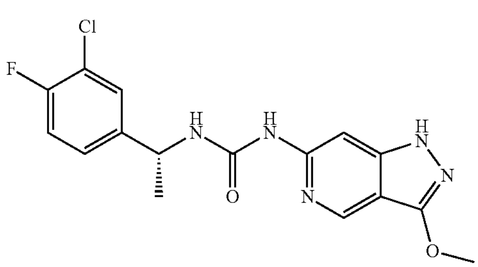 [SMILES: COc1n[nH]c2cc(NC(=O)N[C@H](C)c3ccc(F)c(Cl)c3)ncc12] | 1-[(1R)-1-(3-chloro-4-fluorophenyl)ethyl]-3-(3-methoxy-1H-pyrazolo[4,3-c]pyridin-6-yl)urea | Calc'd 364, found 364 | Scheme 3/ Method A, Example 40 |

TABLE 14-continued

| Ex | Structure | IUPAC Name | Exact Mass [M + H]+ | Route Used (Intermediate Used) |
|---|---|---|---|---|
| 295 | 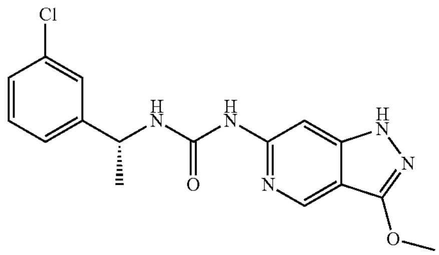 | 1-[(1R)-1-(3-chlorophenyl)ethyl]-3-(3-methoxy-1H-pyrazolo[4,3-c]pyridin-6-yl)urea | Calc'd 346, found 346 | Scheme 3/ Method A, Example 40 |
| 296 | 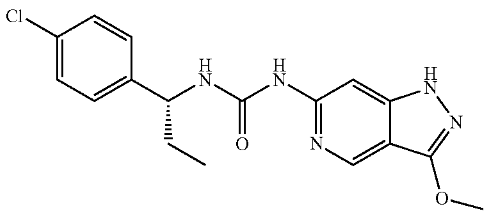 [SMILES: CC[C@@H](NC(=O)Nc1cc2[nH]nc(OC)c2cn1)c1ccc(Cl)cc1] | 1-[(1R)-1-(4-chlorophenyl)propyl]-3-(3-methoxy-1H-pyrazolo[4,3-c]pyridin-6-yl)urea | Calc'd 360, found 360 | Scheme 3/ Method A, Example 40 |
| 297 | 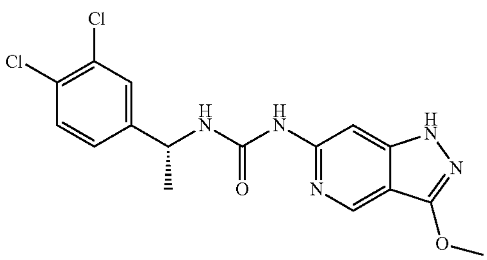 [SMILES: COc1n[nH]c2cc(NC(=O)N[C@H](C)c3ccc(Cl)c(Cl)c3)ncc12] | 1-[(1R)-1-(3,4-dichlorophenyl)ethyl]-3-(3-methoxy-1H-pyrazolo[4,3-c]pyridin-6-yl)urea | Calc'd 380, found 380 | Scheme 3/ Method A, Example 40 |
| 298 | 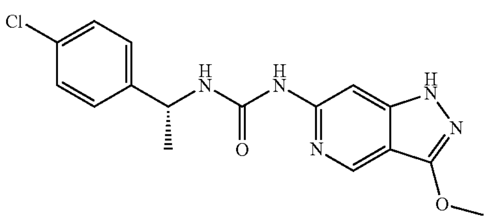 [SMILES: COc1n[nH]c2cc(NC(=O)N[C@H](C)c3ccc(Cl)cc3)ncc12] | 1-[(1R)-1-(4-chlorophenyl)ethyl]-3-(3-methoxy-1H-pyrazolo[4,3-c]pyridin-6-yl)urea | Calc'd 346, found 346 | Scheme 3/ Method A, Example 40 |
| 299 | 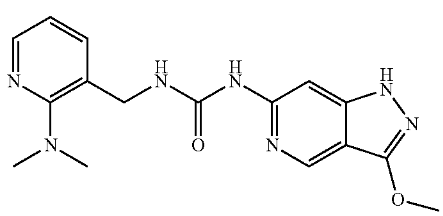 [SMILES: COc1n[nH]c2cc(NC(=O)NCc3cccnc3N(C)C)ncc12] | 1-{[2-(dimethylamino)pyridin-3-yl]methyl}-3-(3-methoxy-1H-pyrazolo[4,3-c]pyridin-6-yl)urea | Calc'd 342, found 342 | Scheme 3/ Method A, Example 40 |
| 300 | 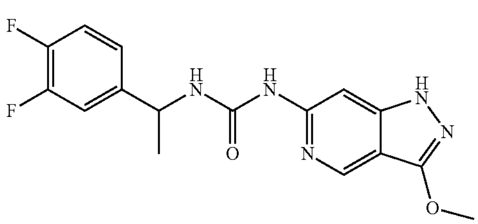 [SMILES: COc1n[nH]c2cc(NC(=O)NC(C)c3ccc(F)c(F)c3)ncc12] | 1-[1-(3,4-difluorophenyl)ethyl]-3-(3-methoxy-1H-pyrazolo[4,3-c]pyridin-6-yl)urea | Calc'd 348, found 348 | Scheme 3/ Method A, Example 40 |

TABLE 14-continued

| Ex | Structure | IUPAC Name | Exact Mass [M + H]+ | Route Used (Intermediate Used) |
|---|---|---|---|---|
| 301 | 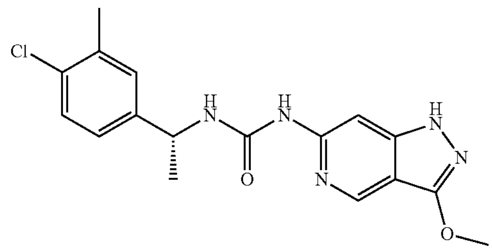 [SMILES: COc1n[nH]c2cc(NC(=O)N[C@H](C)c3ccc(Cl)c(C)c3)ncc12] | 1-[(1R)-1-(4-chloro-3-methylphenyl)ethyl]-3-(3-methoxy-1H-pyrazolo[4,3-c]pyridin-6-yl)urea | Calc'd 360, found 360 | Scheme 3/ Method A, Example 40 |
| 302 | 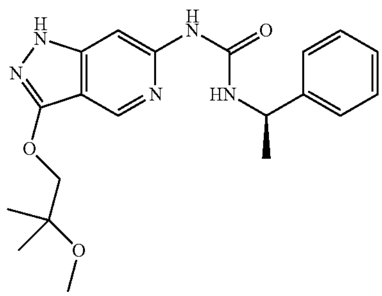 [SMILES: COC(C)(C)COc1n[nH]c2cc(NC(=O)N[C@H](C)c3ccccc3)ncc12] | 1-[3-(2-methoxy-2-methylpropoxy)-1H-pyrazolo[4,3-c]pyridin-6-yl]-3-[(1R)-1-phenylethyl]urea | Calc'd 384, found 384 | Scheme 4, Example 69 |
| 303 | 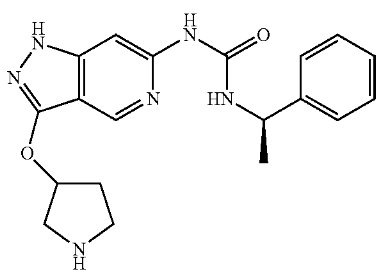 [SMILES: C[C@@H](NC(=O)Nc1cc2[nH]nc(OC3CCNC3)c2cn1)c1ccccc1] | 1-[(1R)-1-phenylethyl]-3-[3-(pyrrolidin-3-yloxy)-1H-pyrazolo[4,3-c]pyridin-6-yl]urea | Calc'd 367, found 367 | Scheme 4, Example 69 |
| 304 | 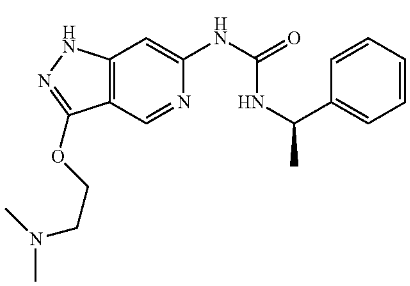 [SMILES: C[C@@H](NC(=O)Nc1cc2[nH]nc(OCCN(C)C)c2cn1)c1ccccc1] | 1-{3-[2-(dimethylamino)ethoxy]-1H-pyrazolo[4,3-c]pyridin-6-yl}-3-[(1R)-1-phenylethyl]urea | Calc'd 369, found 369 | Scheme 4, Example 69 |
| 305 | 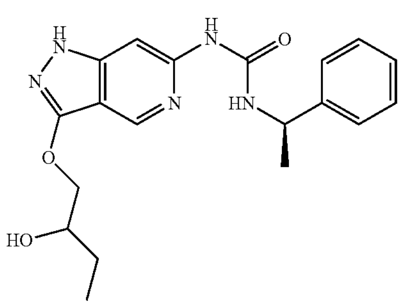 [SMILES: CCC(O)COc1n[nH]c2cc(NC(=O)N[C@H](C)c3ccccc3)ncc12] | 1-[3-(2-hydroxybutoxy)-1H-pyrazolo[4,3-c]pyridin-6-yl]-3-[(1R)-1-phenylethyl]urea | Calc'd 370, found 370 | Scheme 4, Example 69 |

TABLE 14-continued

| Ex | Structure | IUPAC Name | Exact Mass [M + H]+ | Route Used (Intermediate Used) |
|---|---|---|---|---|
| 306 | 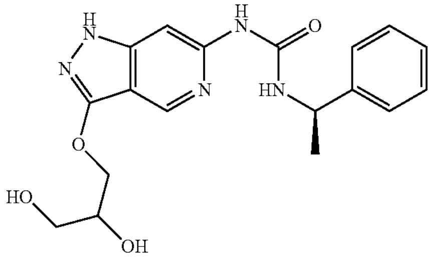 [SMILES: C[C@@H](NC(=O)Nc1cc2[nH]nc(OCC(O)CO)c2cn1)c1ccccc1] | 1-[3-(2,3-dihydroxypropoxy)-1H-pyrazolo[4,3-c]pyridin-6-yl]-3-[(1R)-1-phenylethyl]urea | Calc'd 372, found 372 | Scheme 4, Example 69 |
| 307 | 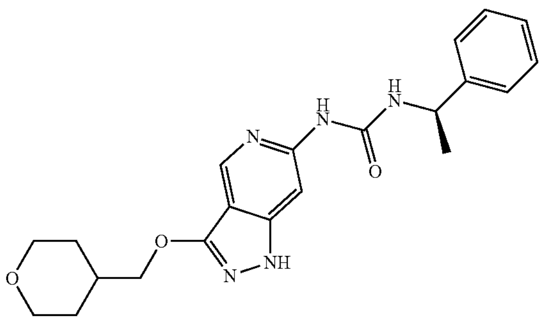 [SMILES: C[C@@H](NC(=O)Nc1cc2[nH]nc(OCC3CCOCC3)c2cn1)c1ccccc1] | 1-[(1R)-1-phenylethyl]-3-[3-(tetrahydro-2H-pyran-4-ylmethoxy)-1H-pyrazolo[4,3-c]pyridin-6-yl]urea | Calc'd 396, found 396 | Scheme 4, Example 69 |
| 308 | 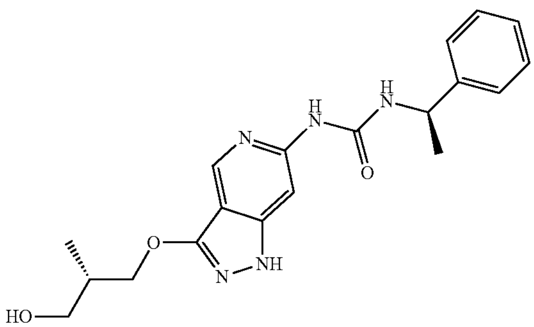 [SMILES: C[C@@H](CO)COc1n[nH]c2cc(NC(=O)N[C@H](C)c3ccccc3)ncc12] | 1-(3-{[(2S)-3-hydroxy-2-methylpropyl]oxy}-1H-pyrazolo[4,3-c]pyridin-6-yl)-3-[(1R)-1-phenylethyl]urea | Calc'd 370, found 370 | Scheme 4, Example 69 |
| 309 | 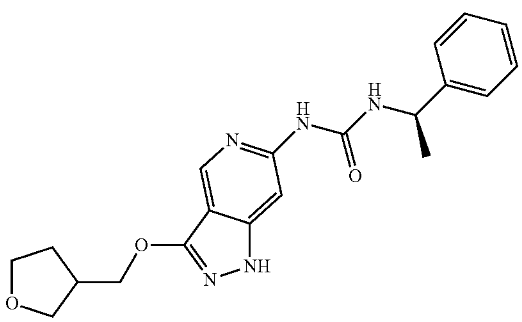 [SMILES: C[C@@H](NC(=O)Nc1cc2[nH]nc(OCC3CCOC3)c2cn1)c1ccccc1] | 1-[(1R)-1-phenylethyl]-3-[3-(tetrahydrofuran-3-ylmethoxy)-1H-pyrazolo[4,3-c]pyridin-6-yl]urea | Calc'd 382, found 382 | Scheme 4, Example 69 |
| 310 | 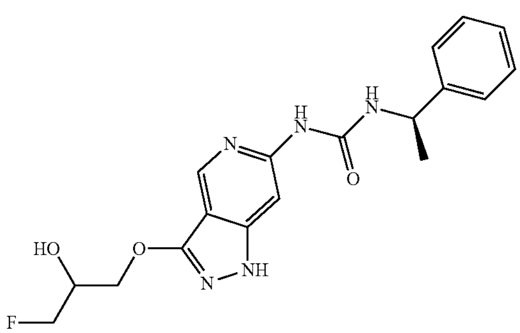 [SMILES: C[C@@H](NC(=O)Nc1cc2[nH]nc(OCC(O)CF)c2cn1)c1ccccc1] | 1-[3-(3-fluoro-2-hydroxypropoxy)-1H-pyrazolo[4,3-c]pyridin-6-yl]-3-[(1R)-1-phenylethyl]urea | Calc'd 374, found 374 | Scheme 4, Example 69 |

| Ex | Structure | IUPAC Name | Exact Mass [M + H]+ | Route Used (Intermediate Used) |
|---|---|---|---|---|
| 311 | 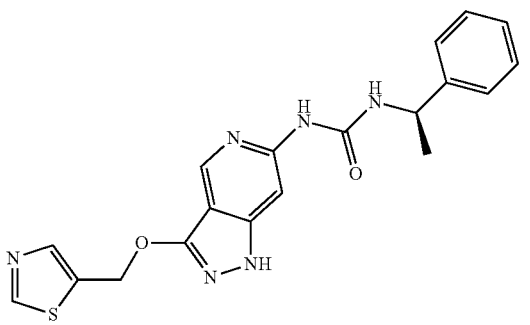 [SMILES: C[C@@H](NC(=O)Nc1cc2[nH]nc(OCc3cncs3)c2cn1)c1ccccc1] | 1-[(1R)-1-phenylethyl]-3-[3-(1,3-thiazol-5-ylmethoxy)-1H-pyrazolo[4,3-c]pyridin-6-yl]urea | Calc'd 395, found 395 | Scheme 4, Example 69 |
| 312 | 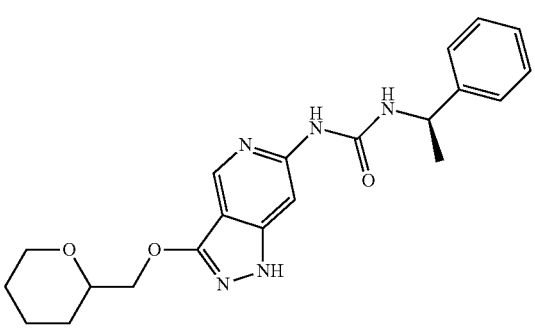 [SMILES: C[C@@H](NC(=O)Nc1cc2[nH]nc(OCC3CCCCO3)c2cn1)c1ccccc1] | 1-[(1R)-1-phenylethyl]-3-[3-(tetrahydro-2H-pyran-2-ylmethoxy)-1H-pyrazolo[4,3-c]pyridin-6-yl]urea | Calc'd 396, found 396 | Scheme 4, Example 69 |
| 313 | 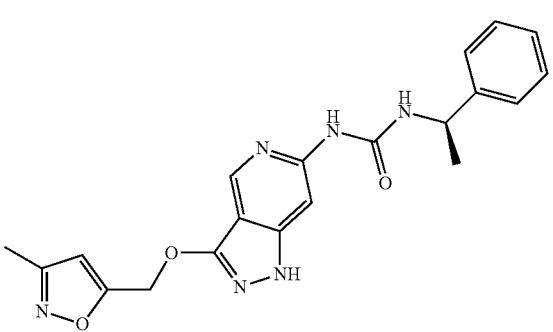 [SMILES: Cc1cc(COc2n[nH]c3cc(NC(=O)N[C@H](C)c4ccccc4)ncc23)on1] | 1-{3-[(3-methylisoxazol-5-yl)methoxy]-1H-pyrazolo[4,3-c]pyridin-6-yl}-3-[(1R)-1-phenylethyl]urea | Calc'd 393, found 393 | Scheme 4, Example 69 |
| 314 | 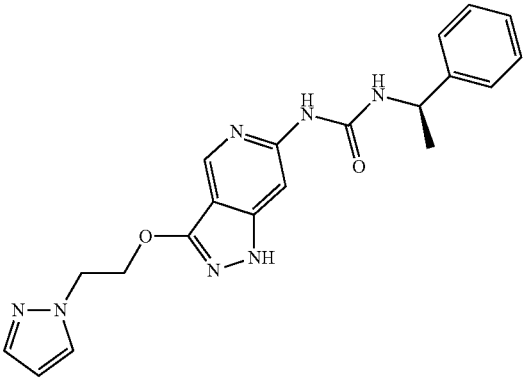 [SMILES: C[C@@H](NC(=O)Nc1cc2[nH]nc(OCCn3cccn3)c2cn1)c1ccccc1] | 1-[(1R)-1-phenylethyl]-3-{3-[2-(1H-pyrazol-1-yl)ethoxy]-1H-pyrazolo[4,3-c]pyridin-6-yl}urea | Calc'd 392, found 392 | Scheme 4, Example 69 |

| Ex | Structure | IUPAC Name | Exact Mass [M + H]+ | Route Used (Intermediate Used) |
|---|---|---|---|---|
| 315 | 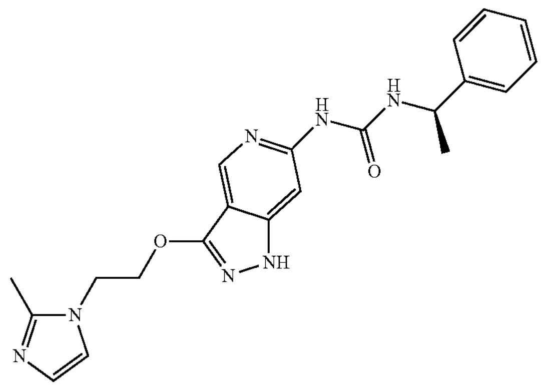 [SMILES: Cc1nccn1CCOc1n[nH]c2cc(NC(=O)N[C@H](C)c3ccccc3)ncc12] | 1-{3-[2-(2-methyl-1H-imidazol-1-yl)ethoxy]-1H-pyrazolo[4,3-c]pyridin-6-yl}-3-[(1R)-1-phenylethyl]urea | Calc'd 406, found 406 | Scheme 4, Example 69 |
| 316 | 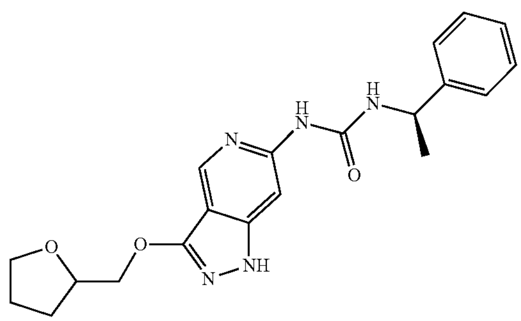 [SMILES: C[C@@H](NC(=O)Nc1cc2[nH]nc(OCC3CCCO3)c2cn1)c1ccccc1] | 1-[(1R)-1-phenylethyl]-3-[3-(tetrahydrofuran-2-ylmethoxy)-1H-pyrazolo[4,3-c]pyridin-6-yl]urea | Calc'd 382, found 382 | Scheme 4, Example 69 |
| 317 | 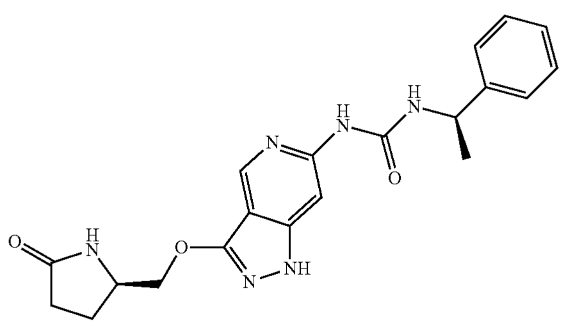 [SMILES: C[C@@H](NC(=O)Nc1cc2[nH]nc(OC[C@H]3CCC(=O)N3)c2cn1)c1ccccc1] | 1-(3-{[(2R)-5-oxopyrrolidin-2-yl]methoxy}-1H-pyrazolo[4,3-c]pyridin-6-yl)-3-[(1R)-1-phenylethyl]urea | Calc'd 395, found 395 | Scheme 4, Example 69 |
| 318 | 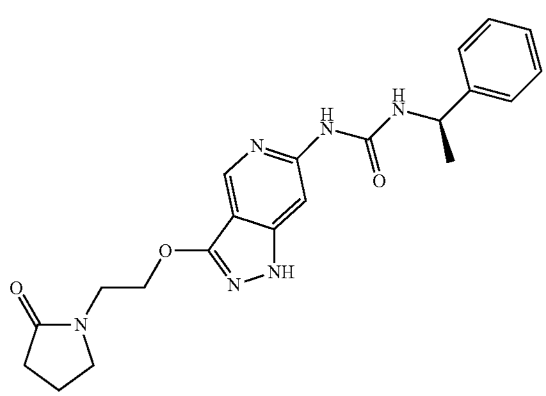 [SMILES: C[C@@H](NC(=O)Nc1cc2[nH]nc(OCCN3CCCC3=O)c2cn1)c1ccccc1] | 1-{3-[2-(2-oxopyrrolidin-1-yl)ethoxy]-1H-pyrazolo[4,3-c]pyridin-6-yl}-3-[(1R)-1-phenylethyl]urea | Calc'd 409, found 409 | Scheme 4, Example 69 |

TABLE 14-continued

| Ex | Structure | IUPAC Name | Exact Mass [M + H]+ | Route Used (Intermediate Used) |
|---|---|---|---|---|
| 319 | 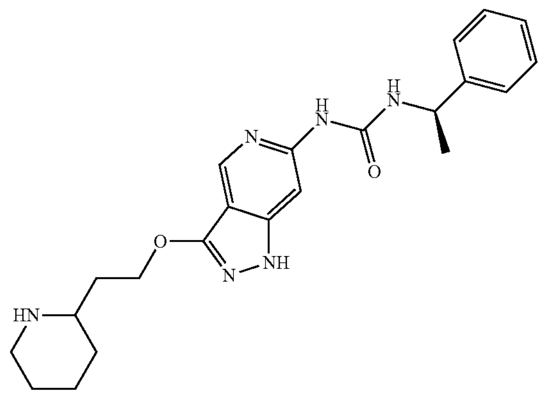 [SMILES: C[C@@H](NC(=O)Nc1cc2[nH]nc(OCCC3CCCCN3)c2cn1)c1ccccc1] | 1-[(1R)-1-phenylethyl]-3-[3-(2-piperidin-2-ylethoxy)-1H-pyrazolo[4,3-c]pyridin-6-yl]urea | Calc'd 409, found 409 | Scheme 4, Example 69 |
| 320 | 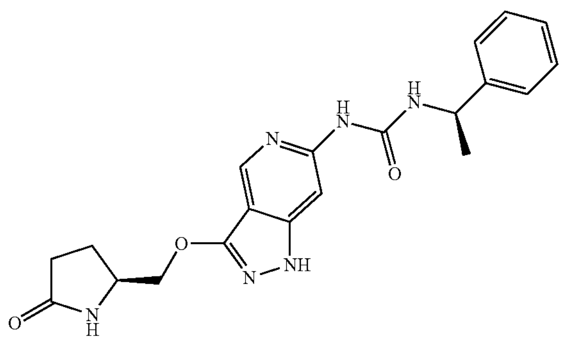 [SMILES: C[C@@H](NC(=O)Nc1cc2[nH]nc(OC[C@@H]3CCC(=O)N3)c2cn1)c1ccccc1] | 1-(3-{[(2S)-5-oxopyrrolidin-2-yl]methoxy}-1H-pyrazolo[4,3-c]pyridin-6-yl)-3-[(1R)-1-phenylethyl]urea | Calc'd 395, found 395 | Scheme 4, Example 69 |
| 321 | 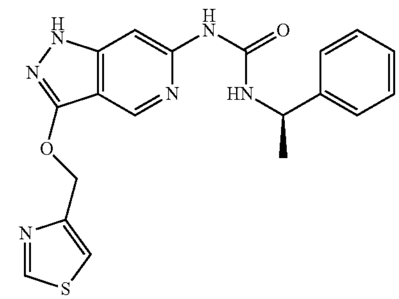 [SMILES: C[C@@H](NC(=O)Nc1cc2[nH]nc(OCc3cscn3)c2cn1)c1ccccc1] | 1-[(1R)-1-phenylethyl]-3-[3-(1,3-thiazol-4-ylmethoxy)-1H-pyrazolo[4,3-c]pyridin-6-yl]urea | Calc'd 395, found 395 | Scheme 4, Example 69 |
| 322 | 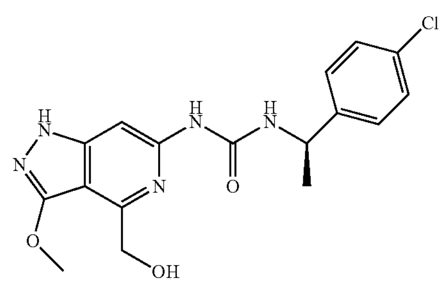 [SMILES: COc1n[nH]c2cc(NC(=O)N[C@H](C)c3ccc(Cl)cc3)nc(CO)c12] | 1-[(1R)-1-(4-chlorophenyl)ethyl]-3-[4-(hydroxymethyl)-3-methoxy-1H-pyrazolo[4,3-c]pyridin-6-yl]urea | Calc'd 376, found 376 | Scheme 3/ Method A, Example 40 (35B) |

TABLE 14-continued

| Ex | Structure | IUPAC Name | Exact Mass [M + H]+ | Route Used (Intermediate Used) |
|---|---|---|---|---|
| 323 | 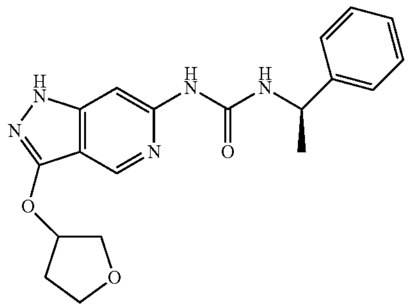 [SMILES: C[C@@H](NC(=O)Nc1cc2[nH]nc(OC3CCOC3)c2cn1)c1ccccc1] | 1-[(1R)-2-phenylethyl]-3-[3-(tetrahydrofuran-3-yloxy)-1H-pyrazolo[4,3-c]pyridin-6-yl]urea, Stereoisomer A | Calc'd 368, found 368 | Scheme 3/ Method A, Example 40 |
| 324 | 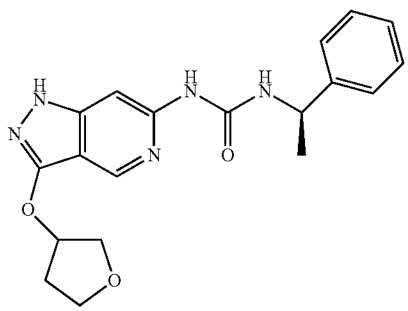 [SMILES: C[C@@H](NC(=O)Nc1cc2[nH]nc(OC3CCOC3)c2cn1)c1ccccc1] | 1-[(1R)-1-phenylethyl]-3-[3-(tetrahydrofuran-3-yloxy)-1H-pyrazolo[4,3-c]pyridin-6-yl]urea, Stereoisomer B | Calc'd 368, found 368 | Scheme 3/ Method A, Example 40 |
| 325 | 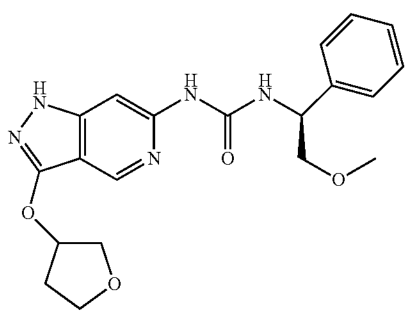 [SMILES: COC[C@@H](NC(=O)Nc1cc2[nH]nc(OC3CCOC3)c2cn1)c1ccccc1] | 1-[(1S)-2-methoxy-1-phenylethyl]-3-[3-(tetrahydrofuran-3-yloxy)-1H-pyrazolo[4,3-c]pyridin-6-yl]urea, Stereoisomer A | Calc'd 398, found 398 | Scheme 3/ Method A, Example 40 |
| 326 | 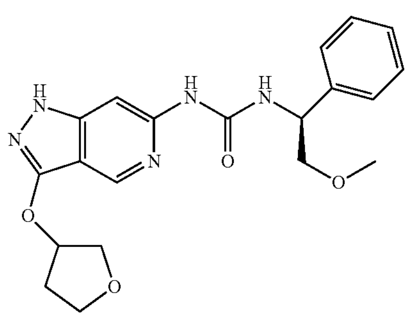 [SMILES: COC[C@@H](NC(=O)Nc1cc2[nH]nc(OC3CCOC3)c2cn1)c1ccccc1] | 1-[(1S)-2-methoxy-1-phenylethyl]-3-[3-(tetrahydrofuran-3-yloxy)-1H-pyrazolo[4,3-c]pyridin-6-yl]urea, Stereoisomer B | Calc'd 398, found 398 | Scheme 3/ Method A, Example 40 |
| 327 | 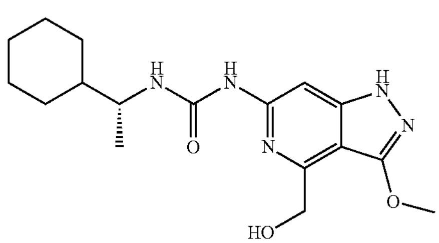 [SMILES: COc1n[nH]c2cc(NC(=O)N[C@H](C)C3CCCCC3)nc(CO)c12] | 1-[(1R)-1-cyclohexylethyl]-3-[4-(hydroxymethyl)-3-methoxy-1H-pyrazolo[4,3-c]pyridin-6-yl]urea | Calc'd 348, found 348 | Scheme 3/ Method A, Example 40 (35B) |

TABLE 14-continued

| Ex | Structure | IUPAC Name | Exact Mass [M + H]+ | Route Used (Intermediate Used) |
|---|---|---|---|---|
| 328 | 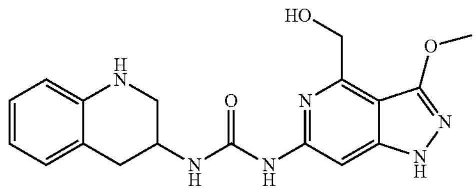 [SMILES: COc1n[nH]c2cc(NC(=O)NC3CNc4ccccc4C3)nc(CO)c12] | 1-[4-(hydroxymethyl)-3-methoxy-1H-pyrazolo[4,3-c]pyridin-6-yl]-3-(1,2,3,4-tetrahydroquinolin-3-yl)urea | Calc'd 369, found 369 | Scheme 3/ Method A, Example 40 (35B) |
| 329 | 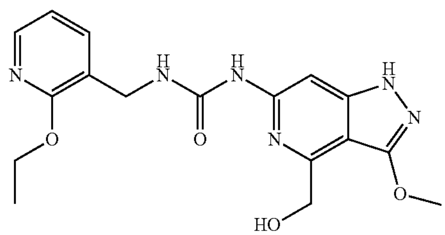 [SMILES: CCOc1ncccc1CNC(=O)Nc1cc2[nH]nc(OC)c2c(CO)n1] | 1-[(2-ethoxypyridin-3-yl)methyl]-3-[4-(hydroxymethyl)-3-methoxy-1H-pyrazolo[4,3-c]pyridin-6-yl]urea | Calc'd 373, found 373 | Scheme 3/ Method A, Example 40 (35B) |
| 330 | 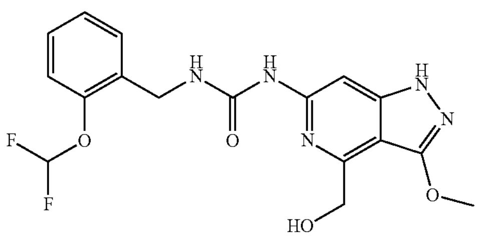 [SMILES: COc1n[nH]c2cc(NC(=O)NCc3ccccc3OC(F)F)nc(CO)c12] | 1-[2-(difluoromethoxy)benzyl]-3-[4-(hydroxymethyl)-3-methoxy-1H-pyrazolo[4,3-c]pyridin-6-yl]urea | Calc'd 394, found 394 | Scheme 3/ Method A, Example 40 (35B) |
| 331 | 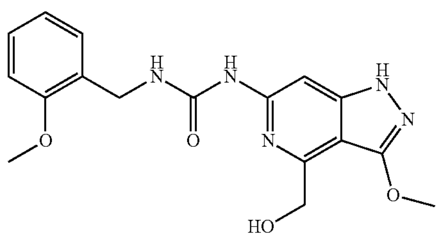 [SMILES: COc1ccccc1CNC(=O)Nc1cc2[nH]nc(OC)c2c(CO)n1] | 1-[4-(hydroxymethyl)-3-methoxy-1H-pyrazolo[4,3-c]pyridin-6-yl]-3-(2-methoxybenzyl)urea | Calc'd 358, found 358 | Scheme 3/ Method A, Example 40 (35B) |
| 332 | 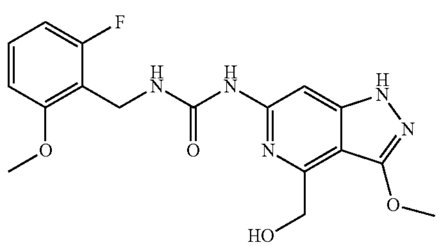 [SMILES: COc1cccc(F)c1CNC(=O)Nc1cc2[nH]nc(OC)c2c(CO)n1] | 1-(2-fluoro-6-methoxybenzyl)-3-[4-(hydroxymethyl)-3-methoxy-1H-pyrazolo[4,3-c]pyridin-6-yl]urea | Calc'd 376, found 376 | Scheme 3/ Method A, Example 40 (35B) |
| 333 | 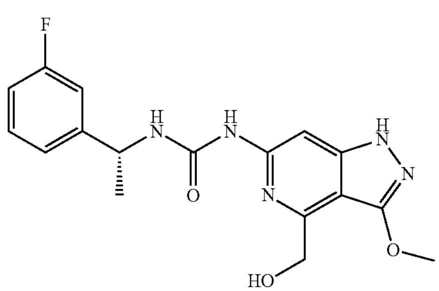 [SMILES: COc1n[nH]c2cc(NC(=O)N[C@H](C)c3cccc(F)c3)nc(CO)c12] | 1-[(1R)-1-(3-fluorophenyl)ethyl]-3-[4-(hydroxymethyl)-3-methoxy-1H-pyrazolo[4,3-c]pyridin-6-yl]urea | Calc'd 360, found 360 | Scheme 3/ Method A, Example 40 (35B) |

TABLE 14-continued

| Ex | Structure | IUPAC Name | Exact Mass [M + H]+ | Route Used (Intermediate Used) |
|---|---|---|---|---|
| 334 | 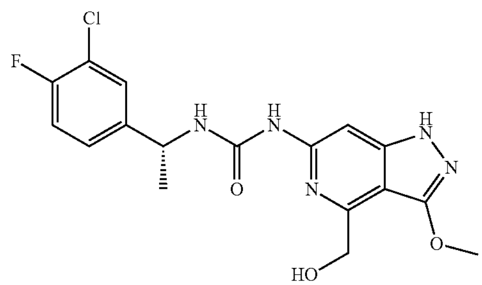 [SMILES: COc1n[nH]c2cc(NC(=O)N[C@H](C)c3ccc(F)c(Cl)c3)nc(CO)c12] | 1-[(1R)-1-(3-chloro-4-fluorophenyl)ethyl]-3-[4-(hydroxymethyl)-3-methoxy-1H-pyrazolo[4,3-c]pyridin-6-yl]urea | Calc'd 394, found 394 | Scheme 3/ Method A, Example 40 (35B) |
| 335 | 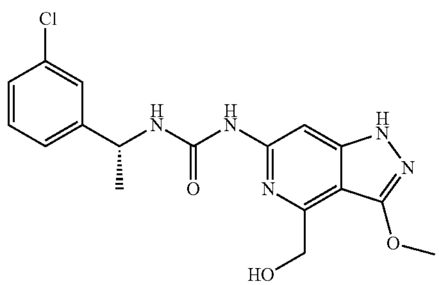 | 1-[(1R)-1-(3-chlorophenyl)ethyl]-3-[4-(hydroxymethyl)-3-methoxy-1H-pyrazolo[4,3-c]pyridin-6-yl]urea | Calc'd 376, found 376 | Scheme 3/ Method A, Example 40 (35B) |
| 336 | 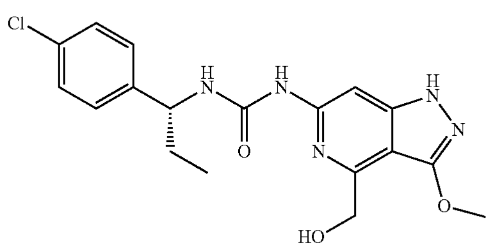 [SMILES: CC[C@@H](NC(=O)Nc1cc2[nH]nc(OC)c2c(CO)n1)c1ccc(Cl)cc1] | 1-[(1R)-1-(4-chlorophenyl)propyl]-3-[4-(hydroxymethyl)-3-methoxy-1H-pyrazolo[4,3-c]pyridin-6-yl]urea | Calc'd 390, found 390 | Scheme 3/ Method A, Example 40 (35B) |
| 337 | 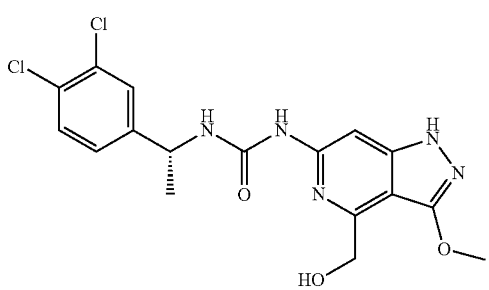 [SMILES: COc1n[nH]c2cc(NC(=O)N[C@H](C)c3ccc(Cl)c(Cl)c3)nc(CO)c12] | 1-[(1R)-1-(3,4-dichlorophenyl)ethyl]-3-[4-(hydroxymethyl)-3-methoxy-1H-pyrazolo[4,3-c]pyridin-6-yl]urea | Calc'd 410, found 410 | Scheme 3/ Method A, Example 40 (35B) |
| 338 | 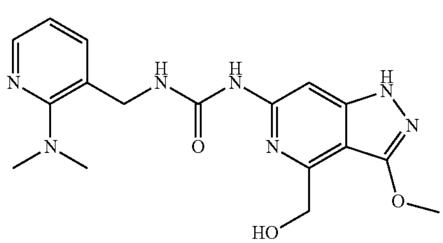 [SMILES: COc1n[nH]c2cc(NC(=O)NCc3cccnc3N(C)C)nc(CO)c12] | 1-{[2-(dimethylamino)pyridin-3-yl]methyl}-3-[4-(hydroxymethyl)-3-methoxy-1H-pyrazolo[4,3-c]pyridin-6-yl]urea | Calc'd 372, found 372 | Scheme 3/ Method A, Example 40 (35B) |

TABLE 14-continued

| Ex | Structure | IUPAC Name | Exact Mass [M + H]+ | Route Used (Intermediate Used) |
|---|---|---|---|---|
| 339 | 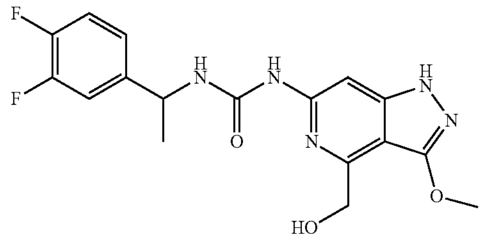 [SMILES: COc1n[nH]c2cc(NC(=O)NC(C)c3ccc(F)c(F)c3)nc(CO)c12] | 1-[1-(3,4-difluorophenyl)ethyl]-3-[4-(hydroxymethyl)-3-methoxy-1H-pyrazolo[4,3-c]pyridin-6-yl]urea | Calc'd 378, found 378 | Scheme 3/ Method A, Example 40 (35B) |
| 340 | 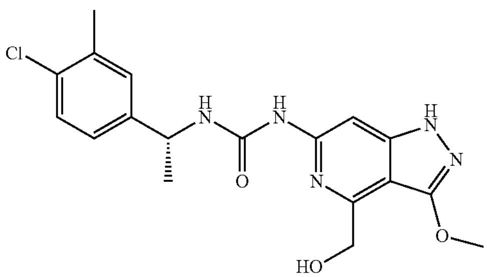 [SMILES: COc1n[nH]c2cc(NC(=O)N[C@H](C)c3ccc(Cl)c(C)c3)nc(CO)c12] | 1-[(1R)-1-(4-chloro-3-methylphenyl)ethyl]-3-[4-(hydroxymethyl)-3-methoxy-1H-pyrazolo[4,3-c]pyridin-6-yl]urea | Calc'd 390, found 390 | Scheme 3/ Method A, Example 40 (35B) |
| 341 | 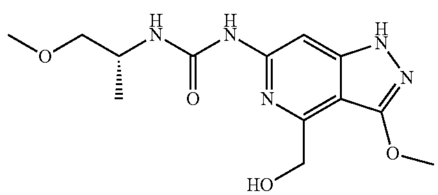 | 1-[4-(hydroxymethyl)-3-methoxy-1H-pyrazolo[4,3-c]pyridin-6-yl]-3-[(1R)-2-methoxy-1-methylethyl]urea | Calc'd 310, found 310 | Scheme 3/ Method A, Example 40 (35B) |
| 342 | 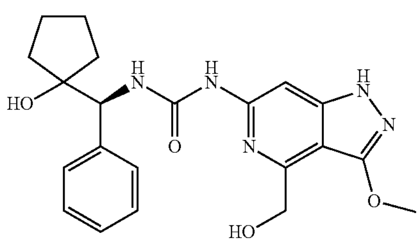 [SMILES: COc1n[nH]c2cc(NC(=O)N[C@@H](c3ccccc3)C3(O)CCCC3)nc(CO)c12] | 1-[(S)-(1-hydroxycyclopentyl)(phenyl)methyl]-3-[4-(hydroxymethyl)-3-methoxy-1H-pyrazolo[4,3-c]pyridin-6-yl]urea | Calc'd 412, found 412 | Scheme 3/ Method A, Example 40 (35B, 55B) |
| 343 | 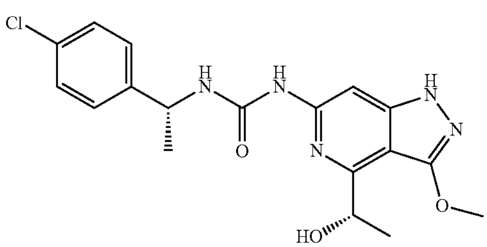 [SMILES: COc1n[nH]c2cc(NC(=O)N[C@H](C)c3ccc(Cl)cc3)nc([C@H](C)O)c12] | 1-[(1R)-1-(4-chlorophenyl)ethyl]-3-{4-[(1S)-1-hydroxyethyl]-3-methoxy-1H-pyrazolo[4,3-c]pyridin-6-yl}urea | Calc'd 390, found 390 | Scheme 3/ Method A, Example 40 (38B) |
| 344 | 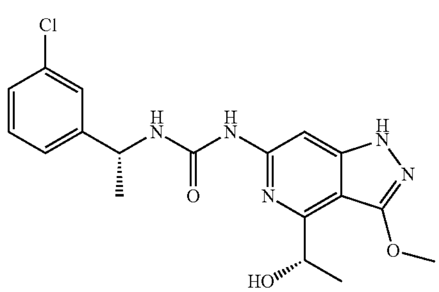 [SMILES: COc1n[nH]c2cc(NC(=O)N[C@H](C)c3cccc(Cl)c3)nc([C@H](C)O)c12] | 1-[(1R)-1-(3-chlorophenyl)ethyl]-3-{4-[(1S)-1-hydroxyethyl]-3-methoxy-1H-pyrazolo[4,3-c]pyridin-6-yl}urea | Calc'd 390, found 390 | Scheme 3/ Method A, Example 40 (38B) |

TABLE 14-continued

| Ex | Structure | IUPAC Name | Exact Mass [M + H]+ | Route Used (Intermediate Used) |
|---|---|---|---|---|
| 345 | 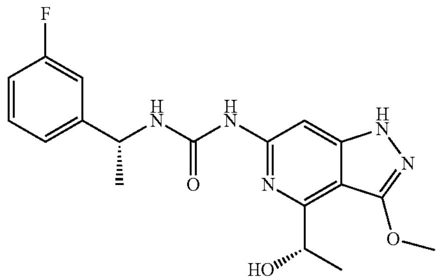 [SMILES: COc1n[nH]c2cc(NC(=O)N[C@H](C)c3cccc(F)c3)nc([C@H](C)O)c12] | 1-[(1R)-1-(3-fluorophenyl)ethyl]-3-{4-[(1S)-1-hydroxyethyl]-3-methoxy-1H-pyrazolo[4,3-c]pyridin-6-yl}urea | Calc'd 374, found 374 | Scheme 3/ Method A, Example 40 (38B) |
| 346 | 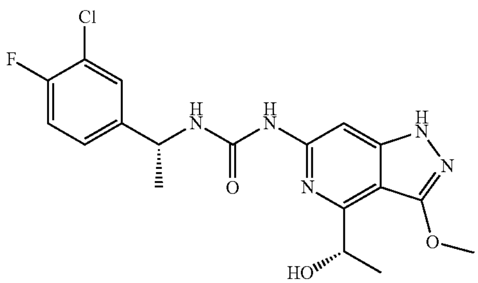 [SMILES: COc1n[nH]c2cc(NC(=O)N[C@H](C)c3ccc(F)c(Cl)c3)nc([C@H](C)O)c12] | 1-[(1R)-1-(3-chloro-4-fluorophenyl)ethyl]-3-{4-[(1S)-1-hydroxyethyl]-3-methoxy-1H-pyrazolo[4,3-c]pyridin-6-yl}urea | Calc'd 408, found 408 | Scheme 3/ Method A, Example 40 (38B) |
| 347 | 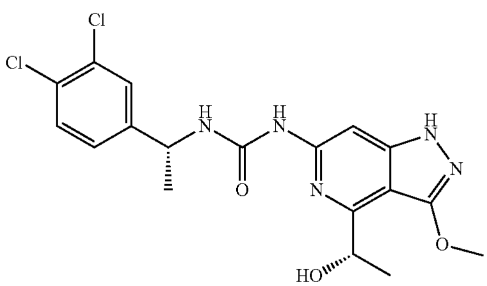 [SMILES: COc1n[nH]c2cc(NC(=O)N[C@H](C)c3ccc(Cl)c(Cl)c3)nc([C@H](C)O)c12] | 1-[(1R)-1-(3,4-dichlorophenyl)ethyl]-3-{4-[(1S)-1-hydroxyethyl]-3-methoxy-1H-pyrazolo[4,3-c]pyridin-6-yl}urea | Calc'd 424, found 424 | Scheme 3/ Method A, Example 40 (38B) |
| 348 | 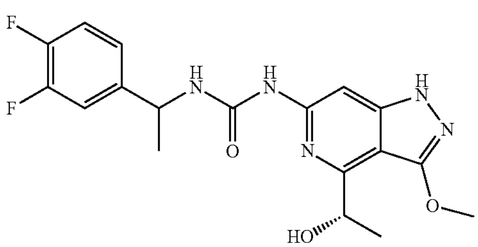 [SMILES: COc1n[nH]c2cc(NC(=O)NC(C)c3ccc(F)c(F)c3)nc([C@H](C)O)c12] | 1-[1-(3,4-difluorophenyl)ethyl]-3-{4-[(1S)-1-hydroxyethyl]-3-methoxy-1H-pyrazolo[4,3-c]pyridin-6-yl}urea | Calc'd 392, found 392 | Scheme 3/ Method A, Example 40 (38B) |
| 349 | 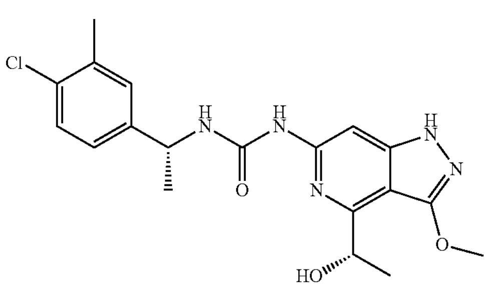 [SMILES: COc1n[nH]c2cc(NC(=O)N[C@H](C)c3ccc(Cl)c(C)c3)nc([C@H](C)O)c12] | 1-[(1R)-1-(4-chloro-3-methylphenyl)ethyl]-3-{4-[(1S)-1-hydroxyethyl]-3-methoxy-1H-pyrazolo[4,3-c]pyridin-6-yl}urea | Calc'd 404, found 404 | Scheme 3/ Method A, Example 40 (38B) |

TABLE 14-continued

| Ex | Structure | IUPAC Name | Exact Mass [M + H]+ | Route Used (Intermediate Used) |
|---|---|---|---|---|
| 350 | 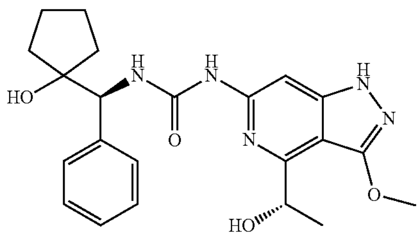 [SMILES: COc1n[nH]c2cc(NC(=O)N[C@@H](c3ccccc3)C3(O)CCCC3)nc([C@H](C)O)c12] | 1-[(S)-(1-hydroxycyclopentyl)(phenyl)methyl]-3-{4-[(1S)-1-hydroxyethyl]-3-methoxy-1H-pyrazolo[4,3-c]pyridin-6-yl}urea | Calc'd 426, found 426 | Scheme 3/ Method A, Example 40 (38B, 55B) |
| 351 | 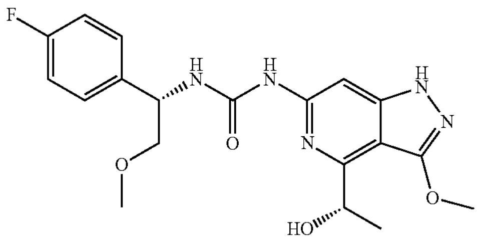 [SMILES: COC[C@@H](NC(=O)Nc1cc2[nH]nc(OC)c2c([C@H](C)O)n1)c1ccc(F)cc1] | 1-[(1S)-1-(4-fluorophenyl)-2-methoxyethyl]-3-{4-[(1S)-1-hydroxyethyl]-3-methoxy-1H-pyrazolo[4,3-c]pyridin-6-yl}urea | Calc'd 404, found 404 | Scheme 3/ Method A, Example 40 (38B) |
| 352 | 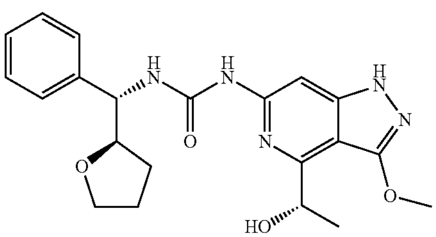 [SMILES: COc1n[nH]c2cc(NC(=O)N[C@@H](c3ccccc3)[C@H]3CCCO3)nc([C@H](C)O)c12] | 1-{4-[(1S)-1-hydroxyethyl]-3-methoxy-1H-pyrazolo[4,3-c]pyridin-6-yl}-3-{(S)-phenyl[(2R)-tetrahydrofuran-2-yl]methyl}urea | Calc'd 412, found 412 | Scheme 3/ Method A, Example 40 (38B) |
| 353 | 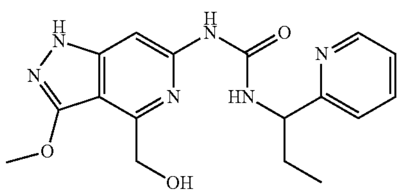 [SMILES: CCC(NC(=O)Nc1cc2[nH]nc(OC)c2c(CO)n1)c1ccccn1] | 1-[4-(hydroxymethyl)-3-methoxy-1H-pyrazolo[4,3-c]pyridin-6-yl]-3-(1-pyridin-2-ylpropyl)urea | Calc'd 357, found 357 | Example 107 (35B) |
| 354 | 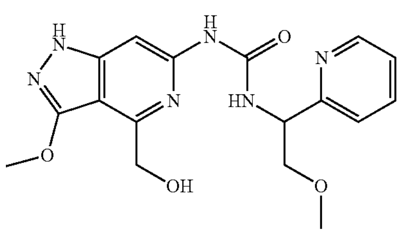 [SMILES: COCC(NC(=O)Nc1cc2[nH]nc(OC)c2c(CO)n1)c1ccccn1] | 1-[4-(hydroxymethyl)-3-methoxy-1H-pyrazolo[4,3-c]pyridin-6-yl]-3-(2-methoxy-1-pyridin-2-ylethyl)urea | Calc'd 373, found 373 | Example 107 (35B) |
| 355 | 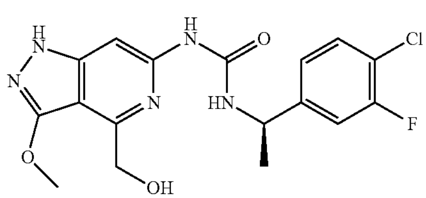 [SMILES: COc1n[nH]c2cc(NC(=O)N[C@H](C)c3ccc(Cl)c(F)c3)nc(CO)c12] | 1-[(1R)-1-(4-chloro-3-fluorophenyl)ethyl]-3-[4-(hydroxymethyl)-3-methoxy-1H-pyrazolo[4,3-c]pyridin-6-yl]urea | Calc'd 394, found 394 | Example 107 (35B) |

TABLE 14-continued

| Ex | Structure | IUPAC Name | Exact Mass [M + H]+ | Route Used (Intermediate Used) |
|---|---|---|---|---|
| 356 | 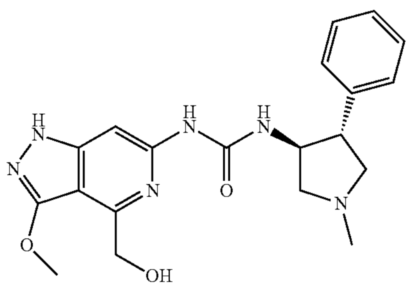 [SMILES: COc1n[nH]c2cc(NC(=O)N[C@@H]3CN(C)C[C@H]3c3ccccc3)nc(CO)c12] | 1-[4-(hydroxymethyl)-3-methoxy-1H-pyrazolo[4,3-c]pyridin-6-yl]-3-[(3S,4R)-1-methyl-4-phenylpyrrolidin-3-yl]urea | Calc'd 397, found 397 | Scheme 3/ Method A, Example 40 (35B) |
| 357 | 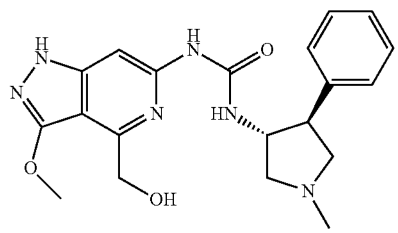 [SMILES: COc1n[nH]c2cc(NC(=O)N[C@H]3CN(C)C[C@@H]3c3ccccc3)nc(CO)c12] | 1-[4-(hydroxymethyl)-3-methoxy-1H-pyrazolo[4,3-c]pyridin-6-yl]-3-[(3R,4S)-1-methyl-4-phenylpyrrolidin-3-yl]urea | Calc'd 397, found 397 | Scheme 3/ Method A, Example 40 (35B) |
| 358 | 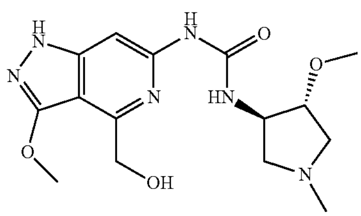 [SMILES: COc1n[nH]c2cc(NC(=O)N[C@@H]3CN(C)C[C@H]3OC)nc(CO)c12] | 1-[4-(hydroxymethyl)-3-methoxy-1H-pyrazolo[4,3-c]pyridin-6-yl]-3-[(3R,4R)-4-methoxy-1-methylpyrrolidin-3-yl]urea | Calc'd 351, found 351 | Scheme 3/ Method A, Example 40 (35B) |
| 359 | 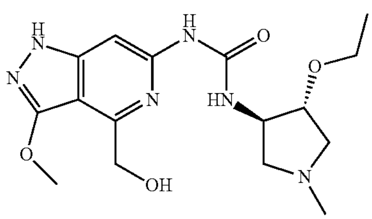 [SMILES: CCO[C@@H]1CN(C)C[C@H]1NC(=O)Nc1cc2[nH]nc(OC)c2c(CO)n1] | 1-[(3R,4R)-4-ethoxy-1-methylpyrrolidin-3-yl]-3-[4-(hydroxymethyl)-3-methoxy-1H-pyrazolo[4,3-c]pyridin-6-yl]urea | Calc'd 365, found 365 | Scheme 3/ Method A, Example 40 (35B) |
| 360 | 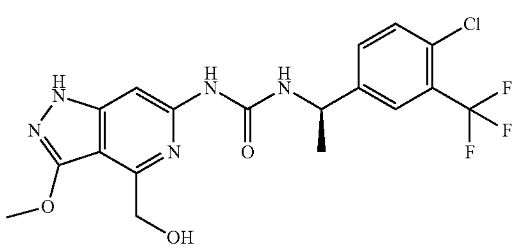 [SMILES: COc1n[nH]c2cc(NC(=O)N[C@H](C)c3ccc(Cl)c(C(F)(F)F)c3)nc(CO)c12] | 1-{(1R)-1-[4-chloro-3-(trifluoromethyl)phenyl]ethyl}-3-[4-(hydroxymethyl)-3-methoxy-1H-pyrazolo[4,3-c]pyridin-6-yl]urea | Calc'd 444, found 444 | Example 107 (35B) |
| 361 | 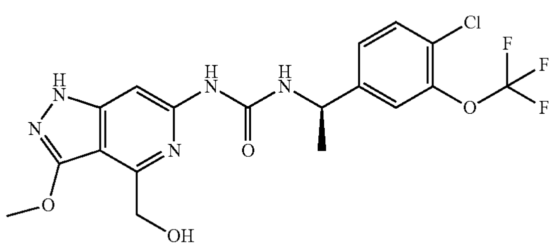 [SMILES: COc1n[nH]c2cc(NC(=O)N[C@H](C)c3ccc(Cl)c(OC(F)(F)F)c3)nc(CO)c12] | 1-{(1R)-1-[4-chloro-3-(trifluoromethoxy)phenyl]ethyl}-3-[4-(hydroxymethyl)-3-methoxy-1H-pyrazolo[4,3-c]pyridin-6-yl]urea | Calc'd 460, found 460 | Example 107 (35B) |

TABLE 14-continued

| Ex | Structure | IUPAC Name | Exact Mass [M + H]+ | Route Used (Intermediate Used) |
|---|---|---|---|---|
| 362 | 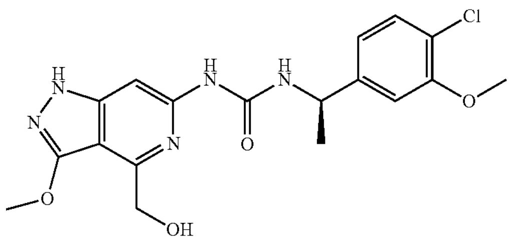 | 1-[(1R)-1-(4-chloro-3-methoxyphenyl)ethyl]-3-[4-(hydroxymethyl)-3-methoxy-1H-pyrazolo[4,3-c]pyridin-6-yl]urea | Calc'd 406, found 406 | Example 107 (35B) |
| 363 | 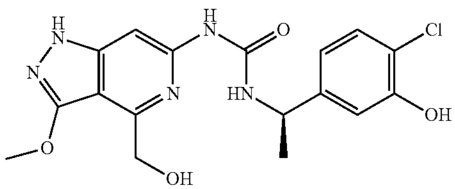 [SMILES: COc1n[nH]c2cc(NC(=O)N[C@H](C)c3ccc(Cl)c(O)c3)nc(CO)c12] | 1-[(1R)-1-(4-chloro-3-hydroxyphenyl)ethyl]-3-[4-(hydroxymethyl)-3-methoxy-1H-pyrazolo[4,3-c]pyridin-6-yl]urea | Calc'd 392, found 392 | Example 107 (35B) |
| 364 | 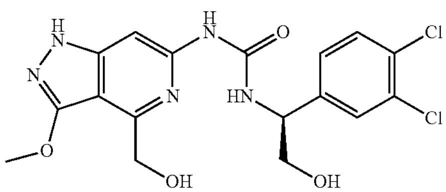 [SMILES: COc1n[nH]c2cc(NC(=O)N[C@H](CO)c3ccc(Cl)c(Cl)c3)nc(CO)c12] | 1-[(1S)-1-(3,4-dichlorophenyl)-2-hydroxyethyl]-3-[4-(hydroxymethyl)-3-methoxy-1H-pyrazolo[4,3-c]pyridin-6-yl]urea | Calc'd 426, found 426 | Example 107 (35B) |
| 365 | 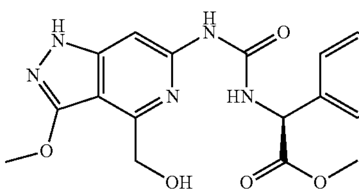 | methyl (2S)-(4-fluorophenyl)({[4-(hydroxymethyl)-3-methoxy-1H-pyrazolo[4,3-c]pyridin-6-yl]carbamoyl}amino)ethanoate | Calc'd 404, found 404 | Example 107 (35B) |
| 366 | 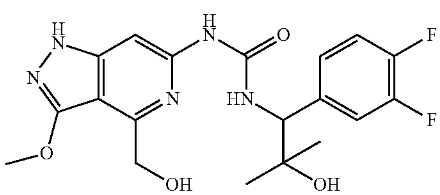 [SMILES: COc1n[nH]c2cc(NC(=O)NC(c3ccc(F)c(F)c3)C(C)(C)O)nc(CO)c12] | 1-[1-(3,4-difluorophenyl)-2-hydroxy-2-methylpropyl]-3-[4-(hydroxymethyl)-3-methoxy-1H-pyrazolo[4,3-c]pyridin-6-yl]urea | Calc'd 422, found | Example 107 (35B) |
| 367 | 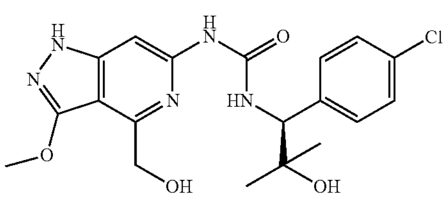 [SMILES: COc1n[nH]c2cc(NC(=O)N[C@@H](c3ccc(Cl)cc3)C(C)(C)O)nc(CO)c12] | 1-[(1S)-1-(4-chlorophenyl)-2-hydroxy-2-methylpropyl]-3-[4-(hydroxymethyl)-3-methoxy-1H-pyrazolo[4,3-c]pyridin-6-yl]urea | Calc'd 420, found 420 | Example 107 (35B) |
| 368 | 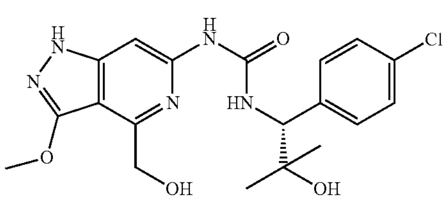 [SMILES: COc1n[nH]c2cc(NC(=O)N[C@H](c3ccc(Cl)cc3)C(C)(C)O)nc(CO)c12] | 1-[(1R)-1-(4-chlorophenyl)-2-hydroxy-2-methylpropyl]-3-[4-(hydroxymethyl)-3-methoxy-1H-pyrazolo[4,3-c]pyridin-6-yl]urea | Calc'd 420, found 420 | Example 107 (35B) |

TABLE 14-continued

| Ex | Structure | IUPAC Name | Exact Mass [M + H]+ | Route Used (Intermediate Used) |
|---|---|---|---|---|
| 369 | 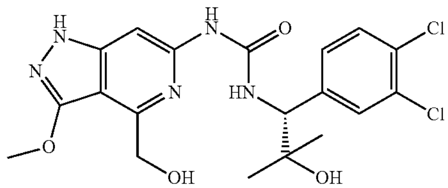 [SMILES: COc1n[nH]c2cc(NC(=O)N[C@H](c3ccc(Cl)c(Cl)c3)C(C)(C)O)nc(CO)c12] | 1-[(1R)-1-(3,4-dichlorophenyl)-2-hydroxy-2-methylpropyl]-3-[4-(hydroxymethyl)-3-methoxy-1H-pyrazolo[4,3-c]pyridin-6-yl]urea | Calc'd 454, found 454 | Example 107 (35B) |
| 370 | 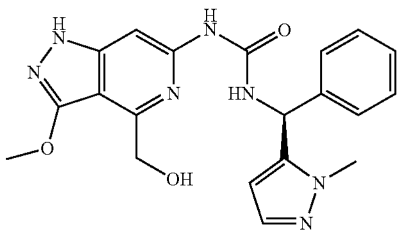 [SMILES: COc1n[nH]c2cc(NC(=O)N[C@@H](c3ccccc3)c3ccnn3C)nc(CO)c12] | 1-[4-(hydroxymethyl)-3-methoxy-1H-pyrazolo[4,3-c]pyridin-6-yl]-3-[(S)-(1-methyl-1H-pyrazol-5-yl)(phenyl)methyl]urea | Calc'd 408, found 408 | Example 107 (35B) |
| 371 | 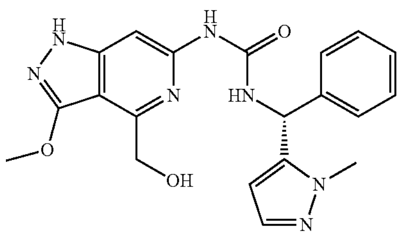 [SMILES: COc1n[nH]c2cc(NC(=O)N[C@H](c3ccccc3)c3ccnn3C)nc(CO)c12] | 1-[4-(hydroxymethyl)-3-methoxy-1H-pyrazolo[4,3-c]pyridin-6-yl]-3-[(R)-(1-methyl-1H-pyrazol-5-yl)(phenyl)methyl]urea | Calc'd 408, found 408 | Example 107 (35B) |
| 372 | 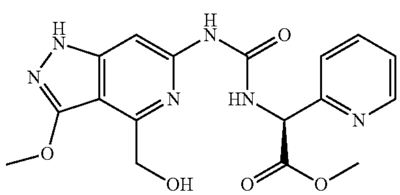 [SMILES: COC(=O)[C@@H](NC(=O)Nc1cc2[nH]nc(OC)c2c(CO)n1)c1ccccn1] | methyl (2S)-({[4-(hydroxymethyl)-3-methoxy-1H-pyrazolo[4,3-c]pyridin-6-yl]carbamoyl}amino)(pyridin-2-yl)ethanoate | Calc'd 387, found 387 | Example 107 (35B) |
| 373 | 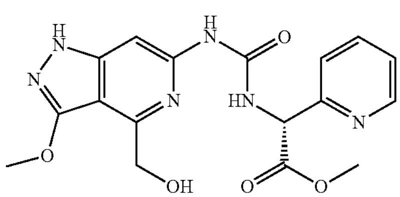 [SMILES: COC(=O)[C@H](NC(=O)Nc1cc2[nH]nc(OC)c2c(CO)n1)c1ccccn1] | methyl (2R)-({[4-(hydroxymethyl)-3-methoxy-1H-pyrazolo[4,3-c]pyridin-6-yl]carbamoyl}amino)(pyridin-2-yl)ethanoate | Calc'd 387, found 387 | Example 107 (35B) |
| 374 | 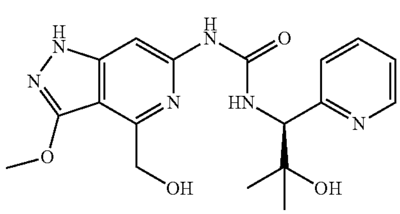 [SMILES: COc1n[nH]c2cc(NC(=O)N[C@@H](c3ccccn3)C(C)(C)O)nc(CO)c12] | 1-[4-(hydroxymethyl)-3-methoxy-1H-pyrazolo[4,3-c]pyridin-6-yl]-3-[(1S)-2-hydroxy-2-methyl-1-pyridin-2-ylpropyl]urea | Calc'd 387, found 387 | Example 107 (35B) |
| 375 | 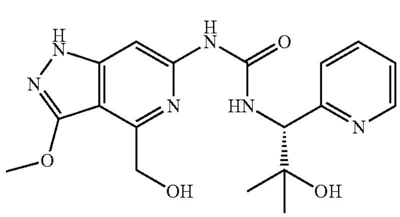 [SMILES: COc1n[nH]c2cc(NC(=O)N[C@H](c3ccccn3)C(C)(C)O)nc(CO)c12] | 1-[4-(hydroxymethyl)-3-methoxy-1H-pyrazolo[4,3-c]pyridin-6-yl]-3-[(1R)-2-hydroxy-2-methyl-1-pyridin-2-ylpropyl]urea | Calc'd 387, found 387 | Example 107 (35B) |

TABLE 14-continued

| Ex | Structure | IUPAC Name | Exact Mass [M + H]+ | Route Used (Intermediate Used) |
|---|---|---|---|---|
| 376 | 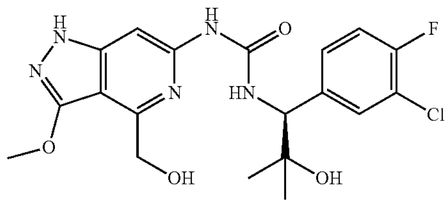 [SMILES: COc1n[nH]c2cc(NC(=O)N[C@@H](c3ccc(F)c(Cl)c3)C(C)(C)O)nc(CO)c12] | 1-[(1S)-1-(3-chloro-4-fluorophenyl)-2-hydroxy-2-methylpropyl]-3-[4-(hydroxymethyl)-3-methoxy-1H-pyrazolo[4,3-c]pyridin-6-yl]urea | Calc'd 438, found 438 | Example 107 (35B) |
| 377 | 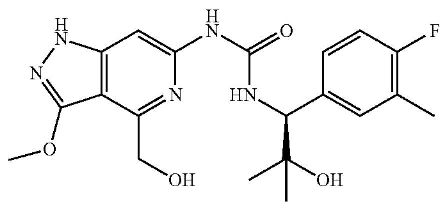 | 1-[(1S)-1-(4-fluoro-3-methylphenyl)-2-hydroxy-2-methylpropyl]-3-[4-(hydroxymethyl)-3-methoxy-1H-pyrazolo[4,3-c]pyridin-6-yl]urea | Calc'd 418, found 418 | Example 107 (35B) |
| 378 | 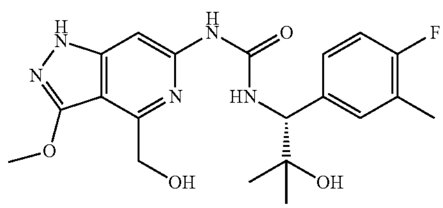 | 1-[(1R)-1-(4-fluoro-3-methylphenyl)-2-hydroxy-2-methylpropyl]-3-[4-(hydroxymethyl)-3-methoxy-1H-pyrazolo[4,3-c]pyridin-6-yl]urea | Calc'd 418, found 418 | Example 107 (35B) |
| 379 | 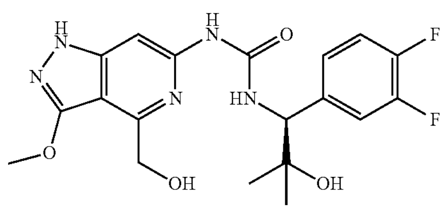 [SMILES: COc1n[nH]c2cc(NC(=O)N[C@@H](c3ccc(F)c(F)c3)C(C)(C)O)nc(CO)c12] | 1-[(1S)-1-(3,4-difluorophenyl)-2-hydroxy-2-methylpropyl]-3-[4-(hydroxymethyl)-3-methoxy-1H-pyrazolo[4,3-c]pyridin-6-yl]urea | Calc'd 422, found 422 | Example 107 (35B) |
| 380 | 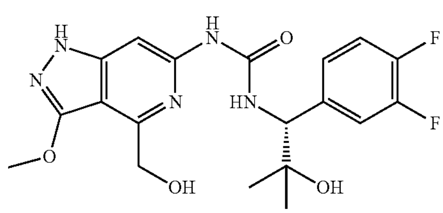 [SMILES: COc1n[nH]c2cc(NC(=O)N[C@H](c3ccc(F)c(F)c3)C(C)(C)O)nc(CO)c12] | 1-[(1R)-1-(3,4-difluorophenyl)-2-hydroxy-2-methylpropyl]-3-[4-(hydroxymethyl)-3-methoxy-1H-pyrazolo[4,3-c]pyridin-6-yl]urea | Calc'd 422, found 422 | Example 107 (35B) |
| 381 | 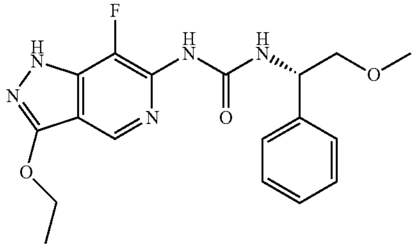 [SMILES: CCOc1n[nH]c2c(F)c(NC(=O)N[C@H](COC)c3ccccc3)ncc12] | 1-(3-ethoxy-7-fluoro-1H-pyrazolo[4,3-c]pyridin-6-yl)-3-[(1S)-2-methoxy-1-phenylethyl]urea | Calc'd 374, found 374 | Scheme 1/ Method B, Ex. 26 (2B) |

TABLE 14-continued

| Ex | Structure | IUPAC Name | Exact Mass [M + H]+ | Route Used (Intermediate Used) |
|---|---|---|---|---|
| 382 | 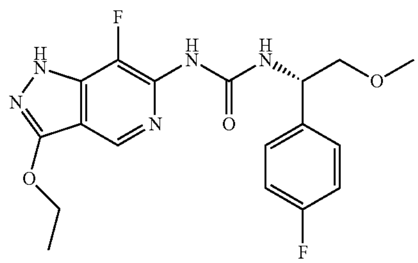 [SMILES: CCOc1n[nH]c2c(F)c(NC(=O)N[C@H](COC)c3ccc(F)cc3)ncc12] | 1-(3-ethoxy-7-fluoro-1H-pyrazolo[4,3-c]pyridin-6-yl)-3-[(1S)-1-(4-fluorophenyl)-2-methoxyethyl]urea | Calc'd 392, found 392 | Scheme 1/ Method B, Ex. 26 (2B) |
| 383 | 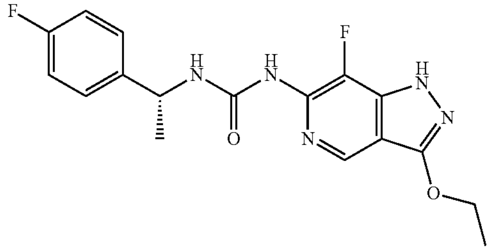 [SMILES: CCOc1n[nH]c2c(F)c(NC(=O)N[C@H](C)c3ccc(F)cc3)ncc12] | 1-(3-ethoxy-7-fluoro-1H-pyrazolo[4,3-c]pyridin-6-yl)-3-[(1R)-1-(4-fluorophenyl)ethyl]urea | Calc'd 362, found 362 | Scheme 1/ Method B, Ex. 26 (2B) |
| 384 | 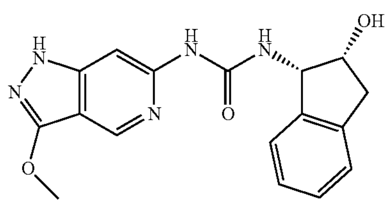 [SMILES: COc1n[nH]c2cc(NC(=O)N[C@H]3c4ccccc4C[C@H]3O)ncc12] | 1-[(1S,2R)-2-hydroxy-2,3-dihydro-1H-inden-1-yl]-3-(3-methoxy-1H-pyrazolo[4,3-c]pyridin-6-yl)urea | Calc'd 340, found 340 | Scheme 10/ Method A, Example 102 |
| 385 | 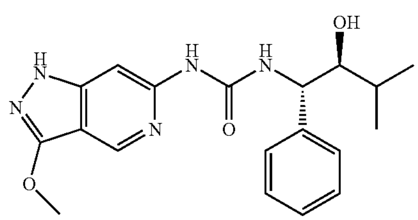 [SMILES: COc1n[nH]c2cc(NC(=O)N[C@@H](c3ccccc3)[C@@H](O)C(C)C)ncc12] | 1-[(1S,2S)-2-hydroxy-3-methyl-1-phenylbutyl]-3-(3-methoxy-1H-pyrazolo[4,3-c]pyridin-6-yl)urea | Calc'd 370, found 370 | Scheme 10/ Method A, Example 102 |
| 386 | 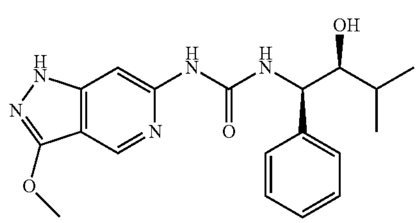 [SMILES: COc1n[nH]c2cc(NC(=O)N[C@H](c3ccccc3)[C@@H](O)C(C)C)ncc12] | 1-[(1R,2S)-2-hydroxy-3-methyl-1-phenylbutyl]-3-(3-methoxy-1H-pyrazolo[4,3-c]pyridin-6-yl)urea | Calc'd 370, found 370 | Scheme 10/ Method A, Example 102 |
| 387 | 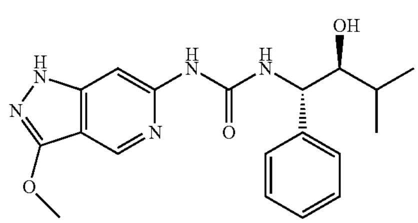 [SMILES: COc1n[nH]c2cc(NC(=O)N[C@@H](c3ccccc3)[C@@H](O)C(C)C)ncc12] | 1-[(1S,2S)-2-hydroxy-3-methyl-1-phenylbutyl]-3-(3-methoxy-1H-pyrazolo[4,3-c]pyridin-6-yl)urea | Calc'd 370, found 370 | Scheme 10/ Method A, Example 102 |

TABLE 14-continued

| Ex | Structure | IUPAC Name | Exact Mass [M + H]+ | Route Used (Intermediate Used) |
|---|---|---|---|---|
| 388 | 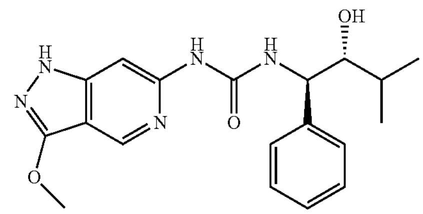 [SMILES: COc1n[nH]c2cc(NC(=O)N[C@H](c3ccccc3)[C@H](O)C(C)C)ncc12] | 1-[(1R,2R)-2-hydroxy-3-methyl-1-phenylbutyl]-3-(3-methoxy-1H-pyrazolo[4,3-c]pyridin-6-yl)urea | Calc'd 370, found 370 | Scheme 10/ Method A, Example 102 |
| 389 | 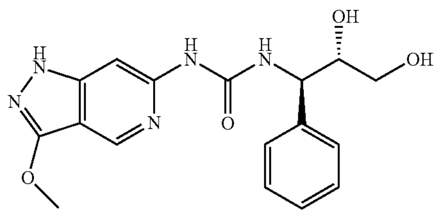 [SMILES: COc1n[nH]c2cc(NC(=O)N[C@H](c3ccccc3)[C@H](O)CO)ncc12] | 1-[(1R,2S)-2,3-dihydroxy-1-phenylpropyl]-3-(3-methoxy-1H-pyrazolo[4,3-c]pyridin-6-yl)urea | Calc'd 358, found 358 | Scheme 10/ Method A, Example 102 |
| 390 | 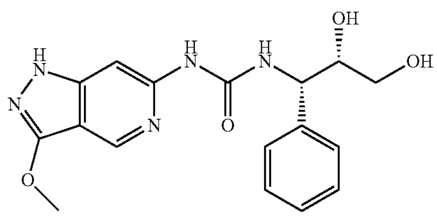 [SMILES: COc1n[nH]c2cc(NC(=O)N[C@@H](c3ccccc3)[C@H](O)CO)ncc12] | 1-[(1S,2S)-2,3-dihydroxy-1-phenylpropyl]-3-(3-methoxy-1H-pyrazolo[4,3-c]pyridin-6-yl)urea | Calc'd 358, found 358 | Scheme 10/ Method A, Example 102 |
| 391 | 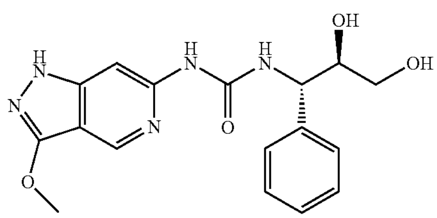 [SMILES: COc1n[nH]c2cc(NC(=O)N[C@@H](c3ccccc3)[C@@H](O)CO)ncc12] | 1-[(1S,2R)-2,3-dihydroxy-1-phenylpropyl]-3-(3-methoxy-1H-pyrazolo[4,3-c]pyridin-6-yl)urea | Calc'd 358, found 358 | Scheme 10/ Method A, Example 102 |
| 392 | 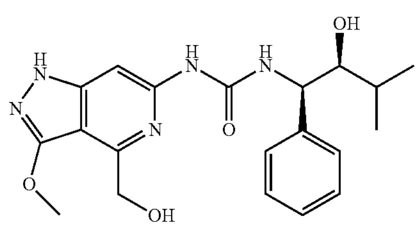 [SMILES: COc1n[nH]c2cc(NC(=O)N[C@H](c3ccccc3)[C@@H](O)C(C)C)nc(CO)c12] | 1-[4-(hydroxymethyl)-3-methoxy-1H-pyrazolo[4,3-c]pyridin-6-yl]-3-[(1R,2S)-2-hydroxy-3-methyl-1-phenylbutyl]urea | Calc'd 400, found 400 | Scheme 10/ Method A, Example 102 |
| 393 | 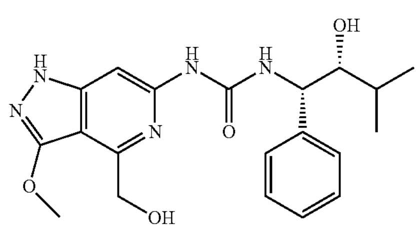 [SMILES: COc1n[nH]c2cc(NC(=O)N[C@@H](c3ccccc3)[C@H](O)C(C)C)nc(CO)c12] | 1-[4-(hydroxymethyl)-3-methoxy-1H-pyrazolo[4,3-c]pyridin-6-yl]-3-[(1S,2R)-2-hydroxy-3-methyl-1-phenylbutyl]urea | Calc'd 400, found 400 | Scheme 10/ Method A, Example 102 |
| 394 | 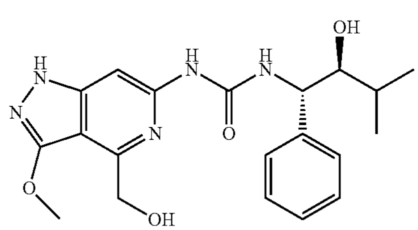 [SMILES: COc1n[nH]c2cc(NC(=O)N[C@@H](c3ccccc3)[C@@H](O)C(C)C)nc(CO)c12] | 1-[4-(hydroxymethyl)-3-methoxy-1H-pyrazolo[4,3-c]pyridin-6-yl]-3-[(1S,2S)-2-hydroxy-3-methyl-1-phenylbutyl]urea | Calc'd 400, found 400 | Scheme 10/ Method A, Example 102 |

TABLE 14-continued

| Ex | Structure | IUPAC Name | Exact Mass [M + H]+ | Route Used (Intermediate Used) |
|---|---|---|---|---|
| 395 | 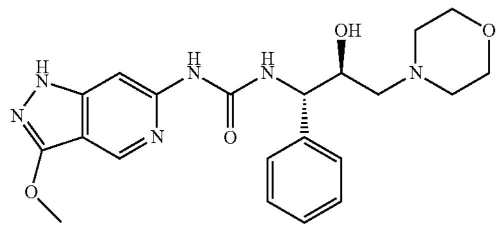 [SMILES: COc1n[nH]c2cc(NC(=O)N[C@@H](c3ccccc3)[C@@H](O)CN3CCOCC3)ncc12] | 1-[(1S,2S)-2-hydroxy-3-morpholin-4-yl-1-phenylpropyl]-3-(3-methoxy-1H-pyrazolo[4,3-c]pyridin-6-yl)urea | Calc'd 427, found 427 | Scheme 10/ Method A, Example 102 |
| 396 | 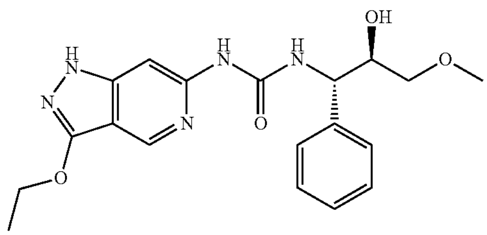 [SMILES: CCOc1n[nH]c2cc(NC(=O)N[C@@H](c3ccccc3)[C@@H](O)COC)ncc12] | 1-(3-ethoxy-1H-pyrazolo[4,3-c]pyridin-6-yl)-3-[(1S,2R)-2-hydroxy-3-methoxy-1-phenylpropyl]urea | Calc'd 386, found 386 | Scheme 10/ Method A, Example 102 |
| 397 | 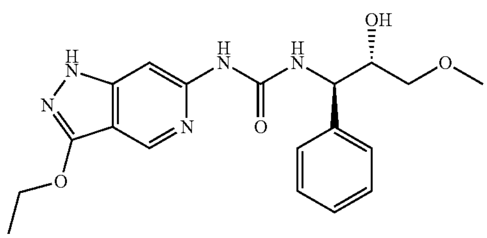 [SMILES: CCOc1n[nH]c2cc(NC(=O)N[C@H](c3ccccc3)[C@H](O)COC)ncc12] | 1-(3-ethoxy-1H-pyrazolo[4,3-c]pyridin-6-yl)-3-[(1R,2S)-2-hydroxy-3-methoxy-1-phenylpropyl]urea | Calc'd 386, found 386 | Scheme 10/ Method A, Example 102 |
| 398 | 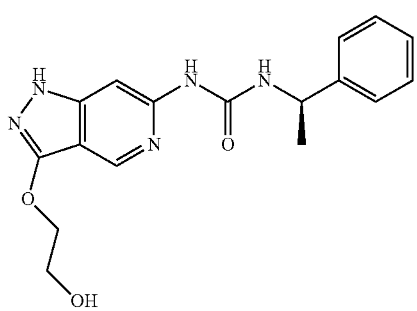 [SMILES: C[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1R)-1-phenylethyl]urea | Calc'd 342, found 342 | Scheme 3/ Method A, Example 40 (58B) |
| 399 | 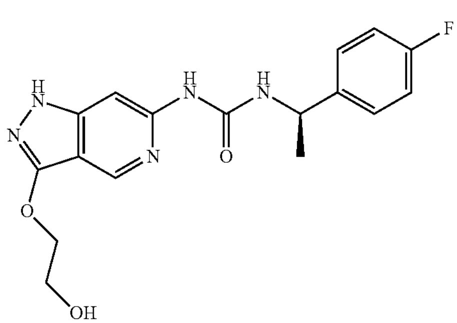 [SMILES: C[C@@H](NC(=O)Nc1cc2[nH]nc(OCCO)c2cn1)c1ccc(F)cc1] | 1-[(1R)-1-(4-fluorophenyl)ethyl]-3-[3-(2-hydroxyethoxy)-1H-pyrazolo[4,3-c]pyridin-6-yl]urea | Calc'd 360, found 360 | Scheme 3/ Method A, Example 40 (58B) |

TABLE 14-continued

| Ex | Structure | IUPAC Name | Exact Mass [M + H]+ | Route Used (Intermediate Used) |
| --- | --- | --- | --- | --- |
| 400 | 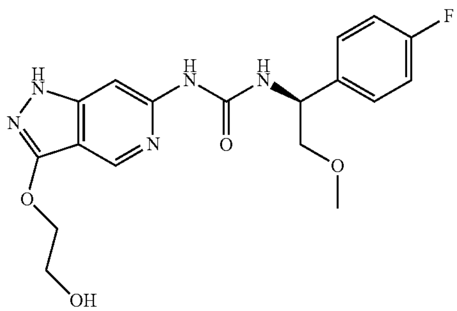 [SMILES: COC[C@@H](NC(=O)Nc1cc2[nH]nc(OCCO)c2cn1)c1ccc(F)cc1] | 1-[(1S)-1-(4-fluorophenyl)-2-methoxyethyl]-3-[3-(2-hydroxyethoxy)-1H-pyrazolo[4,3-c]pyridin-6-yl]urea | Calc'd 390, found 390 | Scheme 3/ Method A, Example 40 (58B) |
| 401 | 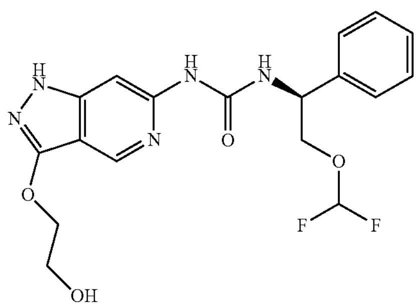 [SMILES: O=C(Nc1cc2[nH]nc(OCCO)c2cn1)N[C@H](COC(F)F)c1ccccc1] | 1-[(1S)-2-(difluoromethoxy)-1-phenylethyl]-3-[3-(2-hydroxyethoxy)-1H-pyrazolo[4,3-c]pyridin-6-yl]urea | Calc'd 408, found 408 | Scheme 3/ Method A, Example 40 (58B, 25B) |
| 402 | 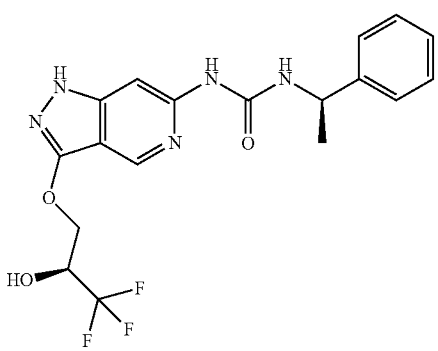 [SMILES: C[C@@H](NC(=O)Nc1cc2[nH]nc(OC[C@H](O)C(F)(F)F)c2cn1)c1ccccc1] | 1-[(1R)-1-phenylethyl]-3-(3-{[(2S)-3,3,3-trifluoro-2-hydroxypropyl]oxy}-1H-pyrazolo[4,3-c]pyridin-6-yl)urea | Calc'd 410, found 410 | Scheme 3/ Method A, Example 40 (3B) |
| 403 | 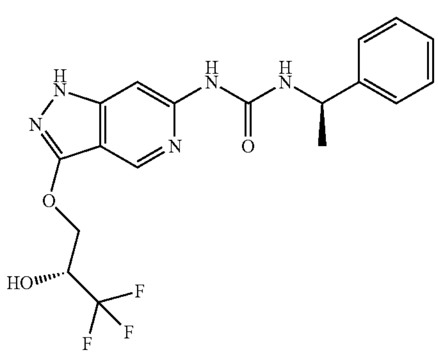 [SMILES: C[C@@H](NC(=O)Nc1cc2[nH]nc(OC[C@@H](O)C(F)(F)F)c2cn1)c1ccccc1] | 1-[(1R)-1-phenylethyl]-3-(3-{[(2R)-3,3,3-trifluoro-2-hydroxypropyl]oxy}-1H-pyrazolo[4,3-c]pyridin-6-yl)urea | Calc'd 410, found 410 | Scheme 3/ Method A, Example 40 (3B) |

TABLE 14-continued

| Ex | Structure | IUPAC Name | Exact Mass [M + H]+ | Route Used (Intermediate Used) |
|---|---|---|---|---|
| 404 | 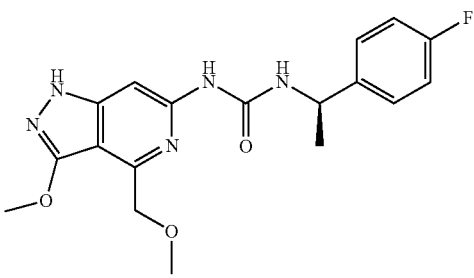 [SMILES: COCc1nc(NC(=O)N[C@H](C)c2ccc(F)cc2)cc2[nH]nc(OC)c12] | 1-[(1R)-1-(4-fluorophenyl)ethyl]-3-[3-methoxy-4-(methoxymethyl)-1H-pyrazolo[4,3-c]pyridin-6-yl]urea | Calc'd 374, found 374 | Scheme 5, Example 73 |
| 405 | 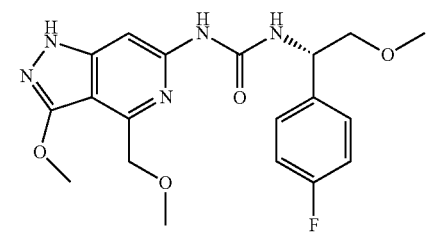 [SMILES: COCc1nc(NC(=O)N[C@H](COC)c2ccc(F)cc2)cc2[nH]nc(OC)c12] | 1-[(1S)-1-(4-fluorophenyl)-2-methoxyethyl]-3-[3-methoxy-4-(methoxymethyl)-1H-pyrazolo[4,3-c]pyridin-6-yl]urea | Calc'd 404, found 404 | Scheme 5, Example 73 |
| 406 | 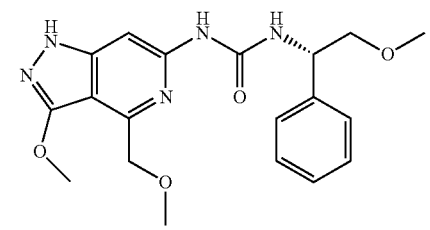 [SMILES: COCc1nc(NC(=O)N[C@H](COC)c2ccccc2)cc2[nH]nc(OC)c12] | 1-[3-methoxy-4-(methoxymethyl)-1H-pyrazolo[4,3-c]pyridin-6-yl]-3-[(1S)-2-methoxy-1-phenylethyl]urea | Calc'd 386, found 386 | Scheme 5, Example 73 |
| 407 | 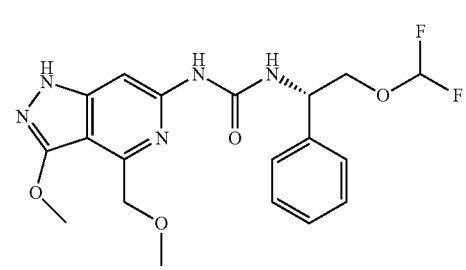 [SMILES: COCc1nc(NC(=O)N[C@H](COC(F)F)c2ccccc2)cc2[nH]nc(OC)c12] | 1-[(1S)-2-(difluoromethoxy)-1-phenylethyl]-3-[3-methoxy-4-(methoxymethyl)-1H-pyrazolo[4,3-c]pyridin-6-yl]urea | Calc'd 422, found 422 | Scheme 5, Example 73 (25B) |
| 408 | 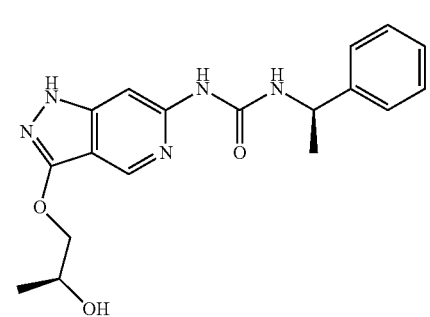 [SMILES: C[C@H](O)COc1n[nH]c2cc(NC(=O)N[C@H](C)c3ccccc3)ncc12] | 1-(3-{[(2S)-2-hydroxypropyl]oxy}-1H-pyrazolo[4,3-c]pyridin-6-yl)-3-[(1R)-1-phenylethyl]urea | Calc'd 356, found 356 | Scheme 3/Method A, Example 40 (3B) |

| Ex | Structure | IUPAC Name | Exact Mass [M + H]+ | Route Used (Intermediate Used) |
|---|---|---|---|---|
| 409 | 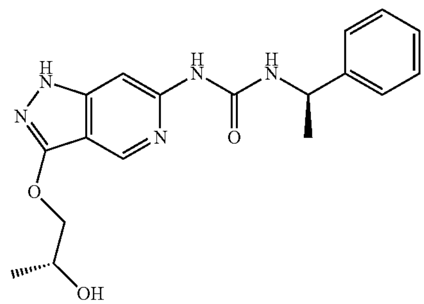 [SMILES: C[C@@H](O)COc1n[nH]c2cc(NC(=O)N[C@H](C)c3ccccc3)ncc12] | 1-(3-{[(2R)-2-hydroxypropyl]oxy}-1H-pyrazolo[4,3-c]pyridin-6-yl)-3-[(1R)-1-phenylethyl]urea | Calc'd 356, found 356 | Scheme 3/ Method A, Example 40 (3B) |
| 410 | 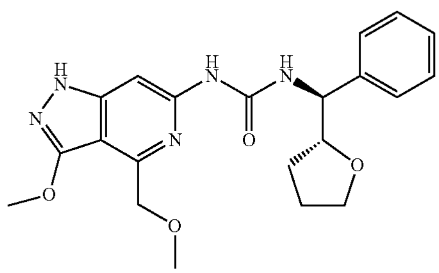 [SMILES: COCc1nc(NC(=O)N[C@@H](c2ccccc2)[C@H]2CCCO2)cc2[nH]nc(OC)c12] | 1-[3-methoxy-4-(methoxymethyl)-1H-pyrazolo[4,3-c]pyridin-6-yl]-3-{(S)-phenyl[(2R)-tetrahydrofuran-2-yl]methyl}urea | Calc'd 412, found 412 | Scheme 5, Example 73 |
| 411 | 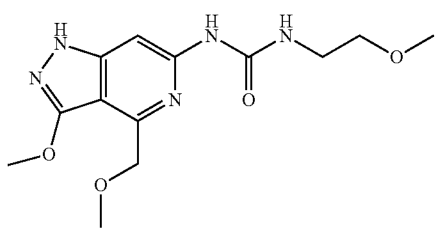 | 1-(2-methoxyethyl)-3-[3-methoxy-4-(methoxymethyl)-1H-pyrazolo[4,3-c]pyridin-6-yl]urea | Calc'd 310, found 310 | Scheme 5, Example 73 |
| 412 | 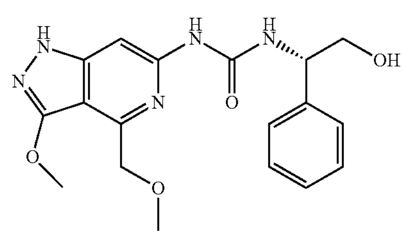 [SMILES: COCc1nc(NC(=O)N[C@H](CO)c2ccccc2)cc2[nH]nc(OC)c12] | 1-[(1S)-2-hydroxy-1-phenylethyl]-3-[3-methoxy-4-(methoxymethyl)-1H-pyrazolo[4,3-c]pyridin-6-yl]urea | Calc'd 372, found 372 | Scheme 5, Example 73 |
| 413 | 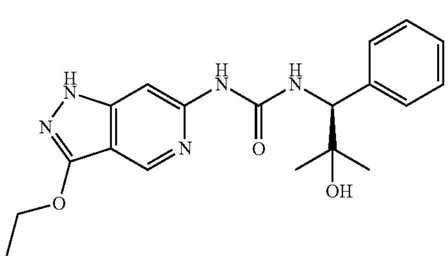 [SMILES: CCOc1n[nH]c2cc(NC(=O)N[C@@H](c3ccccc3)C(C)(C)O)ncc12] | 1-(3-ethoxy-1H-pyrazolo[4,3-c]pyridin-6-yl)-3-[(1S)-2-hydroxy-2-methyl-1-phenylpropyl]urea | Calc'd 370, found 370 | Scheme 3/ Method A, Example 40 (21B) |
| 414 | 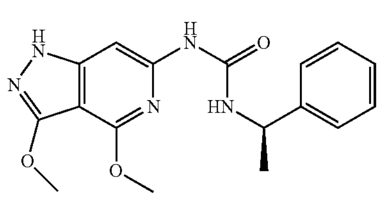 [SMILES: COc1n[nH]c2cc(NC(=O)N[C@H](C)c3ccccc3)nc(OC)c12] | 1-(3,4-dimethoxy-1H-pyrazolo[4,3-c]pyridin-6-yl)-3-[(1R)-1-phenylethyl]urea | Calc'd 342, found 342 | Scheme 3/ Method A, Example 40 (56B) |

TABLE 14-continued

| Ex | Structure | IUPAC Name | Exact Mass [M + H]+ | Route Used (Intermediate Used) |
|---|---|---|---|---|
| 415 | 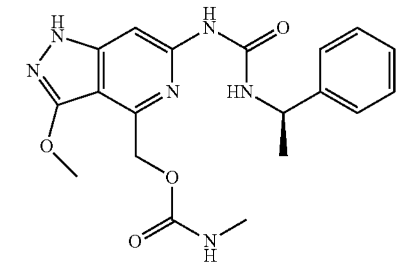 [SMILES: CNC(=O)OCc1nc(NC(=O)N[C@H](C)c2ccccc2)cc2[nH]nc(OC)c12] | [3-methoxy-6-({[(1R)-1-phenylethyl]carbamoyl}amino)-1H-pyrazolo[4,3-c]pyridin-4-yl]methyl methylcarbamate | Calc'd 399, found 399 | Scheme 3/ Method A, Example 40 (57B) |
| 416 | 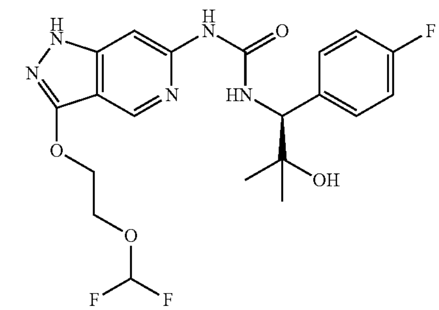 [SMILES: CC(C)(O)[C@@H](NC(=O)Nc1cc2[nH]nc(OCCOC(F)F)c2cn1)c1ccc(F)cc1] | 1-{3-[2-(difluoromethoxy)ethoxy]-1H-pyrazolo[4,3-c]pyridin-6-yl}-3-[(1S)-1-(4-fluorophenyl)-2-hydroxy-2-methylpropyl]urea | Calc'd 454, found 454 | Scheme 3/ Method A, Example 40 (59B, 22B) |
| 417 | 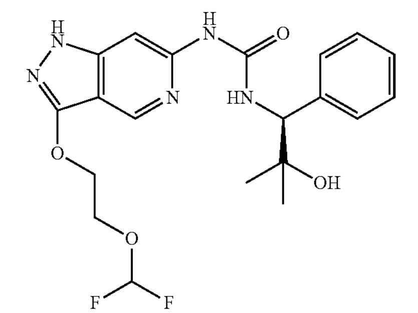 [SMILES: CC(C)(O)[C@@H](NC(=O)Nc1cc2[nH]nc(OCCOC(F)F)c2cn1)c1ccccc1] | 1-{3-[2-(difluoromethoxy)ethoxy]-1H-pyrazolo[4,3-c]pyridin-6-yl}-3-[(1S)-2-hydroxy-2-methyl-1-phenylpropyl]urea | Calc'd 436, found 436 | Scheme 3/ Method A, Example 40 (59B, 21B) |
| 418 | 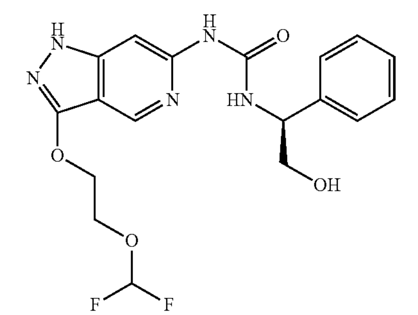 [SMILES: O=C(Nc1cc2[nH]nc(OCCOC(F)F)c2cn1)N[C@H](CO)c1ccccc1] | 1-{3-[2-(difluoromethoxy)ethoxy]-1H-pyrazolo[4,3-c]pyridin-6-yl}-3-[(1S)-2-hydroxy-1-phenylethyl]urea | Calc'd 408, found 408 | Scheme 3/ Method A, Example 40 (59B) |
| 419 | 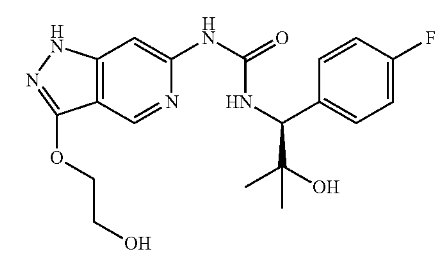 [SMILES: CC(C)(O)[C@@H](NC(=O)Nc1cc2[nH]nc(OCCO)c2cn1)c1ccc(F)cc1] | 1-[(1S)-1-(4-fluorophenyl)-2-hydroxy-2-methylpropyl]-3-[3-(2-hydroxyethoxy)-1H-pyrazolo[4,3-c]pyridin-6-yl]urea | Calc'd 404, found 404 | Scheme 3/ Method A, Example 40 (22B, 58B) |

TABLE 14-continued

| Ex | Structure | IUPAC Name | Exact Mass [M + H]+ | Route Used (Intermediate Used) |
|---|---|---|---|---|
| 420 | 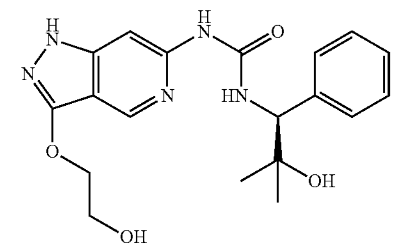 [SMILES: CC(C)(O)[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1S)-2-hydroxy-2-methyl-1-phenylpropyl]urea | Calc'd 386, found 386 | Scheme 3/ Method A, Example 40 (21B, 58B) |
| 421 | 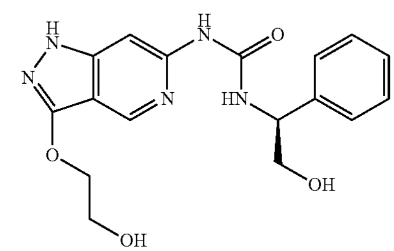 [SMILES: O=C(Nc1cc2[nH]nc(OCCO)c2cn1)N[C@H](CO)c1ccccc1] | 1-[3-(2-hydroxyethoxy)-1H-pyrazolo[4,3-c]pyridin-6-yl]-3-[(1S)-2-hydroxy-1-phenylethyl]urea | Calc'd 358, found 358 | Scheme 3/ Method A, Example 40 (58B) |
| 422 | 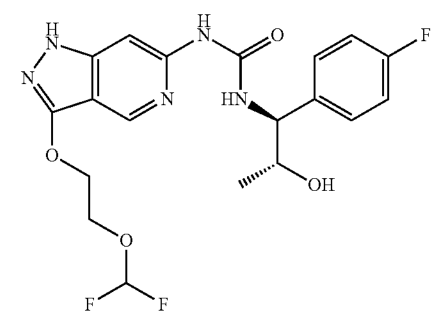 [SMILES: C[C@@H](O)[C@@H](NC(=O)Nc1cc2[nH]nc(OCCOC(F)F)c2cn1)c1ccc(F)cc1] | 1-{3-[2-(difluoromethoxy)ethoxy]-1H-pyrazolo[4,3-c]pyridin-6-yl}-3-[(1S,2R)-1-(4-fluorophenyl)-2-hydroxypropyl]urea | Calc'd 440, found 440 | Scheme 3/ Method A, Example 40 (59B, 24B) |
| 423 | 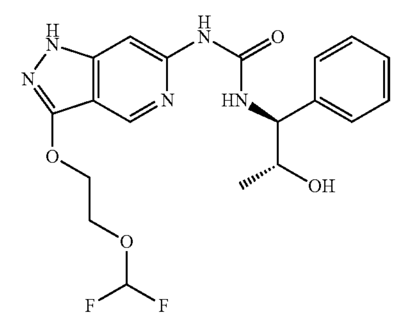 [SMILES: C[C@@H](O)[C@@H](NC(=O)Nc1cc2[nH]nc(OCCOC(F)F)c2cn1)c1ccccc1] | 1-{3-[2-(difluoromethoxy)ethoxy]-1H-pyrazolo[4,3-c]pyridin-6-yl}-3-[(1S,2R)-2-hydroxy-1-phenylpropyl]urea | Calc'd 422, found 422 | Scheme 3/ Method A, Example 40 (59B, 23B) |
| 424 | 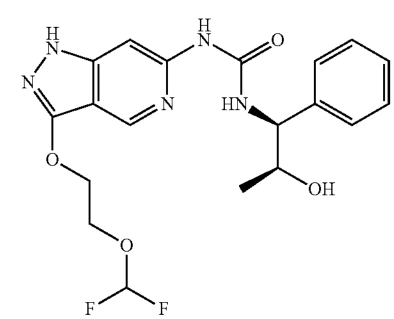 [SMILES: C[C@H](O)[C@@H](NC(=O)Nc1cc2[nH]nc(OCCOC(F)F)c2cn1)c1ccccc1] | 1-{3-[2-(difluoromethoxy)ethoxy]-1H-pyrazolo[4,3-c]pyridin-6-yl}-3-[(1S,2S)-2-hydroxy-1-phenylpropyl]urea | Calc'd 422, found 422 | Scheme 3/ Method A, Example 40 (59B) |

TABLE 14-continued

| Ex | Structure | IUPAC Name | Exact Mass [M + H]+ | Route Used (Intermediate Used) |
|---|---|---|---|---|
| 425 | 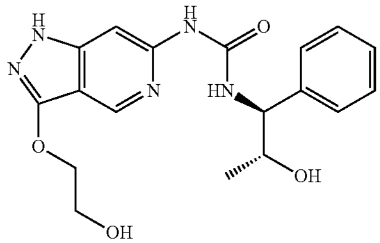 [SMILES: C[C@@H](O)[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1S,2R)-2-hydroxy-1-phenylpropyl]urea | Calc'd 372, found 372 | Scheme 3/ Method A, Example 40 (58B, 23B) |
| 426 | 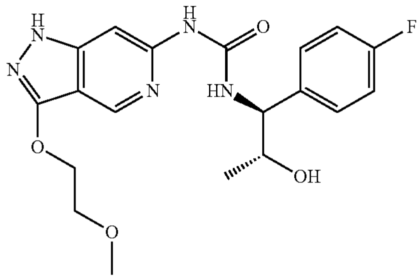 [SMILES: COCCOc1n[nH]c2cc(NC(=O)N[C@@H](c3ccc(F)cc3)[C@@H](C)O)ncc12] | 1-[(1S,2R)-1-(4-fluorophenyl)-2-hydroxypropyl]-3-[3-(2-methoxyethoxy)-1H-pyrazolo[4,3-c]pyridin-6-yl]urea | Calc'd 404, found 404 | Scheme 3/ Method A, Example 40 (24B, see Ex. 1) |
| 427 | 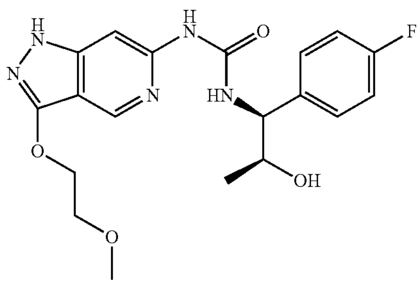 [SMILES: COCCOc1n[nH]c2cc(NC(=O)N[C@@H](c3ccc(F)cc3)[C@H](C)O)ncc12] | 1-[(1S,2S)-1-(4-fluorophenyl)-2-hydroxypropyl]-3-[3-(2-methoxyethoxy)-1H-pyrazolo[4,3-c]pyridin-6-yl]urea | Calc'd 404, found 404 | Scheme 3/ Method A, Example 40 |
| 428 | 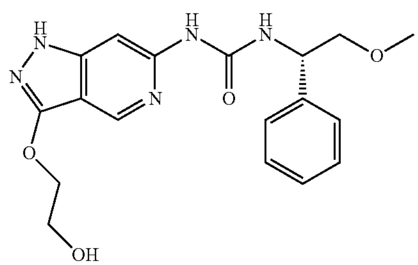 [SMILES: COC[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1S)-2-methoxy-1-phenylethyl]urea | Calc'd 372, found 372 | Scheme 3/ Method A, Example 40 (58B) |
| 429 | 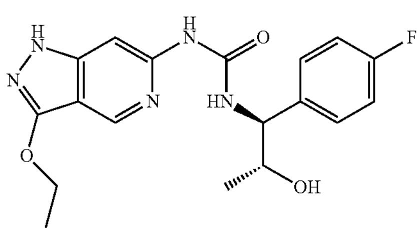 [SMILES: CCOc1n[nH]c2cc(NC(=O)N[C@@H](c3ccc(F)cc3)[C@@H](C)O)ncc12] | 1-(3-ethoxy-1H-pyrazolo[4,3-c]pyridin-6-yl)-3-[(1S,2R)-1-(4-fluorophenyl)-2-hydroxypropyl]urea | Calc'd 374, found 374 | Scheme 3/ Method A, Example 40 (24B) |
| 430 | 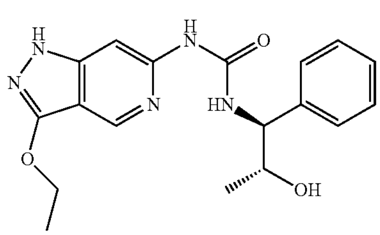 [SMILES: CCOc1n[nH]c2cc(NC(=O)N[C@@H](c3ccccc3)[C@@H](C)O)ncc12] | 1-(3-ethoxy-1H-pyrazolo[4,3-c]pyridin-6-yl)-3-[(1S,2R)-2-hydroxy-1-phenylpropyl]urea | Calc'd 356, found 356 | Scheme 3/ Method A, Example 40 (23B) |

TABLE 14-continued

| Ex | Structure | IUPAC Name | Exact Mass [M + H]+ | Route Used (Intermediate Used) |
|---|---|---|---|---|
| 431 | 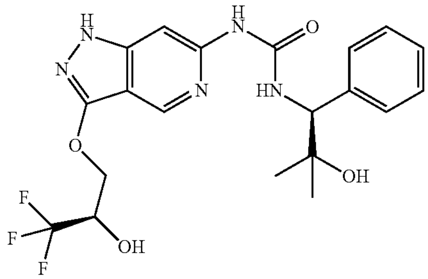 [SMILES: CC(C)(O)[C@@H](NC(=O)Nc1cc2[nH]nc(OC[C@@H](O)C(F)(F)F)c2cn1)c1ccccc1] | 1-[(1S)-2-hydroxy-2-methyl-1-phenylpropyl]-3-(3-{[(2R)-3,3,3-trifluoro-2-hydroxypropyl]oxy}-1H-pyrazolo[4,3-c]pyridin-6-yl)urea | Calc'd 454, found 454 | Scheme 3/ Method A, Example 40 (21B) |
| 432 | 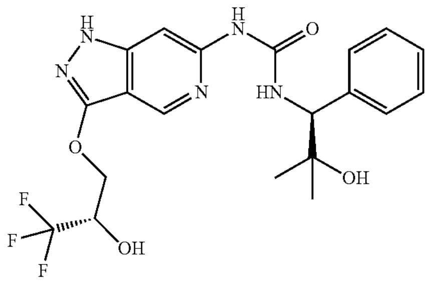 [SMILES: CC(C)(O)[C@@H](NC(=O)Nc1cc2[nH]nc(OC[C@H](O)C(F)(F)F)c2cn1)c1ccccc1] | 1-[(1S)-2-hydroxy-2-methyl-1-phenylpropyl]-3-(3-{[(2S)-3,3,3-trifluoro-2-hydroxypropyl]oxy}-1H-pyrazolo[4,3-c]pyridin-6-yl)urea | Calc'd 454, found 454 | Scheme 3/ Method A, Example 40 (21B) |
| 433 | 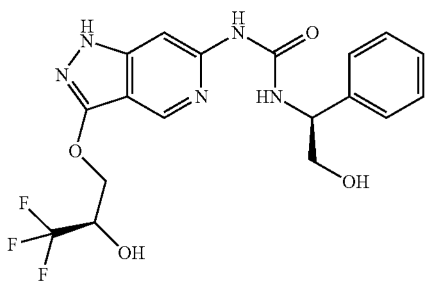 [SMILES: O=C(Nc1cc2[nH]nc(OC[C@@H](O)C(F)(F)F)c2cn1)N[C@H](CO)c1ccccc1] | 1-[(1S)-2-hydroxy-1-phenylethyl]-3-(3-{[(2R)-3,3,3-trifluoro-2-hydroxypropyl]oxy}-1H-pyrazolo[4,3-c]pyridin-6-yl)urea | Calc'd 426, found 426 | Scheme 3/ Method A, Example 40 |
| 434 | 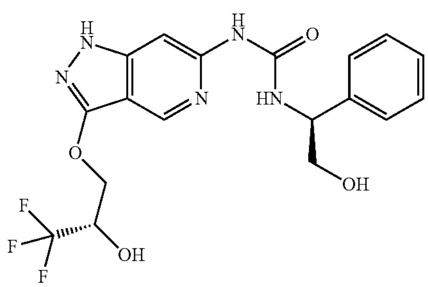 [SMILES: O=C(Nc1cc2[nH]nc(OC[C@H](O)C(F)(F)F)c2cn1)N[C@H](CO)c1ccccc1] | 1-[(1S)-2-hydroxy-1-phenylethyl]-3-(3-{[(2S)-3,3,3-trifluoro-2-hydroxypropyl]oxy}-1H-pyrazolo[4,3-c]pyridin-6-yl)urea | Calc'd 426, found 426 | Scheme 3/ Method A, Example 40 |
| 435 | 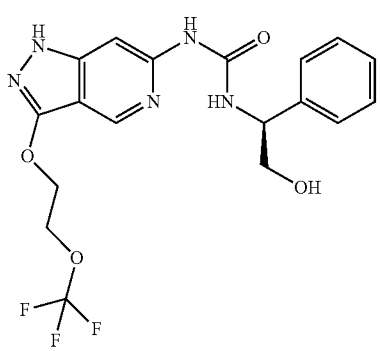 [SMILES: O=C(Nc1cc2[nH]nc(OCCOC(F)(F)F)c2cn1)N[C@H](CO)c1ccccc1] | 1-[(1S)-2-hydroxy-1-phenylethyl]-3-{3-[2-(trifluoromethoxy)ethoxy]-1H-pyrazolo[4,3-c]pyridin-6-yl}urea | Calc'd 426, found 426 | Scheme 3/ Method A, Example 40 (59B) |

TABLE 14-continued

| Ex | Structure | IUPAC Name | Exact Mass [M + H]+ | Route Used (Intermediate Used) |
|---|---|---|---|---|
| 436 | 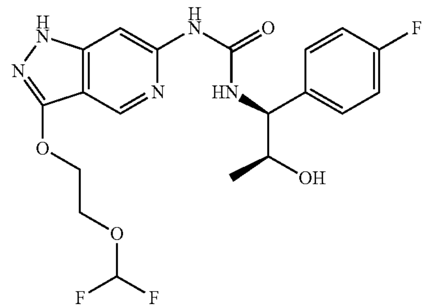 [SMILES: C[C@H](O)[C@@H](NC(=O)Nc1cc2[nH]nc(OCCOC(F)F)c2cn1)c1ccc(F)cc1] | 1-{3-[2-(difluoromethoxy)ethoxy]-1H-pyrazolo[4,3-c]pyridin-6-yl}-3-[(1S,2S)-1-(4-fluorophenyl)-2-hydroxypropyl]urea | Calc'd 440, found 440 | Scheme 3/ Method A, Example 40 (59B) |
| 437 | 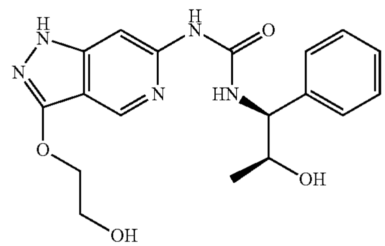 [SMILES: C[C@H](O)[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1S,2S)-2-hydroxy-1-phenylpropyl]urea | Calc'd 372, found 372 | Scheme 3/ Method A, Example 40 (58B) |
| 438 | 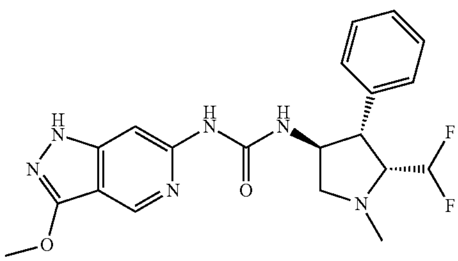 [SMILES: COc1n[nH]c2cc(NC(=O)N[C@@H]3CN(C)[C@@H](C(F)F)[C@H]3c3ccccc3)ncc12] | 1-[(3S,4S,5R)-5-(difluoromethyl)-1-methyl-4-phenylpyrrolidin-3-yl]-3-(3-methoxy-1H-pyrazolo[4,3-c]pyridin-6-yl)urea | Calc'd 417, found 417 | Scheme 3/ Method A, Ex. 40; (Urea from WO 2013/063214) |
| 439 | 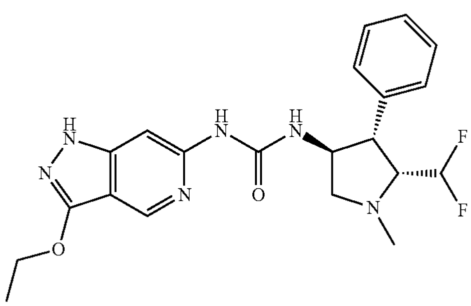 [SMILES: CCOc1n[nH]c2cc(NC(=O)N[C@@H]3CN(C)[C@@H](C(F)F)[C@H]3c3ccccc3)ncc12] | 1-[(3S,4S,5R)-5-(difluoromethyl)-1-methyl-4-phenylpyrrolidin-3-yl]-3-(3-ethoxy-1H-pyrazolo[4,3-c]pyridin-6-yl)urea | Calc'd 431, found 431 | Scheme 3/ Method A, Ex. 40; (Urea from WO 2013/063214) |
| 440 | 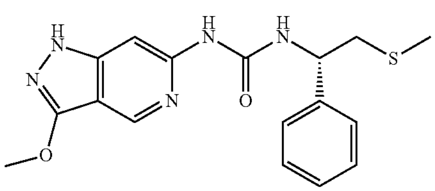 | 1-(3-methoxy-1H-pyrazolo[4,3-c]pyridin-6-yl)-3-[(1S)-2-(methylsulfanyl)-1-phenylethyl]urea | Calc'd 358, found 358 | Scheme 3/ Method A, Ex. 40; (Urea from WO 2013/063214) |
| 441 | 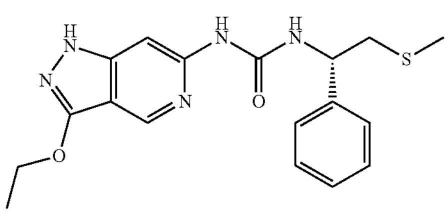 [SMILES: CCOc1n[nH]c2cc(NC(=O)N[C@H](CSC)c3ccccc3)ncc12] | 1-(3-ethoxy-1H-pyrazolo[4,3-c]pyridin-6-yl)-3-[(1S)-2-(methylsulfanyl)-1-phenylethyl]urea | Calc'd 372, found 372 | Scheme 3/ Method A, Ex. 40; (Urea from WO 2013/063214) |

TABLE 14-continued

| Ex | Structure | IUPAC Name | Exact Mass [M + H]+ | Route Used (Intermediate Used) |
|---|---|---|---|---|
| 442 | 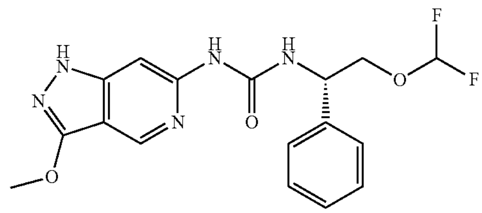 [SMILES: COc1n[nH]c2cc(NC(=O)N[C@H](COC(F)F)c3ccccc3)ncc12] | 1-[(1S)-2-(difluoromethoxy)-1-phenylethyl]-3-(3-methoxy-1H-pyrazolo[4,3-c]pyridin-6-yl)urea | Calc'd 378, found 378 | Scheme 3, Method A/ Example 40 (25B) |
| 443 | 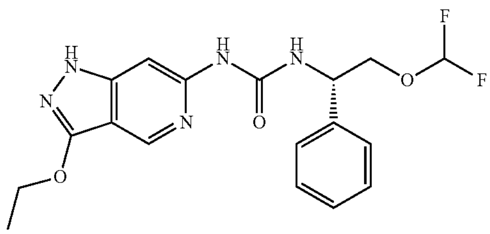 [SMILES: CCOc1n[nH]c2cc(NC(=O)N[C@H](COC(F)F)c3ccccc3)ncc12] | 1-[(1S)-2-(difluoromethoxy)-1-phenylethyl]-3-(3-ethoxy-1H-pyrazolo[4,3-c]pyridin-6-yl)urea | Calc'd 392, found 390 | Scheme 3, Method A/ Example 40 (25B) |
| 444 | 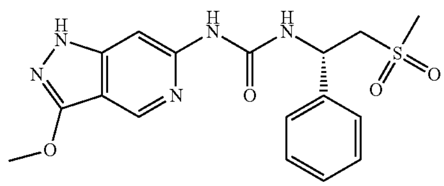 [SMILES: COc1n[nH]c2cc(NC(=O)N[C@H](CS(C)(=O)=O)c3ccccc3)ncc12] | 1-(3-methoxy-1H-pyrazolo[4,3-c]pyridin-6-yl)-3-[(1S)-2-(methylsulfonyl)-1-phenylethyl]urea | Calc'd 390, found 390 | Scheme 3/ Method A, Ex. 40; (Urea from WO 2013/ 063214) |
| 445 | 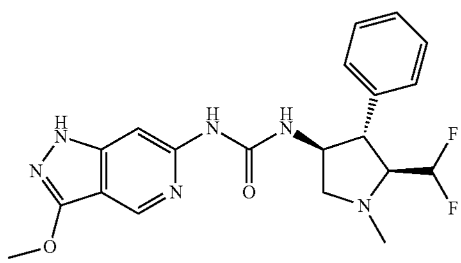 [SMILES: COc1n[nH]c2cc(NC(=O)N[C@@H]3CN(C)[C@H](C(F)F)[C@H]3c3ccccc3)ncc12] | 1-[(3S,4S,5S)-5-(difluoromethyl)-1-methyl-4-phenylpyrrolidin-3-yl]-3-(3-methoxy-1H-pyrazolo[4,3-c]pyridin-6-yl)urea | Calc'd 417, found 417 | Scheme 3/ Method A, Ex. 40; (Urea from WO 2013/ 063214) |
| 446 | 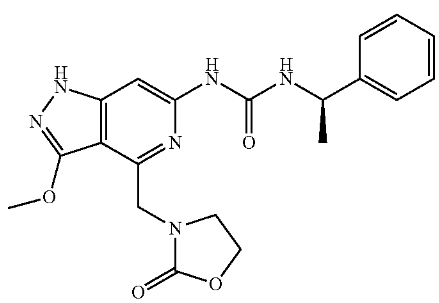 [SMILES: COc1n[nH]c2cc(NC(=O)N[C@H](C)c3ccccc3)nc(CN3CCOC3=O)c12] | 1-{3-methoxy-4-[(2-oxo-1,3-oxazolidin-3-yl)methyl]-1H-pyrazolo[4,3-c]pyridin-6-yl}-3-[(1R)-1-phenylethyl]urea | Calc'd 411, found 411 | Scheme 5, Example 73 |
| 447 | 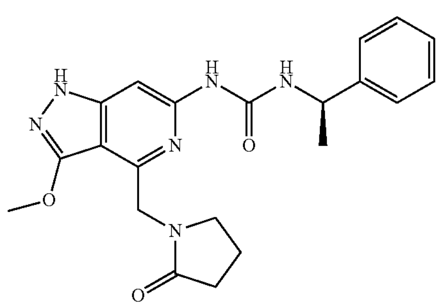 [SMILES: COc1n[nH]c2cc(NC(=O)N[C@H](C)c3ccccc3)nc(CN3CCCC3=O)c12] | 1-{3-methoxy-4-[(2-oxopyrrolidin-1-yl)methyl]-1H-pyrazolo[4,3-c]pyridin-6-yl}-3-[(1R)-1-phenylethyl]urea | Calc'd 409, found 409 | Scheme 5, Example 73 |

TABLE 14-continued

| Ex | Structure | IUPAC Name | Exact Mass [M + H]+ | Route Used (Intermediate Used) |
|---|---|---|---|---|
| 448 | 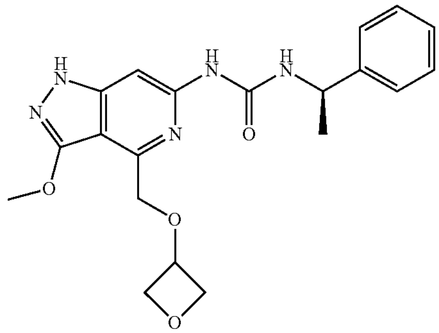 [SMILES: COc1n[nH]c2cc(NC(=O)N[C@H](C)c3ccccc3)nc(COC3COC3)c12] | 1-{3-methoxy-4-[(oxetan-3-yloxy)methyl]-1H-pyrazolo[4,3-c]pyridin-6-yl}-3-[(1R)-1-phenylethyl]urea | Calc'd 398, found 398 | Scheme 5, Example 73 |
| 449 | 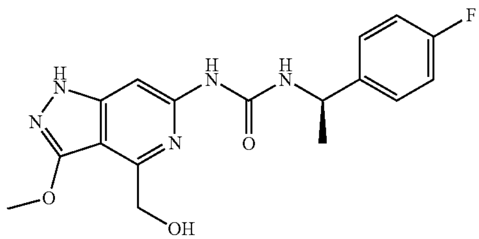 [SMILES: COc1n[nH]c2cc(NC(=O)N[C@H](C)c3ccc(F)cc3)nc(CO)c12] | 1-[(1R)-1-(4-fluorophenyl)ethyl]-3-[4-(hydroxymethyl)-3-methoxy-1H-pyrazolo[4,3-c]pyridin-6-yl]urea | Calc'd 360, found 360 | Scheme 3/ Method A, Ex. 40 (35B) |
| 450 | 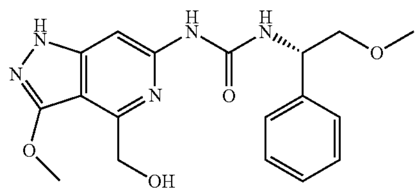 [SMILES: COC[C@@H](NC(=O)Nc1cc2[nH]nc(OC)c2c(CO)n1)c1ccccc1] | 1-[4-(hydroxymethyl)-3-methoxy-1H-pyrazolo[4,3-c]pyridin-6-yl]-3-[(1S)-2-methoxy-1-phenylethyl]urea | Calc'd 372.0, found 372 | Scheme 3/ Method A, Ex. 40 (35B) |
| 451 | 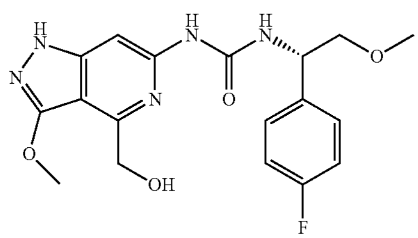 [SMILES: COC[C@@H](NC(=O)Nc1cc2[nH]nc(OC)c2c(CO)n1)c1ccc(F)cc1] | 1-[(1S)-1-(4-fluorophenyl)-2-methoxyethyl]-3-[4-(hydroxymethyl)-3-methoxy-1H-pyrazolo[4,3-c]pyridin-6-yl]urea | Calc'd 390, found 390 | Scheme 3/ Method A, Ex. 40 (35B) |
| 452 | 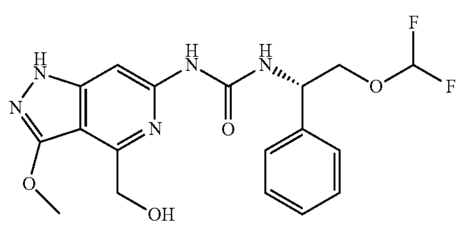 [SMILES: COc1n[nH]c2cc(NC(=O)N[C@H](COC(F)F)c3ccccc3)nc(CO)c12] | 1-[(1S)-2-(difluoromethoxy)-1-phenylethyl]-3-[4-(hydroxymethyl)-3-methoxy-1H-pyrazolo[4,3-c]pyridin-6-yl]urea | Calc'd 408, found 408 | Scheme 3/ Method A/ Ex. 40 (35B, 25B) |
| 453 | 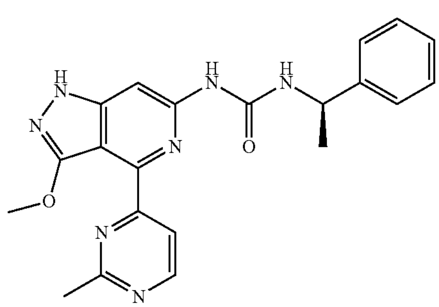 [SMILES: COc1n[nH]c2cc(NC(=O)N[C@H](C)c3ccccc3)nc(-c3ccnc(C)n3)c12] | 1-[3-methoxy-4-(2-methylpyrimidin-4-yl)-1H-pyrazolo[4,3-c]pyridin-6-yl]-3-[(1R)-1-phenylethyl]urea | Calc'd 404, found 404 | Scheme 3/ Method A, Ex. 40 (63B) |

TABLE 14-continued

| Ex | Structure | IUPAC Name | Exact Mass [M + H]+ | Route Used (Intermediate Used) |
|---|---|---|---|---|
| 454 | 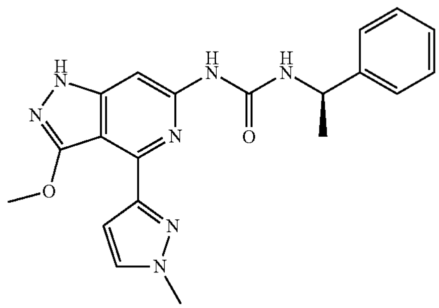 [SMILES: COc1n[nH]c2cc(NC(=O)N[C@H](C)c3ccccc3)nc(-c3ccn(C)n3)c12] | 1-[3-methoxy-4-(1-methyl-1H-pyrazol-3-yl)-1H-pyrazolo[4,3-c]pyridin-6-yl]-3-[(1R)-1-phenylethyl]urea | Calc'd 392, found 392 | Scheme 3/ Method A, Ex. 40 (61B) |
| 455 | 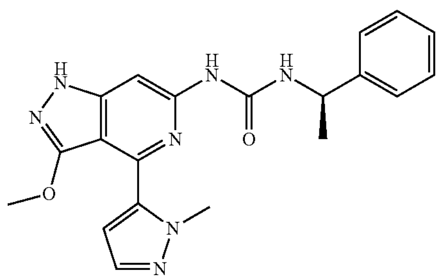 [SMILES: COc1n[nH]c2cc(NC(=O)N[C@H](C)c3ccccc3)nc(-c3ccnn3C)c12] | 1-[3-methoxy-4-(1-methyl-1H-pyrazol-5-yl)-1H-pyrazolo[4,3-c]pyridin-6-yl]-3-[(1R)-1-phenylethyl]urea | Calc'd 392, found 392 | Scheme 3/ Method A, Ex. 40 (62B) |
| 456 | 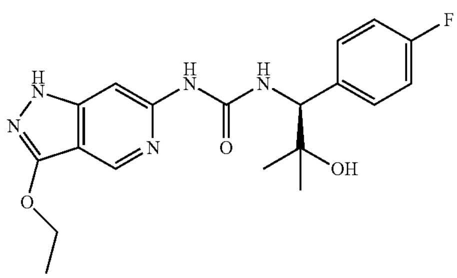 [SMILES: CCOc1n[nH]c2cc(NC(=O)N[C@@H](c3ccc(F)cc3)C(C)(C)O)ncc12] | 1-(3-ethoxy-1H-pyrazolo[4,3-c]pyridin-6-yl)-3-[(1S)-1-(4-fluorophenyl)-2-hydroxy-2-methylpropyl]urea | Calc'd 388, found 388 | Scheme 3/ Method A, Ex. 40 (22B) |
| 457 | 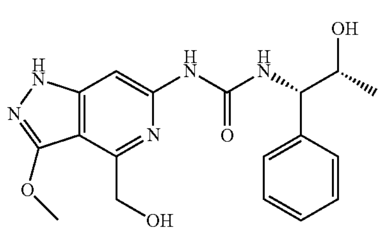 [SMILES: COc1n[nH]c2cc(NC(=O)N[C@@H](c3ccccc3)[C@@H](C)O)nc(CO)c12] | 1-[4-(hydroxymethyl)-3-methoxy-1H-pyrazolo[4,3-c]pyridin-6-yl]-3-[(1S,2R)-2-hydroxy-1-phenylpropyl]urea | Calc'd 372, found 372 | Scheme 3/ Method A, Ex. 40 (35B, 23B) |
| 458 | 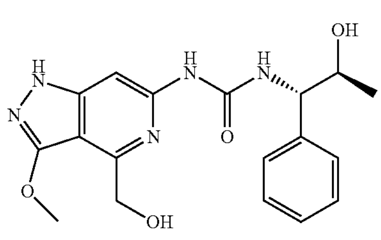 [SMILES: COc1n[nH]c2cc(NC(=O)N[C@@H](c3ccccc3)[C@H](C)O)nc(CO)c12] | 1-[4-(hydroxymethyl)-3-methoxy-1H-pyrazolo[4,3-c]pyridin-6-yl]-3-[(1S,2S)-2-hydroxy-1-phenylpropyl]urea | Calc'd 372, found 372 | Scheme 3/ Method A, Ex. 40 (35B) |

TABLE 14-continued

| Ex | Structure | IUPAC Name | Exact Mass [M + H]+ | Route Used (Intermediate Used) |
|---|---|---|---|---|
| 459 | 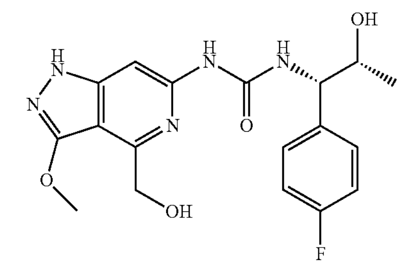 [SMILES: COc1n[nH]c2cc(NC(=O)N[C@@H](c3ccc(F)cc3)[C@@H](C)O)nc(CO)c12] | 1-[(1S,2R)-1-(4-fluorophenyl)-2-hydroxypropyl]-3-[4-(hydroxymethyl)-3-methoxy-1H-pyrazolo[4,3-c]pyridin-6-yl]urea | Calc'd 390, found 390 | Scheme 3/ Method A, Ex. 40 (35B, 24B) |
| 460 | 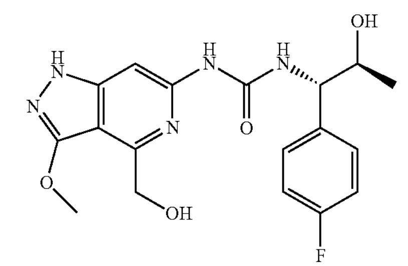 [SMILES: COc1n[nH]c2cc(NC(=O)N[C@@H](c3ccc(F)cc3)[C@H](C)O)nc(CO)c12] | 1-[(1S,2S)-1-(4-fluorophenyl)-2-hydroxypropyl]-3-[4-(hydroxymethyl)-3-methoxy-1H-pyrazolo[4,3-c]pyridin-6-yl]urea | Calc'd 390, found 390 | Scheme 3/ Method A, Ex 40 (35B) |
| 461 | 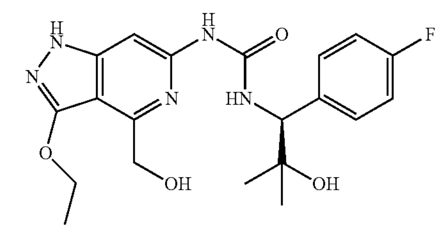 [SMILES: CCOc1n[nH]c2cc(NC(=O)N[C@@H](c3ccc(F)cc3)C(C)(C)O)nc(CO)c12] | 1-[3-ethoxy-4-(hydroxymethyl)-1H-pyrazolo[4,3-c]pyridin-6-yl]-3-[(1S)-1-(4-fluorophenyl)-2-hydroxy-2-methylpropyl]urea | Calc'd 418, found 418 | Scheme 3/ Method A, Ex 40 (22B) |
| 462 | 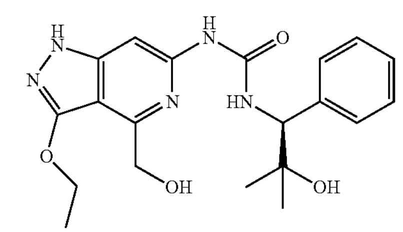 [SMILES: CCOc1n[nH]c2cc(NC(=O)N[C@@H](c3ccccc3)C(C)(C)O)nc(CO)c12] | 1-[3-ethoxy-4-(hydroxymethyl)-1H-pyrazolo[4,3-c]pyridin-6-yl]-3-[(1S)-2-hydroxy-2-methyl-1-phenylpropyl]urea | Calc'd 400, found 400 | Scheme 3/ Method A, Ex 40 (21B) |
| 463 | 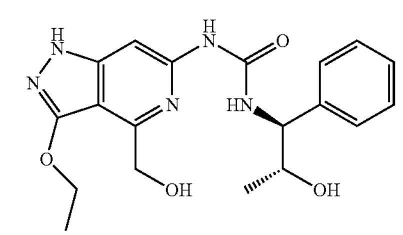 [SMILES: CCOc1n[nH]c2cc(NC(=O)N[C@@H](c3ccccc3)[C@@H](C)O)nc(CO)c12] | 1-[3-ethoxy-4-(hydroxymethyl)-1H-pyrazolo[4,3-c]pyridin-6-yl]-3-[(1S,2R)-2-hydroxy-1-phenylpropyl]urea | Calc'd 386, found 386 | Scheme 3/ Method A, Ex 40 (23B) |
| 464 | 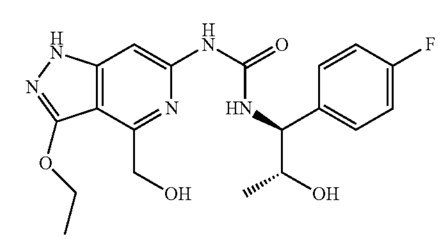 [SMILES: CCOc1n[nH]c2cc(NC(=O)N[C@@H](c3ccc(F)cc3)[C@@H](C)O)nc(CO)c12] | 1-[3-ethoxy-4-(hydroxymethyl)-1H-pyrazolo[4,3-c]pyridin-6-yl]-3-[(1S,2R)-1-(4-fluorophenyl)-2-hydroxypropyl]urea | Calc'd 404, found 404 | Scheme 3/ Method A, Ex 40 (24B) |

TABLE 14-continued

| Ex | Structure | IUPAC Name | Exact Mass [M + H]+ | Route Used (Intermediate Used) |
|---|---|---|---|---|
| 465 | 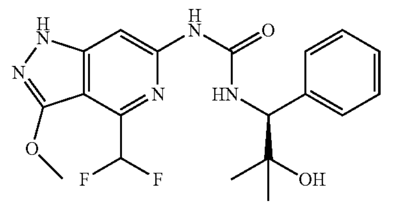 [SMILES: COc1n[nH]c2cc(NC(=O)N[C@@H](c3ccccc3)C(C)(C)O)nc(C(F)F)c12] | 1-[4-(difluoromethyl)-3-methoxy-1H-pyrazolo[4,3-c]pyridin-6-yl]-3-[(1S)-2-hydroxy-2-methyl-1-phenylpropyl]urea | Calc'd 406, found 406 | Scheme 3/ Method A, Ex 40 (64B, 21B) |
| 466 | 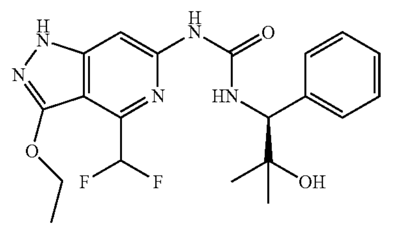 [SMILES: CCOc1n[nH]c2cc(NC(=O)N[C@@H](c3ccccc3)C(C)(C)O)nc(C(F)F)c12] | 1-[4-(difluoromethyl)-3-ethoxy-1H-pyrazolo[4,3-c]pyridin-6-yl]-3-[(1S)-2-hydroxy-2-methyl-1-phenylpropyl]urea | Calc'd 420, found 420 | Scheme 3/ Method A, Ex 40 (21B) |
| 467 | 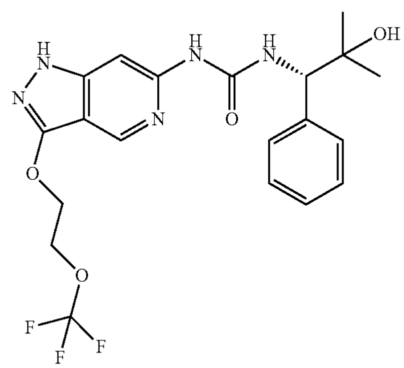 [SMILES: CC(C)(O)[C@@H](NC(=O)Nc1cc2[nH]nc(OCCOC(F)(F)F)c2cn1)c1ccccc1] | 1-[(1S)-2-hydroxy-2-methyl-1-phenylpropyl]-3-{3-[2-(trifluoromethoxy)ethoxy]-1H-pyrazolo[4,3-c]pyridin-6-yl}urea | Calc'd 454, found 454 | Scheme 3/ Method A, Ex 40 |
| 468 | 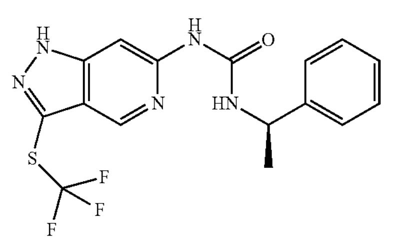 [SMILES: C[C@@H](NC(=O)Nc1cc2[nH]nc(SC(F)(F)F)c2cn1)c1ccccc1] | 1-[(1R)-1-phenylethyl]-3-{3-[(trifluoromethyl)sulfanyl]-1H-pyrazolo[4,3-c]pyridin-6-yl}urea | Calc'd 382, found 382 | Scheme 3/ Method A, Ex 40 (65B) |
| 469 | 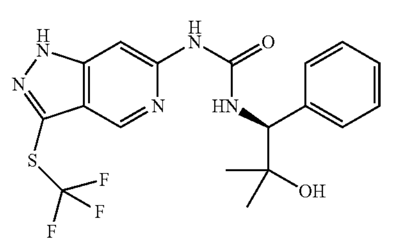 [SMILES: CC(C)(O)[C@@H](NC(=O)Nc1cc2[nH]nc(SC(F)(F)F)c2cn1)c1ccccc1] | 1-[(1S)-2-hydroxy-2-methyl-1-phenylpropyl]-3-{3-[(trifluoromethyl)sulfanyl]-1H-pyrazolo[4,3-c]pyridin-6-yl}urea | Calc'd 426, found 426 | Scheme 3/ Method A, Ex 40 (65B, 21B) |

| Ex | Structure | IUPAC Name | Exact Mass [M + H]+ | Route Used (Intermediate Used) |
|---|---|---|---|---|
| 470 | 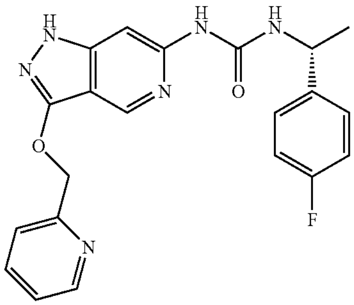 [SMILES: C[C@@H](NC(=O)Nc1cc2[nH]nc(OCc3ccccn3)c2cn1)c1ccc(F)cc1] | 1-[(1R)-1-(4-fluorophenyl)ethyl]-3-[3-(pyridin-2-ylmethoxy)-1H-pyrazolo[4,3-c]pyridin-6-yl]urea | Calc'd 407, found 407 | Scheme 4 |
| 471 | 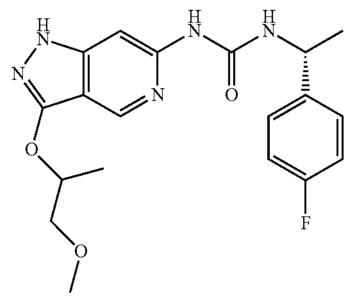 [SMILES: COCC(C)Oc1n[nH]c2cc(NC(=O)N[C@H](C)c3ccc(F)cc3)ncc12] | 1-[(1R)-1-(4-fluorophenyl)ethyl]-3-[3-(2-methoxy-1-methylethoxy)-1H-pyrazolo[4,3-c]pyridin-6-yl]urea | Calc'd 388, found 388 | Scheme 4 |
| 472 | 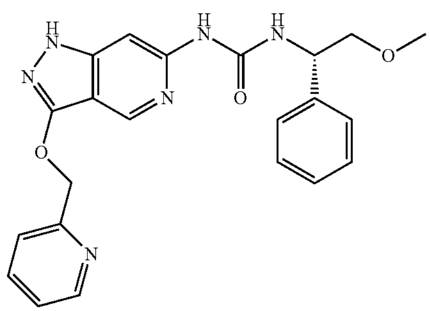 [SMILES: COC[C@@H](NC(=O)Nc1cc2[nH]nc(OCc3ccccn3)c2cn1)c1ccccc1] | 1-[(1S)-2-methoxy-1-phenylethyl]-3-[3-(pyridin-2-ylmethoxy)-1H-pyrazolo[4,3-c]pyridin-6-yl]urea | Calc'd 419, found 419 | Scheme 4 |
| 473 | 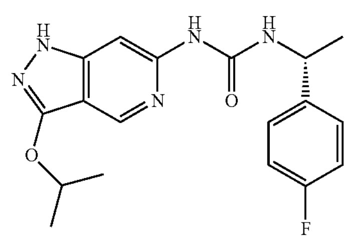 [SMILES: CC(C)Oc1n[nH]c2cc(NC(=O)N[C@H](C)c3ccc(F)cc3)ncc12] | 1-[(1R)-1-(4-fluorophenyl)ethyl]-3-[3-(1-methylethoxy)-1H-pyrazolo[4,3-c]pyridin-6-yl]urea | Calc'd 358, found 358 | Scheme 4 |
| 474 | 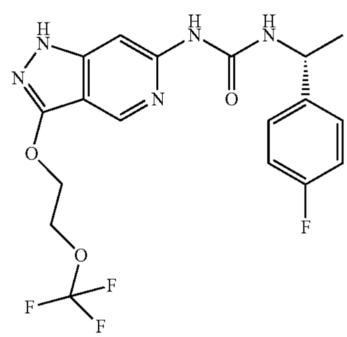 [SMILES: C[C@@H](NC(=O)Nc1cc2[nH]nc(OCCOC(F)(F)F)c2cn1)c1ccc(F)cc1] | 1-[(1R)-1-(4-fluorophenyl)ethyl]-3-{3-[2-(trifluoromethoxy)ethoxy]-1H-pyrazolo[4,3-c]pyridin-6-yl}urea | Calc'd 428, found 428 | Scheme 4 |

TABLE 14-continued

| Ex | Structure | IUPAC Name | Exact Mass [M + H]+ | Route Used (Intermediate Used) |
|---|---|---|---|---|
| 475 | 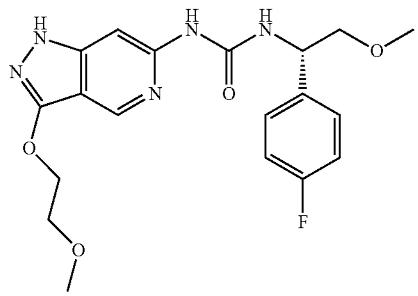 [SMILES: COCCOc1n[nH]c2cc(NC(=O)N[C@H](COC)c3ccc(F)cc3)ncc12] | 1-[(1S)-1-(4-fluorophenyl)-2-methoxyethyl]-3-[3-(2-methoxyethoxy)-1H-pyrazolo[4,3-c]pyridin-6-yl]urea | Calc'd 404, found 404 | Scheme 3/ Method A |
| 476 | 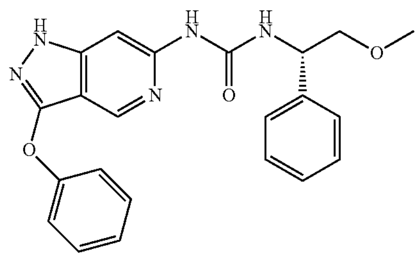 [SMILES: COC[C@@H](NC(=O)Nc1cc2[nH]nc(Oc3ccccc3)c2cn1)c1ccccc1] | 1-[(1S)-2-methoxy-1-phenylethyl]-3-(3-phenoxy-1H-pyrazolo[4,3-c]pyridin-6-yl)urea | Calc'd 404, found 404 | Scheme 3/ Method A (68B) |
| 477 | 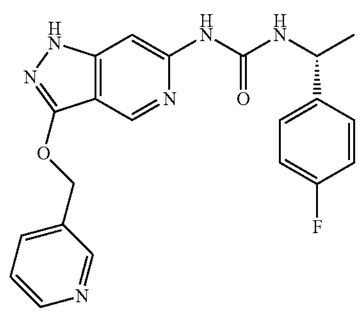 [SMILES: C[C@@H](NC(=O)Nc1cc2[nH]nc(OCc3cccnc3)c2cn1)c1ccc(F)cc1] | 1-[(1R)-1-(4-fluorophenyl)ethyl]-3-[3-(pyridin-3-ylmethoxy)-1H-pyrazolo[4,3-c]pyridin-6-yl]urea | Calc'd 407, found 407 | Scheme 4 |
| 478 | 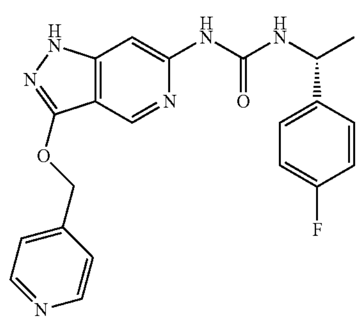 [SMILES: C[C@@H](NC(=O)Nc1cc2[nH]nc(OCc3ccncc3)c2cn1)c1ccc(F)cc1] | 1-[(1R)-1-(4-fluorophenyl)ethyl]-3-[3-(pyridin-4-ylmethoxy)-1H-pyrazolo[4,3-c]pyridin-6-yl]urea | Calc'd 407, found 407 | Scheme 4 |
| 479 | 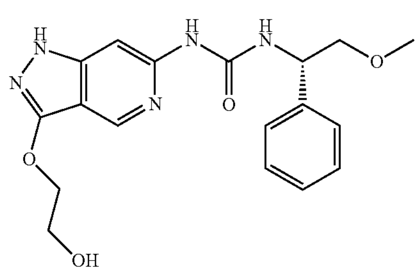 [SMILES: COC[C@@H](NC(=O)Nc1cc2[nH]nc(OCCO)c2cn1)c1ccccc1] | 1-[3-(2-hydroxyethoxy)-1H-pyrazolo[4,3-c]pyridin-6-yl]-3-[(1S)-2-methoxy-1-phenylethyl]urea | Calc'd 372, found 372 | Scheme 4 |

TABLE 14-continued

| Ex | Structure | IUPAC Name | Exact Mass [M + H]+ | Route Used (Intermediate Used) |
|---|---|---|---|---|
| 480 | 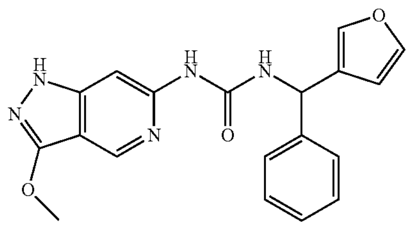 [SMILES: COc1n[nH]c2cc(NC(=O)NC(c3ccccc3)c3ccoc3)ncc12] | 1-[furan-3-yl(phenyl)methyl]-3-(3-methoxy-1H-pyrazolo[4,3-c]pyridin-6-yl)urea | Calc'd 364, found 364 | Scheme 3/ Method B |
| 481 | 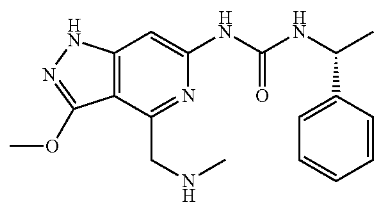 [SMILES: CNCc1nc(NC(=O)N[C@H](C)c2ccccc2)cc2[nH]nc(OC)c12] | 1-{3-methoxy-4-[(methylamino)methyl]-1H-pyrazolo[4,3-c]pyridin-6-yl}-3-[(1R)-1-phenylethyl]urea | Calc'd 355, found 355 | Scheme 5 |
| 482 | 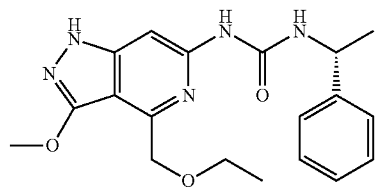 [SMILES: CCOCc1nc(NC(=O)N[C@H](C)c2ccccc2)cc2[nH]nc(OC)c12] | 1-[4-(ethoxymethyl)-3-methoxy-1H-pyrazolo[4,3-c]pyridin-6-yl]-3-[(1R)-1-phenylethyl]urea | Calc'd 370, found 370 | Scheme 5 |
| 483 | 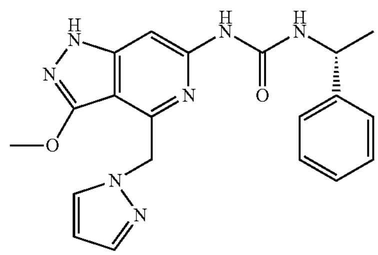 [SMILES: COc1n[nH]c2cc(NC(=O)N[C@H](C)c3ccccc3)nc(Cn3cccn3)c12] | 1-[3-methoxy-4-(1H-pyrazol-1-ylmethyl)-1H-pyrazolo[4,3-c]pyridin-6-yl]-3-[(1R)-1-phenylethyl]urea | Calc'd 392, found 392 | Scheme 5 |
| 484 | 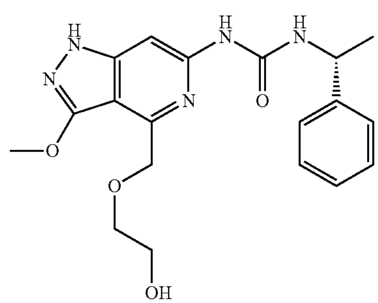 [SMILES: COc1n[nH]c2cc(NC(=O)N[C@H](C)c3ccccc3)nc(COCCO)c12] | 1-{4-[(2-hydroxyethoxy)methyl]-3-methoxy-1H-pyrazolo[4,3-c]pyridin-6-yl}-3-[(1R)-1-phenylethyl]urea | Calc'd 386, found 386 | Scheme 5 |
| 485 | 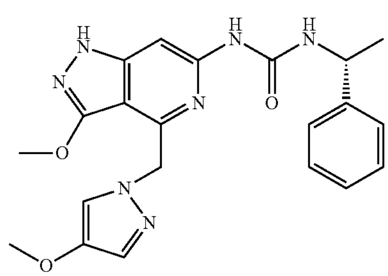 [SMILES: COc1cnn(Cc2nc(NC(=O)N[C@H](C)c3ccccc3)cc3[nH]nc(OC)c23)c1] | 1-{3-methoxy-4-[(4-methoxy-1H-pyrazol-1-yl)methyl]-1H-pyrazolo[4,3-c]pyridin-6-yl}-3-[(1R)-1-phenylethyl]urea | Calc'd 422, found 422 | Scheme 5 |

TABLE 14-continued

| Ex | Structure | IUPAC Name | Exact Mass [M + H]+ | Route Used (Intermediate Used) |
|---|---|---|---|---|
| 486 | 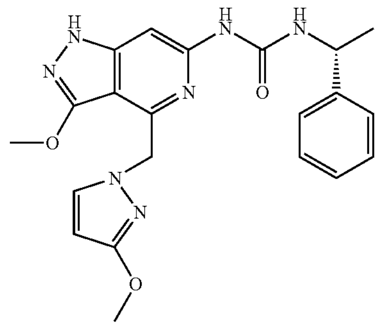 [SMILES: COc1ccn(Cc2nc(NC(=O)N[C@H](C)c3ccccc3)cc3[nH]nc(OC)c23)n1] | 1-{3-methoxy-4-[(3-methoxy-1H-pyrazol-1-yl)methyl]-1H-pyrazolo[4,3-c]pyridin-6-yl}-3-[(1R)-1-phenylethyl]urea | Calc'd 422, found 422 | Scheme 5 |
| 487 | 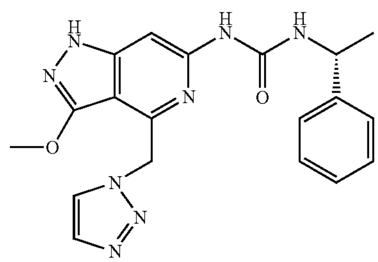 [SMILES: COc1n[nH]c2cc(NC(=O)N[C@H](C)c3ccccc3)nc(Cn3ccnn3)c12] | 1-[3-methoxy-4-(1H-1,2,3-triazol-1-ylmethyl)-1H-pyrazolo[4,3-c]pyridin-6-yl]-3-[(1R)-1-phenylethyl]urea | Calc'd 393, found 393 | Scheme 5 |
| 488 | 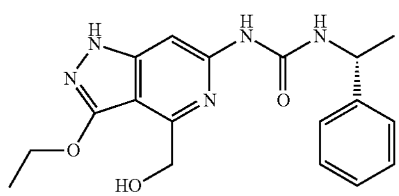 [SMILES: CCOc1n[nH]c2cc(NC(=O)N[C@H](C)c3ccccc3)nc(CO)c12] | 1-[3-ethoxy-4-(hydroxymethyl)-1H-pyrazolo[4,3-c]pyridin-6-yl]-3-[(1R)-1-phenylethyl]urea | Calc'd 356, found 356 | Scheme 3/ Method A, synthesis of 35B |
| 489 | 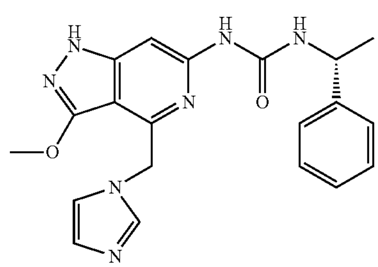 [SMILES: COc1n[nH]c2cc(NC(=O)N[C@H](C)c3ccccc3)nc(Cn3ccnc3)c12] | 1-[4-(1H-imidazol-1-ylmethyl)-3-methoxy-1H-pyrazolo[4,3-c]pyridin-6-yl]-3-[(1R)-1-phenylethyl]urea | Calc'd 392, found 392 | Scheme 5 |
| 490 | 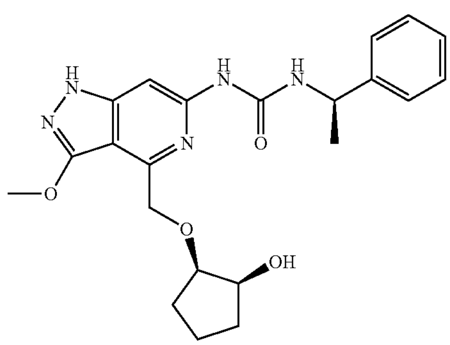 [SMILES: COc1n[nH]c2cc(NC(=O)N[C@H](C)c3ccccc3)nc(CO[C@@H]3CCC[C@@H]3O)c12] | 1-[4-({[(1R,2S)-2-hydroxycyclopentyl]oxy}methyl)-3-methoxy-1H-pyrazolo[4,3-c]pyridin-6-yl]-3-[(1R)-1-phenylethyl]urea | Calc'd 426, found 426 | Scheme 3/ Method A, synthesis of 69B |

| Ex | Structure | IUPAC Name | Exact Mass [M + H]+ | Route Used (Intermediate Used) |
|---|---|---|---|---|
| 491 | 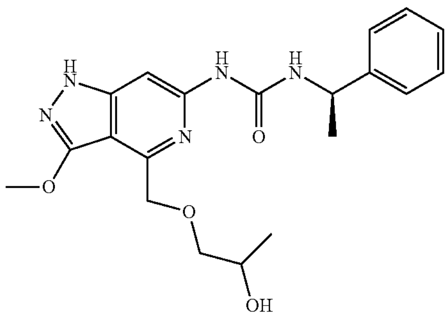 [SMILES: COc1n[nH]c2cc(NC(=O)N[C@H](C)c3ccccc3)nc(COCC(C)O)c12] | 1-{4-[(2-hydroxypropoxy)methyl]-3-methoxy-1H-pyrazolo[4,3-c]pyridin-6-yl}-3-[(1R)-1-phenylethyl]urea | Calc'd 400, found 400 | Scheme 3/ Method A (69B) |
| 492 | 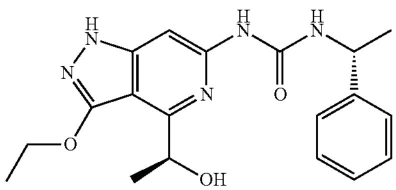 [SMILES: CCOc1n[nH]c2cc(NC(=O)N[C@H](C)c3ccccc3)nc([C@H](C)O)c12] | 1-{3-ethoxy-4-[(1S)-1-hydroxyethyl]-1H-pyrazolo[4,3-c]pyridin-6-yl}-3-[(1R)-1-phenylethyl]urea | Calc'd 370, found 370 | Scheme 3/ Method A, synthesis of 38B |
| 493 | 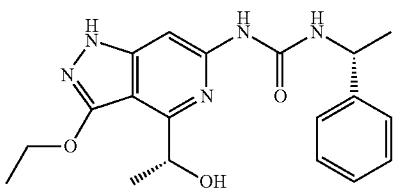 [SMILES: CCOc1n[nH]c2cc(NC(=O)N[C@H](C)c3ccccc3)nc([C@@H](C)O)c12] | 1-{3-ethoxy-4-[(1R)-1-hydroxyethyl]-1H-pyrazolo[4,3-c]pyridin-6-yl}-3-[(1R)-1-phenylethyl]urea | Calc'd 370, found 370 | Scheme 3/ Method A, synthesis of 38B |
| 494 | 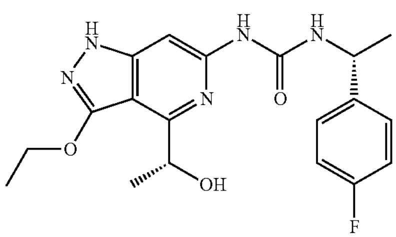 [SMILES: CCOc1n[nH]c2cc(NC(=O)N[C@H](C)c3ccc(F)cc3)nc([C@@H](C)O)c12] | 1-{3-ethoxy-4-[(1R)-1-hydroxyethyl]-1H-pyrazolo[4,3-c]pyridin-6-yl}-3-[(1R)-1-(4-fluorophenyl)ethyl]urea | Calc'd 388, found 388 | Scheme 3/ Method A, synthesis of 38B |
| 495 | 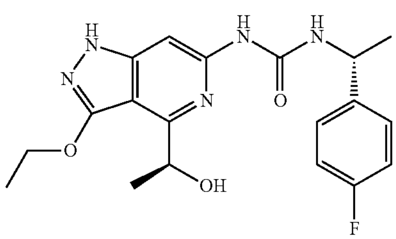 [SMILES: CCOc1n[nH]c2cc(NC(=O)N[C@H](C)c3ccc(F)cc3)nc([C@H](C)O)c12] | 1-{3-ethoxy-4-[(1S)-1-hydroxyethyl]-1H-pyrazolo[4,3-c]pyridin-6-yl}-3-[(1R)-1-(4-fluorophenyl)ethyl]urea | Calc'd 388, found 388 | Scheme 3/ Method A, synthesis of 38B |
| 496 | 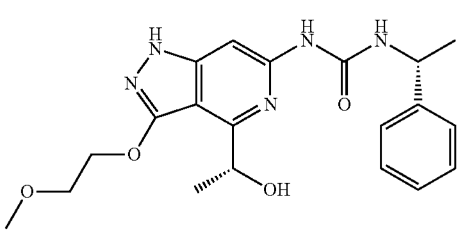 [SMILES: COCCOc1n[nH]c2cc(NC(=O)N[C@H](C)c3ccccc3)nc([C@@H](C)O)c12] | 1-{4-[(1R)-1-hydroxyethyl]-3-(2-methoxyethoxy)-1H-pyrazolo[4,3-c]pyridin-6-yl}-3-[(1R)-1-phenylethyl]urea | Calc'd 400, found 400 | Scheme 3/ Method A, synthesis of 38B |

TABLE 14-continued

| Ex | Structure | IUPAC Name | Exact Mass [M + H]+ | Route Used (Intermediate Used) |
|---|---|---|---|---|
| 497 | 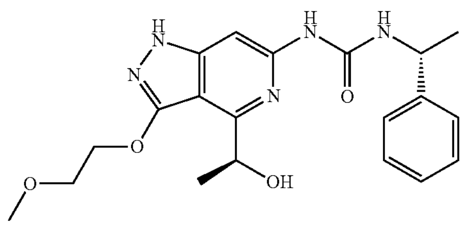 [SMILES: COCCOc1n[nH]c2cc(NC(=O)N[C@H](C)c3ccccc3)nc([C@H](C)O)c12] | 1-[4-[(1S)-1-hydroxyethyl]-3-(2-methoxyethoxy)-1H-pyrazolo[4,3-c]pyridin-6-yl}-3-[(1R)-1-phenylethyl]urea | Calc'd 400, found 400 | Scheme 3/ Method A, synthesis of 38B |
| 498 | 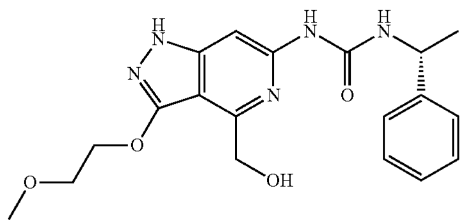 [SMILES: COCCOc1n[nH]c2cc(NC(=O)N[C@H](C)c3ccccc3)nc(CO)c12] | 1-[4-(hydroxymethyl)-3-(2-methoxyethoxy)-1H-pyrazolo[4,3-c]pyridin-6-yl]-3-[(1R)-1-phenylethyl]urea | Calc'd 386, found 386 | Scheme 3/ Method A, synthesis of 35B |
| 499 | 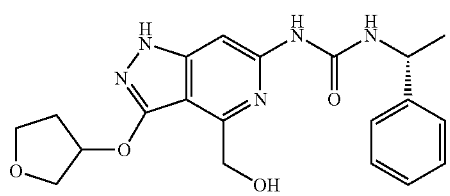 [SMILES: C[C@@H](NC(=O)Nc1cc2[nH]nc(OC3CCOC3)c2c(CO)n1)c1ccccc1] | 1-[4-(hydroxymethyl)-3-(tetrahydrofuran-3-yloxy)-1H-pyrazolo[4,3-c]pyridin-6-yl]-3-[(1R)-1-phenylethyl]urea | Calc'd 398, found 398 | Scheme 3/ Method A, synthesis of 35B |
| 500 | 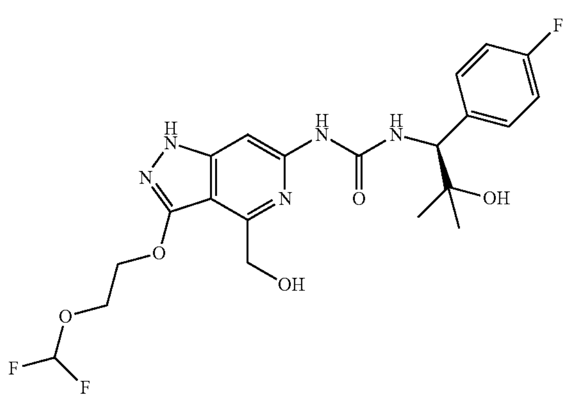 [SMILES: CC(C)(O)[C@@H](NC(=O)Nc1cc2[nH]nc(OCCOC(F)F)c2c(CO)n1)c1ccc(F)cc1] | 1-{3-[2-(difluoromethoxy)ethoxy]-4-(hydroxymethyl)-1H-pyrazolo[4,3-c]pyridin-6-yl}-3-[(1S)-1-(4-fluorophenyl)-2-hydroxy-2-methylpropyl]urea | Calc'd 484, found 484 | Scheme 3/ Method A (67B, 22B) |
| 501 | 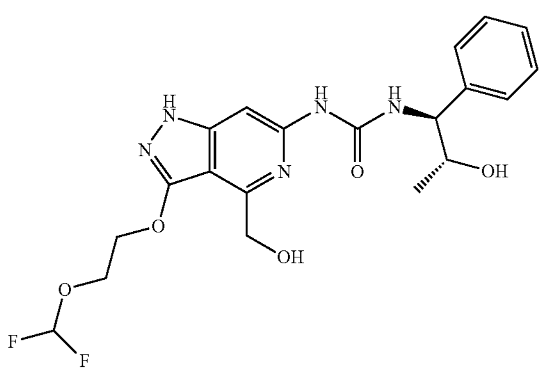 [SMILES: C[C@@H](O)[C@@H](NC(=O)Nc1cc2[nH]nc(OCCOC(F)F)c2c(CO)n1)c1ccccc1] | 1-{3-[2-(difluoromethoxy)ethoxy]-4-(hydroxymethyl)-1H-pyrazolo[4,3-c]pyridin-6-yl}-3-[(1S,2R)-2-hydroxy-1-phenylpropyl]urea | Calc'd 452, found 452 | Scheme 3/ Method A (67B, 23B) |

TABLE 14-continued

| Ex | Structure | IUPAC Name | Exact Mass [M + H]+ | Route Used (Intermediate Used) |
|---|---|---|---|---|
| 502 | 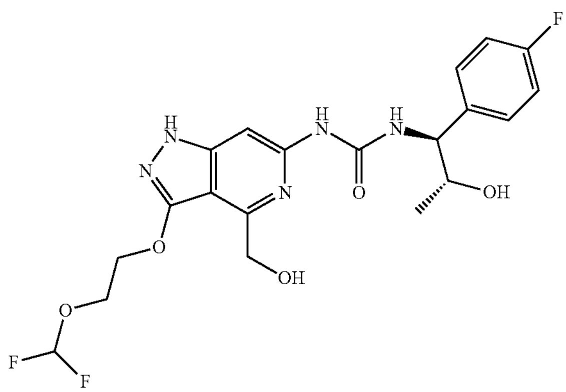 [SMILES: C[C@@H](O)[C@@H](NC(=O)Nc1cc2[nH]nc(OCCOC(F)F)c2c(CO)n1)c1ccc(F)cc1] | 1-{3-[2-(difluoromethoxy)ethoxy]-4-(hydroxymethyl)-1H-pyrazolo[4,3-c]pyridin-6-yl}-3-[(1S,2R)-1-(4-fluorophenyl)-2-hydroxypropyl]urea | Calc'd 470, found 470 | Scheme 3/ Method A (67B, 24B) |
| 503 | 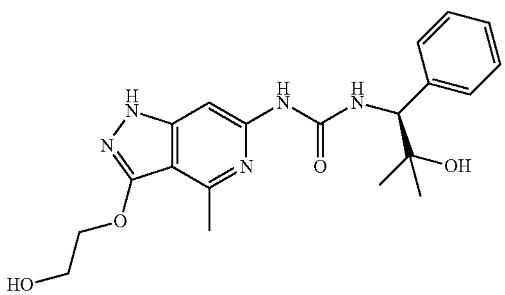 [SMILES: Cc1nc(NC(=O)N[C@@H](c2ccccc2)C(C)(C)O)cc2[nH]nc(OCCO)c12] | 1-[3-(2-hydroxyethoxy)-4-methyl-1H-pyrazolo[4,3-c]pyridin-6-yl]-3-[(1S)-2-hydroxy-2-methyl-1-phenylpropyl]urea | Calc'd 400, found 400 | Scheme 3/ Method A (66B, 21B) |
| 504 | 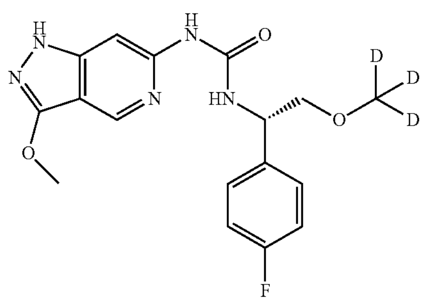 [SMILES: [2H]C([2H])([2H])OC[C@@H](NC(=O)Nc1cc2[nH]nc(OC)c2cn1)c1ccc(F)cc1] | 1-{(1S)-1-(4-fluorophenyl)-2-[(~2~H_3_)methyloxy]ethyl}-3-(3-methoxy-1H-pyrazolo[4,3-c]pyridin-6-yl)urea | Calc'd 363, found 363 | Scheme 3/ Method A |
| 505 | 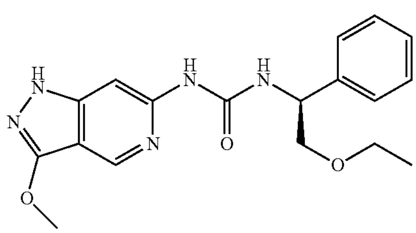 [SMILES: CCOC[C@@H](NC(=O)Nc1cc2[nH]nc(OC)c2cn1)c1ccccc1] | 1-[(1S)-2-ethoxy-1-phenylethyl]-3-(3-methoxy-1H-pyrazolo[4,3-c]pyridin-6-yl)urea | Calc'd 356, found 356 | Scheme 3/ Method A |
| 506 | 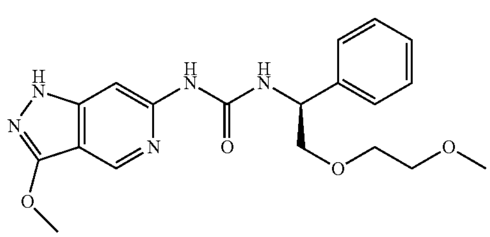 [SMILES: COCCOC[C@@H](NC(=O)Nc1cc2[nH]nc(OC)c2cn1)c1ccccc1] | 1-[(1S)-2-(2-methoxyethoxy)-1-phenylethyl]-3-(3-methoxy-1H-pyrazolo[4,3-c]pyridin-6-yl)urea | Calc'd 386, found 386 | Scheme 3/ Method A |

| Ex | Structure | IUPAC Name | Exact Mass [M + H]+ | Route Used (Intermediate Used) |
|---|---|---|---|---|
| 507 | 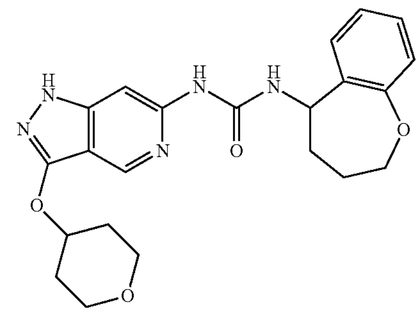 [SMILES: O=C(Nc1cc2[nH]nc(OC3CCOCC3)c2cn1)NC1CCCOc2ccccc21] | 1-(2,3,4,5-tetrahydro-1-benzoxepin-5-yl)-3-[3-(tetrahydro-2H-pyran-4-yloxy)-1H-pyrazolo[4,3-c]pyridin-6-yl]urea | Calc'd 424, found 424 | Scheme 3/ Method A |
| 508 | 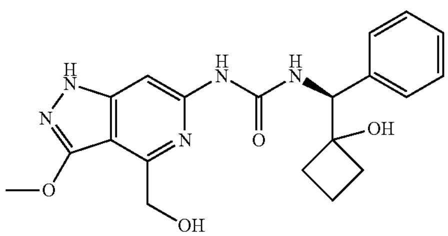 [SMILES: COc1n[nH]c2cc(NC(=O)N[C@@H](c3ccccc3)C3(O)CCC3)nc(CO)c12] | 1-[(S)-(1-hydroxycyclobutyl)(phenyl)methyl]-3-[4-(hydroxymethyl)-3-methoxy-1H-pyrazolo[4,3-c]pyridin-6-yl]urea | Calc'd 398, found 398 | Scheme 3/ Method A |
| 509 | 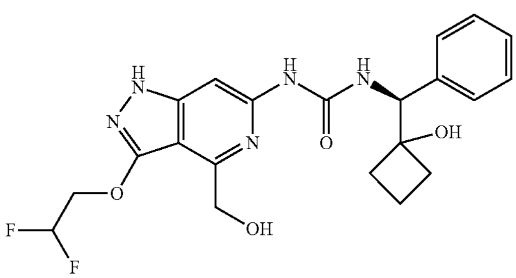 [SMILES: O=C(Nc1cc2[nH]nc(OCC(F)F)c2c(CO)n1)N[C@@H](c1ccccc1)C1(O)CCC1] | 1-[3-(2,2-difluoroethoxy)-4-(hydroxymethyl)-1H-pyrazolo[4,3-c]pyridin-6-yl]-3-[(S)-(1-hydroxycyclobutyl)(phenyl)methyl]urea | Calc'd 448, Found 448 | Scheme 3/ Method A |
| 510 | 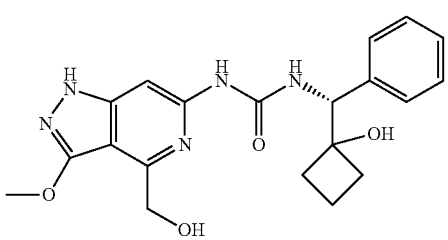 [SMILES: COc1n[nH]c2cc(NC(=O)N[C@H](c3ccccc3)C3(O)CCC3)nc(CO)c12] | 1-[(R)-(1-hydroxycyclobutyl)(phenyl)methyl]-3-[4-(hydroxymethyl)-3-methoxy-1H-pyrazolo[4,3-c]pyridin-6-yl]urea | Calc'd 398, found 398 | Scheme 3/ Method A |
| 511 | 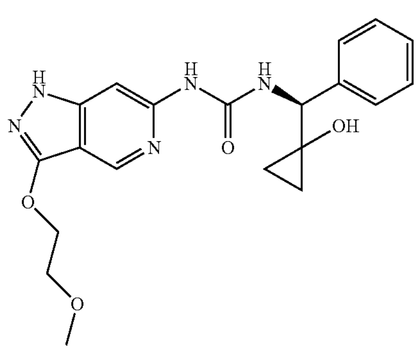 [SMILES: COCCOc1n[nH]c2cc(NC(=O)N[C@@H](c3ccccc3)C3(O)CC3)ncc12] | 1-[(S)-(1-hydroxycyclopropyl)(phenyl)methyl]-3-[3-(2-methoxyethoxy)-1H-pyrazolo[4,3-c]pyridin-6-yl]urea | Calc'd 398, found 398 | Scheme 10, Example 102 (32B) |

TABLE 14-continued

| Ex | Structure | IUPAC Name | Exact Mass [M + H]+ | Route Used (Intermediate Used) |
|---|---|---|---|---|
| 512 | 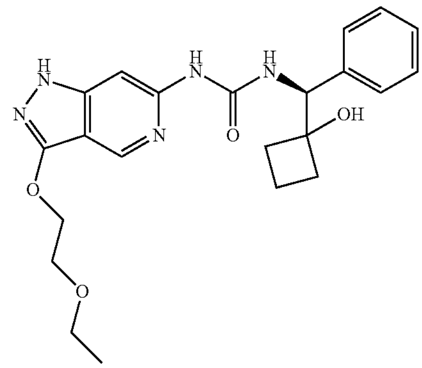 [SMILES: CCOCCOc1n[nH]c2cc(NC(=O)N[C@@H](c3ccccc3)C3(O)CCC3)ncc12] | 1-[3-(2-ethoxyethoxy)-1H-pyrazolo[4,3-c]pyridin-6-yl]-3-[(S)-(1-hydroxycyclobutyl)(phenyl)methyl]urea | Calc'd 426, found 426 | Scheme 10, Example 102 |
| 513 | 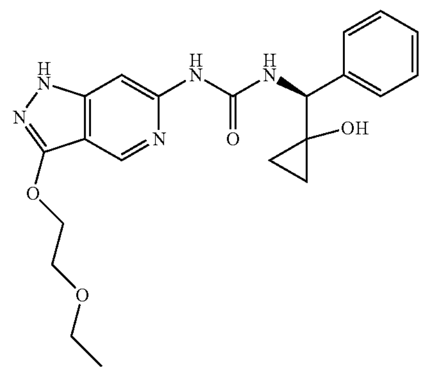 [SMILES: CCOCCOc1n[nH]c2cc(NC(=O)N[C@@H](c3ccccc3)C3(O)CC3)ncc12] | 1-[3-(2-ethoxyethoxy)-1H-pyrazolo[4,3-c]pyridin-6-yl]-3-[(S)-(1-hydroxycyclopropyl)(phenyl)methyl]urea | Calc'd 412, found 412 | Scheme 10, Example 102 |
| 514 | 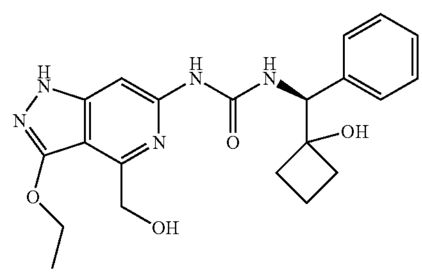 [SMILES: CCOc1n[nH]c2cc(NC(=O)N[C@@H](c3ccccc3)C3(O)CCC3)nc(CO)c12] | 1-[3-ethoxy-4-(hydroxymethyl)-1H-pyrazolo[4,3-c]pyridin-6-yl]-3-[(S)-(1-hydroxycyclobutyl)(phenyl)methyl]urea | Calc'd 412, found 412 | Scheme 3/ Method A |
| 515 | 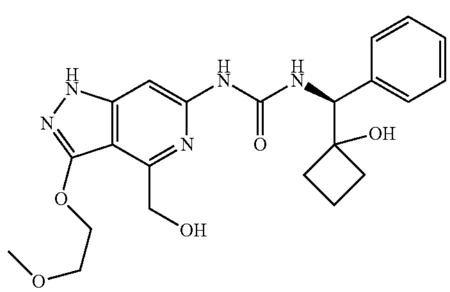 [SMILES: COCCOc1n[nH]c2cc(NC(=O)N[C@@H](c3ccccc3)C3(O)CCC3)nc(CO)c12] | 1-[(S)-(1-hydroxycyclobutyl)(phenyl)methyl]-3-[4-(hydroxymethyl)-3-(2-methoxyethoxy)-1H-pyrazolo[4,3-c]pyridin-6-yl]urea | Calc'd 442, found 4442 | Scheme 3/ Method A |

TABLE 14-continued

| Ex | Structure | IUPAC Name | Exact Mass [M + H]+ | Route Used (Intermediate Used) |
|---|---|---|---|---|
| 516 | 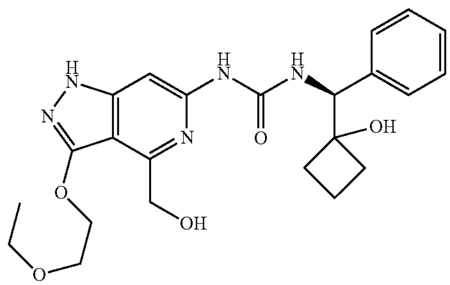 [SMILES: CCOCCOc1n[nH]c2cc(NC(=O)N[C@@H](c3ccccc3)C3(O)CCC3)nc(CO)c12] | 1-[3-(2-ethoxyethoxy)-4-(hydroxymethyl)-1H-pyrazolo[4,3-c]pyridin-6-yl]-3-[(S)-(1-hydroxycyclobutyl)(phenyl)methyl]urea | Calc'd 456, found 456 | Scheme 3/ Method A |
| 517 | 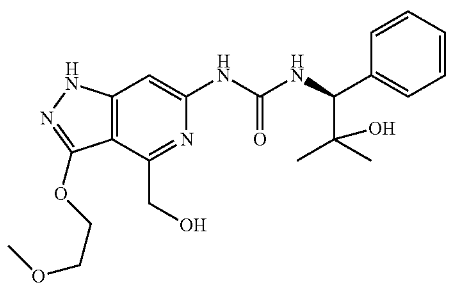 [SMILES: COCCOc1n[nH]c2cc(NC(=O)N[C@@H](c3ccccc3)C(C)(C)O)nc(CO)c12] | 1-[4-(hydroxymethyl)-3-(2-methoxyethoxy)-1H-pyrazolo[4,3-c]pyridin-6-yl]-3-[(1S)-2-hydroxy-2-methyl-1-phenylpropyl]urea | Calc'd 430, found 430 | Scheme 3/ Method A (21B) |
| 518 | 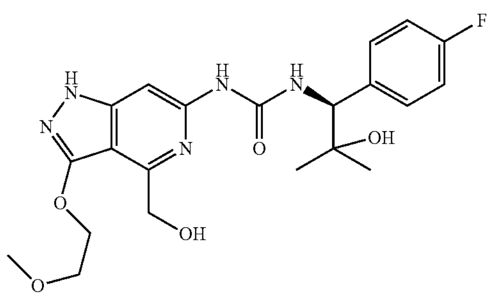 [SMILES: COCCOc1n[nH]c2cc(NC(=O)N[C@@H](c3ccc(F)cc3)C(C)(C)O)nc(CO)c12] | 1-[(1S)-1-(4-fluorophenyl)-2-hydroxy-2-methylpropyl]-3-[4-(hydroxymethyl)-3-(2-methoxyethoxy)-1H-pyrazolo[4,3-c]pyridin-6-yl]urea | Calc'd 448, found 448.4 | Scheme 3/ Method A (22B) |
| 519 | 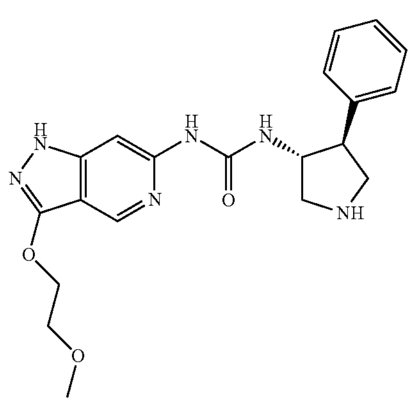 [SMILES: COCCOc1n[nH]c2cc(NC(=O)N[C@H]3CNC[C@@H]3c3ccccc3)ncc12] | 1-[3-(2-methoxyethoxy)-1H-pyrazolo[4,3-c]pyridin-6-yl]-3-[(3R,4S)-4-phenylpyrrolidin-3-yl]urea | Calc'd 397, found 397 | Scheme 10, Example 102 (32B) |

TABLE 14-continued

| Ex | Structure | IUPAC Name | Exact Mass [M + H]+ | Route Used (Intermediate Used) |
|---|---|---|---|---|
| 520 | 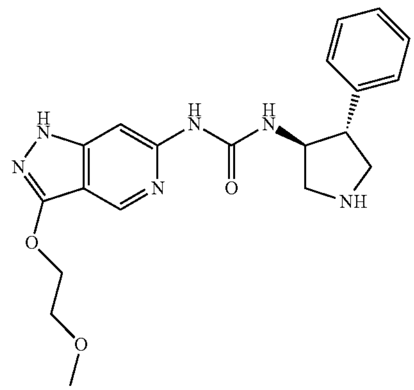 [SMILES: COCCOc1n[nH]c2cc(NC(=O)N[C@@H]3CNC[C@H]3c3ccccc3)ncc12] | 1-[3-(2-methoxyethoxy)-1H-pyrazolo[4,3-c]pyridin-6-yl]-3-[(3S,4R)-4-phenylpyrrolidin-3-yl]urea | Calc'd 397, found 397 | Scheme 10, Example 102 (32B) |
| 521 | 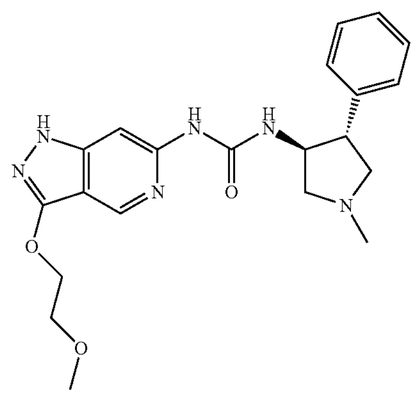 [SMILES: COCCOc1n[nH]c2cc(NC(=O)N[C@@H]3CN(C)C[C@H]3c3ccccc3)ncc12] | 1-[3-(2-methoxyethoxy)-1H-pyrazolo[4,3-c]pyridin-6-yl]-3-[(3S,4R)-1-methyl-4-phenylpyrrolidin-3-yl]urea | Calc'd 411, found 411 | Scheme 3/ Method A, Example 112 |
| 522 | 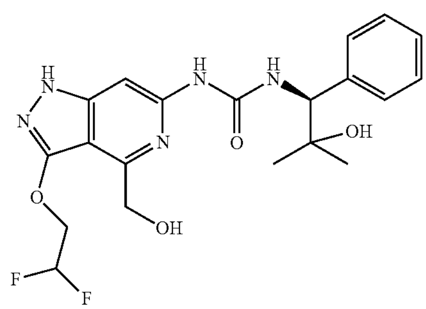 [SMILES: CC(C)(O)[C@@H](NC(=O)Nc1cc2[nH]nc(OCC(F)F)c2c(CO)n1)c1ccccc1] | 1-[3-(2,2-difluoroethoxy)-4-(hydroxymethyl)-1H-pyrazolo[4,3-c]pyridin-6-yl]-3-[(1S)-2-hydroxy-2-methyl-1-phenylpropyl]urea | Calc'd 436, found 436 | Scheme 3/ Method A (21B) |
| 523 | 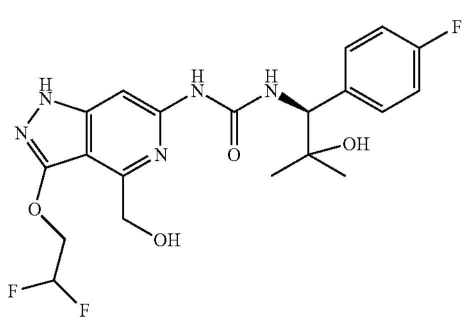 [SMILES: CC(C)(O)[C@@H](NC(=O)Nc1cc2[nH]nc(OCC(F)F)c2c(CO)n1)c1ccc(F)cc1] | 1-[3-(2,2-difluoroethoxy)-4-(hydroxymethyl)-1H-pyrazolo[4,3-c]pyridin-6-yl]-3-[(1S)-1-(4-fluorophenyl)-2-hydroxy-2-methylpropyl]urea | Calc'd 454, found 454 | Scheme 3/ Method A (22B) |

TABLE 14-continued

| Ex | Structure | IUPAC Name | Exact Mass [M + H]+ | Route Used (Intermediate Used) |
|---|---|---|---|---|
| 524 | 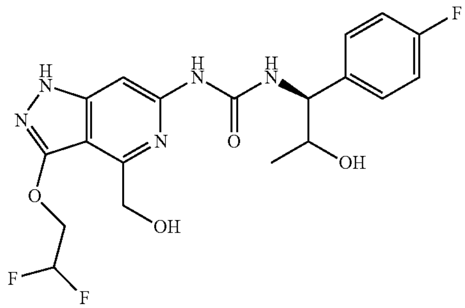 [SMILES: CC(O)[C@@H](NC(=O)Nc1cc2[nH]nc(OCC(F)F)c2c(CO)n1)c1ccc(F)cc1] | 1-[3-(2,2-difluoroethoxy)-4-(hydroxymethyl)-1H-pyrazolo[4,3-c]pyridin-6-yl]-3-[(1S)-1-(4-fluorophenyl)-2-hydroxypropyl]urea | Calc'd 440, found 440 | Scheme 3/Method A, synthesis of 23B |
| 525 | 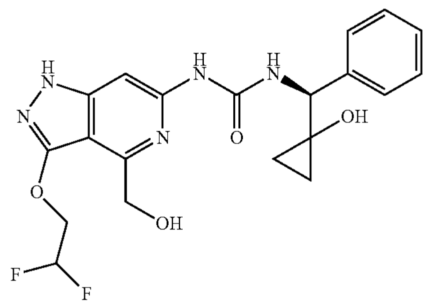 [SMILES: O=C(Nc1cc2[nH]nc(OCC(F)F)c2c(CO)n1)N[C@@H](c1ccccc1)C1(O)CC1] | 1-[3-(2,2-difluoroethoxy)-4-(hydroxymethyl)-1H-pyrazolo[4,3-c]pyridin-6-yl]-3-[(S)-(1-hydroxycyclopropyl)(phenyl)methyl]urea | Calc'd 434, found 434 | Scheme 3/Method A |
| 526 | 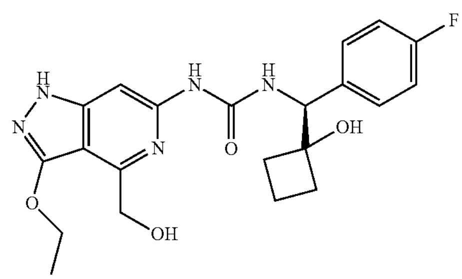 [SMILES: CCOc1n[nH]c2cc(NC(=O)N[C@@H](c3ccc(F)cc3)C3(O)CCC3)nc(CO)c12] | 1-[3-ethoxy-4-(hydroxymethyl)-1H-pyrazolo[4,3-c]pyridin-6-yl]-3-[(S)-(4-fluorophenyl)(1-hydroxycyclobutyl)methyl]urea | Calc'd 430, found 430 | Scheme 3/Method A |
| 527 | 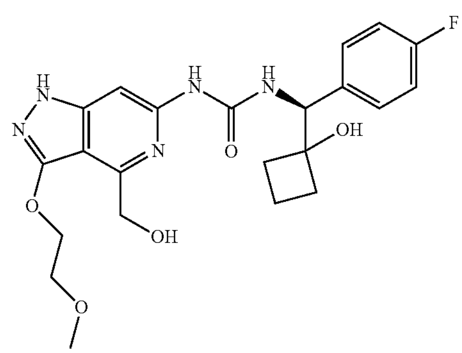 [SMILES: COCCOc1n[nH]c2cc(NC(=O)N[C@@H](c3ccc(F)cc3)C3(O)CCC3)nc(CO)c12] | 1-[(S)-(4-fluorophenyl)(1-hydroxycyclobutyl)methyl]-3-[4-(hydroxymethyl)-3-(2-methoxyethoxy)-1H-pyrazolo[4,3-c]pyridin-6-yl]urea | Calc'd 460, found 460 | Scheme 3/Method A |
| 528 | 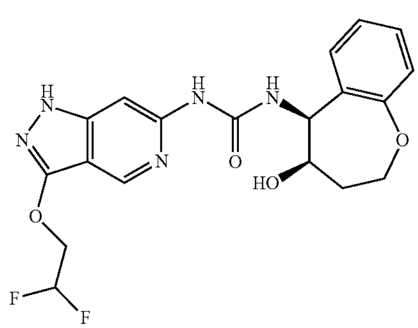 [SMILES: O=C(Nc1cc2[nH]nc(OCC(F)F)c2cn1)N[C@H]1c2ccccc2OCC[C@H]1O] | 1-[3-(2,2-difluoroethoxy)-1H-pyrazolo[4,3-c]pyridin-6-yl]-3-[(4R,5S)-4-hydroxy-2,3,4,5-tetrahydro-1-benzoxepin-5-yl]urea | Calc'd 420, found 420 | Scheme 10, Example 102 |

| Ex | Structure | IUPAC Name | Exact Mass [M + H]+ | Route Used (Intermediate Used) |
|---|---|---|---|---|
| 529 | 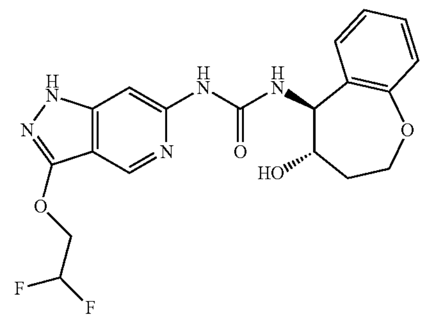 [SMILES: O=C(Nc1cc2[nH]nc(OCC(F)F)c2cn1)N[C@H]1c2ccccc2OCC[C@@H]1O] | 1-[3-(2,2-difluoroethoxy)-1H-pyrazolo[4,3-c]pyridin-6-yl]-3-[(4S,5S)-4-hydroxy-2,3,4,5-tetrahydro-1-benzoxepin-5-yl]urea | Calc'd 420, found 420 | Scheme 10, Example 102 |
| 530 | 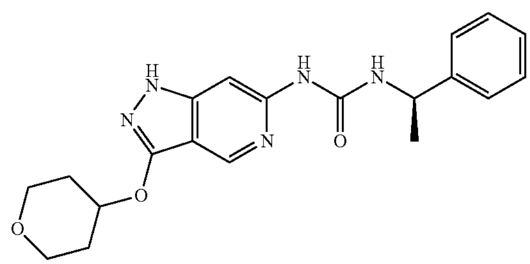 [SMILES: C[C@@H](NC(=O)Nc1cc2[nH]nc(OC3CCOCC3)c2cn1)c1ccccc1] | 1-[(1R)-1-phenylethyl]-3-[3-(tetrahydro-2H-pyran-4-yloxy)-1H-pyrazolo[4,3-c]pyridin-6-yl]urea | Calc'd 382, found 382 | Scheme 1 |
| 531 | 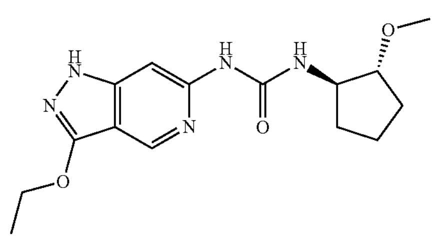 [SMILES: CCOc1n[nH]c2cc(NC(=O)N[C@@H]3CCC[C@H]3OC)ncc12] | 1-(3-ethoxy-1H-pyrazolo[4,3-c]pyridin-6-yl)-3-[(1R,2R)-2-methoxycyclopentyl]urea | Calc'd 320, found 320 | Scheme 1 (28B) |
| 532 | 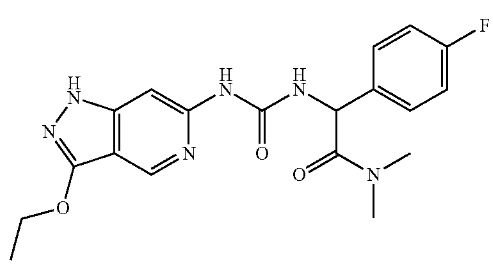 [SMILES: CCOc1n[nH]c2cc(NC(=O)NC(C(=O)N(C)C)c3ccc(F)cc3)ncc12] | 2-{[(3-ethoxy-1H-pyrazolo[4,3-c]pyridin-6-yl)carbamoyl]amino}-2-(4-fluorophenyl)-N,N-dimethylacetamide | Calc'd 401, found 401 | Scheme 1 |
| 533 | 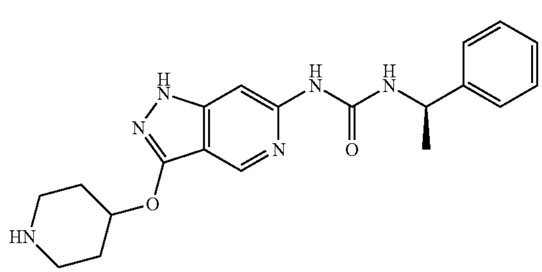 [SMILES: C[C@@H](NC(=O)Nc1cc2[nH]nc(OC3CCNCC3)c2cn1)c1ccccc1] | 1-[(1R)-1-phenylethyl]-3-[3-(piperidin-4-yloxy)-1H-pyrazolo[4,3-c]pyridin-6-yl]urea | Calc'd 381, found 381 | Scheme 1 |

TABLE 14-continued

| Ex | Structure | IUPAC Name | Exact Mass [M + H]+ | Route Used (Intermediate Used) |
|---|---|---|---|---|
| 534 | 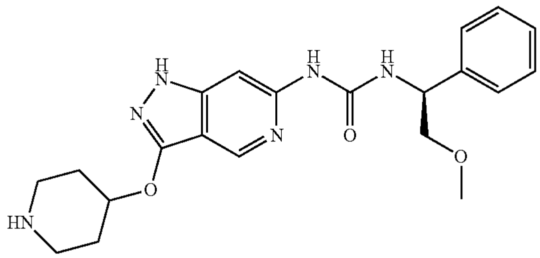 [SMILES: COC[C@@H](NC(=O)Nc1cc2[nH]nc(OC3CCNCC3)c2cn1)c1ccccc1] | 1-[(1S)-2-methoxy-1-phenylethyl]-3-[3-(piperidin-4-yloxy)-1H-pyrazolo[4,3-c]pyridin-6-yl]urea | Calc'd 411, found 411 | Scheme 1 |
| 535 | 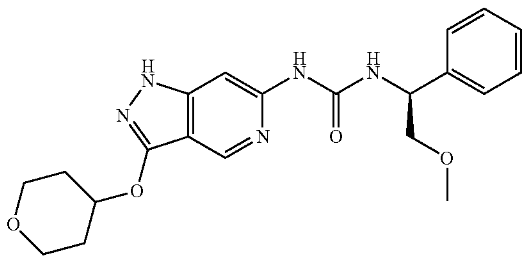 [SMILES: COC[C@@H](NC(=O)Nc1cc2[nH]nc(OC3CCOCC3)c2cn1)c1ccccc1] | 1-[(1S)-2-methoxy-1-phenylethyl]-3-[3-(tetrahydro-2H-pyran-4-yloxy)-1H-pyrazolo[4,3-c]pyridin-6-yl]urea | Calc'd 412, found 412 | Scheme 1 |
| 536 | 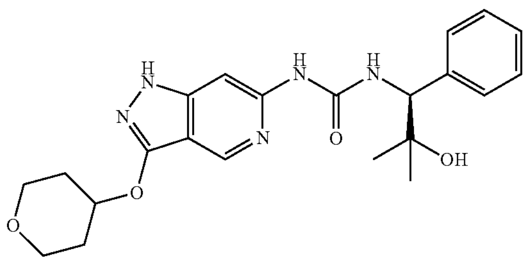 [SMILES: CC(C)(O)[C@@H](NC(=O)Nc1cc2[nH]nc(OC3CCOCC3)c2cn1)c1ccccc1] | 1-[(1S)-2-hydroxy-2-methyl-1-phenylpropyl]-3-[3-(tetrahydro-2H-pyran-4-yloxy)-1H-pyrazolo[4,3-c]pyridin-6-yl]urea | Calc'd 426, found 426 | Scheme 1 |
| 537 | 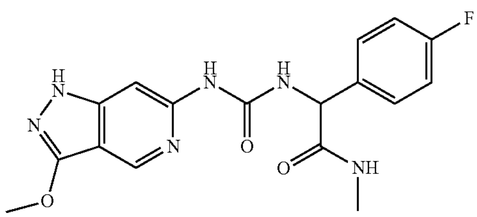 [SMILES: CNC(=O)C(NC(=O)Nc1cc2[nH]nc(OC)c2cn1)c1ccc(F)cc1] | 2-(4-fluorophenyl)-2-{[(3-methoxy-1H-pyrazolo[4,3-c]pyridin-6-yl)carbamoyl]amino}-N-methylacetamide | Calc'd 373, found 373 | Scheme 1 (26B) |
| 538 | 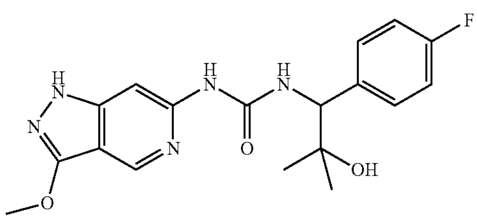 [SMILES: COc1n[nH]c2cc(NC(=O)NC(c3ccc(F)cc3)C(C)(C)O)ncc12] | 1-[1-(4-fluorophenyl)-2-hydroxy-2-methylpropyl]-3-(3-methoxy-1H-pyrazolo[4,3-c]pyridin-6-yl)urea | Calc'd 374, found 374 | Example 62 |
| 539 | 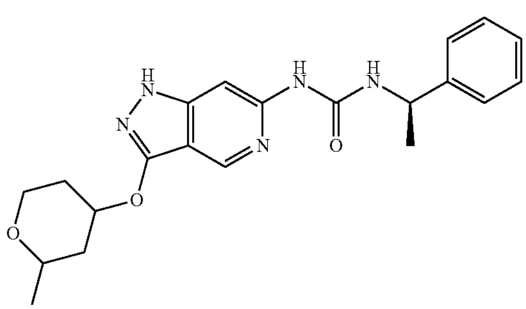 | 1-{3-[(2-methyltetrahydro-2H-pyran-4-yl)oxy]-1H-pyrazolo[4,3-c]pyridin-6-yl}-3-[(1R)-1-phenylethyl]urea, | Calc'd 396, found 396 | Scheme 1 |

Mixture of cis and trans isomers in tetrahydropyran ring

TABLE 14-continued

| Ex | Structure | IUPAC Name | Exact Mass [M + H]+ | Route Used (Intermediate Used) |
|---|---|---|---|---|
| 540 | Mixture of cis and trans isomers in cyclohexane ring | 1-{3-[(4-cyanocyclohexyl)oxy]-1H-pyrazolo[4,3-c]pyridin-6-yl}-3-[(1R)-1-phenylethyl]urea | Calc'd 405, found 405 | Scheme 1 |
| 541 | Mixture of cis and trans isomers in cyclohexane ring | 1-{3-[(4-cyanocyclohexyl)oxy]-1H-pyrazolo[4,3-c]pyridin-6-yl}-3-[(1S)-2-(difluoromethoxy)-1-phenylethyl]urea | Calc'd 471, found 471 | Scheme 1 |
| 542 | 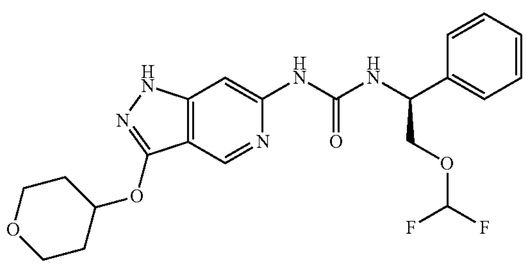 [SMILES: O=C(Nc1cc2[nH]nc(OC3CCOCC3)c2cn1)N[C@H](COC(F)F)c1ccccc1] | 1-[(1S)-2-(difluoromethoxy)-1-phenylethyl]-3-[3-(tetrahydro-2H-pyran-4-yloxy)-1H-pyrazolo[4,3-c]pyridin-6-yl]urea | Calc'd 448, found 448 | Scheme 1 |
| 543 | Mixture of cis and trans isomers in tetrahydropyran ring | 1-((S)-2-methoxy-1-phenylethyl)-3-(3-((3-methyltetrahydro-2H-pyran-4-yl)oxy)-1H-pyrazolo[4,3-c]pyridin-6-yl)urea | Calc'd 396, found 396 | Scheme 1 |
| 544 | Mixture of cis and trans isomers in tetrahydropyran ring | 1-[(1S)-2-methoxy-1-phenylethyl]-3-{3-[(2-methyltetrahydro-2H-pyran-4-yl)oxy]-1H-pyrazolo[4,3-c]pyridin-6-yl}urea | Calc'd 426, found 426 | Scheme 1 |

| Ex | Structure | IUPAC Name | Exact Mass [M + H]+ | Route Used (Intermediate Used) |
|---|---|---|---|---|
| 545 | Mixture of cis and trans isomers in tetrahydropyran ring | 1-((S)-2-methoxy-1-phenylethyl)-3-(3-((3-methyltetrahydro-2H-pyran-4-yl)oxy)-1H-pyrazolo[4,3-c]pyridin-6-yl)urea | Calc'd 426, found 426 | Scheme 1 |
| 546 | Mixture of cis and trans isomers in cyclohexane ring | 1-{3-[(4-cyanocyclohexyl)oxy]-1H-pyrazolo[4,3-c]pyridin-6-yl}-3-[(1S)-2-methoxy-1-phenylethyl]urea | Calc'd 435, found 435 | Scheme 1 |
| 547 | Mixture of cis and trans isomers in cyclohexane ring | 1-{3-[(4-methoxycyclohexyl)oxy]-1H-pyrazolo[4,3-c]pyridin-6-yl}-3-[(1S)-2-methoxy-1-phenylethyl]urea | Calc'd 440, found 440 | Scheme 1 |
| 548 | 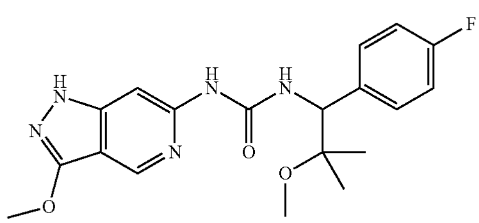 [SMILES: COc1n[nH]c2cc(NC(=O)NC(c3ccc(F)cc3)C(C)(C)OC)ncc12] | 1-[1-(4-fluorophenyl)-2-methoxy-2-methylpropyl]-3-(3-methoxy-1H-pyrazolo[4,3-c]pyridin-6-yl)urea | Calc'd 388, found 388 | Scheme 1 |
| 549 | Mixture of cis and trans isomers in cyclohexane ring | 1-[(1S)-2-(difluoromethoxy)-1-phenylethyl]-3-{3-[(4-methoxy-4-methylcyclohexyl)oxy]-1H-pyrazolo[4,3-c]pyridin-6-yl}urea | Calc'd 490, found 490 | Scheme 1 |

TABLE 14-continued

| Ex | Structure | IUPAC Name | Exact Mass [M + H]+ | Route Used (Intermediate Used) |
|---|---|---|---|---|
| 550 | 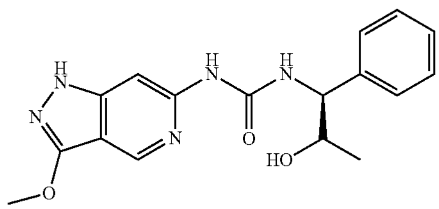 [SMILES: COc1n[nH]c2cc(NC(=O)N[C@@H](c3ccccc3)C(C)O)ncc12] | 1-[(1S,2S)-2-hydroxy-1-phenylpropyl]-3-(3-methoxy-1H-pyrazolo[4,3-c]pyridin-6-yl)urea | Calc'd 342, found 342 | Scheme 1 |
| 551 | Mixture of cis and trans isomers in cyclohexane ring | 1-{3-[(4-methoxy-4-methylcyclohexyl)oxy]-1H-pyrazolo[4,3-c]pyridin-6-yl}-3-[(1S)-2-methoxy-1-phenylethyl]urea | Calc'd 454, found 454 | Scheme 1 |
| 552 | 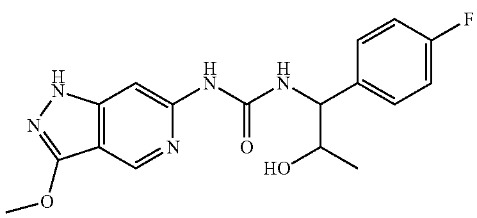 [SMILES: COc1n[nH]c2cc(NC(=O)NC(c3ccc(F)cc3)C(C)O)ncc12] | 1-[1-(4-fluorophenyl)-2-hydroxypropyl]-3-(3-methoxy-1H-pyrazolo[4,3-c]pyridin-6-yl)urea | Calc'd 360, found 360 | Scheme 1 |
| 553 | Mixture of cis (racemic) isomers in tetrahydropyran ring | 1-{3-cis-rac-[(2-methyltetrahydro-2H-pyran-4-yl)oxy]-1H-pyrazolo[4,3-c]pyridin-6-yl}-3-[(1R)-1-phenylethyl]urea | Calc'd 396, found 396 | Scheme 1 |
| 554 | Mixture of trans (racemic) isomers in tetrahydropyran ring | 1-{3-trans-rac-[(2-methyltetrahydro-2H-pyran-4-yl)oxy]-1H-pyrazolo[4,3-c]pyridin-6-yl}-3-[(1R)-1-phenylethyl]urea | Calc'd 396, found 396 | Scheme 1 |

TABLE 14-continued

| Ex | Structure | IUPAC Name | Exact Mass [M + H]+ | Route Used (Intermediate Used) |
|---|---|---|---|---|
| 555 | Mixture of cis (racemic) isomers in tetrahydropyran ring | 1-[(1S)-2-methoxy-1-phenylethyl]-3-{3-cis-rac [(2-methyltetrahydro-2H-pyran-4-yl)oxy]-1H-pyrazolo[4,3-c]pyridin-6-yl}urea | Calc'd 426, found 426 | Scheme 1 |
| 556 | Mixture of trans (racemic) isomers in tetrahydropyran ring | 1-[(1S)-2-methoxy-1-phenylethyl]-3-{3-trans-rac-[(2-methyltetrahydro-2H-pyran-4-yl)oxy]-1H-pyrazolo[4,3-c]pyridin-6-yl}urea | Calc'd 426, found 426 | Scheme 1 |
| 557 | Mixture of racemic cis isomers in tetrahydropyran ring | 1-(3-{[(2R,6S)-2,6-dimethyltetrahydro-2H-pyran-4-yl]oxy}-1H-pyrazolo[4,3-c]pyridin-6-yl)-3-[(1S)-2-methoxy-1-phenylethyl]urea | Calc'd 440, found 440 | Scheme 1 |
| 558 | 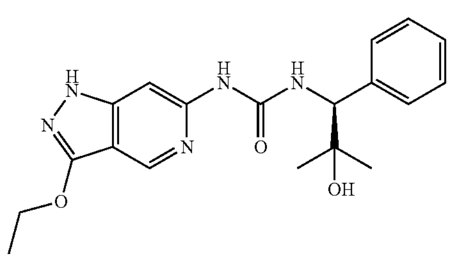 [SMILES: CCOc1n[nH]c2cc(NC(=O)N[C@@H](c3ccccc3)C(C)(C)O)ncc12] | 1-(3-ethoxy-1H-pyrazolo[4,3-c]pyridin-6-yl)-3-[(1S)-2-hydroxy-2-methyl-1-phenylpropyl]urea | Calc'd 370, found 370 | Scheme 1 |
| 559 | 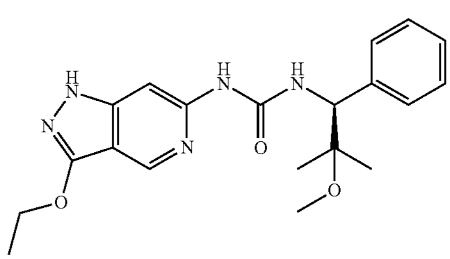 [SMILES: CCOc1n[nH]c2cc(NC(=O)N[C@@H](c3ccccc3)C(C)(C)OC)ncc12] | 1-(3-ethoxy-1H-pyrazolo[4,3-c]pyridin-6-yl)-3-[(1S)-2-methoxy-2-methyl-1-phenylpropyl]urea | Calc'd 384, found 384 | Scheme 1 |

TABLE 14-continued

| Ex | Structure | IUPAC Name | Exact Mass [M + H]+ | Route Used (Intermediate Used) |
|---|---|---|---|---|
| 560 | 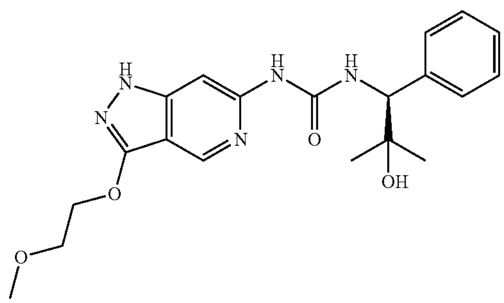 [SMILES: COCCOc1n[nH]c2cc(NC(=O)N[C@@H](c3ccccc3)C(C)(C)O)ncc12] | 1-[(1S)-2-hydroxy-2-methyl-1-phenylpropyl]-3-[3-(2-methoxyethoxy)-1H-pyrazolo[4,3-c]pyridin-6-yl]urea | Calc'd 400, found 400 | Example 62 |
| 561 | Stereoisomer A | 1-[(1S)-2-hydroxy-1-phenylpropyl]-3-(3-methoxy-1H-pyrazolo[4,3-c]pyridin-6-yl)urea, Stereoisomer A | Calc'd 342, found 342 | Scheme 1 |
| 562 | Stereoisomer B | 1-[(1S)-2-hydroxy-1-phenylpropyl]-3-(3-methoxy-1H-pyrazolo[4,3-c]pyridin-6-yl)urea, Stereoisomer B | Calc'd 342, found 342 | Scheme 1 |
| 563 | 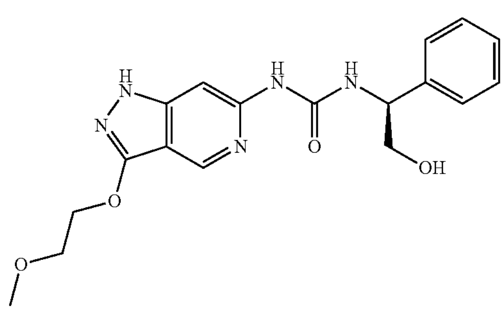 [SMILES: COCCOc1n[nH]c2cc(NC(=O)N[C@H](CO)c3ccccc3)ncc12] | 1-[(1S)-2-hydroxy-1-phenylethyl]-3-[3-(2-methoxyethoxy)-1H-pyrazolo[4,3-c]pyridin-6-yl]urea | Calc'd 372, found 372 | Scheme 1 |
| 564 | 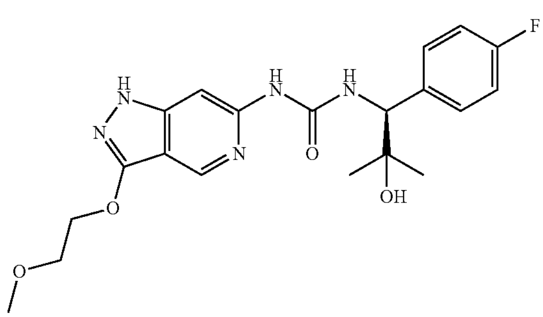 [SMILES: COCCOc1n[nH]c2cc(NC(=O)N[C@@H](c3ccc(F)cc3)C(C)(C)O)ncc12] | 1-[(1S)-1-(4-fluorophenyl)-2-hydroxy-2-methylpropyl]-3-[3-(2-methoxyethoxy)-1H-pyrazolo[4,3-c]pyridin-6-yl]urea | Calc'd 418, found 418 | Scheme 1 |

TABLE 14-continued

| Ex | Structure | IUPAC Name | Exact Mass [M + H]+ | Route Used (Intermediate Used) |
|---|---|---|---|---|
| 565 | mixture of racemic cis isomers in tetrahydropyran ring | 1-{3-[(2,6-dimethyltetrahydro-2H-pyran-4-yl)oxy]-1H-pyrazolo[4,3-c]pyridin-6-yl}-3-[(1S)-2-hydroxy-2-methyl-1-phenylpropyl]urea | Calc'd 454, found 454 | Scheme 1 |
| 566 | 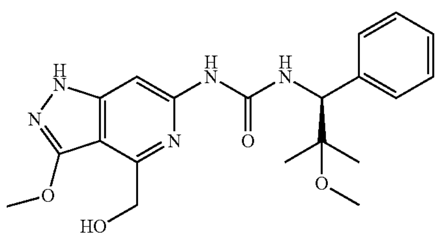 [SMILES: COc1n[nH]c2cc(NC(=O)N[C@@H](c3ccccc3)C(C)(C)OC)nc(CO)c12] | 1-[4-(hydroxymethyl)-3-methoxy-1H-pyrazolo[4,3-c]pyridin-6-yl]-3-[(1S)-2-methoxy-2-methyl-1-phenylpropyl]urea | Calc'd 400, found 400 | Scheme 1 |
| 567 | mixture of cis isomers (racemic) in tetrahydropyran ring | 1-{3-[(2,6-dimethyltetrahydro-2H-pyran-4-yl)oxy]-1H-pyrazolo[4,3-c]pyridin-6-yl}-3-[(1S)-1-(4-fluorophenyl)-2-hydroxy-2-methylpropyl]urea | Calc'd 472, found 472 | Scheme 1 |
| 568 | 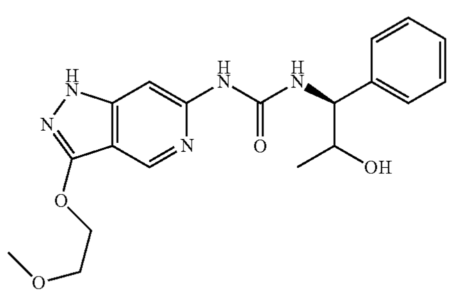 [SMILES: COCCOc1n[nH]c2cc(NC(=O)N[C@@H](c3ccccc3)C(C)O)ncc12] | 1-[(1S)-2-hydroxy-1-phenylpropyl]-3-[3-(2-methoxyethoxy)-1H-pyrazolo[4,3-c]pyridin-6-yl]urea | Calc'd 386, found 386 | Scheme 1 |
| 569 | 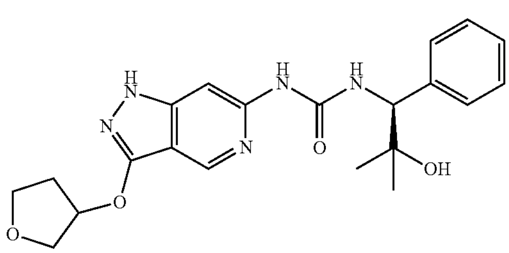 [SMILES: CC(C)(O)[C@@H](NC(=O)Nc1cc2[nH]nc(OC3CCOC3)c2cn1)c1ccccc1] | 1-[(1S)-2-hydroxy-2-methyl-1-phenylpropyl]-3-[3-(tetrahydrofuran-3-yloxy)-1H-pyrazolo[4,3-c]pyridin-6-yl]urea | Calc'd 412, found 412 | Scheme 1 |

TABLE 14-continued

| Ex | Structure | IUPAC Name | Exact Mass [M + H]+ | Route Used (Intermediate Used) |
|---|---|---|---|---|
| 570 | 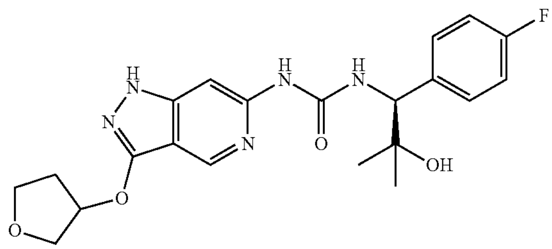 [SMILES: CC(C)(O)[C@@H](NC(=O)Nc1cc2[nH]nc(OC3CCOC3)c2cn1)c1ccc(F)cc1] | 1-[(1S)-1-(4-fluorophenyl)-2-hydroxy-2-methylpropyl]-3-[3-(tetrahydrofuran-3-yloxy)-1H-pyrazolo[4,3-c]pyridin-6-yl]urea | Calc'd 430, found 430 | Scheme 1 |
| 571 | 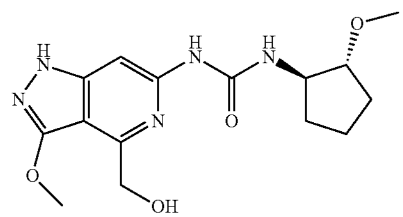 [SMILES: COc1n[nH]c2cc(NC(=O)N[C@@H]3CCC[C@H]3OC)nc(CO)c12] | 1-[4-(hydroxymethyl)-3-methoxy-1H-pyrazolo[4,3-c]pyridin-6-yl]-3-[(1R,2R)-2-methoxycyclopentyl]urea | Calc'd 336, found 336 | Scheme 1 |
| 572 | 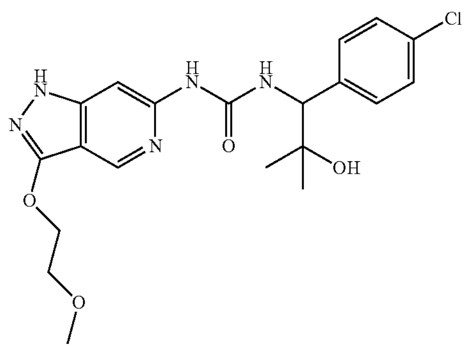 [SMILES: COCCOc1n[nH]c2cc(NC(=O)NC(c3ccc(Cl)cc3)C(C)(C)O)ncc12] | 1-[1-(4-chlorophenyl)-2-hydroxy-2-methylpropyl]-3-[3-(2-methoxyethoxy)-1H-pyrazolo[4,3-c]pyridin-6-yl]urea | Calc'd 434, found 434 | Scheme 1 |
| 573 | 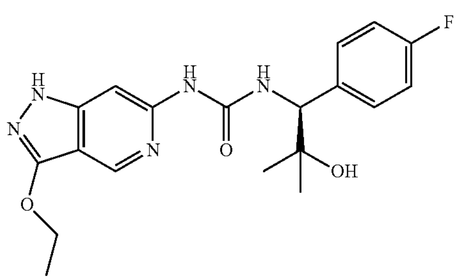 [SMILES: CCOc1n[nH]c2cc(NC(=O)N[C@@H](c3ccc(F)cc3)C(C)(C)O)ncc12] | 1-(3-ethoxy-1H-pyrazolo[4,3-c]pyridin-6-yl)-3-[(1S)-1-(4-fluorophenyl)-2-hydroxy-2-methylpropyl]urea | Calc'd 388, found 388 | Scheme 1 |
| 574 | 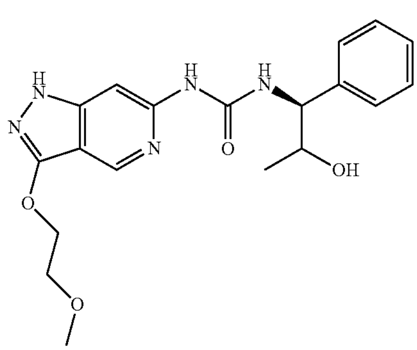 [SMILES: COCCOc1n[nH]c2cc(NC(=O)N[C@@H](c3ccccc3)C(C)O)ncc12] | 1-[(1S)-2-hydroxy-1-phenylpropyl]-3-[3-(2-methoxyethoxy)-1H-pyrazolo[4,3-c]pyridin-6-yl]urea, Stereoisomer A | Calc'd 386, found 386 | Scheme 1 |

TABLE 14-continued

| Ex | Structure | IUPAC Name | Exact Mass [M + H]+ | Route Used (Intermediate Used) |
|---|---|---|---|---|
| 575 | 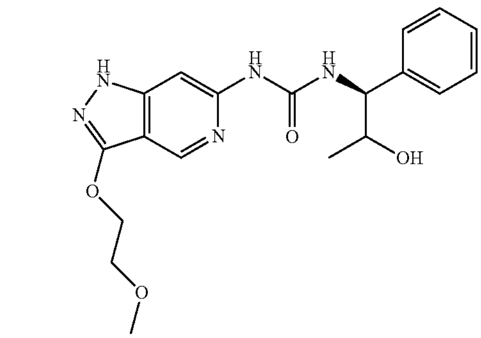 [SMILES: COCCOc1n[nH]c2cc(NC(=O)N[C@@H](c3ccccc3)C(C)O)ncc12] | 1-[(1S)-2-hydroxy-1-phenylpropyl]-3-[3-(2-methoxyethoxy)-1H-pyrazolo[4,3-c]pyridin-6-yl]urea, Stereoisomer B | Calc'd 386, found 386 | Scheme 1 |
| 576 | 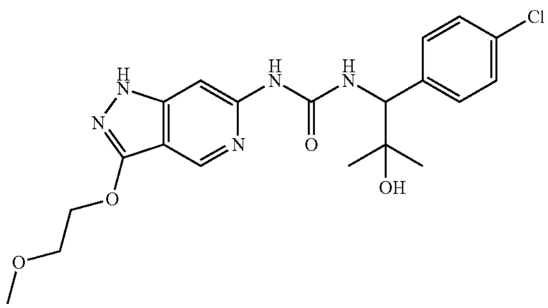 [SMILES: COCCOc1n[nH]c2cc(NC(=O)NC(c3ccc(Cl)cc3)C(C)(C)O)ncc12] | 1-[1-(4-chlorophenyl)-2-hydroxy-2-methylpropyl]-3-[3-(2-methoxyethoxy)-1H-pyrazolo[4,3-c]pyridin-6-yl]urea, Stereoisomer A | Calc'd 434, found 434 | Scheme 1 |
| 577 | 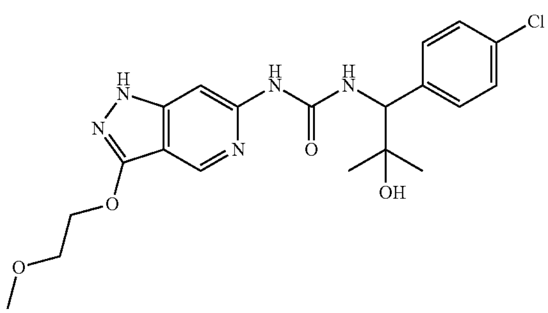 [SMILES: COCCOc1n[nH]c2cc(NC(=O)NC(c3ccc(Cl)cc3)C(C)(C)O)ncc12] | 1-[1-(4-chlorophenyl)-2-hydroxy-2-methylpropyl]-3-[3-(2-methoxyethoxy)-1H-pyrazolo[4,3-c]pyridin-6-yl]ure, Enantiomer B | Calc'd 434, found 434 | Scheme 1 |
| 578 | 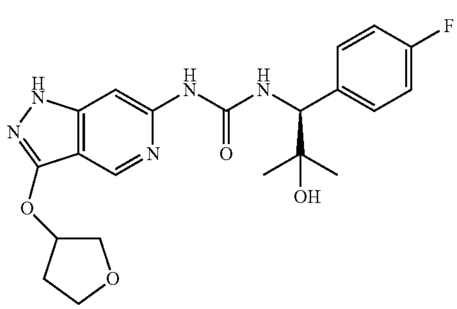 [SMILES: CC(C)(O)[C@@H](NC(=O)Nc1cc2[nH]nc(OC3CCOC3)c2cn1)c1ccc(F)cc1] | 1-[(1S)-1-(4-fluorophenyl)-2-hydroxy-2-methylpropyl]-3-[3-(tetrahydrofuran-3-yloxy)-1H-pyrazolo[4,3-c]pyridin-6-yl]urea, Stereoisomer A | Calc'd 430, found 430 | Scheme 1 |

TABLE 14-continued

| Ex | Structure | IUPAC Name | Exact Mass [M + H]+ | Route Used (Intermediate Used) |
|---|---|---|---|---|
| 579 | 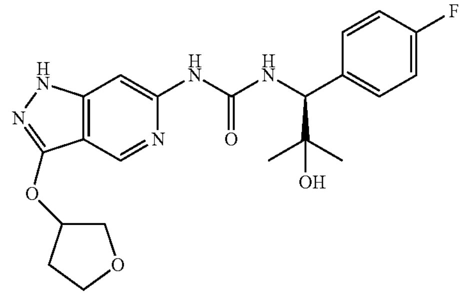 [SMILES: CC(C)(O)[C@@H](NC(=O)Nc1cc2[nH]nc(OC3CCOC3)c2cn1)c1ccc(F)cc1] | 1-[(1S)-1-(4-fluorophenyl)-2-hydroxy-2-methylpropyl]-3-[3-(tetrahydrofuran-3-yloxy)-1H-pyrazolo[4,3-c]pyridin-6-yl]urea, Stereoisomer B | Calc'd 430, found 430 | Scheme 1 |

Assays
Active Human ERK2 (hERK2) Activity Assay:

Activated ERK2 activity was determined in an IMAP-FP assay (Molecular Devices). Using this assay format, the potency ($IC_{50}$) of each compound was determined from a 10 point (1:3 serial dilution, 3 µM starting compound concentration) titration curve using the following outlined procedure. To each well of a black Corning 384-well plate (Corning Catalog #3575), 7.5 nL of compound (3333 fold dilution in final assay volume of 25 µL) was dispensed, followed by the addition of 15 µL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 µL kinase buffer containing 2.45 µM ERK2 IMAP substrate peptides (2.25 µM-unlabeled IPTTPITTTYFFFK-COOH and 200 nM-labeled IPTTPITT-TYFFFK-SFAM (5-carboxyfluorescein)-COOH), and 75 µM ATP. The final reaction in each well of 25 µL consists of 0.5 nM hERK2, 900 nM unlabeled peptide, 80 nM labeled-peptide, and 30 µM ATP. Phosphorylation reactions were allowed to proceed for 60 minutes and were immediately quenched by the addition of 60 µL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer). The AERK2 $IC_{50}$ in nanomolar (nM) for the compounds of Examples 1 to 81 is in Table 15.

TABLE 15

AERK2 $IC_{50}$ In nM

| Ex | $IC_{50}$ | Ex | $IC_{50}$ | Ex | $IC_{50}$ | Ex | $IC_{50}$ |
|---|---|---|---|---|---|---|---|
| 1 | 2.18 | 22 | 18 | 43 | 1.23 | 64 | 1.25 |
| 2 | 1.53 | 23 | 1.21 | 44 | 1.04 | 65 | 8.16 |
| 3 | 1680 | 24 | 30.29 | 45 | 8.16 | 66 | 1570 |
| 4 | 10.44 | 25 | 19.28 | 46 | 1.42 | 67 | 5.80 |
| 5 | 226 | 26 | 4.11 | 47 | 3.29 | 68 | 977.8 |
| 6 | 159.4 | 27 | 21.51 | 48 | 2.77 | 69 | 2.49 |
| 7 | 6.30 | 28 | 1.89 | 49 | 65.75 | 70 | 0.34 |
| 8 | 2.59 | 29 | 0.57 | 50 | 9.34 | 71 | 2.17 |
| 9 | 5.27 | 30 | 12.88 | 51 | 8.88 | 72 | 0.92 |
| 10 | 8.51 | 31 | 3.82 | 52 | 24.1 | 73 | 8.89 |
| 11 | 11.8 | 32 | 6.56 | 53 | 5.29 | 74 | 317.4 |
| 12 | 14.52 | 33 | 6.49 | 54 | 8.23 | 75 | 266.2 |
| 13 | 5.03 | 34 | 0.42 | 55 | 748.4 | 76 | 31.67 |
| 14 | 26.42 | 35 | 22.62 | 56 | 579.6 | 77 | 6.91 |
| 15 | 657.1 | 36 | 3.26 | 57 | 1.64 | 78 | 269.7 |
| 16 | 23.21 | 37 | 8.73 | 58 | 3000 | 79 | 35.89 |
| 17 | 20.6 | 38 | 8.66 | 59 | 362.2 | 80 | 30.64 |

TABLE 15-continued

AERK2 $IC_{50}$ In nM

| Ex | $IC_{50}$ | Ex | $IC_{50}$ | Ex | $IC_{50}$ | Ex | $IC_{50}$ |
|---|---|---|---|---|---|---|---|
| 18 | 38.47 | 39 | 8.03 | 60 | 1410 | 81 | 63.13 |
| 19 | 17.91 | 40 | 17.65 | 61 | 64.03 | | |
| 20 | 9.20 | 41 | 7.36 | 62 | 4.10 | | |
| 21 | 11.96 | 42 | 25.72 | 63 | 169.5 | | |

The AERK2 $IC_{50}$ in nanomolar (nM) for the compounds of Examples 100-113 and 200-579 is in Tables 16-19.

TABLE 16

AERK2 $IC_{50}$ In nM

| Ex | $IC_{50}$ | Ex | $IC_{50}$ | Ex | $IC_{50}$ | Ex | $IC_{50}$ |
|---|---|---|---|---|---|---|---|
| 100 | 19.0 | 216 | 133.3 | 246 | 1036.0 | 275 | 2.3 |
| 101 | 43.0 | 217 | 26.1 | 247 | 7.7 | 276 | 4.3 |
| 102 | 1.2 | 218 | 1260.0 | 248 | 142.6 | 277 | 1.0 |
| 103 | 1.7 | 219 | 73.6 | 249 | 53.0 | 278 | 169.4 |
| 104 | 1212.0 | 220 | 5.8 | 250 | 208.5 | 279 | 227.2 |
| 105 | 1507.0 | 221 | 705.7 | 251 | 40.5 | 280 | 267.3 |
| 106 | 25.6 | 222 | 314.3 | 252 | 64.2 | 281 | 199.1 |
| 107 | 0.4 | 223 | 135.0 | 253 | 29.6 | 282 | 968.3 |
| 108 | 4.6 | 224 | 166.2 | 254 | 5.4 | 283 | 3.4 |
| 109 | 2.1 | 225 | 5.9 | 255 | 11.9 | 284 | 144.2 |
| 110 | 1.8 | 226 | 116.1 | 256 | 21.4 | 285 | 84.9 |
| 111 | 1807.0 | 227 | 1.0 | 256 | 0.7 | 286 | 212.5 |
| 112 | 1.2 | 228 | 181.3 | 257 | 2.5 | 287 | 83.3 |
| 113 | 2.7 | 229 | 1.5 | 258 | 63.2 | 288 | 470.4 |
| 200 | 121.2 | 230 | 0.8 | 259 | 16.3 | 289 | 65.9 |
| 201 | 165.0 | 231 | 135.8 | 260 | 1.9 | 290 | 63.1 |
| 202 | 494.8 | 232 | 1.2 | 261 | 8.4 | 291 | 41.3 |
| 203 | 1610.0 | 233 | 1.8 | 262 | 139.8 | 292 | 14.0 |
| 204 | 80.9 | 234 | 1.2 | 263 | 281.1 | 293 | 97.1 |
| 205 | 0.5 | 235 | 9.4 | 264 | 5.0 | 294 | 53.1 |
| 206 | 0.8 | 236 | 2.0 | 265 | 1.5 | 295 | 42.2 |
| 207 | 0.5 | 237 | 1.4 | 266 | 1.4 | 296 | 29.5 |
| 208 | 0.4 | 238 | 4.0 | 267 | 7.9 | 297 | 20.3 |
| 209 | 0.8 | 239 | 5.9 | 268 | 6.8 | 298 | 160.4 |
| 210 | 0.5 | 240 | 24.8 | 269 | 8.8 | 299 | 300.4 |
| 211 | 189.9 | 241 | 365.7 | 270 | 50.4 | 300 | 77.9 |
| 212 | 1.7 | 242 | 65.9 | 271 | 3.5 | 301 | 73.3 |
| 213 | 20.2 | 243 | 5.7 | 272 | 1.8 | 302 | 27.8 |
| 214 | 4.2 | 244 | 3.4 | 273 | 28.9 | 303 | 109.5 |
| 215 | 463.9 | 245 | 378.2 | 274 | 1402.0 | 304 | 100.7 |

TABLE 17

AERK2 IC$_{50}$ In nM

| Ex | IC$_{50}$ | Ex | IC$_{50}$ | Ex | IC$_{50}$ | Ex | IC$_{50}$ |
|---|---|---|---|---|---|---|---|
| 305 | 7.5 | 334 | 1.5 | 363 | 0.5 | 392 | 41.9 |
| 306 | 1.9 | 335 | 1.5 | 364 | 1583.0 | 393 | 1172.0 |
| 307 | 1.6 | 336 | 5.3 | 365 | 958.3 | 394 | 63.9 |
| 308 | 3.1 | 337 | 1.2 | 366 | 2.1 | 395 | 10.2 |
| 309 | 5.4 | 338 | 544.3 | 367 | 1.4 | 396 | 2.2 |
| 310 | 3.1 | 339 | 4.0 | 368 | 113.1 | 397 | 821.2 |
| 311 | 1.9 | 340 | 1.1 | 369 | 32.3 | 398 | 1.6 |
| 312 | 16.8 | 341 | 614.3 | 370 | 10.7 | 399 | 1.2 |
| 313 | 2.4 | 342 | 2.9 | 371 | 106.0 | 400 | 1.5 |
| 314 | 8.7 | 343 | 30.2 | 372 | 105.4 | 401 | 1.4 |
| 315 | 2.9 | 344 | 13.7 | 373 | 67.0 | 402 | 8.1 |
| 316 | 19.8 | 345 | 30.9 | 374 | 164.4 | 403 | 32.9 |
| 317 | 3.2 | 346 | 18.5 | 375 | 1013.0 | 404 | 11.4 |
| 318 | 5.5 | 347 | 7.4 | 376 | 2.2 | 405 | 17.1 |
| 319 | 211.1 | 348 | 47.8 | 377 | 0.4 | 406 | 15.0 |
| 320 | 17.3 | 349 | 10.4 | 378 | 148.8 | 407 | 8.6 |
| 321 | 85.7 | 350 | 6.2 | 379 | 0.8 | 408 | 6.3 |
| 322 | 2.2 | 351 | 42.5 | 380 | 182.9 | 409 | 5.3 |
| 323 | 6.4 | 352 | 96.6 | 381 | 2.2 | 410 | 133.9 |
| 324 | 4.1 | 353 | 206.1 | 382 | 3.9 | 411 | 524.6 |
| 325 | 1.8 | 354 | 1378.0 | 383 | 9.0 | 412 | 7.7 |
| 326 | 1.1 | 355 | 1.6 | 384 | 71.6 | 413 | 0.9 |
| 327 | 9.2 | 356 | 1.6 | 385 | 44.9 | 414 | 2.3 |
| 328 | 84.0 | 357 | 68.9 | 386 | 1108.0 | 415 | 8.9 |
| 329 | 324.8 | 358 | 104.6 | 387 | 58.5 | 416 | 0.5 |
| 330 | 28.2 | 359 | 39.8 | 388 | 2221.0 | 417 | 0.4 |
| 331 | 49.7 | 360 | 4.6 | 389 | 1254.0 | 418 | 0.6 |
| 332 | 17.4 | 361 | 61.3 | 390 | 3.5 | 419 | 0.5 |
| 333 | 1.6 | 362 | 2.0 | 391 | 3.9 | 420 | 0.7 |
|  |  |  |  |  |  | 421 | 0.5 |

TABLE 18

AERK2 IC$_{50}$ In nM

| Ex | IC$_{50}$ | Ex | IC$_{50}$ | Ex | IC$_{50}$ | Ex | IC$_{50}$ |
|---|---|---|---|---|---|---|---|
| 422 | 0.9 | 449 | 2.5 | 476 | 167.7 | 503 | 0.4 |
| 423 | 0.6 | 450 | 10.1 | 477 | 1.7 | 504 | 10.4 |
| 424 | 0.4 | 451 | 9.3 | 478 | 1.4 | 505 | 4.7 |
| 425 | 0.5 | 452 | 8.6 | 479 | 1.6 | 506 | 12.8 |
| 426 | 0.8 | 453 | 8.9 | 480 | 63.4 | 507 | 0.6 |
| 427 | 0.6 | 454 | 15.2 | 481 | 970.0 | 508 | 2.8 |
| 428 | 1.6 | 455 | 23.7 | 482 | 22.2 | 509 | 0.7 |
| 429 | 0.6 | 456 | 0.5 | 483 | 32.1 | 510 | 2743.0 |
| 430 | 1.3 | 457 | 2.2 | 484 | 4.5 | 511 | 2.0 |
| 431 | 1.1 | 458 | 4.1 | 485 | 23.4 | 512 | 2.4 |
| 432 | 0.7 | 459 | 3.2 | 486 | 68.6 | 513 | 4.3 |
| 433 | 2.0 | 460 | 3.4 | 487 | 8.4 | 514 | 0.7 |
| 434 | 0.5 | 461 | 0.4 | 488 | 1.0 | 515 | 0.5 |
| 435 | 1.0 | 462 | 0.4 | 489 | 9.6 | 516 | 0.6 |
| 436 | 0.4 | 463 | 0.4 | 490 | 49.4 | 517 | 0.3 |
| 437 | 0.6 | 464 | 0.3 | 491 | 19.3 | 518 | 0.3 |
| 438 | 213.7 | 465 | 2.4 | 492 | 12.7 | 519 | 1.1 |
| 439 | 43.2 | 466 | 0.8 | 493 | 1.2 | 520 | 264.6 |
| 440 | 3.8 | 467 | 0.8 | 494 | 1.7 | 521 | 169.1 |
| 441 | 1.1 | 468 | 86.9 | 495 | 13.6 | 522 | 0.5 |
| 442 | 5.5 | 469 | 3.0 | 496 | 7.2 | 523 | 0.7 |
| 443 | 1.3 | 470 | 3.0 | 497 | 0.8 | 524 | 1.0 |
| 444 | 25.4 | 471 | 9.2 | 498 | 0.3 | 525 | 0.8 |
| 445 | 7.6 | 472 | 1.3 | 499 | 0.5 | 526 | 0.5 |
| 446 | 2.7 | 473 | 10.2 | 500 | 0.3 | 527 | 0.4 |
| 447 | 140.0 | 474 | 31.1 | 501 | 0.4 | 528 | 0.6 |
| 448 | 14.7 | 475 | 1.4 | 502 | 0.5 | 529 | 350.2 |

TABLE 19

AERK2 IC$_{50}$ In nM

| Ex | IC$_{50}$ | Ex | IC$_{50}$ | Ex | IC$_{50}$ | Ex | IC$_{50}$ |
|---|---|---|---|---|---|---|---|
| 530 | 2.4 | 543 | 4.9 | 556 | 4.9 | 568 | 1.8 |
| 531 | 103.1 | 544 | 1.8 | 557 | 5.3 | 569 | 0.5 |
| 532 | 430.2 | 545 | 1.9 | 558 | 2.9 | 570 | 0.4 |
| 533 | 128.0 | 546 | 4.1 | 559 | 1.8 | 571 | 358.6 |
| 534 | 21.5 | 547 | 11.8 | 560 | 0.6 | 572 | 0.8 |
| 535 | 0.9 | 548 | 4.2 | 561 | 122.0 | 573 | 0.7 |
| 536 | 0.8 | 549 | 30.3 | 562 | 13.6 | 574 | 0.9 |
| 537 | 276.8 | 550 | 12.2 | 563 | 0.8 | 575 | 0.8 |
| 538 | 10.9 | 551 | 10.6 | 564 | 0.5 | 576 | 1.1 |
| 539 | 1.5 | 552 | 13.4 | 565 | 1.0 | 577 | 119.1 |
| 540 | 25.3 | 553 | 9.8 | 566 | 2.7 | 578 | 0.4 |
| 541 | 6.2 | 54 | 0.5 | 567 | 0.9 | 579 | 1.0 |
| 542 | 0.7 | 555 | 0.3 |  |  |  |  |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

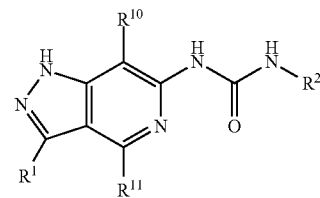

(1.0)

or a pharmaceutically acceptable salt thereof, wherein:
R$^1$ is selected from the group consisting of: —OR$^4$ and —S(O)$_t$R$^5$;
t is 0, 1 or 2;
R$^2$ is selected from the group consisting of: R$^2$ is selected from the group consisting of: H, (C$_6$-C$_{10}$)aryl-(C$_1$-C$_3$alkyl)-heterocycloalkyl-, —(C$_1$-C$_6$alkyl), —(C$_1$-C$_6$alkyl)-O—(C$_1$-C$_6$alkyl), —(C$_1$-C$_6$alkyl)-heterocycloalkyl-(C$_6$-C$_{10}$aryl), —(C$_1$-C$_6$alkyl)(C$_6$-C$_{10}$)aryl, —(C$_1$-C$_4$alkyl)heteroaryl, —(C$_3$-C$_6$cycloalkyl)-(C$_6$-C$_{10}$aryl), -heterocycloalkyl-(C$_6$-C$_{10}$aryl), -fused (heterocycloalkyl)(C$_6$-C$_{10}$)aryl wherein said heterocycloalkyl is a 5 to 8 membered ring (including the two atoms common with said aryl) comprising 1-3 heteroatoms selected from the group consisting of: O, S and N, and wherein the remaining atoms are carbon, -fused ((C$_3$-C$_6$cycloalkyl))(C$_6$-C$_{10}$)aryl, -heterocycloalkyl-C(O)O—(C$_1$-C$_6$alkyl)-(C$_6$-C$_{10}$)aryl, -heterocycloalkyl-(C$_1$-C$_6$alkyl)-heteroaryl, heterocycloalkyl, (C$_3$-C$_6$ cycloalkyl)-(C$_1$-C$_6$alkyl)- and —(C$_3$-C$_6$cycloalkyl);
and wherein said aryl (including the aryl moiety of said fused heterocycloalkylaryl, and fused cycloalkylaryl groups), heterocycloalkyl (including the heterocycloalkyl moiety of said fused heterocycloalkylaryl group), heteroaryl, and cycloalkyl (including the cycloalkyl moiety of said fused cycloalkylaryl group) moieties of said R$^2$ groups are optionally substituted with 1-3 substituents independently selected from the group consisting of: halo, —O—(C$_1$-C$_6$alkyl), —OH, —CF$_3$, —(C$_1$-C$_6$alkyl), —S(O)$_r$(C$_1$-C$_6$alkyl) wherein r is 0, 1 or 2, —(C$_1$-C$_6$alkyl)-(C$_3$-C$_6$ cycloalkyl), —C(O)—(C$_1$-C$_6$alkyl)-OH, (hydroxyl substituted —(C$_1$-C$_6$alkyl)), —(C$_1$-C$_6$alkyl)(C$_6$-C$_{10}$) aryl, —(C$_1$-C$_6$alkyl)(halo substituted (C$_6$-C$_{10}$)aryl), —C(O)O(C$_1$-C$_6$alkyl), —C(O)(C$_1$-C$_6$alkyl), (halo substituted —(C$_1$-C$_6$alkyl)), —O-(halo substituted (C$_1$-C$_6$alkyl)), —C(O)N(C$_1$-C$_6$alkyl)$_2$ wherein each alkyl is selected independently, —C(O)NH(C$_1$-C$_6$alkyl), —N(C$_1$-C$_6$alkyl)$_2$ wherein each alkyl is independently selected, and —NH(C$_1$-C$_6$alkyl);

and wherein said alkyl moieties of said R$^2$ groups are optionally substituted with 1-3 substituents independently selected from the group consisting of: halo, —O—(C$_1$-C$_6$alkyl), —OH and —CF$_3$, —S(O), (C$_1$-C$_6$alkyl) wherein r is 0, 1 or 2, —(C$_3$-C$_6$cycloalkyl), (hydroxy substituted —(C$_3$-C$_6$cycloalkyl)), heteroaryl, -heteroaryl-(C$_1$-C$_6$alkyl), heterocycloalkyl, —S(O)$_t$(C$_1$-C$_6$alkyl) (wherein t is 0, 1, or 2), —C(O)O(C$_1$-C$_6$alkyl), —O-(halo substituted —(C$_1$-C$_6$alkyl)), —O(C$_1$-C$_6$alkyl)-O—(C$_1$-C$_6$alkyl), —N(C$_1$-C$_6$alkyl)$_2$ wherein each alkyl is independently selected, and —NH(C$_1$-C$_6$alkyl);

R$^4$ is selected from the group consisting of: —(C$_1$-C$_6$alkyl)-O—(C$_1$-C$_6$alkyl), —(C$_1$-C$_6$alkyl)(C$_6$-C$_{10}$aryl), —(C$_1$-C$_6$alkyl), —(C$_1$-C$_6$alkyl)-heteroaryl, —(C$_1$-C$_6$alkyl)-C(O)—N(C$_1$-C$_6$alkyl)$_2$ (wherein each alkyl moiety is independently selected), —(C$_1$-C$_6$alkyl)-heterocycloalkyl, heterocycloalkyl, —(C$_1$-C$_6$alkyl)-(C$_3$-C$_6$cycloalkyl), —(C$_1$-C$_6$alkyl)-N(C$_1$-C$_6$alkyl)$_2$ wherein each alkyl is independently selected, -(hydroxy substituted (C$_1$-C$_6$alkyl)), -heteroaryl and —(C$_3$-C$_6$cycloalkyl);

and wherein said aryl, cycloalkyl, heteroaryl, and heterocycloalkyl moieties of said R$^4$ groups are optionally substituted with 1-3 substitutents independently selected from the group consisting of: halo (e.g., F, Br, and Cl, and in one example F), =O, —CN, —O(C$_1$-C$_6$alkyl) and —(C$_1$-C$_6$ alkyl);

and wherein the alkyl moieties of said R$^4$ groups are optionally substituted with 1-3 substituents independently selected from the group consisting of: —OH, halo (e.g., F, Br, and Cl, and in one example F), and —O(C$_1$-C$_6$alkyl);

R$^5$ is selected from the group consisting of: —(C$_1$-C$_6$alkyl), and —(C$_1$-C$_6$alkyl)-O—(C$_1$-C$_6$alkyl); and wherein said alkyl moieties of said R$^5$ groups are optionally substituted with 1-3 substitutents independently selected from the group consisting of: halo, and —O(C$_1$-C$_6$alkyl); and R$^{10}$ and R$^{11}$ are each independently selected from the group consisting of: H, halo, —(C$_1$ to C$_6$alkyl), —(C$_3$-C$_6$ cycloalkyl), hydroxy substituted —(C$_1$-C$_6$alkyl), —(C$_1$-C$_6$alkyl)-O—(C$_1$-C$_6$alkyl), —(C$_1$-C$_6$alkyl)-N(C$_1$-C$_6$alkyl)$_2$ wherein each alkyl is independently selected, —(C$_1$-C$_6$alkyl)-heterocycloalkyl, —NH$_2$, —N(C$_1$-C$_6$alkyl)$_2$ wherein each alkyl is independently selected, —NH(C$_1$-C$_6$alkyl), —(C$_1$-C$_6$alkyl)NH(C$_1$-C$_6$alkyl), —(C$_1$-C$_6$alkyl)NH$_2$, —NHC(O)(C$_1$-C$_6$alkyl), —NH—(C$_6$-C$_{10}$aryl)-O(C$_1$-C$_6$alkyl), —C(O)OH, —CN, heteroaryl, -(heteroaryl-((C$_1$-C$_6$alkyl)-OH), —((C$_1$-C$_6$alkyl)heteroaryl), —C(O)-heterocycloalkyl, -oxoheteroaryl, —C(O)NH$_2$, —C(O)N(C$_1$-C$_6$alkyl)$_2$ wherein each alkyl is independently selected, —C(O)NH(C$_1$-C$_6$alkyl), —(C$_1$-C$_6$alkyl)-(C$_3$-C$_6$cycloalkyl), (hydroxy substituted —(C$_1$-C$_6$alkyl)-(C$_3$-C$_6$cycloalkyl)), —(C$_1$-C$_6$alkyl)-O—C(O)—(C$_1$-C$_6$alkyl), —C(O)—(C$_1$-C$_6$alkyl), —(C$_1$-C$_6$alkyl)-O—C(O)—NH(C$_1$-C$_6$alkyl), —(C$_1$-C$_6$alkyl)-O—C(O)—N(C$_1$-C$_6$alkyl)$_2$ wherein each alkyl is independently selected, —(C$_1$-C$_6$alkyl)-(oxoheterocycloalkyl), —(C$_1$-C$_6$alkyl)-O-heterocyloalkyl, halo substituted (C$_1$-C$_6$alkyl), —(C$_1$-C$_6$alkyl)heteroaryl, —(C$_1$-C$_6$alkyl)-((C$_1$-C$_6$)alkoxy) substituted heteroaryl), —(C$_1$-C$_6$alkyl)-O—(C$_1$-C$_6$alkyl)-OH, —(C$_1$-C$_6$alkyl)-O—(C$_3$-C$_6$ cycloalkyl)-OH, and —(C$_1$-C$_6$alkyl)-OH.

2. The compound of claim 1 wherein R$^1$ is —OR$^4$.

3. The compound of claim 1 wherein R$^1$ is —S(O)$_r$R$^5$.

4. The compound of claim 1 wherein R$^1$ is selected from the group consisting of:

—O—CH$_2$CH$_2$—OCH$_3$, —O—CH$_2$-phenyl, —O—CH$_3$, —O—CD$_3$, —OCH(F)$_2$, —OCH$_2$CH$_3$, —OCH$_2$CHF$_2$, —O(CH$_2$)$_3$CF$_3$, —OCH$_2$C(CH$_3$)$_2$OCH$_3$, —O(CH$_2$)NCH$_3$)$_2$, —OCH$_2$CH(OH)CH$_2$CH$_3$, —OCH$_2$CH(OH)CH$_2$OH, —OCH$_2$CH(CH$_3$)CH$_2$OH, —OCH$_2$CH(CH$_3$)OH, —OCH$_2$CH(OH)CH$_2$F, —OCH$_2$CH(OH)CF$_3$, —OCH$_2$CH$_2$OCHF$_2$, —OCH$_2$CH$_2$OCF$_3$, —O(CH$_2$)$_2$OH, —O(CH$_2$)$_2$OCH$_3$, —OCH(CH$_3$)CH$_2$OCH$_3$, —O(CH$_2$)$_2$OCH$_3$, —O(CH$_2$)$_2$OCH$_2$CH$_3$, —O—CH$_2$-pyridyl, —O—CH$_2$—C(O)—N(CH$_3$)$_2$, —O—CH$_2$-oxetanyl, —O—CH$_2$-tetrahydrofuranyl, —O—CH$_2$-tetrahydropyranyl, —O—CH$_2$-azetidinyl, —O—CH$_2$-pyrrolidinyl, —O—CH$_2$-piperidinyl, —O—CH$_2$-piperazinyl, —O—CH$_2$-morpholinyl, —O—CH$_2$-thietanyl, —O—CH$_2$-tetrahydrothiophenyl (O—CH$_2$-tetrahydrothienyl), —O—CH$_2$-tetrahydrothiopyranyl, —O—CH$_2$-thiazolyl, —O—CH$_2$-methylisoxazolyl, —O—(CH$_2$)$_2$-pyrazolyl, —O—(CH$_2$)$_2$-methylimidazolyl, —OCH$_2$oxopyrrolidinyl, —O(CH$_2$)$_2$oxopyrrolidinyl, —O(CH$_2$)$_2$piperidinyl, —O-phenyl, —Otetrahydrofuranyl, —Opiperidinyl, —Omethyltetrahydro-pyranyl, —Ocyanocyclohexyl, —Omethoxymethylcyclohexyl, —Odimethyltetrahydropyranyl, —O-oxetanyl, —O-tetrahydrofuranyl, —O-tetrahydropyranyl, —O-azetidinyl, —O-pyrrolidinyl, —O-piperidinyl, —O-piperazinyl, —O-morpholinyl, —O-thietanyl, —O-tetrahydrothiophenyl (—O-tetrahydrothienyl), —O-tetrahydrothiopyranyl, —CH$_2$-cyclopropyl, —CH$_2$-cyclobutyl, —CH$_2$-cyclopentyl, —CH$_2$-cyclohexyl, and —O—CH$_2$CH$_2$—OH.

5. The compound of claim 1 wherein R$^1$ is selected from the group consisting of:

—SCH$_3$, —SCH$_2$CH$_3$, —SCH$_2$CH$_2$—O—CH$_3$, and —S(O)$_2$CH$_3$.

6. The compound of claim 1 wherein R$^2$ is selected from the group consisting of:

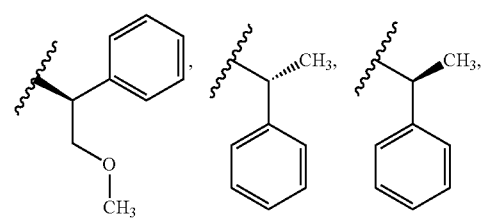

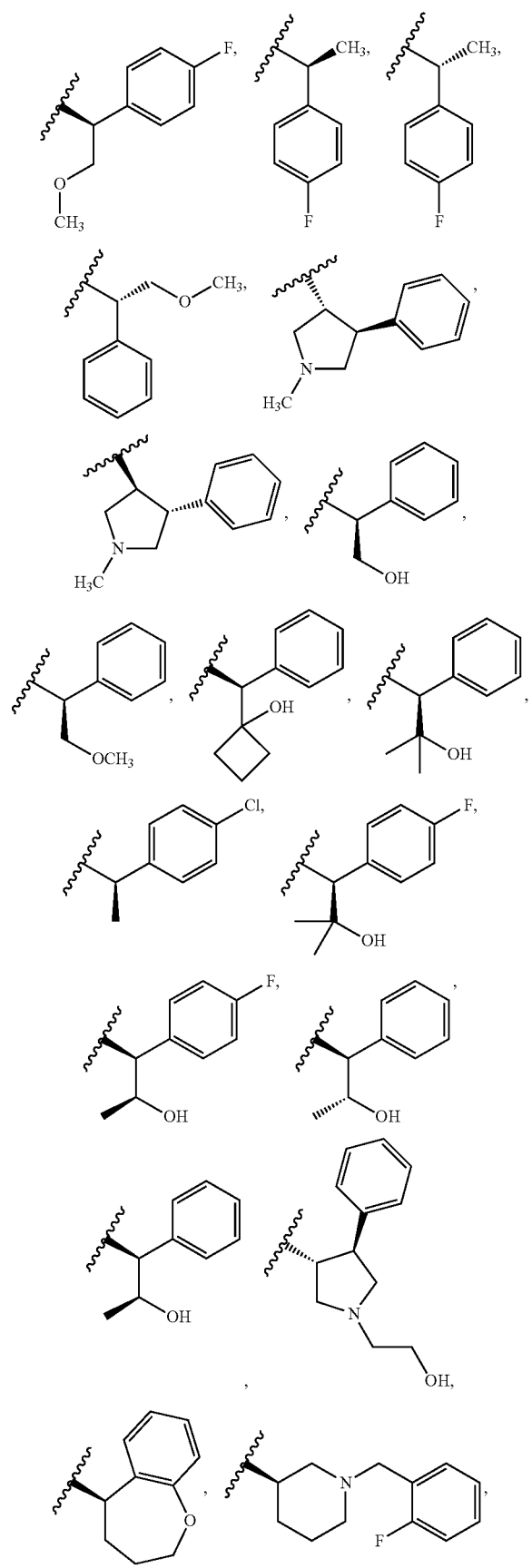
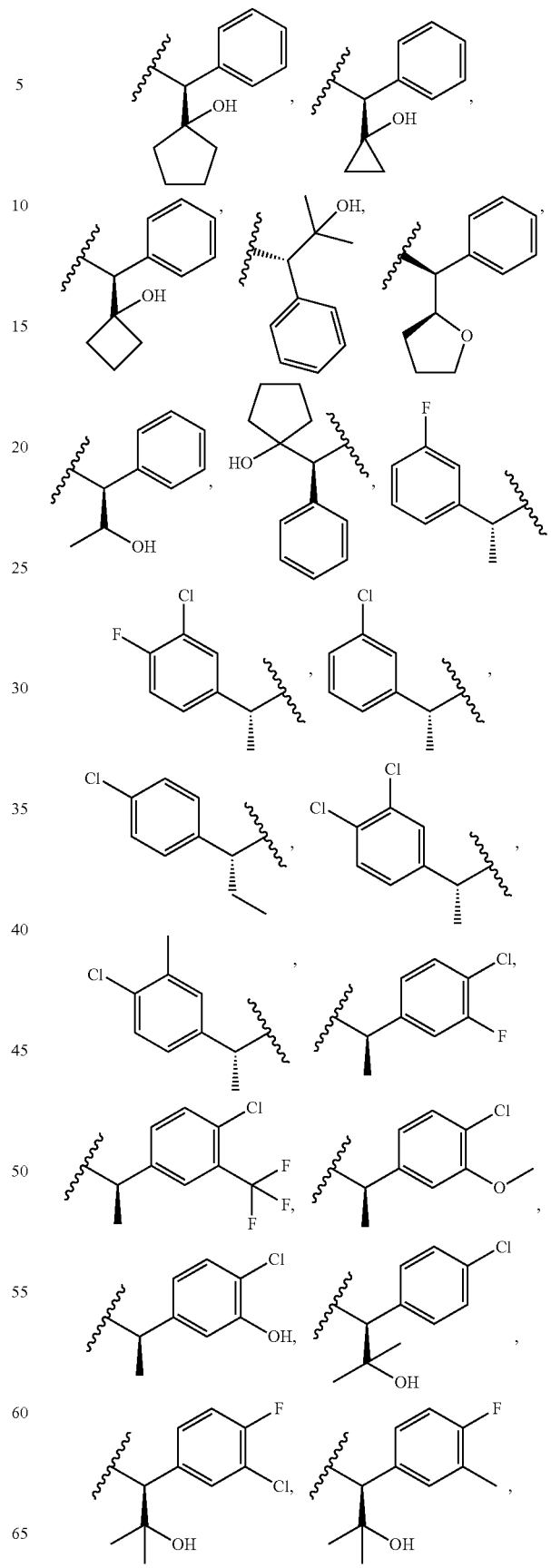

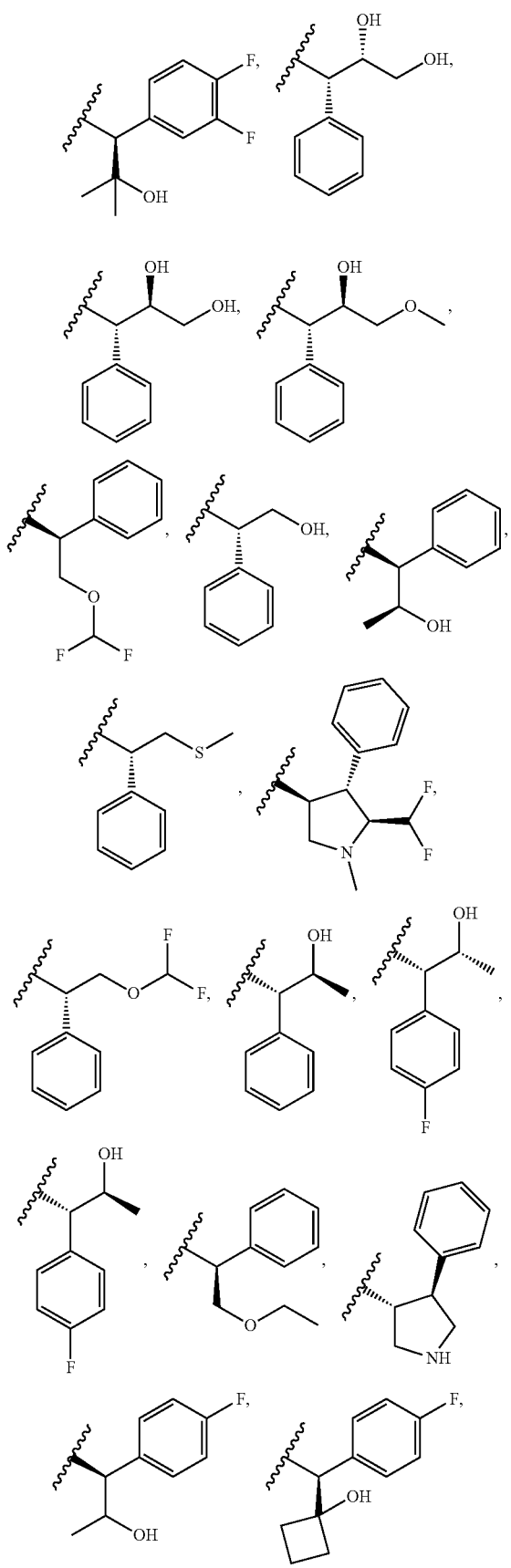
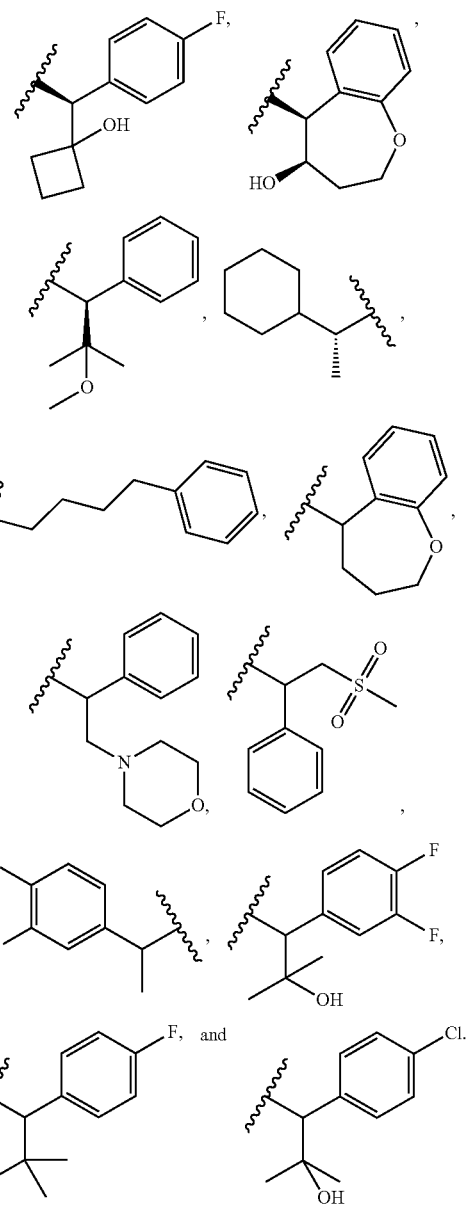

7. The compound of claim 1 wherein (1) $R^1$ is selected from the group consisting of: —O(CH$_2$)$_2$OCH$_3$, —OCH$_3$, —O(CH$_2$)$_2$OH, —OCH$_2$CHF$_2$, —OCH$_2$CH$_3$, —O(CH$_2$)$_3$CF$_3$, —OCH$_2$CH(OH)—CH$_2$CH$_3$, —OCH$_2$CH(CH$_2$OH)OH, —OCH$_2$tetrahydropyranyl, —OCH$_2$CH(CH$_3$)CH$_2$OH, $R^1$ is —OCH$_2$tetrahydrofuranyl, —OCH$_2$CH(OH)CH$_2$F, —Othiazolyl, —O(CH$_2$)$_2$pyrazolyl, —O(CH$_2$)$_2$methylimidazolyl, —O(CH$_2$)$_2$oxopyrrolidinyl, —Otetrahydrofuranyl, —OCH$_2$CH—(OH)CF$_3$, —O(CH$_2$)$_2$OCHF$_2$, —O(CH$_2$)$_2$OCH$_3$, —OCH$_2$C(CF$_3$)OH, —O(CH$_2$)$_2$OCF$_3$, —Otetra-hydropyranyl, —O(CH$_2$)$_2$OCH$_2$CH$_3$, —SCF$_3$, —OCH(CH$_3$)CH$_2$OCH$_3$, —OCH$_2$pyridyly, —Otetra-hydropyranyl, —Ocyanocyclohexyl, —Omethyltetrahydropyranyl, —Odimethyltetrahydropyranyl, —OCH$_2$CH(CH$_3$)OH, —OCH$_2$pyridyl and —O(CH$_2$)$_2$OCH$_2$CH$_3$; (2) $R^2$ is selected from the group consisting of:

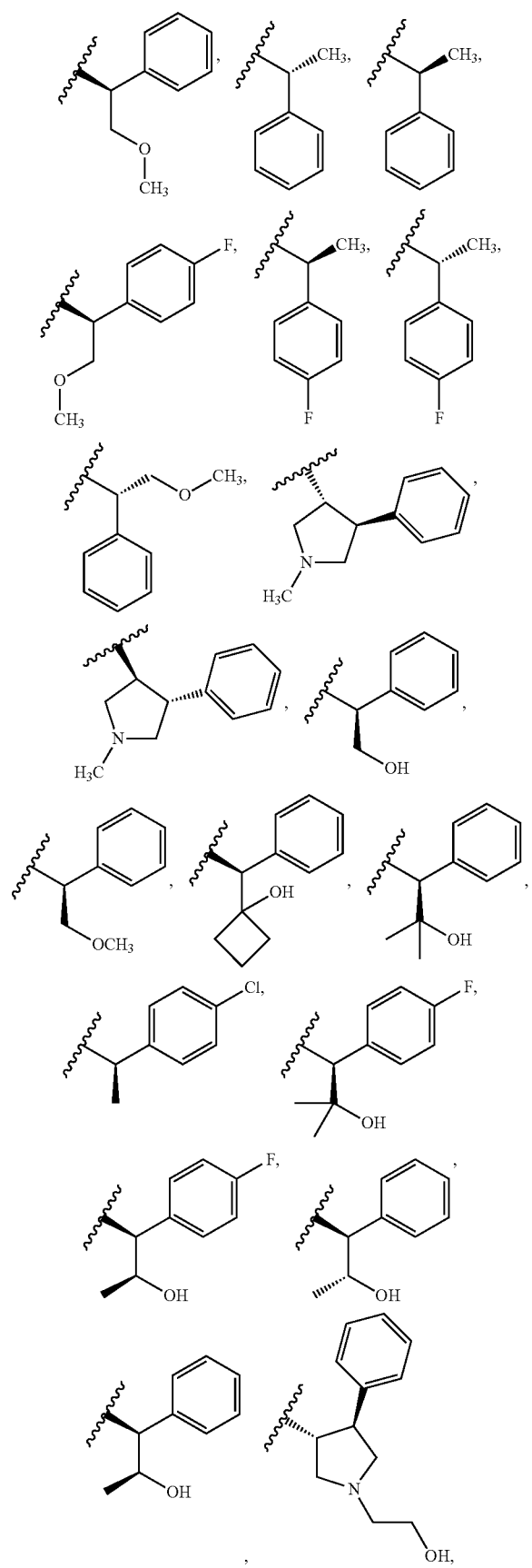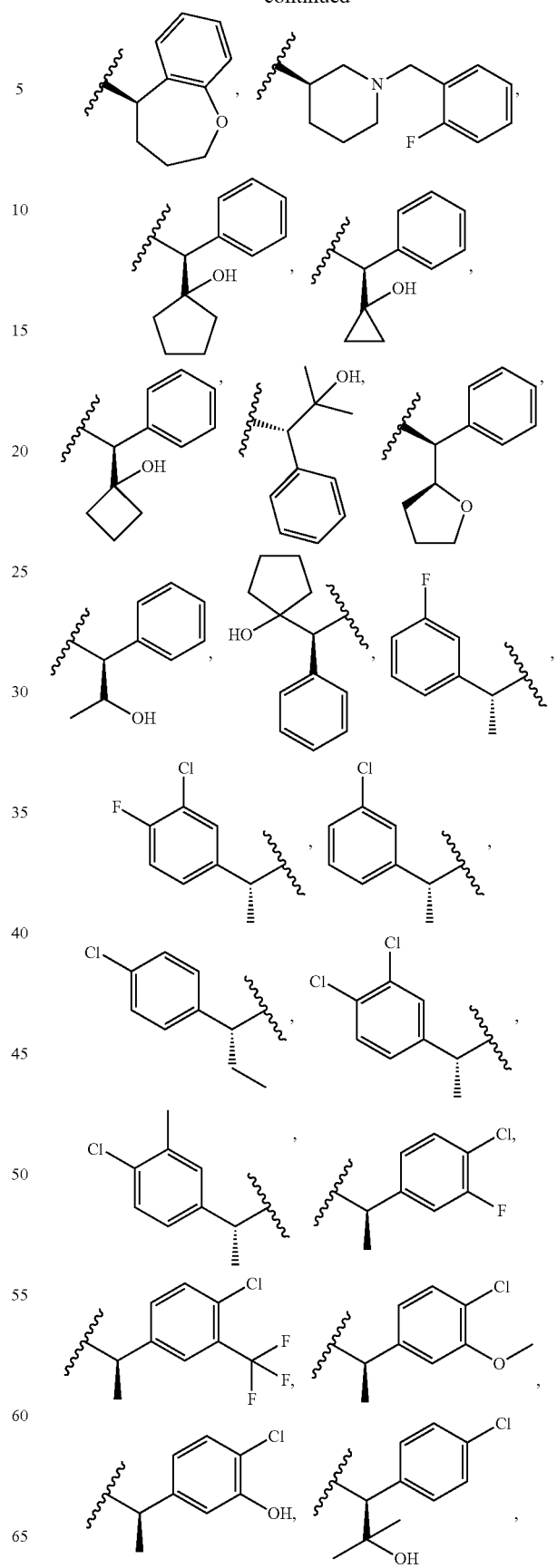

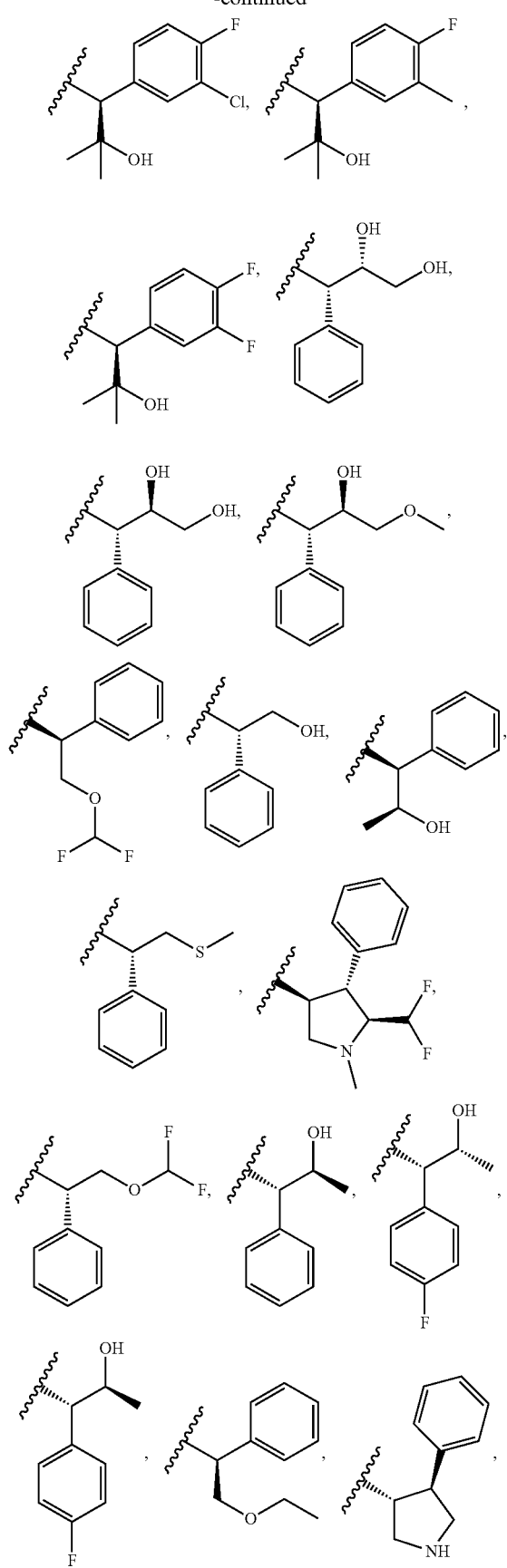
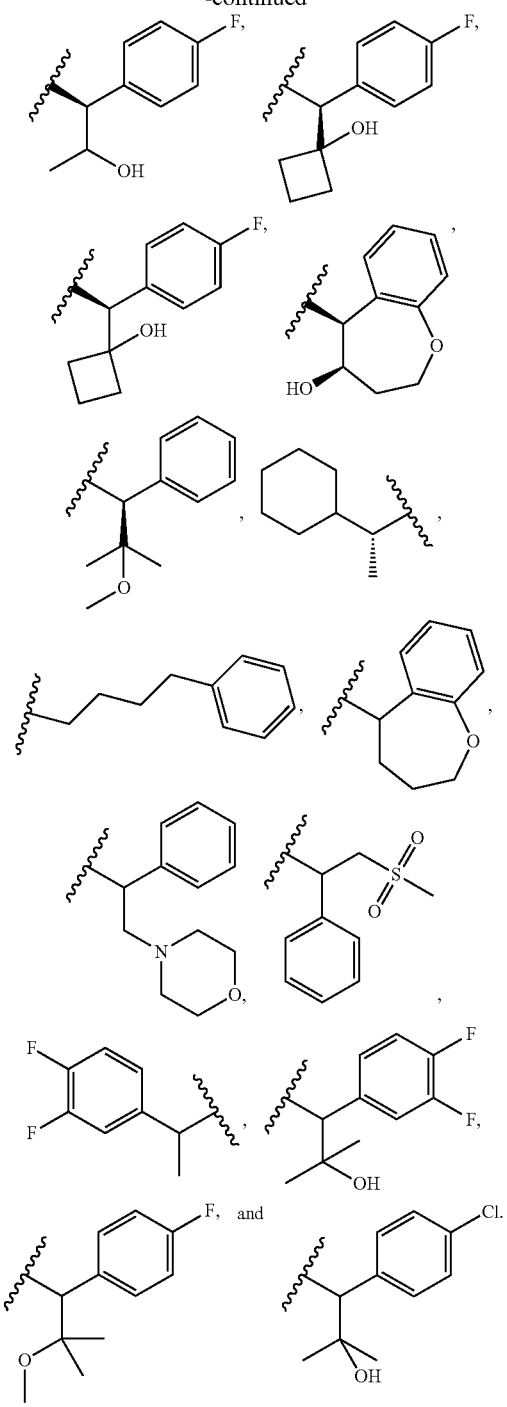

(3) $R^{10}$ is selected from the group consisting of H and F; and (4) $R^{11}$ is selected from the group consisting of: —$CH_2OH$, —$CH(OH)CH_3$, —$CH(OH)CH_3$, —$CH(OH)CH_2CH_3$, -pyridyl-$CH_2OH$, —CH(OH)cyclopropyl, —$CH_2OC(O)CH_3$, -methyloxadiazolyl, -methylthiadiazolyl, —$NH_2$, —$NHCH_3$, —$NHCH_2CH_3$, methylpyridyl, —$NHC(O)CH_3$, pyrazolyl, oxazolyl, $R^{11}$ is methylpyrimidinyl, —$CH_2OC(O)NHCH_3$, —$CH_2$imidazolyl, —$CH_3$, —$CHF_2$, —$CH_2OCH_3$, —$CH_2$oxooxazolidinyl, —$CH_2O(CH_2)_2OH$, —$CH_2$triazolyl and —$CH(CH_3)OH$.

8. The compound of claim 1 wherein $R^{10}$ is selected from the group consisting of: H, F, Cl, Br, methyl, ethyl, isopropyl, cyclopropyl, —CH(OH)CH$_3$, —CH$_2$OCH$_3$, —CH$_2$—N(CH$_3$)$_2$, and —CH$_2$-morpholinyl.

9. The compound of claim 1 wherein $R^{11}$ is selected from the group consisting of: H, F, Cl, Br, —CF$_3$, —CHF$_2$, —CN, —NH$_2$, —NH(CH$_3$), —NH(CH$_3$)$_2$, —NHC(O)CH$_3$, —NH-phenyl-O—CH$_3$, methyl, ethyl, isopropyl, cyclopropyl, —CH$_2$OC(O)OCH$_3$, —CH$_2$OH, —CH(OH)CH$_3$, —CH(OH)CH$_2$CH$_3$, —CH$_2$OCH$_3$, —CH$_2$—N(CH$_3$)$_2$, —CH(OH)cyclopropyl, —C(O)CH$_3$, —CH$_2$-morpholinyl, methyloxadiazolyl-, methylpyridyl-, methylthiadiazolyl-, pyrazolyl, oxodihydrooxadiazolyl-, C(O)NHCH$_3$, —C(O)N(CH$_3$)$_2$, —NH$_2$, —CH$_2$OC(O)NHCH$_3$, —CH$_2$O(CH$_2$)$_2$OH, —CH$_2$oxo-oxazolidinyl, —CH$_2$oxopyrrolidinyl, —CH$_2$—O-oxetanyl, —CH$_2$pyrazolyl, —CH$_2$NHCH$_3$, —CH$_2$OCH$_2$CH$_3$, methylpyrimidinyl-, methylpyrazolyl-, —CH$_2$(methoxypyrazolyl), —CH$_2$triazolyl, —CH$_2$imidazolyl, —CH$_2$O(hydroxycyclopentyl), —CH$_2$OCH$_2$CH(CH$_3$)OH, —CH(CH$_3$)OH.

10. The compound of claim 1 wherein $R^1$ is selected from the group consisting of Group I; $R^2$ is selected from the group consisting of: B1, B2, B3, B5, B8, B10, and B25; $R^{10}$ is selected from the group consisting of: H and F; and $R^{11}$ is selected from the group consisting of: H and —CH$_3$; and wherein Group I represents —OCH$_3$, —OCH$_2$CH$_2$OCH$_3$, —OCH$_2$CH$_3$, —OCH$_2$CH$_2$OH,

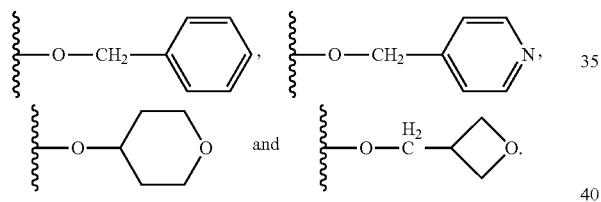

11. The compound of claim 1 wherein $R^1$ is selected from the group consisting of Group I; $R^2$ is selected from the group consisting of: B11, B31, B32, B38, B39, B44, B46, B50, B51, B53, B54, and B62; $R^{10}$ is selected from the group consisting of: H and F; and $R^{11}$ is selected from the group consisting of: H and —CH$_3$; and wherein Group I is as defined above.

12. The compound of claim 1 wherein (1) $R^1$ is selected from the group consisting of: —O(CH$_2$)$_2$OCH$_3$, —OCH$_3$, —O(CH$_2$)$_2$OH, —OCH$_2$CHF$_2$, —OCH$_2$CH$_3$, —O(CH$_2$)$_3$CF$_3$, —OCH$_2$CH(OH)—CH$_2$CH$_3$, —OCH$_2$CH(CH$_2$OH)OH, —OCH$_2$tetrahydropyranyl, —OCH$_2$CH(CH$_3$)CH$_2$OH, —OCH$_2$tetra-hydrofuranyl, —OCH$_2$CH(OH)CH$_2$F, —Othiazolyl, —O(CH$_2$)$_2$pyrazolyl, —O(CH$_2$)$_2$methyl-imidazolyl, —O(CH$_2$)$_2$oxopyrrolidinyl, —Otetrahydro-furanyl, —OCH$_2$CH—(OH)CF$_3$, —O(CH$_2$)$_2$O—CHF$_2$, —O(CH$_2$)$_2$OCH$_3$, —OCH$_2$C(CF$_3$)OH, —O(CH$_2$)$_2$OCF$_3$, —Otetra-hydropyranyl, —O(CH$_2$)$_2$—OCH$_2$CH$_3$, —SCF$_3$, —OCH(CH$_3$)CH$_2$OCH$_3$, —OCH$_2$pyridyly, —Otetra-hydropyranyl, —Ocyanocyclohexyl, —Omethyltetrahydropyranyl, —Odimethyltetrahydropyranyl, —OCH$_2$CH(CH$_3$)OH, —OCH$_2$pyridyl and —O(CH$_2$)$_2$OCH$_2$CH$_3$; (2) $R^2$ is selected from the group consisting of:

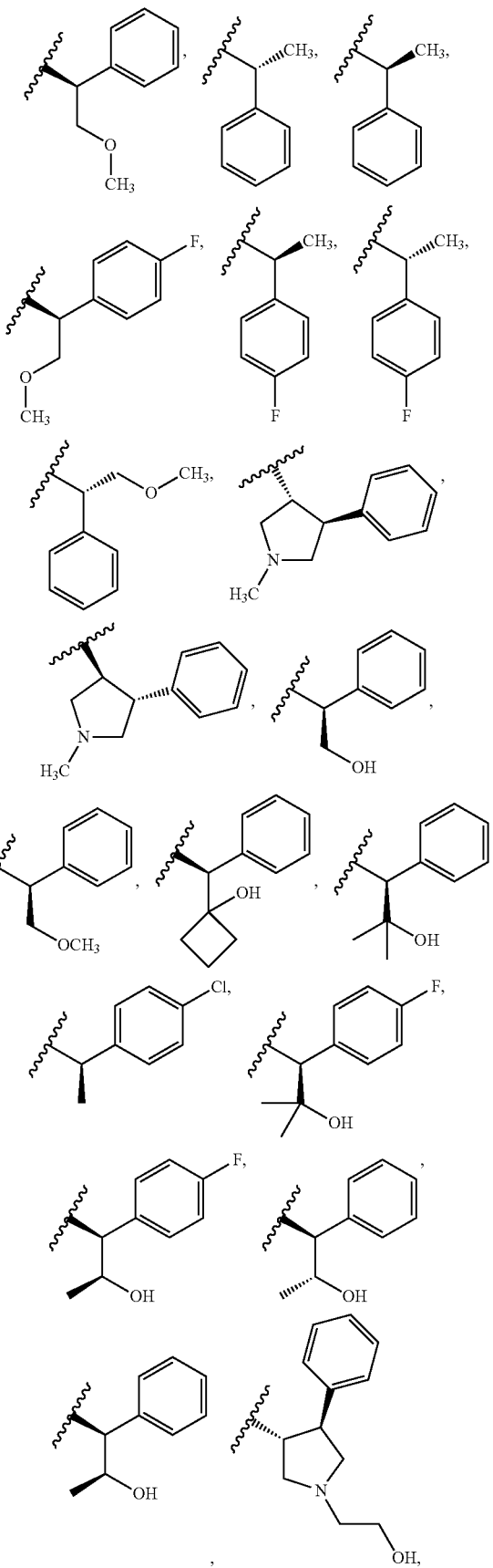

389
-continued
390
-continued
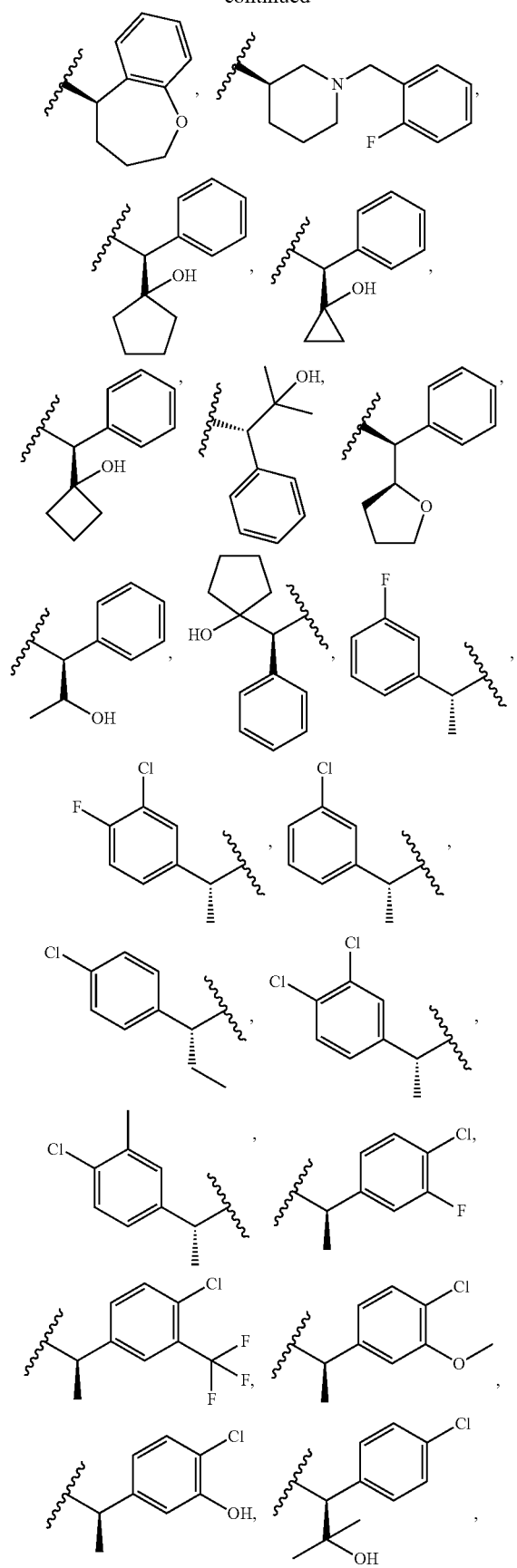
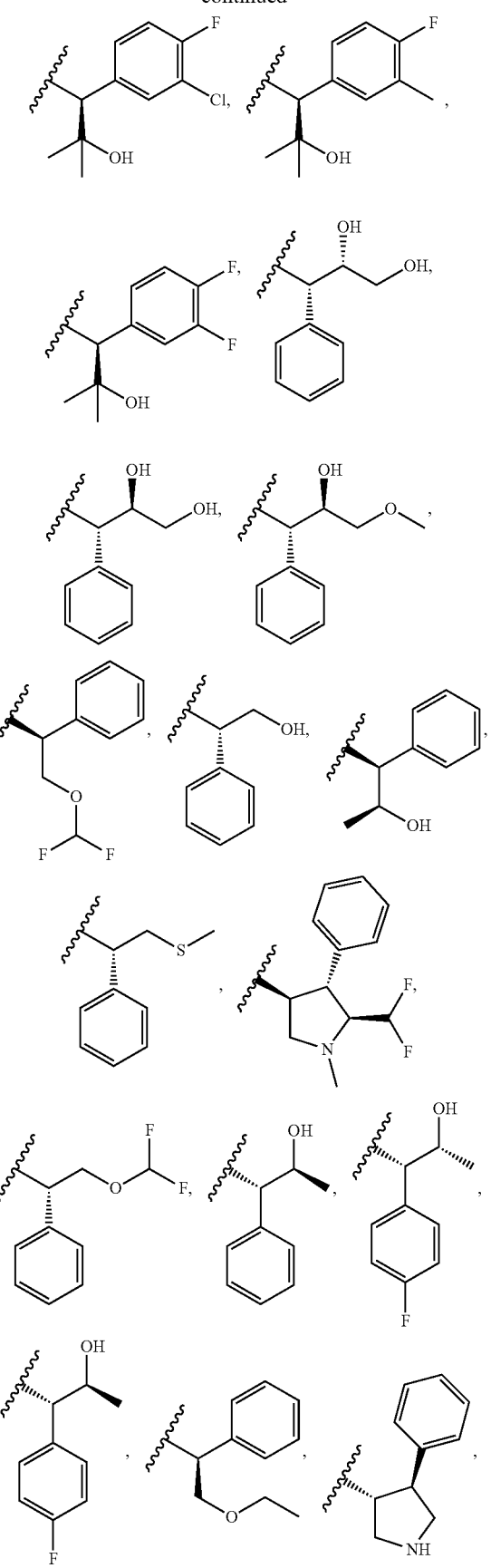

-continued

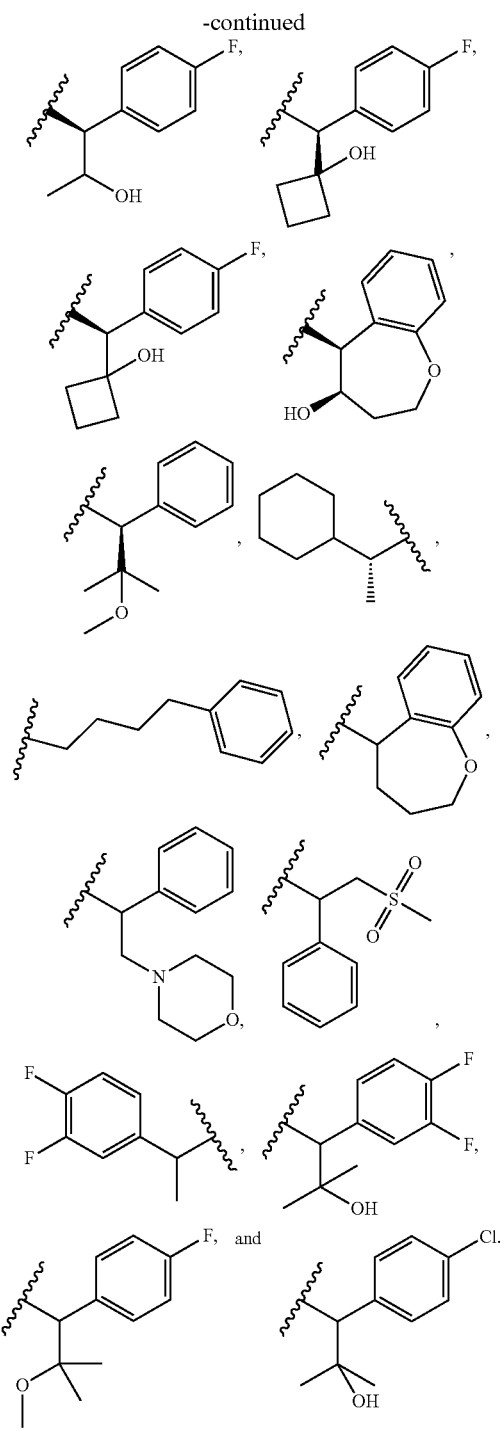

(3) $R^{10}$ is H; and (4) $R^{11}$ is selected from the group consisting of: —CH$_2$OH, —CH(OH)CH$_3$, —CH(OH)CH$_3$, —CH(OH)CH$_2$CH$_3$, -pyridyl-CH$_2$OH, —CH(OH)cyclopropyl, —CH$_2$OC(O)CH$_3$, -methyloxadiazolyl, -methyl-thiadiazolyl, —NH$_2$, —NHCH$_3$, —NHCH$_2$CH$_3$, methylpyridyl, —NHC(O)CH$_3$, pyrazolyl, oxazolyl, $R^{11}$ is methylpyrimidinyl, —CH$_2$OC(O)NHCH$_3$, —CH$_2$imidazolyl, —CH$_3$, —CHF$_2$, —CH$_2$OCH$_3$, —CH$_2$oxooxazolidinyl, —CH$_2$O(CH$_2$)$_2$OH, —CH$_2$triazolyl and —CH(CH$_3$)OH.

13. The compound of claim 1 selected from the group consisting of

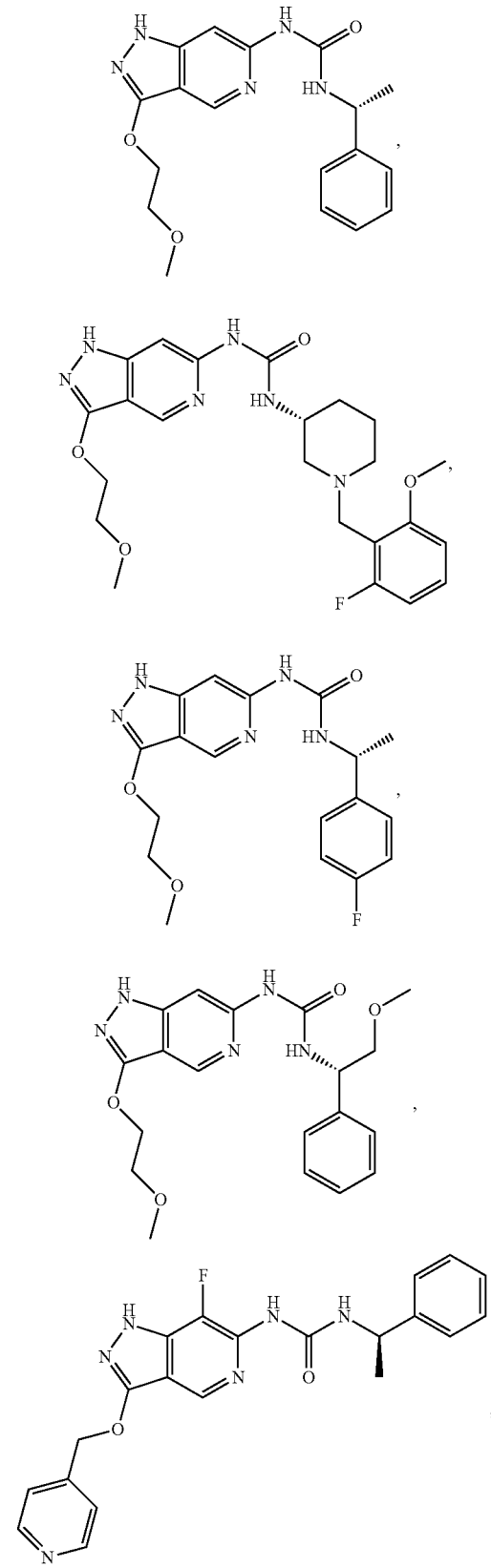

393
-continued
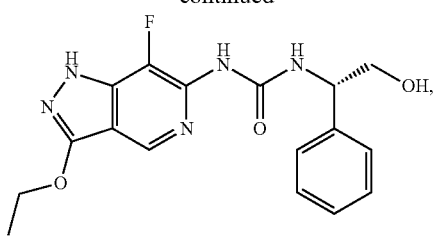
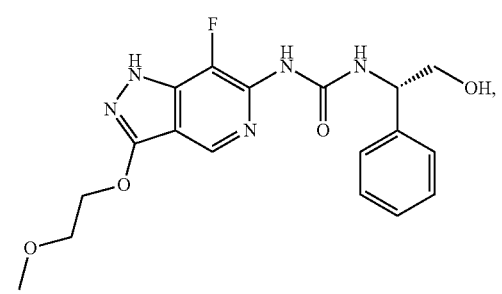
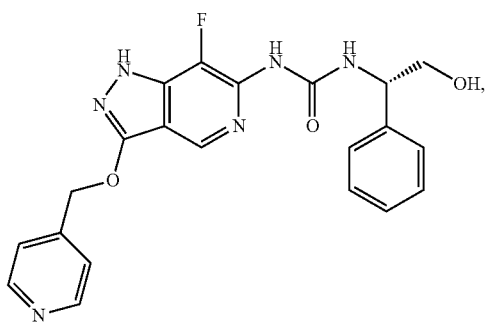
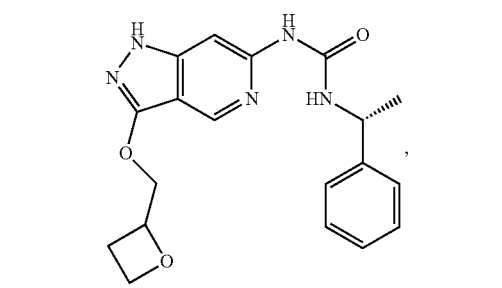
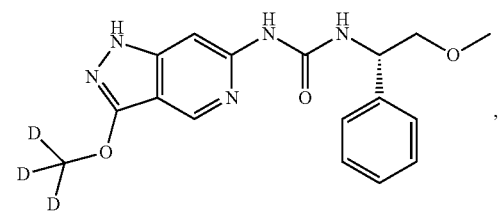
394
-continued
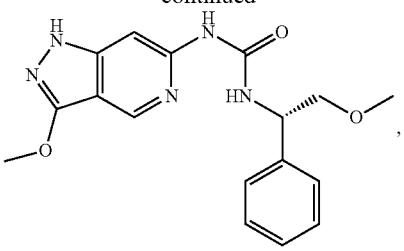
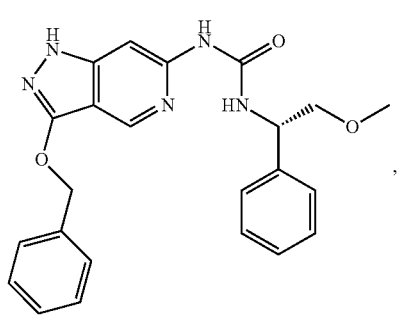
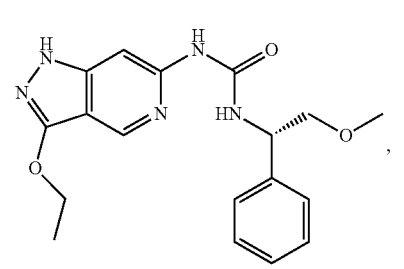
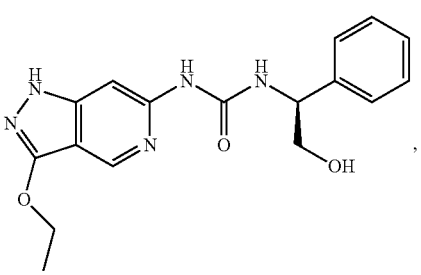
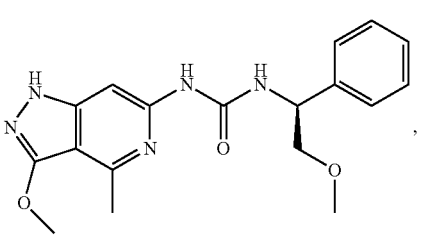
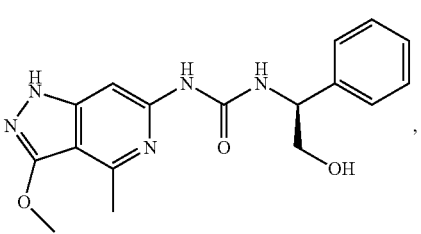

395
-continued
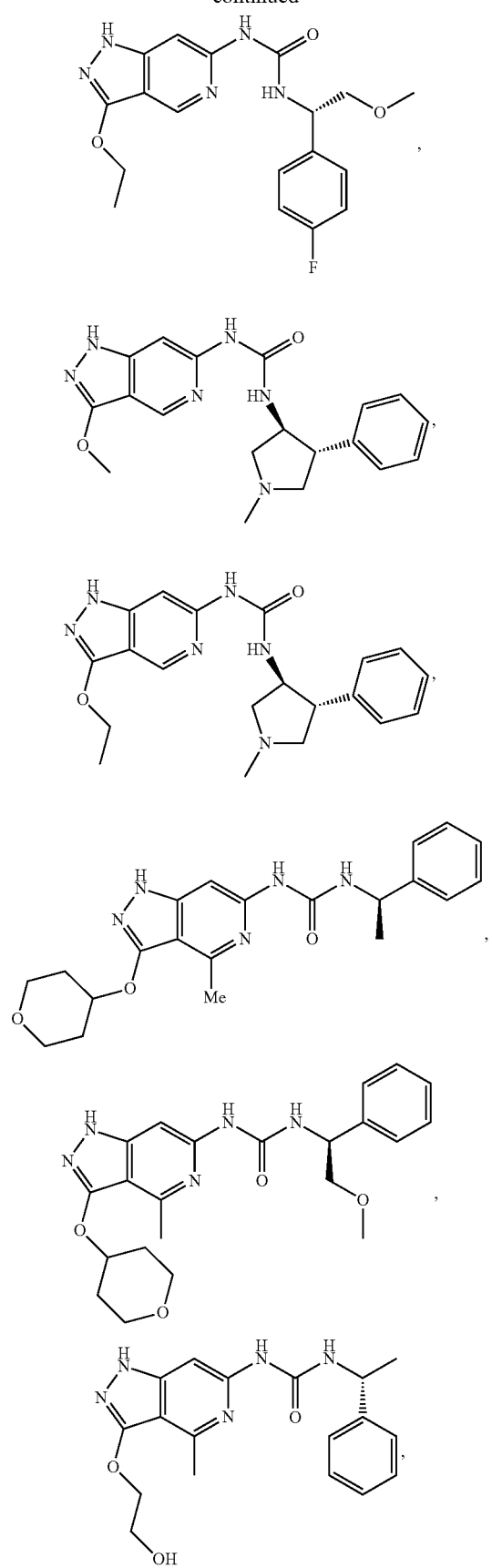
396
-continued
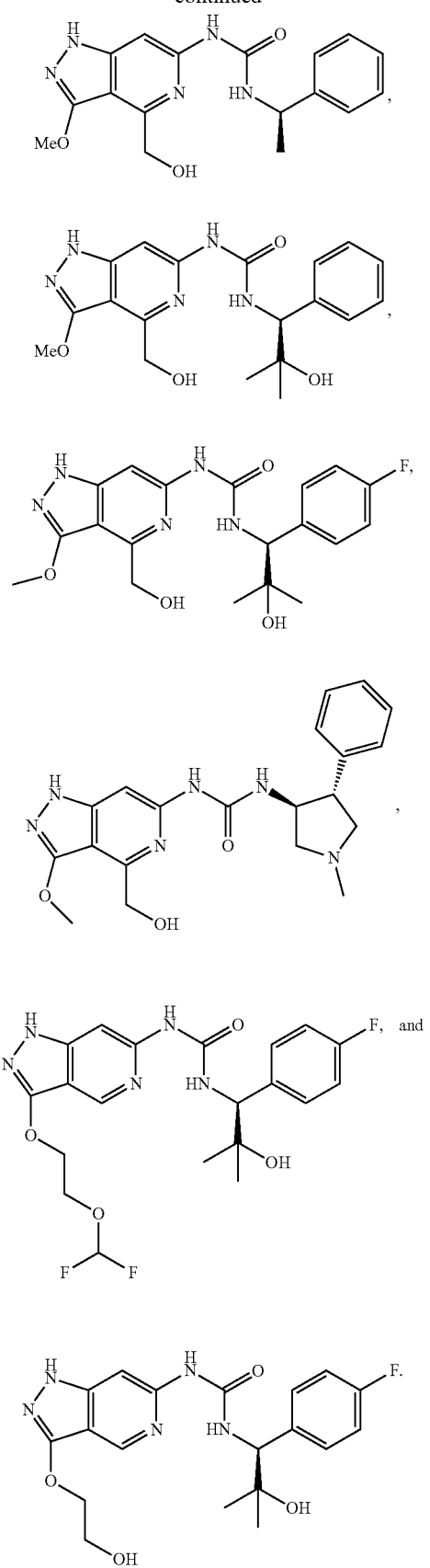

14. The compound of claim 1 selected from the group consisting of
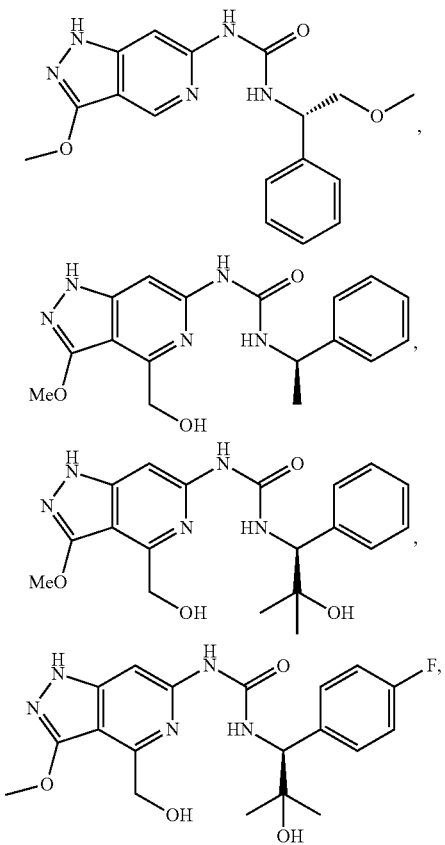
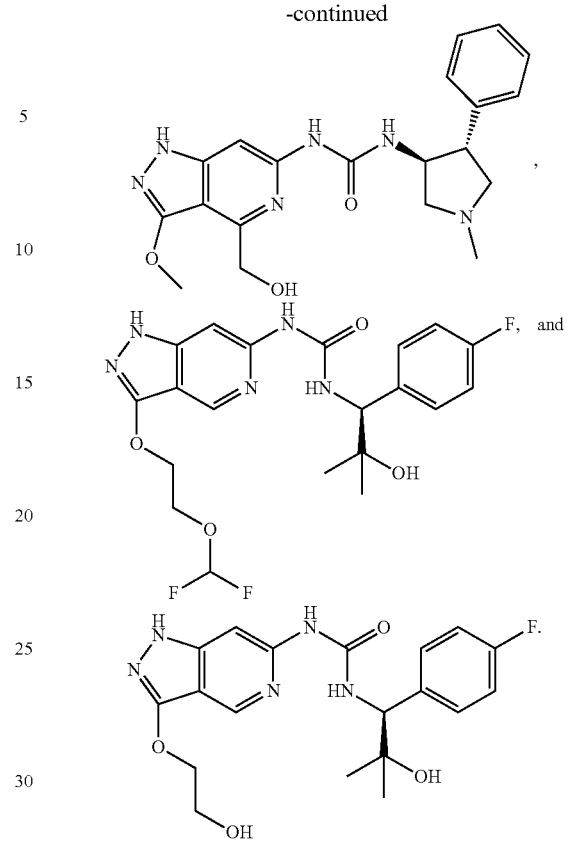
15. A pharmaceutical composition comprising a compound of claim 1 and a pharmaceutically acceptable carrier.
* * * * *